United States Patent [19]

Kitaura et al.

[11] Patent Number: 4,666,890

[45] Date of Patent: *May 19, 1987

[54] PEPTIDE, PROCESS FOR PREPARATION THEREOF AND USE THEREOF

[75] Inventors: Yoshihiko Kitaura, Sakurai; Osamu Nakaguchi, Toyonaka; Keiji Hemmi; Matsuhiko Aratani, both of Suita; Hidekazu Takeno, Tenri; Satoshi Okada, Takatsuki; Hirokazu Tanaka; Masashi Hashimoto, both of Takarazuka; Yoshio Kuroda, Takatsuki; Eiko Iguchi, Osaka; Masanobu Kohsaka, Sakai; Hatsuo Aoki, Ikeda; Hiroshi Imanaka, Osaka, all of Japan

[73] Assignee: Fujisawa Pharmaceutical Co., Ltd., Osaka, Japan

[*] Notice: The portion of the term of this patent subsequent to Jan. 19, 1999 has been disclaimed.

[21] Appl. No.: 380,061

[22] Filed: May 20, 1982

Related U.S. Application Data

[60] Division of Ser. No. 229,072, Jan. 28, 1981, Pat. No. 4,349,466, which is a continuation-in-part of Ser. No. 201,241, Oct. 27, 1980, Pat. No. 4,322,341, which is a continuation-in-part of Ser. No. 171,024, Jul. 22, 1980, abandoned, which is a continuation-in-part of Ser. No. 149,441, May 13, 1980, abandoned, which is a continuation-in-part of Ser. No. 147,710, May 8, 1980, abandoned, which is a continuation-in-part of Ser. No. 110,020, Jan. 7, 1980, abandoned, which is a continuation-in-part of Ser. No. 93,523, Nov. 13, 1979, Pat. No. 4,311,640.

[30] Foreign Application Priority Data

| Nov. 14, 1978 | [GB] | United Kingdom | 44346/78 |
|---|---|---|---|
| Jul. 31, 1979 | [GB] | United Kingdom | 7926705 |
| Oct. 11, 1979 | [GB] | United Kingdom | 7935401 |
| Oct. 15, 1979 | [GB] | United Kingdom | 7935730 |
| Oct. 17, 1979 | [GB] | United Kingdom | 7936000 |
| Oct. 29, 1979 | [GB] | United Kingdom | 7937343 |
| Nov. 7, 1979 | [DK] | Denmark | 4722/79 |
| Nov. 13, 1979 | [AU] | Australia | 52759/79 |
| Nov. 13, 1979 | [CA] | Canada | 339737 |
| Nov. 13, 1979 | [HU] | Hungary | FU 379/13993 |
| Nov. 14, 1979 | [EP] | European Pat. Off. | 79104479.5 |
| Nov. 14, 1979 | [JP] | Japan | 54-147275 |
| Nov. 14, 1979 | [KR] | Rep. of Korea | 79-3985 |
| Nov. 14, 1979 | [ES] | Spain | 485.962 |
| Jul. 22, 1980 | [CA] | Canada | 356887 |
| Jul. 29, 1980 | [AR] | Argentina | 281972 |
| Jul. 29, 1980 | [DK] | Denmark | 3272/80 |
| Jul. 29, 1980 | [ES] | Spain | 493.817 |
| Jul. 30, 1980 | [AU] | Australia | 60939/80 |
| Jul. 30, 1980 | [GR] | Greece | 62571 |
| Jul. 30, 1980 | [MX] | Mexico | 8946 |
| Jul. 31, 1980 | [EP] | European Pat. Off. | 7926705 |
| Jul. 31, 1980 | [JP] | Japan | 55-106279 |
| Jul. 31, 1980 | [KR] | Rep. of Korea | 80-3063 |

[51] Int. Cl.⁴ .................. H61K 37/02; C07K 5/08; C07K 5/10
[52] U.S. Cl. .................. 514/18; 530/330; 530/331
[58] Field of Search .............. 424/177; 260/112.5 R; 514/18; 530/330, 331

[56] References Cited

U.S. PATENT DOCUMENTS

| 4,261,979 | 4/1981 | Jolles et al. | 424/177 |
|---|---|---|---|
| 4,311,640 | 1/1982 | Kuroda et al. | 424/177 |
| 4,349,466 | 9/1982 | Kitaura et al. | 424/177 |

FOREIGN PATENT DOCUMENTS

| 0011283 | 5/1980 | European Pat. Off. |
|---|---|---|
| 0025842 | 1/1981 | European Pat. Off. |
| 2053231 | 2/1981 | United Kingdom |

*Primary Examiner*—Delbert R. Phillips
*Attorney, Agent, or Firm*—Oblon, Fisher, Spivak, McClelland, & Maier

[57] ABSTRACT

The invention relates to novel peptides of enhanced pharmacological activity of the formula:

(Abstract continued on next page.)

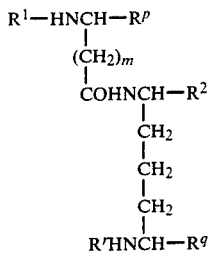

wherein
R$^1$ is alkanoyl;
R$^2$ and R$^q$ are each hydrogen, carboxy, protected carboxy, or a group of the formula:

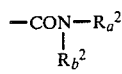

wherein R$_a^2$ is mono- or di-carboxy (or protected carboxy) lower alkyl or ar(carboxy or protected carboxy) lower alkyl whose aryl moiety may be substituted by hydroxy,
R$_b^2$ is hydrogen or lower alkyl;
R$^p$ is hydrogen, carboxy, protected carboxy, with proviso that when one of R$^2$ and R$^q$ is hydrogen, then the other is carboxy or protected carboxy or a group of the formula:

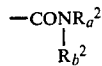

wherein R$_a^2$ and R$_b^2$ are each as defined above;
R$^r$ is hydrogen or amino protective group;
m is an integer 1 to 3;
or its pharmaceutically acceptable salt.

24 Claims, 1 Drawing Figure

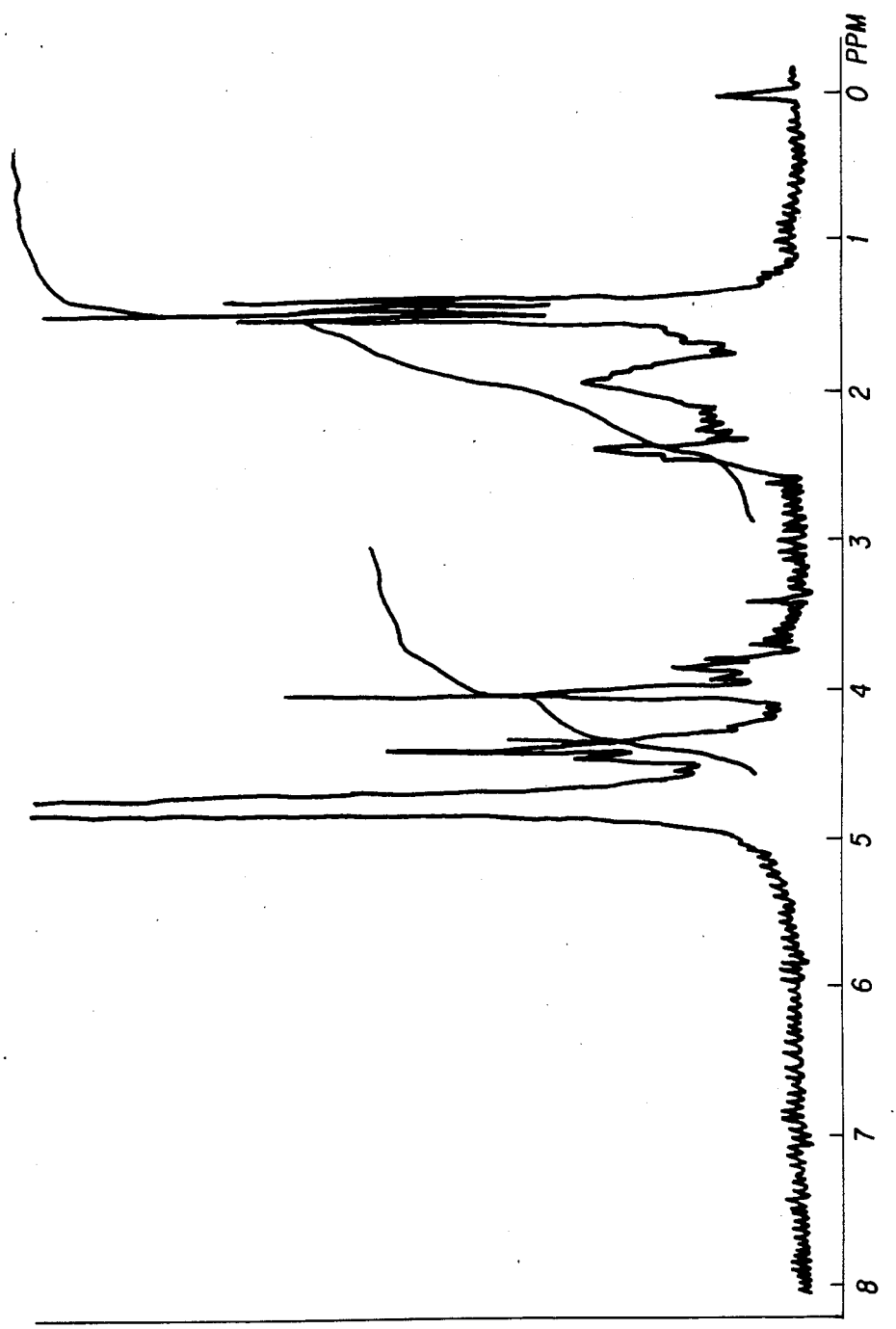

PEPTIDE, PROCESS FOR PREPARATION THEREOF AND USE THEREOF

This application is a division of application Ser. No. 229,072, filed Jan. 28, 1981, now U.S. Pat. No. 3,349,466, which is in turn a continuation-in-part of application Ser. No. 201,241 filed Oct. 27, 1980, now U.S. Pat. No. 4,322,341, which is in turn a continuation-in-part of application Ser. No. 171,024 filed July 22, 1980, now abandoned, which is a continuation-in-part of application Ser. No. 149,441, filed on May 13, 1980, now abandoned, which is a continuation-in-part of application Ser. No. 147,710, filed on May 8, 1980, now abandoned which is a continuation-in-part of application Ser. No. 110,020, filed on Jan. 7, 1980, now abandoned, which is a continuation-in-part of application Ser. No. 093,523 filed on Nov. 13, 1979, now U.S. Pat. No. 4,311,640, Jan 19, 1982.

This invention relates to a new peptide. More particularly, this invention relates to a new peptide and the pharmaceutically acceptable salt thereof, which have pharmacological activities, to processes for the preparation thereof and to a new intermediate for preparing the active peptide, and to the pharmaceutical composition comprising the same and a method of use thereof.

Firstly, it is to be noted that this invention is originated from and based on the first and new discovery of the new active peptide, i.e. FR-900156 substance. That is, the FR-900156 substance was firstly and newly isolated in pure form from a culture broth obtained by fermentation of a new strain belonging to the genus Streptomyces and characterized by the physico-chemical properties.

Thereafter, as a result of extensive study, the inventors of this invention succeeded in determining the chemical structure thereof by commanding physical and chemical techniques so that they could give the sequential structure of the formula (If) indicated below to FR-900156 substance and proposed with a firm belief the possible stereoisomeric structure of the formula (Ie) as indicated below for the same.

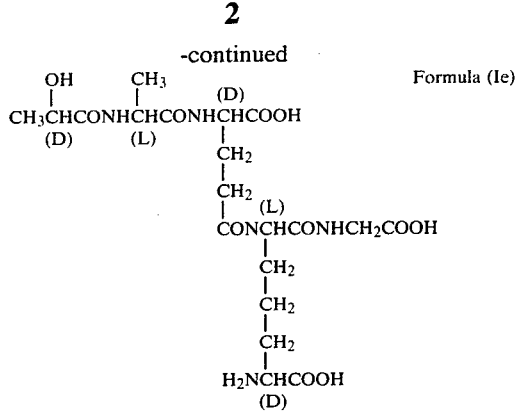

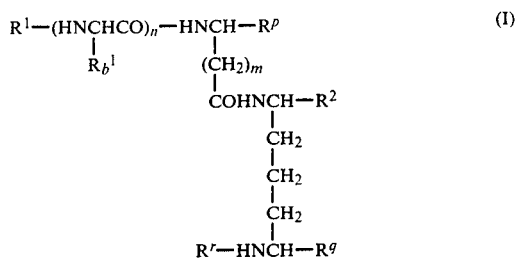

(D—Lactyl-L—alanyl-γ-D—glutamyl-(L)—meso-diaminopimelyl (L)—glycine).

BRIEF DESCRIPTION OF THE DRAWING

The FIGURE of the drawing reproduces the nuclear magnetic resonance absorption spectrum of FR-900156.

Further, after the structural elucidation of FR-900156 as explained above, the inventors of this invention have continued extensive studies on total syntheses of the compound of the formula (If) including the compound of the formula (Ie) so that they have succeeded in completing the industrially advantageous and applicable synthetic processes for preparation of the same, and further have synthetized a lot of related compounds.

A new peptide of this invention is represented by the following formula (I):

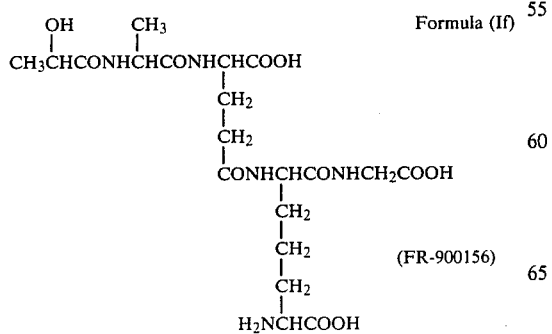

wherein
R¹ is hydrogen or acyl;
$R_b^1$ is hydrogen, methyl, isopropyl, hydroxymethyl, protected hydroxymethyl or benzyl;
$R^2$ and $R^q$ are each hydrogen, carboxy, protected carboxy, or a group of the formula:

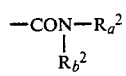

wherein
$R_a^2$ is mono- or di-carboxy (or protected carboxy) lower alkyl or ar(carboxy or protected carboxy) lower alkyl whose aryl moiety may be substituted by hydroxy,
$R_b^2$ is hydrogen or lower alkyl;
$R^p$ is hydrogen, carboxy, protected carboxy with proviso that when one of $R^2$ and $R^q$ is hydrogen, then the other is carboxy or protected carboxy or a group of the formula:

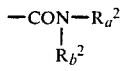

wherein $R_a^2$ and $R_b^2$ are each as defined above;
$R^r$ is hydrogen or amino protective group,
m is an integer 1 to 3; and
n is an integer 0 to 2,
provided that when $R^1$ is hydrogen, t-butoxycarbonyl or N-acetylmuramyl,
$R_b^1$ is methyl, m is an integer 2 and n is an integer 1, then
$R^2$ is hydrogen, protected carboxy or a group of the formula:

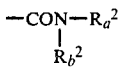

wherein $R_a^2$ is mono- or di-carboxy (or protected carboxy) lower alkyl having 1 and 3 to 6 carbon atoms, α-carboxyethyl, α-protected carboxyethyl, ar-(carboxy or protected carboxy) lower alkyl whose aryl moiety may be substituted by hydroxy and $R_b^2$ is as defined above.

Particulars of the various definitions, which are mentioned hereinabove, and hereinafter and preferred examples thereof are explained in the following.

The term "lower" is intended to mean a group having 1 to 6 carbon atom(s), unless otherwise provided.

(1) Re. Acyl for $R^1$ and $R_c^1$

Generally, "acyl" may be an acyl group derived from an acid such as organic carboxylic acid, carbonic acid, or carbamic acid, or the thio acid or imidic acid corresponding to each of the preceeding acids, or an organic sulfonic acid, each of which includes an aliphatic, an aromatic and/or a heterocyclic groups in its molecule; carbamoyl; or carbamimidoyl.

Suitable examples of said acyl are illustrated below.
Aliphatic acyl means an acyl group derived from an aliphatic acid includes:

alkanoyl (e.g. formyl, acetyl, propionyl, butyryl, isobutyryl, valeryl, isovaleryl, pivaloyl, hexanoyl, α-ethylhexanoyl, heptanoyl, lauroyl, stearoyl, docosanoyl, 2-heneicosylpentacosanoyl, hexacosanoyl[CE$_3$(CH$_2$)$_{24}$CO], tetrapentacontanoyl[CH$_3$(CH$_2$)$_{52}$CO], 2-hexadecyloctadecanoyl[[CH$_3$(CH$_2$)$_{15}$]$_2$CHCO], n-tetracosanoyl[CE$_3$(CH$_2$)$_{22}$CO], 2-docosyltetracosanoyl[[CH$_3$(CH$_2$)$_{21}$]$_2$CHCO], etc.);

cycloalkanecarbonyl (e.g. cyclopentanecarbonyl, cyclopropanecarbonyl, cyclohexanecarbonyl, cycloheptanecarbonyl, etc.);

bridgedalicycliccarbonyl such as bicyclic or tricyclic alkane or alkenecarbonyl (e.g. norbornane carbonyl, adamantanecarbonyl, etc.);

alkenoyl (e.g. acryloyl, methacryloyl, crotonoyl, oleoyl, arachidonyl, etc.);

lower alkylthio(lower)alkanoyl (e.g. methylthioacetyl, ethylthioacetyl, etc.);

lower alkoxycarbonyl (e.g. methoxycarbonyl, ethoxycarbonyl, propoxycarbonyl, butoxycarbonyl, t-butoxycarbonyl, t-pentoxycarbonyl, etc.);

lower alkanesulfonyl(lower)alkoxycarbonyl (e.g. 2-(mesyl)ethoxycarbonyl, etc.);

lower alkylthio(lower)alkoxycarbonyl (e.g. 2-(ethylthio)ethoxycarbonyl, etc.);

lower alkenyloxycarbonyl (e.g. allyloxycarbonyl, etc.)

alkatetraenoyl (e.g. 3,7-dimethylnona-2,4,6,8-tetraenoyl, etc);

lower alkynyloxycarbonyl (e.g. 1,1-dimethylpropargyloxycarbonyl, etc.);

lower alkylcarbamoyl (e.g. methylcarbamoyl, etc.);
(N-lower alkyl)thiocarbamoyl [e.g. (N-methyl)thiocarbamoyl, etc.];

lower alkylcarbamimidoyl (e.g. methylcarbamimidoyl, etc.);

oxalo;

alkoxalyl (e.g. methoxalyl, ethoxalyl, propoxalyl, etc.).

In the above exemplified aliphatic acyl, the aliphatic hydrocarbon moiety, particularly the alkyl group and alkane moiety and the alkenyl group and alkene moiety may have optionally one or more suitable substituent(s) such as amino, halogen (e.g. fluorine, chlorine, bromine, etc.), hydroxy, hydroxyimino, carboxy, lower alkoxy (e.g. methoxy, ethoxy, propoxy, etc.), lower alkoxycarbonyl, acylamino such as lower alkanoylamino (e.g. acetylamino, propionylamino, etc.), ar(lower)alkoxycarbonylamino (e.g. benzyloxycarbonylamino, etc.), etc. or acyloxy such as lower alkanoyloxy (e.g. acetoxy, propoxy, etc.), ar(lower)alkanoyloxy (e.g. benzylcarbonyloxy, etc.), aroyloxy (e.g. benzoyloxy, etc.), or 5- or 6-membered cycloalkenyl (e.g. 1,3,3-trimethyl-1-cyclohexen-2-yl, etc.).

Preferred examples of aliphatic acyl having such substituents may be exemplified by
hydroxyalkanoyl (e.g. glycoloyl, lactoyl, 2-hydroxybutyl, mycoloyl, 2-hydroxyhexacosanoyl

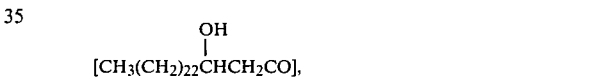

etc
lower alkoxy(lower)alkanoyl (e.g. methoxyacetyl, 2-methoxypropionyl, etc.), carboxy(lower)alkanoyl (e.g. carboxyacetyl, carboxypropionyl, etc.), (lower)alkoxycarbonyl(lower)alkanoyl (e.g. methoxalyl, ethoxalyl, methoxycarbonylacetyl, propoxycarbonylpropionyl, ethoxycarbonylbutyryl, etc.), halo(lower)alkoxycarbonyl (e.g. chloromethoxycarbonyl, tribromoethoxycarbonyl, trichloroethoxycarbonyl, etc.), 6-membered cycloalkenyl-alkatetraenoyl (e.g. retinoyl, etc.),
and the like.

Aromatic acyl means an acyl group derived from an acid having substituted or unsubstituted aryl group, in which the aryl group may include phenyl, tolyl, xylyl, naphthyl and the like, and suitable examples thereof are illustrated as follows:

aroyl (e.g. benzoyl, toluoyl, xyloyl, naphthoyl, phthaloyl, etc.);

ar(lower)alkanoyl (e.g. phenylacetyl, diphenylacetyl, etc.);

ar(lower)alkenoyl (e.g. cinnamoyl, etc.);
aryloxy(lower)alkanoyl (e.g. phenoxyacetyl, etc.);
arylthio(lower)alkanoyl (e.g. phenylthioacetyl, etc.);
arylamino(lower)alkanoyl (e.g. N-phenylglycyl, etc.);

arenesulfonyl (e.g. benzenesulfonyl, tosyl, naphthalenesulfonyl, etc.);

aryloxycarbonyl (e.g. phenoxycarbonyl, tolyloxycarbonyl, etc.);

aralkoxycarbonyl (e.g. benzyloxycarbonyl, benzhydryloxycarbonyl, trityloxycarbonyl, α-naphthylethoxycarbonyl, etc.);

arylcarbamoyl (e.g. phenylcarbamoyl, tolylcarbamoyl, naphthylcarbamoyl, etc.);

arylglyoxyloyl (e.g. phenylglyoxyloyl, etc.);

arylthiocarbamoyl (e.g. phenylthiocarbamoyl, etc.);

arylcarbamimidoyl (e.g. phenylcarbamimidoyl, etc.); and the like.

In the above exemplified aromatic acyl, the aromatic hydrocarbon moiety (particularly, aryl moiety) and/or aliphatic hydrocarbon moiety (particularly, alkane moiety) may have optionally one or more suitable substituent(s), such as the same as those exemplified as the suitable substituent for alkyl group and alkane moiety as mentioned above.

Preferred example of aromatic acyl having such substituents may be exemplified by hydroxyaroyl (e.g. salicyloyl, etc.)

haloaroyl (e.g. chlorobenzoyl, etc.), haloar(lower)alkanoyl (e.g. chlorophenylacetyl, etc.), hydroxyar(lower)alkanoyl (e.g. mandelyl, etc.), methoxyaralkanoyl [e.g. 10-(2,3,4-trimethoxy-6-methylphenyl)-decanoyl, etc].

Heterocyclic acyl means an acyl group derived from an acid having heterocyclic group and includes:

heterocyclic carbonyl, in which the heterocycle moiety is 5 to 6 membered heterocycle containing at least one hetero atom selected from nitrogen, oxygen and sulfur (e.g. thenoyl, furoyl, pyrrolecarbonyl, 5-oxo-2-pyrrolidinecarbonyl, nicotinoyl, etc.);

heterocyclo(lower)alkanoyl, in which the heterocycle moiety is 5 to 6 membered heterocycle containing at least one hetero atom selected from nitrogen, oxygen and sulfur (e.g. thienylacetyl, furylacetyl, imidazolylpropionyl, tetrazolylacetyl, 2-(2-amino-4-thiazolyl)-2-methoxyiminoacetyl, N-acetylmuramyl, etc.); and the like. In the above exemplified heterocyclic acyl, heterocycle moiety and/or the aliphatic hydrocarbon moiety may have optionally one or more suitable substituent(s) such as the same as those exemplified as the suitable substituent for aliphatic acyl as mentioned above.

Further, in the above exemplified acyl, in case that these acyls have one or more functional group such as hydroxy, amino, carboxy and the like, such groups may be protected by conventional protective groups(s).

(2) Re. Protected carboxy for $R^2$, $R^p$, $R_1^p$ and $R^q$:

A protective group of the protected carboxy includes a conventional protective group for tentatively protecting a carboxy group which is conventionally used in the field of amino acid and peptide chemistry.

As preferred examples of protected carboxy, there may be exemplified an ester such as an ester with silyl compound (hereinafter referred to as silyl ester), an ester with an aliphatic hydroxy compound (hereinafter referred to as apliphatic ester) and an ester with a hydroxy compound containing an aromatic group (hereinafter referred to as aromatic ester), and a protected carbazoyl of the formula: —COHNNHY (wherein Y is hydrogen or an amino protective group).

Concrete examples of such a protected carboxy are exemplified as follows.

suitable silyl ester such as trialkylsilyl (e.g. trimethylsilyl, triethylsilyl, etc.) ester, halo-alkylsilyl (e.g. chloro-dimethylsilyl, dichloromethylsilyl, etc.) ester, trihalosilyl (e.g. trichlorosilyl, etc.) ester, alkylalkoxysilyl (e.g. methyl-diethoxysilyl, etc.) ester, trialkoxysilyl (e.g. tris(2-chloroethoxy)silyl, etc.) ester, and the like;

suitable aliphatic hydrocarbon ester such as alkyl (e.g. methyl, ethyl, propyl, isopropyl, butyl, tert-butyl, etc.) ester, cycloalkyl (e.g. cyclopentyl, cyclohexyl, etc.) ester and the like; and suitable ester containing an aromatic group such as aryl (e.g. phenyl, tolyl, xylyl, etc.) ester, aralkyl (e.g. benzyl, diphenylmethyl, phenethyl, etc.) ester, aryloxyalkyl (e.g. phenoxymethyl, phenoxyethyl, etc.) ester, aroylalkyl (e.g. phenacyl, toluoylethyl, etc.) ester, and the like.

The ester forming group (e.g. substituted silyl, aliphatic hydrocarbon residue, aryl, aralkyl, aryloxyalkyl, aroylalkyl and the like, as exemplified above) may optionally have one or more appropriate substituent(s) such as alkyl (e.g. methyl, ethyl, etc.), cycloalkyl (e.g. cyclopropyl, cyclohexyl, etc.), alkoxy (e.g. methoxy, ethoxy, etc.), alkanoyloxy (e.g. acetoxy, etc.), alkylthio (e.g. methylthio, etc.), halogen (e.g. chlorine, etc.), cyano, nitro, etc.

Examples of such substituted esters may be mono(di or tri)haloalkyl (e.g. chloromethyl, bromoethyl, dichloromethyl, 2,2,2-trichloroethyl, 2,2,2-tribromoethyl, 2,2,2-trifluoroethyl, etc.) ester, cyanoalkyl (e.g. cyanomethyl, cyanoethyl, etc.) ester, cycloalkyl-substituted-alkyl (e.g. 1-cyclopropylethyl, etc.) ester, mono(di, tri, tetra or penta)halophenyl (e.g. 4-chlorophenyl, 3,5-dibromophenyl, 2,4,5-trichlorophenyl, 2,4,6-trichlorophenyl, pentachlorophenyl, etc.) ester, and the like.

With regard to the term "protected carboxy" for $R^2$, $R^p$, $R_1^p$ and $R^q$, it is to be understood that this group bear the meaning not only in synthetic manufacture of the object compound by chemical process(es), but also in physiological and pharmaceutical properties of the object compound per se.

That is, in the meaning of the synthetic manufacture, free carboxy group for $R^2$, $R^p$, $R_1^p$ and $R^q$ may be transformed into the "protected carboxy" group as mentioned above before conducting the process(es) for preventing any possible undesired side reaction(s), and the "protected carboxy" group in the resultant compound may be transformed into free carboxy group after the reaction is conducted. This will be apparent from the explanation of the processes in the following.

On the other hand, in the meaning of the physiological and pharmaceutical properties of the object compound, the compound bearing the "protected carboxy" group for $R^2$, $R^p$, $R_1^p$ and/or $R^q$ is optionally used for the physiologically and pharmaceutically active compound per se. More particularly, as such a protected carboxy group, "esterified carboxy" group is optionally given as a preferable example, including a conventional esterified carboxy. As suitable examples of the "esterified carboxy", there may be exemplified the same esterified carboxy as illustrated above for explanation of the protected carboxy, among which, as preferred examples, there may be given an aliphatic hydrocarbon ester such as alkyl ester, i.e. alkoxycarbonyl (e.g. methoxycarbonyl, ethoxycarbonyl, propoxycarbonyl, isopropoxycarbonyl, butoxycarbonyl, t-butoxycarbonyl, etc.) and the like.

(3) Re. A group of the formula:

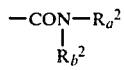

for $R^2$ and $R^q$:

Suitable example of lower alkyl for $R_b^2$ and lower alkyl moiety of mono- or di-carboxy(lower)alkyl and of ar(carboxy)lower alkyl for $R_a^2$ is one having 1–6 carbon atoms such as methyl, ethyl, propyl, isopropyl, butyl, isobutyl, pentyl, isopentyl and the like.

Suitable example of aryl moiety of ar(carboxy)lower alkyl for $R_a^2$ is phenyl, tolyl, xylyl, naphthyl and the like. In this respect, it is to be noted that "ar(carboxy)-lower alkyl" can alternatively expressed by the wording "lower alkyl" which is substituted by carboxy and aryl group.

Carboxy in "mono- or di-carboxy lower alkyl" for $R_a^2$ and "ar(carboxy)lower alkyl whose aryl moiety may be substituted by hydroxy" for $R_a^2$ may be protected by a conventional protective group; namely, $R_a^2$ includes within its definition also protected carboxy-lower alkyl and ar(protected carboxy)lower alkyl which may be substituted by hydroxy. Suitable example of such a protected carboxy is the same as that exemplified for $R^p$ and $R^q$.

Most preferred examples of a group of the formula:

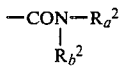

are illustrated as follows:

$$-CONHCH_2COOH, \quad -CONH\underset{L}{\overset{CH_3}{C}}HCOOH, \quad -CONH\underset{D}{\overset{CH_3}{C}}HCOOH,$$

$$-CONHCH_2CH_2COOH, \quad -CONHCH_2CH_2CH_2COOH,$$

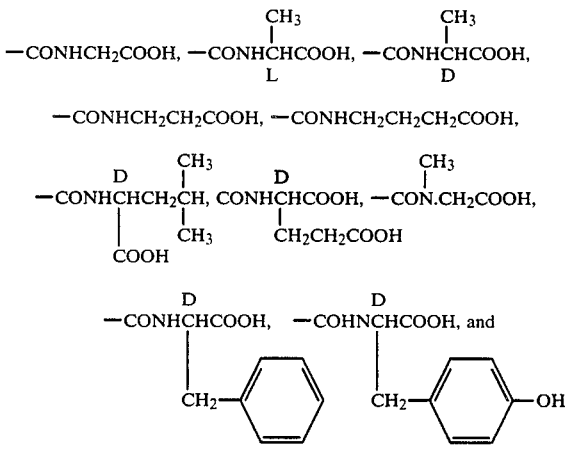

the corresponding group, in which the carboxy group is protected by a conventional carboxy protective group.

(4) Re. Protected hydroxymethyl for $R_b^1$:

Hydroxy group of hydroxymethyl for $R_b^1$ may be protected by a conventional hydroxy protective group; namely, $R_b^1$ includes protected hydroxymethyl.

Some preferred examples of the hydroxy protective group may be exemplified by an acyl such as substituted or unsubstituted alkanoyl (e.g. formyl, acetyl, propionyl, butyryl, isobutyryl, valeryl, bromoacetyl, dichloroacetyl, trifluoroacetyl, etc.), substituted or unsubstituted aroyl (e.g. benzoyl, toluoyl, xyloyl, nitrobenz-oyl, bromobenzoyl, salicyloyl, etc.), arylalkyl (e.g. benzyl) or the like.

(5) Re. Amino protective group for $R^r$, $R_1^r$ and Y:

The amino protective group includes a conventional protective group for tentatively protecting an amino group, which is used in the field of amino acid and peptide chemistry. That is, in the peptide synthesis, it is understood that, for bonding a desired "reactive" amino group (—NH$_2$) with a desired "reactive" carboxy group (—COOH) to form a desired peptide bond (—CONH—) between them, it is preferable to tentatively protect the other undesired "reactive" amino group to convert it into an unreactive or less reactive protected amino group in the reaction in order to avoid the side reaction between the undesired "reactive" amino group and desired "reactive" carboxy groups. Further, it is understood that it is preferable that a protective group in such protected amino group is easily eliminable according to the necessity in the post treatment of the object peptide. Accordingly, an amino protective group to meet the above requirements can be used and suitable one should be selected according to the kind and property of the component to be used in this invention.

As preferred examples of the amino protective group, the following examples are illustrated:

Acyl, particularly organic acyl, for example, substituted or unsubstituted aliphatic hydrocarbon-oxycarbonyl such as alkoxycarbonyl (e.g. methoxycarbonyl, ethoxycarbonyl, propoxycarbonyl, butoxycarbonyl, t-butoxycarbonyl, t-pentoxycarbonyl, etc.), haloalkoxycarbonyl (e.g. chloromethoxycarbonyl, tribromoethoxycarbonyl, trichloroethoxycarbonyl, etc.), an alkane- or arene-sulfonylalkoxycarbonyl (e.g. 2-(mesyl)ethoxycarbonyl, 2-(p-toluenesulonyl)ethoxycarbonyl, etc.), an alkylthio- or arylthioalkoxycarbonyl (e.g. 2-(ethylthio)ethoxycarbonyl, 2-(p-tolylthio)ethoxycarbonyl, etc.), substituted or unsubstituted alkanoyl such as halo(lower)alkanoyl (e.g. formyl, trifluoroacetyl, etc), a monocyclic or fusedcyclic-alicyclic oxycarbonyl (e.g. cyclohexyloxycarbonyl, adamantyloxycarbonyl, isobornyloxycarbonyl, etc.), substituted or unsubstituted alkenyloxycarbonyl (e.g. allyoxycarbonyl, etc.), substituted or unsubstituted alkynyloxycarbonyl (e.g. 1,1-dimethylpropargyloxycarbonyl, etc.) or the like, substituted or unsubstituted aryloxycarbonyl (e.g. phenoxycarbonyl, p-methylphenoxycarbonyl, etc.), substituted or unsubstituted aralkoxycarbonyl (e.g. benzyloxycarbonyl, p-nitrobenzyloxycarbonyl, p-phenylazobenzyloxycarbonyl, p-(p-methoxyphenylazo)benzyloxycarbonyl, p-chlorobenzyloxycarbonyl, p-bromobenzyloxycarbonyl, α-naphthylmethoxycarbonyl, p-biphenylisopropoxycarbonyl, etc.);

substituted or unsubstituted arenesulfonyl (e.g. benzenesulfonyl, p-toluenesulfonyl, etc.);

substituted or unsubstituted dialkylphosphoryl (e.g. dimethylphosphoryl, etc.);

substituted or unsubstituted diaralkylphosphoryl (e.g. O,O-dibenzylphosphoryl, etc.);

substituted or unsubstituted aryloxyalkanoyl (e.g. phenoxyacetyl, p-chlorophenoxyacetyl, 2-nitrophenoxyacetyl, 2-methyl-2-(2-nitrophenoxy)propyonyl, etc.) or the like;

substituted or unsubstituted aryl such as phenyl, tolyl or the like;

substituted or unsubstituted aralkyl such as benzyl, diphenylmethyl, trityl, nitrobenzyl, or the like;

substituted or unsubstituted alkylidene (e.g. ethylene, isopropylidene, etc.) or the like;

substituted or unsubstituted aralkylidene such as benzylidene, 2-hydroxybenzylidene, 2-hydroxy-5-chlorobenzylidene or the like;

substituted or unsubstituted arylthio such as phenylthio, nitrophenylthio, dinitrophenylthio, trichlorophenylthio or the like; and substituted or unsubstituted aralkylthio such as tritylthio or the like.

(6) Esterified carboxy for $R_3{}^p$, $R_c{}^2$ and $R_4{}^q$:

The esterified carboxy and esterified carboxy moiety for $R_3{}^p$, $R_c{}^2$ and $R_4{}^q$ include a conventional esterified carboxy.

As suitable examples of the esterified carboxy, there may be exemplified the same esters as illustrated above for explanation of protected carboxy for $R^2$, $R^p$, $R_1{}^p$ and $R^q$, among which, as preferred examples, there may be given an aliphatic hydrocarbon ester such as alkyl ester, i.e. alkoxycarbonyl (e.g. methoxycarbonyl, ethoxycarbonyl, propoxycarbonyl, isopropoxycarbonyl, butoxycarbonyl, t-butoxycarbonyl, etc.) and the like.

A pharmaceutically acceptable salt of the new peptides of the formula (I) may include a salt with an inorganic or organic base such as an alkali metal salt (e.g. sodium salt, potassium salt, etc.), an alkaline earth metal salt (e.g. calcium salt, etc.), ammonium salt, ethanolamine salt, triethylamine salt, dicyclohexylamine salt or the like, and an acid addition salt with organic or inorganic acid such as methane sulfonate, hydrochloride, sulfate, nitrate, phosphate or the like.

With regard to the formula (I) of the compound of this invention the following is to be noted. That is, partial formula:

in the formula (I) particularly means
$R^1$—, when n is an integer 0,

when n is an integer 1, and

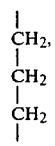

when n is an integer 2.
Further, partial formula

in the formula (I) particularly means

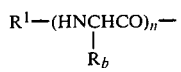

when m is an integer 1,

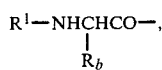

when m is an integer 2, and

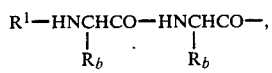

when m is an integer 3.

The compound (I) of this invention including FR-900156 can be prepared by chemical synthetic methods and fermentation method, details of which will be apparent from the following description.

[1]

SYNTHESIS:

(1) Process 1: Peptide bond formation 1

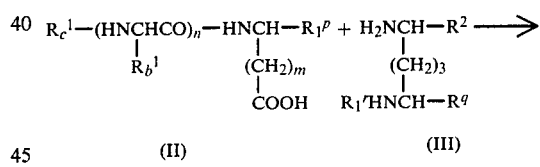

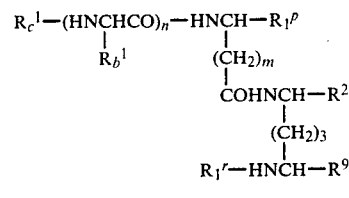

(2) Process 2: Selective deacylation

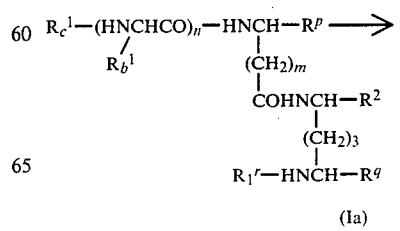

-continued

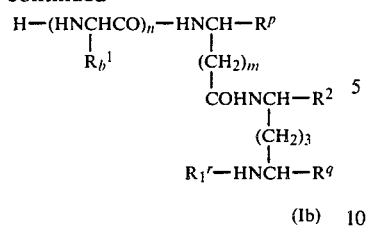

(Ib)

(3) Process 3: Acylation

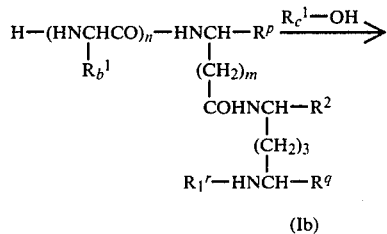

(Ib)

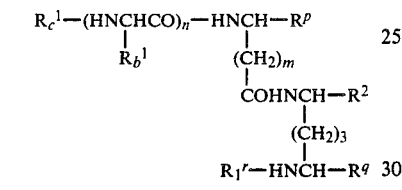

(Ia)

(4) Process 4: Elimination of protective groups

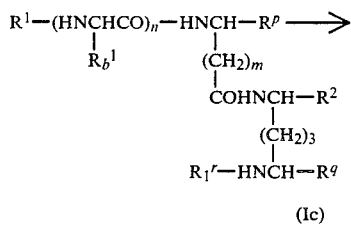

(Ic)

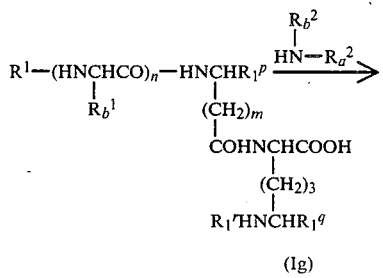

(Id)

(5) Process 5: Peptide bond formation 2

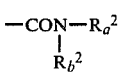

(Ig)

-continued

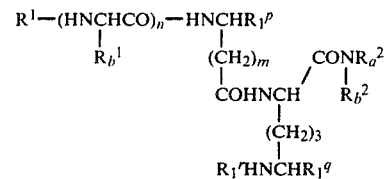

(Ih)

(6) Process 6: Aminoprotection

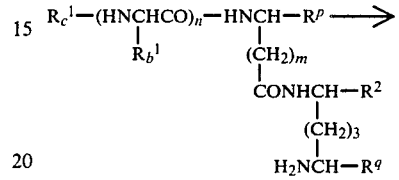

(Ij)

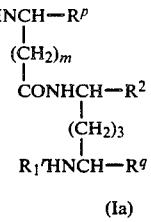

(Ia)

(7) Process 7: Esterification

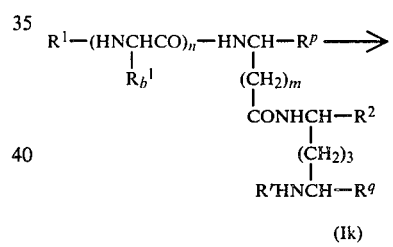

(Ik)

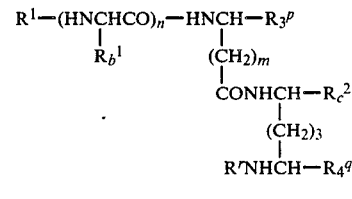

(Il)

[$R^1$, $R_b^1$, $R^p$, $R^2$, $R^q$, $R^r$, m and n are each as defined above provided that at least one of $R^p$, $R^2$ and $R^q$ is carboxy, or alternatively at least $R_a^2$ is mono- or di-carboxy lower alkyl or ar(carboxy)lower alkyl whose aryl moiety may be substituted by hydroxy; and $R_c^2$ and $R_4^q$ are each hydrogen, carboxy, protected carboxy, esterified carboxy or a group of the formula:

$$-CON-R_a^2$$
$$\phantom{-CON-}R_b^2$$

wherein $R_a^2$ is mono- or di-carboxy (or protected carboxy)lower alkyl, esterified carboxy lower alkyl, ar(carboxy or protected carboxy)lower alkyl whose aryl moiety may be substituted by hydroxy or ar(esterified carboxy)lower alkyl whose aryl moiety may be substituted by hydroxy and $R_b^2$ is as defined above, $R_3^p$ is hydrogen, carboxy, protected carboxy or esterified carboxy provided that at least one of $R_c^2$, $R_4^q$ and $R_3^p$ is esterified carboxy, or alternatively at least $R_a^2$ is mono- or di-esterified carboxy lower alkyl or ar(esterified carboxy)lower alkyl whose aryl moiety may be substituted by hydroxy.]

[2]

FERMENTATION

A strain belonging to the genus Streptomyces→

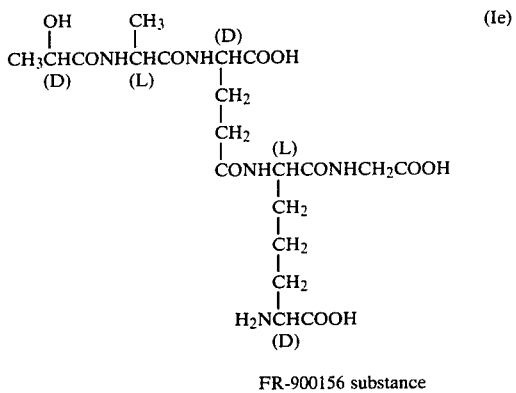

FR-900156 substance

In the above formulae, $R_c^1$ is acyl, $R_1^p$ is hydrogen or protected carboxy, $R_2^p$ is hydrogn or carboxy, $R_1^q$ is hydrogen or protected carboxy, $R^2$ and $R_7^q$ are hydrogen, carboxy or a group of the formula:

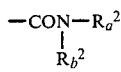

wherein $R_a^2$ is mono- or di-carboxy lower alkyl or ar(carboxy)lower alkyl whose aryl moiety may be substituted by hydroxy, and $R_b^2$ is as defined above, $R_1^r$ is amino protective group and m, n, $R^1$, $R^2$, $R^p$, $R^q$, $R^r$, $R_a^2$ and $R_b^2$ are each as defined above.

Detailed explanation of processes for preparation of a new peptide of the formula (I) will be made in following.

[1]

SYNTHESIS (1) Process 1: Peptide bond formation

Compound (II)+Compound (III)→Compound (Ia)

This process relates to a method for preparing Compound (Ia) by reacting Compound (II) or its salt with a Compound (III) or its salt.

The reaction of this process can be conducted as follows. That is, in one case, as the first step, the carboxy group of Compound (II) or its salt is usually activated in a conventional manner, for example, in the form of its acid halide, azide, acid anhydride or a mixed anhydride, activated ester, and the like, and is reacted with the Compound (III) to give Compound (Ia), and in the other case, the Compound (II) or its salt is reacted with the Compound (III) or its salt directly in the presence of a conventional condensing agent such as N,N-dicyclohexylcarbodiimide and the like. Among these activation methods, preferred activation method for the carboxy group of the Compound (II) into its activated form and preferred condensing agent as mentioned above are selected according to kinds of the carboxy protective group(s) of the Compound (II) and (III) and to the reaction conditions (e.g. the kinds of the reaction solvent, reaction temperature and so on).

This reaction is preferably carried out in a solvent such as methylene chloride, chloroform, tetrahydrofuran, dioxane, ethyl acetate, methanol, ethanol, water or the like under ice-cooling to at ambient temperature and the reaction in the presence of a condensing agent is usually carried out in an anhydrous, but not critical, conditions.

(2) Process 2: Selective deacylation

Compound (Ia)→Compound (Ib)

This process relates to a method for preparing Compound (Ib) or its salt by removing selectively an acyl group for $R_c^1$ of Compound (Ia) or its salt.

This process is applied to case that the acyl group for $R_c^1$ reveals a different chemical property from that of the amino protective group for $R_1^r$ against each kind of the removal methods and can selectively be removable by a method to be employed.

This reaction is carried out by conventional methods such as catalytic reduction method, liquidammoniaalkalimetal method, acid method, zinc acid method, base method, hydrazine method and the like. Among these methods, preferred one is selected according to kind of the acyl group for $R_c^1$ of Compound (Ia).

Each of the above methods is explained as follows.

(i) Catalytic reduction method:

This method is preferably applied to case that the acyl group for $R_c^1$ of Compound (Ia) are one which is removable by catalytic reduction. As preferred examples of such an acyl group for $R_c^1$, there may be exemplified substituted or unsubstituted aralkoxycarbonyl (e.g. benzyloxycarbonyl, p-phenylazobenzyloxycarbonyl, p-(p'-methoxyphenylazo)benzyloxycarbonyl, p-nitrobenzyloxycarbonyl, etc.); substituted or unsubstituted alkenyl- or alkynyloxycarbonyl (e.g. allyloxycarbonyl, 1,1-dimethylproparglyloxycarbonyl, etc.); substituted or unsubstituted aryloxyalkanoyl (e.g. 2-nitrophenoxyacetyl, 2-methyl-2-(2-nitrophenoxy)propionyl, etc.); and the like.

This catalytic reduction is carried out in a conventional manner, and suitable catalysts to be used in catalytic reduction are conventional ones such as platinum catalyst (e.g. platinum plate, spongy platinum, platinum black, colloidal platinum, platinum oxide or platinum wire, etc.), palladium catalyst (e.g. spongy palladium, palladium black, palladium oxide, palladium on carbon, colloidal palladium, palladium on barium sulfate, palladium on barium carbonate, etc.), nickel catalyst (e.g. reduced nickel, nickel oxide, Raney nickel, etc.), cobalt catalyst (e.g. reduced cobalt, Raney cobalt, etc.), iron catalyst (e.g. reduced iron, Raney iron, etc.), copper catalyst (e.g. reduced copper, Raney copper, Ullman copper, etc.) or the like.

The reduction is usually carried out in a solvent. A suitable solvent to be used may be, e.g. water, methanol, ethanol, propanol, ethyl acetate, tetrahydrofuran, dioxane, N,N-dimethylformamide, acetic acid, a mixture of water and alcohol (e.g. methanol, ethanol, etc.) tetrahydrofuran, dioxane or ethyl acetate, and other conventional organic solvent or a mixture thereof. Further, the reduction is preferably carried out in the presence of an acid such as acetic acid or the like.

The reaction is preferably carried out under somewhat milder conditions such as cooling or warming.

In this method, in case that $R^q$ is a group of the formula: —CONHNHY and an amino protective group for Y is the same as the acyl for $R_c{}^1$, then such an amino protective group also is simultaneously removed to give a Compound (Ib) wherein $R^q$ is a group of the formula: —CONHNH$_2$. Further, in case that a protected carboxy group for $R^p$ is, for example, substituted or unsubstituted aralkyl ester type one (e.g. benzyl ester p-nitrobenzyl ester, p-chlorobenzyl ester, p-phenylazobenzyl ester, etc.), such a protective group also is simultaneously removed in this process to give a Compound (Ib) wherein $R^p$ is carboxy.

(ii) Acid method:

(ii)-1 Method of use of trifluoroacetic acid or formic acid:

This method is preferably applied to case that the acyl group for $R_c{}^1$ is one which is removable by treating with trifluoro-acetic acid or formic acid. Preferred examples of such an acyl group may be exemplified by a group such as branched- or alicyclicoxycarbonyl, (e.g. t-butoxycarbonyl, t-pentoxycarbonyl, t-amyloxycarbonyl, adamantyloxycarbonyl, isobornyloxycarbonyl, etc.); substituted or unsubstituted aralkoxycarbonyl (e.g. p-methoxybenzyloxycarbonyl, etc.).

This reaction is conventionally carried out in a solvent such as methylene chloride, chloroform, acetic acid, water and the like in the presence of trifluoroacetic acid or formic acid, and anisole is preferably added thereto.

Trifluoroacetic acid and formic acid are also used as the solvent.

This reaction is usually carried out under ice-cooling to ambient temperature.

In this method, in case that $R^q$ is a group of the formula: —CONHNHY and an amino protective group for Y is the same as the acyl for $R_c{}^1$, then such an amino protective group also is simultaneously removed to give a Compound (Ib) wherein $R^q$ is a group of the formula: —CONHNH$_2$. Further, in case that a protected carboxy group for $R^p$ is, for example, a branched alkyl ester (e.g. t-butyl ester, etc.), or substituted or unsubstituted aralkyl ester (e.g. diphenylmethyl ester, p-methoxybenzyl ester, etc.), such a protective group also is simultaneously removed to give a Compound (Ib) wherein $R^p$ is carboxy.

(ii)-2 Method of use of hydrochloric acid or p-toluenesulfonic acid:

This method is preferably applied to case that an acyl group for $R_c{}^1$ is one which is removed by treating with hydrochloric acid or p-toluenesulfonic acid.

Preferred examples of such an acyl group may be exemplified by e.g. substituted or unsubstituted branched alkoxycarbonyl (e.g. t-butoxycarbonyl, 1-(p-biphenyl)-1-methylethoxycarbonyl, etc.) and the like in addition to one as illustrated in the above (ii)-1.

This reaction is carried out in a solvent such as ethyl acetate, methylene chloride, chloroform, tetrahydrofuran and the like in the presence of an inorganic or organic strong acid such as hydrochloric acid, p-toluenesulfonic acid or the like, and anisole is preferably added thereto.

This reaction is preferably carried out under ice-cooling to at ambient temperature.

In this method, in case that $R^q$ is a group of the formula: —CONHNHY and an amino protective group for Y is the same as the acyl for $R_c{}^1$, then such an amino protective group also is simultaneously removed to give a Compound (Ib) wherein $R^q$ is a group of the formula: —CONHNH$_2$. Further, in case that a protected carboxy group for $R^p$ is, for example, a branched alkyl ester (e.g. t-butyl ester etc.) or substituted or unsubstituted aralkyl ester (e.g. diphenylmethyl ester, p-methoxybenzyl ester, etc.), such a protective group also is simultaneously removed to give a Compound (Ib) wherein $R^p$ is carboxy.

(ii)-3 Method of use of hydrogen bromide:

This method is preferably applied to case that an acyl group for $R_c{}^1$ is one which is removable by treating with hydrogen bromide.

Preferred examples of such an acyl group may be exemplified by substituted or unsubstituted aralkoxycarbonyl (e.g. benzyloxycarbonyl, p-chlorobenzyloxycarbonyl, p-bromobenzyloxycarbonyl, p-tolyloxycarbonyl, p-phenylazobenzyloxycarbonyl, α-naphthylmethoxycarbonyl, etc.) and an alkoxycarbonyl (e.g. isopropoxycarbonyl, etc.) in addition to one as illustrated in the above (ii)-1 and (ii)-2.

This reaction is usually carried out in a solvent such as ethyl acetate, acetic acid, trifluoroacetic acid or the like in the presence of hydrogen bromide.

This reaction is preferably carried out under ice-cooling to at ambient temperature.

In this method, in case that $R^q$ is a group of the formula: —CONHNHY and an amino protective group for Y is the same as the acyl for $R_c{}^1$, then such an amino protective group also is simultaneously removed to give Compound (Ib) wherein $R^q$ is a group of the formula: —CONHNH$_2$. Further, in case that a protected carboxy group for $R^p$ is, for example, a branched alkyl ester or (e.g. t-butyl ester, etc.), substituted or unsubstituted aralkyl ester (e.g. diphenylmethyl ester, p-methoxybenzyl ester, etc.), such a protective group is simultaneously removed to give a Compound (Ib) wherein $R^p$ is carboxy.

(iii) Liquid-ammonia-alkali metal method:

This method is preferably applied to case that the acyl group for $R_c{}^1$ is one which is removable by treating with liquid ammonia-alkali metal. As preferred examples of such an acyl group, there may be exemplified substituted or unsubstituted aralkoxycarbonyl (e.g. benzyloxycarbonyl, etc.), substituted or unsubstituted aryloxycarbonyl (e.g. phenoxycarbonyl, p-methylphenoxycarbonyl, etc.), an arenesulfonyl (e.g. benzenesulfonyl, p-toluenesulfonyl, etc.) and the like.

This reaction is usually carried out by dissolving Compound (Ia) into liquid ammonia and then alkali metal is added thereto.

This reaction is preferably carried out at a lower temperature, e.g. at $-78°$ C. to at boiling point of liquid ammonia.

In this method, in case that $R^q$ is a group of the formula: —CONHNHY and amino protective group for Y is the same as the acyl for $R_c{}^1$, then such an amino protective group also is simultaneously removed to give a Compound (Ib) wherein $R^q$ is a group of the formula: —CONHNH$_2$.

(iv) Hydrazine method:

This method is preferably applied to case that the acyl group for $R_c^1$ is one which is removable by treating with a hydrazine compound or an amine compound. As preferred examples of such an acyl group, there may be exemplified phthaloyl, formyl, acetoacetyl, etc.

Preferred examples of hydrazine compound are exemplified by hydrazine, methylhydrazine, phenylhydrazine and the like and those of amine compound are exemplified by hydroxylamine, dialkylaminoalkylamine (e.g. N,N-dimethylaminopropylamine, etc.) and the like.

This reaction is usually carried out by treating Compound (Ia) with the hydrazine compound or amine compound in a solvent such as water, alcohol (e.g. methanol, ethanol, etc.) tetrahydrofuran, dioxane or the like at ambient temperature to under reflux.

In this method, in case that $R^q$ is a group of the formula: —CONHNHY and an amino protective group for Y is the same as the acyl for $R_c^1$, then such an amino protective group also is simultaneously removed to give a Compound (Ib) wherein $R^q$ is a group of the formula: —CONHNH$_2$.

(v) Zinc-acid method:

This method is preferably applied to case that the acyl group for $R_c^1$ is one which is removable by treating with zinc acid. As preferred examples of such an acyl group, there may be exemplified trichloroethoxycarbonyl, 4-piperidyloxycarbonyl, 1-methyl-1-(4-pyridyl)ethoxycarbonyl and the like.

This method is carried out by treating Compound (Ia) with zinc in the presence of a weak acid such as formic acid, acetic acid and the like. The reaction may be carried out in a solvent such as methylene chloride, chloroform, tetrahydrofuran, ethyl acetate, alcohol (e.g. methanol, ethanol, etc.), dimethylformamide and the like, and in this case a weak acid as mentioned above is added to such a solvent. The reaction is usually carried out at $-10°$ C. to ambient temperature.

In this reaction, in case that $R^q$ is a group of the formula: —CONHNHY and an amino protective group for Y is the same as the acyl for $R_c^1$, then such an amino protective group also is simultaneously removed to give a Compound (Ib) wherein $R^q$ is a group of the formula: —CONHNH$_2$. Further, in case that a protected carboxy group for $R^p$ of Compound (Ia) is, for example, a halo-alkyl ester type of group (e.g. trichloroethyl, etc.), sych a carboxy protective group also is simultaneously removed to give a Compound (Ib) wherein $R^p$ is carboxy.

(vi) Base method:

This method is preferably applied to case that the acyl group for $R_c^1$ is one which is removable by treating with a base. As preferred examples of such an acyl group, there may be exemplified haloalkanoyl (e.g. trifluoroacetyl, etc.), substituted or unsubstituted alkoxycarbonyl (e.g. 2-(p-toluenesulfonyl)ethoxycarbonyl, 2-(p-tolylthio)ethoxycarbonyl, etc.), substituted or unsubstituted aryloxycarbonyl (e.g. 2-nitrophenoxycarbonyl, etc.) and the like.

This method is carried out in the presence of a base under ice-cooling to at ambient temperature.

Suitable base is an inorganic base such as alkali metal hydroxide or alkaline earth metal hydroxide, or the corresponding carbonate or bicarbonate (e.g. sodium hydroxide, potassium hydroxide, sodium carbonate, potassium carbonate, lithium carbonate, sodium bicarbonate, calcium hydroxide, magnesium hydroxide, etc.), ammonium hydroxide or the like; an organic base such as an alkoxide or phenoxide of the above metal (e.g. sodium ethoxide, sodium methoxide, lithium phenoxide, etc.), an amine such as mono-, di- or trialkylamine (e.g. methylamine, ethylamine, propylamine, isopropylamine, butylamine, N,N-dimethyl-1,3-propanediamine, trimethylamine, triethylamine, etc.), unsubstituted, mono- or disubstituted arylamine (e.g. aniline, N-methylaniline N,N-dimethylaniline, etc.), a heterocyclic base (e.g. pyrrolidine, morpholine, N-methylmorpholine, N-methylpiperidine, N,N-dimethylpiperazine, pyridine, etc.) or the like; a basic ion exchange resin and the like.

This method is preferably conducted under somewhat milder conditions such as coolind or warming and usually in any solvent which does not have an adverse influence on the reaction, e.g. water, a hydrophilic solvent such as alcohol (e.g. methanol, ethanol, propanol, etc.), N,N-dimethylformamide, tetrahydrofuran, dioxane, dimethylsulfoxide, etc. or a mixture thereof. In case that the above-mentioned bases are in liquid, they can also be used as a solvent.

In this method, in case that $R^q$ is a group of the formula: —CONHNHY and an amino protective group for Y is the same as the acyl for $R_c^1$, then such an amino protective group also is simultaneously removed to give a Compound (Ib) wherein $R^q$ is a group of the formula: —CONHNH$_2$. Further, in case that a protected carboxy group for $R^p$ of Compound (Ia) is, for example, an alkyl ester type of group (e.g. methyl ester, ethyl ester, etc.), an aralkyl ester type group (e.g. benzyl ester, etc.), such a protective group also is simultaneously removed to give a Compound (Ib) wherein $R^p$ is carboxy.

(3) Process 3:

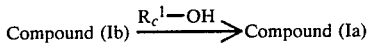

Compound (Ib) $\xrightarrow{R_c^1-OH}$ Compound (Ia)

This process relates to a method for preparing Compound (Ia) by reacting Compound (Ib) with an acylating agent.

The acylating agent to be used in this reaction includes an organic acid ($R_c^1$—OH wherein $R_c^1$ is acyl group) such as monobasic or dibasic organic carboxylic acid, an organic carbonic acid or an organic carbamic acid and the corresponding thio acid or imidic acid; and an organic sulfonic acid, and more particularly, aliphatic, aromatic or heterocyclic carboxylic acid, and the corresponding carbonic, carbamic, thiocarboxylic, thiocarbonic, thiocarbamic, carboximidic, carbamimidic acid, and sulfonic acid; their reactive derivatives; and also includes an isocyanate (e.g. potassium-, alkyl- or aryl-isocyanate), isothiocyanate (e.g. alkylisothiocyanate) and an isothiourea (e.g. ethyl isothiourea). Suitable examples of these organic acid ($R_c^1$—OH wherein $R_c^1$ is acyl group) are the corresponding organic acid to those comprising the acyl group as exemplified hereinabove in details in the descriptions of suitable examples of acyl groups for $R^1$ and $R_c^1$ of the compound (I).

Said organic acid as an acylating agent can be used in the form of an activated organic acid, i.e. as a reactive derivative of the acid. As such reactive derivatives of said organic acids, there may be exemplified an acid halide, an acid azide, an acid anhydride, an activated amide, an activated ester, etc., and additionally isocyanate and isothiocyanate can preferably be used as reactive derivative of carbamic and thiocarbamic acids, respectively. Preferred examples of such reactive derivatives are illustrated by:

an acid halide (e.g. acid chloride, acid bromide etc.);

an acid azide;

an acid anhydride including a mixed acid anhydride with an acid such as dialkylphosphoric acid, phenylphosphoric acid, diphenylphosphoric acid, dibenzylphosphoric acid, halogenated phosphoric acid, dialkylphosphorous acid, sulfurous acid, thiosulfuric acid, sulfuric acid, monoalkylcarbonic acid, aliphatic carboxylic acid (e.g. acetic acid, pivalic acid, pentanoic acid, isopentanoic acid, 2-ethylbutyric acid, trichloroacetic acid, etc.), aromatic carboxylic acid (e.g. benzoic acid, etc.) or the like, and symmetrical acid anhydride;

an activated amide with pyrazole, imidazole, 4-substituted imidazole, dimethylpyrazole, triazole or tetrazole; and an activated ester such as substituted or unsubstituted alkylthio ester (e.g. methylthio ester, carboxymethyl thioester, etc.), substituted or unsubstituted aryl thioester (e.g. phenyl thioester, p-nitrophenyl thioesther, p-cresyl thioester, etc.), heterocyclic ester (e.g. pyranyl ester, pyridyl ester, piperidyl ester, 8-quinolyl thioester, etc.) or ester with N,N-dimethylhydroxylamine, 1-hydroxy-2-(1H)-pyridone, N-hydroxysuccinimide, N-hydroxyphthalimide or 1-hydroxy-6-chlorobenzotriazole, or the like.

The above reactive derivative is selected according to the kind of the acid to be used.

In the reaction, when free acid is used as an acylating agent, the acylation reaction may preferably be conducted in the presence of a condensing agent such as carbodiimidic compound (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), N,N'-carbonyldi(2-methylimidazole), pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus compound (e.g. phosphorus oxychloride, phosphorus trichloride, etc.), thionyl chloride, oxalyl chloride, 2-ethyl-7-hydroxybenzisoxazolium salt, 2-ethyl-5-(m-sulfophenyl)isoxazolium hydroxide, (chloromethylene)dimethylammonium chloride, 2,2,4,4,6,6-hexachloro-1,3,5,2,4,6-triazatriphosphorine, 1-benzenesulphonyloxy-6-chloro-1H-benzotriazole, p-toluenesulfonyl chloride, isopropoxybenzenesulfoxyl chloride or the like; or a mixed condensing agent such as a mixture of triphenylphosphine and a carbon tetrahalide (e.g. carbon tetrachloride, carbon tetrabromide, etc.), a complex of N,N-dimethylformamide with phosphoryl chloride, phosgene or thionyl chloride, etc., or the like.

The reaction is usually conducted in a solvent such as water, alcohol (e.g. methanol, ethanol, propanol, etc.), acetone, ethyl ether, dioxane, acetonitrile, ethylacetate, N,N-dimethylformamide, dimethylsulfoxide, tetrahydrofuran, dichloromethane, chloroform, etc. or pyridine, N-methylmorpholine, N-methylpyrrolidine or other conventional solvents, or a mixture thereof.

The reaction can also be conducted preferably in the presence of an organic or inorganic base such as alkali metal (e.g. sodium, potassium, etc.), alkaline earth metal (e.g. calcium, etc.), alkali or alkaline earth metal hydride (e.g. sodium hydride, calcium hydride, etc.), alkali or alkaline earth metal hydroxide (e.g. sodium hydroxide, potassium hydroxide, calcium hydroxide, etc.), alkali or alkaline earth metal carbonate or bicarbonate (e.g. sodium carbonate, potassium carbonate, sodium bicarbonate, lithium carbonate, etc.), alkali or alkaline earth metal alkoxide (e.g. sodium ethoxide, lithium methoxide, magnesium methoxide, etc.), trialkylamine (e.g. triethylamine, etc.), pyridine, bicyclodiaza compound (e.g. 1,5-diazabicyclo[3,4,0]nonene-5, 1,5-diazabicyclo[5,4,0]undecene-5, etc.) or the like. Among said base, a liquid one can also be used as a solvent.

There is no limitation to this reaction temperature, and this reaction may preferably be conducted within the range of cooling to ambient temperature.

(4) Process 4: Elimination of protective groups

Compound (Ic)→Compound (Id)

This process relates to a method for preparing Compound (Id) by subjecting Compound (Ic) to removal reaction of protective groups of protected carboxy groups for $R^p$ and $R^q$ and or amino protective group for $R^r$, details of which are explained as follows:

Process 4-1: Elimination of an amino protective group for $R^r$

The elimination of an amino protective group for $R_1^r$ is carried out substantially in the same manner as that of Process 2, and accordingly the detailed explanation for Process 2 as made hereinabove is to be referred to.

Process 4-2: Removal of carboxy protective group of protected carboxy for $R^p$ and $R^q$ The reaction for removal of protective group of the protected carboxy group is carried out by a conventional method such as hydrolysis and reduction or the like, details of which are explained in the following.

(i) For hydrolysis which refers to the same meanings as solvolysis including, for example, acidolysis, alcoholysis, aminolysis, hydroxinolysis, etc.:

Hydrolysis is preferably carried out in the presence of an acid or base.

Suitable acid includes an inorganic acid (e.g. hydrochloric acid, hydrobromic acid, sulfuric acid, etc.), an organic acid (e.g. formic acid, acetic acid, trifluoroacetic acid, propionic acid, benzenesulfonic acid, p-toluenesulfonic acid, etc.), an acidic ion-exchange resin and the like.

Suitable base includes an inorganic base such as alkali or alkaline earth metal hydroxide or the corresponding carbonate or bicarbonate (e.g. sodium hydroxide, potassium hydroxide, sodium carbonate, potassium carbonate, lithium carbonate, sodium bicarbonate, calcium hydroxide, magnesium hydroxide, etc.), ammonium hydroxide or the like; an organic base such as an alkoxide or phenoxide of the above metal (e.g. sodium ethoxide, sodium methoxide, lithium phenoxide, etc.), an amine such as mono-, di- or tri-alkylamine (e.g. methylamine, ethylamine, propylamine, isopropylamine, butylamine, N,N-dimethyl-1,3-propanediamine, trimethylamine, triethylamine, etc.), unsubstituted, mono- or disubstituted arylamine (e.g. aniline, N-methylaniline, N,N-dimethylaniline, etc.), a heterocyclic base (e.g. pyrrolidine, morpholine, N-methylmorpholine, N-methylpiperidine, N,N-dimethylpiperazine, pyridine, etc.), hydrazines (e.g. hydrazine, methylhydrazine, ethylhydrazine, etc.) or the like; a basic ion-exchange resin and the like.

The hydrolysis is preferably conducted under somewhat milder conditions such as cooling or warming and usually in a solvent which does not have adverse influence to the reaction, e.g. water, a hydrophilic solvent such as alcohol (e.g. methanol, ethanol, propanol, etc.), acetone, N,N-dimethylformamide, tetrahydrofuran, dioxane, dimethylsulfoxide, etc. or a mixture thereof, and other hydrophobic solvent such as benzene diethylether, etc. may also be used as a solvent. A liquid abovementioned acid or base can also be used as solvent.

(ii) For reduction:

Reduction, including chemical reduction and catalytic reduction, is carried out in a conventional manner.

Suitable reducing agents to be used in chemical reduction are a metal (e.g. tin, zinc, iron, etc.), or a combination of such metal and/or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum platinum black, colloidal platinum, platinum oxide or platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Rabey nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) or the like.

The reduction is usually carried out in a solvent. A suitable solvent to be used may be, e.g. water, alcohol (e.g. methanol, ethanol, propanol, etc.) and other conventional organic solvent or a mixture thereof. Additionally, the afore-mentioned liquid acids to be used in chemical reduction can also be used as solvent. Further, a suitable solvent to be used in catalytic reduction may be, e.g. the above-mentioned solvent, and other conventional solvent, such as diethyl ether, dioxane, tetrahydrofuran, etc. or a mixture thereof.

The reaction is preferably carried out under somewhat milder conditions such as cooling or warming.

Among these methods for removal of protective groups, preferred one and appropriate combination methods are to be selected according to kinds of the protective groups of carboxy group and amino protective group to be removed off.

It is noted that this process includes the following cases of removal of protective groups and amino protective group, that is, one case that all of the carboxy protective groups for $R^p$ and $R^q$ and the amino protective group for $R^r$ in the Compound (Ic) are simultaneously removed by a method to be employed to the reaction, and the other case that the carboxy protective groups and the amino protective group are sequentially and stepwise removed by a method which is appropriately selected according to the kinds of the protective group to be removed.

Process 4-3: Removal of hydrazino group

A protected carbazoyl of the formula: —CONHNHY wherein Y is an amino protective group can be removed by subjecting the Compound (Ic) at first to the reaction of Process 4-1 for eliminating amino protective group (i.e. Y) to give —CO.NHNH$_2$ group and then subjecting the reaction product to the reaction of this step to give —COOH group, and particular of this reaction step is as follows.

The reaction of this step is carried out in a conventional manner by treating the Compound (Ic) with a conventional oxidizing agent which is capable of oxidizing a group of the formula: —CONHNH$_2$ to form into a group of the formula: —COOH and accordingly preferred example of such an oxidizing agents may be halogen such as iodine, bromine etc., perhalogenic acid such as periodic acid or its salt (e.g. sodium salt, potassium salt, etc.), perchloric acid, etc., N-haloimide such as N-bromosuccinimide, etc., lead tetraacetate, hydrogen peroxide or its salt (e.g. nickel peroxide, etc.), metal oxide such as mercuric oxide, manganese dioxide, nickel peroxide, etc., cupric compound (e.g. cupric acetate, cupric sulfate, etc.) and the like.

This reaction is usually carried out in a solvent such as water, acetic acid, methanol, ethanol, tetrahydrofuran, dioxane and the like and a mixture thereof, which should be appropriately selected in accordance with the kind of oxidizing agent to be used.

This reaction is usually carried out under ice-cooling to at ambient temperature, or under reflux.

As to Process 4 for Elimination of protective groups (i.e. Process 4-1, Process 4-2 and Process 4-3), it is to be noted that, in case that acyl for $R^1$ has one or more protective groups for hydroxy, amino and (or) carboxy, such protective groups also may be simultaneously removed and such a case is included within the scope of this process.

(5) Process 5: Peptide bond formation 2

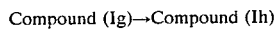
Compound (Ig)→Compound (Ih)

This process relates to a method for preparing Compound (Ih) by reacting Compound (Ig) or its salt with a compound of the formula:

$$\begin{array}{c} R_b{}^2 \\ | \\ HN-R_a{}^2 \end{array}$$

or its salt (wherein $R_a{}^2$ and $R_b{}^2$ are each as defined above).

This reaction is carried out in substantially the same manner as that of Process 1, and accordingly the detailed explanation for Process 1 as made hereinabove is to be referred thereto.

(6) Process 6: Aminoprotection

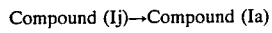
Compound (Ij)→Compound (Ia)

This process relates to a method for preparing Compound (Ia) by reacting Compound (Ij) with an amino protecting agent.

The amino protecting agent to be used in this reaction is the same as one illustrated in Process 6$^s$ explained hereinafter.

The reaction is carried out substantially in the same manner as that of Process 3.

(7) Process 7: Esterification

This process relates to a method for preparing Compound (II) by reacting Compound (Ik) with an esterifying agent.

An esterifying agent to be used in this reaction may include a conventional one such as alcohol (e.g. methanol, ethanol, propanol, butanol, benzylalcohol etc.) or its reactive equivalent (e.g. halide, sulfate, aliphatic or aromatic sulfonate or the corresponding diazo compound, etc.) and the like.

This reaction is carried out in a conventional manner and in case of using alcohol as an esterifying agent the reaction is usually carried out in the presence of an acid such hydrochloric acid, sulfuric acid, methanesulfonic acid or the like, and in case of using alkyl halide as an esterifying agent the reaction is usually carried out in the presence of a base as illustrated in the aforementioned Process 2.

(2) Fermentation: A strain of Streptomyces→Compound (Ie)

This compound (Ie) (hereinafter referred to as FR-900156 substance) can be produced by fermentation of a FR-900156 substance producing strain belonging to the genus Streptomyces in a nutrient medium, details of which are explained in the following.

The microorganism which can be used for the production of the FR-900156 substance is a strain belonging to the genus Streptomyces, among which a strain of *Streptomyces olivaceogriseus* and *Streptomyces violaceus* have been newly isolated from a soil sample as a suitable strain of a FR-900156 substance-producing strain belonging to the genus Streptomyces.

It is to be understood that, for the production of the FR-900156 substance, this invention is not limited to the use of the particular organism as described herein, which is given for illustrative purpose only. This invention also includes the use of any mutants which are capable of producing the FR-900156 substance, including natural mutants which are produced by natural mutation of the organisms as well as artificial mutants which can be produced from the described organism by conventional means, such as X-rays, ultra-violet radiation, nitrogen mustard oils and the like.

I. Re. *Streptomyces olivaceogriseus* nov. sp.C-353:

*Streptomyces olivaceogriseus* nov. sp.C-353 has been isolated from a soil sample collected at Kochi Prefecture, Japan and deposited with and added to a permanent stock culture collection of the America Type Culture Collection under the number ATCC 31427.

*Streptomyces olivaceogriseus* nov. sp. C-353 (ATCC 31427) has the following morphological, cultural and physiological characteristics.

(1) Morphological characteristics:

Microscopic observations were made on cultures which were grown from 10 to 14 days on sucrose-nitrate agar, glycerin-asparagine agar, yeast-malt extract agar, oatmeal agar, starch-inorganic salts agar and Bennett agar. Sporophore morphology was observed on undisturbed plates cultures.
1. Type of branching of spore-forming hyphae: Monopodial branching
2. Form of spore-forming hyphae: Retinaculiaperti (closed spirals, loops)
3. Numbers of spores: 5–20 spores
4. Surface appearance and size of spores:
   Smooth
   $0.6-1.2 \times 1.0-1.9$ micron
5. Existence of zoospores: Not observed
6. Existence of sporangium: Not observed
7. Formation of spores: At aerial mycelium
8. Fragmentation of substrate mycelium: Not observed (2) Cultural characteristics:

The following observations were made on slant cultures which were grown on various media at 30° C. for 10–14 days.

| Medium | Aerial mass color | Reverse side of colony | Soluble Pigment |
|---|---|---|---|
| Sucrose-nitrate agar | none or very thin, powdery | pale yellow, small colonies | none |
| Glucose-asparagine agar | light gray to greenish gray, powdery | pale yellow to pale yellowish brown, small colonies | none |
| Glycerin-asparagine agar | thin, powdery light gray | pale yellowish brown, small colonies | none or trace |
| Starch-inorganic salts agar | olive gray, powdery | grayish yellow brown, small colonies | none |
| Tyrosine agar | light olive gray, thin powdery | yellowish brown, small colonies | light brown |
| Nutrient agar | none | pale yellow, flat | none |
| Yeast-malt extract agar | greenish gray, powdery | yellowish brown, wrinkled colonies | none |
| Oatmeal agar | light gray to greenish gray, powdery | colorless, small colonies | none |
| Peptone-yeast iron agar | none | colorless to pale yellow, slightly wrinkled | light brown |
| Glucose-peptone gelatin stab | white, thin powdery, | colorless to pale yellow, wrinkled colonies | brown |
| Milk | white, very thin powdery | colorless, surface ring growth | none |

(3) Biological and physiological properties:
1. Temperature requirements (on Bennett agar slants) growth from 15° C. to 40° C. optimum 28° C.
2. Hydrolysis of startch (on starch-inorganic salts agar) hydrolyzed weakly
3. Liquefaction of gelatin (on glucose-peptone gelatin stab)
   negative
4. Action on milk:
   no coagulation
   no peptonization
5. Production of melanin (on tyrosine agar, peptone-yeast iron agar and tryptone-yeast broth): positive
6. Utilization of various carbon compounds (on Pridham-Gottlieb basal agar medium)
   L-Arabinose: —
   D-Xylose: ±
   D-Glucose: +
   D-Fructose: +
   D-Galactose: +
   Sucrose: +
   Glycerin: +
   Inositol: +
   Lactose: +
   L-Rhamnose: —
   Maltose: +
   Raffinose: —
   D-Mannitol: +
   D-Mannose: +
   Salicin: —
   Symbols: +, good utilization; ±, doubtful utilization; —, no utilization
7. Cell wall pattern I (LL-diaminopimelic acid)

As a result of looking up the strain possessing the characteristics mentioned above by referring to the literature, namely "Bergey's Manual of Determinative Bacteriology" eighth edition (1975), and "The International Streptomyces Project Reports" written by E. B. Shirling and D. Gottlieb Cf. International Journal of Systematic Bacteriology Vol. 18, pages 69 and 279 (1968), Vol. 19, pages 391 (1969) and Vol. 22, pages 265 (1972), *Streptomyces eurythermus* and *Streptomyces galbus* (Okami) have been detected as species having relatively analogous characteristics to those of the strain ATCC 31427.

The strain ATCC 31427, however, is different from these analogous species in the following:

*Streptomyces eurythermus* (Okami):

A strain of the species can assimilate arabinose and can not assimilate inositol. Assimilation of rhamnose and raffinose by a strain of the species is indefinite. Loops are not formed. Straights or flexous mycelium are sometimes observed.

*Streptomyces galbus:*

Open-spirals are generally formed. A strain of the species produces a soluble yellow-yellow green pigment, and can not assimilate sucrose.

In view of the result of the observation, the strain ATCC 31427 can be judged to be a new species belonging to the genus Streptomyces and this has been designated as *Streptomyces olivaceogriseus* nov. sp. C-353.

II. Re. *Streptomyces violaceous* No.6724

*Streptomyces violaceus* No.6724 was isolated from a soil sample collected at Ishigaki island, at Okinawa Prefecture, Japan, and deposited with and added to a permanent stock culture collection of the American Type Culture Collection under the number ATCC 31481.

*Streptomyces violaceus* No.6724 has following morphological, cultural and physiological characteristics.

(1) Morphological characteristics

Microscopic observations were made on cultures which were grown on sucrose-nitrate agar, glycerin-asparagine agar, starch-inorganic salts agar, yeast-malt extract agar and oatmeal agar at 30° C. for 10 to 14 days.

1. Type of branching of spore-forming hyphae: Monopodial branching
2. Form of spore-forming hyphae: Spirales
3. Numbers of spores: 10–50
4. Surface appearance and size of spore: Spiny 0.3–0.7×0.6–1.1μ
5. Existence of zoospore and sporangium: Not observed
6. Formation of spores: At aerial mycelium
7. Fragmentation of substrate mycelium: Not observed.

(2) Cultural characteristics

The following observations were made on cultures which were grown on various madia at 30° C. for 10 to 14 days.

| Medium | Aerial mass color | Reverse side of colony | Soluble Pigment |
|---|---|---|---|
| Sucrose-nitrate agar | purplish white, powdery | small colonies | purple |
| Glucose-asparagine agar | purplish white, powdery | yellowish red, small colonies | pink |
| Glycerin-asparagine agar | pinkish white-pink, powdery | Yellowish red, small colonies, slightly wrinkled | pink-red |
| Starch-inorganic salts agar | whitish red, short cottony | yellowish red, slightly wrinkled | red |
| Tyrosine agar | none | red, wrinkled colonies | none or trace |
| Nutrient agar | none or very thin powdery | colorless-purple, flat | reddish purple |
| Yeast-malt extract agar | pink-purplish pink, short cottony | reddish brown-purplish brown, wrinkled colonies | reddish purple |
| Oatmeal agar | pink-purplish pink, powdery | colorless-purplish pink, small colonies | pink-purple |
| Peptone-yeast iron agar | none | colorless, wrinkled colonies | brown |
| Glucose-peptone gelatin stab | white, thin powdery | red, wrinkled colonies | faint brown |
| Milk | thin powdery | red growth on surface | reddish yellow |

Reverse mycelium pigment is pH indicator, changing from red to violet (purple) with addition of 0.05N NaOH or from violet to red (pink) with addition of 0.05N HCl. Soluble pigment is also pH sensitive, showing the same changes noted for revere mycelium pigment.

(3) Biological and physiological properties

1. Temperature reguirements (on Bennett agar slants): growth from 15° C. to 40° C. (optimum 28° C.)
2. Liquefaction of gelatin (on glucose-peptone gelatin stab): negative
3. Hydrolysis of starch (on starch-inorganic salts agar): positive
4. Action on milk: coagulation, no peptonization
5. Production of melanoid pigment: (on tyrosine agar, peptone-yeast iron agar and tryptone-yeast extract broth): positive
   very weak or not on tyrosine agar
6. Utilization of various carbon compounds (on Pridham-Gottlieb basal agar medium)
   L-Arabinose: +
   D-Xylose: +
   L-Rhamnose: +
   D-Glucose: +
   D-Fructose: +
   D-Mannose: +
   D-Galactose: +
   Sucrose: +
   Lactose: +
   Maltose: +
   Raffinopse: +
   Inulin: ±
   Cellulose: −
   Chitin: −
   Glycerin: +
   D-Mannitol: +
   Salicin: +
   Inositol: +
   Na-Acetate: −
   Na-Citrate: +
   Na-Succinate: +

Symbols: +, good utilization ±, doubtful utilization −, no utilization.

The FR-900156 substance of this invention is produced when the FR-900156 substance-producing strain belonging to the genus Streptomyces (e.g. *Streptomyces olivaceogriseus* nov. sp. C-353 and *Streptomyces violaceus*, etc.) is grown in a nutrient medium containing sources of assimilable carbon and nitrogen under aerobic conditions (e.g. shaking culture, submerged culture, etc.).

The preferred sources of carbon in the nutrient medium are carbohydrates such as glucose, fructose, glycerin, starch and the like. Other sources which may be included are lactose, arabinose, xylose, dextrin, molasses and the like.

The preferred sources of nitrogen are yeast extract, peptone, gluten meal, cottonseed meal, soybean meal, corn steep liquor, dried yeast, wheat germ, etc., as well as inorganic and organic nitrogen compounds such as ammonium salts (e.g. ammonium nitrate, ammonium sulphate, ammonium phosphate, etc.), urea, amino acid and the like.

The carbon and nitrogen sources, though advantageously employed in combination, need not be used in their pure form because less pure materials, which contain traces of growth factors and considerable quantitites of mineral nutrients, are also suitable for use. When desired, there may be added to the medium mineral salts such as calcium carbonate, sodium or potassium phosphate, sodium or potassium chloride, magnesium salts, copper slats and the like. If necessary, especially when the culture medium foams seriously a defoaming agent, such as liquid paraffin, fatty oil, plant oil, mineral oil or silicone may be added.

As in the case of the preferred methods used for the production of other antibiotics in massive amounts, submerged aerobic cultural conditions are preferred for the production of the FR-900156 substance in massive amounts. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of the FR-900156 substance. Accordingly, it is desirable first to produce a vegetative inoculum of the organism by inoculating a relatively small quantity of culture medium with spores or mycelia of the organism and culture them and then to transfer the cultured vegetative inoculum aseptically to large tanks. The medium, in which the vegerative inoculum is produced, is substantially the same as or different from the medium utilized for the production of the FR-900156 substance.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 40° C., preferably 30° C., for a period of about 50 hours to 100 hours.

The FR-900156 substance can be recovered from the culture medium by conventional means which are commonly used for the recovery of other known antibiotics.

In general, most of the FR-900156 substance produced are found in the cultured broth, and accordingly the FR-900156 substance can be separated from the filtrate, which is obtained by filtering of centrifuging the culture broth, by a conventional method such as concentration under reduced pressure, lyophilization, pH adjustment, treatment with a resin (e.g. anion or cation exchange resin, non-ionic adsorption resin, etc.), treatment with an adsorbent (e.g. activated charcoal, silicic acid, silica gel, cellulose, alumina, etc.), crystallization, recrystallization and the like.

The FR-900156 substance thus produced in the culture brotth can be isolated in the free form, i.e., FR-900156 substance per se and when the solution or its concentrate containing the FR-900156 substance is treated with a base, i.e. with an inorganic base such as an alkali metal compound (e.g. sodium hydroxide, sodium carbonate, sodium bicarbonate, potassium hydroxide, etc.), an alkaline earth metal compound (e.g. calcium hydroxide, magnesium hydroxide, etc.), ammonia and the like, with an organic base (e.g. ethanolamine, triethylamine, dicyclohexylamine, etc.); or with an acid i.e. with an inorganic acid (e.g. hydrochloric acid, sulfuric acid, phosphoric acid, etc.); or with an organic acid (e.g. formic acid, acetic acid, p-toluenesulfonic acid, citric acid, tartaric acid etc.) during operation of the processes, e.g. extraction, isolation or purification processes, the FR-900156 substance may be transformed into and isolated in the form of the corresponding salts thereof. Alternatively, thus prepared salts of the FR-900156 substance can easily be converted to the free form, i.e. FR-900156 substance per se in a conventional manner.

Further, the FR-900156 substance obtained in the free form may be converted to the corresponding salts thereof with a base or an acid as mentioned above in a conventional manner.

Accordingly, it is to be understood that this invention includes within the scope thereof the FR-900156 substance as well as salts thereof as mentioned above.

The FR-900156 substance possesses the following physical and chemical properties (The following data are those of the product obtained by Example 94 (3):)

(1) Form and color: White powder (2) Nature of substance: Amphoteric (3) Color reaction:

Positive; each reaction with ninhydrin, potassium permanganate and sulfuric acid Negative; Dragendorff reaction and Ehrlich reaction (4) Solubility:

Soluble; water

Sparingly soluble; methanol

Insoluble; ethanol, acetone, ethyl acetate, benzene, hexane, chloroform (5) MP; 143–148 (dec.)

(6) Specific rotation $[\alpha]_D^{25} = -27.1$ (c=0.4 in water)

(7) Ultraviolet absorption spectrum: end absorption (8) Infrared absorption spectrum (KBr): 1050, 1130, 1235, 1340, 1400, 1450, 1535, 1660, 1735, 2950, 2980, 3080, 3350 cm$^{-1}$.

(9) Elementary analysis: Qualitative analysis revealed that the FR-900156 substance comprises the following elements:

Carbon, Hydrogen, Nitrogen and Oxygen.

(10) Thin layer chromatography:

| Stationary phase | Developing Solvent | Rf Value |
| --- | --- | --- |
| Eastman cellulose sheet*[1] | BuOH, Acetic acid Water(4:1:2) | 0.35 |
| Silicagel sheet Merck*[2] | 60% i-propanol-water | 0.65 |

Note
*[1]Trade name, made by Eastman Kodak Co.
*[2]Trade name, made by Merck & Co.

(11) Molecular weight: Mass spectrometory (Field desorption method): M=519 (base peak: M+1=520)

(12) Nuclear magnetic resonance absorption spectrum: As shown in the Figure of accompanying drawing. (Solvent: D$_2$O, Reference: TMSP)

(13) Amino acid analysis:

| | Molar ratio |
|---|---|
| Glycine | 1.00 |
| Glutamic acid | 1.06 |
| Alanine | 1.04 |
| α, ε-Diaminopimelic acid | 1.03 |

(Molar ratio is expressed as assuming Glycine = 1.00)

(14) Molecular formula:

$$C_{20}H_{33}N_5O_{11}$$

Further, physical and chemical properties of more purified sample of FR-900156 substance (i.e. a product obtained by Example for fermentation (4)) was measured, as a result of which MP of said sample 147°–153° C. (dec.) and other properties thereof were the same as the above.

From analysis of the above physicochemical properties and the further investigation for elucidation of chemical structure, the chemical structure of the FR-900156 substance has been elucidated as follows:

```
    OH          CH3
    |           |        (D)
CH3CHCONHCHCONHCHCOOH
   (D)        (L)    |
                     CH2
                     |
                     CH2
                     |     (L)
                     CONHCHCONHCH2COOH
                          |
                          CH2
                          |
                          CH2
                          |
                          CH2
                          |
                          H2NCHCOOH
                              (D)
```

(D—Lactyl-L—alanyl-γ-D—glutamyl-(L)—meso-diaminopimelyl(L)—glycine)

PREPARATION OF STARTING COMPOUNDS (II) AND (III)

The starting Compounds (II) and (III) each include new compound and can be prepared by methods as described below. Among the Compound (III), a new compound is represented by the following formula:

$$\begin{array}{c} R_b^2 \\ | \\ R^1-HNCHCON-R_a^2 \\ | \\ (CH_2)_3 \\ | \\ R'HNCHR^q \end{array}$$

wherein
R$^1$, R$_a^2$, R$_b^2$, R$^q$ and R$^r$ are each as defined above, provided that when R$^1$ is hydrogen or t-butoxycarbonyl and R$_b^2$ is hydrogen,
then R$_a^2$ is mono- or di-carboxy lower alkyl having 1 and 3 to 6 carbon atoms, α-carboxyethyl or ar(carboxy)lower alkyl whose aryl moiety may be substituted by hydroxy.

Detailed explanation of preparation of the starting Compounds (II) and (III) are made in the following.

PREPARATION OF COMPOUND (III), I.E. COMPOUNDS (III-1) TO (III-15)

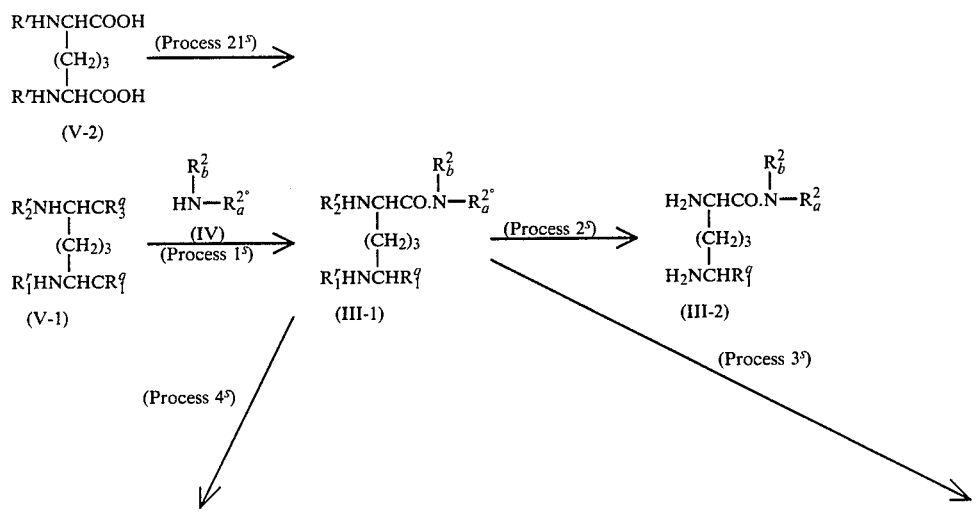

-continued
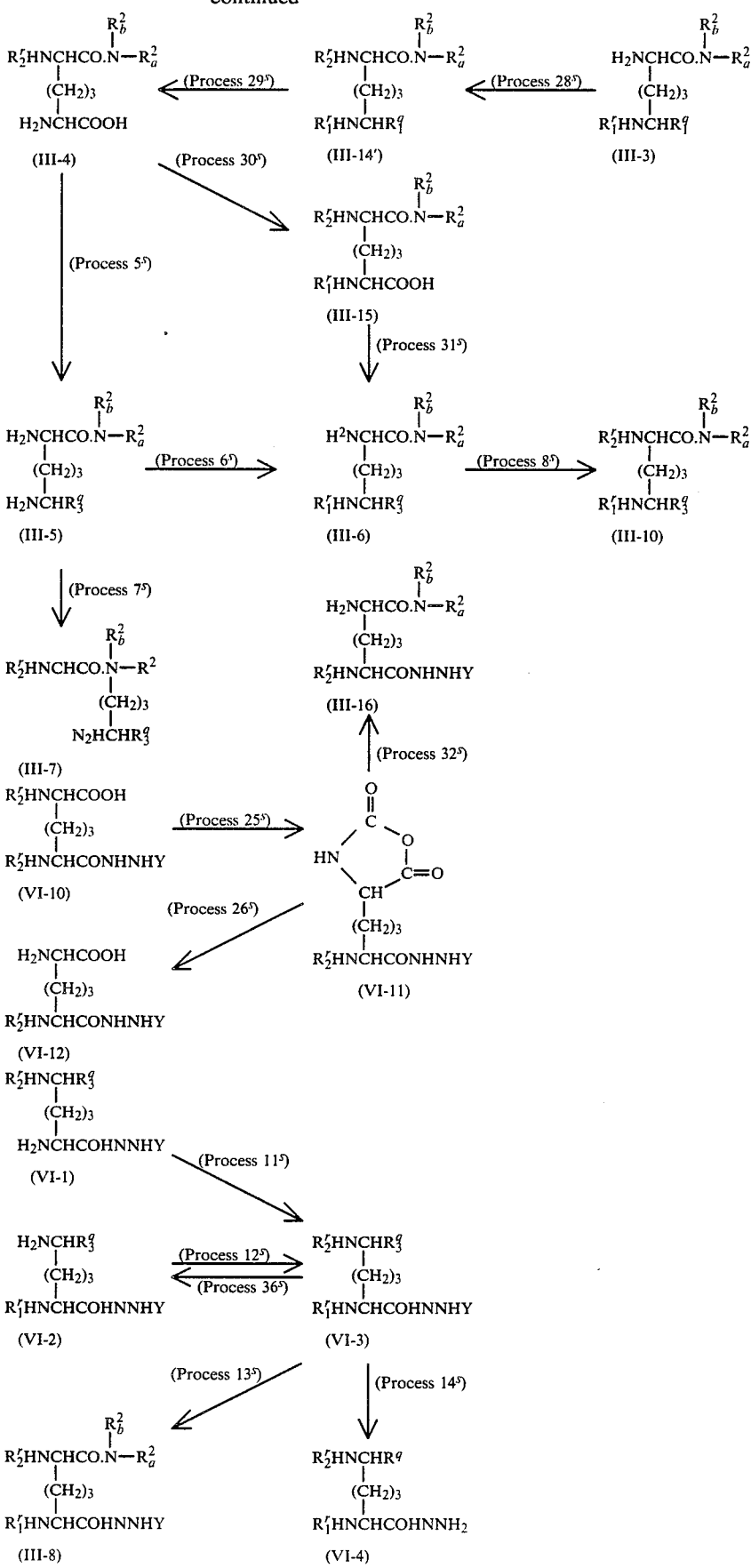

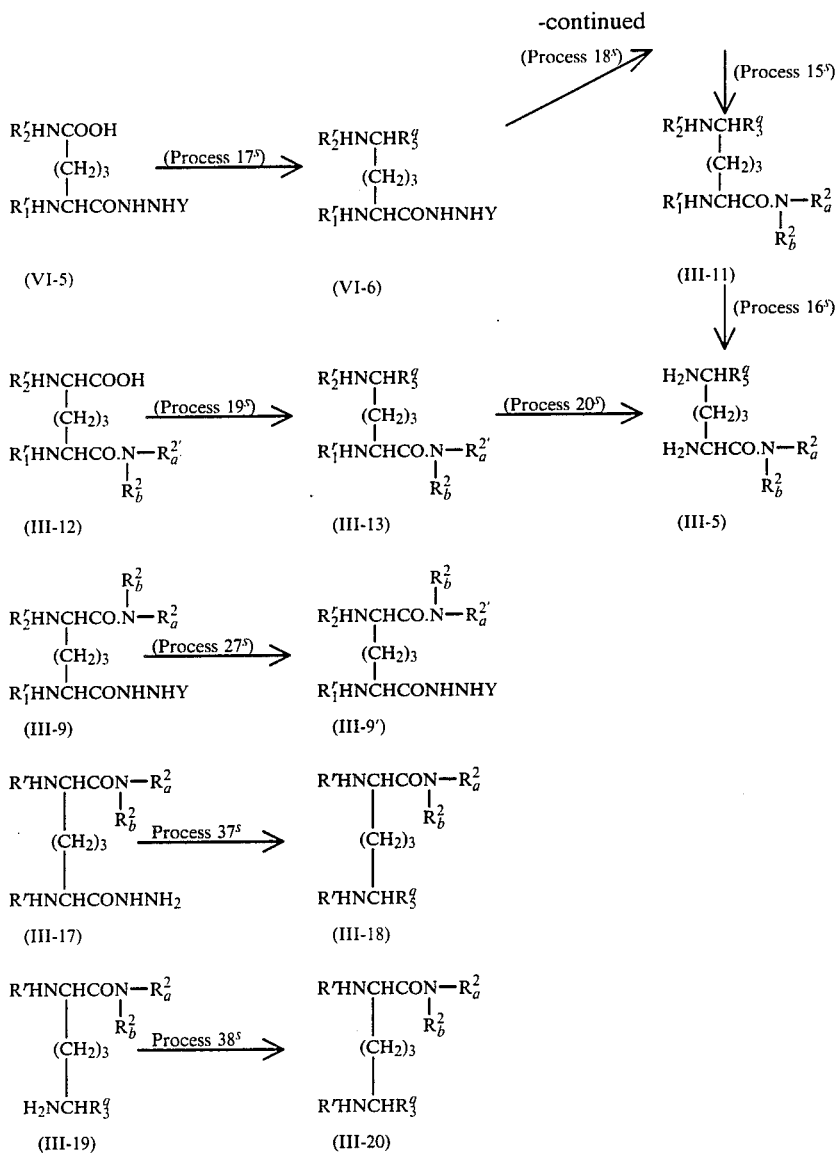
PREPARATION OF COMPOUND (II)
(i) Process 33$^s$:
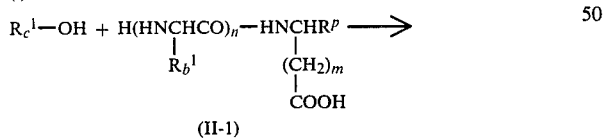
(ii) Process 34$^s$:
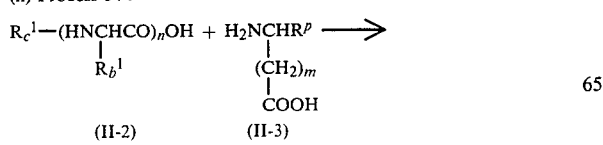
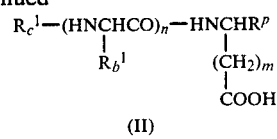
(iii) Process 35$^s$:
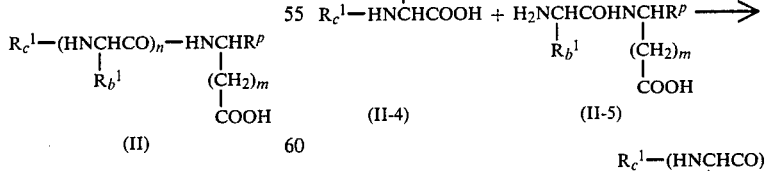

In the above formula,
$R_2^r$ is an amino-protective group, $R_a{}^{2'}$ is mono or di-protected carboxy-lower alkyl or ar(protected carboxy)lower alkyl whose aryl moiety may be substituted by hydroxy, $R_3{}^q$ is carboxy or protected carboxy excepting protected carbazoyl, $R_5{}^q$ is esterified carboxy, and $R_c{}^1$, $R_b{}^1$, $R^p$, $R_1{}^r$, $R_1{}^q$, $R_b{}^2$, Y, m and n are each as defined above.

Particulars of the definitions for $R_2{}^r$, and $R_a{}^{2'}$ and preferred example thereof are the same as those for $R_1{}^r$ and $R_a{}^2$, respectively, and preferred example of esterified carboxy for $R_5{}^q$ is the same as those for $R_3{}^p$, $R_c{}^2$ and $R_4{}^q$.

(1) Process $1^s$

Compound (V-1)+Compound (IV)→Compound (III-1)

This process relates to a method for preparing Compound (III-1) by reacting Compound (V-1) or its salt with a Compound (IV) or its salt.

The starting Compound (V-1) includes a known one described in e.g. Biochemistry, vol. 9, pages 823–831, 1971, and new one which can be prepared according to the method as described in said literature.

This reaction is carried out in substantially the same manner as that of Process 1 as explained hereinabove.

(2) Process $2^s$

Compound (III-1)→Compound (III-2)

This process relates to a method for preparing Compound (III-2) by subjecting Compound (III-1) to elimination reaction of both of amino protective groups for $R_1{}^r$ and $R_2{}^r$.

This process is applied to case that both amino protective groups for $R_1{}^r$ and $R_2{}^r$ are ones which can be removed by a method to be employed in this process.

This reaction is carried out by conventional methods such as catalytic reduction method, liquid ammonia-alkalimetal method, acid method, zinc-acid method, base method, hydrazine method and the like. Among these methods, preferred one is selected according to kind of the amino protective groups for $R_1{}^r$ and $R_2{}^r$ of Compound (III-1).

This reaction is carried out in substantially the same manner as that of Process 2 as explained hereinabove.

(3) Process $3^s$

Compound (III-1)→Compound (III-3)

This process relates to a method for preparing Compound (III-3) or its salts by removing selectively an amino protective group for $R_2{}^r$ of Compound (III-1) or its salt.

This process is applied in case that the amino protective group for $R_2{}^r$ reveals a different chemical property from that for $R_1{}^r$ against each kind of the removal methods as mentioned in the foregoing Process 2 and can selectively be removable by a method to be employed.

This reaction is carried out by conventional methods as mentioned in explanation for Process 2. Among these methods, preferred one is selected according to kinds fo the amino protective group for $R_2{}^r$. Each of such a method and the kinds of such amino protective group are to be referred to explanations in Process 2.

(4) Process $4^s$

Compound (III-1)→Compound (III-4)

This process relates to a method for preparing Compound (III-4) or its salt by removing selectively an amino protective group for $R_1{}^r$ of Compound (III-1) or its salt.

This process is applied to case that the amino protective group for $R_1{}^r$ and the amino protective group of the protected carbazoyl for $R_1{}^q$ reveals mutually the same chemical property and they reveal a different chemical property from that for $R_2{}^r$ against each kind of the removal methods as mentioned in the foregoing Process 2 and they can selectively be removable by a method to be employed.

(5) Process $5^s$

Compound (III-4)→Compound (III-5)

This process relates to a method for preparing Compound (III-5) for its salt by removing an amino protective group for $R_2{}^r$ or its salt.

This reaction is carried out in substantially the same manner as that of Process $3^s$ as explained hereinabove.

(6) Process $6^s$

Compound (III-5)→Compound (III-6)

This process relates to a method for preparing Compound (III-6) by reacting Compound (III-5) with an amino protective agent.

The amino protecting agent includes organic carboxylic, sulfonic, sulfinic, phosphoric and carbonic acids, aldehyde and ketone compounds which are composed of the same protective group as explained for the amino protective group for $R^r$, $R_1{}^r$ and Y and their reactive derivatives.

The reactive derivatives include conventional ones such as halides, activated amides, activated esters, acid azide and the like.

When a free acid form of such an amino protecting agent is employed, the reaction is preferably carried out in the presence of a condensing agent conventionally used in the field of amino acid and peptide chemistry.

This reaction is carried out in water or an aqueous organic solvent in the presence of a metal compound such as cupric chloride, cupric sulfate cupric carbonate, cupric acetate or the like.

(7) Process $7^s$

Compound (III-5)→Compound (III-7)

This process relates to a method for preparing Compound (III-7) by reacting Compound (III-5) with an amino protecting agent.

The amino protecting agent to be used in this reaction is the same as one illustrated in Process $6^s$.

This reaction is carried out in a conventional solvent, preferably within the range of pH 6–9, more preferably at pH of around neutrality under ice-cooling to at ambient temperature.

(8) Process $8^s$

Compound (III-6)→Compound (III-10)

This process relates to a method for preparing Compound (III-10) by reacting Compound (III-6) with an amino protecting agent.

The amino protecting agent is the same as that of Process $6^s$ and the reaction condition is the same as those of Process 3 as explained hereinabove.

(9) Process 9$^s$

Compound (VI)→Compound (VI-1)

This process relates to a method for preparing Compound (VI-1) by reacting Compound (VI) with an amino protecting agent.

In this reaction, it is necessary that such an amino protecting group to be introduced into one of two amino groups of the Compound (VI) be different from the amino protecting group for Y in case of obtaining stereospecific compound.

The amino protecting agent to be used is the same as the one illustrated in Process 6$^s$.

This reaction is carried out in substantially the same manner as that of Process 6$^s$.

(10) Process 10$^s$:

Compound (VI)→Compound (VI-2)

This process relates to a method for preparing Compound (VI-2) by reacting Compound (VI) with an amino protecting agent.

In this reaction, such an amino protective group to be introduced into the amino group may be the same as or different from that for Y.

Preferred examples of an amino protecting agent are the same as that of Process 6$^s$.

This reaction is carried out in water or an aqueous organic solvent and preferably within the range of pH 6-9, more preferably at pH of around neutrality under ice-cooling to at ambient temperature.

(11) Process 11$^s$:

Compound (VI-1)→Compound (VI-3)

This process relates to a method for preparing Compound (VI-3) by reacting Compound (VI-1) with a amino protecting agnet.

In this reaction, it is necessary that such an amino protective group to be introduced into the amino group is different from that for R$_2^r$ of Compound (VI-1) in case of obtaining stereospecific compound, but may be the same as that for Y.

This reaction is preferably carried out at neutral-alkaline condition, and other reaction conditions are the same as that of Process 3 as explained hereinabove.

(12) Process 12$^s$:

Compound (VI-2)→Compound (VI-3)

This process relates to a method for preparing Compound (VI-3) by reacting Compound (VI-2) with an amino protecting agent.

In this reaction, it is necessary that such an amino protective group to be introduced into the amino group (VI-3) is different from that for R$_1^r$ and Y of Compound (VI-2) in case of obtaining stereospecific compound.

Reaction conditions are the same as those of Process 11$^s$.

(13) Process 13$^s$:

Compound (VI-3)→Compound (III-8)

This process relates to a method for preparing Compound (III-8) by reacting Compound (VI-3) with a compound of the formula (IV):

or its salt.

This reaction is carried out in substantially the same manner as that of Process 1 as explained hereinabove.

(14) Process 14$^s$:

Compound (VI-3)→Compound (VI-4)

This process relates to a method for preparing Compound (VI-4) by removing selectively an amino protective group for Y of Compound (VI-3).

This process is applied to case that the amino protective group for Y reveals a different chemical property from that for R$_1^r$ and R$_2^r$ against each kind of the removal methods as mentioned in the foregoing Process 2 and can selectively be removed by a method to be employed.

This reaction is carried out in substantially the same manner as that of Process 2 as explained hereinabove.

(15) Process 15$^s$:

Compound (VI-4)→Compound (III-11)

This process relates to a method for preparing Compound (III-11) by reacting Compound (VI-4) or its salt with a compound of the formula:

or its salt.

This reaction is carried out in substantially the same manner as that of Process 1$^s$.

(16) Process 16$^s$:

Compound (III-11)→Compound (III-5)

This process relates to a method for preparing Compound (III-5) by removing both of amino protective groups for R$_1^r$ and R$_2^r$ of Compound (III-11).

This reaction is carried out in substantially the same manner as that of Process 2$^s$.

(17) Process 17$^s$:

Compound (VI-5)→Compound (VI-6)

This process relates to a method for preparing Compound (VI-6) by reacting Compound (VI-5) with an esterifying agent.

An esterifying agent to be used in this reaction is the same as one illustrated in the aforementioned Process 7 and the reaction is carried out substantially in the same manner as that of Process 7.

(18) Process 18$^s$:

Compound (VI-6)→Compound (VI-4)

This process relates to a method for preparing Compound (VI-4) by removing selectively an amino protective group for Y of Compound (VI-6).

This reaction is carried out in substantially the same manner as that of Process 14$^s$.

(19) Process 19$^s$:

Compound (III-12)→Compound (III-13)

This process relates to a method for preparing Compound (III-13) by reacting Compound (III-12) with an esterifying agent.

An esterifying agent to be used in this process is the same as that of Process $17^s$.

This reaction is carried out in substantially the same manner as that of Process $17^s$.

(20) Process $20^s$:

Compound (III-13)→Compound (III-5)

This process relates to a method for preparing Compound (III-5) by removing both of amino protective groups for $R_2{}^r$ and $R_1{}^r$ of Compound (III-13).

This reaction is carried out in substantially the same manner as that of Process $16^s$.

(21) Process $21^s$:

Compound (V-2)→Compound (VI-7)

This process relates to a method for preparing Compound (VI-7) by reacting Compound (V-2) with a halogenating agent.

A halogenating agent to be used in this reaction is to be such a halogenating agent as being capable of halogenating a carboxy group to provide the corresponding acid halide and may include a conventional one such as phosphorus trihalide (e.g. phosphorus trichloride, etc.), phosphorus pentahalide (e.g. phosphorus pentachloride, etc.), thionyl, halide (e.g. thionyl chloride, etc.), phosgene and the like.

In this reaction, the following are to be noted: That is, in case that a Compound (V-2), wherein both of $R^r$ and $R^r$ are a carbonic acyl group (e.g. alkoxy-carbonyl, etc.), is employed as a starting compound, all of the halogenatig agent as exemplified above can be used, and the reaction is conducted by reacting Compound (V-2) with the halogenating agent under warming or heating. On the other hand, in case that a compound (V-2) wherein both of $R^r$ and $R^r$ are hydrogen, is employed as a starting compound, phosgene only is used as a halogenating agent, and the reaction is carried out by reacting Compound (V-2) with phosgene under cooling to warming.

(22) Process $22^s$:

Compound (VI-7)→Compound (VI-8)

This process relates to a method for preparing Compound (VI-8) by reacting Compound (VI-7) or its salt with a compound of the formula: $H_2NNHY$ or its salt.

This reaction is preferably carried out in the presence of a weak acid such as acetic acid, oxalic acid or the like. This reaction is carried out in a conventional solvent under ice-cooling to at ambient temperature.

(23) Process $23^s$:

Compound (VI-8)→Compound (VI-9)

This process relates to a method for preparing Compound (VI-9) by reacting Compound (VI-8) with a conventional leucineaminopeptidase.

This reaction is preferably carried out in a conventional solvent, e.g. water, a hydrophilic solvent such as alcohol (e.g. methanol, ethanol, etc.), acetone or the like or a mixture thereof within the range of pH 7 to 10, preferably pH 8 to 9, at 20° to 40° C., preferably 37° C.

(24) Process $24^s$:

Compound (VI-9)→Compound (VI-10)

This process relates to a method for preparing Compound (VI-10) with an amino protecting agent.

An amino protecting agent to be used are same as that of Process $6^s$.

This reaction is carried out in substantially the same manner as that of Process 3 as explained hereinabove.

(25) Process $25^s$:

Compound (VI-10)→Compound (VI-11)

This process relates to a method for preparing Compound (VI-11) by reacting Compound (VI-10) with a halogenating agent.

A halogenating agent is the same as that of Process $21^s$.

This reaction is carried out in substantially the same manner as that of Process $21^s$. In this respect, it is to be noted that, in case that a compound (VI-10), wherein $R_2{}^r$ is a carbonic acyl (e.g., alkoxycarbonyl), is employed as a starting compound, all of the halogenating agent as exemplified in the explanation for Process $21^s$ can be explained.

(26) Process $26^s$:

Compound (VI-11)→Compound (VI-12)

This process relates to a method for preparing compound (VI-12) by subjecting compound (VI-11) to hydrolysis.

This reaction is carried out substantially the same manner as that of Process 4-2 as explained hereinabove.

(27) Process $27^s$:

Compound (III-9)→Compound (III-9')

This process relates to a method for preparing compound (III-9') by reacting compound (III-9) with an esterifying agent.

An esterifying agent to be used is the same as that of Process $17^s$.

This reaction is carried out in substantially the same manner as that of Process $17^s$.

(28) Process $28^s$:

Compound (III-3)→Compound (III-14')

This process relates to a method for preparing compound (III-14') by reacting compound (III-3) with an amino protecting agent.

An amino protecting agent to be used is the same as that of Process $6^s$.

This reaction is carried out in substantially the same manner as that of Process $8^s$.

(29) Process $29^s$:

Compound (III-14')→Compound (III-4)

This process relates to a method for preparing compound (III-4) by removing selectively an amino protective group for $R_1{}^r$.

This reaction is carried out substantially the same manner as that of Process $4^s$.

(30) Process $30^s$:

Compound (III-4)→Compound (III-15)

This process relates to a method for preparing Compound (III-15) by reacting compound (III-4) with an amino protecting agent.

An amino protecting agent to be used is the same as that of Process 6$^s$.

This reaction is carried out in substantially the same manner as that of Process 8$^s$.

(31) Process 31$^s$:

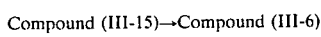
Compound (III-15)→Compound (III-6)

This process relates to a method for preparing compound (III-6) by removing selectively an amino protective group for $R_2{}^r$.

This reaction is carried out in substantially the same manner as that of Process 3$^s$.

(32) Process 32$^s$:

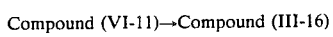
Compound (VI-11)→Compound (III-16)

This process relates to a method for preparing compound (III-16) by reacting compound (VI-11) with a Compound of the formula:

$$R_b{}^2$$
$$HN-R_a{}^2$$

or its salt.

This reaction is carried out substantially the same manner as that of Process 22$^s$.

(33) Process 33$^s$:

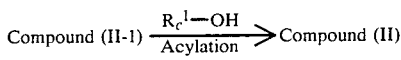
Compound (II-1) $\xrightarrow[\text{Acylation}]{R_c{}^1-OH}$ Compound (II)

This process relates to a method for preparing Compound (II) by reacting Compound (II-1) with an acylating agent.

The starting Compound (II-1) includes known one (e.g. Journal of Med. Chemistry, vol. 9, 971 (1966)) and new one, and said new compound can be prepared according to the method described in such literature.

The acylating agent to be used in this reaction is the same as illustrated in the aforementioned Process 3.

The acylating is carried out in substantially the same manner as that of Process 3 as explained hereinabove.

(34) Process 34$^s$:

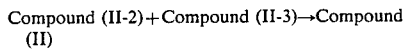
Compound (II-2)+Compound (II-3)→Compound (II)

This process relates to a method for preparing Compound (II) or its salt by reacting Compound (II-2) or its salt with Compound (II-3) or its salt.

This reaction is carried out in substantially the same manner as that of Process 1 as explained hereinabove.

(35) Process 35$^s$:

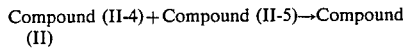
Compound (II-4)+Compound (II-5)→Compound (II)

This process relates to a method for preparing Compound (II) or its salt by reacting Compound (II-4) or its salt with Compound (II-5) or its salt.

This reaction is carried out in substantially the same manner as that of Process 1 as explained hereinabove.

(36) Process 36$^s$:

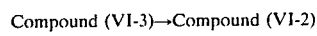
Compound (VI-3)→Compound (VI-2)

This process relates to a method for preparing Compound (VI-2) or its salt by removing relectively an amino protective group for $R_1{}^r$ of Compound (VI-3).

This reaction is carried out in substantially the same manner as that of Process 3$^s$ and accordingly the detailed explanation for Process 3$^s$ as made hereinabove is to be referred thereto.

(37) Process 37$^s$:

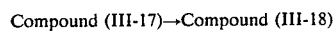
Compound (III-17)→Compound (III-18)

This process relates to a method for preparing Compound (III-18) by reacting Compound (III-17) with an oxidizing agent in the presence of alcohol.

The oxidizing agent to be used in thiis process is the same as one illustrated in Process 4-3.

The alcohol to be used in this process is a conventional one such as methanol, ethanol, propanol, butanol, benzylalcohol or the like.

The reaction is carried out in substantially the same manner as that of Process 4-3.

(38) Process 38$^s$:

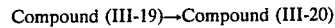
Compound (III-19)→Compound (III-20)

This process relates to a method for preparing Compound (III-20) by reacting Compound (III-19) with an amino protecting agent.

An amino protecting agent to be used is the same as that of Process 6$^s$.

This reaction is carried out in substantially the same manner as that of Process 8$^s$.

As to the object Compound (I) and starting Compounds (II) and (III) which are prepared according to the aforementioned Processes, it is to be noted that each of said compounds includes one or more stereoisomers which in due to the asymmetric carbon atoms in their molecule and all of such isomers are included within the scope this invention.

The new peptide (I) and its pharmaceutically acceptable salts of this invention have been found to possess enhancing activities of immune response (i.e., enhancing activities of cellular immunity and humoral antibody production) and reticuloendotherial system, mitogenic activity, inducing activity of interferon, protective efficacy in experimental infection and anticancer activity.

Accordingly, the new peptide (I) and its pharmaceutically acceptable salts are useful for the therapeutic treatment of infectious diseases caused by pathogenic microorganism, especially gram-negative bacteria and gram-positive bacteria and fugi, and of cancer in animals.

Further, Compounds (II) and (III) are useful as intermediate for preparing Compound (I) having biologically active properties as mentioned above.

For the purpose of showing pharmaceutical utility of the new peptide (I), pharmacological test data thereof are illustrated in the following.

1. BLOOD STREAM CLEARANCE OF CARBON

Reagents

1. Carbon suspension. Rotoring drawing ink (170 mg carbon/ml.) was diluted to 1/5 of the original concentration in saline containing 1% gelatin.
2. 0.1% aqueous sodium carbonate solution.

Procedure

Mice (DDY male 5-6 W) were injected via the tail vein with a dose of 0.01 ml/g body weight of carbon. Blood samples were taken by means of a pointed capillary pippet calibrated to hold a 50 μl and previously washed in heparin. This was plunged into the retrooribital venous sinus at the nasal angle of the eye. The samples were removed at 3 and 6 min. The blood was immediately discharged into 3.0 ml. of the sodium carbonate solution. This hemolyszed the blood and allowed the quantitation of carbon. The samples were then read in a spectrophotometer at 660 nm, the log concentration being obtained from a previously determined standard curve. The clearance value K may be determined by plotting log carbon concentration against time according to the following relationship;

$$K = \frac{(\log C_1 - \log C_2)}{T_2 - T_1}$$

in which $T_1$ and $T_2$ represent the time in min when the sample were withdrawn and $C_1$ and $C_2$ represent the concentrations of carbon in the blood at the time $T_1$ and $T_2$, respectively.

EXAMINATION OF EFFECT OF THE NEW PEPTIDE ON CARBON CLEARANCE

The aqueous solution of the test compound as given was administered subcutaneously to mice. Twenty four hours later, blood stream clearance of carbon was measured. K value obtained with treated mice was compared with that of control mice. The test results are shown in Table 1 to 3.

Test compound (1)

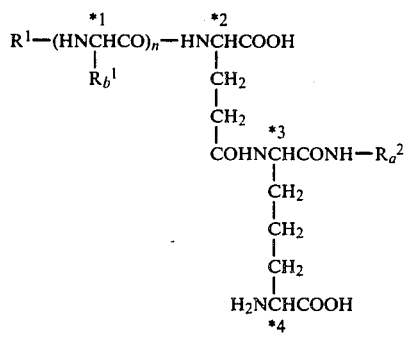

TABLE 1

| $R^1$ | $R_b^1$ | n | $R_a^2$ | *1 | *2 | *3 | *4 | Dose (mg/kg) | $\frac{K_{treated}}{K_{control}}$ | Reference compound $\frac{K_{treated}}{K_{control}}$ |
|---|---|---|---|---|---|---|---|---|---|---|
| OH<br>\|<br>CH₃CHCO<br>D | CH₃ | 1 | CH₃<br>\|<br>—CHCOOH<br>L | L | D | L | D | 1<br>0.1 | 1.3<br>1.0 | 1.3<br>0.9 |
| " | " | " | CH₂—⌬<br>\|<br>—CHCOOH<br>D | " | " | " | " | 1<br>0.1 | 1.6<br>1.1 | 1.3<br>0.9 |
| " | " | " | CH₃<br>\|<br>—CH—COOH<br>D | " | " | " | " | 1<br>0.1 | 2.8<br>2.6 | 2.3<br>1.2 |
| H | — | 0 | —CH₂COOH | — | " | " | " | 100<br>1 | 1.8<br>1.5 | —<br>2.4 |
| CH₃CO | " | " | " | " | " | " | " | 1<br>0.1 | 1.2<br>0.8 | 1.0<br>0.8 |
| ⌬(O=/N(Z)/CO)—L pyrrolidinone | " | " | " | " | " | " | " | 1<br>0.1 | 1.8<br>1.9 | 1.8<br>1.9 |
| ⌬(O=/N(H)/CO)—L pyrrolidinone | " | " | " | " | " | " | " | 100<br>1 | 1.7<br>1.5 | —<br>1.8 |
| H | " | " | CH₃<br>\|<br>—CHCOOH<br>D | " | " | " | " | 100<br>1 | 2.7<br>1.1 | —<br>1.8 |

TABLE 1-continued

| $R^1$ | $R_b^1$ | n | $R_a^2$ | *1 | *2 | *3 | *4 | Dose (mg/kg) | $\dfrac{K_{treated}}{K_{control}}$ | Reference compound $\dfrac{K_{treated}}{K_{control}}$ |
|---|---|---|---|---|---|---|---|---|---|---|
| 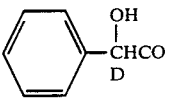 | " | " | " | " | " | " | " | 1<br>0.1 | 1.6<br>1.7 | 1.8<br>1.7 |
| $CH_3(CH_2)_5CO$ | " | " | " | " | " | " | " | 1<br>0.1 | 1.9<br>2.5 | 1.8<br>1.7 |
| $CH_3(CH_2)_{10}CO$ | " | " | " | " | " | " | " | 1<br>0.1 | 1.7<br>2.1 | 1.8<br>1.9 |
| $CH_3(CH_2)_{16}CO$ | $CH_3$ | 1 | $CH_2COOH$ | " | " | " | " | 1<br>0.1 | 1.5<br>1.2 | 1.3<br>— |
| 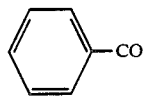 | " | 2 | " | " | " | " | " | 1<br>0.1 | 1.3<br>1.5 | 1.3<br>0.9 |
| $CH_3CO$ | " | " | " | " | " | " | " | 100<br>1 | 4.2<br>4.7 | —<br>4.5 |
| 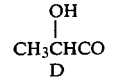 | H | 1 | " | " | " | " | " | 100<br>1 | 2.0<br>0.9 | —<br>2.0 |
| " | $CH_2OH$ | " | " | " | " | " | " | 100<br>1 | 2.3<br>1.1 | —<br>2.0 |
| " |  | " | " | " | " | " | " | 100<br>1 | 2.3<br>1.7 | —<br>2.0 |
| " | 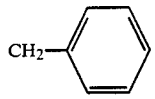 | " | " | " | " | " | " | 100<br>1 | 2.9<br>1.6 | —<br>2.3 |
| 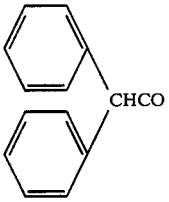 | $CH_3$ | " | " | " | " | " | " | 1<br>0.1 | 1.4<br>1.8 | 1.8<br>1.9 |
| 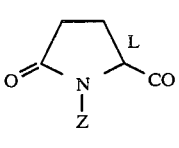 | " | " | " | " | " | " | " | 1<br>0.1 | 2.0<br>1.6 | 1.8<br>1.2 |
| 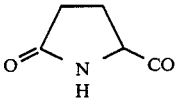 | " | " | " | " | " | " | " | 100<br>1 | 2.2<br>1.5 | —<br>1.8 |
| 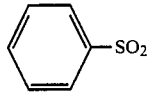 | " | " | " | " | " | " | " | 1<br>0.1 | 1.2<br>1.6 | 1.8<br>1.7 |
| 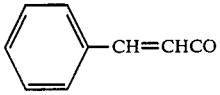 | " | " | " | " | " | " | " | 1<br>0.1 | 2.0<br>1.3 | 1.8<br>1.9 |

TABLE 1-continued

| $R^1$ | $R_b^1$ | n | $R_a^2$ | *1 | *2 | *3 | *4 | Dose (mg/kg) | $\frac{K_{treated}}{K_{control}}$ | Reference compound $\frac{K_{treated}}{K_{control}}$ |
|---|---|---|---|---|---|---|---|---|---|---|
| CH$_3$CH(OH)CO— D | " | " | —CH$_2$CH$_2$COOH (CH$_2$CH$_2$ side with COOH) | " | " | " | " | 1<br>0.1 | 1.8<br>1.5 | 1.8<br>1.7 |
| " | " | " | —CH(COOH)CH$_2$CH$_2$COOH D | " | " | " | " | 1<br>0.1 | 1.8<br>1.2 | 1.8<br>1.9 |
| HOCH$_2$CO— | CH$_3$ | 1 | CH$_2$COOH | " | " | " | " | 100<br>1 | 2.5<br>0.9 | —<br>2.1 |
| CH$_3$CH(OH)CO— L | " | " | " | " | " | " | " | 1<br>0.1 | 2.3<br>1.5 | 2.4<br>1.4 |
| CH$_3$CH(NH$_2$)CO— D | " | " | " | " | " | " | " | 100<br>1 | 2.0<br>1.8 | —<br>2.0 |
| 2-thienyl-CH$_2$CO— | " | " | " | " | " | " | " | 100<br>1 | 1.6<br>1.9 | —<br>2.2 |
| C$_6$H$_5$NHCO— | " | " | " | " | " | " | " | 100<br>1 | 2.1<br>1.9 | —<br>2.2 |
| C$_6$H$_5$CH$_2$OCO— | " | " | " | " | " | " | " | 100<br>1 | 1.6<br>2.2 | —<br>1.7 |
| N-acetylmuramyl residue (HO, HO, OH, NHCOCH$_3$, H$_3$CCHCO—) | " | " | " | " | " | " | " | 100<br>1 | 1.9<br>0.7 | —<br>2.0 |
| (CH$_3$)$_3$CCO— | " | " | " | " | " | " | " | 100<br>1 | 2.9<br>2.3 | —<br>1.8 |
| 1-adamantyl-CO— | " | " | " | " | " | " | " | 100<br>1 | 2.1<br>2.0 | —<br>2.2 |
| CH$_3$(CH$_2$)$_{10}$CO— | " | " | " | " | " | " | " | 1<br>0.1 | 1.7<br>1.6 | 1.3<br>0.9 |
| 2-hydroxyphenyl-CO— | " | " | " | " | " | " | " | 1<br>0.1 | 1.6<br>1.2 | 1.3<br>0.9 |
| DL CH$_3$(CH$_2$)$_3$CH(C$_2$H$_5$)CO— | " | " | " | " | " | " | " | 1<br>0.1 | 3.0<br>1.7 | 3.6<br>1.6 |

TABLE 1-continued

| $R^1$ | $R_b^1$ | n | $R_a^2$ | *1 | *2 | *3 | *4 | Dose (mg/kg) | $\dfrac{K_{treated}}{K_{control}}$ | Reference compound $\dfrac{K_{treated}}{K_{control}}$ |
|---|---|---|---|---|---|---|---|---|---|---|
| ![3-pyridyl]-CO (nicotinoyl) | " | " | " | " | " | " | " | 1 | 2.1 | 1.6 |
|  |  |  |  |  |  |  |  | 0.1 | 1.0 | 1.1 |
| H | CH$_3$ | 1 | CH$_2$COOH | " | " | " | " | 100 | 2.1 | — |
|  |  |  |  |  |  |  |  | 1 | 0.8 | 2.1 |
| OH<br>\|<br>CH$_3$CHCO<br>D | " | " | " | " | " | " | " | 100 | 1.0 | — |
|  |  |  |  |  |  |  |  | 1 | 0.7 | 1.0 |
| " | " | " | " | " | " | " | L | 10 | 4.3 | 5.0 |
|  |  |  |  |  |  |  |  | 1 | 1.2 | 4.5 |
| " | " | " | " | " | L | " | D | 100 | 2.8 | — |
|  |  |  |  |  |  |  |  | 1 | 1.4 | 3.6 |
| OH<br>\|<br>CH$_3$CHCO<br>L | " | " | " | " | D | " | " | 100 | 2.6 | — |
|  |  |  |  |  |  |  |  | 1 | 2.4 | 2.2 |
|  |  |  |  |  |  |  |  | 1 | 2.2 | 1.8 |
| OH<br>\|<br>CH$_3$CHCO<br>D | " | " | " | D | " | " | " | 0.1 | 1.9 | 1.2 |
| CH$_3$CH$_2$CO | " | " | " | L | " | " | " | 100 | 2.0 | — |
|  |  |  |  |  |  |  |  | 1 | 1.6 | 2.1 |
| CH$_3$CO | " | " | " | " | " | " | " | 100 | 2.0 | — |
|  |  |  |  |  |  |  |  | 1 | 1.1 | 2.2 |
| CH$_3$(CH$_2$)$_5$CO | " | " | " | " | " | " | " | 1 | 2.3 | 2.0 |
|  |  |  |  |  |  |  |  | 0.1 | 1.4 | 1.1 |
| CH$_3$\<br>   \>CHCO<br>CH$_3$/ | " | " | " | " | " | " | " | 100 | 2.0 | — |
|  |  |  |  |  |  |  |  | 1 | 2.4 | 1.7 |
| C$_6$H$_5$—CO (benzoyl) | " | " | " | " | " | " | " | 100 | 2.3 | — |
|  |  |  |  |  |  |  |  | 1 | 2.0 | 2.6 |
| C$_6$H$_5$—CH(OH)CO<br>D | " | " | " | " | " | " | " | 1 | 2.5 | 2.0 |
|  |  |  |  |  |  |  |  | 0.1 | 1.3 | 1.1 |
| OCH$_3$<br>\|<br>CH$_3$CHCO<br>DL | " | " | " | " | " | " | " | 100 | 1.5 | — |
|  |  |  |  |  |  |  |  | 1 | 1.3 | 1.4 |
| C$_6$H$_5$—OCH$_2$CO | " | " | " | " | " | " | " | 100 | 1.5 | — |
|  |  |  |  |  |  |  |  | 1 | 1.3 | 1.4 |

Note: Reference compound is a compound wherein $R^1$ is CH$_3$CH(OH)CO (D), $R_b^1$ is CH$_3$, n is 1, $R_a^2$ is CH$_2$COOH, *1 is L, *2 is D, *3 is L and *4 is D.

TABLE 2

| Drug | Dose (mg/mouse) | $K_{treated}/K_{control}$ |
|---|---|---|
| Krestin | 10 | 1.1 |
|  | 1 | 1.0 |
| Levamisol | 10 | — (death) |
|  | 1 | 0.5 |
| Tuftsin | 400 | 1.4 |
|  | 125 | 1.0 |
| FR-900156 substance | 0.25 | 2.9 |
|  | 0.06 | 1.5 |

TABLE 2-continued

| Drug | Dose (mg/mouse) | $K_{treated}/K_{control}$ |
|---|---|---|
| Control (saline) | | 1.0 |

(2) Test Compound 2

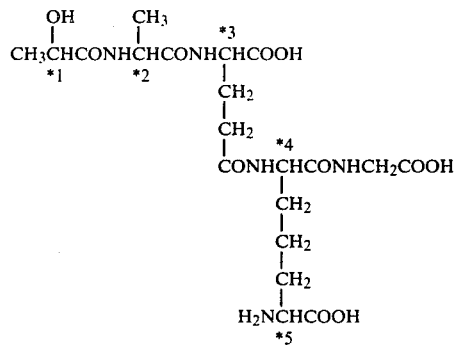

TABLE 3

| Test Compound *1 *2 *3 *4 *5 | Dose (mg/kg) | $K_{treated}/K_{control}$ | Reference Compound FR-900156 substance |
|---|---|---|---|
| D L L L D | 100 | 2.0 | — |
| | 1 | 0.9 | 1.9 |
| D D L L D | 100 | 1.7 | — |
| | 1 | | 1.6 |
| D L D L L | 100 | 2.7 | — |
| | 1 | 0.9 | 2.5 |
| L L D L D | 100 | 2.6 | — |
| | 1 | 2.4 | 2.2 |
| D D D L D | 1 | 2.2 | 1.8 |

TABLE 3-continued

| Test Compound *1 *2 *3 *4 *5 | Dose (mg/kg) | $K_{treated}/K_{control}$ | Reference Compound FR-900156 substance |
|---|---|---|---|
| | 0.1 | 1.9 | 1.2 |

2.

ENHANCING ACTIVITIES OF CELLULAR IMMUNITY AND HUMORAL ANTIBODY PRODUCTION

Guinea pigs (groups of five) were given 0.1 ml of FIA (Freund's Incomplete Adjuvant) emulsion containing 500 μg of ovalbumin in both posterior footpads. Control groups received antigen in FIA only, whereas the test groups received the antigen with the following test compounds in FIA. The animals were skin-tested on day 14 and bled on day 16.

(1) Test Compound (1)

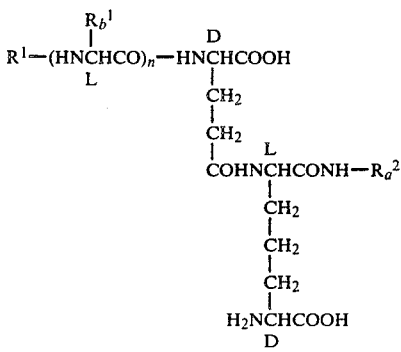

TABLE 4

| $R^1$ | $R_b^1$ | n | $R_a^2$ | Dose (μg/site) | Cellular immunity *1 skin reaction (mm diameter, M ± S.E.) | Humoral hemagglutination titer (M ± S.E. log$_2$) *2 | immunity hemolysin titer (M ± S.E. log$_2$) *2 |
|---|---|---|---|---|---|---|---|
| H | CH$_3$ | 1 | CH$_2$COOH | 1 | 1.8 ± 0.7 *3 | 11.9 ± 0.5 *3 | 5.6 ± 0.5 |
| | | | | 10 | 8.9 ± 0.9 *3 | 12.3 ± 0.2 *3 | 6.6 ± 0.3 |
| | | | | 100 | 10.8 ± 3.3 *3 | 12.0 ± 0.3 *3 | 6.7 ± 0.5 |
| CH$_3$CH$_2$CO | " | " | " | 1 | 2.0 ± 2.0 | 12.3 ± 0.2 *3 | 7.3 ± 0.4 *3 |
| | | | | 10 | 8.6 ± 1.0 *3 | 11.4 ± 0.5 *3 | 7.8 ± 0.3 *3 |
| | | | | 100 | 3.1 ± 1.3 *3 | 9.7 ± 0.4 | 7.2 ± 0.3 *3 |
| HOCH$_2$CO | " | " | " | 1 | 10.4 ± 2.4 *3 | 11.8 ± 0.5 *3 | 7.4 ± 0.6 *3 |
| | | | | 10 | 14.6 ± 1.1 *3#2 | 12.4 ± 0.5 *3 | 7.3 ± 0.5 *3 |
| | | | | 100 | 6.6 ± 1.1 *3 | 10.8 ± 0.2 *3 | 6.0 ± 0.2 |
| Control | | | | 0 | 0 | 9.4 ± 0.4 | 5.4 ± 0.5 |
| $\underset{L}{\overset{OH}{\underset{|}{CH_3CHCO}}}$ | " | " | " | 1 | 6.7 ± 0.8 *3 | 8.2 ± 0.1 *3 | |
| | | | | 10 | 10.2 ± 1.6 *3 | 7.6 ± 0.5 *3 | |
| ⟨phenyl⟩—CO | " | " | " | 1 | 8.7 ± 1.8 *3 | 8.9 ± 0.2 *3 | |
| | | | | 10 | 7.7 ± 2.4 *3 | 8.7 ± 0.2 *3 | |
| Control | " | " | " | 0 | 0 | 6.8 ± 0.3 | |
| ⟨phenyl⟩—CHCO, OH, D | " | " | " | 1 | 11.5 ± 2.1 *3#1 | 10.8 ± 0.3 *3 | 7.1 ± 0.4 *3 |
| | | | | 10 | 11.1 ± 0.7 *3#2 | 12.3 ± 0.5 *3 | 8.5 ± 0 *3 |
| | | | | 100 | 1.1 ± 1.1 | 9.1 ± 0.6 | 4.3 ± 6 *3 |
| Control | | | | 0 | 0 | 9.2 ± 0.3 | 5.9 ± 0.1 |

TABLE 4-continued

| $R^1$ | $R_b^1$ | n | $R_a^2$ | Dose (μg/site) | Cellular immunity *1 skin reaction (mm diameter, M ± S.E.) | Humoral hemagglutination titer (M ± S.E. log$_2$) *2 | immunity hemolysin titer (M ± S.E. log$_2$) *2 |
|---|---|---|---|---|---|---|---|
| OH<br>\|<br>CH$_3$CHCO<br>D | H | " | " | 1<br>10<br>100 | | 10.0 ± 0.3 *3<br>9.6 ± 0.3<br>10.0 ± 0.4 | 5.9 ± 0.3<br>6.9 ± 0.5 *3<br>7.0 ± 0.4 *3 |
| " | CH$_3$<br>\ <br>CH<br>/<br>CH$_3$ | " | " | 1<br>10<br>100 | | 10.6 ± 0.3 *3<br>9.9 ± 1.0 *3<br>10.5 ± 0.4 *3 | 6.9 ± 0.3 *3<br>7.0 ± 0.4 *3<br>6.3 ± 0.5 *3 |
| " | HOCH$_2$ | " | " | 1<br>10<br>100 | 10.1 ± 1.1 *3#2<br>10.7 ± 1.3 *3<br>5.4 ± 2.2 | 10.5 ± 0.2 *3<br>9.8 ± 0.4<br>9.6 ± 0.4 | 7.8 ± 0.3 *3<br>7.3 ± 0.3 *3<br>7.1 ± 0.2 *3 |
| Control | | | | 0 | 0.9 ± 0.9 | 8.5 ± 0.5 | 5.5 ± 0.3 |
| NH$_2$<br>\|<br>CH$_3$CHCO<br>D | CH$_3$ | " | " | 1<br>10 | 5.0 ± 2.2<br>7.1 ± 0.9 *3 | 8.5 ± 0.2 *3<br>7.9 ± 0.4 *3 | |
| HO—sugar ring with OH, NHCOCH$_3$, H$_3$CCHCO— | " | " | " | 1<br>10 | 5.4 ± 2.2 *3<br>12.6 ± 0.9 *3 | 7.6 ± 0.4 *3<br>8.4 ± 0.2 *3 | |
| Control | | | | 0 | 0 | 5.8 ± 0.3 | |
| CH$_3$(CH$_2$)$_5$CO | " | " | " | 1<br>10 | 10.01 ± 1.2 *3<br>7.5 ± 2.2 *3 | 9.5 ± 0.4 *3<br>9.2 ± 0.6 *3 | |
| CH$_3$\ <br>CHCO<br>CH$_3$/ | " | " | " | 1<br>10 | 5.5 ± 1.4 *3<br>8.5 ± 1.0 *3 | 8.7 ± 0.5 *3<br>7.4 ± 0.6 *3 | |
| Control | | | | 0 | 0 | 6.6 ± 0.6 | |
| ⌬—OCH$_2$CO | " | " | " | 1<br>10 | 10.2 ± 1.1 *3<br>6.3 ± 1.3 *3 | 8.3 ± 0.3 *3<br>7.7 ± 0.3 *3 | |
| CH$_3$CO | "<br>D<br>L | 2 | " | 1<br>10 | 9.0 ± 1.0 *3<br>8.1 ± 2.5 *3 | 7.7 ± 0.5<br>8.4 ± 0.5 *3 | |
| OCH$_3$<br>\|<br>CH$_3$CHCO<br>DL | CH$_3$ | 1 | " | 1<br>10 | 8.0 ± 1.1 *3<br>11.9 ± 2.5 *3 | 8.8 ± 0.3 *3<br>8.3 ± 0.3 *3 | |
| Control | | | | 0 | 0 | 7.1 ± 0.1 | |
| ⌬—CH$_2$OCO | " | " | " | 0.1<br>1<br>10 | 11.2 ± 1.1 *3<br>7.6 ± 2.2 *3<br>6.4 ± 2.5 | 10.4 ± 0.3 *3<br>10.2 ± 0.3 *3<br>9.3 ± 0.2 *3 | |
| (thiophene)—CH$_2$CO | " | " | " | 0.1<br>1<br>10 | 6.4 ± 2.7<br>10.2 ± 2.6 *3<br>8.6 ± 1.8 *3 | 9.9 ± 0.5 *3<br>10.6 ± 0.3 *3<br>10.6 ± 0.3 *3 | |
| ⌬—NHCO | " | " | " | 0.1<br>1<br>10 | 10.5 ± 2.9 *3<br>9.3 ± 0.7 *3<br>4.2 ± 1.3 | 9.1 ± 0.4<br>9.1 ± 0.4<br>9.8 ± 0.2 | |

TABLE 4-continued

| R[1] | R[1]_b | n | R[2]_a | Dose (μg/site) | Cellular immunity *1 skin reaction (mm diameter, M ± S.E.) | Humoral hemagglutination titer (M ± S.E. log_2) *2 | immunity hemolysin titer (M ± S.E. log_2) *2 |
|---|---|---|---|---|---|---|---|
| Control | | | | 0 | 0.9 ± 0.9 | 8.5 ± 0.4 | |
| CH_3CO | — | 0 | " | 1 | 6.4 ± 2.1 *3 | 8.8 ± 0.3 | |
| | | | | 10 | 8.7 ± 1.0 *3 | 9.1 ± 0.4 | |
| OH<br>\|<br>CH_3CHCO<br>D | CH_3 | 1 | CH_3<br>\|<br>CHCOOH<br>L | 1<br>10 | 13.7 ± 1.6 *3<br>10.8 ± 0.8 *3 | 11.1 ± 0.5<br>10.7 ± 0.3 | |

(2) Test Compound (2)

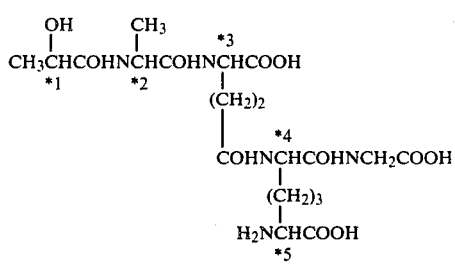

TABLE 5

| Test Compound | | | | | Dose (μg/site) | Cellular immunity*1 skin reaction (mm diameter, M ± S.E.) | Humoral Hemagglutination titer (M ± S.E. log_2)*2 | immunity hemolysin titer (M ± S.E. log_2)*2 |
|---|---|---|---|---|---|---|---|---|
| *1 | *2 | *3 | *4 | *5 | | | | |
| D | L | D | L | D | 0 | 0 | 9.1 ± 0.19 | 4.5 ± 0.45 |
| | | | | | 0.1 | 8.2 ± 2.8*3 | 9.9 ± 0.10*3 | 6.4 ± 0.76 |
| | | | | | 1 | 14.5 ± 2.1*3 | 11.5 ± 0.61*3 | 7.7 ± 0.64*3 |
| | | | | | 10 | 11.0 ± 1.3*3 | 12.2 ± 0.56*3 | 7.1 ± 0.58 |
| | | | | | 100 | 4.2 ± 1.7*3 | 10.0 ± 1.01 | 5.9 ± 0.89 |
| D | L | L | L | D | 0 | 0.9 ± 0.9 | 8.5 ± 0.4 | — |
| | | | | | 1 | 2.4 ± 1.5 | 10.4 ± 0.5*3 | — |
| | | | | | 10 | 7.9 ± 2.1*3 | 11.0 ± 0*3 | — |
| D | L | D | DL | | 0 | 0 | 9.2 ± 0.3 | 5.9 ± 0.1 |
| | | | | | 1 | 4.3 ± 1.8*3 | 10.2 ± 1.1*3 | 6.5 ± 0.4 |
| | | | | | 10 | 9.0 ± 3.2*3 | 10.4 ± 0.3*3 | 7.5 ± 1.2*3 |
| | | | | | 100 | 6.4 ± 1.7*3 | 10.9 ± 0.2*3 | 6.7 ± 1.2*3 |
| L | L | D | L | D | 0 | 0 | 6.8 ± 0.3 | — |
| | | | | | 1 | 6.7 ± 0.8*3 | 8.2 ± 0.1*3 | — |
| | | | | | 10 | 10.2 ± 1.6*3 | 7.6 ± 0.5*3 | — |

Note:
*1 The skin test was performed on the back by intradermal injection of 5 μg of antigen dissolved in 0.1 ml of saline. Skin reaction of the test site was measured at 48 hours.
*2 Antibody estimation was carried out as follows:
Ovalbumin-coated sheep red blood cells were prepared by chromium chloride.
Antibody titer was expressed as the reciprocal of the highest dilution of serum evoking threshold hemogglutination and hemolysin.
The results were converted to log_2 unit.
*3 Significance was calculated by Student's t-test; $P < 0.05$
1: 2/5 of animal, Central necrosis
2: 1/5 of animal, Central necrosis

3. MITOGENIC ACTIVITIES FOR MOUSE SPLEEN CELLS (Materials and Methods)

(1) Animal:

Mice used for this experiment were male BALB/C Strain, aged 13 weeks (Test 1) or female BALB/C strain, aged 9 weeks (Test 2).

(2) Tissue Culture Medium:

The tissue culture medium employed was a complete medium designated Roswell Park Memorial Institute (RRMI)-1640. All media employed contained 100 units/ml of penicillin G and 100 μg/ml of streptomycin sulfate and 10% fetal calf serum.

(3) Cell Preparation:

Spleens were removed under sterile conditions, and washed with Hanks solution and then teased in the tissue culture medium. The cells were suspended in the tissue culture medium to contain $8 \times 10^6$ cells/ml.

(4) Culture Conditions:

Into each hole of Microtest II tissue culture plate (8×12 hole) (maker: Falcon Plastics Co.) were poured 0.1 ml of the above cells suspension and 0.1 ml of the prescribed concentrate of the test compound as described below and then the cultures were incubated intriplicate at 37° C. in a humidified atmosphere (95% air, 5% CO_2) for 48 hours.

The control culture contained 0.1 ml of the culture medium instead of the medium containing the test compound.

(5) (3H) Thymidine uptake:

In all tests, 20 μl of 10 micro-curine (μCi)/ml of tritiated thymidine (3H-thymidine) was added to each hole for the final 24 hours of culture. After the culture was completed, the resultant cells were filtered with a filter paper, Whatman GF83 and washed successively with saline and with 5% trichloroacetic acid. The filter paper was dried and placed in a scintillator (toluene 1 l, containing 0.1 g of p-bis(5-phenyloxazoyl]benzene and 4 g of 2,5-diphenyloxazoyl), and 3H-thymidine incorporated into DNA was measured.

(6) Stimulation Index $$\text{Stimulation Index} = \frac{\text{3H—thymidine uptake (net cpm) at treatment}}{\text{3H—thymidine uptake (net cpm) at control}}$$

(7) Test Compound (1)

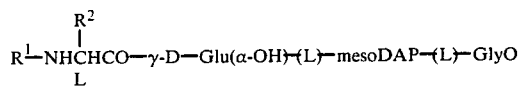

(Results)
(1) Test 1

TABLE 6

| $R^1$ | $R^2$ | Concentration (μg/ml) | 3H—thymidine uptake net cpm: av ± S.E. | Stimulation Index |
|---|---|---|---|---|
| CH$_3$(CH$_2$)$_5$CO | CH$_3$ | 100 | 2,728 ± 73 | 5.2 |
| | | 10 | 2,660 ± 45 | 5.0 |
| | | 1 | 2,899 ± 126 | 5.5 |
| CH$_3$CHCO (OH) D | —⟨phenyl⟩—CH$_2$ | 100 | 2,174 ± 142 | 4.1 |
| | | 10 | 1,547 ± 79 | 2.9 |
| | | 1 | 1,103 ± 76 | 2.1 |
| (CH$_3$)$_2$CHCO | CH$_3$ | 100 | 2.234 ± 170 | 4.2 |
| | | 10 | 2,046 ± 138 | 3.9 |
| | | 1 | 1.378 ± 112 | 2.6 |
| ⟨phenyl⟩—CH$_2$OCO | CH$_3$ | 100 | 2,312 ± 158 | 4.4 |
| | | 10 | 2,388 ± 97 | 4.5 |
| | | 1 | 1,775 ± 94 | 3.4 |
| Control | — | — | 528 ± 28 | 1.0 |
| ⟨phenyl⟩—CHCO (OH) D | CH$_3$ | 100 | 2,306 ± 54 | 5.5 |
| | | 10 | 1,788 ± 314 | 4.3 |
| | | 1 | 1,928 ± 87 | 4.6 |
| HOCH$_2$CO | CH$_3$ | 100 | 2,605 ± 117 | 6.2 |
| | | 10 | 1,725 ± 86 | 4.1 |
| | | 1 | 1,120 ± 55 | 2.7 |

TABLE 6-continued

| $R^1$ | $R^2$ | Concentration (μg/ml) | 3H—thymidine uptake net cpm: av ± S.E. | Stimulation Index |
|---|---|---|---|---|
| CH$_3$CH$_2$CO | CH$_3$ | 100 | 2,023 ± 142 | 4.9 |
| | | 10 | 1,474 ± 44 | 3.5 |
| | | 1 | 732 ± 28 | 1.8 |
| CH$_3$CHCO (OH) D | H | 100 | 1,541 ± 73 | 3.7 |
| | | 10 | 1,119 ± 63 | 2.7 |
| | | 1 | 937 ± 30 | 2.2 |
| CH$_3$CHCO (OH) D | (CH$_3$)$_2$CH | 100 | 1,675 ± 22 | 4.0 |
| | | 10 | 1,679 ± 98 | 4.0 |
| | | 1 | 1,019 | 2.4 |
| CH$_3$CHCO (OH) D | HOCH$_2$ | 100 | 1,541 ± 41 | 3.7 |
| | | 10 | 1,468 ± 12 | 3.5 |
| | | 1 | 927 ± 33 | 2.2 |
| CH$_3$CHCO (NH$_2$) D | CH$_3$ | 100 | 1,635 ± 192 | 3.9 |
| | | 10 | 1,573 ± 69 | 3.8 |
| | | 1 | 1,001 ± 73 | 2.4 |
| Control | — | — | 417 ± 13 | 1.0 |
| ⟨phenyl⟩—OCH$_2$CO | CH$_3$ | 100 | 1.979 ± 174 | 5.0 |
| | | 10 | 2,343 ± 22 | 5.9 |
| | | 1 | 1,469 ± 224 | 3.7 |
| CH$_3$CHCO (OCH$_3$) DL | CH$_3$ | 100 | 1,537 ± 113 | 3.9 |
| | | 10 | 1,788 ± 30 | 4.5 |
| | | 1 | 1,144 ± 142 | 2.9 |
| CH$_3$CONHCHCO (CH$_3$) D | CH$_3$ | 100 | 1.627 ± 38 | 4.1 |
| | | 10 | 1,837 ± 138 | 4.6 |
| | | 1 | 1.338 ± 74 | 3.4 |
| ⟨phenyl⟩—NHCO | CH$_3$ | 100 | 1,528 ± 122 | 3.8 |
| | | 10 | 1,225 ± 42 | 3.1 |
| | | 1 | 866 ± 37 | 2.2 |
| ⟨thienyl⟩—CH$_2$CO | CH$_3$ | 100 | 1,588 ± 167 | 4.0 |
| | | 10 | 1,469 ± 87 | 3.7 |
| | | 1 | 1,065 ± 89 | 2.7 |
| Control | — | — | 399 ± 51 | 1.0 |

(2) Test 2

TABLE 7

| $R^1$ | $R^2$ | Concentration (μg/ml) | 3H—thymidine uptake net cpm:av ± S.E | Stimulation Index |
|---|---|---|---|---|
| CH$_3$CO | CH$_3$ | 100 | 1,920 ± 135 | 4.2 |
| | | 10 | 1,067 ± 63 | 2.4 |
| | | 1 | 785 ± 33 | 1.7 |
| CH$_3$CHCO (OH) L | CH$_3$ | 100 | 2,772 ± 215 | 6.1 |
| | | 10 | 2.326 ± 140 | 5.1 |
| | | 1 | 1,713 ± 102 | 3.8 |
| ⟨phenyl⟩—CO | CH$_3$ | 100 | 2,979 ± 199 | 6.6 |
| | | 10 | 2,177 ± 66 | 4.8 |
| | | 1 | 1,477 ± 46 | 3.3 |

TABLE 7-continued

| R$^1$ | R$^2$ | Concentration ($\mu$g/ml) | 3H—thymidine uptake net cpm:av ± S.E | Stimulation Index |
|---|---|---|---|---|
| 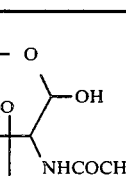 | CH$_3$ | 100 | 2,186 ± 164 | 4.8 |
| | | 10 | 1,370 ± =58 | 3.0 |
| | | 1 | 756 ± 42 | 1.7 |
| Control | | — | 452 ± 30 | 1.0 |
|  | CH$_3$ | 100 | 4.227 ± 217 | 4.2 |
| | | 10 | 3,664 ± 122 | 3.7 |
| | | 1 | 2,809 ± 83 | 2.8 |
| CH$_3$(CH$_2$)$_{10}$CO | CH$_3$ | 100 | 4,027 ± 217 | 4.0 |
| | | 10 | 3,963 ± 198 | 4.0 |
| | | 1 | 4,210 ± 255 | 4.2 |
| 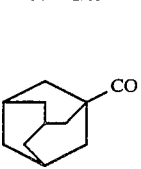 | CH$_3$ | 100 | 3,967 ± 348 | 4.0 |
| | | 10 | 2,933 ± 126 | 2.9 |
| | | 1 | 2,134 ± 32 | 2.1 |
| Control | | — | 1,000 ± 94 | 1.0 |

(8) Test Compound (2)

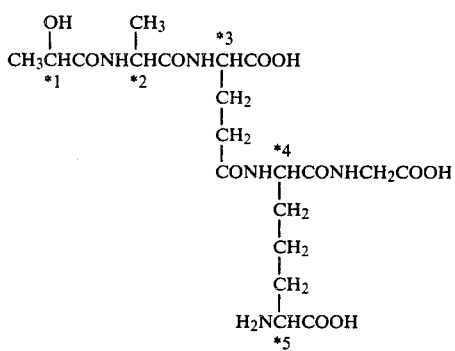

TABLE 8

| Test Compound | | | | | Test | Concentration ($\mu$g/ml) | 3H—thymidine uptake net com: av ± S.E. | Stimulation Index |
|---|---|---|---|---|---|---|---|---|
| *1 | *2 | *3 | *4 | *5 | | | | |
| D | L | D | L | D | 1 | 100 | 2,028 ± 89 | 4.9 |
| | | | | | | 10 | 1,486 ± 120 | 3.6 |
| | | | | | | 1 | 835 ± 64 | 2.0 |
| | | | | | | 0 | 417 ± 13 | 1.0 |
| | | | | | 2 | 100 | 3,666 ± 42 | 4.1 |
| | | | | | | 10 | 3,223 ± 402 | 3.6 |
| | | | | | | 1 | 2,741 ± 319 | 3.0 |
| | | | | | | 0 | 901 ± 105 | 1.0 |
| D | L | D | DL | | 1 | 100 | 1,284 ± 131 | 3.1 |
| | | | | | | 10 | 1,414 ± 38 | 3.4 |
| | | | | | | 1 | 996 ± 35 | 2.4 |
| | | | | | | 0 | 417 ± 13 | 1.0 |
| L | L | D | L | D | 2 | 100 | 2,772 ± 215 | 6.1 |
| | | | | | | 10 | 2,326 ± 140 | 5.1 |
| | | | | | | 1 | 1,713 ± 102 | 3.8 |
| | | | | | | 0 | 452 ± 30 | 1.0 |
| D | L | D | L | L | 1 | 100 | 1,271 ± 29 | 3.2 |
| | | | | | | 10 | 1,003 ± 50 | 2.5 |
| | | | | | | 1 | 742 ± 61 | 1.9 |
| | | | | | | 0 | 399 ± 51 | 1.0 |

4. PROTECTIVE EFFICACY IN EXPERIMENTAL INFECTION IN MICE (1) In determining the protective efficacy against experimental infections in mice, the test compound was dissoloed in and diluted with sterile saline to provide prescribed concentrations of drug.

Male ICR-strain mice, aged 4 weeks were used in groups of ten mice. E. coli 22 was cultivated overnight at 37° C. on trypticase soy agar and then were suspended in a sterile saline to obtain microbial cell concentration of 9.0×10$^7$ CFU/ml. Mice were inoculated intraperitoneally with 0.2 ml of the suspension. Each of the test drugs was given intraperitoneally in various doses to a group of ten mice 24 hours before challenge.

Survival percent were found from the number of the surviving animals after four days of injection. Results are shown in Table 9.

(1) Test Compound (1):

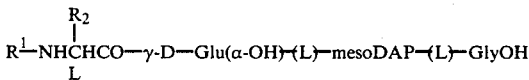

TABLE 9

| | | Survival (%) | |
|---|---|---|---|
| R$^1$ | R$^2$ | Dose 10 mg/kg | Dose 1 mg/kg |
| CH$_3$(CH$_2$)$_5$CO | CH$_3$ | 60 | 70 |
| (CH$_3$)$_3$CCO | CH$_3$ | 70 | 70 |
| CH$_3$(CH$_2$)$_{10}$CO | CH$_3$ | 50 | 60 |
| CH$_3$COHNCHCO<br>D<br>(CH$_3$) | CH$_3$ | 100 | 88.9 |

TABLE 9-continued

| R¹ | R² | Survival (%) Dose 10 mg/kg | Survival (%) Dose 1 mg/kg |
|---|---|---|---|
| CH₃CHCO (OCH₃) DL | CH₃ | 88.9 | 100 |
| Ph-OCH₂CO | CH₃ | 100 | 88.9 |
| Ph-CHCO (OH) D | CH₃ | 87.5 | 75.0 |
| Ph-CO | CH₃ | 30 | 50 |
| (CH₃)₂CHCO | CH₃ | 20 | 60 |
| Ph-CH₂OCO | CH₃ | 50 | 30 |
| Ph-NHCO | CH₃ | 70 | 70 |
| adamantyl-CO | CH₃ | 50 | 50 |
| Ph-COHNCHCO (CH₃) D | CH₃ | 50 | 50 |
| 2-HO-Ph-CO | CH₃ | 80 | 60 |
| CH₃CHCO (OH) D | CH₂-Ph | 60 | 60 |
| 2-thienyl-CH₂CO | CH₃ | 40 | 70 |
| HOCH₂CO- | CH₃ | 75 | 100 |
| CH₃CH₂CO | CH₃ | 100 | 87.5 |
| CH₃CHCO (OH) D | (CH₃)₂CH | 87.5 | 100 |
| CH₃CHCO (OH) D | HOCH₂ | 87.5 | 87.5 |
| CH₃CHCO (OH) D | H | 100 | 100 |
| CH₃CHCO (OH) L | CH₃ | 87.5 | 62.5 |
| CH₃CHCO (NH₂) D | CH₃ | 100 | 87.5 |
| N-acetylmuramyl (HO, O, OH, HO, NHCOCH₃, CH₃CHCO) | CH₃ | 100 | 87.5 |
| CH₃CO | CH₃ | 62.5 | 25.0 |

(2) Test Compound (2)

$$R^1-(HNCHCO)_n\overset{*2}{-}HNCHCOOH$$
$$\underset{R_b^1}{|}^{*1} \quad \underset{CH_2}{|}$$
$$\underset{CH_2}{|}$$
$$\underset{COHNCHCONH-R_a^2}{|}^{*3}$$
$$\underset{CH_2}{|}$$
$$\underset{CH_2}{|}$$
$$\underset{CH_2}{|}$$
$$\underset{H_2NCHCOOH}{|}$$
$$^{*4}$$

TABLE 10

| R[1] | R$_b^1$ | n | R$_a^2$ | *1 | *2 | *3 | *4 | Survival (%) Dose 10 mg/kg | Survival (%) Dose 1 mg/kg |
|---|---|---|---|---|---|---|---|---|---|
| (C$_6$H$_5$)$_2$CHCO— | CH$_3$ | 1 | CH$_2$COOH | L | D | L | D | 75.0 | 50.0 |
| 5-oxo-1-Z-pyrrolidin-2-yl-CO— (L) | " | " | " | " | " | " | " | 87.5 | 75.0 |
| 5-oxo-pyrrolidin-2-yl-CO— (L, NH) | " | " | " | " | " | " | " | 75.0 | 87.5 |
| C$_6$H$_5$—SO$_2$— | " | " | " | " | " | " | " | 75.0 | 87.5 |
| C$_6$H$_5$—CH=CHCO— | " | " | " | " | " | " | " | 87.5 | 62.5 |
| CH$_3$CH(OH)CO— (D) | " | " | —CH$_2$CH(COOH)— | " | " | " | " | 87.5 | 87.5 |
| CH$_3$CH(OH)CO— (D) | " | " | —CH(CH$_3$)COOH (L) | " | " | " | " | 70.0 | 70.0 |
| " | " | " | —CH(CH$_2$C$_6$H$_5$)COOH (D) | " | " | " | " | 90.0 | 80.0 |
| " | " | " | —CH(CH$_3$)—COOH (D) | " | " | " | " | 60 | 60 |
| H | — | 0 | —CH$_2$COOH | — | " | " | " | 66.6 | 22.2 |
| CH$_3$CO | " | " | " | " | " | " | " | 100 | 88.9 |
| 5-oxo-1-Z-pyrrolidin-2-yl-CO— (L) | " | " | " | " | " | " | " | 87.5 | 75.0 |
| 5-oxo-pyrrolidin-2-yl-CO— (L, NH) | " | " | " | " | " | " | " | 87.5 | 50.0 |

TABLE 10-continued

| R¹ | $R_b^1$ | n | $R_a^2$ | *1 | *2 | *3 | *4 | Survival (%) Dose 10 mg/kg | Dose 1 mg/kg |
|---|---|---|---|---|---|---|---|---|---|
| H | " | " | CH₃<br>\|<br>—CHCOOH<br>D | " | " | " | " | 75.0 | 87.5 |
| 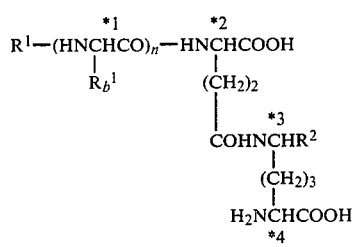 | " | " | " | " | " | " | " | 62.5 | 50.0 |
| CH₃(CH₂)₅CO | " | " | " | " | " | " | " | 62.5 | 62.5 |
| CH₃(CH₂)₁₀CO | " | " | " | " | " | " | " | 87.5 | 100 |
| H | " | " | CH₂COOH | " | " | " | " | 87.5 | 100 |
| DL<br>\|<br>CH₃(CH₂)₃CHCO<br>\|<br>C₂H₅ | CH₃ | 1 | " | L | " | " | " | 87.5 | 50.0 |
| OH<br>\|<br>CH₃CHCO<br>D | " | " | " | " | " | " | L | 100 | 88.9 |
| " | " | " | " | " | L | " | D | — | 50.0 |
| OH<br>\\<br>CH₃CHCO<br>D | " | " | " | D | " | " | " | 100 | 87.5 |
| " | " | " | " | " | D | " | " | 75.0 | 75.0 |
| CH₃(CH₂)₅CO | " | " | CH₃<br>\|<br>—CHCOOH<br>D | L | " | " | " | 100 | 44.4 |

(2) Test Compound (2)

$$R^1-(HNCHCO)_n^{*1}-HNCHCOOH^{*2}$$
$$\hspace{1cm} | \hspace{2cm} |$$
$$\hspace{0.5cm} R_b^1 \hspace{1.5cm} (CH_2)_2$$
$$\hspace{3cm} |^{*3}$$
$$\hspace{2.5cm} COHNCHR^2$$
$$\hspace{3.5cm} |$$
$$\hspace{3cm} (CH_2)_3$$
$$\hspace{3.5cm} |$$
$$\hspace{2.5cm} H_2NCHCOOH$$
$$\hspace{4cm} *4$$

(2) In determining the protective efficacy against experimental infections in mice, the FR-900156 substance was dissolved and diluted in sterile water to provide three-fold concentrations of drug for testing.

Male DDY-strain mice, aged 6 weeks and averaging 24–26 g in weight, were used in groups of four mice each.

Overnight cultures of *Escherichia coli* No. 22 in Difco Nutrient Broth was diluted to 1/100 in fresh medium and incubated at 30° C. with shaking. When the cell density of $1 \times 10^8$/ml was obtained, 0.2 ml of the culture was injected intraperitoneally. All the animals receiving the challenge and not treated with the drug died within 48 hours of the infection.

TABLE 10

| R¹ | $R_b^1$ | n | R² | *1 | *2 | *3 | *4 | Survival Dose 10 mg/kg | Dose 1 mg/kg |
|---|---|---|---|---|---|---|---|---|---|
| CH₃(CH₂)₅CO | CH₃ | 1 | COOH | L | D | L | D | 66.6 | 88.9 |
| " | — | 0 | " | — | " | " | " | 88.9 | 100 |
| H | " | " | " | " | " | " | " | 88.9 | 88.9 |
| OH<br>\|<br>CH₃CHCO<br>D | CH₃ | 1 | " | L | " | " | " | 100 | 62.5 |
| " | " | " | CH₃<br>\|<br>CONCOOH | " | " | " | " | 87.5 | 75.0 |
| " | " | " | H | " | " | — | " | 40.0 | 60.0 |

One-fifth ml of the FR-900156 substance solution was injected subcutaneously, 1,4,5, and 6 days before the infection.

Two days after infection, the test was considered complete and survival records of that day were made. The test results are shown in Table 11

TABLE 11

| Dose (mg/mouse/day) | Survival/infected |
|---|---|
| 0.01 | 10/10 |
| 0.003 | 10/10 |
| 0.001 | 10/10 |
| 0.0003 | 8/10 |
| 0.0001 | 4/10 |
| Control | 0/10 |

5-1 ANTICANCER ACTIVITY

Female rats of Donru Strain, aged 6 weeks, were used in groups of three rats each.

Suspension of ascites hepatoma AH 66 in 0.5 ml of Hank's solution was transplanted intraperitoneally ($5 \times 10^4$ cells/rat). About 13 days later, all the control animals dies of ascites. Prolongation of survival time in comparison with the controls is the criterion of effectiveness.

Therapy was given 5, 6, 7, 8, 9, days before tumor transplantation. The FR-900156 substance was dissolved and diluted in sterile saline water to provide three-fold dilutions for testing and the said sterile saline solution of the FR-900156 substance was given intraperitoneally to the animals. The test results are shown in Table 12.

TABLE 12

| Dose (mg/rat/day) | Life span (days) |
|---|---|
| 1.0 | 14, >30, >30 |
| 0.3 | 13, >30, >30 |
| 0.1 | 13, >30, >30 |
| 0.03 | 13, 13, 13 |
| Control (saline) | 13, 13, 13 |

5-2 ANTITUMOR ACTIVITY

Methylcholanthlene-induced fibrosarocoma (Meth-A) was used.

A mixture of the tumor cells ($1 \times 10^5$) and the test compound was suspended in a 0.5% methylcellulose saline solution. The suspension was inoculated intradermally in male BALB/c mice.

Four weeks after inoculation, tumor size was measused. Results are shown in the following table.

Test Compound:

| Test compound R$^1$ | R$^p$ | R$_a^2$ | R$^q$ | Dose μg/site | Suppression of Meth-A growth |
|---|---|---|---|---|---|
| CH$_3$(CH$_2$)$_{16}$CO | H | H | H | 10 | 8/10 |
| Control | — | | | | 1/20 |
| CH$_3$(CH$_2$)$_{16}$CO | H | CH$_3$ | CH$_3$ | 100 | 10/10 |
| Control | — | | | | 1/20 |
| [CH$_3$(CH$_2$)$_{21}$]$_2$CHCO | 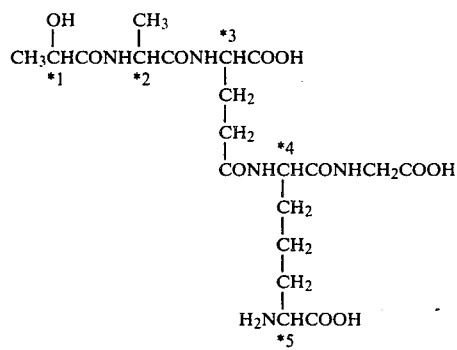 | CH$_3$ | CH$_3$ | 100 | 7/10 |
| Control | — | | | | 1/20 |

Note:
Values gives Number of tumor-free mice/Number of mice tested, provided that when the perpendicular diameter of the tumor was less than 5 mm, the animal was defined as free of tumor.

6. INDUCING ACTIVITY OR INTERFERON

Test Compound:

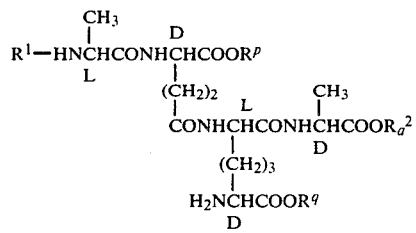

Male ICR strain mice aged 4 to 6 weeks were used in these experiments. Spleens of these mice were removed and the capacity of spleen cells to produce interferon in vitro by the treatment of test compound was tested.

Single spleen cell subpensious were prepared in medium RPMI-1640 supplement with streptomycin (100γ/ml), penicillin G (100 γ/ml), 1% glutamine and 2-mercaptoethanol ($5 \times 10^{-5}$M).

These were cultured at 37° C. at a concentration of $4 \times 10^7$ cells/ml with or without test compound dissolved with culture medium (dose: 100, 10, 1 μg/ml). After 24 hours, supernatants of these cultures were collected and those interferon activities were titrated by cytopathic effect (CPE) inhibition test in L cell-VSV system. Antiviral titer was expressed in IU/ml base on standard interferon.

The results are as the following table 13.

TABLE 13

| Test Compound |   |   |   |   | Dose (μg/ml) | IF Titer (IU/ml) |
|---|---|---|---|---|---|---|
| *1 | *2 | *3 | *4 | *5 |   |   |
| D | L | D | L | D | 100 | 14 |
|   |   |   |   |   | 10 | 16 |
|   |   |   |   |   | 1 | 10 |
|   |   |   |   |   | 0 | <6.5 |
| D | L | D | DL |   | 100 | 62 |
|   |   |   |   |   | 10 | 40 |
|   |   |   |   |   | 1 | 39 |
|   |   |   |   |   | 0 | 7.5 |
| D | D | D | L | D | 100 | 29 |
|   |   |   |   |   | 10 | 23 |
|   |   |   |   |   | 1 | 11 |
|   |   |   |   |   | 0 | <11 |
| D | D | L | L | D | 100 | 38 |
|   |   |   |   |   | 10 | 11 |
|   |   |   |   |   | 1 | <11 |
|   |   |   |   |   | 0 | <11 |

7. ACUTE TOXICITY IN MICE of FR-900156

1 g/kg (i.v.): no toxicity.

8. CELL TOXICITY (mouse L cell) of FR-900156

500 μg/ml: no toxic effect.

The pharmaceutical composition of this invention can be used in the form of a pharmaceutical preparation, for example, in solid, semisolid or liquid form, which contains an active substance of this invention in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, collidal silica, potato starch, urea and other carriers suitable for use in manufacturing preparations, in solid, semisolid, or liquid form, and in addition auxiliary, stabilizing, thickening and coloring agents and perfumes may be used. The pharmaceutical compositions can also contain preservative or bacteriostatic agents to keep the active ingredient in the desired preparations stable in activity. The active object compound is included in the pharmaceutical composition in an amount sufficient to produce the desired therapeutic effect upon the process or condition of diseases.

For applying this composition to humans, it is preferably to apply it by intravenous, intramuscular or oral administration. While the dosage or therapeutically effective amount of the object compound of this invention varies from and also depends upon the age and condition of each individual patient to be treated, a daily dose of about 2-100 mg of the active ingredient/kg of a human being or an animal is generally given for treating diseases, and an average single dose of about 50 mg, 100 mg, 250 mg, and 500 mg is generally administered.

The following examples are given for purpose of illustrating this invention.

In the following examples, starting compounds and object compounds are expressed by using the following abbreviations:

Lac: Lactyl
Ala: Alanyl
Glu: Glutamyl
Gly: Glycyl
DAP: α,ε-Diaminopimelyl
Z: benzyloxycarbonyl
Boc: t-butoxycarbonyl
Bzl: benzyl
Me: methyl
Et: ethyl
Su: N-hydroxysuccinimide
Bzh: benzhydryl
Ac: acetyl
Val: Valyl
Ser: Seryl
Phe: Phenylalanyl
Asp: Aspartyl
Lys: Lysyl
Leu: Leucyl
Sar: Sarcosyl
γ-Abu: γ-Aminobutyryl
Aad: 2-Aminoadipyl
Tyr: Tyrosyl
Tfa: Trifluoroacetyl.

PREPARATION 1

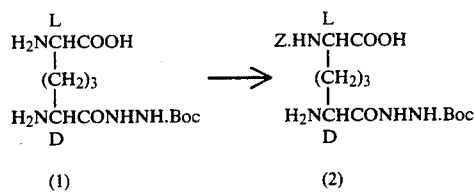

meso—DAP(D)—NHNH.Boc (1) (5.4 g) and cupric chloride (dihydrate) (1.52 g) were dissolved in a mixture of water (30 ml) and 0.5N aqueous sodium hydroxide (60 ml). The solution was stirred for thirty minutes at ambient temperature. The solution was cooled to 0° C. and benzyloxycarbonyl chloride (4.6 g) was added dropwise thereto in the course of twenty minutes, maintaining the pH over 11. The stirring was continued for an additional one hour at the same temperature. After the reaction was completed, the solution was adjusted to pH 7 with 5% aqueous hydrochloric acid and then hydrogen sulfide gas was passed through the solution for about fifteen minutes. To the reaction mixture was added ethyl acetate (50 ml) and the mixture was adjusted to pH 4 with 5% aqueous hydrochloric acid. The ethyl acetate layer and the aqueous layer were divided out, and the ethyl acetate layer was extracted four times with water (30 ml). All of the aqueous layers were combined and concentrated to 40 ml under reduced pressure to give a crystals. The crystals were collected by filtration, washed with water to give Z-(L)meso-DAP(D)-NHNH.Boc (2) (3.5 g). The mother liquor and the washings were collected and extracted twice with n-butanol (40 ml). The extracts were combined and concentrated under reduced pressure to give a residue. The residue was triturated with ether and collected by filtration to give additional Z—(L)meso—DAP(-D)—NHNH.Boc (2) (1.2 g) as a crude solid, which was recrystallized from water. mp 194-196 (dec.).

N.M.R. (CD$_3$OD), δ(ppm): 1.67 (9H, s), 1.6-2.1 (6H, m), 3.6-4.2 (2H, m), 5.12 (2H, s), 7.43 (5H, s).

$[\alpha]_D = -20.8°$ (C:0.5 methanol).

PREPARATION 2

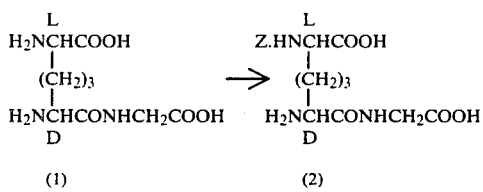

3N Aqueous sodium hydroxide (6.0 ml) was added to a solution of meso—DAP—(D)—GlyOH (1) (1.85 g) and cupric chloride (dihydrate) (1.28 g) in water (190 ml) at 5° C. To the solution was added benzyloxycarbonyl chloride (5.4 ml), and the resulting solution was stirred at 5° C., maintaining the pH 11-12 with 3N aqueous sodium hydroxide. The stirring was continued for 4.5 hours and an additional benzyloxycarbonyl chloride (3.2 ml) was added to the reaction mixture. The mixture was stirred at 5° C. for six hours, maintaining the pH 11-12 with 3N aqueous sodium hydroxide.

The reaction mixture was acidified to pH 2 with 3N aqueous hydrochloric acid and washed twice with ether. The separated aqueous layer was adjusted to pH 4.5 with 3N aqueous sodium hydroxide and buffled with hydrogen sulfide and then filtered. The filtrate was concentrated to about 100 ml and the concentrate was allowed to stand in a refrigerator to give crystals. The crystals were collected by filtration and washed successively with water, methanol and ether to give Z—(L-)—meso—DAP—(D)—GlyOH (2) (230 mg). mp 161.5–162.0 (dec.).

N.M.R. (CD$_3$OD-D$_2$O) δ(ppm): 1.2–2.2 (6H, m), 3.7–4.3 (4H, m), 5.10 (2H, s), 7.39 (5H, s).

$[\alpha]_D = -25.3°$ (C: 0.5 methanol).

The filtrate was concentrated and chromatographed on a macroporous non-ionic adsorption resin, HP20 (trade mark, maker: Mitsubishi Chemical Industry Co., Ltd.) (125 ml). After washing with water, elution was carried out with 50% aqueous methanol and then 80% aqueous methanol. The eluates were combined and evaporated to dryness and the crude crystals thus obtained was dissolved in hot methanol (80 ml) and filtered. To the filtrate was added water (15 ml) and the solution was concentrated to give crude crystals. The crude crystals were washed successively with isopropanol and ether to give Z—(L)—meso—DAP—(D)—GlyOH (2) (2.22 g). The same object compound (2) (165 mg) was additionally obtained from the mother liquor.

PREPARATION 3

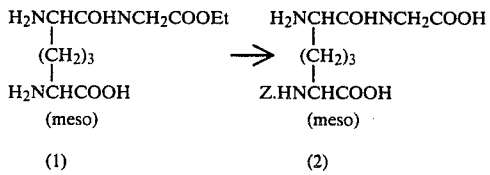

meso DAP(OE)GlyOEt (1) (4.10 g) was dissolved in water (30 ml) and cupric chloride (dihydrates) (2.08 g) was added to the solution. The mixture was stirred at 5°–7° C. for five hours, maintaining pH 11 with 2% aqueous sodium hydroxide.

To the reaction mixture was added benzyloxycarbonyl chloride (10.0 g) and the resulting mixture was stirred at 5°–7° C. for five hours, maintaining pH 11. An additional benzyloxycarbonyl chloride (4.0 g) was added to the reaction mixture. The resulting mixture was stirred for four hours and adjusted to pH 1 with dil hydrochloric acid and washed with ethyl acetate. The aqueous layer was adjusted to pH 7 and hydrogen sulfide gas was passed through the solution. The precipitates were filtered off and the filtrate was concentrated. The concentrate was adjusted to pH 3.2–3.4 and passed through a column packed with a macroporous non-ionic adsorption resin, HP20 (180 ml). Elution was carried out with 50% aqueous methanol and the eluate was evaporated to dryness to give Z-meso DAP(OH)-GlyOH (2) (4.3 g) as a solid.

N.M.R. (D$_2$O+NaHCO$_3$) δ(ppm): 1.38–1.88 (6H, m), 3.75 (2H, s), 3.79 (1H, t, J=4 Hz), 3.96 (1H, t, J=4 Hz), 5.11 (2H, s), 7.44 (5H, s).

PREPARATION 4

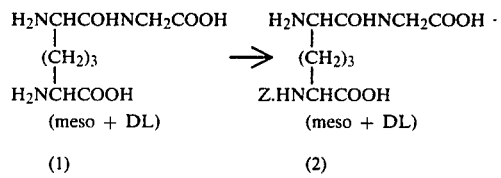

Cupric carbonate (1.173 g) was added to a solution of DAP(OH)GlyOH (1) (1.7 g) in water (50 ml) and the mixture was refluxed for two hours. The reaction mixture was filtered and the filtrate was adjusted to pH 11.5 with 2N aqueous sodium hydroxide. Benzyloxycarbonyl chloride (3.23 ml) was added to the reaction mixture at 0° C. and the resulting mixture was stirred at 0° C. for six hours, maintaining pH 11.5. The reaction mixture was neutralized with dil. aqueous hydrochloric acid and dechelated by hydrogen sulfide gas. The resulting mixture was filtered and the filtrate was chromatographed on a macroporous non-ionic adsorption resin, HP20 (100 ml). Elution was carried out with 80% aqueous methanol and the eluate was evaporated to dryness to give Z—DAP(OH)GlyOH (2) (1.4 g) as a solid.

N.M.R. (CD$_3$OD) δ(ppm): 1.38–1.88 (6H, m), 3.75 (2H, s), 3.79 (1H, t, J=4 Hz), 3.96 (1H, t, J=4 Hz), 5.11 (2H, s), 7.44 (5H, s).

PREPARATION 5

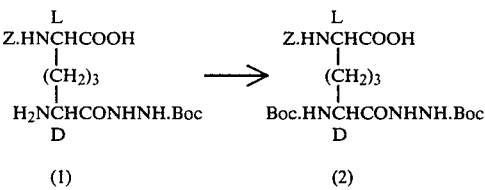

(1) Preparation 5-1

Z—(L)meso—DAP(D)—NHNHBoc (1) (5.0 g), t-butylcarbonic anhydride (3.0 g) and triethylamine (2.54 g) in a mixture of water (50 ml) and dioxane (50 ml) were stirred for three hours at ambient temperature. Dioxane was distilled off under reduced pressure and the resulting aqueous layer was washed with ether. The aqueous layer was adjusted to pH 2 with 5% aqueous hydrochloric acid and extracted with ethyl acetate. The extract was washed with saturated aqueous sodium chloride and then dried over anhydrous magnesium sulfate to give Z—(L)—Boc(D-

)meso—DAP(D)NHNHBoc (2) (6.0 g), which was recrystallized from isopropyl ether. mp 146-148 (dec).

N.M.R. (CDCl₃), δ(ppm): 1.4-2.1 (6H, m), 1.67 (9H, s), 4.1-4.5 (2H, m), 5.13 (2H, s), 5.50 (1H, broad s), 6.0 (1H, broad s), 7.05 (1H, broad s), 7.35 (5H, s), 8.37 (1H, broad s), 8.90 (1H, broad s).

(2) Preparation 5-2

Z—(L)—Boc(D)meso—DAP(D)—NHNHBoc (2) (0.50 g) was obtained from Z—(L)meso—DAP(-D)—NHNHBoc (1) (438 mg) by substantially the same manner as that of Example 5-1 provided that t-butyl S-4,6-dimethylpyrimidine-2-ylthiocarbonate (288 mg) was employed in place of t-butylcarbonic anhydride.

PREPARATION 6

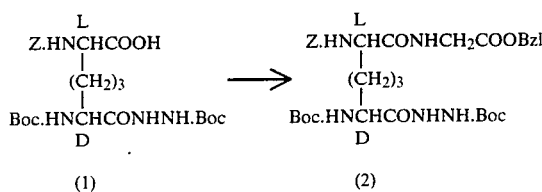

Z—(L)—Boc(D)meso—DAP(D)—HNHNHBoc (1) (10.8 g) and N-methyl-morpholine (2.02 g) were dissolved in methylene chloride (110 ml) and stirred at −10°— −15° C. Isobutyl chlorocarbonate (2.73 g) was added dropwise to the solution and the mixture was stirred for thirty minutes at ambient temperature. To the solution was added dropwise a solution of glycine benzyl ester p-toluenesulfonate (6.75 g) and N-methyl morpholine (2.02 g) in methylene chloride (110 ml). The solution was stirred for two hours at −10°— −15° C. and for an hour at ambient temperature. Methylene chloride was distilled off under reduced pressure and the residue was dissolved into a mixture of ethyl acetate (150 ml) and 1% aqueous hydrochloric acid (60 ml). The ethyl acetate layer was separated and washed successively with water 2% aqueous sodium bicarbonate and aqueous sodium chloride in turn. The ethyl acetate layer was dried over anhydrous magnesium sulfate and evaporated to dryness under reduced pressure. The residue thus obtained was recrystallized from ether to give Z—(L)—Boc(D)—meso—DAP(L)GlyoBzl—(D)—NHNHBoc. (Z)(12.3 g), mp. 85-87.

N.M.R. (CDCl₃), δ(ppm): 1.43 (18H, s), 1.5z-2.2 (6H, m), 4.10 (2H, d, J=6 Hz), 4.1-4.5 (2H, m), 5.10 (2H, s), 5.17 (2H, s), 5.40 (1H, d, J=8 Hz), 5.90 (1H, d, J=8 Hz), 6.73 (1H, broad s), 7.33 (10H, s), 7.73 (1H, broad s), 8.4-8.6 (1H, m).

PREPARATION 7

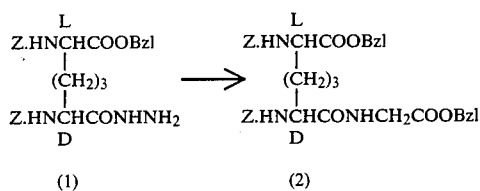

To a solution of di—Z—meso—DAP(L)oBzl—(D)—NHNH₂ trifluoroacetic acid salt (1) (6.435 g) in dimethylformamide (25 ml) was added 3.29N hydrochloric acid in dimethylformamide (5.80 ml) at −50° C. and then isoanylnitrite (1.41 ml) was added. The solution was allowed to warm to −20° C. and then stirred for ten minutes. The resulting solution was cooled to −50° C. and triethylamine (3.97 ml) was added thereto. To the solution was added a mixture of glycine benzyl ester p.toluensulfonate (6.41 g) and triethylamine (7.95 ml) in dimethylformamide (12 ml). The heterogeneous mixture was stirred at 3°-7° C. for six hours and allowed to stand in a refrigerator for 48 hours. The reaction mixture was diluted with a mixture of ethyl acetate (170 ml) and methylene chloride (30 ml) and washed successively with 5% aqueous phosphoric acid, water dil. sodium bicarbonate, water, and brine. The mixture was dried over anhydrous magnesium sulfate and the solvent was evaporated to dryness to give crystalline materials (6.4 g). The crystalline materials were chromatographed on silica gel (90 g) and eluted with a mixture of methylene chloride and ethyl acetate (5:1). The eluate was evaporated to give a residue. Crystallization was carried out from ethyl acetate to give crude crystals of di—Z—meso—DAP(L)oBzl—(D)—GLyoBzl (2) (5.32 g). mp 131°-133° C.

An aliquote (450 mg) of the above crystals were further purified by chromatography on silica gel (eluted with a mixture of methylene chloride and ethyl acetate (1:3), followed by recrystallization from a mixture of ethyl acetate and ether (5:2) to give fine needles. mp 138°-139.5° C.

[α]$_D^{20}$= +4.5° (C−1, chloroform).

N.M.R. (CDCl₃), δ(ppm): 1.1.-2.1 (6H, m), 3.98 (2H, d, J=6 Hz), 3.8-4.5 (2H, m), 5.04 (4H, s), 5.08 (2H, s), 5.10 (2H, s), 5.49 (2H, t, J=7 Hz), 6.64 (1H, t, J=6 Hz), 7.28 (20H, s).

PREPARATION 8

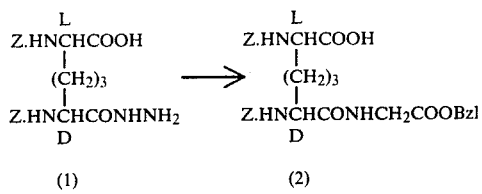

A solution of sodium nitrite (0.97 g) in water (10 ml) was added to a two-phase solution of di-—Z—meso—DAP(D)—NHNH₂ (6.50 g) in a mixture of 1N aqueous hydrochloric acid (42 ml) and ethyl acetate (30 ml) at 0° C. The resulting mixture was stirred at 0° C. for five minutes and a cooled ethyl acetate (30 ml) was added thereto. The ethyl acetate layer was collected and washed four times with dil. sodium chloride, dried over anhydrous magnesium sulfate and then filtered. To the filtrate was added a solution of H—GlyoBzl in methylene chloride (30 ml), which was prepared by desalting glycine benzyl ester p-toluenesulfonate (11.6 g) with potassium carbonate in a mixture of methylene chloride and water in a conventional manner, and then triethylamine (1.92 ml) was added. The resulting mixture was kept at 4° C. for 20 hours. The reaction mixture was washed successively with dil, hydrochloric acid and (three times), brine, dried over anhydrous magnesium sulfate and evaporated to dryness to give an oil (6.5 g), which was chromatographed on silica gel (45 g). Elution was carried out with a mixture of methylene chloride and methanol (100:5) to give amorphous solid (5.15 g). The solid was crystallized from a mixture of ethyl acetate and ether (1:2) to give di—Z—meso—DAP(D)GlyoBzl (2)(1.54 g)

N.M.R. (acetone-d$_6$), δ(ppm): 1.3-2.4 (6H, m), 3.9-4.6 (2H, m), 4.06 (2H, d, J=6 Hz), 5.12 (4H, s), 5.18 (2H, s), 6.3-6.9 (2H, broad d, J=8 Hz), 7.38 (15H, s), 7.77 (1H, t, J=6 Hz).

PREPARATION 9

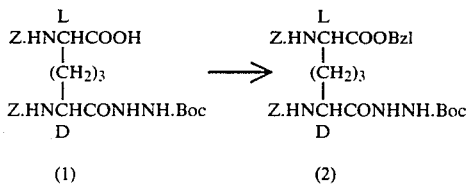

A mixture of di—Z—meso—DAP(D)—NHNHBoc (1) (8.83 g), benzyl bromide (3.66 ml) and triethylamine (4.30 ml) in dimethylformamide (40 ml) was stirred at ambient temperature for 19 hours. The reaction mixture was diluted with ethyl acetate (150 ml) and the solution was washed successively with dil. phosphoric acid, water, dil. sodium bicarbonate, water and brine. The solution was dried over anhydrous magnesium sulfate and evaporated to give an amorphous solid (9.0 g), which was purified by column chromatography using silica gel (90 g), and fractions eluted with a mixture of methylene chloride and ethyl acetate (1:3) were combined and evaporated to dryness to give a solid (8.65 g). Recrystallization from a mixture of ether and hexane gave di—Z—meso—DAP(L)oBzl—(D)—NHNHBoc (2)(7.40 g).

N.M.R. (CDCl$_3$), δ(ppm): 1.40 (9H, s), 1.1-2.0 (6H, m), 4.0-4.7 (2H, m), 5.17 (4H, s), 5.23 (2H, s), 6.87 (1H, broad s), 7.48 (15H, s), 8.57 (1H, broad s).

$[\alpha]_D^{23} = +13.2°$ (C=1, chloroform).

PREPARATION 10

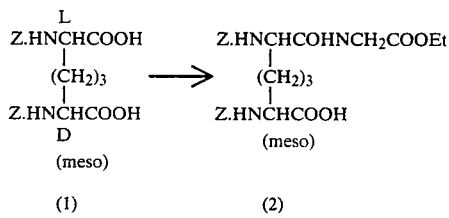

To a cold mixture of di—Z—(D)meso—DAP (1)(13.8 g) and triethylamine (6.1 g) in methylene chloride (150 ml) was added dropwise in the course of five minutes a cold solution of isobutoxycarbonyl chloride (5.33 g) in methylene chloride (30 ml) at −10° C. The mixture was stirred at −10° C.~−12° C. for twenty five minutes. To the mixture was added dropwise a solution of glycine ethyl ester hydrochloride (5.44 g) and triethylamine (3.94 g) in methylene chloride (200 ml) at −10° C.~−12° C. in the course of twenty minutes. The solution was stirred at −10° C. for thirty minutes. To the reaction mixture was added water and the mixture was adjusted to pH 2 with 1N aqueous hydrochloric acid, and then washed with saturated aqueous sodium chloride and with 5% aqueous sodium bicarbonate. The methylene chloride layer was washed with water and then concentrated. To the concentrate was added ethyl acetate and insoluble materials were filtered off and the filtrate was extracted three times with 5% aqueous sodium bicarbonate (pH 8). The extract was adjusted to pH 2 with 1N aqueous hydrochloric acid and then extracted three times with ethyl acetate. The extract was washed twice with water and dried over anhydrous magnesium sulfate. The extract was filtered and the filtrate was concentrated. The oil residue thus obtained was allowed to stand in a refrigerator to give crystals. The crystals was washed with isopropyl ether and dried over anhydrous magnesium sulfate to give di—Z—meso—DAP(OH)GlyOBt (7.73 g).

N.M.R. (DMSO-d$_6$), δ(ppm): 1.20 (3H, t, J=7 Hz), 1.0-1.9 (6H, m), 3.7-4.2 (2H, m) 3.80 (2H, d, J=6 Hz), 4.03 (2H, q, J=7 Hz), 5.00 (4H, s), 7.33 (10H, s).

PREPARATION 11

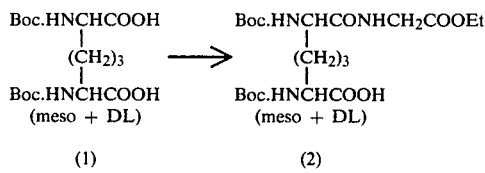

A mixture of di—Boc—meso—DAP di-dicyclohexylamine salt (1)(18.5 g) in methylene chloride (160 ml) was added to a solution of triethylamine hydrochloride (8.0 g) in methylene chloride (200 ml) and the mixture was stirred at ambient temperature for two hours and cooled to −10° C. To the cold mixture was added dropwise a solution of ethoxycarbonyl chloride (3.46 g) in methylene chloride (10 ml), maintaining the temperature at −10° C. The solution was stirred at −10° C. for thirty minutes. To the reaction mixture was added dropwise a mixture of glycinethyl ester hydrochloride (4.45 g) and triethylamine (3.23 g) in methylene chloride (200 ml) in the course of thirty minutes, maintaining the temperature at −10° C. The mixture was stirred at the same temperature for thirty minutes. The reaction mixture was adjusted to pH 2 with 1N aqueous hydrochloric acid and then washed twice with water and twice with saturated aqueous sodium chloride. The organic layer was concentrated and the concentrate was dissolved in ethyl acetate. Extraction was carried out twice with 5% aqueous sodium bicarbonate. The extract was adjusted to pH 2 with 1N aqueous hydrochloric acid. Extraction was carried out with ethyl acetate and the organic layer was washed successively with saturated aqueous sodium chloride, 5% aqueous sodium bicarbonate, and further washed with saturated aqueous sodium chloride. The organic layer was dried over anhydrous magnesium sulfate and filtered. The filtrate was concentrated to give an oily di—Boc—meso—DAP(OH)GlyOBt (2)(5.16 g).

N.M.R. (CDCl$_3$), δ(ppm: 1.30 (3H, t, J=7 Hz), 1.43 (18H, s), 1.1-2.1 (6H, m), 4.07 (2H, t, J=6 Hz), 3.8-4.5 (2H, m), 4.15 (2H, q, J=7 Hz).

PREPARATION 12

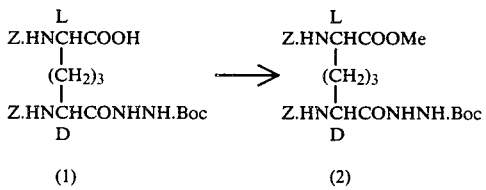

A solution of diazomethane (1 g/100 ml, 6 ml) was added to a solution of di—I—meso—DAP—(D)—NHNHBoc (1)(0.62 g) in ether (15 ml) at 0° C. until the solution became yellow. The reaction mixture was evaporated to dryness and the residue was chromatographed on silica gel (14 g) and elution was carried out with a mixture of methylene chloride and ethyl acetate (5:3) to give di—A—meso—DAP(-L)oME—(D)NHNHBoc.

N.M.R. (CDCl₃), δ(ppm): 1.2-2.2 (6H, m), 1.33 (9H, s), 3.73 (3H, s), 4.1-4.6 (2H, m), 5.12 (4H, s), 5.74 (1H, d, J=8 Hz), 5.78 (1H, d, J=8 Hz), 6.68 (1H, broad s), 7.35 (10H, s), 8.50 (1H, broad s).

$[\alpha]_D^{23} = +12.7°$ C. (C=1, ethanol).

PREPARATION 13

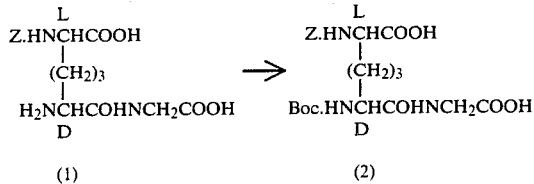

To a suspension of Z—(L)—meso—DAP—(D)—GlyOH (1) (2.072 g) in water (20 ml) was added triethylamine (2.90 ml) and the mixture was stirred at 0° C. for a few minute. A solution of t-butylcarbonic anhydride (1.54 g) in dioxane (20 ml) was added to the resulting solution. The solution was stirred at ambient temperature for 6.5 hours and concentrated. The concentrate was diluted with water (50 ml) and ethyl acetate (100 ml) was added thereto. The mixture was cooled to 0° C. and acidified to pH 2 with 1N aqueous hydrochloric acid.

The organic layer was separated and washed with water and brine, dried over magnesium sulfate and then evaporated to give Z—(L)—Boc(D)meso—DAP(D)-GlyOH (2) (2.88 g) as an amorphous solid.

N.M.R. (DMSO-d₆), δ(ppm): 1.37 (9H, s), 1.1-1.9 (6H, m), 3.6-4.2 (2H, m), 3.73 (2H, d, J=5.5 Hz), 5.02 (2H, s), 6.75 (1H, m), 7.33 (5H, s), 7.50 (1H, broad d, J=9 Hz), 8.07 (1H, broad t, J=5.5 Hz), 12.6 (2H, m).

PREPARATION 14

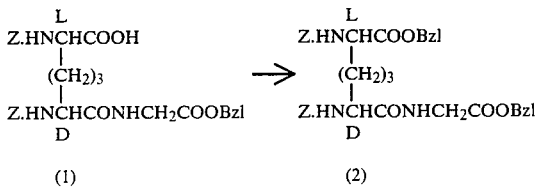

Triethylamine (0.84 ml) was added to a solution of di—Z—meso—DAP—(D)—GlyOBzl (1)(3.0 g) in dimethylformamide (15 ml) at 0° C. and then benzyl bromide (0.72 ml) was added thereto. The mixture was stirred at ambient temperature for 7.5 hours and triethylamine (0.42 ml) and benzyl bromide (0.36 ml) were added thereto. The mixture was stirred at ambient temperature overnight and poured into dil. phosphoric acid and then extracted with ethyl acetate (100 ml). The extract was washed successively with dil. phosphoric acid, water, dil. sodium bicarbonate, dil. sodium chloride and saturated sodium chloride, and then dried over anhydrous magnesium sulfate. The solvent was evaporated to give an oil (3.4 g). The oil was chromatographed on silica gel (55 g) and elution was carried out with a mixture of ethyl acetate and methylene chloride (35.65 g) to give crude crystals. The crude crystals were recrystallized from ethyl acetate to give di-—Z—meso—DAP(L)oBzl—(D)—GlyOBzl (2) (1.38 g).

N.M.R. (CDCl₃), δ(ppm): 1.1-2.1 (6H, m), 3.98 (2H, d, J=6 Hz), 3.8-4.5 (2H, m), 5.04 (4H, s), 5.08 (2H, s), 5.10 (2H, s), 5.49 (2H, t, J=7 Hz), 6.64 (1H, t, J=6 Hz), 7.28 (20H, s).

PREPARATION 15

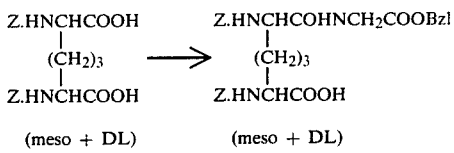

Di—Z—DAP(OH)₂ (1)(4.58 g) was dissolved in tetrahydrofuran (50 ml) and N-hydroxysuccinimide (1.15 g) was added to the solution. To the resulting solution was added a mixture of glycine benzyl ester p-toluenesulfonate (3.21 g) and triethylamine (1.4 ml) in tetrahydrofuran. N,N'-Dicyclohexylcarbodiimide (2.06 g) was added to the resulting solution under ice-cooling and the solution was stirred at ambient temperature. N,N'-Dicyclohexylurea was filtered off and the filtrate was evaporated to dryness. The residue was dissolved in ethyl acetate and washed successively with dil. hydrochloric acid, saturated sodium chloride, saturated sodium bicarbonate and saturated sodium chloride, in turn. The organic layer was dried over magnesium sulfate and concentrated. The concentrate was chromatographed on silica gel (100 g) and eluted with a mixture of chloroform and methanol (10:1). The eluate was concentrated to dryness to give crystals of di-—Z—DAP(OH)GlyoBzl (2)(2.67 g).

N.M.R. (CDCl₃), δ(ppm): 0.83-2.0 (6H, m), 3.3-4.5 (4H, m), 4.97 (6H, broad s), 5.0-5.6 (2H, m), 5.8-6.6 (2H, m), 7.18 (15H, m).

PREPARATION 16

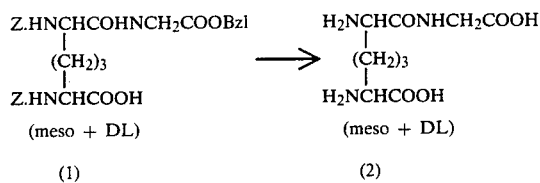

A solution of di—Z—DAP(OH)GlyoBzl (1)(5.1 g) in methanol (80 ml) was hydrogenated over 5% palladium black (2 g). The reaction mixture was filtered and the filtrate was evaporated to give DAP(OH)GlyOH (2)(1.77 g).

N.M.R. (D₂O), δ(ppm): 1.3-2.3 (6H, m), 3.73 (1H, t, J=5.5 Hz), 3.80 (2H, s), 4.00 (1H, t, J=6 Hz).

PREPARATION 17

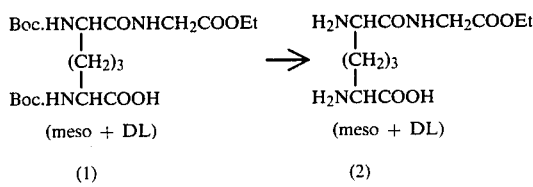

To a solution of di—Boc—DAP(OH)GlyOEt (1)(6.0 g) in ethyl acetate (10 ml) was added 6N hydrochloric acid/ethyl acetate (20 ml) under cooling. The mixture was stirred under cooling for four hours to give crystals. The crystals were collected and washed with ethyl acetate to give DAPGlyOEt-di-hydrochloric acid salt monohydrate (2) (4.18 g).

N.M.R. (D$_2$O), δ(ppm): 1.20 (3H, t, J=7 Hz), 1.1–2.2 (6H, m), 3.8–4.3 (2H, m), 4.11 (2H, s), 4.26 (2H, q, J=7 Hz).

PREPARATION 18

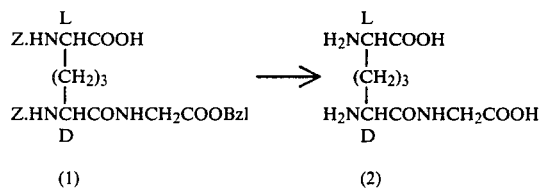

A mixture of di—Z—meso—DAP—GlyoBzl (1)(60 mg) and 10% palladium black (25 mg) in acetic acid (1 ml) was stirred at ambient temperature under hydrogen atmosphere for 4.5 hours. The reaction mixture was filtered through Celite. The filtrate was evaporated to give meso—DAP(D)GlyOH (2) (39 mg).

N.M.R. (D$_2$O), δ(ppm): 1.3–2.3 (6H, m), 3.73 (1H, t, J=5.5 Hz), 3.80 (2H, s), 4.00 (1H, t, J=6 Hz).

PREPARATION 19

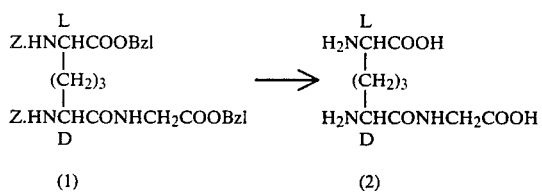

To a solution of di—Z—meso—DAP(L)oBzl—(D-)—GlyoBzl (1) (6.20 g) in acetic acid (100 ml) was added 10% palladium black (1.73 g) and the mixture was stirred at ambient temperature under hydrogen atmosphere for twenty hours. The reaction mixture was filtered and the catalyst was washed with acetic acid. The filtrate and the washing were combined and concentrated. The concentrate was dissolved in a small amount of water and the solution was evaporated to dryness. This operation was repeated twice. The residue was chromatographed on a macroporous non-ionic adsorption resin, HP20 (150 ml) and elution was carried out with water. The desired fraction was evaporated. The residue was dissolved in a small amount of water and lyophilized to give amorphous solid (2.28 g). A 300 mg portion of this amorphous solid was dissolved in water (3 ml) and the solution warmed to 50° C. and then methanol was added thereto until becoming cloudy. Occasional addition of methanol was required for completion of crystallization. The crystals were collected by filtration to give meso—DAP—(D)GlyOH (2)(270 mg). mp 235° C. (dec).

N.M.R. (D$_2$O), δ(ppm): 1.3–2.3 (6H, m), 3.73 (1H, t, J=5.5 Hz), 3.80 (2H, s), 4.00 (1H, t, J=6 Hz),
[α]$_D^{20}$= −60.6 (C=0.507, water).

PREPARATION 20

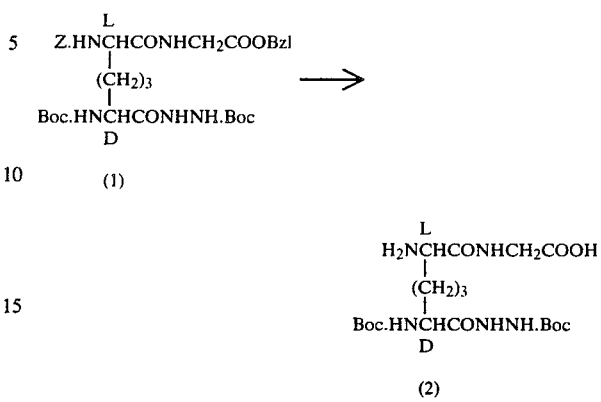

Z—(L)—Boc(D)—meso—DAP(L)—GlyoBzl—(D-)—NHNHBoc (1) (12.0 g) was hydrogenated in a mixture of methanol (100 ml) and acetic acid (2.4 ml) over 10% palladium black (2 g). After completion of the reaction, the catalyst was removed by filtration and the filtrate was evaporated to dryness under reduced pressure. To the residue was added water (30 ml) and the solution was evaporated to dryness. This operation was repeated three times. The residue thus obtained was triturated with ether to give Boc(D)—meso—DAP(L)-GlyOH—(D)—NHNHBoc (2)(7.80 g). mp 130°–138° C. (dec).

N.M.R. (CD$_3$OD), δ(ppm): 1.60 (9H, s), 1.63 (9H, s), 1.7–2.0 (6H, m), 3.92 (2H, s), 3.8–4.1 (2H, m).

PREPARATION 21

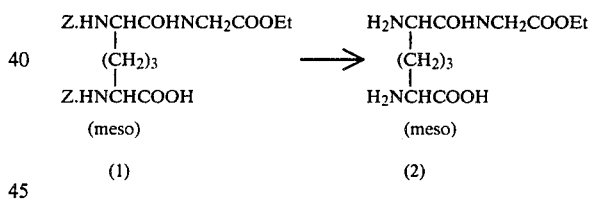

Di—Zmeso—DAP(OH)GlyOEt (1)(9.33 g) was hydrogenated in acetic acid (80 ml) with 10% palladium black (0.93 g) under conditions of two atmospheric pressure of hydrogen. The reaction mixture was filtered and the filtrate was concentrated. Ethyl acetate was added to the concentrate and dried over magnesium sulfate to give meso—DAPGlyOEt acetic acid salt (2) (5.74 g). mp 188°–189° C. (dec.)

N.M.R. (D$_2$O), δ(ppm): 1.44 (3H, t, J=7 Hz), 1.2–2.2 (6H, m), 1.93 (3H, s), 3.76 (1H, t, J=6 Hz), 3.9–4.2 (1H, m), 4.10 (2H, s), 4.20 (2H, q, J=7 Hz).

PREPARATION 22

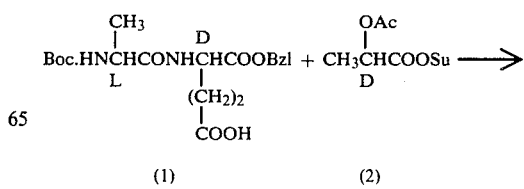

-continued

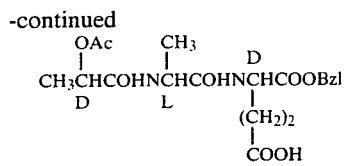

(3)

Boc—L—Ala—D—Glu(α—oBzl) (1) (298 mg) and anisole (0.2 ml) were added to trifluoroacetic acid (1 ml) at 0° C. and the mixture was stirred at the same temperature for two hours. Trifluoroacetic acid was evaporated to dryness and the residue was triturated with ether. The resulting compound was dissolved in water (3 ml) and adjusted to pH 7 with triethylamine and additional 0.1 ml of triethylamine was added to the solution. To the resulting solution was added a solution of Lac(oAc)OSu (2) (167 mg) in dimethylformamide (3 ml) at 0° C. The resulting mixture was stirred overnight at ambient temperature and the reaction mixture was acidified with a diluted aqueous hydrochloric acid and then extracted with ethyl acetate. The extract was washed with water and evaporated to dryness. The residue thus obtained was purified by preparative thin layer chromatography using a pre-coated silica gel plate, developing with a mixture of chloroform and methanol (8:2) to give D—Lac(oAc)—L—Ala—γ—D—Glu(OH)(α—oBzl) (3) (270 mg).

N.M.R. (CD$_3$OD), δ(ppm): 1.40 (3H, d, J=7 Hz), 1.47 (3H, d, J=7 Hz), 2.13 (3H, s), 2.1–2.5 (4H, m), 4.4–5.3 (3H, m), 5.20 (2H, s), 7.40 (5H, s).

PREPARATION 23

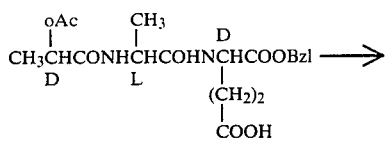

(1)

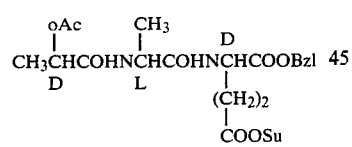

(2)

Dicyclohexylcarbodiimide (32 mg) was added to a mixture of D—Lac(oAc)—L—Ala—D—Glu(α—oBzl)(OH) (1) (65 mg) and N-hydroxysuccinimide (18 mg.) in dioxane (3 ml) at 0° C. The resulting mixture was stirred overnight at ambient temperature and filtered. The filtrate was evaporated to dryness to give D—Lac(oAc)—L—Ala—D—Glu(α—oBzl)(oSu) (2) (80 mg).

PREPARATION 24

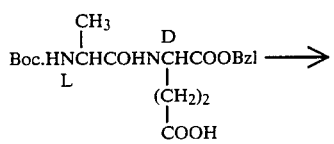

(1)

-continued

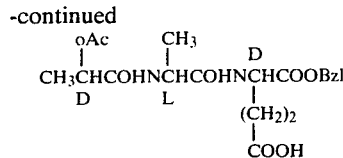

(2)

Boc—L—Ala—D—Glu(α—oBzl)(OH) (1) (65 g) was dissolved in trifluoroacetic acid (260 ml) and the solution was stirred for fifteen minutes at ambient temperature. The solution was evaporated under reduced pressure. The residue thus obtained was dissolved in 50% aqueous acetone (600 ml).

O-acetyl-D-lactic chloride (28.8 g) was added dropwise to the solution while stirring under ice-cooling, maintaining the pH 7-8.

The stirring was continued for an hour at the same temperature and then acetone was evaporated under reduced pressure. The resulting aqueous solution was washed with ethyl acetate (300 ml) and adjusted to pH 2 with 10% aqueous hydrochloric acid. Extraction was carried out twice with ethyl acetate (600 ml and 300 ml). The ethyl acetate layer was washed with saturated aqueous sodium chloride solution and dried over anhydrous magnesium sulfate and then evaporated under reduced pressure to give D—Lac(oAc)—L—Ala—γ—D—Glu(α—oBzl)(OH) (2) (64.7 g).

N.M.R. (CDCl$_3$), δ(ppm): 1.40 (3H, d, J=7 Hz), 1.47 (3H, d, J=7 Hz), 2.13 (3H, s), 2.1–2.5 (4H, m), 4.4–5.3 (3H, m), 5.20 (2H, s), 7.40 (5H, s).

PREPARATION 25

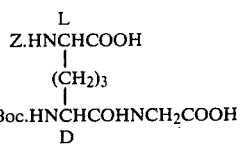

(1)

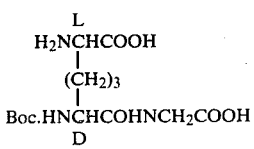

(2)

Z—(L)—Boc—(D)meso—DAP—(D)GlyOH (1) (2.80 g) was hydrogenated in methanol (56 ml) over 10% palladium black (0.82 g) under conditions of ordinary atmospheric pressure of hydrogen at ambient temperature for four hours. To the reaction mixture was added methanol (50 ml) and the resulting mixture was warmed to 40° C. and then filtered. The catalyst was washed well with methanol and filtered. The filtrate and washings were combined and concentrated to give crystals. The crystals was diluted with isopropanol and cooled in a refrigerator and then washed with ether to give —Boc—(D)meso—DAP(D)GlyOH (2) (1.678 g)

N.M.R. (CD$_3$OD+D$_2$O), δ(ppm): 1.3–2.2 (6H, m), 1.40 (9H, s), 3.66 (1H, t, J=5 Hz), 3.7–4.2 (1H, m), 3.88 (2H, s).

[α]$_D^{23}$ = +12.2° (C=0.5, methanol).

PREPARATION 26

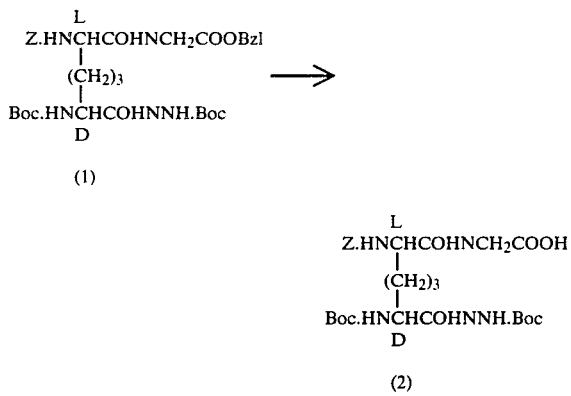

To a solution of Z—(L)—Boc—(D-)—mesoDAP—(D)—NHNHBoc—(L)—GlyoBzl (1) (105 mg) in methanol was added 0.1N aqueous sodium hydroxide (1.5 ml). The mixture was stirred at ambient temperature for two hours and evaporated. The resulting aqueous solution was acidified to pH 2 with 5% aqueous hydrochloric acid and extracted with ethyl acetate. The extract was washed with water, dried over magnesium sulfate and evaporated to give Z—(L-)—Boc—(D)—mesoDAP(D)—NHNHBoc—(L)-GLyOH (2) (85 mg).

N.M.R. (CDCl$_3$), δ(ppm): 1.43 (18H, s), 1.3-2.1 (6H, m), 3.9-4.5 (4H, m), 5.10 (2H, s), 6.2-6.4 (4H, m), 7.10 (1H, broad s), 7.33 (5H, s), 8.95 (1H, broad s).

PREPARATION 27

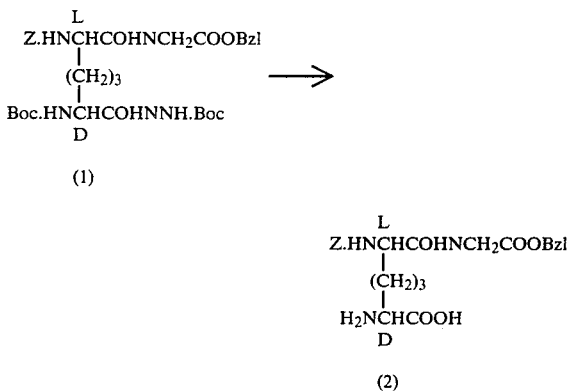

Z—(L)—Boc—(D)—mesoDAP—(D)—NHNH-Boc—(L)—GlyoBzl (1) (2.0 g). was added to trifluoroacetic acid (10 ml) and the mixture was stirred at ambient temperature for 15 minutes. Trifluoroacetic acid was distilled off and the residue was dissolved in 50% aqueous dioxane (30 ml) and then cooled to 0° C. To this solution was added N-bromosuccinimide (1.04 g) and the mixture was stirred at the same temperature for an hour. Dioxane was distilled off and the residue was adjusted to pH 6 with saturated aqueous sodium bicarbonate. The precipitated crystalline solid was filtered and washed with water to give Z—(L-)—mesoDAP—(L)—GlyoBzl (2)(1.15 g).

N.M.R. (DMSO-d$_6$), δ(ppm): 1.2-2.0 (6H, m), 3.8-4.2 (4H, m), 5.05 (2H, s), 5.15 (2H, s), 7.40 (10H, s).

PREPARATION 28

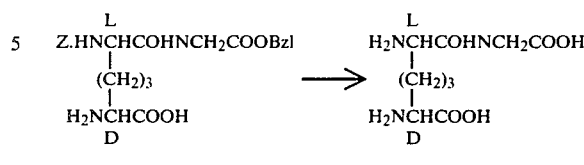

A solution of Z—(L)—mesoDAP—(L)GlyoBzl (1) (100 mg) in a mixture of methanol (10 ml) and water (3 ml) was hydrogenated over 10% palladium-black (50 mg) under an ordinary atmospheric pressure of hydrogen. The reaction mixture was filtered and the filtrate was evaporated. The residue was pulvelized to give mesoADAP—(L)GlyOH (2) (44 mg).

N.M.R. (D$_2$O), δ(ppm): 1.3-2.1 (6H, m), 3.73 (1H, t, J=6 Hz), 3.80 (2H, s), 4.01 (1H, t, J=6 Hz).

PREPARATION 29

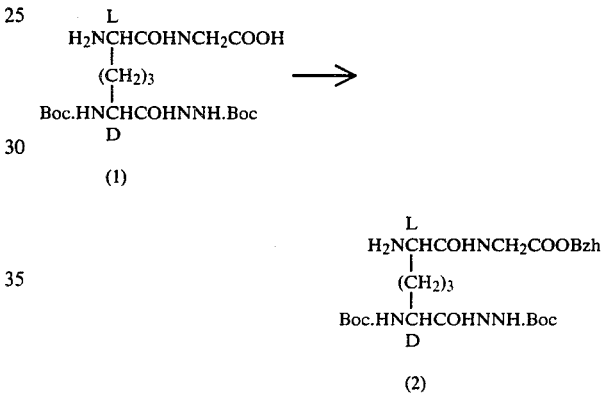

p-Toluenesulfonic acid (monohydrate) (0.56 g) was added to a solution of Boc—(D)—mesoDAP—(D-)—NHNHBoc—(L)—GlyOH (1) (1.39 g). To the mixture was added a solution of diphenyldiazomethane (0.62 g) in methanol (1 ml). The resulting mixture was stirred at ambient temperature for 30 minutes.

To the reaction mixture was added an additional diphenyldiazomethane (0.78 g) until the starting material (1) was disappeared on thin layer chromatography.

An excess of the reagent was distroyed by adding acetic acid and the mixture was adjusted to pH 8 with saturate aqueous sodium bicarbonate and then evaporated. The residue was dissolved in ether (3 ml) and triturated with n-hexane (5 ml). The solvents were removed by decantation. This operation was further repeated twice. The residue was put on a column of silicagel (30 g) and eluted with a mixture of ethyl acetate and methanol (10:1).

The fractions containing the object compound (2) were combined and evaporated to give a solid, which was purified by reprecipitation from a mixture of ether and n-hexane (1:2) to give Boc—(D)—mesoDAP—(D-)—NHNHBoc—(L)—GlyoBzh (2) (1.22 g).

N.M.R. (CDCL$_3$), δ(ppm): 1.33 (18H, s), 1.1-1.8 (6H, m), 3.1-3.5 (1H, m), 3.9-4.3 (3H, m), 5.2-5.5 (1H, m), 6.75 (1H, s), 7.3 (10H, s), 7.6-8.0 (1H, m).

PREPARATION 30

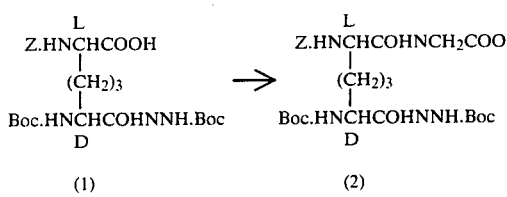

To a mixture of Z—(L)—Boc—(D-)—mesoDAP—(D)—NHNHBoc (1) (1.40 g) and glycine methyl ester hydrochloride (392 mg) in dimethyl formamide (10 ml) were added N-hydroxysuccinimide (0.45 g) and dicyclohexylcarbodiimide (0.645 g) at 0° C., and the resulting mixture was stirred at the same temperature for 30 minutes and at ambient temperature for overnight. The resulting precipitate was filtered off and the filtrate was concentrated. The concentrate was dissolved in ethyl acetate (50 ml) and the solution was washed successively with 0.5N hydrochloric acid, water, 2.5% sodium bicarbonate and water. The organic layer was dried over magnesium sulfate and evaporated to give Z—(L)—Boc—(D)—mesoDAP—(D-)—NHNHBoc—(L)GlyoMe (2) (1.45 g).

N.M.R. (CDCl₃), δ(ppm): 1.40 (18H, s), 1.5-2.0 (6H, m), 3.70 (3H, s), 3.98 (2H, d, J=6 Hz), 4.0-4.5 (2H, m), 5.07 (2H, s), 5.45 (1H, d, J=8 Hz), 5.93 (1H, d, J=8 Hz), 6.83 (1H, broad s), 7.1-7.3 (1H, m), 7.33 (5H, s), 8.63 (1H, broad s).

PREPARATION 31

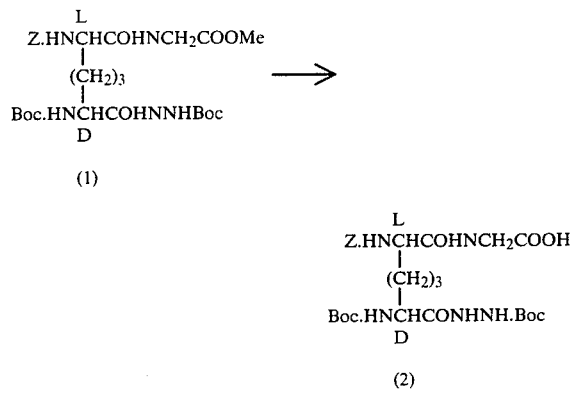

To a solution of Z—(L)—Boc—(D-)—mesoDAP—(D)—NHNHBoc—(L)—GlyOMe (1) (1.41 g) in a mixture of water (14 ml) and methanol (10 ml) was added 1N sodium hydroxide (2.3 ml) at 0° C.

The mixture was stirred at the same temperature for 30 minutes and at ambient temperature for 3.5 hours. Methanol was distilled off and the resulting solution was washed with ethyl acetate. The aqueous layer was adjusted to pH 3 with 5% hydrochloric acid and extracted with ethyl acetate.

The extract was washed with a saturated sodium chloride, dried over magnesium sulfate and then evaporated to give Z—(L)—Boc—(D)—mesoDAP—(D-)—NHNHBoc—(L)—GlyOH (2) (1.24 g).

N.M.R. (CDCl₃), δ(ppm): 1.43 (18H, s), 1.3-2.1 (4H, m), 3.9-4.5 (4H, m), 5.10 (2H, s), 6.2-6.4 (4H, m), 7.10 (1H, broad s), 7.33 (5H, s), 8.95 (1H, broad s).

PREPARATION 32

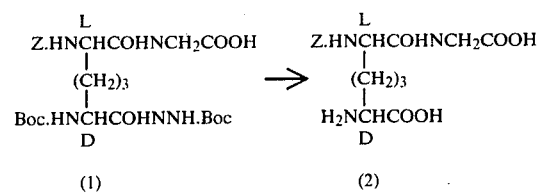

Z—(L)—Boc—(D)—mesoDAP—(D)—NHNH-Boc—(L)—GlyOH (1) (270 mg) was added to trifluoroacetic acid (5) and the mixture was stirred at ambient temperature for 15 minutes.

Trifluoroacetic acid was distilled off and the residue was pulverized with ether. The solvent was removed by decantation and the solid material thus obtained was dissolved in 60% aqueous acetic acid (30 ml) and manganese dioxide (180 mg) was added to the solution. The resulting mixture was stirred at ambient temperature for an hour. The reaction mixture was filtered and the filtrate was evaporated. The seridue was dissolved in water and the solution was evaporated.

The residue was dissolved in 50% ethanol (60 ml) and adjusted to pH 9 with dil. aqueous ammonia and stored in a refrigerator. The solution was treated with an active carbon (30 mg) and filtered. The filtrate was concentrated and the concentrate was dissolved in water (20 ml) and put on a column of carbon (15 ml).

The column was washed with water and eluted with 70% aqueous acetone. The extract was evaporated to give Z—(L)—mesoDAP—(L)—GlyOH (2) (85 mg).

M.p. 210° C. (dec.).

I.R. (Nujol): 3300, 2600-2400 (shoulder), 1710 (shoulder), 1680, 1640 cm⁻¹.

N.M.R. (DMSO-d₆), δ(ppm): 1.10-2.20 (6H, m), 3.30 (1H, m), 3.65 (2H, d, J-7 Hz), 4.00 (1H, m), 5.00 (2H, s), 7.30 (5H, s).

PREPARATION 33

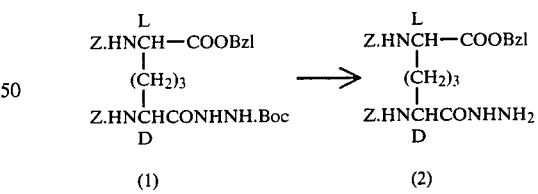

A solution of di—Z—meso—DAP(L)oBzl—(D-)—NHNHBoc (1) (6.68 g) in trifluoroacetic acid (30 ml) was stirred at ambient temperature for twenty minutes. The resulting solution was concentrated and the residue was dissolved in methylenechloride. The solution was evaporated under reduced pressure and the residue was crystallized from ether to give di—Z—meso—DAP(-L)oBzl—(D)—NHNH₂ trifluoroacetic acid salt. (2) (6.627 g). mp 113°-114° C.

N.M.R. (DmSo-d₆) δ(ppm) 1.1-2.0 (6H, m), 3.6-4.3 (2H, m) 5.03 (4H, s), 5.11 (2H, s), 7.33 (15H, s), 7.1-8.4 (6H, m).

PREPARATION 34

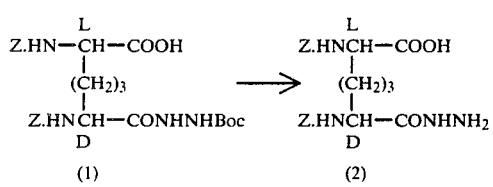

A mixture of di—Z—meso—DAP(D)—NHNHBoc (1) (6.41 g) and anisole (3 ml) in trifluoroacetic acid (17 ml) was stirred at 0° C. for 1.5 hours. The reaction mixture was concentrated under reducing pressure and ether (50 ml) was added to the concentrate. The ether solution was triturated to give precipitates. The precipitates were washed twice with ether and pumped to give di—Z—meso—DAP(D)NHNH$_2$ trifluoroacetic acid salt. (2) (7.0 g).

N.M.R. (CD$_3$OD) δ(ppm): 1.2–2.1 (6H, m), 3.9–4.5 (2H, m), 5.05 (4H, s), 7.25 (10H, s).

PREPARATION 35

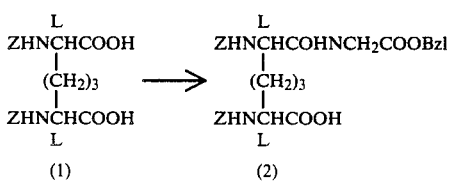

To a mixture of di—Z—L—DAP (1) (4.59 g) and N-methylmorpholine (2.2 ml) in methylene chloride (50 ml) was added iso-butoxycarbonyl chloride (1.69 ml) at −20° C. and the mixture was stirred at −10° C.∼−15° C. for 30 minutes. The reaction mixture was cooled to −30° C. and a mixture of H-GlyoBzl p-toluenesulfonate (4.38 g) and N-methylmorpholine (1.43 ml) in methylene chloride (25 ml) was added thereto. The mixture was stirred at −10° C. for an hour and then allowed to warm to ambient temperature. The reaction mixture was concentrated and the concentrate was poured into a mixture of ethyl acetate and dil. hydrochloric acid. Insoluble materials were filtered off and the organic layer was separated and washed successively with dil. sodium bicarbonate, dil. hydrochloric acid, water and brine. During this operation, crystals were separated out which was collected by filtration to give di-—Z—L—DAP—mono—GlyoBzl (2) (0.79 g). The filtrate was dried over magnesium sulfate and evaporated. The residue was combined with the insoluble materials described above and then recrystallized from ethyl acetate to give additional di-—Z—L—DAP—mono—GlyoBzl (2) (2.55 g).

N.M.R. (DmSo-d$_6$): 1.1–1.9 (6H, m), 3.89 (2H, broad d, J=5 Hz), 3.7–4.4 (2H, m), 5.00 (4H, s), 5.10 (2H, s), 7.1–7.6 (2H, m), 7.32 (15H, s), 8.31 (1H, t, J=5 Hz).

PREPARATION 36

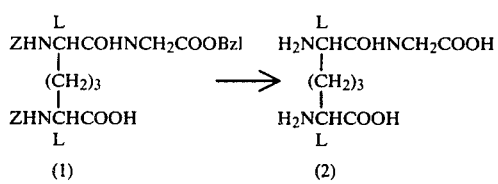

Di—Z—L—DAP—mono—GlyoBzl (1) (3.12 g) was dissolved in a mixture of methanol (10 ml) and acetic acid (60 ml) by warming. To the solution was added 10% palladium black (850 mg) and the mixture was stirred under an atmospheric pressure of hydrogen overnight, during which time an white precipitate was appeared. The catalyst and the precipitate were collected by filtration and the filter cake was washed with 50% aqueous acetic acid and water. The filtrate and the washings were combined and evaporated. The residue was dissolved in water and the solution was evaporated in order to remove acetic acid. This operation was repeated twice and the residue was triturated with hot water and then methanol was added thereto. The suspension was cooled in a refrigerator and the resulting precipitate was filtered and washed with methanol and ether to give L—DAP—monoGlyOH (2) (1.295 g).

I.R. (Nujol): 1660, 1640 (shoulder), 1590 (broad), 1530 cm$^{-1}$.

N.M.R. (D$_2$O) δ(ppm): 1.2–2.3 (6H, m), 3.5–4.3 (2H, m), 3.87 (2H, s).

PREPARATION 37

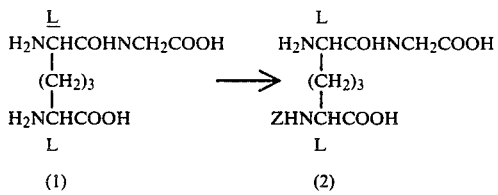

To a mixture of L—DAP—monoGlyOH (1) (1.25 g) and cupric chloride (dihydrate (1) (0.86 g) in water (120 ml) were added 3N sodium hydroxide (5.5 ml) and carbobenzyloxy chloride (3.6 ml) at 5° C. The mixture was stirred at 5° C. for 4.25 hours, during which time the pH of the reaction mixture was kept at 11–11.5 by adding 3N sodium hydroxide.

To the reaction mixture was added an additional carbobenzyloxy chloride (1.08 ml) and the resulting mixture was stirred at the same temperature for 6 hours, maintaining pH 11–11.5 with 3N sodium hydroxide. Another portion of carbobenzyloxy chloride (1.08 ml) was added to the reaction mixture and the resulting mixture was stirred at 5° C. for 2.5 hours, keeping the pH at 11–11.5. The reaction mixture was acidified to pH 2 with dil. hydrochloric acid and washed twice with ether. The aqueous layer was adjusted to pH 4.5 with dil. sodium hydrochloride and then hydrogen sulfide gas was bubbled at 5° C. The resulting precipitate was filtered off and the filtrate was concentrated to 50 ml. The concentrate was adjusted to pH 2 and chromatographed on a column of a macroporous non-ionic adsorption resin, HP 20 (70 ml). Fractions eluted with 50% aqueous methanol were collected and evaporated. The residue was triturated with ether containing a small amount of methanol to give Z—(α)—L—DAP—(ε)—GlyOH (2) (1.30 g).

N.M.R. (D₂O), δ(ppm): 1.2-2.2 (6H, m), 3.88 (2H, d, J=2.5 Hz), 3.8-4.3 (2H, m), 5.10 (2H, s), 7.43 (5H, s).

PREPARATION 38

(1) Step 1

```
         D
H₂NCHCOOBzl
    |
   (CH₂)₂        + BocHNCH₂COOSu  ⟶
    |
   COOH
    (1)              (2)
```

```
              D
BocHNCH₂COHNCHCOOBzl
              |
             (CH₂)₂
              |
             COOH
              (3)
```

D—Glu(α—oBzl) (1) (4.74 g) was dissolved in a mixture of dioxane (60 ml) and water (60 ml) containing triethylamine (2.02 g). To this solution was added Boc—Gly—N—Su (2) (5.16 g), and the mixture was allowed to stand overnight at ambient temperature. The resulting reaction mixture was evaporated to give an oily residue which was dissolved in ethyl acetate and then washed with water. The organic layer was dried over magnesium sulfate and evaporated. to give an oily residue (5.40 g). Analytical sample of the compound (3) was purified as dicyclohexylamine salt which was recrystallized from ethyl acetate-diisopropyl ether to give dicyclohexylamine salt of Boc—Gly—D—Glu(α—oBzl). mp 127°-129° C.

N.M.R. (CDCl₃), δ(ppm): 1.40 (9H, s), 0.84-2.40 (24H, m), 2.92 (2H, m), 3.80 (2H, d, J=7 Hz), 4.08 (1H, q, J=7 Hz), 4.48 (1H, m), 5.12 (2H, s), 5.64 (1H, m), 7.32 (5H, s), 8.54 (1H, d, J=7 Hz), 9.18 (1H, s).

(2) Step 2

```
               OAc
                |              D
               CH₃CHCONHCH₂COHNCHCOOBzl
Compound (3) ⟶ D              |
                              (CH₂)₂
                               |
                              COOH
                               (4)
```

Boc—Gly—D—Glu(α—oBzl) (3) (4.30 g) was dissolved in trifluoroacetic acid (20 ml) and the solution was kept at ambient temperature for 30 minutes. Evaporation of the solvent under reduced pressure gave an oily residue, to which toluene was added and evaporated in vacuo. The resulting oily residue was dissolved in 50% aqueous acetone (20 ml) and the solution was adjusted to pH 7.0-8.0 by adding saturated sodium bicarbonate solution. To this stirred solution cooled in an ice-bath, was added dropwise acetyl-D-lactyl chloride (1.97 g) and the mixture was stirred at the same temperature for an hour. The reaction mixture was extracted with ethyl acetate and the aqueous layer was treated with conc.hydrochloric acid to adjust the pH to 3.0. The aqueous layer was extracted with ethyl acetate and the organic layer was washed with water, dried over magnesium sulfate and evaporated to give an oily residue (2.8 g). The residue was purified as dicyclohexylamine salt which was recrystallized from ethyl acetate-diisopropyl ether to give D—Lac(oAc)—Gly—D—Glu(α—oBzl) (4) (2.1 g). mp 117°-118° C.

N.M.R. (CDCl₃), δ(ppm): 0.80-2.52 (24H, m), 1.48 (3H, d, J=7 Hz), 2.14 (3H, s), 2.96 (2H, m), 3.96 (2H, d, J=7 Hz), 4.46 (1H, q, J=7 Hz), 5.16 (2H, s), 5.20 (1H, q, J=7 Hz), 7.32 (5H, s), 8.92-9.28 (3H, m).

The following compounds were prepared in substantially the same manner as that of Steps 1 and 2 of Preparation 38.

PREPARATION 39

(1) Step 1

Dicyclohexylamine salt of Boc—L—Val—D—Glu(α—oBzl) mp. 130° C.

N.M.R. (CDCl₃), δ(ppm): 0.91 (3H, d, J=7 Hz), 0.94 (3H, d, J=7 Hz), 1.0-2.60 (25H, m), 2.96 (2H), 4.00 (1H, m), 4.44 (1H, m), 5.14 (2H, s), 5.36 (1H, m), 7.24 (1H, m), 7.32 (5H, s), 8.54 (1H), 9.38 (1H, s).

(2) Step 2

Dicyclohexylamine salt of D—Lac(oAc)—L—Val—D—Glu(α—oBzl). mp. 121°-122° C.

N.M.R. (CDCl₃), δ(ppm): 0.91 (3H, d, J=7 Hz), 0.94 (3H, d, J=7 Hz), 1.00-2.60 (25H, m), 1.46 (3H, d, J=7 Hz), 2.14 (3H, s), 3.00 (2H, m), 4.28-4.60 (2H, m), 5.16 (2H, s), 5.20 7.00 (1H, d, J=7 Hz), 7.32 (5H, s), 9.04 (1H, d, J=7 Hz), 9.28 (1H, s)

PREPARATION 40

(1) Step 1

Boc—L—Ser(oBzl)—D—Glu(α—oBzl). mp 84°-85° C.

N.M.R. (CDCl₃), δ(ppm): 1.44 (9H, s), 1.76-2.48 (4H, m), 3.60, 3.65 (2H, doublet of AB quartet, J=4 Hz, 7 Hz), 4.36 (1H), 4.52 (2H, s), 4.68 (1H), 5.16 (2H, s), 5.56 (1H), 7.28 (5H, s), 7.32 (5H, s), 7.04-7.40 (1H, m), 9.62 (1H, broad s).

(2) Step 2

Dicyclohexylamine salt of D—Lac(oAc)—L—Ser(oBzl)—D—Glu(α—oBzl). mp 124°-125° C.

N.M.R. (CDCl₃), δ(ppm): 1.00-2.40 (24H, m), 1.46 (3H, d, J=7 Hz), 2.12 (3H, s), 2.92 (2H, m), 3.62, 3.88 (2H, doublet of AB quartet, J=4 Hz, 10 Hz), 4.40-4.72 (2H, m), 4.52 (2H, s), 5.16 (2H, s), 5.17 (1H, q, J=7 Hz), 7.12 (1H, d, J=7 Hz), 7.28 (5H, s), 7.32 (5H, s), 8.44 (1H, d, J=7 Hz), 8.56 (1H, broad s).

PREPARATION 41

(1) Step 1

Boc—L—Phe—D—Glu(α—oBzl). mp 131° C.

N.M.R. (DMSO-d₆), δ(ppm): 1.30 (9H, s), 1.60-2.33 (4H, m), 2.67-3.0 (2H, m), 3.90-4.66 (2H, m), 5.13 (2H, s), 7.21 (5H, s), 7.33 (5H, s), 8.30 (1H, d, J=7 Hz).

(2) Step 2

D—Lac(oAc)—L—Phe—D—Glu(α—oBzl). mp 148°-150° C. (dec.)

N.M.R. (DMSO-d₆), δ (ppm): 1.13 (3H, d, J=7 Hz), 2.00 (3H, s), 1.80-2.40 (4H, m), 2.67-3.30 (2H, m), 4.20-4.83 (2H, m), 4.91 (1H, q, 7 Hz), 5.17 (2H, s), 7.23 (5H, s), 7.36 (5H, s), 8.25 (2H, t, J=7 Hz).

PREPARATION 42

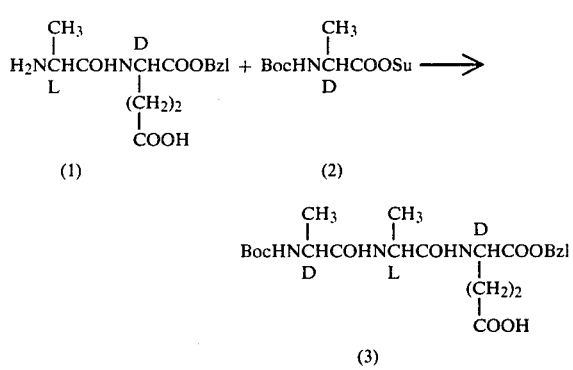

To a solution of L—Ala—D—Glu(α—oBzl) (1) hydrochloric acid salt (5.40 g) in 50% aqueous dioxane (100 ml) were added triethylamine (3.16 g) and Boc—D—AlaoSu (4.48 g), and the mixture was stirred overnight at ambient temperature. After evaporation of dioxane, the aqueous layer was acidified to pH 1 with dil hydrochloric acid and extracted with ethyl acetate. The extract was washed with water, dried over magnesium sulfate and evaporated. The residue was crystallized from a mixture of ethyl acetate and ether and filtered to give Boc—D—Ala—L—Ala—D—Glu(α—oBzl) (3) (6.90 g).

N.M.R. (acetone-d$_6$), δ(ppm): 1.32 (6H, d, J=7 Hz), 1.40 (9H, s), 2.09–2.54 (4H, m), 3.88–4.72 (3H, m), 5.15 (2H, s), 6.17 (1H, d, J=7 Hz), 7.37 (5H, s), 7.34–7.67 (2H, m).

PREPARATION 43

(1) Step 1

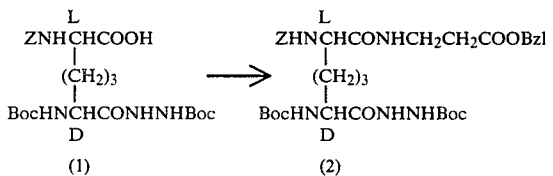

To a solution of Z—(L)—Boc—(D)—mesoDAP (D)—NHNHBoc (2) (1.50 g.) and N-methylmorpholine (0.32 ml.) in methylenechloride (15 ml.) was added isobutyl chlorocarbonate (0.375 ml.) at −25° C. After stirring at −15° C. for 30 minutes, the solution was cooled to −45° C. To the resulting solution were added a solution of B—AlaOBzl. P-toluenesulfonate (1.075 g.) and N-methylmorpholine (0.34 ml.) in methylenechloride-dimethylformamide (10 ml.-1 ml.). The reaction mixture was stirred at −15° C.--10° C. for an hour, allowed to warm to ambient temperature and then concentrated. The concentrate was taken up into ethyl acetate (600 ml.) and washed in turn with dil hydrochloric acid, water (×2), dil sodiumbicarbonate, water and brine. The concentrate was dried over magnesium sulfate and the solvent was distilled off to give Z—(L-)—Boc—(D)—meso DAP—(L)—β—AlaOBzl—(D-)—NHNHBoc (2) (2.00 g.).

N.M.R. (DMSO-d$_6$), δ (ppm): 1.1–1.9 (6H, m), 3.1–3.5 (2H, m), 3.7–4.1 (2H, m), 4.98 (2H, s), 5.06 (2H, s), 6.5–6.8 (1H, m), 7.3 (1H, m), 7.95 (1H, m), 8.66 (1H, broad s), 9.53 (1H, broad s).

(2) Step 2

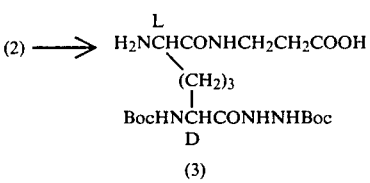

A suspension of 10% of palladium-carbon (0.50 g.) in water (5 ml.) was added to a solution of compound (2) (1.95 g.) in methanol (40 ml.). The mixture was stirred under hydrogen atmosphere. The reaction mixture was filtered and the filtrate was concentrated. Water was coevaporated with ethanol to give an amorphous solid. Trituration with ether and filtration gave Boc (D) mesoDAP—(L)—β—AlaOH—(D)—NHNHBoc (3) (1.25 g.).

N.M.R. (D$_2$O), δ (ppm): 1.0–2.2 (6H, m), 1.45 (18H, s), 2.41 (2H, t, J=7 Hz), 3.47 (2H, t, J=7 Hz), 3.7–4.2 (2H, m).

The following compounds were prepared in substantially the same manner as steps 1 and 2 of Preparation 43.

PREPARATION 44

(2) Step 1

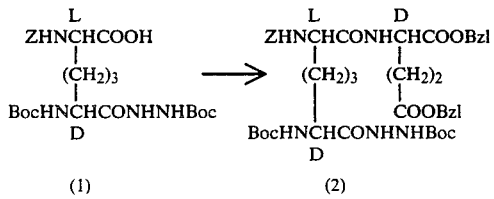

N.M.R. (DMSO-d$_6$), δ (ppm): 1.1–2.5 (10H, m), 1.35 (18H, s), 3.5–4.6 (3H, m), 4.97 (2H, s), 5.01 (2H, s), 5.07 (2H, s), 6.6–6.8 (1H, m), 7.30 (15H, s), 7.7–8.8 (2H, m).

(2) Step 2

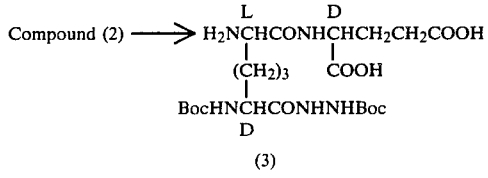

N.M.R. (D$_2$O), δ(ppm): 0.6–2.6 (28H, m), 3.5–4.4 (3H, m).

PREPARATION 45

(1) Step 1

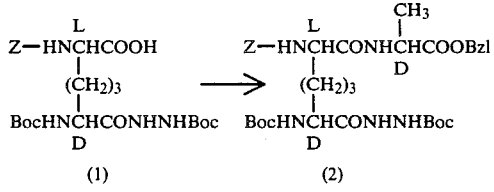

N.M.R. (DMSO-d$_6$), δ (ppm): 1.33 (18H, s), 1.25–2.00 (9H, m), 3.66–4.50 (3H, m), 5.02 (2H, s), 5.11 (2H, s), 7.33 (10H, s).

(2) Step 2

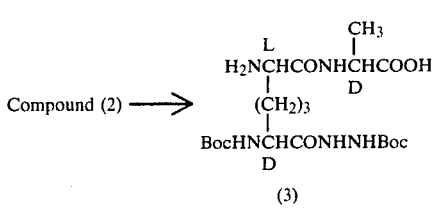

N.M.R. (D₂O), δ (ppm): 1.50 (18H, s), 1.15–2.15 (9H, m), 3.83–4.33 (3H, m).

PREPARATION 46

(1) Step 1

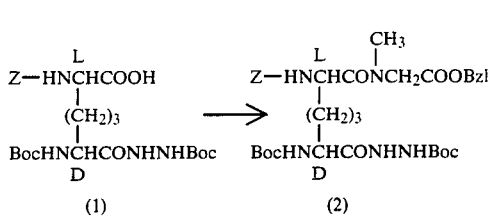

I.R. (Nujol): 3270, 1695 (broad), 1640 cm⁻¹.

(2) Step 2

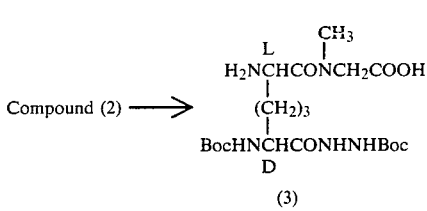

N.M.R. (D₂O), δ (ppm): 1.2–2.2 (6H, m), 1.41 (18H, s), 2.93 and 3.10 (3H, a pair of singlets), 3.5–4.5 (4H, m).

PREPARATION 47

(1) Step 1

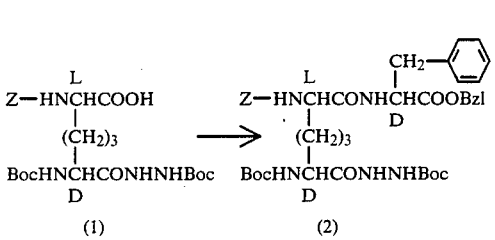

N.M.R. (DMSO), δ (ppm): 1.0–1.9 (6H, m), 1.37 (18H, s), 2.8–3.2 (2H, m), 3.5–4.3 (2H, m), 4.3–4.8 (1H, m), 4.99 (2H, s), 5.08 (2H, s), 6.4–6.8 (1H, m), 7.1 (1H, m), 7.15 (5H, s), 7.28 (10H, m), 8.28 (1H, broad d, J=7 Hz), 8.4–8.8 (1H, m), 9.50 (1H, broad s).

(2) Step 2

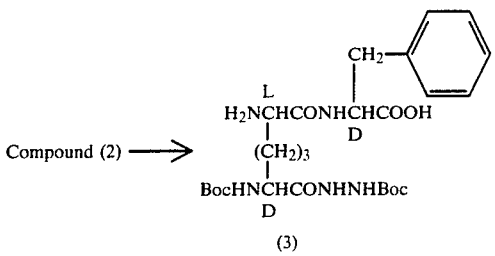

N.M.R. (D₂O), δ (ppm): 0.8–2.0 (6H, m), 1.53 (18H, s), 2.5–4.2 (5H, m), 7.41 (5H, s).

PREPARATION 48

(1) Step 1

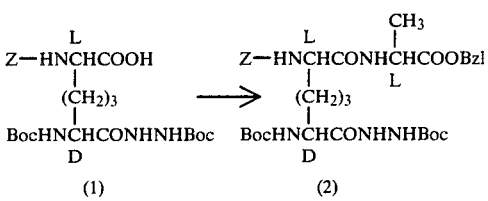

N.M.R. (DMSO-d₆), (ppm): 1.0–2.0 (9H, m) 1.42 (18H, s), 3.7–4.7 (3H, m), 5.05 (2H, s), 5.15 (2H, s), 6.6–7.0 (1H, s), 7.1–7.8 (1H, m), 7.38 (10H, s), 8.40 (1H, broad s, J-7 Hz), 8.5–8.9 (1H, m), 9.65 (1H, broad s).

(2) Step 2

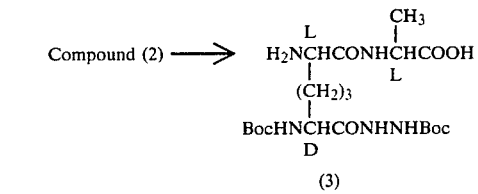

N.M.R. (CD₃OD-D₂O), δ(ppm): 1.38 (3H, d, J=7 Hz), 1.44 (9H, s), 1.46 (9H, s), 1.1–2.2 (6H, m), 3.8–4.3 (3H, m).

PREPARATION 49

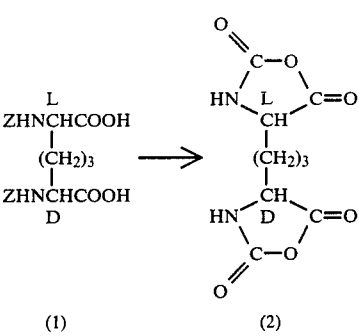

To a cooled solution of di—Z—mesoDAP (1) (3.50 g.) in methylene chloride (70 ml.) was added phosphorus pentachloride (3.50 g.) at 0° C., and the mixture was stirred at the same temperature for 15 minutes. The temperature was raised to ambient temperature and then the mixture was stirred for 15 minutes. The reaction mixture was then warmed to 50° C. and stirred for 20 minutes. After standing for 20 minutes at 0° C., the resulting crystalline solid was filtered and washed with methylene chloride to give mesoDAP—N—carboxylic anhydride (2) (1.68 g.).

I.R. (Nujol): 3250, 1840, 1765 cm⁻¹.

N.M.R. (DMSO-d₆), δ(ppm): 1.2 2.0 (6H, m), 4.43 (2H, t, J=5 Hz), 9.06 (2H, s).

PREPARATION 50

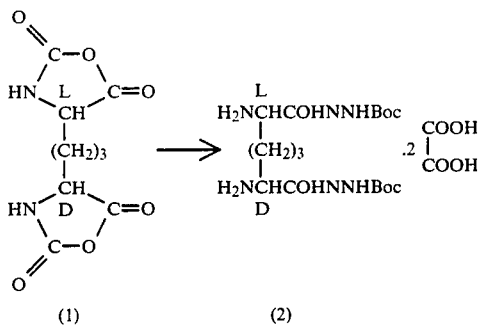

To a cooled mixture of t-butylcarbazate (1.58 g.) and oxalic acid hydrate (1.26 g.) in methanol (7 ml.) was added a solution of mesoDAP N-carboxylic anhydride (1.23 g.) in methyl cyanide (7 ml.). After stirring at 0° C. for 10 minutes, methyl cyanide (7 ml.) was added to the solution and the mixture was stirred at the same temperature for 30 minutes. The resulting crystalline solid was filtered and washed with methyl cyanide to give mesoDAP—di NHNHBoc oxalate (2) (2.66 g.).

I.R. (Nujol): 3600-2200, 1720, 1680, 1610 cm⁻¹.

N.M.R. (D₂O), δ(ppm): 1.47 (18H, s), 1.3 2.3 (6H, m), 4.10 (2H, t, J=6 Hz).

PREPARATION 51

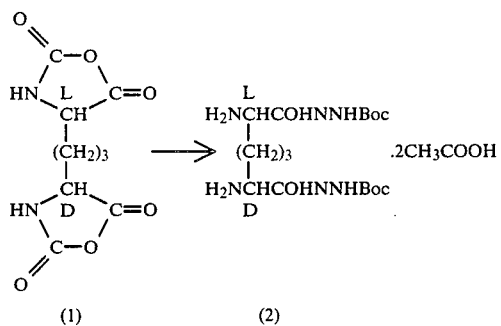

MesoDAP di—NHNH Boc acetate (2) was prepared from mesoDAP N-carboxylic anhydride (1) in substantially the same manner as that of Preparation 50.

N.M.R. (D₂O), δ(ppm): 1.52 (18H, s), 1.95 (6H, s), 1.4-2.3 (6H, m), 4.08 (2H, t, J=7 Hz).

PREPARATION 52

(1) Step 1

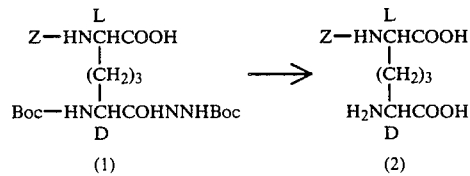

Z—(L)—Boc—(D)—mesoDAP—(D)—NHNHBoc (1) (2.26 g) was added to trifluoroacetic acid (6 ml) and stirred for 15 minutes at room temperature. After evaporation of trifluoroacetic acid, the resulting oily residue was dissolved in 0.1N sulfuric acid (42 ml) and cooled in an icebath. To this solution was added a solution of sodium periodate (1.078 g) in water (15 ml) and the mixture was stirred for 1 hour at the same temperature. The reaction mixture was treated with an aqueous solution of sodium bisulfite until the dark color was clear. After adjusting the pH of the solution to 7.0, the solution was concentrated to about 10 ml and the pH was adjusted to 2.0. This solution was applied to a column of a macroporous nonionic adsorption resin, HP-20 (100 ml), which was eluted with water and then with water-methanol (3:2). Evaporation of the latter fractions gave Z—(L)—mesoDAP (2) (1.0 g) as a white crystalline residue.

m.p. ~245° C. (dec).

I.R. (Nujol): 3500, 3350, 3200, ~2600 (broad), 1690 cm⁻¹.

N.M.R. (DMSO-d₆): δ (ppm): 1.16~2.0 (6H, m), 3.30 (1H, broad signal), 3.90 (1H, broad signal), 5.00 (2H, s), 7.33 (5H, s).

(2) Step 2

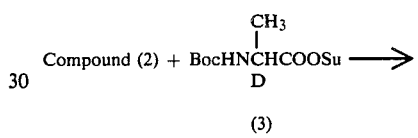

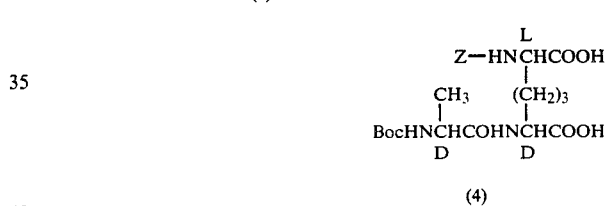

To a mixture of Z—(L)—mesoDAP (2) (1.50 g) and triethylamine (1.0 g) in aqueous dioxane (dioxane 30 ml and water 20 ml) was added Boc—D—Ala—OSu (3) (1.32 g) and the mixture was allowed to stand overnight at room temperature. Dioxane was evaporated, and the resulting aqueous solution was acidified with diluted hydrochloric acid and extracted with ethyl acetate. The extract was washed with water, dried over magnesium sulfate and evaporated to give Boc—D—Ala—(D-)—Z—(L)—mesoDAP (4) (1.90 g) as a white foam.

I.R. (Nujol): 3300, 1700 (broad) cm⁻¹.

N.M.R. (DMSO-d₆), δ (ppm): 1.20~2.0 (18H, m), 3.70-4.40 (3H, m), 5.00 (2H, s), 7.37 (5H, s).

(3) Step 3

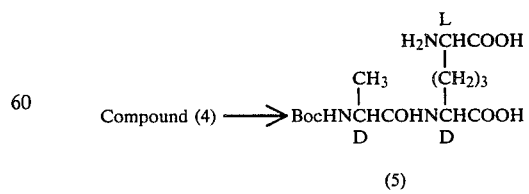

A solution of Boc—D—Ala—(D)—Z—(L-)—mesoDAP (4.1 g.) in acetic acid (40 ml.) was hydrogenated over 10% palladium-charcoal (0.40 g.). The catalyst was removed by filtration and the filtrate was evaporated to give a pasty residue, to which toluene was added and evaporated to give Boc—D—Ala—(D-)—mesoDAP (5) (1.50 g.) as a white powder.

I.R. (Nujol): 3300, 2600~2400 (broad), 1720 1600 (broad) cm$^{-1}$.

N.M.R. (D$_2$O), δ(ppm): 1.17~2.0 (18H, m), 3.30 (1H, broad signal), 3.80~4.30 (2H, m).

PREPARATION 53

(1) Step 1

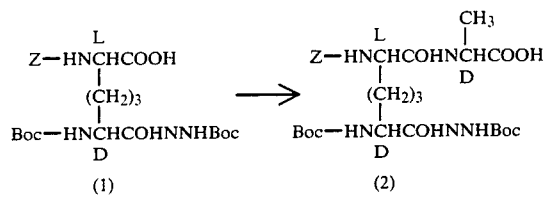

To a suspension of D-alanine (2.89 g) in a mixture of methylene chloride (30 ml) and dimethylformamide (12 ml) was added bis(trimethylsilyl)acetamide (30 ml) and the mixture was stirred for 15 hours at room temperature to give a clear solution. To a solution of the mixed anhydride of Z—(L)—Boc—(D)—mesoDAP—(D-)—NHNHBoc (1) (13.45 g) in methylene chloride (140 ml), prepared by adding N-methylmorphorine (3.03 g) and isobutyl chloroformate (4.10 g) at −15° and stirring the mixture for 40 minutes at the same temperature, was added in one portion the above solution of D-alanine trimethylsilyl ester at −40° C. Then the reaction mixture was allowed to warm up to 0° C. and stirred for 2 hours. The reaction mixture was evaporated and the residue was dissolved in water, acidified with diluted hydrochloric acid and extracted with ethyl acetate. The extract was washed with water, dried over magnesium sulfate and concentrated to give a white powder (12.25 g) of Z—(L)—Boc—(D)—mesoDAP—(D)—NHNH-Boc—(L)—D—AlaOH (2).

I.R. (Nujol): 3300, 2600-2400(broad), 1720-1640(-broad) cm$^{-1}$.

NMR (DMSO-d$_6$), δ(ppm): 1.20-2.00(27H, m), 3.70-4.40 (3H, m), 5.00(2H, s), 7.36(5H, s).

(2) Step 2

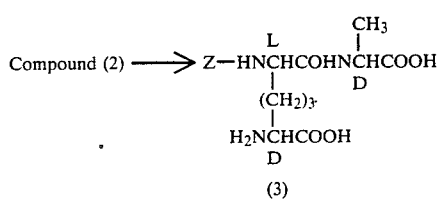

Z—(L)—Boc—(D)—mesoDAP—(D)—NHNH-Boc—(L)—D—AlaOH (2) (14.60 g) was dissolved in trifluoroacetic acid (20 ml) and stirred for 15 minutes at room temperature. Trifluoroacetic acid was removed by evaporation and the residual oil was dissolved in a mixture of 1N sulfuric acid (25 ml) and water (30 ml). The resulting solution was treated with a solution of sodium periodate (5.60 g) in water (20 ml) under cooling in an ice-bath and kept for 1 hour at the same temperature. The reaction mixture was then treated with an aqueous sodium bisulfite solution until the color of the solution became clear. This solution was applied to a column of HP-20, an macroporous non-ionic adsorption resin (300 ml), which was eluted successively with water and methanol-water (1:2). Evaporation of the latter fractions gave a crystalline residue (6.80 g) of Z—(L)—mesoDAP—(L)—D—AlaOH (3).

m.p. ~150° C. (dec).

I.R (Nujol): 3300, 2600-2400(broad), 1720(shoulder), 1700, 1640 cm$^{-1}$.

NMR (DMSO-d$_6$), δ(ppm): 1.30 (3H, d, J=7 Hz), 1.10-2.30 (6H, m), 3.43 (1H, broad s), 3.80-4.50 (2H, m), 5.10 (2H, s), 7.40 (5H, s).

(3) Step 3

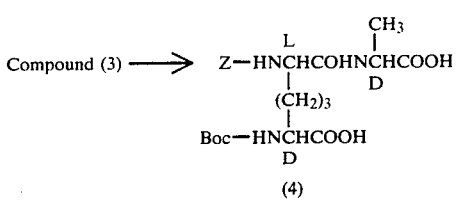

To a mixture of Z—(L)—mesoDAP—(L-)—D—AlaOH (3) (5.70 g) and triethylamine (4.50 g) in water (50 ml) was added a solution 2-t-butoxycarbonyloxyimino-2-phenylacetonitrile (3.55 g) in aceton (50 ml) and the mixture was stirred for 1 hour at room temperature. After standing overnight at the same temperature, the reaction mixture was concentrated and the resulting aqueous solution was washed with ethyl acetate. The aqueous layer was acidified with 1N hydrochloric acid and extracted with ethyl acetate. The extract was washed with water, dried over magnesium sulfate and evaporated to give a white foam (6.0 g) of Z—(L)—Boc—(D)—mesoDAP—(L)—D—AlaOH (4).

I.R. (Nujol): 3300, 2600-2400, 1720-1620 (broad) cm$^{-1}$.

NMR (DMSO-d$_6$), δ(ppm): 1.30-2.0 (18H, m), 3.70-4.3 (3H, m), 5.10 (2H, s), 7.40 (5H, s).

(4) Step 4

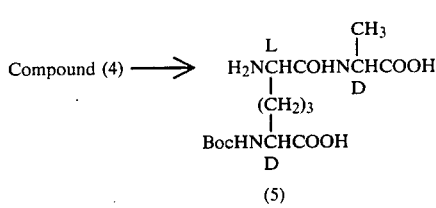

Z—(L)—Boc—(D)—mesoDAP—(L)—D—AlaOH (4) (5.80g) was dissolved in acetic acid (60 ml) and hydrogenated over 10% palladium-charcoal (0.50 g). The catalyst was removed by filtration and the filtrate was evaporated to give an oily residue, which was dissolved in water (30 ml) and applied to a column of HP-20 (150 ml), a macroporous non-ionic adsorption resin. The column was eluted successively with water and methanol-water (3:7). The latter fractions were combined and evaporated to give a white powder (3.80 g) of Boc—(D)—mesoDAP—(L)—D—AlaOH (5).

I.R (Nujol): 3250, 2600-2400 (broad), 1720 (shoulder), 1670 cm$^{-1}$.

NMR (D$_2$O), δ(ppm): 1.20-2.20 (18H, m), 4.00 (2H, t, J=7 Hz), 4.30 (1H, q, J=7 Hz).

PREPARATION 54

(1) Step 1

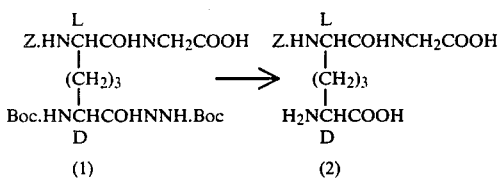

Z—(L)—mesoDAP—(L)—GlyOH(2) was prepared from Z—(L)—Boc—(D)—mesoDAP—(D)—NHNH-Boc—(L)—GlyOH(1) in substantially the same manner as that of preparation 27

M.p. ~210° C. (dec.).

I.R. (Nujol): 3300, 2600-2400(shoulder), 1710 (shoulder), 1680, 1640 cm$^{-1}$.

N.M.R. (DMSO-d$_6$), δ(ppm): 1.10-2.20(6H, m) 3.30 (1H, m), 3.65(2H, d, J=7 Hz), 4.00(1H, m), 5.00(2H, s), 7.30(5H, s).

(2) Step 2

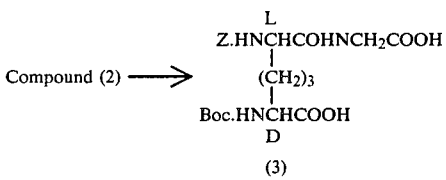

Z—(L)—Boc—(D)—mesoDAP—(L)—GlyOH (3) was prepared from Z—(L)—mesoDAP—(L)—GlyOH (2) in substantially the same manner as preparation 5-1.

N.M.R. (DMSO-d$_6$), δ(ppm): 1.30-2.30(15H, m), 3.80(2H, d, J=7 Hz), 3.80-4.3(2H, m), 5.05(2H, s), 7.40(5H, s).

(3) Step 3

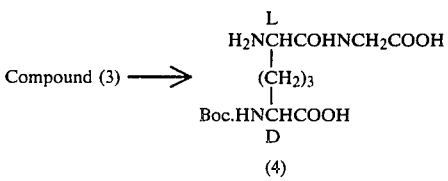

Boc—(D)—mesoDAP—(L)—GlyOH (4) was prepared from Z—(L)—Boc—(D)—mesoDAP—(L)—GlyOH (3) in substantially the same manner as that of Preparation 20.

I.R. (Nujol): 3300, 2600-2400 (broad), 1680 (broad) cm$^{-1}$.

N.M.R. (D$_2$O), δ(ppm): 1.10-2.20 (15H, m), 3.86 (2H, s), 3.80-4.20 (2H, m).

PREPARATION 55

(1) Step 1

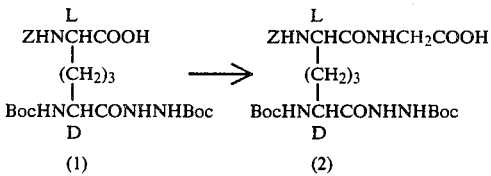

To a solution of Z—(L)—BOC—(D)mesoDAP—(D)—NHNHBoc (1) (5.72 g) and N-methylmorpholine (1.18 g) in methylene chloride (60 ml) was added isobuthylchloroformate (1.60 g) at −10° to −15° C., and the mixture was stirred at the same temperature for an hour. To the reaction mixture was added a solution of glycine trimethylsilyl ester (0.96 g) was added and stirred for 1.5 hours at −10° to −15° C. Methylene chloride was removed in vacuo, and the residue was dissolved in a mixture of ethyl acetate (60 ml) and 2.5% hydrochloric acid. The organic layer was washed with 2.5% hydrochloric acid (50 ml) and water (50 ml) and dried over magnesium sulfate. The solvent was removed in vacuo and the residue was triturated successively with ethyl acetate (10 ml) and isopropylether (120 ml) and the precipitate was filtered and washed with isopropylether to give Z—(L)—Boc—(D)—mesoDAP—(D)—NHNHBoc—(L)—GlyOH (2)(6.1 g).

NMR (CDCl$_3$), δ(ppm): 1.43 (18H, s), 1.3-2.1 (6H, m), 3.9-4.5 (4H, m), 5.10 (2H, s), 6.2-6.4 (4H, m), 7.10 (1H, broad s), 7.33 (5H, s), 8.95 (1H, broad s).

(2) Step 2

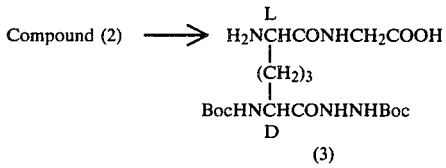

Boc(D)—mesoDAP(L)GlyOH—D—NHNHBoc (3) was obtained in substantially the same manner as that of Preparation 20.

NMR (CD$_3$OD), δ(ppm): 1.60 (9H, s), 1.63 (9H, s), 1.7-2.0 (6H, m), 3.92 (2H, s), 3.8-4.1 (2H, m).

PREPARATION 56

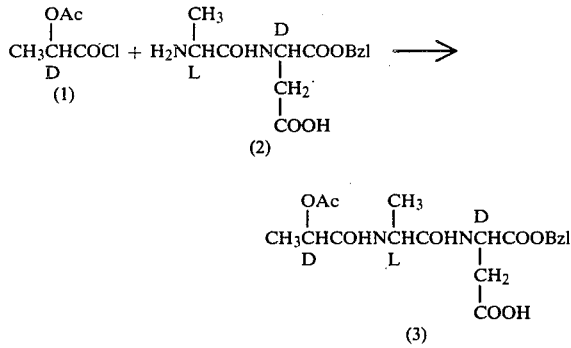

D—Lac(OAc)—L—Ala—D—Asp(OH)OBzl (3) was prepared from L—Ala—D—Asp(OH)OBzl (2) and acetyl—D—lactyl chloride (1) in substantially the same manner as that of Preparation 22.

m.p. 109°-111° C. (dec.).

I.R. (Nujol): 3400, 3300, 1740, 1720, 1670 1550, 1520 cm$^{-1}$.

NMR (CDCl$_3$), δ(ppm): 1.36 (3H, d, J=7 Hz), 1.45 (3H, d, J=7 Hz), 2.15 (3H, s), 3.00 (2H, m), 4.4-5.4 (3H, m), 5.20 (2H, s), 7.16 (1H, d, J=8 Hz), 7.33 (5H, s), 7.60 (2H, d, J=8 Hz), 8.56 (1H, s).

PREPARATION 57

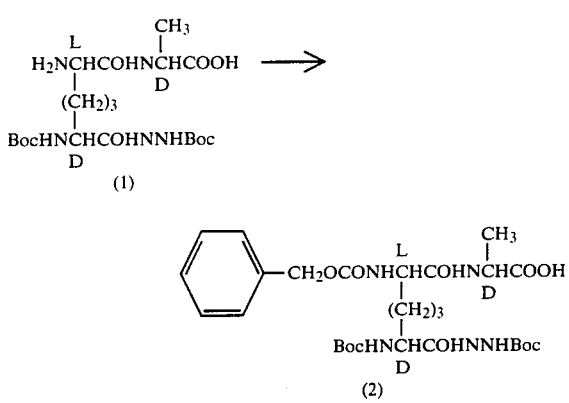

Boc—(D)—mesoDAP—(D)—NHNHBoc—(L-)—D—Ala (1) (14.60 g) was dissolved in a mixture of acetone (60 ml) and water (60 ml). The pH of the solution was adjusted to about 8.0 with sodiumbicarbonate. The solution was stirred and cooled, and carbobenzyloxy chloride (5.30 g) was added thereto. The mixture was reacted for an hour at the same temperature. Removal of acetone under reduced pressure gave an aqueous layer which was acidified with 1N hydrochloric acid and extracted with ethyl acetate. The organic layer was washed with water, dried over magnesium sulfate and evaporated to give Z—(L)—Boc—(D-)—MesoDAP—(D)—NHNHBoc—(L)—D—Ala (2) (14.60 g).

NMR (DMSO-$d_6$), $\delta$(ppm): 1.0–2.0 (27H, m), 3.70–4.50 (3H, m), 5.03 (2H, s), 6.70 (1H, d, J=7 Hz), 7.20 (1H, broad), 7.33 (5H, s), 8.10 (1H, d, J=7 Hz), 8.63 (1H, s), 9.63 (1H, s).

PREPARATION 58

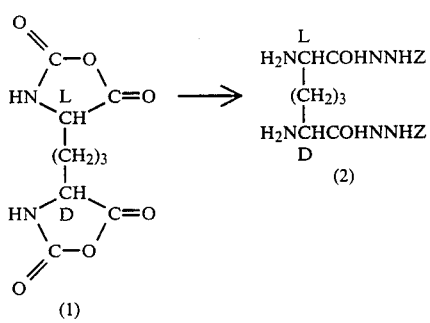

A solution of mesoDAP N-carboxyanhydride (1) (17.0 g) in acetonitrile (130 ml) was cooled to 10° C. and a solution of carbobenzyloxyhydrazine (24.0 g) in acetic acid (80 ml) was added. The mixture was stirred for 30 minutes at the same temperature. After concentration of the reaction mixture, the resulting residue was pulverized with ether to give mesoDAP—di—NHNHZ. 2ACOH (2) (40.3 g)

m.p. 65°–70° C.

I.R. (Nujol): 3600–2200, 1700 cm$^{-1}$.

NMR (CD$_3$OD) $\delta$ 1.5–1.9 (6H, m), 1.92 (6H, s), 3.70 (2H, t, J=5 Hz), 5.13 (4H, s), 7.38 (10H, s).

Acetic acid salt of mesoDAP—di—NHNHZ was dissolved in water and neutralized with 1N sodium hydroxide and then the resulting oil was crystallized from water to give mesoDAP—di—NHNHZ.

m.p. 93°–95° C.

I.R. (Nujol): 3260, 1750, 1720, 1660 cm$^{-1}$.

NMR (CD$_3$OD), $\delta$1.5–1.8 (6H, m), 3.30 (2H, m), 5.13 (4H, s), 7.35 (10H, s).

PREPARATION 59

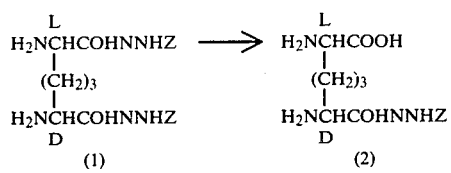

A solution of mesoDAP—di—NHNHZ (1) (40.2 g) in a mixture of water (1.2 l) and acetonitril (0.6 l) was adjusted to pH 8.5 with 1N sodium hydroxide. To this solution was added leucine amino peptidase (from hog kidney) (Boehringer Manheim GmbH) (20 mg) and the mixture was shaken for 6 hours at 37° C. After evaporation of methanol, the resulting aqueous layer was washed with ethyl acetate and concentrated to about 200 ml. The concentrate was applied to a column of HP-20 resin (800 ml). The column was washed with water and eluted with 50% aqueous methanol. The eluate was evaporated and the residue was pulverized with ether to give mesoDAP—(D)—NHNHZ (2) (15.0 g)

m.p. 205°–209° C. (dec).

I.R. (Nujol): 3600–2200, 1720, 1640, 1580 cm$^{-1}$.

NMR (CD$_3$OD), $\delta$ 1.4–2.1 (6H, m), 3.50 (2H, m), 5.17 L (2H, s), 7.40 (5H, s).

PREPARATION 60

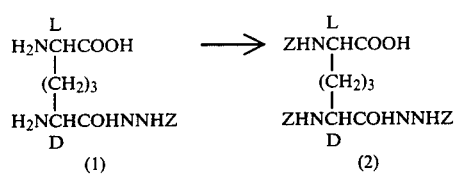

To a suspension of mesoDAP—(D)—NHNHZ (1.40 g) in methylene chloride (30 ml) was added bis(trimethylsilyl)acetamide (6 ml) and the mixture was stirred for 1 hour at room temperature. The resulting solution was cooled to −15° C. and carbobenzyloxy chloride (2.00 g) was added.

After stirring for 1 hour at the same temperature, the mixture was poured into a mixture of ethyl acetate (100 ml) and 2.5% hydrochloric acid (50 ml). The organic layer was separated, washed with saturated aqueous solution of sodium chloride, dried over magnesium sulfate and evaporated. The residue was crystallized from chloroform to give di—Z—mesoDAP—(D-)—NHNHZ (2) (2.20 g)

m.p. 139°–141° C.

I.R. (Nuj 1): 3300, 1740, 1720, 1695, 1660 cm$^{-1}$.

NMR (CD$_3$OD), $\delta$: 1.40–2.0(6H, m), 4.10 (2H, m), 5.10 (6H, s), 7.33 (15H, s).

PREPARATION 61

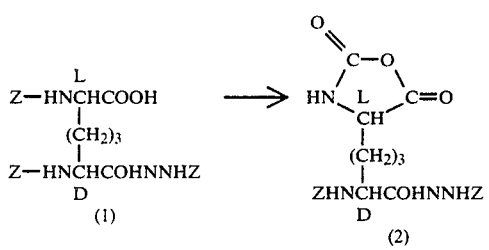

di—Z—mesoDAP—(D)—NHNHZ (1) (0.40 g) was added to thionyl chloride (4 ml) and the mixture was stirred for 30 minutes at room temperature. Evaporation gave Z—(D)—mesoDAP—(D)—NHNHZ—(L-)—N—carboxyanhydride (2) as an oil.

I.R. ($CH_2Cl_2$): 3400, 3270, 1850, 1780, 1700 cm$^{-1}$.

PREPARATION 62

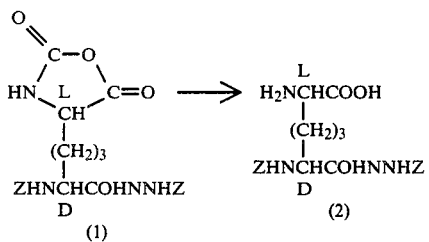

Z—(D)—mesoDAP—(D)—NHNHZ—(L-)—N—carboxyanhydride (1), prepared from 0.40 g of di—Z—mesoDAP—(D)—NHNHZ as described above in Preparation 60, was dissolved in a mixture of acetic acid (4 ml) and 1N hydrochloric acid (2 ml) and the mixture was stirred for 6 hours at room temperature. The reaction mixture was concentrated and the residue was dissolved in water (3 ml) and neutradized with dilute aqueous sodium bicarbonate. The precipitated crrystalline solid was filtered and washed with water to give Z—(D)—mesoDAP(D)—NHNHZ (2) (0.25 g).

m.p. 205°–209° C. (dec).

I.R. (Nujol): 3300, 1715, 1690, 1665, 1605 cm$^{-1}$.

NMR ($CF_3COOH$), δ: 1.6–2.5 (6H, m), 4.43 (2H, m), 5.20 (2H, s), 5.25 (2H, s), 7.38 (10H, s).

PREPARATION 63

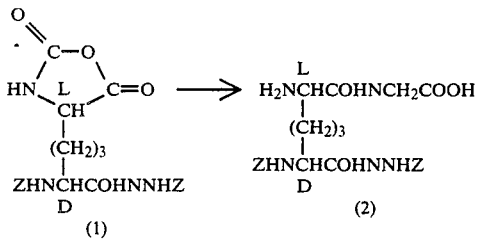

A mixture, of glycine (80 mg) and sodium carbonate (200 mg) in a mixture of 1N sodium hydroxide (1 ml) and water (5 ml) was cooled to −5° C. and a solution of Z—(D)—mesoDAP—(D)—NHNHZ—(L)—N—carboxyanhydride, prepared from di—Z—mesoDAP—(d-)—NHNHZ (1) (602 mg), in acetonitrile (5 ml) was added. The mixture was stirred for 2 hours at the same temperature and overnight at room temperature. The aqueous layer was separated and the organic layer was extracted with 2% aqueous sodium chloride (5 ml). The aqueous layers were combined and neutralized with 1N hydrochloric acid. The precipitated crystalline solid was filtered and washed with water to give Z—(D-)—mesoDAP—(D)—NHNHZ—(L)—GlyOH (2) (120 mg)

m.p. 204°–7° C. (dec).

I.R. (Nujol): 3600–2200, 3250, 1720, 1700, 1690, 1660 cm$^{-1}$.

NMR ($CF_3CO_2H$) δ: 1.5–2.5 (6H, m), 4.0–4.6 (4H, m), 5.30 (4H, s), 7.38 (10H, s).

PREPARATION 64

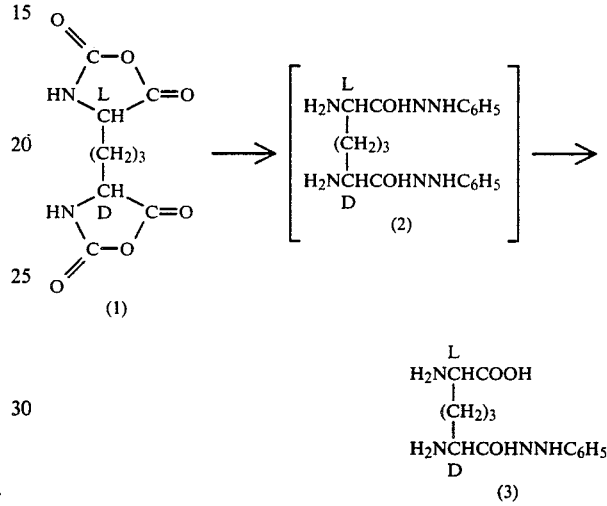

A solution of phenylhydrazine (4.30 g) in acetic acid (10 ml) was cooled to 10° C. and a solution of mesoDAP N-carboxyanhydride (4.80 g) in acetonitrile (35 ml) was added. The mixture was stirred for 1 hour at the same temperture and the solvent was evaporated. The residue was pulverized with ether to give mesoDAP—di—NHNH$C_6H_5$ (acetic acid salt) (2) (10.10 g).

The compound (2) was dissolved in a mixture of water (300 m) and methanol (150 ml) and the pH was adjusted to 8.5. This solution was treated with leucine amino peptidase (from Hog Kidney) (5 mg) at 37° C. for 5 hours. After evaporation of methanol, the resulting aqueous layer was washed with ethyl acetate and concentrated to about 100 ml. The concentrate was applied to a column of HP-20 resin (200 ml). The column was eluted with 50% aqueous methanol. The eluate was evaporated to give mesoDAP—(D)—NHNH$C_6H_5$ (3) (2.50 g).

I.R. (Nujol): 3600–2200, 1640, 1600 cm$^{-1}$.

NMR ($CF_3CO_2H$)δ: 1.9–2.6(6H), 4.0–4.5(2H, m), 7.43 (5H, s).

PREPARATION 65

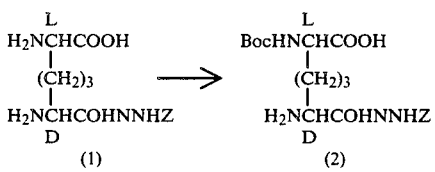

A mixture of mesoDAP—(D)—NHNHZ (1) (3.38 g) and cupric chloride dihydrate (853 mg) in 0.25N sodium hydroxide (50 ml) was cooled to 0° C. and di—t—butyl-dicarbonate (2.83 g) was added. The mixture was stirred for 2 hours at the same temperature, during which time the pH of the reaction mixture was maintained at 9.5-10.0 by adding 1N sodium hydroxide. Hydrogen sulfide was bubbled into the mixture for 10 minutes and the precipitate was filtered off. The filtrate was neutralized to pH 5 with 1N hydrochloric acid and washed with ethyl acetate. The aqueous layer was concentrated to about 10 ml and stood overnight at 5° C. The precipitated crystalline solid was filtered and washed with water to give Boc—(L)—mesoDAP—(D)—NHNHZ (2) (2.92 g).

m.p. 201°-3° C. (dec).

I.R. (Nujol): 3300, 3280, 1725, 1700 cm$^{-1}$.

NMR (CD$_3$OD) δ: 1.40(9H, s) 1.3-2.1(6H, m), 3.8-4.1(2H, m), 5.17 (2H, s), 7.38 (5H, s).

EXAMPLE 1

(1) Step 1

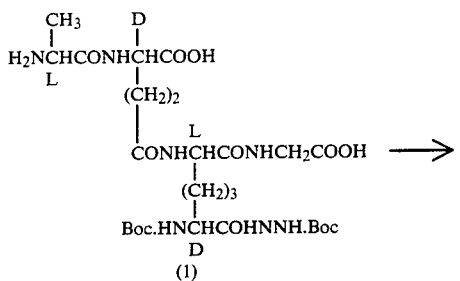

(1)

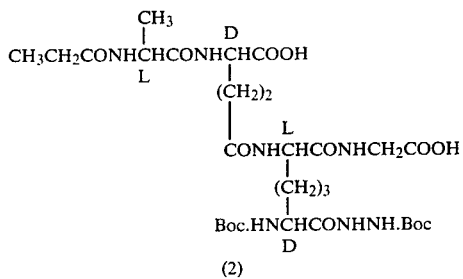

(2)

L—Ala—γ—D—Glu(α—OH)—(L)—Boc—(D)—mesoDAP—(D)—NHNHBoc—(L)—GlyOH(1) (662 mg.) was dissolved in 50% aqueous acetone (8 ml.) and sodium bicarbonate (168 mg.) was added to the solution. To the mixture was added propionic chloride (408 mg.) at 0° C. and the resulting mixture was reacted at the same temperature for an hour, maintaining the pH 7-8 with sodium bicarbonate. The reaction mixture was adjusted to pH 3.0 with 1N hydrochloric acid and concentrated to about 2 ml. in vacuo. To the resulting residue were added ethyl acetate (150 ml.), methanol (10 ml.) and brine (30 ml.).

The organic layer was separated, dried over sodium sulfate and then concentrated to dryness in vacuo. The concentrate was treated with ether to give propionyl—L—Ala—γ—D—Glu(α—OH)—(L)—Boc—(D)—mesoDAP—(D)—NHNHBoc—(L)—GlyOH (2) (400 mg) as a white powder.

IR (Nujol): 3250, 1720(sholder), 1650 cm$^{-1}$.

NMR (CD$_3$OD), δ(ppm): 1.0~2.5 (36H, m), 3.97 (2H, s), 3.90~4.60 (4H, m).

Step (2)

Compound (2) ⟶

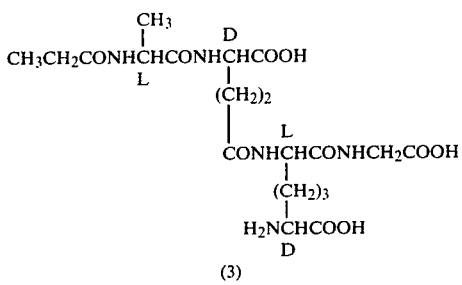

(3)

Trifluoroacetic acid (1.8 ml) was added to propionyl—L—Ala—γ—D—Glu(α—OH)—(L)—Boc—(D)—mesoDAP—(D)—NHNHBoc—(L)—GlyOH (2) (350 mg) and the mixture was allowed to stand at ambient temperature for 15 minutes. The reaction mixture was evaporated in vacuo and the residual oil was triturated with ether to give a white solid. The solid was dissolved in water (10 ml) and to the solution were added 0.1N sulfuric acid (12.2 ml) and a solution of sodium periodate (260 mg) in water (4 ml) with stirring under ice-cooling. The stirring was continued for two hours and sodium bisulfite was added to the reaction mixture until the iodine colour was disappeared. The resulting mixture was evaporated to about 3 ml and the concentrate was adjusted to pH 2.5 with 1N hydrochloric acid, and then chromatographed on a macroporous non-ionic adsorption resin, HP20 (50 ml) (trade mark, maker: Mitsubishi Chemical Industry Co., Ltd.). Elution was carried out with a mixture of water and methanol (9:1). The fractions containing the object compound (3) were collected and freeze-dried to give propionyl—L—Ala—γ—D—Glu(α—OH)—(L)—mesoDAP—(L)—GlyOH (3) (102 mg) as a white solid.

NMR (D$_2$)), δ(ppm): 1.11 (3H, t, J=8 Hz), 1.39 (3H, d, J=8 Hz), 2.31 (2H, q, J=8 Hz), 3.81 (1H, t, J=8 Hz), 3.96 (2H, s), 4.15~4.40 (3H, m).

[α]$_D$= −37.0° (C=0.20 water).

The following compounds were prepared in substantially the same manner as that of Steps 1 and 2 of Example 1, respectively.

EXAMPLE 2

(1) Step 1

Acetyl—L—Ala—γ—D—Glu(α—OH)—(L)—Boc—(D) mesoDAP—(D)—NHNHBoc—(L)—GlyOH.

I.R (Nujol): 3250, 1720, 1630, 1525 cm$^{-1}$

NMR (CD$_3$OD), δ(ppm): 2.00 (3H, s), 3.91 (2H, s).

(2) Step 2

Acetyl-L-Ala-γ-D-Glu(α—OH)—(L)—mesoDAP—(L)—GlyOH.

mp 110°~114° C. (dec.).

[α]$_D$= −28.3° (C=0.36, water).

NMR (D$_2$O), δ(ppm): 1.39 (3H, d, J=7 Hz), 2.03 (3H, s), 3.79 (1H, t, J=7 Hz), 4.02 (2H, s), 4.20~4.50 (3H, m).

EXAMPLE 3

(1) Step 1

Heptanoyl—L—Ala—γ—D—Glu(α—OH)—(L)—Boc—(D)—mesoDAP—(D)—NHNHBoc—(L)—GlyOH.

I.R (Nujol): 3280, 1720, 1650, 1520 cm$^{-1}$.

NMR (CD$_3$OD), δ(ppm): 0.70~1.07 (3H, t), 3.92 (2H, s), 4.15~4.60 (3H, m).

(2) Step 2

Heptanoyl—L—Ala—γ—D—Glu(α—OH)—(L-)—mesoDAP—(L)—GlyOH.

mp 175°~180° C.

NMR (D$_2$O+NaHCO$_3$), δ(ppm): 0.83 (3H, t), 1.40 (3H, d, J=8 Hz), 3.77 (2H, s), 4.1~4.5 (3H, m).

EXAMPLE 4

(1) Step 1

Isobutyryl—L—Ala—γ—D—Glu(α—OH)—(L-)—Boc—(D)—mesoDAP—(D)—NHNHBoc—(L)—GlyOH.

I.R (Nujol): 3260, 1720, 1650 cm$^{-1}$.

NMR (CD$_3$OD), δ(ppm): 1.13 (3H, d, J=7 Hz), 1.24 (3H, d, J=7 Hz), 3.96 (2H, s).

(2) Step 2

Isobutyryl—L—Ala—γ—D—Glu(α—OH)—(L-)—mesoDAP—(L)—GlyOH.

NMR (D$_2$O), δ(ppm): 1.07 (6H, d, J=7 Hz), 1.31 (3H, d, J=7 Hz), 2.50 (1H, hept, J=7 Hz), 3.83 (1H, t, J=7 Hz), 3.98 (2H, s), 4.2~4.5 (3H, m).

[α]$_D$= −31.2° (C=0.17, water).

EXAMPLE 5

(1) Step 1

Benzoyl—L—Ala—γ—D—Glu(α—OH)—(L-)—Boc—(D)—mesoDAP—(D)—NHNHBoc—(L)—GlyOH.

I.R (Nujol), δ(ppm): 3260, 1720, 1640 (broad), 1530 cm$^{-1}$.

NMR (CD$_3$OD), δ(ppm): 3.94 (2H, s), 7.45~7.70 (3H, m), 7.88~8.04 (2H, m).

(2) Step 2

Benzoyl—L—Ala—γ—D—Glu(α—OH)—(L-)—mesoDAP—(L)—GlyOH. [α]$_D$= −4.2° (C=0.19, water).

NMR (D$_2$O), δ(ppm): 1.53 (3H, d, J=7 Hz), 3.83 (1H, t, J=7 Hz), 3.98 (2H, s), 4.15~4.60 (3H, m), 7.40~7.65 (3H, m), 7.70~7.90 (2H, m).

EXAMPLE 6

(1) Step 1

D—mandelyl—L—Ala—γ—D—Glu(α—OH)—(L-)—Boc—(D)—mesoDAP—(D)—NHNHBoc—(L)—GlyOH.

I.R (Nujol): 3280, 1720, 1650, 1520 cm$^{-1}$.

NMR (CD$_3$OD), δ(ppm): 3.94 (2H, s), 4.25~4.55 (3H, m), 5.12 (1H, s), 7.40 (5H, m).

(2) Step 2

D—mandelyl—L—Ala—γ—D—Glu(α—OH)—(L-)—mesoDAP—(L)—GlyOH.

[α]$_D$= −40.5 (C=0.19, water).

NMR (D$_2$O), δ(ppm): 1.46 (3H, d, J=7 Hz), 3.83 (1H, t, J=7 Hz), 3.97 (2H, s), 4.13~4.50 (3H, m), 5.23 (1H, s), 7.48 (5H, s).

EXAMPLE 7

(1) Step 1

2—Methoxypropionyl—L—Ala—γ—D—Glu(α—OH)—(L)—Boc—(D)—mesoDAP—(D-)—NHNHBoc—(L)—GlyOH.

NMR (CD$_3$OD), δ(ppm): 3.41 (3H, s), 3.80 (1H, q, J=7 Hz), 3.95 (2H, s), 4.25~4.55 (3H, m).

(2) Step 2

2-Methoxypropionyl—L—Ala—γ—D—Glu(α—OH)—(L)—mesoDAP—(L)—GlyOH.

[α]$_D$= −30.0° (C=0.21, water).

NMR (D$_2$O), δ(ppm): 1.33 (3H, d, J=7 Hz), 1.41 (3H, d, J=7 Hz), 3.36 (3H, s), 3.75~4.03 (2H, m), 3.96 (2H, s), 4.2~4.5 (3H, m).

EXAMPLE 8

(1) Step 1

Phenoxyacetyl—L—Ala—γ—D—Glu(α—OH-)—(L)—Boc—(D)—mesoDAP—(D)—NHNH-Boc—(L)—GlyOH.

I.R (Nujol): 3280, 1650, 1520 cm$^{-1}$.

NMR (CD$_3$OD), δ(ppm): 3.92 (2H, s), 4.58 (2H, s), 6.85~7.10 (3H, m), 7.20~7.40 (2H, m).

(2) Step 2

Phenoxyacetyl—L—Ala—γ—D—Glu(α—OH-)—(L)—mesoDAP—(L)—GlyOH.

[α]$_D$= −19.6° (C=0.23, water).

NMR (D$_2$O), δ(ppm): 1.43 (3H, d, J=7 Hz), 3.82 (1H, t, J=7 Hz), 3.96 (2H, s), 4.20~4.55 (3H, m), 4.64 (2H, s), 6.97~7.15 (3H, m), 7.30~7.43 (2H, m).

EXAMPLE 9

(1) Step 1

$$\underset{L}{H_2NCHCONHCHCOOH} \overset{CH_3}{\underset{\underset{\underset{\underset{Boc.HNCHCONHNH.Boc}{D}}{(CH_2)_3}}{\underset{L}{CONHCHCONHCH_2COOH}}}{\overset{|}{\underset{|}{(CH_2)_2}}} \longrightarrow$$

(1)

$$\underset{L}{CH_3COOCH_2CONHCHCONHCHCOOH} \overset{CH_3}{\underset{\underset{\underset{\underset{Boc.HNCHCONHNH.Boc}{D}}{(CH_2)_3}}{\underset{L}{CONHCHCONHCH_2COOH}}}{\overset{|}{\underset{|}{(CH_2)_2}}}$$

(2)

Acetyloxyacetyl—L—Ala—γ—D—Glu(α—OH-)—(L)—Boc—(D)—mesoDAP—(D)—NHNH-Boc—(L)—GlyOH (2)(570 mg) was prepared from L—Ala—γ—D—Glu(α—OH)—(L)—Boc—(D-)—meso—DAP—(D)—NHNHBoc—(L)—GlyOH (1) (794 mg) and acetylglycolic chloride of (246 mg) in substantially the same manner as that Step 1 of Example 1.

I.R (Nujol): 3270, 1710, 1650, 1525 cm$^{-1}$.

NMR (DMDO-d$_6$), δ(ppm): 1.24 (3H, d, J=7 Hz), 2.08 (3H, s).

(2) Step 2

Compound (2) ⟶

-continued

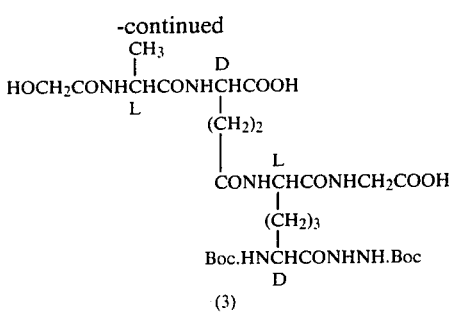

(3)

Acetyloxyacetyl—L—Ala—γ—D—Glu(α—OH)—(L)—Boc—(D)—mesoDAP—(D)—NHNHBoc—(L)—GlyOH (2) (490 mg) was dissolved in 50% aqueous methanol (20 ml) and the solution was adjusted to pH 9.0 with 5% potassium carbonate and then allowed to stand at ambient temperature for an hour. The solution was adjusted to pH 5 and concentrated in vacuo and then water (1 ml) was added to the concentrate. The mixture was adjusted to pH 2.5 with 1N hydrochloric acid and chromatographed on a column of macroporous non-ionic adsorption resin, HP 20 (20 ml). After washing the column with water, elution was carried out with 50% aqueous methanol. The fractions containing the object compound (3) were collected and concentrated to give hydroxyacetyl—L—Ala—γ—D—Glu(α—OH)—(L)—Boc—(D)—meso—DAP—(D)—NHNHBoc—(L)—GlyOH (3) (370 mg) as a white solid.

I.R (Nujol): 3300, 1720 (shoulder), 1650, 1530 cm$^{-1}$.
NMR (D$_2$O), δ(ppm): 3.95 (2H, s), 4.11(2H, s).

(3) Step 3

Compound (3) ⟶

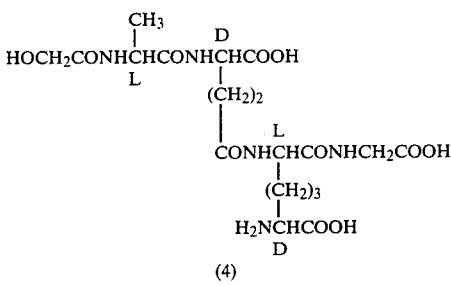

(4)

Hydroxyacetyl—L—Ala—γ—D—Glu(α—OH)—(L)—meso—DAP—(L)—GlyOH (4) (234 mg) was prepared from hydroxyacetyl—L—A Ala—γ—D—Glu(α—OH)—(L)—Boc—(D)—meso—DAP—(D)—NHNHBoc—(L)—GlyOH (3) (345 mg) in substantially the same manner as that of Step 2 of Example 1.
[α]$_D$= −25.2° (C=0.21, water).
NMR (D$_2$O), δ(ppm): 1.43 (3H, d, J=7 Hz), 3.91 (1H, t, J=7 Hz), 3.99 (2H, s), 4.15 (2H, s), 4.20∼4.55 (3H, m).

EXAMPLE 10

The following compounds were prepared in substantially the same manner as that of steps 1 and 2 of Example 1.

(1) Step 1
L—Lac(oAc)—L—Ala—γ—D—Glu(α—OH)—(L)—Boc—(D)—mesoDAP (L)—GlyOH—(D)—NHNHBoc.

I.R(Nujol): 3300, 1720, 1650 cm$^{-1}$.
NMR (CD$_3$OD), δ(ppm): 2.13 (3H, s), 3.93 (2H, s).

(2) Step 2
L—Lac—L—Ala—γ—D—Glu(α—OH)—(L)—mesoDAP—(L)—GlyOH.
mp 170°-174° C. (dec.).
[α]$_D$= −33.2° (C=0.25, water).
NMR (D$_2$O), δ(ppm): 1.38 (3H, d, J=7 Hz), 1.45 (3H, d, J=7 Hz), 3.89 (1H, t, J=7 Hz), 4.01 (2H, s), 4.20∼4.55 (4H, m).

EXAMPLE 11

(1) Step 1

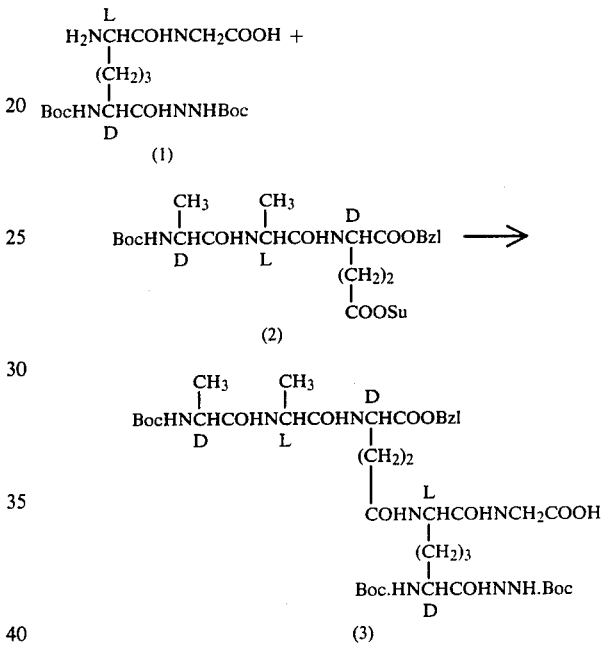

To a mixture of Boc—(D)—mesoDAP—(D)—NHNHBoc—(L)—GlyOH (1) (0.922 g) and triethylamine (0.202 g) in 50% aqueous dioxane (30 ml) was added Boc—D—Ala—L—Ala—D—Glu(oSu)oBzl. The resulting mixture was stirred at ambient temperature overnight and then evaporated. The residue was adjusted to pH 8 with dil sodium bicarbonate and washed with ethyl acetate. The aqueous layer was acidified to pH 1 with dil hydrochloric acid and then extracted with ethyl acetate. The extract was washed with water, dried over magnesium sulfate and evaporated. The residue was crystallized from a mixture of ethyl acetate and ether, and then filtered. The crystal was washed with ether to give Boc—D—Ala—L—Ala—γ—D—Glu(α—oBzl)—(L)—Boc—(D)—mesoDAP—(D)—NHNHBoc—(L)—GlyOH (3) (1.45 g).
NMR (CD$_3$OD), δ(ppm): 1.29 (3H, d, J=7 Hz), 1.32 (3H, d, J=7 Hz), 1.40 (27H, s), 3.87∼4.47 (4H, m), 5.14 (2H, s), 7.32 (5H, s).

(2) Step 2

Compound (3) ⟶

-continued

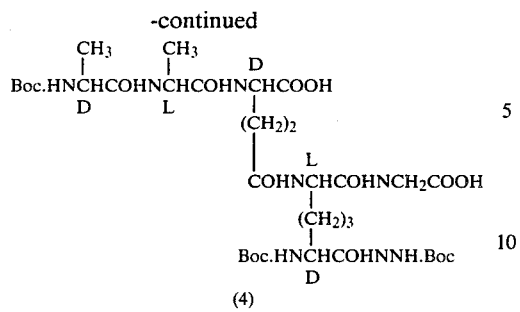

(4)

A solution of Boc—D—Ala—L—Ala—γ—D—Glu(α—OBzl)—(L)—Boc—(D)—meso—DAP—(D-)—NHNHBoc—(L)—GlyOH (3) (1.2 g) in a mixture (25 ml) of methanol and water (2:1) was hydrogenated over 5% palladium-black (0.2 g) at two atmospheric pressures of hydrogen gas. After the reaction was completed, the catalyst was filtered off and the filtrate was evaporated. The residue was pulverized with isopropyl ether and filtered to give Boc—D—Ala—L—Ala—γ—D—Glu(α—OH)—(L-)—Boc—(D)—meso—DAP—(D)—NHNHBoc—(L-)—GlyOH (4) (1.1 g).

NMR (CD$_3$OD), δ(ppm): 1.24 (3H, d, J=7 Hz), 1.35 (3H, d, J=7 Hz), 1.44 (27H, s), 1.34~2.50 (10H, m), 3.94 (2H, s), 3.87~4.50 (4H, m).

(3) Step 3

Compound (4) ⟶

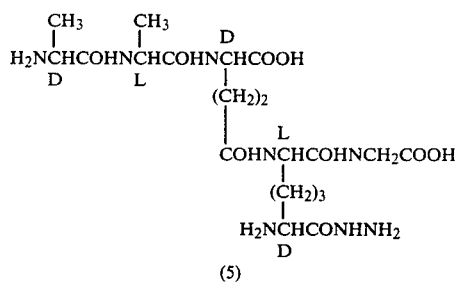

(5)

Boc—D—Ala—L—Ala—γ—D—Glu(α—OH)—(L-)—Boc—(D)—meso—DAP—(D)—NHNHBoc—(L-)—GlyOH (4) (1.0 g) was dissolved in trifluoroacetic acid (5 ml) and the solution was stirred at ambient temperature for 30 minutes. The reaction mixture was evaporated and the residue was pulverized with ethyl acetate and filtered to give D—Ala—L—Ala—γ—D—Glu(α—OH)—(L)—meso—DAP—(D)—NHNH$_2$—(L)—GlyOH (5) trifluoroacetic acid salt (0.81 g).

NMR (D$_2$O), δ(ppm): 1.42 (3H, d, J=7 Hz), 1.57 (3H, d, J=7 Hz), 1.34~2.50 (10H, m), 3.74 (2H, s), 3.67~4.27 (4H, m).

(4) Step 4

Compound (5) ⟶

-continued

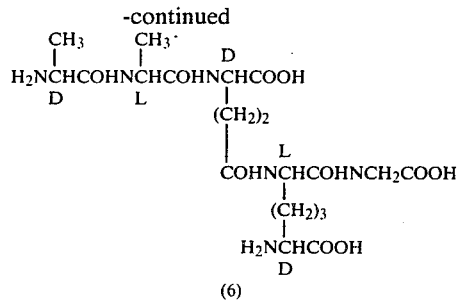

(6)

N-Bromosuccinimide (178 mg) was added to a solution of D—Ala—L—Ala—γ—D—Glu(α—OH)—(L-)—meso—DAP—(D)—NHNH$_2$—(L)—GlyOH (5) trifluoroacetic acid salt (532 mg) in 50% aqueous dioxane (10 ml). The mixture was stirred at ambient temperature for an hour and adjusted to pH 3.5 with dil sodium bicarbonate and then evaporated. The residue was dissolved in water and chromatographed on a column of a macroporous non-ionic adsorption resin, HP 20 (150 ml) and then eluted with water. Eluates containing the object compound (6) were combined and evaporated. The residue was washed with methanol and dissolved in water. The solution was adjusted to pH 3.0 and chromatographed again on a column of macroporous non-ionic adsorption resin, HP 20 (100 ml) and eluted with water. Fractions containing the object compound (6) were combined and evaporated to give a solid. The solid was dissolved in water and lyophilized to give D—Ala—L—Ala—γ—D—Glu(α—OH)—(L)—meso—DAP—(L)—GlyOH (6) (120 mg).

NMR (D$_2$O), δ(ppm): 1.45 (3H, d, J=7 Hz), 1.57 (3H, d, J=7 Hz), 1.34~2.34 (10H, m), 3.88 (2H, s), 3.74~4.50 (4H, m).

EXAMPLE 12

(1) Step 1

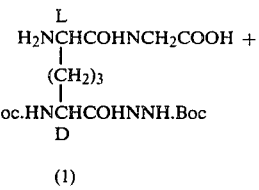

(1)

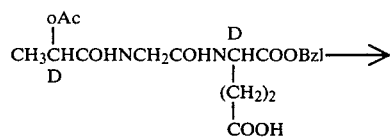

(2)

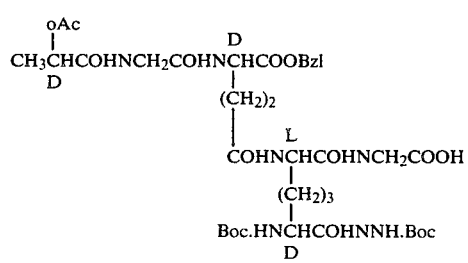

(3)

D—Lac(oAc)—Gly—γ—D—GluoBzl dicyclohexylamine salt (2) (1.20 g) was dissolved in a mixture of ethyl acetate (40 ml) and methylene chloride (10 ml). To the solution was added 1N hydrochloric acid (2 ml) and the precipitates thus formed were filtered off. The organic layer was washed with water, dried over magnesium sulfate and then evaporated to give an oily residue. The residue was dissolved in methylene chloride (20 ml) and to the solution were added N-methyl morpholine (200 mg) and isobutyl chlorocarbonate (270 mg) at 0° C. The mixture was reacted at the same temperature for 20 minutes. To the reaction mixture was added a solution of Boc—(D)—mesoDAP—(D)—NHNH-Boc—(L)—GlyOH (1) (860 mg) in a mixture of methylene chloride (40 ml) and dimethylformamide (50 ml) containing bis(trimethylsilyl)acetamide (2 ml) at 0° C. The resulting mixture was stirred at the same temperature for two hours and concentrated in vacuo to give an oily residue. The residue was dissolved in ethyl acetate and the solution was washed with 2% hydrochloric acid. The organic layer was washed with successively with water and aqueous saturated sodium chloride solution and dried and then evaporated. The residue was throughly washed with ether and collected by filtration to give D—Lac(oAc)—Gly—γ—D—Glu(α—oBzl)—(L)—Boc—(D)—mesoDAP—(D)—NHNH-Boc—(L)—Gly(OH) (3) (1.0 g).

NMR (DMSO-d$_6$), δ(ppm): 0.80~2.60 (3H, m), 2.06 (3H, s), 3.76 (4H, broad s), 3.60~4.52 (3H, m), 5.00 (1H, q, J=7 Hz), 5.12 (2H, s), 6.70 (1H, d, J=7 Hz), 7.38 (5H, s), 7.80~8.80 (5H, m), 9.58 (1H, s).

(2) Step 2

Compound (3)——>

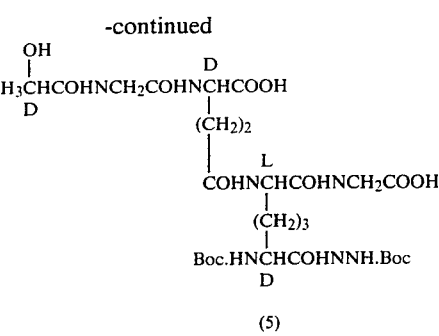

(4)

D—Lac(oAc)—Gly—γ—D—Glu(α—oBzl)—(L)—Boc—(D)—mesoDAP—(D)—NHNHBoc—(L)—GlyOH (3) (0.9 g) was dissolved in glacial acetic acid (9 ml) and hydrogenated over 10% palladium black (200 mg) at ambient temperature for 1.5 hours. The catalyst was filtered off and the filtrate was evaporated in vacuo to give an oily residue which was pulverized with ether to give D—Lac(oAc)—Gly—γ—D—Glu(α—OH-)—(L)—Boc—(D)—mesoDAP—(D)—NHNH-Boc—(L)—GlyOH (4) (0.76 g).

NMR (DMSO-d$_6$), δ(ppm): 0.80~2.80 (31H, m), 2.08 (3H, s), 3.72 (4H, broad s), 3.60~4.36 (3H, m), 5.00 (1H, q, J=7 Hz), 6.76 (1H, m), 7.72~8.40 (5H, m), 8.70 (1H, m), 9.60 (1H, s).

(3) Step 3

Compound (4)——>

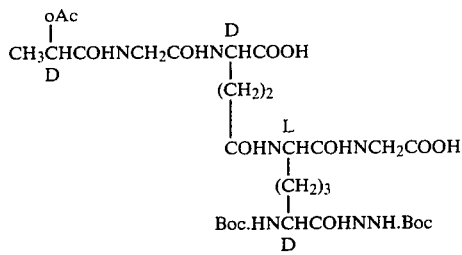

(5)

D—Lac(oAc)—Gly—γ—D—Glu(α—OH)—(L)—Boc—(D)—mesoDAP—(D)—NHNHBoc—(L)—GlyOH (4) (0.70 g) was dissolved in 50% aqueous methanol (20 ml) and the solution was adjusted to pH 9.0 with 5% aqueous potassium carbonate. The solution was allowed to stand at ambient temperature for 3 hours and adjusted to pH 7.0 with 5% hydrochloric acid. The solution was chromotographed on a column of macroporous non-ionic adsorption resin, HP 20 (25 ml) and eluted successively with water (100 ml) and 50% aqueous methanol (100 ml). The latter fraction was evaporated to give a posty residue which was pulverized with ether to give D—Lac—Gly—γ—D—Glu(α—OH-)—(L)—Boc—(D)—mesoDAP—(D)—NHNH-Boc—(L)—GlyOH (5) (0.40 g), I.R (Nujol): 3300, 1730, 1690 1650 (broad) cm$^{-1}$.

NMR (D$_2$O), δ(ppm): 1.0~2.60 (31H, m), 4.00 (4H, s), 4.20~4.60 (4H, m).

(4) Step 4

Compound (5)——>

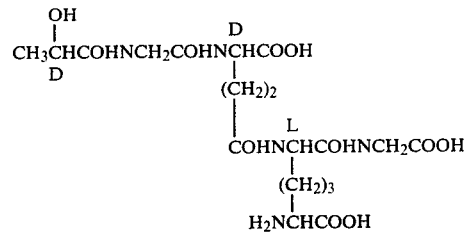

(6)

D—Lac—Gly—γ—D—Glu(α—OH)—(L)—Boc—(D)—mesoDAP—(D)—NHNHBoc—(L)—GlyOH (5) (335 mg) was dissolved in trifluoroacetic acid (3 ml) and the solution was stirred at ambient temperature for 15 minutes. The solution was evaporated in vacuo and the residue thus obtained was pulverized with ether to give a white powder. The powder was dissolved in a mixture of water (8 ml) and 0.1N sulfuric acid (11.6 ml) and the solution was cooled in an icebath. To the solution was added an aqueous sodium metaperiodate solution (240 mg in 3 ml of water) and allowed to react at 0° C. for an hour. The resulting reaction mixture was treated with an aqueous sodium bicarbonate until the purple color of the solution was disappeared. The solution was adjusted to pH 3.0 and concentrated to about 3 ml. The concentrate was adjusted to pH 2.0 and then chromatographed on a column of macroporous non-ionic adsorption resin, HP 20 (80 ml) and eluted with water. Fractions containing the object compound (6) were collected and evaporated in vacuo to give a posty residue which was dissolved in water and lyophilized to give D—Lac—Gly—γ—D—Glu(α—OH)—(L)—mesoDAP—(L)—GlyOH (6) (0.150 g).

$[\alpha]_D = -5.0°$ (C=0.2 in water).

NMR (D₂O), δ(ppm): 1.38 (3H, d, J=7 Hz), 1.20~2.60 (10H, m), 3.82 (1H, t, J=7 Hz), 3.96 (2H, s), 4.00 (2H, s), 3.68~4.52 (3H, m).

EXAMPLE 13

(1) Step 1

L
H₂NCHCOHNCH₂COOH +
|
(CH₂)₃
|
Boc.HNCHCOHNNH.Boc
D (1)

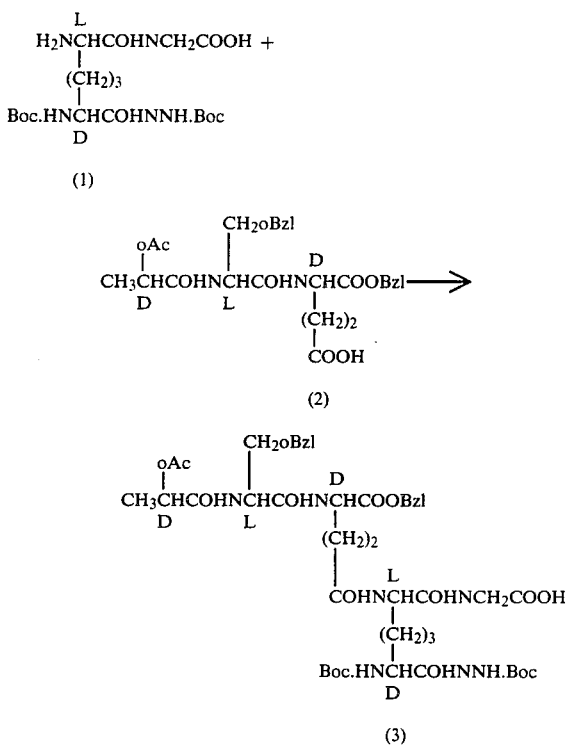

(2)

(3)

D—Lac(oAc)—L—Ser(oBzl)—D—GluoBzl (2) dicyclohexylamine salt (1.40 g) was dissolved in a mixture of ethyl acetate (40 ml) and chloroform (10 ml). To the solution was added 1H hydrochloric acid (2 ml) and the precipitates thus formed were filtered off. The organic layer was separated, washed with water, dried over magnesium sulfate and then evaporated to give an oily residue (1.08 g). The residue was dissolved in methylene chloride (20 ml) and the solution was treated with N-methylmorpholine (198 mg) and cooled to −10° C. and then isobutylchlorocarbonate (270 mg) was added thereto. To the mixture was added Boc—(D-)—mesoDAP—(D)—NHNHBoc—(L)—GlyOH (1) (860 mg) in a mixture of methylene chloride (40 ml) and dimethylformamide (50 ml) containing bis(trimethylsilyl)acetamide (2 ml). The resulting mixture was allowed to react at −10° C. for two hours. The reaction mixture was concentrated in vacuo to give an oily residue which was dissolved in ethyl acetate. The solution was washed with 2% aqueous hydrochloric acid and the ethyl acetate layer was separated, washed with water and dried over magnesium sulfate, and then evaporated. The crystalline residue thus obtained was washed with ether to give D—Lac—(oAc)—L—Ser-(oBzl)—γ—D—Glu(α—oBzl)—(L)—Boc—(D-)—mesoDAP—(D)—NHNHBoc—(L)—GlyOH (3) (1.55 g).

NMR (DMSO-d₆), δ(ppm): 1.00~2.36 (10H, m), 1.38 (18H, s), 1.32 (3H, d, J=7 Hz), 2.04 (3H, s), 3.44~4.84 (8H, m), 4.48 (2H, s), 5.06 (1H, q, J=7 Hz), 5.14 (2H, s), 6.72 (1H, broad s), 7.34 (5H, s), 7.40 (5H, s), 7.92 (1H, broad s), 8.04~8.44 (4H, m), 8.72 (1H, broad s), 9.60 (1H, s)

Successively, the following compounds were prepared in substantially the same manner as that of Steps 2 to 4 of Example 12, respectively.

(2) Step 2

D—Lac(oAc)—L—Ser(OH)—γ—Glu(α—OH-)—(L)—Boc—(D)—mesoDAP—(D)—NHNH-Boc—(L)—GlyOH

NMR (DMSO-d₆), δ(ppm): 1.00~2.40 (10H, m), 1.38 (18H, s), 1.32 (3H, d, J=7 Hz), 2.08 (3H, s), 3.40~4.52 (8H, m), 5.06 (1H, q, J=7 Hz), 6.76 (1H, d, J=7 Hz), 7.64~8.32 (4H, m), 8.72 (1H, s), 9.60 (1H, s).

(3) Step 3

D—Lac—L—Ser—γ—D—Glu(α—OH)—(L-)—Boc—(D)—mesoDAP—(D)—NHNHBoc—(L)—GlyOH.

NMR (D₂O), δ(ppm): 1.00~2.60 (10H, m), 1.42 (3H, d, J=7 Hz), 1.44 (18H, s), 3.60~5.00 (9H, m).

(4) Step 4

D—Lac—L—Ser—γ—D—Glu(α—OH)—(L-)—mesoDAP—(L)—GlyOH.

$[\alpha]_D = -18.5°$ (C=0.2 water).

NMR (D₂O), δ(ppm): 1.20~2.60 (10H, m), 1.40 (3H, d, J=7 Hz), 3.60~5.10 (7H, m), 3.98 (2H, s).

EXAMPLE 14

(1) Step 1

L
H₂NCHCOHNCH₂COOH +
|
(CH₂)₃
|
Boc.HNCHCOHNNH.Boc
D (1)

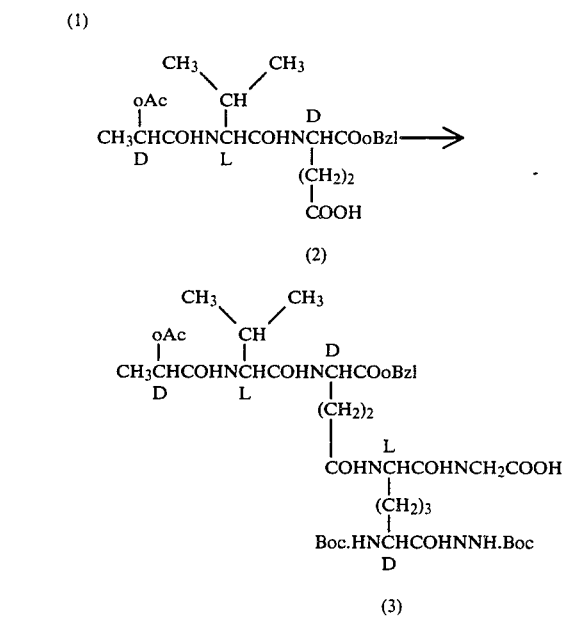

(3)

D—Lac(oAc)—L—Val—γ—D—Glu(α—oBzl)—(L)—Boc—(D)—mesoDAP(D)—NHNHBoc—(L-

)—GlyOH (3) (1.20 g) was prepared from Boc—(D-)—mesoDAP—(D)—NHNHBoc—(L)—GlyOH (1) (800 mg) and D—Lac(oAc)—L—Val—γ—D—GluOBzl (2) (0.90 g) in substantially the same manner as that of Step 1 of Example 12.

NMR (DMSO-d$_6$), δ(ppm): 0.80 (3H, d, J=7 Hz), 0.84 (3H, d, J=7 Hz), 1.83 (18H, s), 1.0~2.40 (14H, m), 2.04 (3H, s), 3.60~4.48 (6H, m), 5.08 (1H, q, J=7 Hz), 5.14 (5H, s), 6.74 (1H, d, J=7 Hz), 7.36 (5H, s), 7.80~8.40 (5H, m), 8.68 (1H, s), 9.54 (1H, s).

Successively, the following compounds were prepared in substantially the same manner as that of Steps 2 to 4 of Example 12, respectively.

(2) Step 2

D—Lac(oAc)—L—Val—γ—D—Glu(α—OH)—(L-)—Boc—(D)—mesoDAP—(D)—NHNHBoc—(L)—GlyOH

NMR (DMSO-d$_6$), δ(ppm): 0.82 (3H, d, J=7 Hz), 0.86 (3H, d, J=7 Hz), 1.00~2.40 (14H, m), 2.04 (3H, s), 3.60~4.40 (6H, m), 5.04 (1H, q, J=7 Hz), 6.76 (1H, d, J=7 Hz), 7.80~8.40 (4H, m), 8.70 (1H, s), 9.60 (1H, s).

(3) Step 3

D-Lac-L-Val-γ-D-Glu(α—OH)—(L)—Boc—(D-)—mesoDAP—(D)—NHNHBoc—(L)—GlyOH.

NMR (D$_2$O), δ(ppm); 0.96 (6H, d, J=7 Hz), 1.12~2.56 (32H, m), 3.96 (2H, s), 3.80~4.52 (5H, m).

(4) Step 4

D—Lac—L—Val—γ—D—Glu(α—OH)—(L-)—mesoDAP(L)—GlyOH.

[α]$_D$= −28.0° (C=0.2, water).

NMR (D$_2$O), δ(ppm): 0.96 (6H, d, J=7 Hz), 1.37 (3H, d, J=7 Hz), 1.20~2.60 (11H, m), 3.96 (2H, s), 3.68~4.50 (5H, m).

The following compounds were prepared in substantially the same manner as that of Steps 1 and 2 of Example 1, respectively.

EXAMPLE 15

(1) Step 1

Thienylacetyl—L—Ala—γ—D—Glu(α—OH)—(L-)—Boc—(D)—mesoDAP—(D)—NHNHBoc—(L)—GlyOH.

NMR (CD$_3$OD), δ(ppm): 3.76 (2H, s), 3.87 (2H, s), 4.15~4.40 (3H, m), 6.90 (2H, m), 7.20 (1H, m).

(2) Step 2

Thienylacetyl—L—Ala—γ—D—Glu(α—OH)—(L-)—mesoDAP—(L)—GlyOH.

[α]$_D$= −33.5° (C=0.20 water).

NMR (D$_2$O), δ(ppm): 1.40 (3H, d, J=7 Hz), 3.81 (3H, t, J=7 Hz), 3.89 (2H, s), 3.97 (2H, s), 4.13~4.44 (3H, m), 7.02 (2H, m), 7.35 (1H, m).

EXAMPLE 16

(1) Step 1

Phenylcarbamoyl—L—Ala—γ—D—Glu(α—OH-)—(L)—Boc—(D)—mesoDAP—(D)—NHNH-Boc—(L)—GlyOH.

I.R. (Nujol): 3300, 1730, 1650, 1595, 1540 cm$^{-1}$.

NMR (CD$_3$OD), δ(ppm): 3.95 (2H, s), 4.2~4.6 (3H, m), 69~7.1 (5H, m).

(2) Step 2

Phenylcarbamoyl-L-Ala-γ-D-Glu(α—OH)—(L-)—mesoDAP—(L)—GlyOH.

[α]$_D$= −38.5° (C=0.20, DMSO).

NMR (D$_2$O+NaHCO$_3$), δ(ppm): 1.43 (3H, d, J=7 Hz), 3.96 (1H, m), 3.76 (2H, s), 4.05~4.5 (3H, m), 7.35 (5H, m).

EXAMPLE 17

(1) Step 1

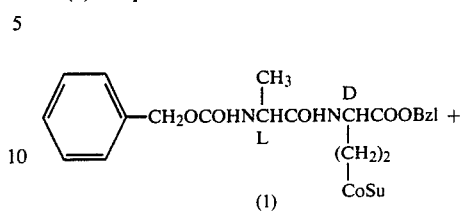

(1)

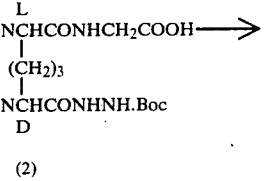

(2)

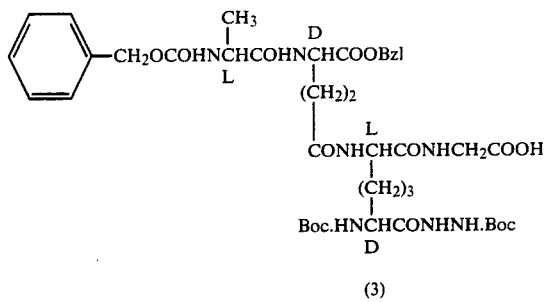

(3)

Triethylamine (720 mg) and benzyloxycarbonyl—L—Ala—D—Glu(oSu)oBzl (1) (3.51 g) was added to a solution of Boc—(D)—meso—DAP—(D-)—NHNHBoc—(L)—GlyOH (2) (3.00 g) in a mixture of dioxane (90 ml) and water (70 ml). The resulting mixture was allowed to stand at ambient temperature for 18 hours, and concentrated to about 50 ml. The concentrate was adjusted to pH 3 with 1N hydrochloric acid and extracted with ethyl acetate (300 ml) containing methanol (20 ml). The organic layer was washed with brine (100 ml), dried over sodium sulfate and then evaporated in vacuo. The residue was washed with ether and filtered to give benzyloxycarbonyl—L—Ala—γ—D—Glu(α—oBzl)—(L-)—Boc—(D)—meso—DAP—(D)—NHNHBoc—(L-)—GlyOH (3) (5.53 g).

NMR (DMSO-d$_6$), δ(ppm): 1.07 (3H, d, J=7 Hz), 3.64~4.48 (6H, m), 5.04 (2H, s), 5.12 (2H, s), 6.56 (1H, d, J=8 Hz), 7.35 (10H, s), 7.95 (1H, d, J=8 Hz), 8.15 (1H, m), 8.35 (1H, d, J=8 Hz), 8.70 (1H, s), 9.56 (1H, s)

(2) Step 2

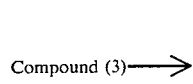

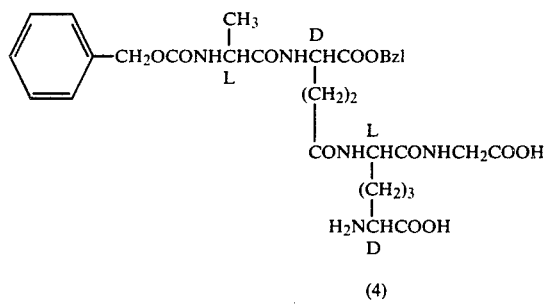

(4)

Benzyloxycarbonyl—L—Ala—γ—D—Glu(α—oBzl)—(L)—Boc—(D)—meso—DAP—(D)—NHNH-Boc—(L)—GlyOH (3) (1.43 g) was added to trifluoroacetic acid (6 ml) and the mixture was stood at ambient temperature for an hour. The mixture was evaporated in vacuo and the residual oil was triturated with isopropyl ether to give a solid. The solid was dissolved in a mixture of water (35 ml) and methanol (10 ml). To this solution were added 1N sulfuric acid (40 ml) and sodium periodate (860 mg) at 0° C. The mixture was stirred at the same temperature for 1.5 hours and concentrated to 10 ml and adjusted to pH 4 with 1N sodium hydroxide. The precipitate thus obtained was collected and dried over phosphorus pentoxide to give benzyloxycarbonyl—L—Ala—γ—D—Glu(α—oBzl)—(L)—mesoDAP—(L)—GlyOH (4) (1.09 g).

I.R. (Nujol): 3300, 1700, 1660, 1540 cm$^{-1}$.

NMR (D$_2$O+NaHCO$_3$), δ(ppm): 3.78 (2H, s), 5.04 (2H, s), 5.13 (2H, s), 7.40 (10H, m).

(3) Step 3

Compound (4)⟶

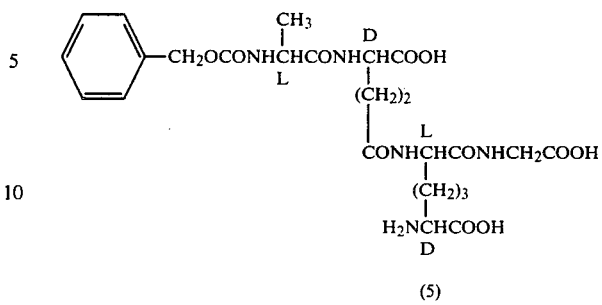

(5)

To a suspension of benzyloxycarbonyl—L—Ala—γ—D—Glu(α—oBzl)—(L)—mesoDAP—(L)—GlyOH (4) (600 mg) in water (10 ml) was added 1N sodium hydroxide (35 ml). The mixture was stood at ambient temperature for an hour. The reaction mixture was adjusted to pH 2.0 with 1N hydrochloric acid and concentrated to about 3 ml. The residual solution was chromatographed on a column of a macroporous non-ionic adsorption resin, HP 20 (60 ml) and eluted with in a mixture of water and methanol (7:3). The fraction containing the object compound (5) was collected and concentrated to dryness in vacuo to give benzyloxycarbonyl—L—Ala—γ—D—Glu(α—OH)—(L)—mesoDAP—(L)—GlyOH (5) (190 mg).

mp 205°–207° C.

[α]$_D$ = −12.1° (C=0.19, water).

NMR (D$_2$O), δ(ppm): 1.37 (3H, d, J=7 Hz), 3.78 (1H, m), 3.93 (2H, s), 4.05∼4.40 (3H, m), 5.14 (2H, s), 7.45 (5H, s).

EXAMPLE 18

(1) Step 1

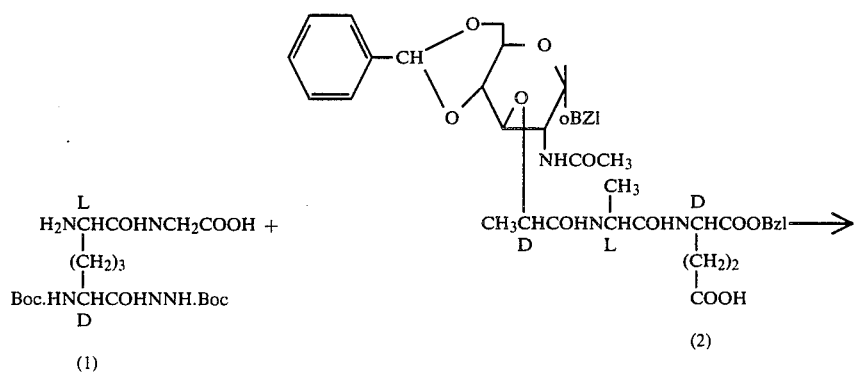

-continued

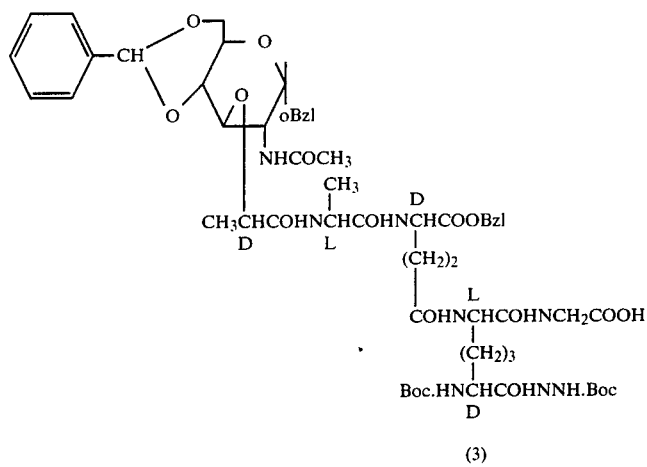

(3)

To a mixture of 1—O—α—benzyl—4,6—O—benzylidene—N—acetyl—muramyl—L—Ala—γ—D—GluoBzl (2) (0.76 g) and triethylamine (0.10 g) in methylene chloride (5 ml) was added dropwise iso-butyl chloroformate (0.13 g) at −18° C. The resulting mixture was stirred at −15° C. for 50 minutes and to this mixture was added at −28° C. silyl ester of Boc—(D-)—mesoDAP—(D)—NHNHBoc—(L)—GlyOH (1) which was prepared from Boc-(D)-mesoDAP—(D-)—NHNHBoc—(L)—GlyOH (0.46 g) and bis(trimethylsilyl)acetamide in a mixture (5 ml) of methylene chloride and dimethylformamide (5:1) with stirring at ambient temperature. The mixture was stirred at −15° C. for 1.5 hours and allowed to warm up to ambient temperature. The solution was distilled off and to the residue thus obtained was added 2% aqueous hydrochloric acid (10 ml) to give a powder. The powder was collected by filtration and washed with water to give 1—O—α-benzyl—4,6—O—benzylidene—N—acetyl—muramyl—L—Ala—γ—Glu(α—oBzl)—(L)—Boc—(D)—mesoDAP—(D-)—NHNHBoc—(L)—GlyOH (3) (1.14 g).

NMR (DMSO-d$_6$), δ(ppm): 1.48 (18H, s), 1.1∼1.6 (8H, m), 1.85 (3H, s), 1.8∼2.3 (8H, m), 3.7∼4.0 (8H, m), 4.0∼4.5 (5H, m), 4.7 (2H, m), 4.90 (1H, d, J=7 Hz), 5.15 (2H, s), 5.72 (1H, s), 7.33 (5H, s), 7.40 (5H, s), 7.34 (5H, s), 8.1∼8.3 (4H, m), 8.3∼8.7 (3H, m).

(2) Step 2

Compound (3) ⟶

-continued

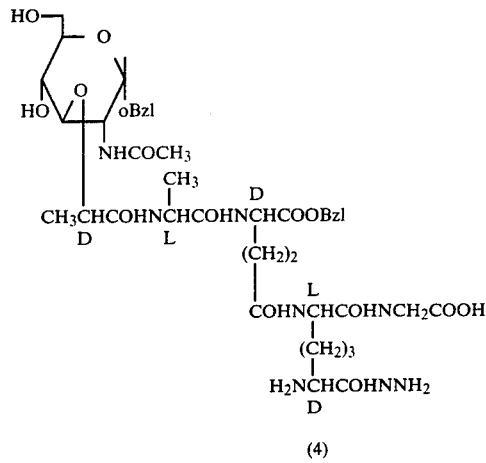

(4)

1—O—α—benzyl—4,6—O—benzylidene—N—acetylmuramyl—L—Ala—γ—D—Glu(α—oBzl)—(L)—Boc—(D)—mesoDAP—(D-)—NHNHBoc—(L)—GlyOH (3) (0.81 g) was added to trifluoroacetic acid (4 ml) and the mixture was stirred at ambient temperature for 15 minutes. The solvent was distilled off and the residue was pulvelized with ether and filtered to give 1-O—α—benzyl—N—acetyl—muramyl—L—Ala—γ—D—Glu(α—oBzl)—(L)—mesoDAP—(D)—NHNH$_2$—(L-)—GlyOH (4) trifluoroacetic acid salt (0.65 g).

NMR (D$_2$O), δ(ppm): 1.38 (6H, d, J=7 Hz), 1.84 (3H, s), 1.2∼1.5 (2H, m), 1.7∼2.1 (6H, m), 2.2∼2.4 (2H, m) 3.6∼4.0 (8H, m), 4.2∼4.5 (5H, m), 5.18 (2H, s), 7.4 (10H, s).

(3) Step 3

Compound (4) ⟶

-continued

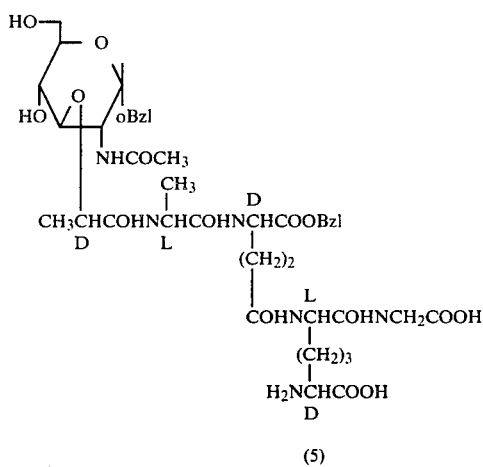

(5)

To a solution of 1—O—α—benzyl—N—acetyl-muramyl—L—Ala—γD—Glu(α—αBzl)—(L-)—mesoDAP—(D)—NHNH$_2$—(L)—GlyOH (4) trifluoroacetic acid salt (0.58 g) in 60% aqueous acetic acid was added manganese dioxide (0.15 g) and the mixture was stirred at ambient temperature for 4 hours. The reaction mixture was filtered and the filtrate was concentrated. The concentrate was dissolved in water (3 ml) and the solution was adjusted to pH 8 with conc. ammonium hydroxide. To the solution was added methanol (3 ml) and the mixture was allowed to stand in a refrigerator. An additional 14 ml of 5% aqueous methanol was added to the mixture and the resulting mixture was filtered. The filtrate was concentrated and the concentrate was dissolved in 1N acetic acid (30 ml) and the solution was put on a column of a chelate resin. The column was eluted with water and the fractions containing the object compound (5) were collected and concentrated to give an oil. The oil was dissolved in water and the solution was adjusted to pH 2.6 and put on a column of a macroporous non-ionic adsorption resin, HP 20. The column was washed with water and eluted with 50% aqueous methanol. The fractions containing the object compound (5) were combined and concentrated to give 1—O—α—benzyl—N—acetyl-muramyl—L—Ala—γ—D—Glu(α—oBzl)—(L-)—mesoDAP—(L)—GlyOH (5) (0.25 g).

NMR (D$_2$O), δ(ppm): 1.35 (3H, d, J=7 Hz), 1.38 (3H, d, J=7 Hz), 1.2~1.6 (2H, m), 1.80 (3H, s), 1.6~2.0 (6H, m), 2.2~2.4 (2H, m), 3.5~3.9 (8H, m), 4.2~4.5 (5H, m), 4.90 (1H, d, J=7 Hz), 5.20 (2H, s), 7.38 (5H, s), 7.40 (5H, s).

(4) Step 4

Compound (5) ⟶

-continued

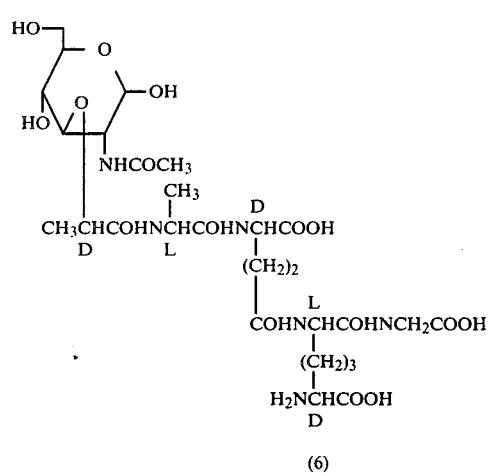

(6)

A solution of 1—O—α—benzyl—N—acetyl-muramyl—L—Ala—γ—D—Glu(α—oBzl)—(L-)—mesoDAP—(L)—GlyOH (5) (0.20 g) in a mixture of water (20 ml) and acetic acid (1.5 ml) was hydrogenated over 10% palladium black (0.10 g) under an atmospheric pressure of hydrogen. The catalyst was filtered off and the filtrate was evaporated to give a white solid (0.15 g). The solid was dissolved in water (2 ml) and lyophilized to give N—acetyl-muramyl—L—Ala—γ—D—Glu(α—OH)—(L-)—mesoDAP—(L)—GlyOH (6) (0.12 g).

NMR (D$_2$O), δ(ppm): 1.38 (3H, d, J=7 Hz), 1.41 (3H, d, J=7 Hz), 1.2~1.6 (2H, m), 1.99 (3H, s), 1.6~2.2 (6H, m), 2.2~2.4 (2H, m), 3.4~4.0 (5H, m), 3.82 (2H, s), 4.1~4.5 (6H, m), 5.19 (1H, m).

EXAMPLE 19

(1) Step 1

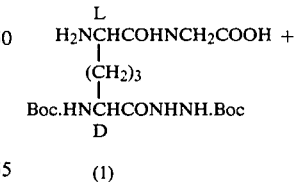

(1)

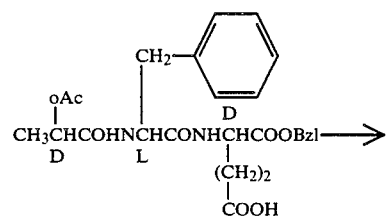

(2)

-continued

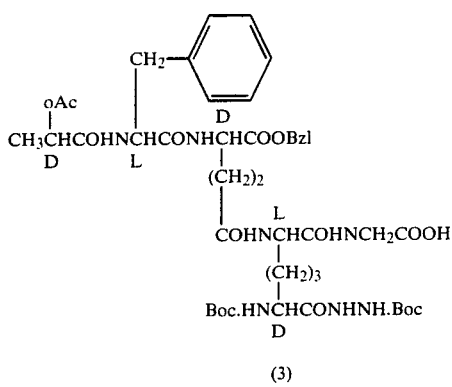

(3)

D—Lac(OAc)—L—Phe—D—GluoBzl (2) (1.0 g) was dissolved in methylene chloride (40 ml) and N-methylmorpholine (200 mg) was added thereto. To this stirred solution cooled at −10° C. in an ice salt-bath, isobutylchlorocarbonate (270 mg) was added and the mixture was allowed to react at the same temperature for 20 minutes. To the reaction mixture was added the silyl ester prepared from Boc—(D)—mesoDAP—(D-)—NHNHBoc—(L)—GlyOH (1) (920 mg) in a mixture of methylene chloride (20 ml) and dimethylformamide (10 ml) containing bis(trimethylsilyl)acetamide (2 ml). The reaction mixture was stirred for 2 hours and concentrated under reduced pressure to give an oily residue which was dissolved in ethyl acetate and washed with 2% hydrochloric acid. The organic layer was washed successively with water and saturated sodium chloride and then dried. Evaporation of the solvent gave a residue which was throughly washed with ether and collected by filtration to give D—Lac(oAc)—L—Phe—γ—D—Glu(α—oBzl)—(L)—Boc—(D-)—mesoDAP—(D)—NHNHBo—(L)—GlyOH (3) (1.660 g).

NMR (DMSO-d$_6$), δ(ppm): 1.10 (2H, d, J=7 Hz), 1.23~2.43 (28H, m), 2.00 (3H, s), 2.86~3.23 (2H, m), 3.73~4.70 (6H, m), 5.17 (2H, s), 7.23 (5H, s), 7.36 (5H, s), 7.70~8.90 (5H, m) 9.60 (1H, s).

(2) Step 2

Compound (3)⟶

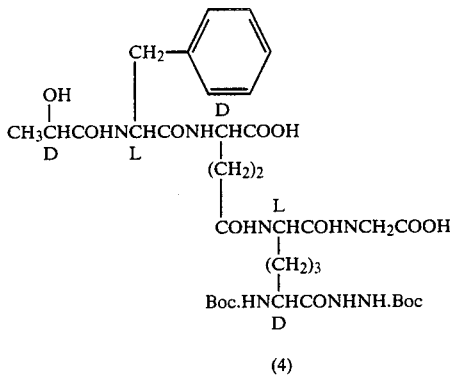

(4)

D—Lac(oAc)—L—Phe—γ—D—Glu(α—oBzl)—(L)—Boc—(D)—mesoDAP—(D)—NHNH-Boc—(L)—GlyOH (3) (1.50 g) was dissolved in 50% aqueous methanol (20 ml). To this solution was added 1N sodium hydroxide (5 ml) and the resulting solution was allowed to stand at ambient temperature for 2 hours. The solution was concentrated to about 3.0 ml after adjusting the pH of the solution to pH 7.0. The pH of the solution was adjusted again to about 2.0 and the precipitates thus formed was extracted with ethyl acetate. The organic layer was washed with saturated sodium chloride and dried over magnesium sulfate and then the solvent was evaporated to give D—Lac-(OH—L—Phe—γ—D—Glu(α—OH)—(L-)—Boc—(D)—mesoDAP—(D)—NHNHBoc—(L)—GlyOH (4) (0.960 g).

NMR (DMSO-d$_6$), δ(ppm): 1.12 (3H, d, J=7 Hz), 1.0~2.32 (28H, m), 2.72~3.20 (2H, m), 3.60~4.80 (7H, m), 6.72 (1H, m), 7.20 (5H, s), 7.48~8.80 (5H, m), 9.52 (1H, s).

(3) Step 3

Compound (4)⟶

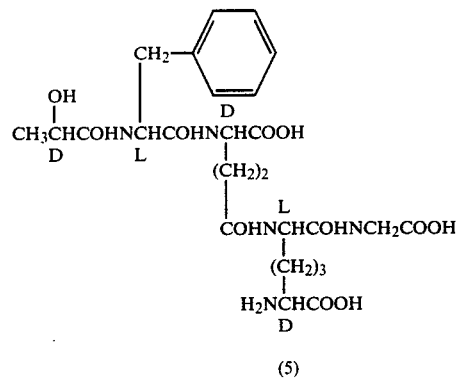

(5)

D—Lac(OH)—L—Phe—γ—D—Glu(α—OH)—(L-)—Boc—(D)—mesoDAP—(D)—NHNHBoc—(L)—GlyOH (4) was dissolved in trifluoroacetic acid (5 ml) and the solution was stirred at ambient temperature for 15 minutes. Evaporation of the solvent under reduced pressure gave an oily residue, which was pulverized with ether to give a white powder. The powder was dissolved in a mixture of water (15 ml) and 0.1N sulfuric acid and the solution was cooled in an ice-bath. To this stirred solution was added an aqueous sodium periodate solution (528 mg in 8 ml of water) and the mixture was allowed to react at the same temperature for an hour. The resulting reaction mixture was treated with sodium bisulfite until the brown color of the mixture became clear and the pH of the solution was adjusted to about 3.0. Then, the solution was concentrated to about 4 ml and the pH of the solution was adjusted again to pH 2.0 The solution was applied to a column of a macroporous non-ionic adsorption resin, HP 20 (60 ml) and eluted with water. Evaporation of fractions containing the object compound (5) was carried out to give D—Lac-(OH)—L—Phe—γ—D—Glu(α—OH)—(L-)—mesoDAP—(L)—GlyOH (5) (0.45 g).

$[\alpha]_D = -5.0°$ (C=0.2, water).

NMR (D$_2$O), δ(ppm): 1.28 (3H, d, J=7 Hz), 1.32~2.28 (10H, m), 3.08 (2H, ABq, J=16 Hz), 3.80 (1H, t, J=7 Hz), 3.96 (2H, s), 4.0~4.44 (4H, m), 7.32 (5H, s).

The following compounds were prepared in substantially the same manner as that of Steps 1 and 2 of Example 1, respectively.

EXAMPLE 20

(1) Step 1

Pivaloyl—L—Ala—γ—D—Glu(α—OH)—(L-)—Boc—(D)—mesoDAP—(D)—NHNHBoc—(L)—GlyOH.

N.M.R. (CD₃OD), δ(ppm): 1.22 (9H, s), 1.38 (2H, d, J=7 Hz), 1.48 (18H, s), 1.34–2.42 (10H, m), 3.95 (2H, s), 4.27–4.60 (4H, m).

(2) Step 2

Pivaloyl—L'Ala—γ—D—Glu(α—OH)—(L-)—mesoDAP—(L)—GlyOH.

N.M.R. (D₂O), δ(ppm): 1.20 (9H, s), 1.37 (3H, d, J=7 Hz), 1.34–2.42 (10H, m), 3.80 (2H, s), 4.10–4.45 (4H, m).

EXAMPLE 21

(1) Step 1

Adamantane—1—carbonyl—L—Ala—γ—D—Glu(α—OH)—(L)—Boc—(D)—mesoDAP—(D-)—NHNHBoc—(L)—GlyOH.

I.R. (Nujol): 3280, 1720 (shoulder), 1630, 1520 cm⁻¹.

(2) Step 2

Adamantane—1—carbonyl—L—Ala—γ—D—Glu(α—OH)—(L)—mesoDAP—(L)—GlyOH.

$[\alpha]_D = -18.9°$ (c=0.18, water).

N.M.R. (D₂O), δ(ppm): 1.46 (3H, d, J=7 Hz), 3.83 (1H, t, J=7 Hz), 3.98 (2H, s), 4.25–4.5 (3H, m).

EXAMPLE 22

(1) Step 1

Lauroyl—L—Ala—γ—D—Glu(α—OH)—(L-)—Boc—(D)—mesoDAP—(D)—NHNHBoc—(L)—GlyOH.

I.R. (Nujol): 3300, 1730 (shoulder), 1650, 1520 cm⁻¹.
N.M.R. (CD₃OD), δ(ppm): 0.96 (3H, m), 3.96 (2H, s).

(22) Step 2

Lauroyl—L'Ala—γ—D—Glu(α—OH)—(L-)—mesoDAP—(L)—GlyOH.

$[\alpha]_D = -30.0°$ (c=0.14, 1N, NaOH).

N.M.R. (D₂O+NaHCO₃), δ(ppm): 0.88 (3H, m), 3.65–3.85 (3H, m), 4.10–4.60 (3H, m).

EXAMPLE 23

(1) Step 1

Salicyloyl(oBzl)—L—Ala—γ—D—Glu(α—OH-)—(L)—Boc—(D)—mesoDAP(D)—NHNHBoc—(L-)—GlyOH.

N.M.R. (CD₃OD), δ(ppm): 1.42 (9H, s), 1.44 (9H, s), 3.87 (2H, s), 5.23 (2H, s), 6.93–7.55 (8H, m), 7.94 (1H, d, d, J=2 and 7 Hz).

(2) Step 2

Salicyloyl—L—Ala—γ—D—Glu(α—OH)—(L-)—mesoDAP—(L)—GlyOH.

$[\alpha]_D = 4.6°$ (c=0.13 water).

N.M.R. (D₂O), δ(ppm): 1.51 (3H, d, J=7 Hz), 3.77 (1H, t, J=7 Hz), 3.91 (2H, s), 6.97–7.10 (2H, m), 7.40–7.55 (1H, m), 7.71–7.79 (1H, m).

EXAMPLE 24

(1) Step 1

α—ethylhexanoyl—L—Ala—γ—D—Glu(α—OH-)—(L)—Boc—(D)—mesoDAP—(D)—NHNH-Boc—(L)—GlyOH.

N.M.R. (CD₃OD), δ(ppm), δ(ppm): 0.88 (6H, t, J=7 Hz), 1.42 (9H, s), 1.54 (9H, s), 1.80–2.36 (19H, m), 3.94 (2H, s).

(2) Step 2

α—ethylhexanoyl—L—Ala—γ—D—Glu(α—OH-)—(L)—mesoDAP—(L)—GlyOH.

$[\alpha]_D = -46.7$ (c=0.12, water).

N.M.R. (D₂O), δ(ppm): 0.81 (6H, t, J=7 Hz), 1.37 (2H, d, J=7 Hz), 3.81 (1H, t, J=7 Hz), 3.96 (2H, s), 4.2–4.5 (3H, m).

EXAMPLE 25

(1) Step 1

Nicotinoyl—L—Ala—γ—D—Glu(α—OH)—(L-)—Boc—(D)—mesoDAP—(D)—NHNHBoc—(L)—GlyOH

N.M.R. (CD₃OD), δ(ppm): 1.40 (18H, m), 3.90 (2H, s), 7.50 (1H, d, d, J=8 and 5 Hz), 8.31 (1H, s), 8.69 (1H, m), 9.11 (1H, m).

(2) Step 2

Nicotinoyl—L—Ala—γ—D—Glu(α—OH)—(L-)—mesoDAP—(L)—GlyOH.

$[\alpha]_D = -7.7°$ (c=0.22, water).

N.M.R. (D₂O), δ(ppm): 1.56 (3H, d, J=7 Hz), 3.83 (1H, t, J=6 Hz), 3.95 (2H, s), 7.94 (1H, d, d, J=8 and 4 Hz), 8.85 (1H, m), 9.10 (1H, m).

EXAMPLE 26

(1) Step 1

Stearoyl—L—Ala—65 —D—Glu(α—OH)—(L-)—Boc—(D)—mesoDAP—(L)—GlyOH.

I.R. (Nujol): 3300, 1720, 1630, 1530 cm⁻¹.

N.M.R. (CD₃OD+CDCl₃), δ(ppm): 0.80 (3H, m) 3.95 (2H, s).

(2) Step 2

Stearoyl—L—Ala—γ—D—Glu(α—OH)—(L-)—mesoDAP—(L)—GlyOH $[\alpha]_D = -30.8°$ (c=0.13, 1N NaOH).

I.R. (Nujol): 3280, 1730, 1630, 1530 cm⁻¹.

NMR (NaoD+D₂o) δ(ppm) 0.83 (3H, m), 3.24 (1H, m), 3.82 (2H, s).

EXAMPLE 27

(1) Step 1

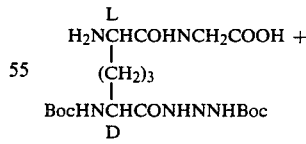

(1)

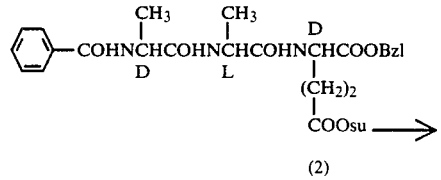

(2)

-continued

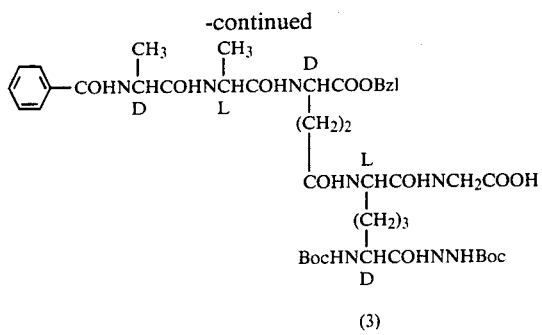

(3)

To a mixture of Boc—(D)—mesoDAP—(D-)—NHNHBoc—(L)—GlyOH (1) (0.46 g) and triethylamine (0.11 g) in a mixture (20 ml) of dioxane and water (2:1) was added benzoyl—D—Ala—L—Ala—D—Glu(γ—OSu)oBzl (2) (0.58 g).

The resulting mixture was stirred at ambient temperature for 18 hours. After evaporation of dioxane, the remaining aqueous layer was acidified to pH 1 with dil. hydrochloric acid and extracted with ethyl acetate.

The extract was washed with water, dried and evaporated. The residue was triturated with ether to give benzoyl—D—Ala—L—Ala—γ—D—Glu(α—oBzl)—(L)—Boc—(D)—meso—DAP—(D)—NHNH-Boc—(L)—GlyOH (3) (0.64 g).

I.R. (Nujol): 3290, 1720, 1680, 1640 cm⁻¹.

(2) Step 2

Compound (3) ⟶

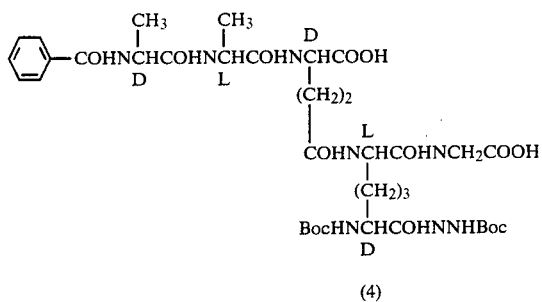

(4)

To a solution of benzoyl—D—Ala—L—Ala—γ—D—Glu(α—oBzl)—(L)—Boc—(D)—mesoDAP—(D)—NHNHBoc—(L)—GlyOH (3) (0.58 g) in a mixture (30 ml) of methanol and water (2:1) was added 10% palladium carbon and the mixture was shaken under three atmospheric pressure of hydrogen for 3 hours. The catalyst was filtered off and the filtrate was evaporated. The residue was triturated with ether to give benzol—D—Ala—L—Ala—γ—D—Glu(α—OH)—(L-)—Boc—(D)—mesoDAP—(D)—NHNHBoc—(L)—GlyOH (4) (0.44 g).

I.R. (Nujol): 3250, 1720, 1660-1360 cm⁻¹.

(3) Step 3

Compound (4) ⟶

-continued

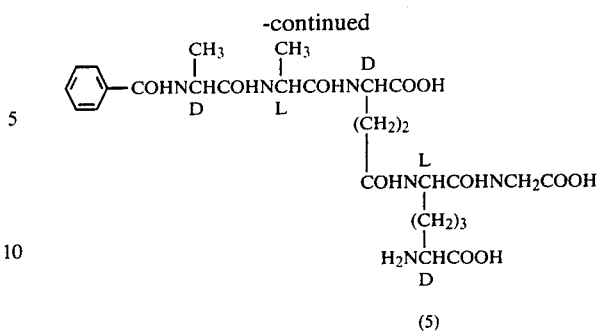

(5)

Benzoyl—D—Ala—L—Ala—γ—D—Glu(α—OH-)—(L)—Boc—(D)—mesoDAP—(D)—NHNH-Boc—(L)—GlyOH (0.40 g) was dissolved in trifluoroacetic acid (6 ml) at 0° C. and the solution was stirred at the same temperature for an hour. After evaporation of trifluoroacetic acid, a small amount of benzene was added to the residue and the mixture was evaporated. The residue was dissolved in water (3 ml) and the solution was acidified with 1N sulfuric acid (0.5 ml). To the solution was added dropwise a solution of sodium periodate (0.14 g) in water (3 ml) at 0° C. After stirring for an hour, sodium bisulfate was added thereto until the color of the reaction mixture became clear. After adjustment of the pH to 3.2, the reaction mixture was concentrated to about 4 ml. The concentrate was put on a column of a macroporous non-ionic adsorption resin, HP 20 (20 ml) and, after washing with water, eluted with 30% aqueous methanol. The fractions containing the object compound (5) were concentrated and the concentrate was lyophilized to give benzoyl—D—Ala—L—Ala—γ—D—Glu(α—OH)—(L-)—mesoDAP—(L)—GlyOH (5) (120 mg).

N.M.R. (D₂O), δ(ppm): 1.50 (3H, d, J=7 Hz), 1.57 (3H, d, J=7 Hz), 1.42-2.42 (10H, m), 3.95 (2H, s), 3.37-4.67 (5H, m), 7.54-7.95 (5H, m).

The following compounds were prepared in substantially the same manner as that of Steps 1-3 of Example 27.

EXAMPLE 28

(1) Step 1

Acetyl—D—Ala—L—Ala—γ—D—Glu(α—oBzl)—(L)—Boc—(D)—mesoDAP—(D)—NHNH-Boc—(L)—GlyOH.

N.M.R. (CD₃OD), δ(ppm): 1.40 (18H, s), 1.33 (6H, d, J=7 Hz), 1.92 (3H, s), 1.84-2.30 (10H, m), 3.88 (2H, s), 3.84-4.25 (5H, m), 5.12 (2H, s), 7.30 (5H, m).

(2) Step 2

Acetyl—D—Ala—L—Ala—γ—D—glu(α—oBzl)—(L)—mesoDAP—(L)—GlyOH.

N.M.R. (CD₃OD), δ(ppm): 1.32 (6H, d, J=7 Hz), 1.34-2.32 (10H, m), 1.90 (3H, s), 3.79-4.25 (5H, m), 3.89 (2H, s), 5.12 (2H, s), 7.30 (5H, s).

(3) Step 3

Acetyl—D—Ala'L—Ala—γ—D—Glu(α—OH-)—(L)'mesoDAP—(L)—GlyOH.

N.M.R. (D₂O), δ(ppm): 1.32 (3H, d, J=7 Hz), 1.40 (3H, d, J=7 Hz), 1.25-2.38 (10H, m), 3.80 (1H, t, J=6 Hz), 3.96 (2H, s), 4.24-4.42 (4H, m).

EXAMPLE 29

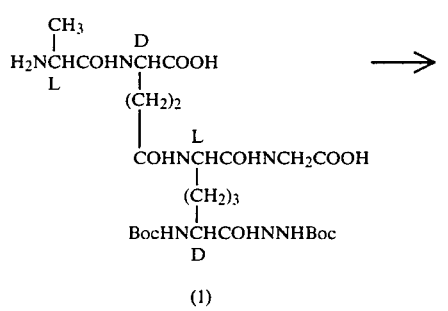

(1)

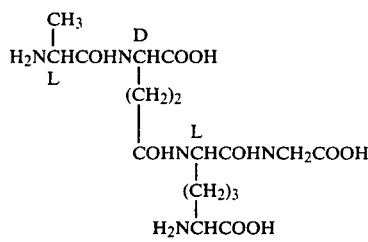

(2)

L—Ala—γ—D—Glu(α—OH)—(L)—Boc—(D-)—mesoDAP—(D)—NHNHBoc—(L)—GlyOH (1) (662 mg) was added to trifluoroacetic adid (4 ml) and the mixture was stirred at ambient temperature for 50 minutes. After removal of trifluoroacetic acid by evaporation, the residue was dissolved in water (20 ml) and cooled to 0° C. To this cooled solution were added 0.1N sulfuric acid (25 ml) and a solution of sodium periodate (535 mg) in water (5 ml). The mixture was stirred at the same temperature for an hour, during which time the reaction solution turned dark brown. Sodium bisulfate was added until the color was clear and the mixture was adjusted to pH 3 with dil. sodium bicarbonate. After concentration of the mixture, the residue was dissolved in a small amount of water and adjusted again to pH 3. The solution was put on a column of a macroporous non-ionic adsorption resin, HP 20 (130 ml) and eluted with water. The fraction containing the object compound (2) was concentrated. This chromatograph operation was repeated, and the fraction containing the object compound (2) was lyophilized to give an amorphous solid (220 mg). A 180 mg portion of the solid was further purified by column chromatograph using an active carbon (20 ml) and eluted with a mixture of water and acetone (4:1). The eluate was evaporated and the residue was pulverized with acetone to give L—Ala—γ—D—Glu(α—OH)—(L)—mesoDAP—(L-)—GlyOH (2) (90 mg).

$[α]_D = -10.6$ (C=0.34 water).

N.M.R. (D$_2$O), δ(ppm): 1.55 (3H, d, J=7 Hz), 3.75 (1H, t, J=7 Hz), 3.86 (2H, s), 4.05–4.45 (m).

EXAMPLE 30

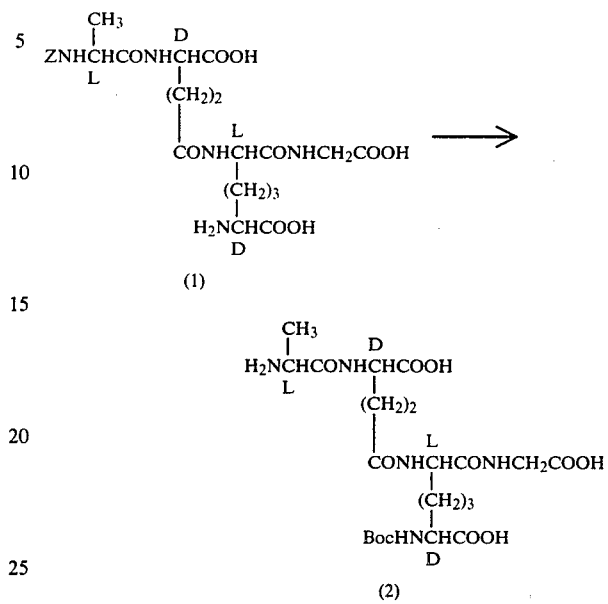

To a solution of Z—L—Ala—γ—D—Glu(α—OH-)—(L)—mesoDAP—(L)—GlyOH (1) (2.04 g) and sodium bicarbonate (890 mg) in a 50% aqueous dioxane (40 ml) was added ditertbutyldicarbonate (1.53 g). After stirring for 4 hours at ambient temperature, additional ditertbutyldicarbonate (770 mg) 1N sodium hydroxide (0.6 ml) was added thereto and the mixture was stirred for 2.5 hours. To the mixture was added acetic acid (5 ml) and the resulting mixture was hydrogenated over 10% palladium black (300 mg) under an atmospheric pressure of hydrogen.

After the catalyst was filtered off, the filtrate was evaporated in vacuo. The residue was dissolved in water (5 ml) and put on a column of macroporous non-ionic adsorption resin, HP 20 (120 ml). The fractions eluted with a mixture of water and methanol (7:3) were combined and concentrated to give L—Ala—γ—D—Glu(α—OH)—(L)—Boc—(D)—mesoDAP—(L)—GlyOH (2) (1.17 g).

I.R. (Nujol): 3280, 1650 (shoulder), 1520 (shoulder).
N.M.R. (D$_2$O), δ(ppm): 1.42 (9H, s), 1.55 (3H, d, J=7 Hz), 3.93 (2H, s), 4.04–4.50 (4H, m).

EXAMPLE 31

(1) Step 1

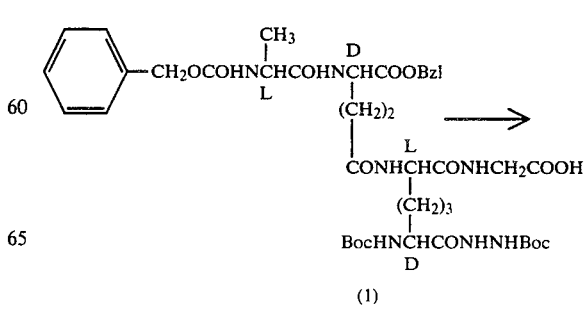

(1)

-continued

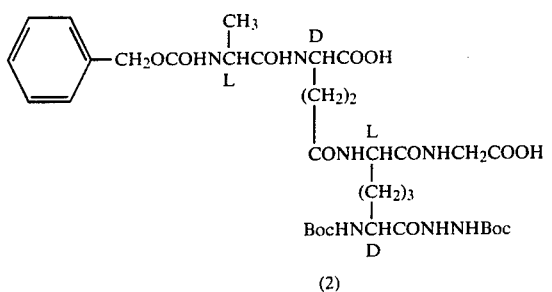

(2)

To a suspension of benzyloxycarbonyl—L—Ala—γ—D—Glu(α—oBzl)—(L-)—Boc—(D)—mesoDAP—(D)—NHNHBoc—(L)—GlyOH (1) (4.43 g) in a mixture of 50% aqueous methanol was added 1N sodium hydroxide (11 ml) at 0° C. After stirring for an hour at the same temperature, the reaction mixture was concentrated to about 30 ml, adjusted to pH 2 with 1N hydrochloric acid, and then extracted with ethyl acetate (300 ml). The organic layer was washed with 0.5N hydrochloric acid (30 ml) and brine, dried over magnesium sulfate and then concentrated in vacuo to give a white powder which was washed with ether. The powder was collected by filtration to give benzyloxycarbonyl—L—Ala—γ—D—Glu(α—OH)—(L)—Boc—(D)—mesoDAP—(D)—NHNHBoc—(L)—GlyOH (2) (3.46 g).

N.M.R. (CD$_3$OD), δ(ppm): 1.50 (18H, s), 3.98 (2H, s), 4.00–4.70 (4H, m), 5.17 (2H, s), 7.40 (5H, s).

(2) Step 2

Compound (2) ⟶

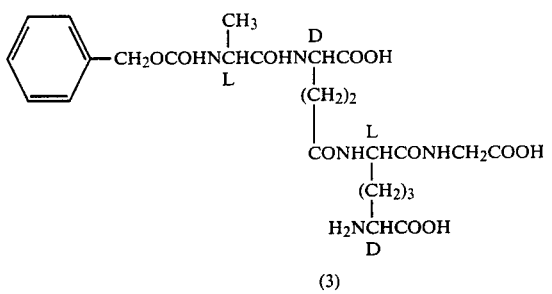

(3)

Benzyloxycarbonyl—L—Ala—γ—D—Glu(α—OH)—(L)—Boc—(D)—mesoDAP—(D)—NHNH-Boc—(L)—GlyOH (2) (3.30 g) was added to trifluoroacetic acid (15 ml) and the mixture was allowed to stand at ambient temperature for 30 minutes. The mixture was evaporated in vacuo and the residual oil was triturated with ether to give a powder (3.38 g). The solid was dissolved in water (60 ml) and to the solution were added 1N sulfuric acid and sodium periodate (1.78 g) at 0° C. After stirring at the same temperature for an hour, the reaction mixture was treated with sodium bisulfite, concentrated to about 5 ml, adjusted to pH 2 with 1N sodium hydroxide and put on a column of macroporous non-ionic adsorption resin, HP 20 (400 ml). The fraction eluted with a mixture of water and methanol (6:4) were combined and evaporated in vacuo to give benzyloxycarbonyl—L—Ala—γ—D—Glu(α—OH)—(L-)—mesoDAP—(L)—GlyOH (3) (1.03 g).

mp 205°–207° C.

N.M.R. (D$_2$O), δ(ppm): 1.37 (3H, d, J=7 Hz), 3.78 (1H, m), 3.93 (2H, s), 4.05–4.40 (3H, m), 5.14 (2H, s), 7.45 (5H, s).

EXAMPLE 32

(1) Step 1

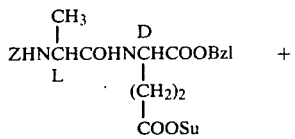

(1)

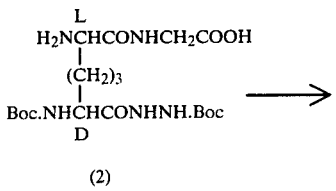

(2)

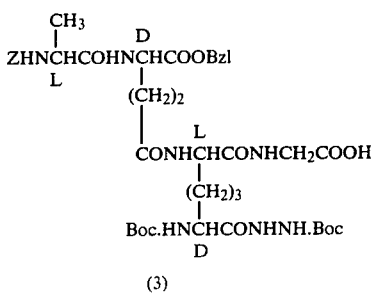

(3)

Triethylamine (720 mg) and Z—L—Ala—D—Glu(oSu)oBzl (1) (3.51 g) was added to a solution of Boc—(D)—meso—DAP—(D)—NHNHBoc—(L)—GlyOH (2) (3.00 g) in a mixture of dioxane (90 ml) and water (70 ml). The resulting mixture was allowed to stand at ambient temperature for 18 hours, and concentrated to about 50 ml. The concentrate was adjusted to pH 3 with 1N hydrochloric acid and extracted with ethyl acetate (300 ml) containing methanol (20 ml). The organic layer was washed with brine (100 ml), dried over sodium sulfate and then evaporated in vacuo. The residue was washed with ether and filtered to give Z—L—Ala—γ—D—Glu(α—oBzl)—(L)—Boc—(D-)—meso—DAP—(D)—NHNHBoc—(L)—GlyOH (3) (5.53 g).

N.M.R. (DMSO-d$_6$), δ(ppm): 1.07 (3H, d, J=7 Hz), 3.65–4.48 (6H, m), 5.04 (2H, s), 5.12 (2H, s), 6.56 (1H, d, J=8 Hz), 7.35 (10H, s), 7.95 (1H, d, J=8 Hz), 8.15 (1H, m), 8.35 (1H, d, J=8 Hz), 8.70 (1H, s), 9.56 (1H, s).

(2) Step 2

Compound (3) ⟶

-continued

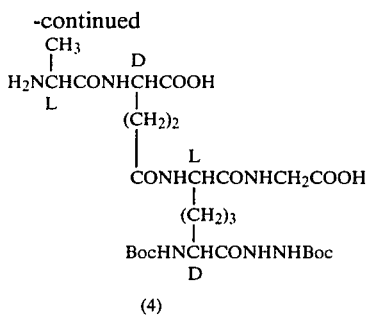
(4)

A solution of compound (3) (5.26 g) in acetic acid (120 ml) was hydrogenated over 10% palladium black (2.0 g) under an atmospheric pressure of hydrogen. After the catalyst was filtered off and washed with acetic acid, the filtrate and the washings were combined and then evaporated in vacuo. The residual oil was triturated with ether to give L—Ala—γ—D—Glu(α—OH)—(L)—Boc—(D)—mesoDAP—(D-)—NHNHBoc—(L)—GlyOH (4) (3.90 g).

I.R. (Nujol): 3250, 1660 (shoulder), 1515 cm$^{-1}$.

N.M.R. (D$_2$O), δ(ppm): 1.54 (3H, d, J=8 Hz), 3.88 (2H, s), 3.95–4.50 (4H, m).

The following compounds were prepared in substantially the same manner as that of Steps 1 and 2 of Example 1, respectively.

EXAMPLE 33

(1) Step 1

Diphenylacetyl—L—Ala—γ—D—Glu(α—OH-)—(L)—Boc—(D)—mesoDAP—(D)—NHNH-Boc—(L)—GlyOH.

N.M.R. (CD$_3$OD), δ(ppm): 1.42 (18H, s), 3.92 (2H, s), 3.83–4.52 (4H, m), 5.08 (1H, s), 7.29 (10H, s).

(2) Step 2

Diphenylacetyl—L—Ala—γ—D—Glu(α—OH-)—(L)—mesoDAP—(L)—GlyOH.

N.M.R. (D$_2$O+NaHCO$_3$), δ(ppm): 1.40 (3H, d, J=7 Hz), 1.20–2.25 (10H, m), 3.71 (1H, m), 3.80 (2H, s), 4.10–4.50 (3H, m), 5.17 (1H, s), 7.35 (10H, s).

EXAMPLE 34

(1) Step 1

N—(N—Benzyloxycarbonyl—L—5—oxo—2—pyrrolidine—carbonyl)—L—Ala—γ—D—Glu(α—OH-)—(L)—Boc—(D)—mesoDAP—(D)—NHNH-Boc—(L)—GlyOH.

N.M.R. (CD$_3$OD), δ(ppm): 1.47 (18H, s), 3.97 (2H, s), 5.27 (2H, s), 7.39 (5H, s)

(2) Step 2

N—(N—Benzyloxycarbonyl—L—5—oxo—2—pyrrolidinecarbonyl)—L—Ala—γ—D—Glu(α—OH-)—(L)—mesoDAP—(L)—GlyOH

[α]$_D$= −55.0° (C=0.14, water).

N.M.R. (D$_2$O), δ(ppm): 1.18 (3H, d, J=7 Hz), 1.3–2.8 (14H, m), 3.80 (1H, t, J=7 Hz), 3.94 (2H, s), 5.19 (2H, ABq), 7.39 (5H, s).

(3) Step 3

L—5—oxo—2—pyrrolidinecarbonyl—L—Ala—γ—D—Glu(α—OH)—(L-)—mesoDAP—(L)—GlyOH.

N.M.R. (D$_2$O), δ(ppm): 1.42 (3H, d, J=7 Hz), 3.79 (1H, t, J=7 Hz), 3.95 (2H, s), 4.15–4.50 (4H, m).

EXAMPLE 35

(1) Step 1

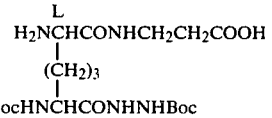
(1)

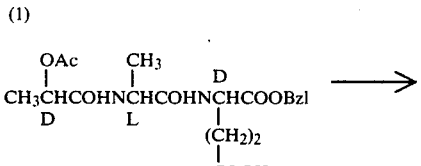
(2)

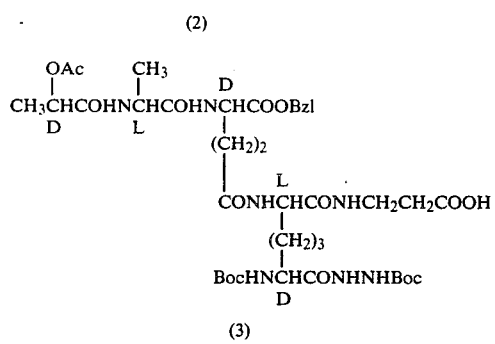
(3)

D—Lac(OAc)—L—Ala—γ—D—Glu(α—OBzl)—(L)—Boc—(D)—mesoDAP—(D)—NHNH-Boc—(L)—β—AlaOH(3) was prepared in substantially the same manner as the step 1 of Example 12 from compound (1) and (2).

N.M.R. (DMSO-d$_6$) δ (ppm): 0.9–2.6(16H, m), 1.38(18H, S), 2.05(3H, S), 2.9–4.7(8H, m), 5.00 (1H, q, J=7 HZ), 5.14(2H, S), 6.5–6.7(1H, m), 7.39(5H, S), 7.7–8.4(4H, m), 8.65(1H, broad S), 9.55(1H, broad S).

(2) Step 2

Compound (3) ⟶

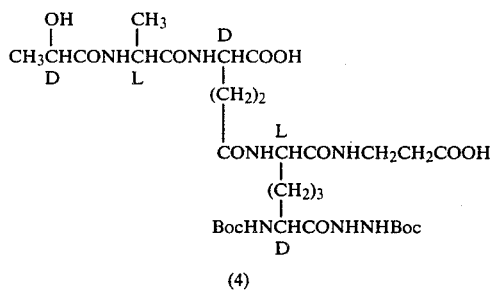
(4)

D—Lac—L—Ala—γ—D—Glu(α—OH)—(L-)—Boc—(D)—mesoDAP—(D)—NHNHBoc—(L-)—β—AlaOH (4) was prepared in substantially the same manner as the step 2 of Example 12 from compound (3).

N.M.R. (D$_2$O), δ(ppm): 1.1–2.8(16H, m), 1.38(18H, S), 2.55(2H, t, J=7 HZ), 3.43(2H, t, J=7 HZ), 3.8–4.5(5H, m).

(3) Step 3

Compound (4) ⟶

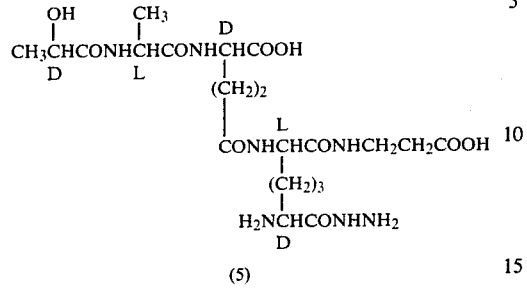

(5)

Di-trifluoroacetic acid salt of D—Lac—L—Ala—γ—D—Glu(α—OH)—(L-)—mesoDAP—(D)—NHNH$_2$—(L)—β—AlaOH (5) was prepared in substantially the same manner the step 3 of Example 12 from compound (4).

N.M.R. (D$_2$O), δ(ppm): 1.1–2.8(10H, m), 1.37(3H, d, J=7 HZ), 1.42(3H, d, J=7 HZ), 2.58(2H, t, J=6 HZ), 3.47(2H, t, J=6 HZ), 2.9–4.6(5H, m).

(4) Step 4

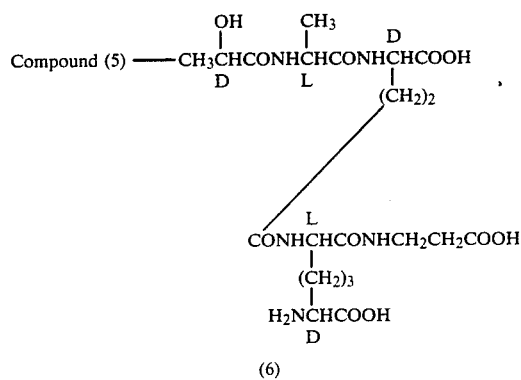

(6)

D—Lac—L—Ala—γ—D—Glu(α—OH)—(L-)—mesoDAP—(L)—β—AlaOH (6) was prepared in substantially the same manner as the step 4 of Example 12 for compound (5).

N.M.R. (D$_2$O), δ(ppm): 1.37(3H, d, J=7 HZ), 1.44(3H, d, J=7 HZ), 1.2–2.7(10H, m), 2.61(2H, t, J=7 HZ), 3.47(2H, t, J=7 HZ), 3.83(1H, t, J=6 HZ), 4.0–4.6(4H, m).

EXAMPLE 36

(1) Step 1

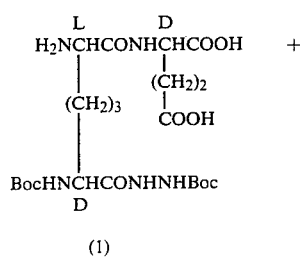

(1)

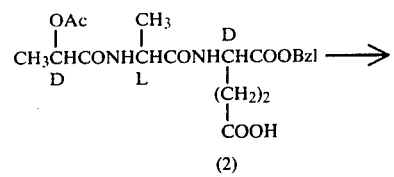

(2)

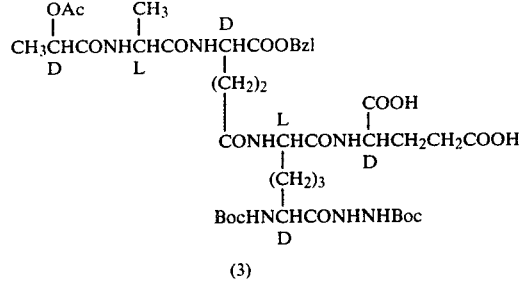

(3)

D—Lac(OAc)—L—Ala—γ—D—Glu(α—OBz-l)—(L)—Boc—(D)—mesoDAP—(D)—NHNH-Boc—(L)—D—GluOH(3) was prepared in substantially the same manner as the step 1 of Example 12 from compounds (1) and (2).

N.M.R. (DMSO-d$_6$), δ(ppm): 0.9–2.5(14H, m), 1.40(18H, S), 2.07(3H, S), 3.6–4.6(5H, m), 4.99(1H, q, J=7 HZ), 5.15(2H, S), 6.5–6.9(1H, m), 7.39(5H, S), 7.7–9.1(5H, m), 9.55(1H, broad S).

(2) Step 2

Compound (3) ⟶

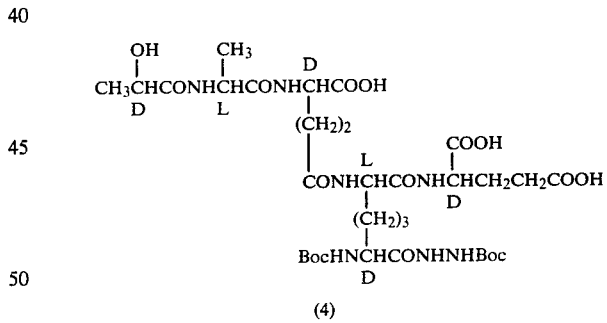

(4)

D—Lac(OH)—L—Ala—γ—D—Glu(α—OH)—(L-)—Boc—(D)—mesoDAP—(D)—NHNHBoc—(L-)—D—GluOH (4) was prepared in substantially the same manner as the step 2 of Example 12 from compound (3).

N.M.R. (D$_2$O), δ(ppm): 1.3–2.8(14H, m), 1.45(18H, S), 3.9–4.6(6H, m).

(3) Step 3

Compound (4) ⟶

-continued

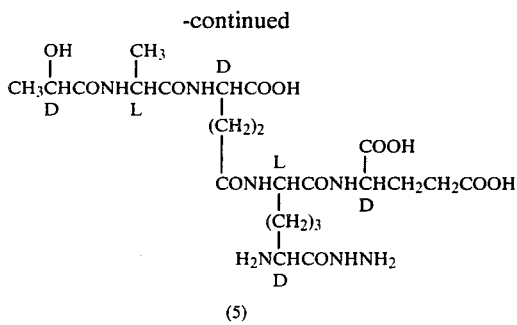

(5)

Di-trifluoroacetic acid salt of D—Lac—L—Ala—γ—D—Glu(α—OH)—(L-)—mesoDAP—(D)—NHNH$_2$—(L)—D—GluOH (5) was prepared in substantially the same manner as the step 3 of Example 12 from compound (4).

N.M.R. (D$_2$O), δ(ppm): 1.1–2.7(m), 1.35(3H, d, J=7 HZ), 1.42(3H, d, J=7 HZ), 3.9–4.6(6H, m).

(4) Step 4

Compound (5) ⟶

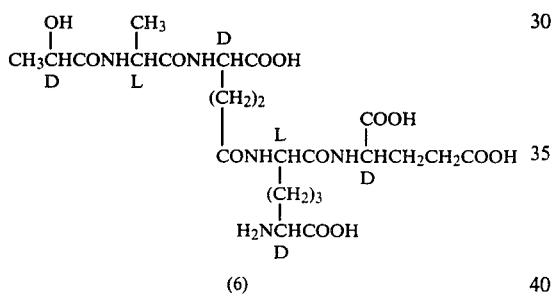

(6)

D—Lac—L—Ala—γ—D—Glu(α—OH)—(L-)—mesoDAP—(L)—D—GluOH (6) was prepared in substantially the same manner as the step 4 of Example 12 from compound (5).

EXAMPLE 37

(1) Step 1

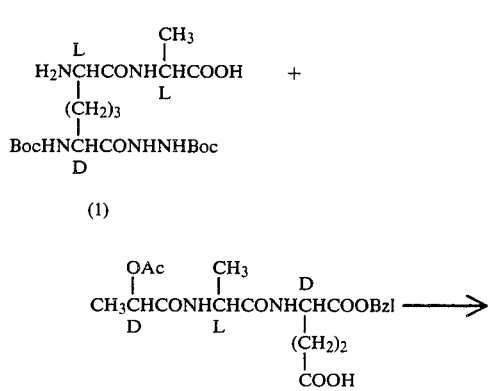

-continued

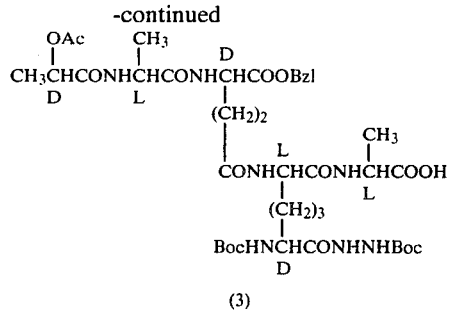

(3)

D—Lac(OAc)—L—Ala—γ—D—Glu(α—OBzl)—(L)—Boc—(D)—mesoDAP—(D)—NHNHBoc—(L)—L—AlaOH (3) was prepared in substantially the same manner as the step 1 of Example 12 from compounds (1) and (2).

N.M.R. (DMSO-D$_6$), δ(ppm): 1.0–2.4(19H, m), 1.43(18H, S), 2.10(3H, S), 3.8–4.8(5H, m), 5.04(1H, q, J=7 HZ), 5.19(2H, S), 6.5–7.10(1H, m), 7.42(5H, S), 7.7–8.9(5H, m), 9.61(1H, broad S).

(2) Step 2

Compound (3) ⟶

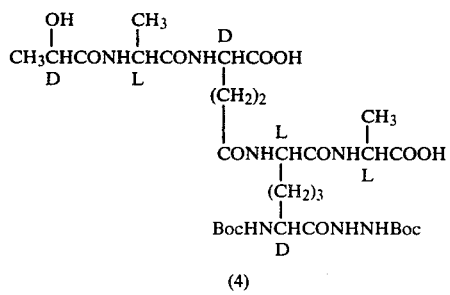

(4)

D—Lac(OH)—L—Ala—γ—D—Glu(α—OH)—(L-)—Boc—(D)—mesoDAP—(D)—NHNHBoc—(L-)—L—AlaOH (4) was prepared in substantially the same manner as the step 2 of Example 12.

N.M.R. (D$_2$O), δ(ppm): 1.3–2.8(19H, m), 1.45(18H, S), 3.9–4.6(6H, m).

(3) Step 3

Compound (4) ⟶

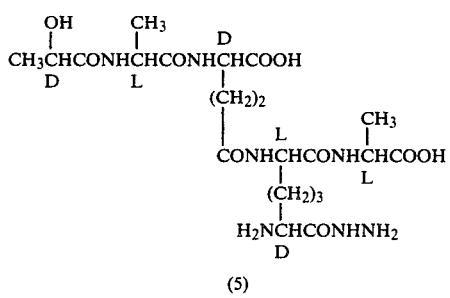

(5)

Di-trifluoroacetic acid salt of D—Lac(OH-)—L—Ala—γ—D—Glu(α—OH)—(L-)—mesoDAP—(D)—NHNH$_2$—(L)—Ala(OH) (5) was prepared in substantially the same manner as the step 3 of Example 12 from compound (4).

N.M.R. (D₂O), δ(ppm): 1.2-2.7(10H, m), 1.39(3H, d, J=7 HZ), 1.44(6H, d, J=7 HZ), 3.9-4.7(6H, m).
(4) Step 4

N.M.R. (D₂O), δ(ppm): 1.37(3H, d, J=7 HZ), 1.43(6H, d, J=7 HZ), 1.2-2.5(10H, m), 3.8(1H, t, J=6 HZ), 4.1-4.5(5H, m).

EXAMPLE 38
(1) Step 1

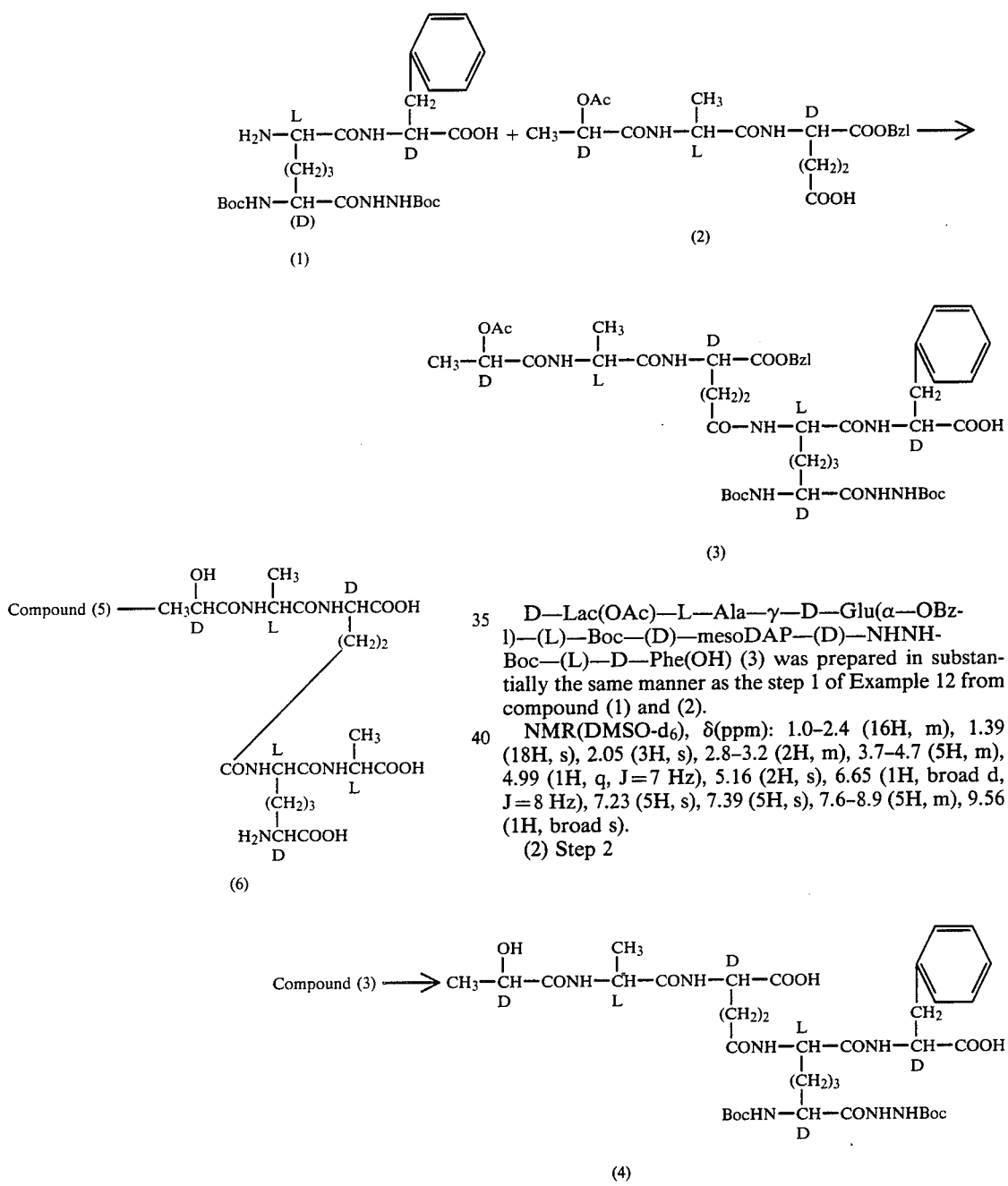

D—Lac(OAc)—L—Ala—γ—D—Glu(α—OBzl)—(L)—Boc—(D)—mesoDAP—(D)—NHNHBoc—(L)—D—Phe(OH) (3) was prepared in substantially the same manner as the step 1 of Example 12 from compound (1) and (2).

NMR(DMSO-d₆), δ(ppm): 1.0-2.4 (16H, m), 1.39 (18H, s), 2.05 (3H, s), 2.8-3.2 (2H, m), 3.7-4.7 (5H, m), 4.99 (1H, q, J=7 Hz), 5.16 (2H, s), 6.65 (1H, broad d, J=8 Hz), 7.23 (5H, s), 7.39 (5H, s), 7.6-8.9 (5H, m), 9.56 (1H, broad s).

(2) Step 2

D—Lac(OH)—L—Ala—γ—D—Glu(α—OH)—(L)—Boc—(D)—mesoDAP—(D)—NHNHBoc—(L)—D—PheOH (4) was prepared in substantially the same manner as step 2 of Example 12 from compound (3).

I.R. (Nujol): 3270, 1720 (shoulder), 1645 (broad), 1520 (broad) cm⁻¹.

(3) Step 3

D—Lac(OH)—L—Ala—γ—D—Glu(α—OH)—(L)—mesoDAP—(L)—L—Ala(OH) (6) was prepared in substantially the same manner as the step 4 of Example 12 from compound (5).

[α]_D = −41.0(C=0.42, water).

Compound (4) ⟶ 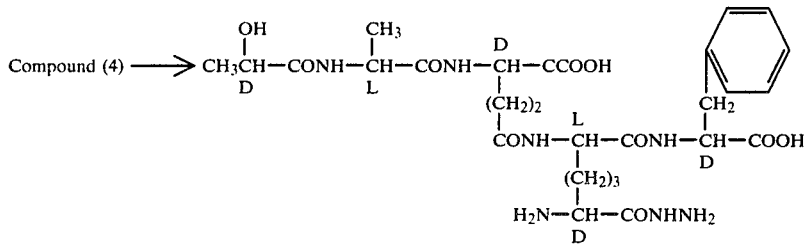

(5)

Di-trifluoroacetic acid salt of D—Lac(OH-)—L—Ala—γ—D—Glu (α—OH)—(L-)—mesoDAP—(D)—NHNH₂—(L)—D—PheOH (5) was prepared in substantially the same manner as the step 3 of Example 12 from compound (4).

N.M.R. (D₂O), δ(ppm): 1.1–2.7(10 H, m), 1.46(3H, d, J=7 Hz), 1.50 (3H, d, J=7 Hz), 2.8–3.5 (2H, m), 3.9–4.7 (6H, m), 7.41 (5H, s).

(4) Step 4

Compound (5) ⟶ 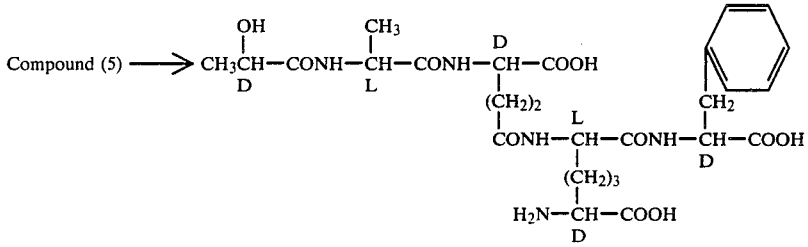

D—Lac(OH)—L—Ala—γ—D—Glu(α—OH)—(L-)—mesoDAP—(L)—D—PheOH (6) was prepared in substantially the same manner as the step 4 of Example 12 from compound (5).

[α]$_D$ = −28.6° (c=0.511 water).

N.M.R. (D₂O), δ(ppm): 1.1–2.5 (10H, m), 1.36 (3H, d, J=7 Hz), 1.42 (3H, d, J=7 Hz), 3.14 (2H), 4.0–4.5 (5H, m), 7.1–7.5 (5H, m).

EXAMPLE 39

(1) Step 1

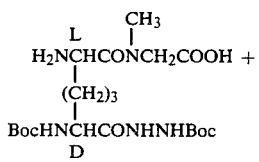

(1)

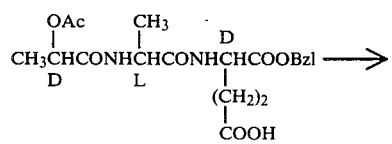

(2)

-continued

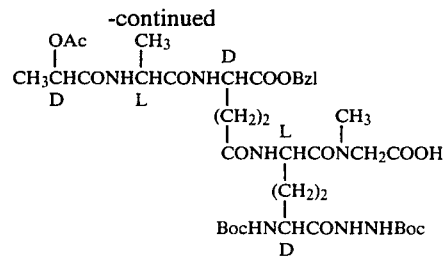

(3)

D—Lac(oAc)—L—Ala—γ—D—Glu(α-oBzl)—(L-)—Boc—(D)—mesoDAP—(D)—NHNHBoc—(L-)—SarOH (3) was prepared in substantially the same manner as the step 1 of Example 12 from compounds (1) and (2).

N.M.R. (DMSO-d6), δ(ppm): 1.0–2.4 (16H, m), 1.35 (18H, s), 2.03 (3H, s), 2.80 and 3.05 (3H, a pair of singlets), 3.6–4.5 (6H, m), 4.98 (1H, q, J=7 Hz), 5.13 (2H, s), 6.5–7.0 (1H, m), 7.3 (1H, m), 7.35 (5H, s), 7.7–9.0 (4H, m).

(2) Step 2

Compound (3) ⟶

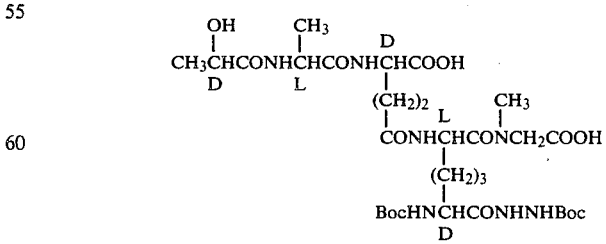

(4)

D—Lac(OH)—L—Ala—γ—D—Glu(α—OH)—(L-)—Boc—(D)—mesoDAP—(D)—NHNHBoc—(L)—

Sar OH (4) was prepared in substantially the same manner as the step 2 of Example 12 from compound 3.

N.M.R. (D$_2$O), δ(ppm): 1.1–2.5 (16H, m), 1.41 (9H, s), 1.43 (9H, s), 2.93 and 3.18 (3H, a pair of singlets), 3.7–4.5 (7H, m).

(3) Step 3

Compound (4) ⟶

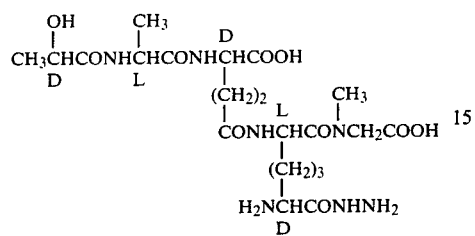

(5)

Di-trifluoroacetric acid salt of D—Lac(OH-)—L—Ala—γ—D—Glu(α—OH)—(L-)—mesoDAP—(D)—NHNH$_2$—(L)—Sar OH (5) was prepared in substantially the same manner as step 3 of Example 12 from Compound (4).

N.M.R. (D$_2$O), (ppm): 1.0–2.6 (10H, m), 1.35 (3H, d, J=7 Hz), 1.41 (3H, d, J=7 Hz), 2.93 and 3.17 (3H, a pair of singlets), 3.8–4.6 (7H, m).

(4) Step 4

Compound (5) ⟶

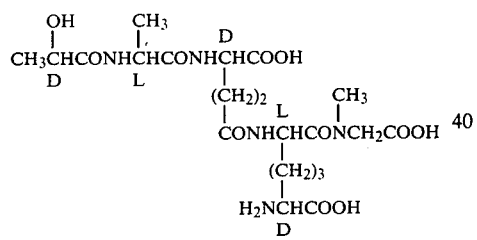

(6)

D—Lac(OH)—L—Ala—γ—D—Glu(α—OH)—(L-)—mesoDAP—(L)—Sar OH (6) was prepared in substantially the same manner as the step 4 of Example 12 from compound (5).

[α]$_D$ = −37.6° (C=0.402, water).

N.M.R. (D$_2$O), δ(ppm): 1.1–2.5 (10H, m), 1.35 (3H, d, J=7 Hz), 1.41 (3H, d, J=7 Hz), 2.96 and 3.20 (3H, a pair of singlet), 3.70–4.0 (1H, m), 4.0–4.6 (6H, m).

EXAMPLE 40

(1) Step 1

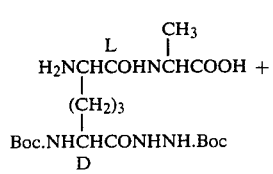

(1)

-continued

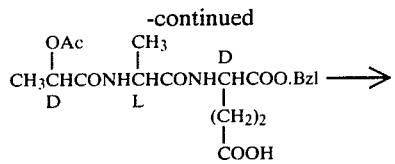

(2)

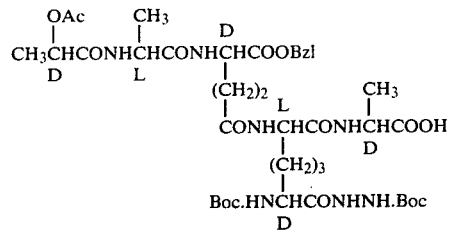

(3)

D—Lac(OAc)—L—Ala—γ—D—Glu(α—OBz-l)—(L)—Boc—(D)—(D)—meso DAP—(D)—NHNH-Boc—(L)—D—AlaOH (3) was prepared in substantially the same manner as step 1 of Example 12 from compounds (1) and (2).

NMR (DMSO-d$_6$), δ(ppm): 0.9–2.6(37H, m), 2.10(3H, s), 3.7–4.7(5H, m), 5.01(1H, q, J=7 Hz), 5.19(2H, s), 6.6–7.0(1H, m), 7.42 (5H, s), 7.7–8.9(5H, m), 9.60(1H, broad s).

(2) Step 2

Compound (3) ⟶

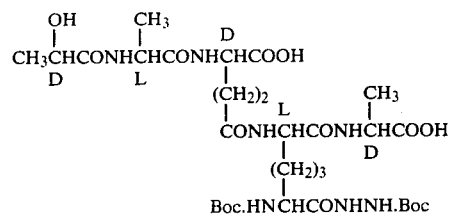

(4)

D—Lac(OH)—L—Ala—γ—D—Glu(α—OH)—(L-)—Boc—(D)—meso DAP—(D)—NHNH.Boc—(L-)—D—AlaOH (4) was prepared in substantially the same manner as the step 2 of Example 12 from compound (3).

NMR (D$_2$O), δ(ppm): 1.3–2.7(19H, m), 1.48(18H, s), 3.9–4.7(6H, m).

(3) Step 3

Compound (4) ⟶

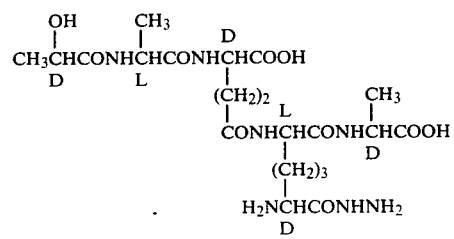

Di-trifluoroacetic acid salt of D—Lac(OH-)—L—Ala—γ—D—Glu(α—OH)—(L)—meso DAP—(D)—NHNH₂—(L)—D—AlaOH (5) was prepared in substantially the same manner as the step 3 of Example 12 from compound (4).

NMR(D₂O), δ(ppm): 1.36(3H, d, J=7 Hz), 1.41(6H, d, J=7 Hz), 1.1–2.7(10H, m), 3.9–4.7(6H, m).

(4) Step 4

Compound (5) ⟶

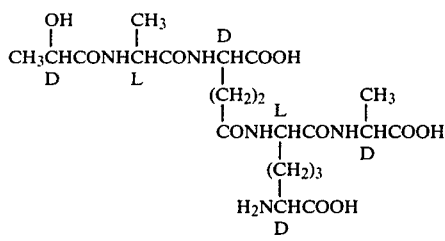

(6)

D—Lac(OH)—L—Ala—γ—D—Glu(α—OH)—(L)—mesoDAP—(L)—D—AlaOH (6) was prepared in substantially the same manner as the step 4 of Example 12.

[α]_D = −17.4° (C=0.305, water).

NMR(D₂O), δ(ppm): 1.38(3H, d, J=7 Hz), 1.41(3H, d, J=7 Hz), 1.44(3H, d, J=7 Hz), 1.2–2.6(10H, m), 3.84(1H, t, J=6 Hz), 4.1–4.6(5H, m).

The following compounds were prepared in substantially the same manner as that of Steps 1 and 2 of Example 1, respectively.

EXAMPLE 41

(1) Step 1

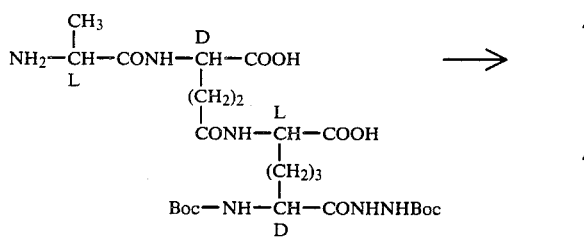

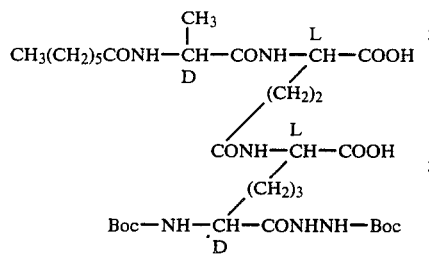

N.M.R. (DMSO-d₆), δ(ppm): 0.80–2.40 (44H, m), 3.67–4.67 (4H, m), 6.70 (1H, d, J=7 Hz), 7.83 (1H, d, J=7 Hz), 8.03 (2H, d, J=7 Hz), 8.60 (1H, s), 9.53 (1H, s).

(2) Step 2

Compound (2) ⟶

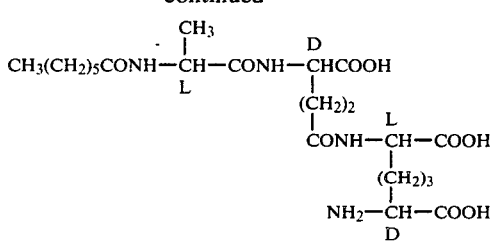

(3)

N.M.R. (D₂O), δ(ppm): 0.84 (3H, t, J=7 Hz), 1.36 (3H, d, J=7 Hz), 1.0–2.60 (20H, m), 3.80 (1H, t, J=7 Hz), 4.10–4.52 (3H, m).

EXAMPLE 42

(1) Step 1

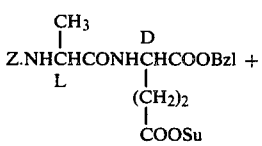

(1)

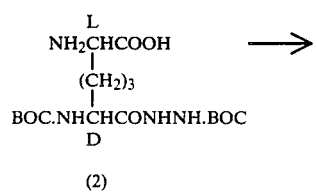

(2)

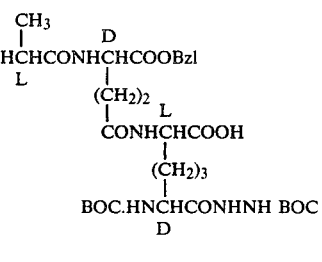

(3)

The compound (3) was prepared in substantially the same manner as the step 1 of Example 12.

N.M.R. (DMSO-d6), δ(ppm): 1.00–2.40 (10H, m), 1.24 (3H, t, J=7 Hz), 1.40 (18H, s), 3.80–4.48 (4H, m), 5.04 (2H, s), 5.12 (2H, s), 6.74 (1H, d, J=7 Hz), 7.36 (10H, s), 8.04 (1H, d, J=7 Hz), 8.32 (1H, d, J=7 Hz), 8.68 (1H, broad s), 9.60 (1H, s).

(2) Step 2

Compound (3) $\xrightarrow{\text{AcOH}}$

-continued

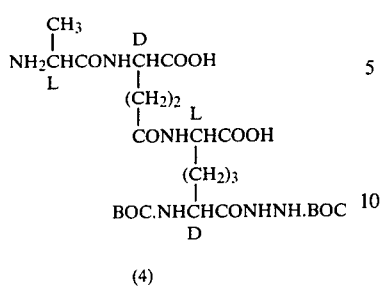

(4)

The compound (4) was prepared in substantially the same manner as the step 2 of Example 12.

N.M.R. (D2O), δ(ppm): 1.36-2.66 (13H, m), 1.43 (18H, s), 3.83-4.43 (4H, m).

(3) Step 3

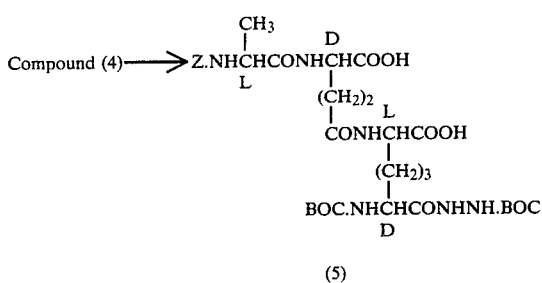

(5)

The compound (5) was prepared in substantially the same manner as the step 1 of Example 1.

N.M.R. (DMSO-d6), δ(ppm): 1.25 (3H, d, J=7 Hz), 1.40 (18H, s), 1.30-2.40 (10H, m), 3.83-4.50 (4H, m), 5.06 (2H, s), 6.76 (1H, d, J=7 Hz). 7.38 (5H, s), 8.13 (2H, d, J=7 Hz), 8.70 (1H, broad s), 9.60 (1H, s).

(4) Step 4

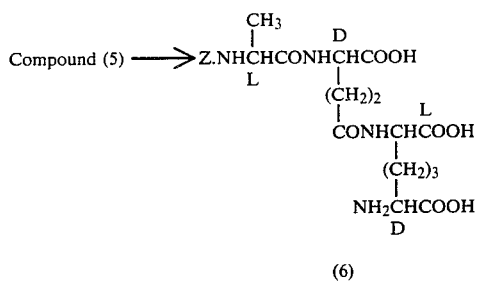

(6)

The compound (6) was prepared in substantially the same manner as the step 4 of Example 12.

N.M.R. (D2O), δ(ppm): 1.34 (3H, d, J=7 Hz), 1.10-2.43 (10H, m) 3.71 (1H, t, J=7 Hz), 3.91-4.30 (3H, m), 5.10 (2H, s), 7.40 (5H, s).

(5) Step 5

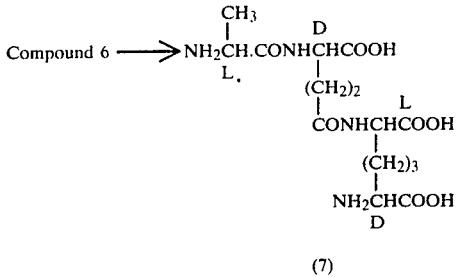

(7)

The compound (7) was prepared in substantially the same manner as the Step 2 of Example 11.

N.M.R. (D2O), δ(ppm): 1.52 (3H, d, J=7 Hz), 1.20-2.52 (10H, m), 3.76 (1H, t, J=7 Hz), 4.00-4.40 (3H, m).

The following compounds were prepared in substantially the same manner as step 1 to 4 of Example 12, respectively.

EXAMPLE 43

(1) Step 1
D—Lac(oAc)—L—Ala—γ—D—Glu(α—oBz-l)—(L)—Boc—(D)—mesoDAP—(D)—NHNHBoc.

N.M.R. (DMSO-D6), δ(ppm): 1.1-2.5 (16H, m), 1.38 (18H, s), 2.04 (3H, s), 3.8-4.7 (4H, m), 4.95 (1H, q, J=7 Hz), 5.10 (2H, s), 7.30 (5H, s), 8.08 (2H, broad t, J=8 Hz).

(2) Step 2
D—Lac(OH)—L—Ala—γ—D—Glu(α—OH)—(L-)—Boc—(D)—mesoDAP—(D)—NHNHBoc.
I.R. (Nujol): 1720, 1650, 1525 cm$^{-1}$.

(3) Step 3
D—Lac(OH)—L—Ala—γ—D—Glu(α—OH)—(L-)—mesoDAP—(D)—NHNH2 (trifluoroacetic acid salt).

N.M.R. (D2O), δ(ppm): 1.40 (3H, d, J=7 Hz), 1.45 (3H, d, J=7 Hz), 1.2-2.7 (10H, m), 4.0-4.7 (5H, m).

(4) Step 4
D—Lac(OH)—L—Ala—γ—D—Glu(α—OH)—(L-)—mesoDAP.
$[\alpha]_D = -21.3°$ (c=0.258, water).
N.M.R. (D2O), δ(ppm): 1.1-2.5 (10H, m), 1.35 (3H, d, J=7 Hz), 1.42 (3H, d, J=7 Hz), 3.88 (1H, t, J=6 Hz), 4.0-4.5 (4H, m).

EXAMPLE 44

(1) Step 1
Benzyloxycarbonyl—L—Ala—γ—D—Glu(α—OBzl)—(L)—Boc—(D)—mesoDAP—(D-)—NHNHBoc—(L)—D—AlaOH.
I.R. (Nujol): 3290, 1720, 1650, 1630, 1530 cm$^{-1}$.
N.M.R. (CD3OD), δ(ppm): 1.39 (18H, s), 3.75-4.55 (5H, m), 5.06 (2H, s), 5.12 (2H, s), 7.23 (10H, s).

(2) Step 2
L—Ala—γ—D—Glu(α—OH)—(L)—Boc—(D-)—mesoDAP—(D)—NHNH—Boc—(L-)—D—AlaOH.
m.p. 174° (dec).
I.R. (Nujol): 3300, 1655, 1525 cm$^{-1}$.
N.M.R. (D2O), δ(ppm): 1.45 (18H, s), 3.98-4.60 (5H, m).

(3) Step 3
Heptanoyl L—Ala—γ—D—Glu(α—OH)—(L-)—Boc—(D)—mesoDAP—NHNHBoc—(L-)—D—AlaOH.

I.R. (Nujol): 3300, 1720, (shoulder), 1650 cm$^{-1}$.

N.M.R. (DMSO-d$_6$), δ(ppm): 0.88 (3H, t, J=7 Hz), 1.0–2.4 (44H, m), 4.0–4.6 (5H, m).

(4) Step 4

Heptanoyl—L—Ala—γ—D—Glu(α—OH)—(L-)—mesoDAP—(L)—D—AlaOH.

[α]$_D$= −26.0° (c=0.2, water).

I.R. (Nujol): 3250, 1720, 1640 cm$^{-1}$.

N.M.R. (D$_2$O), δ(ppm): 0.86 (3H, t, J=7 Hz), 1.0–2.5 (26H, m), 3.84 (1H, t, J=7 Hz), 4.2–4.56 (4H, m).

The following compounds were prepared in the substantially same manner as steps 1 and 2 of Example 1, respectively.

EXAMPLE 45

(1) Step 1

Acetoxyacetyl—L—Ala—γ—D—Glu(α—OH-)—(L)—Boc—(D)—meso—DAP—(D)—NHNH-Boc—(L)—D—AlaOH.

I.R. (Nujol): 3280, 1720, 1650, 1520 cm$^{-1}$.

N.M.R. (CD$_3$OD), δ(ppm): 1.47, (18H, s), 2.14 (3H, s), 4.07–4.70 (5H, m), 4.63 (2H, s).

(2) Step 2

Glycoloyl—L—Ala—γ—Glu(α—OH)—(L-)—mesoDAP—(L)—D—AlaOH.

I.R. (Nujol): 3280, 1720, 1630, 1530 cm$^{-1}$.

N.M.R. (D$_2$O), δ(ppm): 1.41, (3H, d, J=7 Hz), 1.43 (3H, d, J=7 Hz), 3.83 (1H, t, J=7 Hz), 4.14 (2H, s), 4.2–4.55 (4H, m).

EXAMPLE 46

(1) Step 1

O—Acetyl—D—Mandelyl—L—Ala—γ—D—Glu(α—OH)—(L)—Boc—(D)—mesoDAP—(D-)—NHNHBoc—(L)—D—AlaOH.

I.R. (Nujol): 3280, 1720, 1650, 1520 cm$^{-1}$.

N.M.R. (CD$_3$OD), δ(ppm): 1.39, (18H, s), 2.15 (3H, s), 3.9–4.6 (5H, m), 5.87 (1H, s), 7.38 (5H, s).

(2) Step 2

D—Mandelyl—L—Ala—γ—D—Glu(α—OH)—(L-)—mesoDAP—(L)—D—AlaOH.

I.R. (Nujol): 3270, 1715, 1640, 1520 cm$^{-1}$.

N.M.R. (D$_2$O), δ(ppm): 1.35 (3H, d, J=7 Hz), 1.42 (3H, d, J=7 Hz), 3.80, (1H, t, J=7 Hz), 4.1–4.5 (4H, m), 5.18 (1H, s), 7.32 (5H, s).

EXAMPLE 47

(1) Step 1

Phenylacetyl—L—Ala—γ—D—Glu(α—OH)—(L-)—Boc—(D)—meso—DAP—(D)—NHNHBoc—(L-)—D—AlaOH.

I.R. (Nujol): 3280, 1720, (shoulder), 1650, 1520 cm$^{-1}$.

N.M.R. (CD$_3$OD), δ(ppm): 1.40 (18H, s), 3.59 (2H, s), 3.94–4.50 (5H, m), 7.27 (5H, s).

(2) Step 2

Phenylacetyl—L—Ala—γ—D—Glu(α—OH)—(L-)—mesoDAP—(L)—D—AlaOH.

I.R. (Nujol): 3250, 1715, 1640, 1530 cm$^{-1}$.

N.M.R. (D$_2$O), γ(ppm): 1.36 (3H, d, J=7 Hz), 1.40 (3H, d, J=7 Hz), 3.65 (2H, s), 3.80 (1H, t, J=7 Hz), 4.20–4.55 (4H, m), 7.36 (5H, s).

EXAMPLE 48

(1) Step 1

Benzyloxycarbonyl—L—Ala—γ—D—Glu(α—OH-)—(L)—Boc—(D)—mesoDAP—(D)—NHNH-Boc—(L)—D—AlaOH.

I.R. (Nujol): 3270, 1715 (shoulder), 1650, 1520 cm$^{-1}$.

N.M.R. (CD$_3$OD), δ(ppm): 1.41 (18H, s), 3.95–4.50 (5H, m), 5.07 (2H, s), 7.28 (5H, s).

(2) Step 2

Benzyloxycarbonyl—L—Ala—γ—D—Glu(α—OH-)—(L)—mesoDAP—(L)—D—AlaOH.

[α]$_D$= −57.4° (c=0.24, water).

I.R. (Nujol): 3250, 1700(shoulder), 1640, 1520 cm$^{-1}$.

N.M.R. (D$_2$O), δ(ppm): 1.40 (6H, d, J=8 Hz), 3.86 (1H, t, J=6 Hz), 4.07–4.50 (4H, m), 5.10 (2H, s), 7.40 (5H, s).

EXAMPLE 49

(1) Step 1

Benzyloxycarbonyl—γ—D—Glu(α—OBzl)—(L-)—Boc—(D)—meso—DAP—(L)—GlyOH.

I.R. (Nujol): 3260, 1730–1630 (broad) cm$^{-1}$.

N.M.R. (DMSO-d$_6$), δ(ppm): 1.20–2.40 (10H, m), 1.40 (18H, s), 3.76 (2H, d, J=7 Hz), 4.0–4.5 (3H, m) 5.08 (2H, s), 5.15 (2H, s), 7.40 (10H, s).

(2) Step 2

γ—D—Glu(α—OH)—(L)—Boc—(D-)—mesoDAP—(D)—NHNHBoc—(L)—GlyOH.

I.R. (Nujol): 3250 (broad), 1720–1620 (broad) cm$^{-1}$.

N.M.R. (D$_2$O), δ(ppm): 1.20–2.70 (28H, m), 3.83 (1H, t, J=7 Hz), 3.94 (2H, s), 4.0–4.5 (2H, m).

(3) Step 3

Heptanoyl—γ—D—Glu(α—OH)—(L)—Boc—(D-)—mesoDAP—(D)—NHNHBoc—(L)—GlyOH.

I.R. (Nujol): 3250, 1720 (shoulder), 1650 (broad) cm$^{-1}$.

N.M.R. (DMSO-d$_6$), δ(ppm): 0.86 (3H, t, J=7 Hz), 1.0–2.4 (38H, m), 3.70 (2H, d, J=7 Hz), 4.0–4.5 (3H, m).

(4) Step 4

Heptanoyl—γ—D—Glu(α—OH)—(L-)—mesoDAP—(L)—GlyOH.

[α]$_D$= −18.0° (c=0.2, water).

I.R. (Nujol): 3300, 1720, 1640 (broad) cm$^{-1}$.

N.M.R. (D$_2$O), δ(ppm): 0.84 (3H, t, J=7 Hz), 1.0–2.60 (20H, m), 3.80 (1H, t, J=7 Hz), 3.96 (2H, s), 4.20–4.48 (2H, m).

EXAMPLE 50

(1) Step 1

$$\begin{array}{c}
\text{L} \quad \overset{\text{CH}_3}{|} \quad \text{D} \\
\text{H}_2\text{NCHCONHCHCOOH} + \text{Z—HNCHCOOBzl} \longrightarrow \\
| \quad \text{D} \quad \quad \quad | \\
(\text{CH}_2)_3 \quad \quad \quad \quad (\text{CH}_2)_2 \\
| \quad \quad \quad \quad \quad \quad | \\
\text{BocHNCHCOOH} \quad \quad \text{COOSu} \\
\text{D} \\
(1) \quad \quad \quad \quad \quad \quad (2)
\end{array}$$

$$\begin{array}{c}
\text{D} \\
\text{Z—HNCHCOOBzl} \\
| \\
(\text{CH}_2)_2 \quad \quad \text{CH}_3 \\
| \quad \text{L} \quad | \\
\text{COHNCHCOHNCHCOOH} \\
| \quad \quad \quad \quad \text{D} \\
(\text{CH}_2)_3 \\
| \\
\text{BocHNCHCOOH} \\
\text{D} \\
(3)
\end{array}$$

To a mixture of Boc—(D)—mesoDAP—(L-)—D—AlaOH (1) (361 mg.) and triethylamine (202 mg.) in 50% aqueous dioxane (20 ml.) was added Z—D—Glu(OSu)OBZl (2) (440 mg.) and the reaction mixture was concentrated and washed with ethyl acetate. The organic layer was acidified with diluted hydrochloric acid and extracted with ethyl acetate. The extract was washed with water, dried over magnesium sulfate and evaporated to give a foamy residue, which was pulverized with isopropyl ether and collected by filtration to give a white powder (520 mg.) of Z—γ—D—Glu(α—OBzl)—(L)—Boc—(D)—mesoDAP—(L)—D—AlaOH (3).

I.R. (Nujol): 3300, 1720, 1690, 1640, 1530 cm$^{-1}$.

N.M.R. (DMSO-d$_6$), δ(ppm): 1.38 (9H, s), 1.00~2.66 (13H, m), 3.66~4.50 (4H, m), 5.07 (2H, s), 5.15 (2H, s), 7.38 (10H, s).

(2) Step 2

Compound (3) ⟶

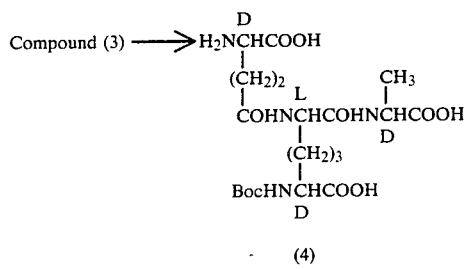

(4)

Z—γ—D—Glu(α—OBzl)—(L)—Boc—(D)—mesoDAP—(L)—D—AlaOH (3) (502 mg) was dissolved in acetic acid (20 ml) and hydrogenated over 10% palladium-charcoal (100 mg). The catalyst was removed by filtration and the filtrate was evaporated to give an oil, to which toluene was added and evaporated to give a pasty residue. This residue was dissolved in water and submitted to a column of HP-20 (50 ml), a macroporous non-ionic adsorption resin. The column was eluted successively with water and methanol-water (1:4). Evaporation of the latter fractions gave a white foam, which was dissolved in water and lyophillized to give a white powder (290 mg) of γ—D—Glu(α—OH)—(L)—Boc—(D)—mesoDAP—(L)—D—AlaOH (4).

I.R. (Nujol): 3250, 1720~1630 (broad), 1530 cm$^{-1}$.

N.M.R. (D$_2$O), δ(ppm): 1.48 (9H, s), 1.10~2.66 (13H, m), 3.77 (1H, t, J=7 Hz), 4.00~4.66 (3H, m).

(3) Step 3

Compound (4) ⟶

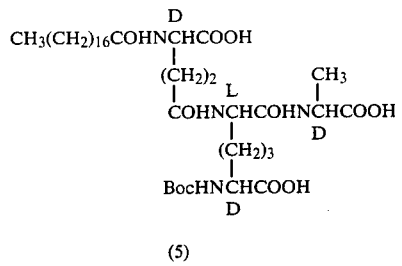

(5)

To a mixture of γ—D—Glu(α—OH)—(L)—Boc—(D)—mesoDAP—(L)—D—AlaOH (4) (280 mg) and triethylamine (175 mg) in methanol (5 ml) was added a solution of stearic anhydride (478 mg) in chloroform (10 ml) and the mixture was kept for 3 days at room temperature. The reaction mixture was concentrated and the residue was dissolved in ethyl acetate. The ethyl acetate was washed successively with diluted hydrochloric acid and water, dried over magnesium sulfate and evaporated to give a foamy residue, which was pulverized with ether and collected to give a white powder (310 mg) of stearoyl—γ—D—Glu(α—OH)—(L)—Boc—(D)—mesoDAP—(L)—D—AlaOH (5).

I.R. (Nujol): 3300, 1710, 1695, 1660 1620 (broad), 1540 cm$^{-1}$.

N.M.R. (CD$_3$OD), δ(ppm): 0.90 (3H, t, J=5 Hz), 1.33 (30H, s), 1.44 (9H, s), 1.16~2.66 (15H, m), 3.66~4.66 (4H, m).

(4) Step 4

Compound (5) ⟶

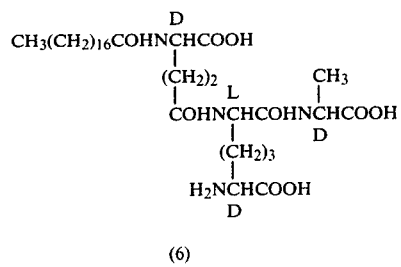

(6)

Stearoyl—γ—D—Glu(α—OH)—(L)—Boc—(D)—mesoDAP—(L)—D—AlaOH (5) (308 mg) was added to trifluoroacetic acid (5 ml) and the mixture was stirred for 1 hour at room temperature. The reaction mixture was concentrated and triturated with ether to give a white powder, which was washed with ether and methanol to give stearoyl—γ—D—Glu(α—OH)—(L)—mesoDAP—(L)—D—AlaOH (6) (230 mg.) as a white powder.

I.R. (Nujol): 3300, 1730, 1640, 1530 cm$^{-1}$.

N.M.R. (D$_2$O+NaOD), δ(ppm): 0.86 (3H, t, J=6 Hz), 1.30 (30H, m), 1.00-2.66 (15H, m), 3.21 (1H, t, J=7 Hz), 4.00~4.20 (3H, m).

EXAMPLE 51

(1) Step 1

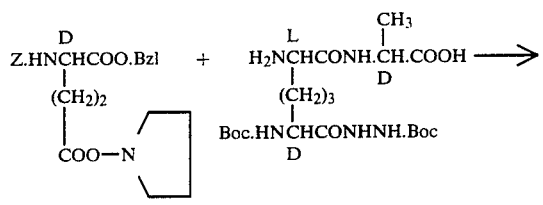

(1)        (2)

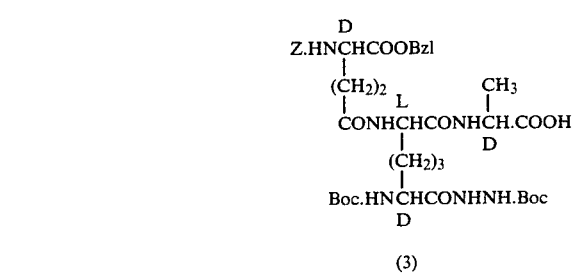

(3)

Compound (2) (4.75 g) was dissolved in a mixture of dioxane (30 ml) and water (30 ml) containing triethylamine (1.01 g). To this solution, there was added compound (1) (4.4 g) and the resulting solution was left for 1 day at ambient temperature. The reaction mixture was concentrated and the concentrates were subjected to extraction with ethylacetate. The organic layer was washed with water, dried over magnesium sulfate (MgSO₄) and then evaporated to give a formy residues, which were pulverized with diisopropylether and collected by filtration to give compound (3) (5.77 g) as white powder.

I.R. (Nujol): 3270, 1730-1620 (broad).

N.M.R. (DMSO-d₆), δ(ppm): 1.37 (18H, s), 1.18-2.33 (13H, m), 3.66-3.84 (4H, m), 5.06 (2H, s), 5.16 (2H, s), 7.36 (10H, s).

(2) Step 2

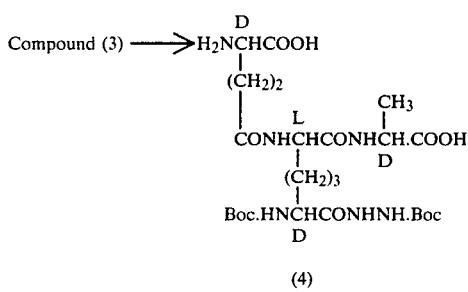

Compound (3) (3.88 g) was dissolved in acetic acid (100 ml) and hydrogenated over palladium-charcoal (300 mg). Catalyst, i.e. palladium-charcoal was removed by filtration and the filtrate was evaporated under reduced pressure to give an oily paste, to which toluene was added. The resulting solution was evaporated to give white powder residues, which were washed with diisopropylether and collected by filtration to give compound (4) (2.10 g) as white powder.

I.R. (Nujol): 3300-2300 (broad), 1720-1620 (broad).

N.M.R. (D₂O), δ(ppm): 1.47 (18H, s), 1.33-2.66 (13H, m), 3.66-4.50 (4H, m).

EXAMPLE 52

(1) Step 1

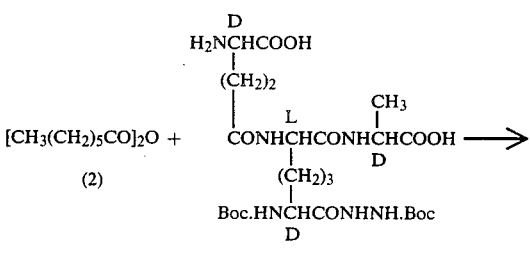

Compound (1) (596 mg) was dissolved in methanol (30 ml), and to this solution, there were added triethylamine (202 mg) and heptanoic anhydride (2) (363 mg) successively. The reaction mixture was kept for 3 days at ambient temperature, and then concentrated. The concentrates were subjected to extraction with ethylacetate. The organic layer was washed with 10% aqueous hydrochloric acid and water, and dried over magnesium sulfate (Mg SO₄) and then evaporated to give a foamy residue, which was pulverized with ether and collected by filtration to give compound (3) (470 mg) as white powder.

I.R. (Nujol): 3300, 1740-1730 (broad).

N.M.R. (DMSO-d₆), δ(ppm): 0.89 (3H, t, J=7 Hz), 1.00-2.40 (23H, m), 3.66-4.66 (4H, m).

(2) Step 2

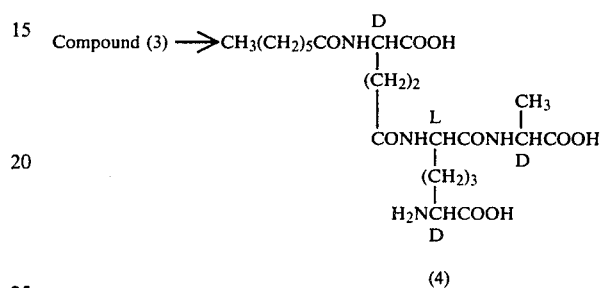

Compound (3) (430 mg) was dissolved in trifluoroacetic acid (10 ml) and the solution was kept for 30 minutes at ambient temperature. The solution was evaporated to give an oily paste, which was dissolved in 0.1N-sulfuric acid (13 ml) and water (8 ml) and cooled in an ice-bath. To this solution, there was added aqueous NaIO₄ (278 mg in 5 ml water) under stirring, and the stirring was continued for 1 hour.

The resulting reaction mixture was treated with aqueous NaHSO₃ solution untill purple color of the solution disappeared. The pH of the solution was made neutral by addition of aqueous NaHCO₃ solution and the whole volume of the solution was concentrated. The pH of the solution was adjusted again to 2.0 and the whole solution was submitted to column of HP-20 resin (50 ml). The column was eluted with water and then methanol-water (1:2). The latter fractions were evaporated gave a white formy substance, which was dissolved in water and then the solution was lyophillized to give compound (4) (240 mg) as white powder.

I.R. (Nujol): 3250, 1740, 1666-1640 (broad).

N.M.R.(D₂O), δ(ppm): 0.82 (3H, t, J=6 Hz), 1.00-2.60 (20H, m), 1.35 (3H, d, J=8 Hz), 3.81 (1H, t, J=7 Hz), 4.40-4.80 (3H, m).

EXAMPLE 53

(1) Step 1

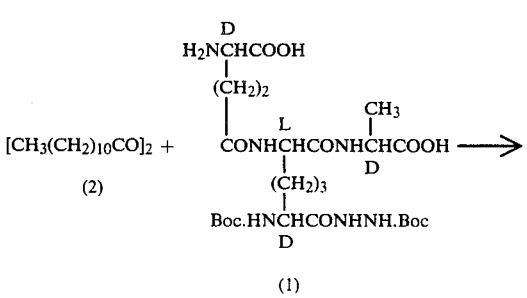

-continued

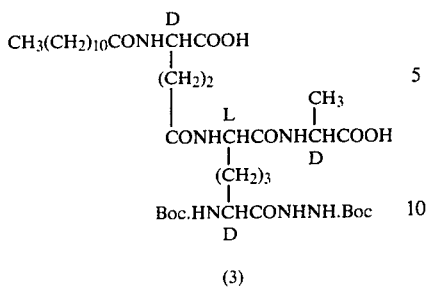

(3)

Compound (1) (596 mg) was dissolved in methanol (30 ml) and chloroform (5 ml), and to this solution, there were added triethylamine (202 mg) and lauric anhydride (2) (609 mg) successively. The reaction mixture was treated substantially in the same manner as the Step 1 of Example 52 to give compound (3) (570 mg) as white powder.

I.R. (Nujol): 3250, 1725–1610 (broad).

N.M.R. (DMSO-$d_6$), δ(ppm): 0.84 (3H, t, J=7 Hz), 1.30 (18H, s), 1.00–2.40 (33H, m), 3.80–4.40 (3H, m).

(2) Step 2

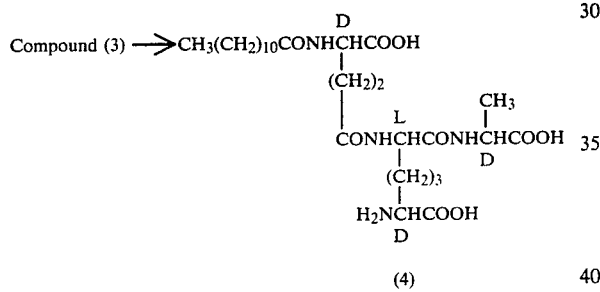

(4)

Compound (3) (510 mg) was dissolved in trifluoroacetic acid (10 ml) and the solution was kept for 30 minutes at ambient temperature. Hereafter, the reaction mixture was treated substantially in the same manner as the Step 2 of Example 52 to give compound (4) (250 mg) as white powder.

I.R. (Nujol): 3300, 1720, 1660–1620 (broad).

N.M.R. (CD$_3$OD), δ(ppm): 0.90 (3H, t, J=7 Hz), 1.00–2.60 (33H, m), 3.75 (1H, t, J=7 Hz), 4.20–4.80 (3H, m).

EXAMPLE 54

(1) Step 1

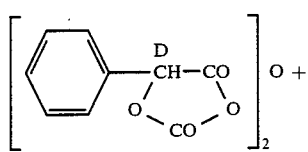

(2)

-continued

H$_2$NCHCOOH
|
D
(CH$_2$)$_2$
|
CONHCHCONHCHCOOH ⟶
         L    |        |
              CH$_3$   D
              (CH$_2$)$_3$
              |
              Boc.HNCHCONHNH.Boc
              |
              D (1)

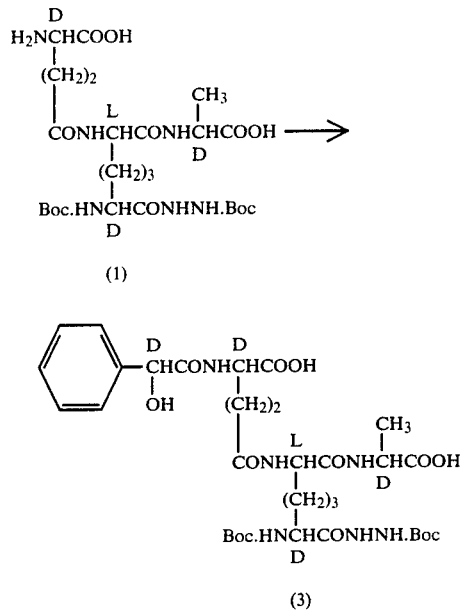

(3)

Compound (1) (596 mg) was dissolved in methanol (30 ml), and to this solution, there were added triethylamine (202 mg) and manderic anhydride (2) (267 mg) successively. The reaction mixture was treated substantially in the same manner as the Step 1 of Example 52 to give Compound (3) (330 mg) as white powder.

IR(Nujol): 3300, 1730–1640(broad).

NMR(DMSO-$d_6$), δppm: 1.39(18H, s), 1.16–2.33(13H, m), 3.70–4.50(4H, m), 5.00(1H, broad s), 7.40(5H, broad s).

(2) Step 2

Compound (3) ⟶

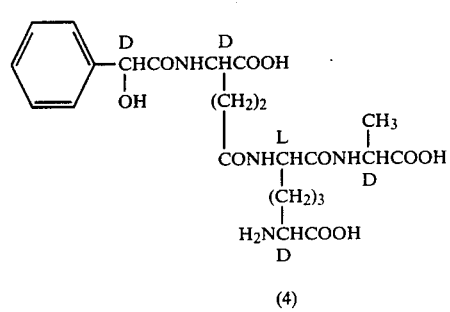

(4)

Compound (3) (479 mg) was dissolved in trifluoroacetic acid (10 ml) and the solution was kept for 30 minutes at ambient temperature. Hereafter, the reaction mixture was treated substantially in the same manner as the Step 2 of Example 53 to give Compound (4) (190 mg) as white powder.

IR(Nujol): 3250, 1720, 1660–1620(broad).

NMR(D$_2$O), δppm: 1.36(3H, d, J=7 Hz), 1.20–2.60 (10H, m), 3.80(1H, t, J=6 Hz), 4.10–4.60 (3H, m), 5.20(1H, s), 7.42(5H, s).

EXAMPLE 55

(1) Step 1

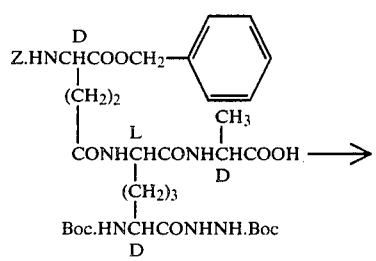

(1)

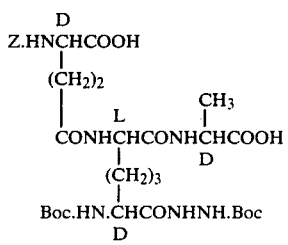

(2)

Compound (1) (1.51 g) was dissolved in a mixture of methanol (15 ml) and water (10 ml). To this solution, there was added 1N-NaOH solution (4.0 ml) and the solution was kept for 2 hours at ambient temperature. The reaction mixture was concentrated after adjusting the pH of the solution of 7.0. The residual aqueous solution was diluted with water. After extraction with ether, aqueous layer was acidified to pH 2 with 1N-HCl to separate an oily product, which was extracted with ethylacetate. The organic layer was washed with H₂O and dried over Mg SO₄. Evaporation of the solvent gave a white foam, which was pulverized with diisopropyl ether to give Compound (2) (1.16 g) as white powder.

I.R. (Nujol): 3250, 1740–1620 (broad).

N.M.R. (DMSO-d₆), δ(ppm): 1.36 (18H, s), 1.00–2.40 (13H, m), 3.66–4.50 (4H, m), 5.03 (2H, s), 7.36 (5H, s).

(2) Step 2

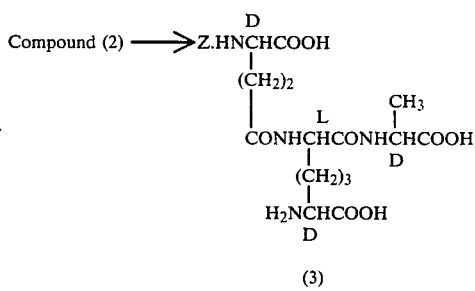

(3)

Compound (2) (1.03 g.) was dissolved in trifluoroacetic acid (10 ml.) and the solution was kept for 30 minutes at ambient temperature. Hereafter, the reaction mixture was treated substantially in the same manner as the Step 2 of Example 2 to give Compound (3) (0.6 g.) as white power.

I.R. (Nujol): 3300, 1700, 1660~1620 (broad).

N.M.R. (D₂O), δ(ppm) 1.36 (3H, d, J=7 Hz), 1.20~2.60 (10H, m), 3.76 (1H, t, J=7 Hz), 3.96~4.50 (3H, m), 5.08 (2H, s), 7.40 (5H, s).

(3) Step 3

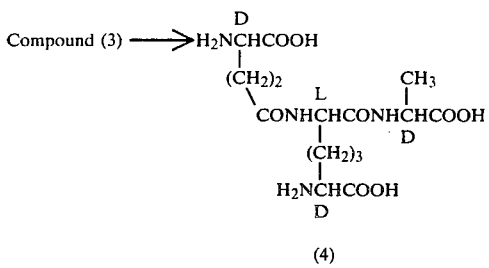

(4)

Compound (3) (374 mg.) was dissolved in acetic acid (30 ml.) and hydrogenated over palladium-charcoal (100 mg.). Catalyst was removed by filtration and the filtrate was evaporated under reduced pressure to give an oily paste, to which toluene was added. Evaporation of toluene gave white powder residue. The residue was dissolved in water and submitted to column of HP-20 resin (100 ml.). The column was eluted with water. Evaporation of the fractions containing the product was evaporated to give a pasty residue, which was dissolved in H₂O and the solution was lyophillized to give Compound (4) (200 mg.) as white powder.

I.R. (Nujol): 3250~2500 (broad) 1680~1500 (broad).

N.M.R. (D₂O), δ(ppm): 1.36 (3H, d, J=7 Hz), 1.20~2.60 (10H, m), 3.75 (1H, t, J=7 Hz), 3.80 (1H, t, J=7 Hz), 4.00~4.50 (2H, m).

EXAMPLE 56

(1) Step 1

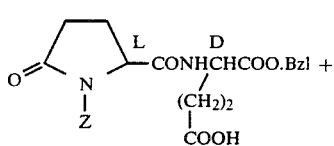

(1)

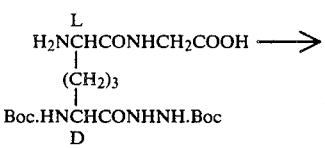

(2)

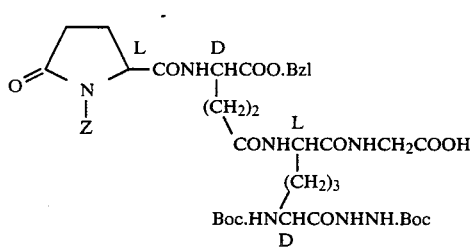

(3)

Compound (1) was dissolved in dichloromethane (20 ml.) and N-methyl-morpholine (308 mg.) was added. This solution was cooled in a dry ice-acetone bath (−17°~−19° C.) under stirring, and to the solution, isobutylchlorocarbonate (417 mg.) was added. The reaction mixture was allowed to react for 20 minutes at the same temperature. To the resulting reaction mixture was added to the solution of Compound (2) (1.41 g.) in a mixture of dichloromethane (40 ml.) and N,N-dimethylformamide (4 ml) containing bis(trimethylsilyl)acetamide (3 ml.). The reaction mixture was stirred for 2 hours at 31 18° C.-10° C. and concentrated under reduced pressure to give an oily residue, which was dissolved in ethylacetate (100 ml.) and washed with 0.5N-Hcl. The organic layer was washed with brine and dried over MgSO4. Evaporation of the solvent gave a white foam which was thoroughly washed with ether to afford Compound (3) (2.42 g.) as white powder, mp. 145°~149° C. (decomp.)

I.R. (Nujol): 3280, 1780. 1720. 1650.

N.M.R. (CD₃OD), δ(ppm): 3.93 (2H, s), 5.18 (4H, s), 7.38 (10H, s).

(2) Step 2

Compound (3) ⟶

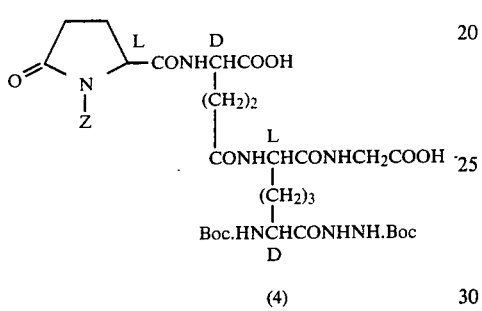

(4)

To a solution of Compound (3) (2.36 g.) in methanol (25 ml.), there was added 1N-NaOH (5.6 ml.) and the mixture was stirred for 5 hours at ambient temperature. The reaction mixture was concentrated in vacuum, and to the residue, there was added 1N-HCl (6 ml.) and the solution was subjected to extraction with ethylacetate. The organic layer was washed with 0.5N-HCl (30 ml.), dried over MgSO4 and evaporated in vacuum. The residual oil was treated with diethyl ether to give Compound (4) (1.86 g.) as white powder.

I.R. (Nujol): 3300, 1680 (broad), 1625.

N.M.R. (CD₃OD), δ(ppm): 1.46 (18H, s), 3.95 (2H, s), 4.00~4.50 (4H, m), 5.13 (2H, s), 7.45 (5H, s).

(3) Step 3

Compound (4) ⟶

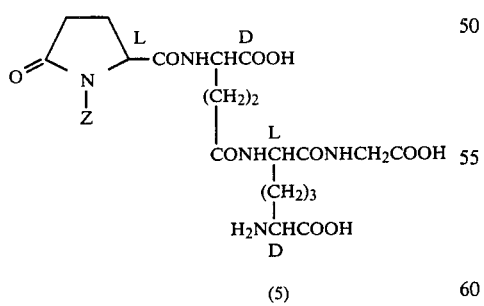

(5)

Compund (4) (1.8 g.) was added to trifluoroacetic acid (10 ml.) and the mixture was stood for 100 minutes at ambient temperature. The reaction mixture was evaporated and the residue was triturated with ethyl ether to give a solid.

The solid was dissolved in water (45 ml). To this solution, was added 1N-H2SO4 (4.4 ml.) and NaIO4 (930 mg.) at 0° C. After stirring for 2 hours at 0° C., the reaction mixture was treated with aqueous NaHSO3, concentrated to about 10 ml, adjusted to pH 2 with 1N-NaOH and submitted to column of HP-20 resin (200 ml.). The column was eluted with water-methanol (3:2) and the fractions were combined and evaporated, and then the residue was lyophilized to give Compound (5) (680 mg.).

I.R. (Nujol): 3270, 1700, 1640, 1520.

N.M.R. (D₂O), δ(ppm): 1.3~2.6 (14H, m), 3,83 (1H, t, J=7 Hz), 3.95 (2H, s), 4.05~4.50 (3H, m), 5.11 (2H, s), 7.40 (5H, s).

(4) Step 4

Compound (5) ⟶

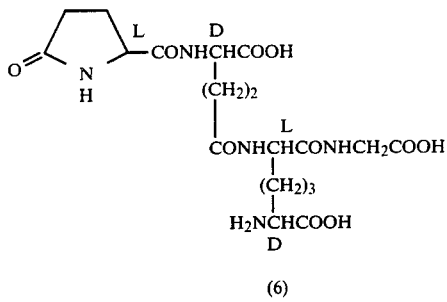

(6)

A solution of Compound (5) (550 mg.) in water (6 ml.) was hydrogenated over 10% palladium-carbon (180 mg.) under an atmospheric pressure of hydrogen gas. After the catalyst was filtered off, the filtrate was evaporated in vacuum and lyophilized to give Compound (6) (450 mg).

I.R. (Nujol): 3250, 1720 (shoulder), 1630, 1530.

N.M.R. (D₂O), δ(ppm): 1.3~2.6 (14H, m), 3.74 (1H, t, J=6 Hz), 3.85 (2H, s), 3.99~4.50 (3H, m).

EXAMPLE 57

(1) Step 1

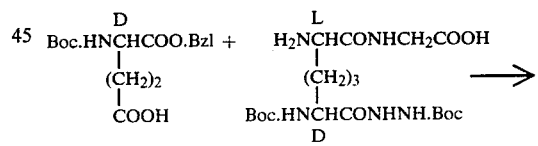

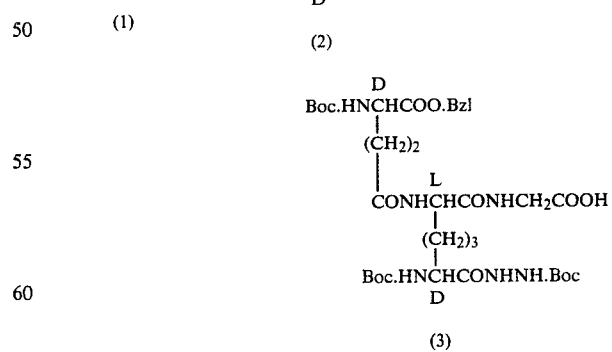

(3)

To a mixture of Compound (1) (674 mg.) and N-methylmorpholine (202 mg.) in dichloromethane (30 ml.), there was added isobutyl chloroformate (273 mg.) at −15°~−20° C. and the mixture was stirred for 30 minutes at the same temperature. The mixture was cooled to −40° C., and to this, there was added trimethyl silyl ester of Compound (2), which was prepared from Compound (2) (910 mg.) and bis(trimethylsilyl)acetamide (3 ml.) by stirring in a mixture of dichloromethane (20 ml.) and N,N-dimethylformamide (2 ml.). This mixture was stirred for 1 hour at −15°∼−20° C., and after evaporation of the solvent, the residue was dissolved in thylacetate (100 ml.), and then the solution was washed successively with 2%-HCl and water, dried over MgSO4 and evaporated. The residue was pulverized with isopyropyl ether to give Compound (3) (1.25 g.).

N.M.R. (CDCl3), δ(ppm): 1.43 (27H, s), 1.3∼2.4 (10H, m), 3.8∼4.5 (5H, m), 5.13 (2H, s), 7.33 (5H, s).

(2) Step 2

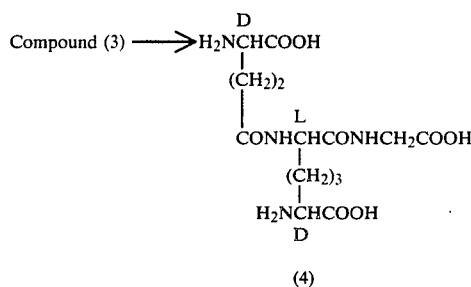

(4)

To a solution of Compound (3) (1.08 g.) in 50% aqueous methanol (10 ml.) was added 1N-NaOH (3 ml.) and the mixture was stirred for 3 hours at ambient temperature. The reaction mixture was neutralized with 1N hydrochloric acid (3 ml.) and evaporated. The residue was dissolved in trifluoroacetic acid (5 ml.) and stirred for 15 minutes at ambient temperature. After evaporation of trifluoroacetic acid, the residue was pulverized with diethyl ether. The powder thus obtained was dissolved in water (10 ml.), and 1N hydrochloric acid (1.7 ml.) was added thereto. To this solution, was added a solution of NaIO4 (354 mg.) in water (2 ml.) at 0° C., and the mixture was stirred for 1 hour at the same temperature. After excess of NaIO4 was decomposed by adding sodium sulfite, the reaction mixture was adjusted to pH 4 with 1N aqueous solution of sodium hydroxide and then concentrated to about 3 ml. The concentrate was subjected to column chromatography on non-ionic adsorption resin "Diaion HP-20: (Trade Mark, manufactured by Mitsubishi Chemical Industries Ltd.) (60 ml.) and elution was carried out with water. The fractions containing the object compound was lyophilized to give compound (4) (140 mg.).

I.R. (KBr): 3500∼2500, 1720, 1650.

N.M.R. (D2O), δ(ppm): 1.3∼2.7 (10H, m), 3.90∼4.50 (2H, m), 4.00 (2H, s).

EXAMPLE 58

(1) Step 1

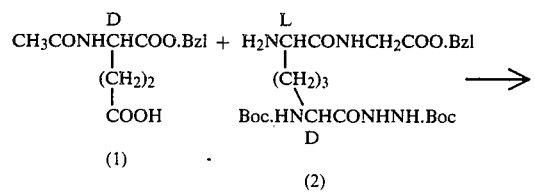

-continued

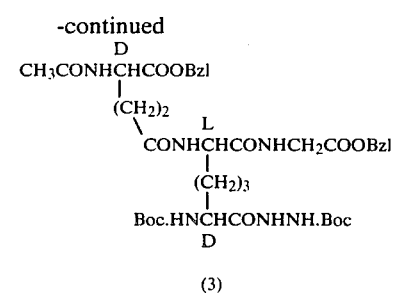

(3)

To a mixture of Compound (1) (560 mg.) and N-methylmorpholine (202 mg.) in dichloromethane (30 ml.), there was added isobutyl chloroformate (273 mg.) at −15°∼−20° C. and the mixture was stirred for 30 minutes at the same temperature. The mixture was cooled to −40° C. and, to this, there was added trimethylsilyl ester of Compound (2), which was prepared from Compound (2) (910 mg.) and bis(trimethylsilyl)acetamide (3 ml.) by stirring in a mixture of dichloromethane (20 ml.) and N,N-dimethylformamide (2 ml.). The mixture was stirred for 1 hour at −15°∼−20° C., and then treated in the same manner as the Step 1 of Example 57 to give Compound 3 (1.8 g.).

I.R. (Nujol): 3300, 1740, 1660.

N.M.R. (CD3OD), δ(ppm): 1.58 (18H, s), 1.95 (3H, s), 1.50∼2.50 (10H, m), 3.88 (2H, s), 3.8∼4.5 (3H, m).

(2) Step 2

(4)

Compound (3) (0.95 mg.) was added to trifluoroacetic acid (5 ml.) and the solution was stirred for 15 minutes at ambient temperature. A evaporation of CF3COOH, the residue was dissolved in water (10 ml) and 1N-HCl (1.7 ml) was added thereto. This solution was cooled to 0° C. and a solution of NaIO4 (364 mg) in water (5 ml) was added thereto and the mixture was stirred for 1 hour at the same temperature. An excess of the reagent was decomposed, by adding Na2SO3, and then the mixture was neutralized to pH 3 with 1N-NaOH and submitted to column of HP-20 (20 ml.). The column, after washing with H2O, was eluted with methanol: water (1:1). The fractions were concentrated, and the residue was dissolved in 50% aq. acetic acid (10 ml.) and hydrogenated over 10% palladium carbon (100 mg). After removal of the catelyst, the filtrate was cncentrated. The residue was dissolved in H2O and evaporated in order to remove a trace of acetic acid. This operation was repeated further two times. The residue was lyophilized to give Compound (4) (200 mg).

I.R. (Nujol): 3250, 1715, 1640.

N.M.R. (D2O), δ(ppm): 1.5∼2.1 (10H, m), 2.1 (3H, s), 3.8∼4.5 (3H, m), 4.0 (2H, s).

EXAMPLE 59

(1) Step 1

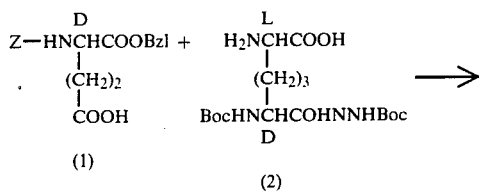

(1)

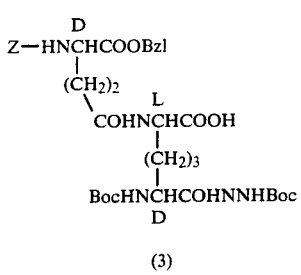

(3)

To a cooled mixture of Compound (1) (2.43 g.) and N-methylmorpholine (0.71 g.) in methylene chloride (40 ml.) was added dropwise isobutyl chloroformate (960 mg.) and the mixture was stirred for 20 minutes at 0° C. To this mixture was added a solution of Compound (2) (2.83 g.) in a mixture of methylene chloride (20 ml.) and dimethylformamide (10 ml.) containing bis(trimethylsilyl)acetamide (2 ml.). The reaction mixture was stirred for 2 hours and then concentrated to give an oily residue, which was dissolved in ethyl acetate, washed with water and dried over magnesium sulfate. Evaporation of the solvent gave a white foam, which was pulverized with isopropyl ether to give Compound (3) (4.20 g.) as white powder.

I.R. (Nujol): 3300, 1740–1640 (broad) cm$^{-1}$.

N.M.R. (DMSO-d6), δ(ppm): 1.37 (18H, s), 1.17~2.40 (10H, m), 3.70–4.40 (3H, m), 5.03 (2H, s), 5.17 (2H, s), 7.37 (10H, s).

(2) Step 2

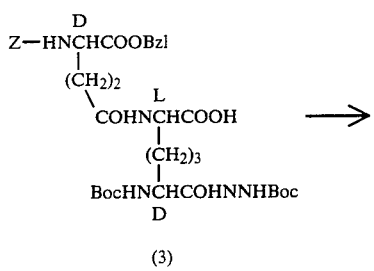

To a solution of Compound (3) (1.46 g.) in 50% aqueous methanol (10 ml.) was added 1N sodium hydroxide (4.10 ml.) and the mixture was stirred for 2 hours at room temperature. The reaction mixture was concentrated and the resulting aqueous solution was diluted with water. After washing with ether, the aqueous layer was acidified with 1N hydrochloric acid to pH 2 and extracted with ethyl acetate. The extract was washed with water, dried over magnesium sulfate to give a white foam, which was pulverized with isopropyl ether to give Compound (4) (1.20 g.) as white powder.

I.R. (Nujol): 3400, 1740 1650 (broad) cm$^{-1}$.

N.M.R. (DMSO-d6), δ(ppm): 1.37 (18H, s), 1.17~2.40 (10H, m), 3.70~4.33 (3H, m), 5.03 (2H, s), 7.37 (5H, s).

(3) Step 3

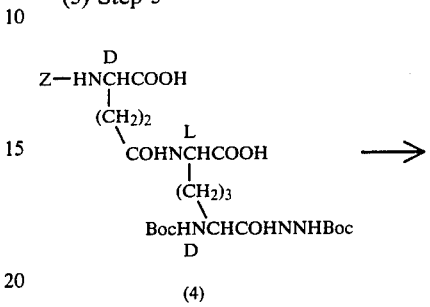

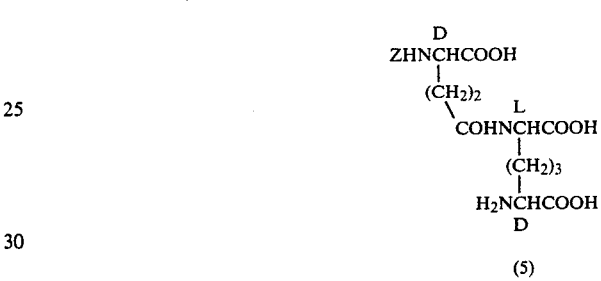

Compound (4) (1.05 g.) was dissolved in trifluoroacetic acid (5 ml.) and stirred for 15 minutes at room temperature. Evaporation of the solvent gave an oily residue, to which toluene was added and evaporated. The residue was dissolved in 0.1N sulfuric acid (35 ml.) and cooled in an ice-bath. To this solution was added a solution of sodium periodate (640 mg.) in water (5 ml.) and the mixture was stirred for 1 hour at the same temperature. The reaction mixture was treated with aqueous sodium bisulfite solution until the dark brown color of the solution was disappeared. After adjusting the pH of the solution to 4.0, the solution was concentrated to about 4 ml. and the pH was adjusted to 2.0. This solution was applied to a column of HP-20 (60 ml.) and eluted with water. Subsequent elution with 50% aqueous methanol gave fractions containing the object product, which were combined and evaporated to give a pasty residue. This residue was dissolved in water and lyophillized to give Compound (5) (0.453 g.) as white powder.

N.M.R. (D$_2$O), δ(ppm): 1.17~2.70 (10H, m), 3.83 (1H, t, J=7 Hz), 4.0~4.60 (2H, m), 5.13 (2H, s), 7.43 (5H, s).

(4) Step 4

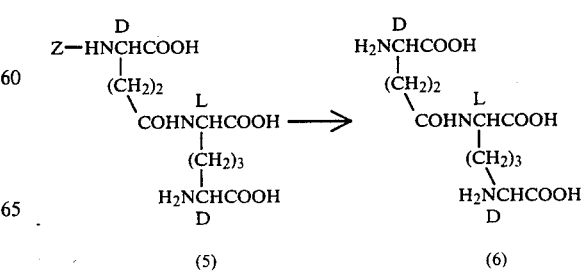

Compound (5) (0.40 g.) was dissolved in water (20 ml.) and hydrogenated over 10% palladium-charcoal (50 mg.). The calalyst was removed by filtration and the filtrate was applied to a column of HP-20 (50 ml.) and eluted with water. Evaporation of the fractions containing the object compound gave a pasty residue, which was dissolved in water and lyophillized to give Compound (6) (260 mg.) as white powder.

I.R. (Nujol): 3500~2500 (broad), 1710 (shoulder), 1620 cm$^{-1}$.

N.M.R. (D$_2$O), δ(ppm): 1.20~2.60 (10H, m), 3.60~3.92 (2H, m), 4.0–4.20 (1H, m).

EXAMPLE 60

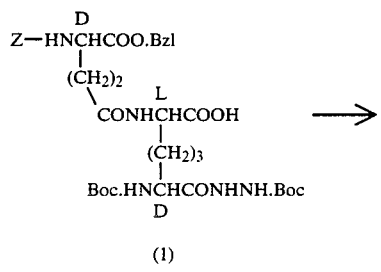

(1)

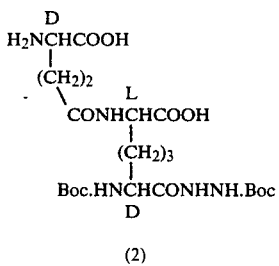

(2)

Compound (1) (2.30 g.) was dissolved in acetic acid (40 ml.) and hydrogenated over 10%-palladium-charcoal (300 mg.). The catelyst was removed by filtration and the filtrate was evaporated under reduced pressure to give an oily paste, to which toluene was added. Evaporation of toluene afforded white powder residue, which was throughly washed with diisopropyl ether and collected by filtration to give Compound (2) (1.70 g.) as white powder.

I.R. (Nujol): 3500~2500 (broad), 1740–1650 (broad).

N.M.R. (D$_2$O), d(ppm): 1.50 (18H, s), 1.16–2.83 (10H, m), 3.83 (1H, t, J=7 Hz), 4.0–4.50 (2H, m).

(2) Step 2

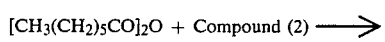

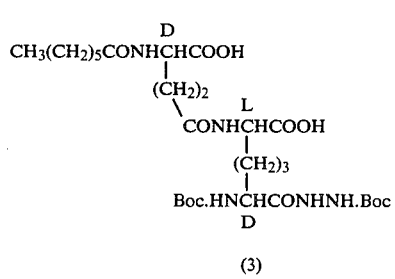

(3)

Compound (2) (800 mg.) was dissolved in methanol (10 ml.) and heptanoic anhydride (380 mg.) was added thereto. The reaction mixture was kept overight at ambient temperature. Evaporation of the solvent gave an oily paste, which was triturated with diisopropyl ether to give Compound (3) (800 mg.) as white powder.

I.R. (Nujol): 3300, 1740–1650 (broad).

N.M.R. (DMSO-d6), δ(ppm): 0.83–2.40 (41H, m), 3.83–4.50 (3H, m).

(3) Step 3

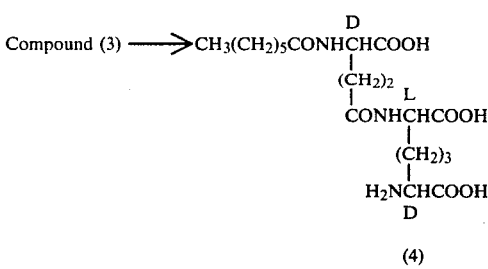

(4)

Compound (3) (750 mg.) was dissolved in trifluoroacetic acid (4 ml.) and kept for 15 minutes at ambient temperature. Evaporation of trifheoroacetic acid gave an oily paste, which was suspended in toluene. Evaporation of toluene afforded white foamy residue, which was dissolved in 0.1N-H$_2$SO$_4$ (30 ml.) and cooled in an ice bath. To this stirred solution, there was added aqueous NaIO$_4$ (350 mg. in 10 ml. H$_2$O) and stirring was continued for 1 hour. The resulting reaction mixture was treated with aqueous NaHSO$_3$ solution until the purple color of the solution disappeared. pH of the solution was made neutral by adding solid NaHCO$_3$ and the whole volume was concentrated to about 5 ml. pH of the solution was adjusted again to 2.0 and the whole solution was submitted to Column of HP-20 resin (100 ml.). The column was eluted with water and then Methanol-water (4:6). Evaporation of the latter fractions collected gave white foam, which was dissolved in water and lyophilized to give Compound (4) (180 mg.) as white powder.

I.R. (Nujol): 3300-2400 (broad), 1720, 1630.

N.M.R. (D$_2$O), δ(ppm): 0.84 (3H, t, J=7 Hz), 1.0–2.60 (20H, m), 3.80 (1H, t, J=7 Hz), 4.20–4.40 (2H, m).

EXAMPLE 61

(1) Step 1

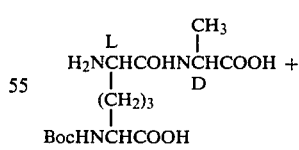

(1)

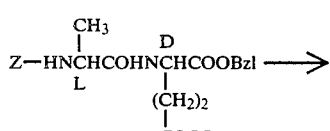

(2)

-continued

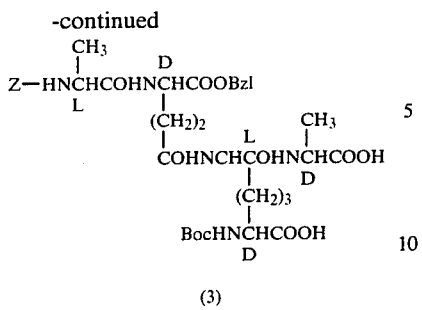
(3)

To a mixture of Boc—(D)—mesoDAP—(L-)—D—AlaOH(1) (3.40 g) and triethylamine (1.90 g) in 50% aqueous dioxane (80 ml) was added Z—L—Ala—D—Glu(γ-OSu)OBzl(2) (5.10 g) and the mixture was left overnight at room temperature. After evaporation of dioxane, the remaining aqueous solution was acidified with 1N hydrochloric acid and extracted with ethyl acetate. The extract was washed with water, dried over magnesium sulfate and evaporated to give Z—L—Ala—γ—D—Glu(α—OBzl)—(L)—Boc—(D-)—mesoDAP—(L)—D—AlaOH(3) (7.30 g) as white foam.

I.R. (Nujol): 3300, 2600–2400, 1710, 1650 cm$^{-1}$.

N.M.R. (DMSO-d$_6$), δ: 1.0–2.50 (25H, m), 3.80–4.50 (5H, m), 5.05 (2H, S), 5.15 (2H, S), 7.40 (10H, S).

(2) Step 2

Compound (3) ⟶
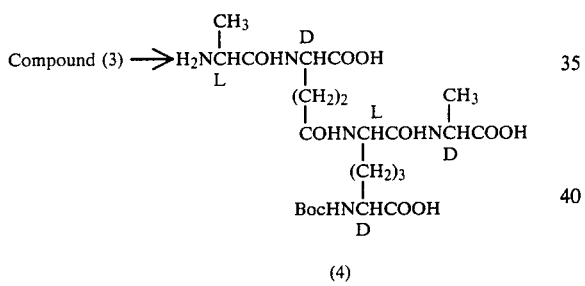
(4)

A solution of Z—L—Ala—γ—D—Glu(α—OBzl)—(L)—Boc—(D)—mesoDAP—(L)—D—AlaOH(3) (7.0 g) in acetic acid (60 ml) was hydrogenated over 10% palladium-charcoal (0.50 g). The catalyst was removed by filtration and the filtrate was evaporated to give a white foam, which was dissolved in water (40 ml) and applied to a column of HP-20 (150 ml). The column was washed with water and eluted with methanol-water (3:7). The eluate was concentrated and lyophillized to give L—Ala—γ—D—Glu(α—OH)—(L)—Boc—(D-)—mesoDAP—(L)—D—AlaOH(4) (4.30 g) as white powder.

I.R. (Nujol): 3300, 2600–2400, 1720 (shoulder), 1660 (broad)cm$^{-1}$.

N.M.R. (D$_2$O), δ: 1.20–2.50 (10H, m), 1.40 (9H, S), 1.36 (3H, d, J=7 Hz), 1.54 (3H, d, J=7 Hz), 3.90–4.50 (4H, m).

(3) Step 3

Compound (4) ⟶

-continued

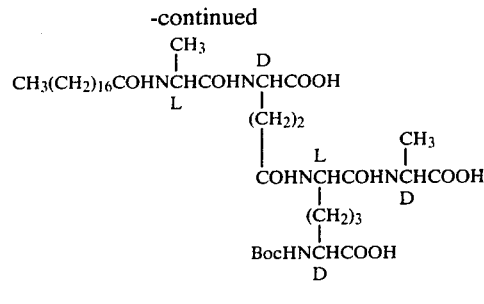
(5)

Stearoyl—L—Ala—γ—D—Glu(α—OH)—(L-)—Boc—(D)—mesoDAP—(L)—D—AlaOH(5) was prepared from L—Ala—γ—D—Glu(α—OH)—(L-)—Boc—(D)—mesoDAP—(L)—D—AlaOH(4) and stearic anhydride in substantially the same manner as that of Step 1 of Example 1.

I.R. (Nujol): 3300, 1710, 1635, 1520 cm$^{-1}$.

N.M.R. (CD$_3$OD-CDCl$_3$), δ: 0.90 (3H, t, J=7 Hz), 1.33 (30H, S), 1.43 (9H, S), 1.00–2.66 (18H, m), 3.60–4.60 (5H, m).

(4) Step 4

Compound (5) ⟶
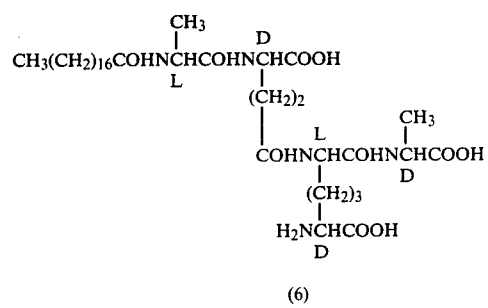
(6)

Stearoyl—L—Ala—γ—D—Glu(α—OH)—(L-)—mesoDAP—(L)—D—AlaOH(6) was prepared from Stearoyl—L—Ala—γ—D—Glu(α—OH)—(L-)—Boc—(D)—mesoDAP—(L)—D—AlaOH(5) in substantially the same manner as that of Step 2 of Example 1.

I.R. (Nujol): 3300, 1730, 1650–1620, 1530 cm$^{-1}$.

N.M.R. (D$_2$O+NaOD), δ: 0.90 (3H, t, J=7 Hz), 1.00–2.66 (51H, m), 3.24 (1H, t, J=7 Hz), 4.00–4.66 (4H, m).

EXAMPLE 62

(1) Step 1

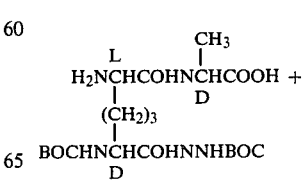
(1)

-continued

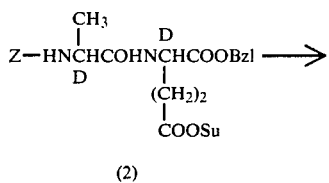

(2)

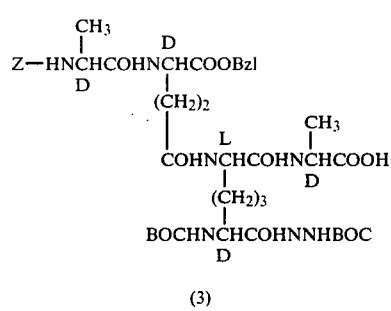

(3)

Z—D—Ala—γ—D—Glu(α—OBzl)—(L-)—Boc—(D)—mesoDAP—(D)—NHNHBoc—(L-)—D—AlaOH(3) was prepared from Boc—(D-)—mesoDAP—(D)—NHNHBoc—(L-)—D—AlaOH(1) and Z—D—Ala—D—Glu(-γ—OSu)OBzl(2) in substantially the same manner as that of Step 1 of Example 1.

I.R. (Nujol): 3300, 2600 (shoulder), 1730, 1670, 1630 cm⁻¹.

N.M.R. (DMSO-d$_6$), δ: 1.00–2.60 (34H, m), 3.88–4.40 (5H, m).

(2) Step 2

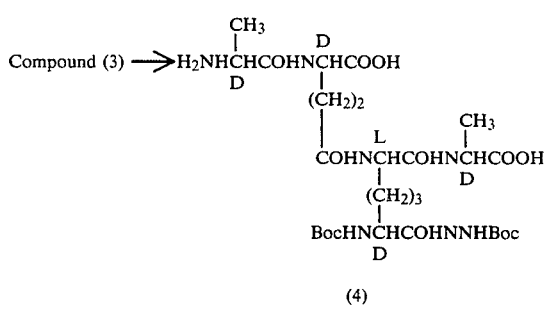

(4)

D—Ala—γ—D—Glu(α—OH)—(L)—Boc—(D-)—mesoDAP—(D)—NHNHBoc—(L-)—D—AlaOH(4) was prepared from Z—D—Ala—γ—D—Glu(α—OBzl)—(L)—Boc—(D-)—mesoDAP—(D)—NHNHBoc—(L-)—D—AlaOH(3) in substantially the same manner as that of Step 2 of Example 63.

I.R. (Nujol): 3300, 2600–2400 (shoulder), 1720 (shoulder), 1660 cm⁻¹.

N.M.R. (D$_2$O), δ: 1.00–2.60 (34H, m), 3.88–4.40 (5H, m).

(3) Step 3

Compound (4) ⟶

-continued

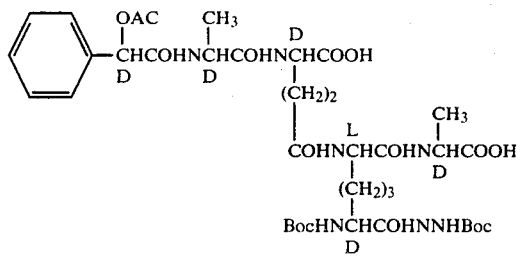

(5)

To a cooled solution of D—Ala—γ—D—Glu(α—OH)—(L)—Boc—(D)—mesoDAP—(D-)—NHNHBoc—(L)—D—AlaOH(4) (1.35 g) in 50% aqueous acetone (10 ml) was added 1N sodium hydroxide. O-Acetyl-D-mandelyl chloride (0.61 g) was added dropwise at 0° C., during which time the pH was maintained at 8.0–9.0. After stirring for 1 hour at the same time, the reaction mixture was adjusted to pH 7.0 with 1N hydrochloric acid and acetone was evaporated. The resulting aqueous solution was adjusted to pH 2.0 with 1N hydrochloric acid and extracted with ethyl acetate. The extract was washed with water, dried over magnesium sulfate and concentrated to give a residue, which was pulverized with ether to give O—acetyl—D—mandelyl—D—Ala—γ-D—Glu(α—OH)—(L)—Boc—(D-)—mesoDAP—(D)—NHNHBoc—(L-)—D—AlaOH(5) (1.35 g) as a solid.

I.R. (Nujol): 3300, 1720, 1650, 1520 cm⁻¹.

N.M.R. (CD$_3$OD), δ: 1.43 (18H, S), 1.00–2.66 (16H, m), 2.15 (3H, S), 4.00–5.00 (5H, m), 5.95 (1H, S), 7.35 (5H, S).

(4) Step 4

Compound (5) ⟶

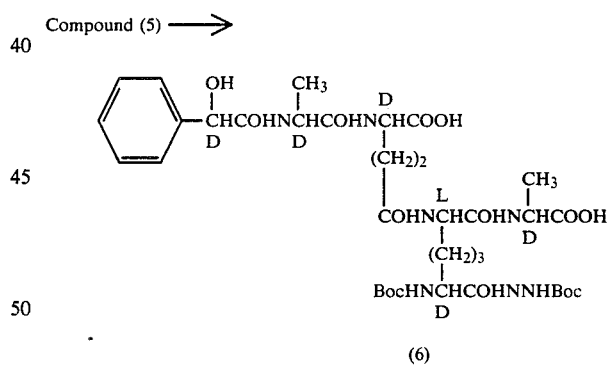

(6)

To a solution of O—acetyl—D—mandelyl—D—Ala—γ—D—Glu(α—OH)—(L-)—Boc—(D)—mesoDAP—(D)—NHNHBoc—(L-)—D—AlaOH(6) (1.25 g) in a mixture of methanol (20 ml) and water (10 ml) was added 1N sodium hydroxide (4.5 ml). After stirring the mixture for 1 hour at room temperature, the pH of the mixture was adjusted to 6.0. After evaporation of methanol, the resulting aqueous solution was adjusted to pH 2.0 with 1N hydrochloric acid and extracted with ethyl acetate. The extract was washed with water, dried over magnesium sulfate and concentrated. The residue was washed with ether to give D—mandelyl—D—Ala—γ—D—Glu(α—OH-)—(L)—Boc—(D)—mesoDAP—(D)—NHNH-Boc—(L)—D—AlaOH(6) (0.96 g) as a solid.

I.R. (Nujol): 3280, 1720–1650, 1520 cm⁻¹.

N.M.R. (CD₃OD), δ: 1.43 (18H, S), 1.00–2.66 (16H, m), 3.83–4.66 (5H, m), 5.10 (1H, S), 7.17–7.66 (5H, m).

(5) Step 5

Compound (6) ⟶

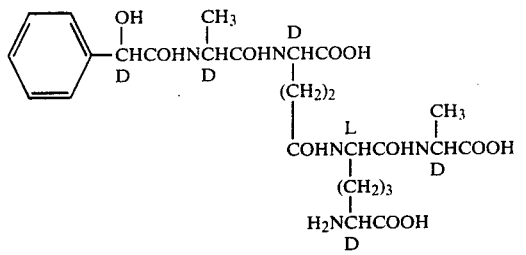

(7)

D—Mandelyl—D—Ala—γ—D—Glu(α—OH)—(L-)—mesoDAP—(L)—D—AlaOH(7) was prepared from D—mandelyl—D—Ala—γ—D—Glu(α—OH)—(L-)—Boc—(D)—mesoDAP—(D)—NHNHBoc—(L-)—D—AlaOH(6) in substantially the same manner as that of Step 2 of Example 1.

I.R. (Nujol): 3280, 1720, 1630–1610, 1520 cm⁻¹.

N.M.R. (D₂O), δ: 1.32 (3H, d, J=7 Hz), 1.40 (3H, d, J=7 Hz), 1.20–2.40 (10H, m), 3.74 (1H, t, J=6 Hz), 4.00–4.50 (4H, m), 5.18 (1H, S), 7.42 (5H, S).

EXAMPLE 63

(1) Step 1

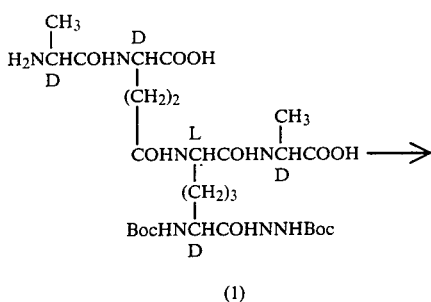

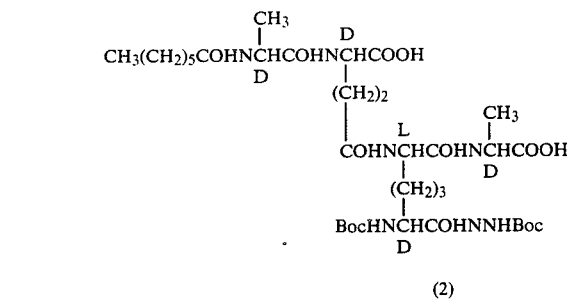

(2)

Heptanoyl—D—Ala—γ—D—Glu(α—OH)—(L-)—Boc—(D)—mesoDAP—(D)—NHNHBoc—(L-)—D—AlaOH(2) was prepared from D—Ala—γ—D—Glu(α—OH)—(L)—Boc—(D-)—mesoDAP—(D)—NHNHBoc—(L-)—D—AlaOH(1) in substantially the same manner as that of Step of 1 of Example 1.

I.R. (Nujol): 3250, 1720, 1660–1640, 1530 cm⁻¹.

N.M.R. (CD₃OD), δ: 0.90 (3H, t, J=7 Hz), 1.00–2,60 (44H, m), 3.90–4.60 (5H, m).

(2) Step 2

Compound (2) ⟶

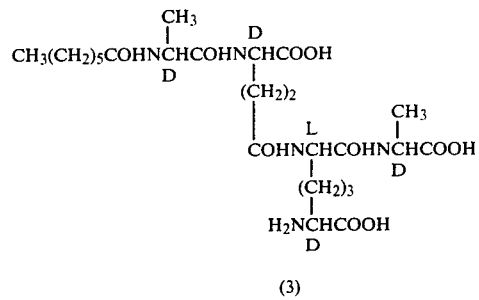

(3)

Heptanoyl—D—Ala—γ—D—Glu(α—OH)—(L-)—mesoDAP—(L)—D—AlaOH(3) was prepared from heptanoyl—D—Ala—γ—D—Glu(α—OH)—(L-)Boc—(D)—mesoDAP—(L)—D—AlaOH(2) in substantially the same manner as that of Step 2 of Example 1.

I.R. (Nujol): 3300, 1720, 1620, 1520 cm⁻¹.

N.M.R. (D₂O), δ: 0.80 (3H, t, J=6 Hz), 1.36 (6H, d, J=7 Hz), 1.00–2.60 (18H, m), 3.76 (1H, t, J=7 Hz), 4.00–4.50 (4H, m).

EXAMPLE 64

(1) Step 1

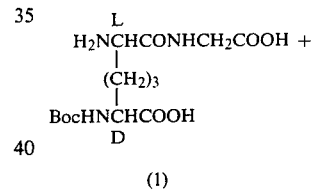

(1)

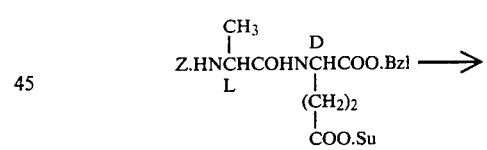

(2)

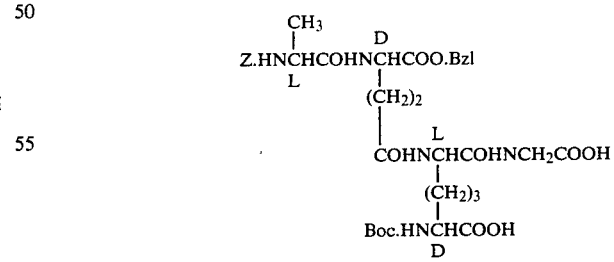

(3)

Z—L—Ala—γ—D—Glu(α—OBzl)—(L)Boc—(D-)—mesoDAP—(L)—GlyOH (3) was prepared from Boc—(D)—mesoDAP—(L)—GlyOH—(1) and Z—L—Ala—(D)Glu(α—Osu)OBzl (2) in substantially the same manner as that of Step 1 of Example 61.

I.R. (Nujol): 3300, 2600–2400, 1720, 1690, 1650 cm⁻¹.

N.M.R. (DMSO-d$_6$), δ(ppm): 1.30 (3H, d, J-7 Hz), 1.10-2.50 (19H, m), 3.80 (2H, d, J=7 Hz), 3.80-4.50 (4H, m), 5.05 (2H, s), 5.18 (2H, s), 7.40 (10H, s).

(2) Step 2

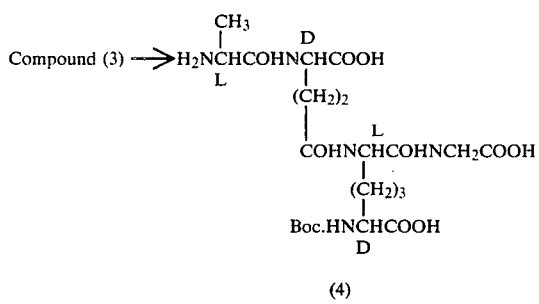

L—Ala—γ—D—Glu(α—OH)—(L-)—Boc—(D-)—mesoDAP—(L)—GlyOH (4) was prepared from Z—L—Ala—γ—D—Glu(α—OBzl)—(L)—Boc—(D-)—mesoDAP—(L)—GlyOH (3) in substantially the same manner as that of Step 2 of Example 61.

I.R. (Nujol): 3300, 2600-2400 (broad), 1720, 1650, (broad) cm$^{-1}$.

N.M.R. (D$_2$O), δ(ppm): 1.56 (3H, d, J-7 Hz), 1.40 (9H, s), 1.20-2.50 (10H, m), 3.92 (2H, s), 4.0-4.40 (4H, m).

(3) Step 3

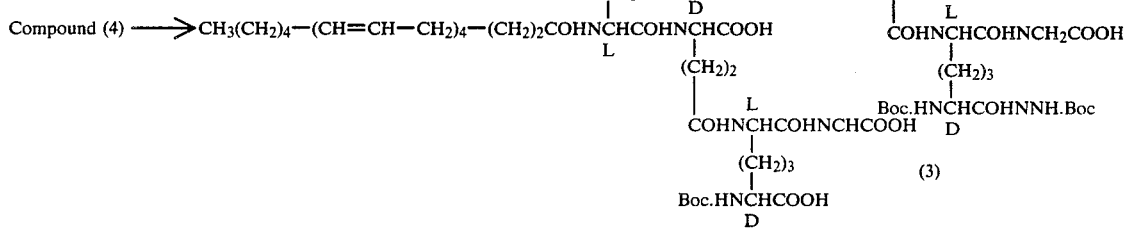

Arachidonyl—L—Ala—γ—D—Glu(α—OH)—(L-)—Boc—(D)—meso—DAP—(L)—GlyOH (5) was prepared from L—Ala—γ—D—Glu(α—OH)—(L-)—Boc—(D)—mesoDAP—(L)—GluOH (4) and N-hydroxyphthalimido ester of arachidonic acid in substantially the same manner as that of Step 3 of Example 61.

I.R. (Nujol): 3300, 1720, 1640, 1530 cm$^{-1}$.

N.M.R. (DMSO-d$_6$), δ(ppm): 0.83 (3H, m), 1.1-2.9 (42H, m), 3.82 (2H, s), 4.05-4.50 (4H, m), 5.20-5.50 (8H, m).

(4) Step 4

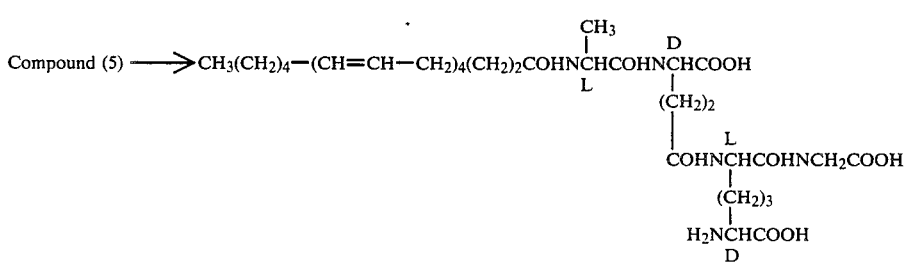

Arachidonyl—L—Ala—γ—D—Glu(α—OH)—(L-)—mesoDAP—(L)—GlyOH (6) was prepared from arachidonyl—L—Ala—γ—D—Glu(α—OH)—(L-)—Boc—(D)—mesoDAP—(L)—GlyOH (5) in substantially the same manner as the Step 2 of Example 1.

I.R. (Nujol): 3270, 1720, 1635, 1530 cm$^{-1}$.

N.M.R. (D$_2$O=NaOD), δ(ppm): 0.85 (3H, m), 1.1-2.0 (33H, m), 3.23 (1H, t, J=7 Hz), 3.76 (2H, s), 4.1-4.5 (3H, m), 5.32 (8H, m).

EXAMPLE 65

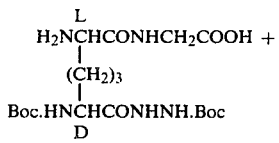

(1)

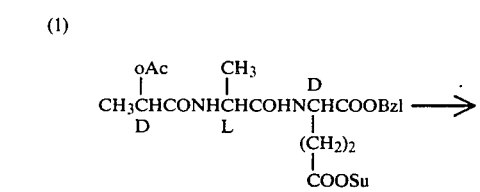

(2)

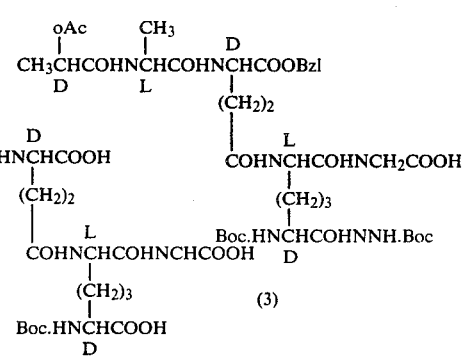

(3)

(1) Example 65-1

Boc(D)—meso—DAP(L)GlyOH—(D)—NHNH-Boc (1) (7.7 g) was dissolved in water (150 ml) and the solution was adjusted to pH 8 with N-methylmorpholine. To the solution was added a dioxane solution (180 ml) of D—Lac(oAc)—L—Ala—γ—D—Glu(α—oBzl-)(oSu) (2) (containing 26.7 m mole of compound (2) as activated ester). The mixture was stirred for four hours at ambient temperature. Dioxane was distilled off under reduced pressure and the resulting mixture was washed with ether (100 ml) and adjusted to pH 3 with 5% aqueous hydrochloric acid. The solution was extracted with ethyl acetate (300 ml and 150 ml) and the extract was washed with water and dried over anhydrous magnesium sulfate and then evaporated to dryness. The residue was crystallized from a mixture of chloroform and ether (1:3) to give D—Lac(oAc)—L—Ala—γ—D—Glu(α—oBzl)—(L)—Boc—(D)—meso—DAP(L)-GlyOH—(D)—NHNHBoc (3) (10.8 g). mp 105°-113° C. (dec.).

N.M.R. (CD$_3$OD), δ(ppm): 1.3-1.8 (30H, m), 2.08 (3H, s), 2.1-2.4 (4H, m), 3.92 (2H, s), 4.2-4.6 (4H, m), 4.8-5.1 (1H, m), 5.17 (2H, s), 7.33 (5H, s).

(2) Example 65-2

D—Lac(oAc)—L—Ala—γ—D—Glu(OH)oBzl (5.2 g) was dissolved in methylene chloride (60 ml) and N-methylmorpholine (1.10 g) was added thereto. To the mixture was added dropwise isobutyl chloroformate (1.50 g) at −10°—−15° C. and the mixture was stirred at −10°—−15° C. for thirty minutes. To the mixture was added a solution prepared by dissolving bis(trimethylsilyl)acetamide (9 ml) and Boc(D)meso—DAP(L)-GlyOH—(D)—NHNHBoc (1) (4.60 g) in a mixture of methylene chloride (50 ml) and dimethylformamide (10 ml). The resulting solution was stirred at −10°—−15° C. for two hours and at 0° C. for an hour and then concentrated to about 30 ml. To the concentrate were added ethyl acetate (200 ml) and 2% aqueous hydrochloric acid (100 ml). The ethyl acetate layer was separated and washed with water and then dried over anhydrous magnesium sulfate. Ethyl acetate was evaporated to dryness under reduced pressure and the residue thus obtained was washed with ether to give D—Lac(oAc-)—L—Ala—γ—D—Glu(α—oBzl)—(L)—Boc—(D-)—meso—DAP(L)GlyOH—(D)—NHNHBoc (3) (8.2 g) of which N.M.R. spectrum was identical with that of the product prepared in Example 65-1.

EXAMPLE 66

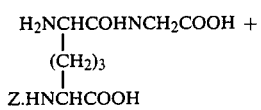

(meso + DL)

(1)

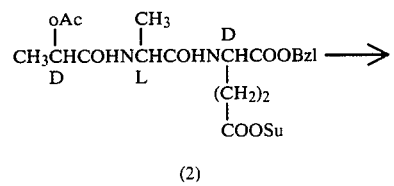

(2)

-continued

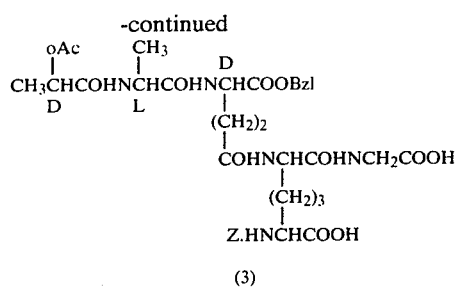

(3)

ZDAP(OH)GlyOH (1) (80 mg) was added to a solution of D—Lac(oAc)—L—Ala—γ—D—Glu(oSu)oBzl (2) (59 mg) in dimethylformamide (4 ml) containing triethylamine (0.03 ml) at 0° C. The mixture was stirred overnight at ambient temperature and then evaporated to dryness. To the residue thus obtained was added dil. hydrochloric acid and then extraction was carried out with ethyl acetate. The extract was washed with water and evaporated to dryness. The residue was recrystallized from a mixture of hexane and chloroform to give D—Lac—(OAC)—L—Ala—γ—D—Glu(α—oBzl)—Z—DAP(OH)GlyOH (3) (86 mg).

N.M.R. (CD$_3$OD), δ(ppm): 1.35 (3H, d, J=7 Hz), 1.43 (3H, d, J=7 Hz), 1.3-2.2 (8H, m), 2.12 (3H, s), 2.30 (2H, m), 3.95 (2H, s), 4.0-4.6 (4H, m), 5.12 (2H, s), 5.18 (2H, s), 7.36 (10H, s).

EXAMPLE 67

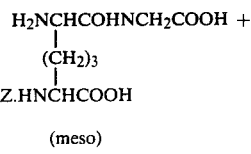

(meso)

(1)

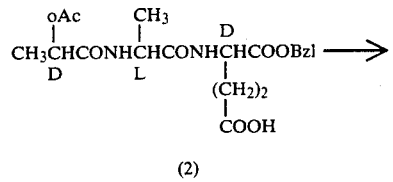

(2)

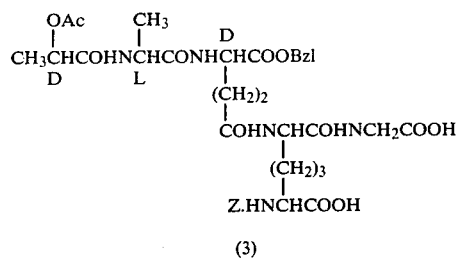

(3)

Z—meso—DAPGlyOH (1) (1.23 g) and bis(trimethylsilyl)acetamide (4.00 g) were suspended in methylene chloride (50 ml) and the suspension was stirred at ambient temperature for four hours. On the other hand, D—Lac—(oAc)—L—Ala—γ—D—Glu(OH)oBzl (2) dicyclohexylamine salt (2.34 g) was dissolved in methylene chloride (30 ml), and triethylamine hydrochloric acid salt (0.54 g) was added at ambient temperature to the solution while stirring. The stirring was continued for two hours and the reaction mixture was cooled to −30° C. and a solution of isobutyl chloroformate (0.53 g) in methylene chloride (50 ml) was added dropwise thereto. The resulting mixture was reacted for twenty minutes at the same temperature. To the reaction mixture was added dropwise a methylene chloride solution of Z—meso—DAPGlyOH prepared above and the resulting mixture was stirred at −30° C. for an hour. The reaction mixture was reacted at ambient temperature for four hours and filtered. The filtrate was washed with 10% aqueous hydrochloric acid and concentrated under reduced pressure and the residue thus obtained was extracted with ethyl acetate. The ethyl acetate layer was washed with water and dried over anhydrous magnesium sulfate and concentrated under reduced pressure to give an oily D—Lac-(oAc)—L—Ala—γ—D—Glu(α—oBzl)—Z—meso—DAP-GlyOH (3 g).

N.M.R. (CD₃OD), δ(ppm): 1.35 (3H, d, J=7 Hz), 1.43 (3H, d, J=7 Hz), 1.3–2.2 (8H, m), 2112 (3H, s), 2.30 (2H, m), 3.95 (2H, s), 4.0–4.6 (4H, m), 5.12 (2H, s), 5.18 (2H, s), 7.36 (10H, s).

ether, acidified to pH 2 with a diluted aqueous hydrochloric acid and extracted with a mixture of ethyl acetate and methylene chloride, containing 1N hydrochloric acid, water and brine, dried over magnesium sulfate and evaporated to give an amorphous solid (660 mg) which was dissolved in chloroform and triturated with ether to give D—Lac(oAc)—L—Ala—γ—D—Glu(α—oBzl)—(D)—Z—(L)—mesoDAP—(D)—GlyOH (3) (450 mg)

N.M.R. (CDCl₃-CD₃OD), δ(ppm): 1.37 (3H, d, J=7 Hz), 1.45 (3H, d, J=7 Hz), 1.2–1.9 (6H, m), 2.0–2.5 (4H, m), 3.93 (2H, broad s), 4.1–4.7 (3H, m), 5.10 (2H, s), 5.17 (2H, s).

EXAMPLE 68

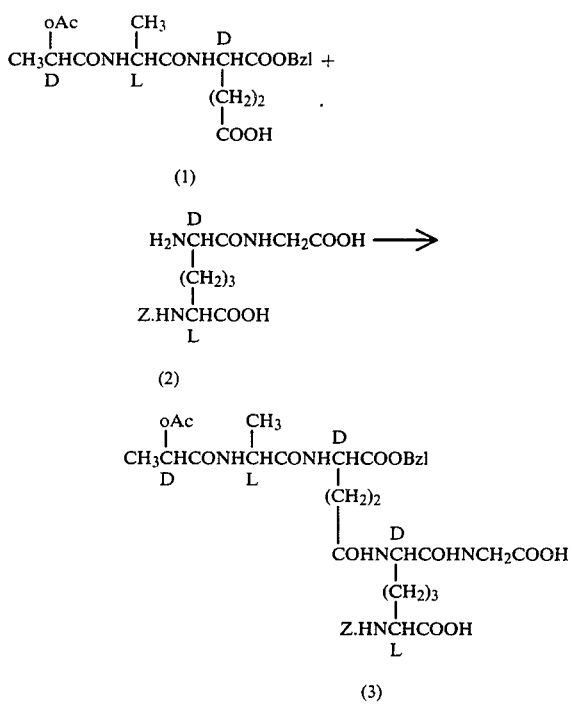

EXAMPLE 69

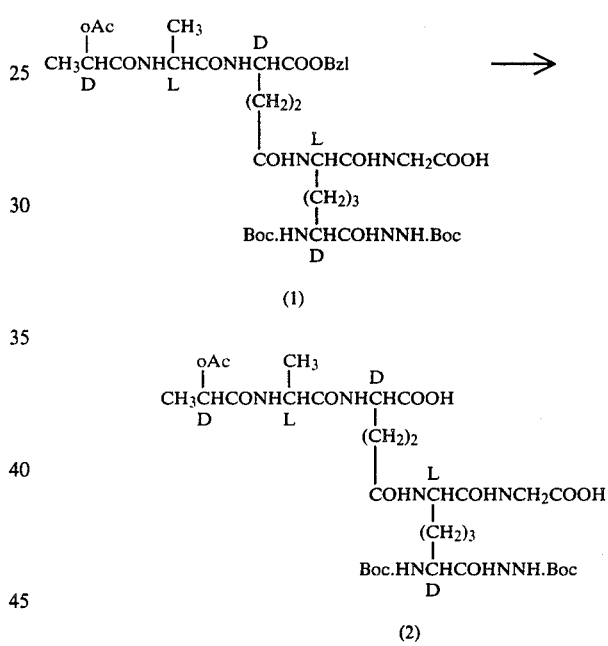

To a mixture of D—Lac(oAc)—L—Ala—γ—D—Glu(OH)(α—oBzl) (1) (653 mg) and N-hydroxysuccinimide (178 mg) in dioxane (7 ml) was added N,N′-dicyclohexylcarbodiimide (320 mg).

The mixture was stirred at 10° C. for ten minutes and further stirred at ambient temperature for 14 hours. The reaction mixture was filtered and the filtrate was evaporated to dryness and the residue was dissolved in dioxane (4.5 ml). A 3 ml portion of this solution was added to a mixture of Z—(L)—mesoDAP—(D)GlyOH (280 mg) and N-methyl-morpholine (156 μl) in dioxane (4 ml) and the mixture was stirred at ambient temperature. After 4.5 hours, a 0.9 ml portion of the above dioxane solution and N-methylmorpholine (100 μl) was added and the mixture was stirred at the same temperature. After 4.5 hours an additional 0.6 ml of the above dioxane solution was added and the mixture was stirred for 1.25 hours. The reaction mixture was washed with D—Lac(oAc)—L—Ala—γ—D—Glu(α—oBzl)—(L)—Boc—(D)meso—DAP(L)GlyOH—(D-)—NHNHBoc (1) (9.4 g) was hydrogenated in acetic acid (100 ml) over 10% palladium black (2.0 g) for 2 hours under 1.5 hydrogen atmospheric pressure at ambient temperature. After completion of the reaction, the catalyst was filtered off and the filtrate was evaporated to dryness under reduced pressure. The residue was triturated with ether to give D—Lac(oAc-)—L—Ala—γ—D—Glu(α—OH)—(L)—Boc—(D-)—meso—DAP—(L)GlyOH—(D)—NHNHBoc (2) (7.50 g).

N.M.R. (CD₃OD), δ(ppm): 1.3–1.9 (m), 2.10 (3H, s), 2.1–2.4 (4H, m), 3.90 (2H, s), 4.2–4.6 (4H, m), 4.8–5.1 (1H, m).

EXAMPLE 70

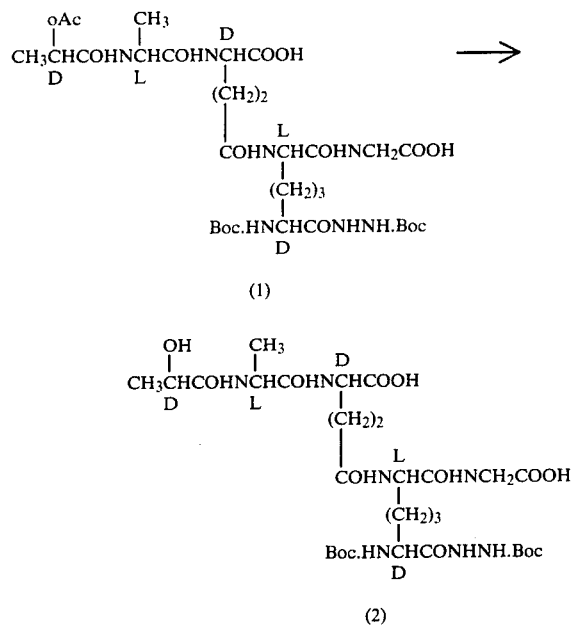

D—Lac(oAc)—L—Ala—γ—D—Glu(α—OH)—(L-)—Boc—(D)—meso—DAP(L)—Gly—(OH)—(D-)—NHNHBoc (1) (1.65 g) was dissolved in 50% aqueous methanol (32 ml) and the solution was stirred for 2.5 hours at ambient temperature, maintaining the pH at 9.0 with 5% aqueous solution of potassium carbonate. The solution was evaporated to dryness under reduced pressure. The residue was adjusted to pH 3 with 5% aqueous hydrochloric acid and then passed through a column packed with a macroporous non-ionic adsorption resin, HP20 (500 ml). The resin was washed with water (200 ml) and eluted with a mixture of methanol and water (1:1 volume). The eluate was evaporated to dryness and the residue was washed with ether to give D—Lac—L—Ala—γ—D—Glu(α—OH)—(L-)—Boc—(D)—meso—DAP(L)GlyOH—(D-)—NHNHBoc (2) (1.24 g).

I.R. (Nujol): 3270, 3200–2600, 1720, 1640 cm$^{-1}$.

N.M.R. (CD$_3$OD), δ(ppm): 1.47 (18H, s), 3.93 (2H, s).

EXAMPLE 71

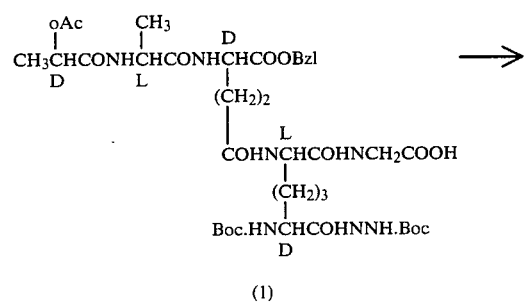

-continued

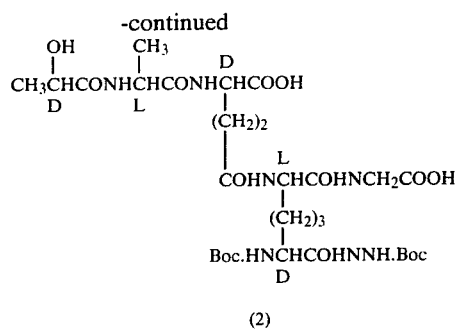

D—Lac(oAc)—L—Ala—γ—D—Glu(α—oBz-l)—(L)—Boc—(D)—meso—DAP(L)GlyOH—(D-)—NHNHBoc (1) (1.0 g) was dissolved in 50% aqueous methanol (20 ml), and 1N aqueous sodium hydroxide (3.7 ml) was added thereto. The resulting solution was stirred for two hours at ambient temperature and concentrated to about 5 ml. The concentrate was adjusted to pH 3 and passed through a column packed with a macroporous non-ionic adsorption resin, HP20 (24 ml). The column was washed with water (100 ml) and eluted with a mixture of methanol and water (1:1) and the eluate was evaporated to dryness under reduced pressure. The residue thus obtained was washed with ether to give D—Lac—L—Ala—γ—D—Glu(α—OH)—(L-)—Boc—(D)—meso—DAP(L)GlyOH—(D-)—NHNHBoc. (2) (660 mg) which was identified with the product prepared in Example 70.

EXAMPLE 72

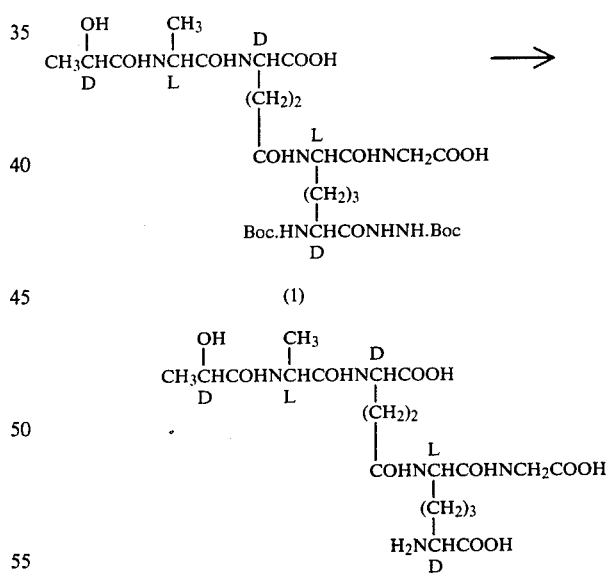

(1) Example 72-1

D—Lac—L—Ala—γ—D—Glu(α—OH)—(L-)—Boc—(D)—meso—DAP(L)—GlyOH—(D-)—NHNHBoc (1) (200 mg) was dissolved in trifluoroacetic acid (1 ml) and the solution was stirred for fifteen minutes at ambient temperature. The solution was evaporated to dryness under reduced pressure. The residue was triturated with ether. The powder thus obtained was dissolved in water (5 ml) and 0.1N aqueous sulfuric acid (6.8 ml) was added. To the mixture was added dropwise a solution of sodium periodate (146 mg) in water (2 ml). The mixture was stirred for an hour under ice-cooling and then the excess reagent was decomposed with sodium bisulfite. The resulting solution was adjusted to pH 3 with an aqueous saturated sodium bicarbonate and concentrated to 1 ml under reduced pressure. The concentrate was passed through a column packed with a macroporous non-ionic adsorption resin, HP20 and eluted with water. The eluate was lyophilized to give D—Lac—L—Ala—γ—D—Glu(α—OH-)—(L)—meso—DAP(L)GlyOH (2) (86 mg) as a solid.

N.M.R. (D$_2$O), δ(ppm): 1.40 (3H, d, J=7 Hz), 1.46 (3H, d, J=7 Hz), 3.88 (1H, t, J=5 Hz), 4.02 (2H, s).

[α] = −30.0 (c=0.4, water).

(2) Example 72-2

D—Lac—L—Ala—γ—D—Glu(α—OH)—(L-)—Boc—(D)—meso—DAP(L)—GlyOH—(D-)—NHNHBoc (1) (220 mg) was dissolved in trifluoroacetic acid (1.5 ml) and the solution was stirred for fifteen minutes at ambient temperature. The trifluoroacetic acid was evaporated to dryness under reduced pressure and the residue thus obtained was triturated with ether. The powder was dissolved in a mixture of water (5 ml) and dioxane (7 ml), and N-bromosuccinimide (110 mg) was added under ice-cooling thereto and the solution was stirred for an hour. The reaction mixture was concentrated to about 1 ml and the concentrate was adjusted to pH 2.5 with 5% aqueous sodium bicarbonate. The solution was passed through a column packed with a macroporous non-ionic adsorption resin, HP20 (16 ml) and elution was carried out with water and the eluate was lyophilized to give D—Lac—L—Ala—γ—D—Glu(α—OH)—(L-)—meso—DAP(L)GlyOH (2) (150 mg), which was identified with the product prepared in Example 72-1.

(3) Example 72-3

D—Lac—L—Ala—γ—D—Glu(α—OH)—(L-)—Boc—(D)—meso—DAP(L)—GlyOH—(D-)—NHNHBoc (1) (200 mg) was dissolved in trifluoroacetic acid (1 ml) and the solution was stirred at ambient temperature for fifteen minutes. Trifluoroacetic acid was evaporated to dryness under reduced pressure. The residue thus obtained was triturated and the powder was dissolved in 60% aqueous acetic acid (15 ml). To the solution was added manganese dioxide (65 mg) while stirring at ambient temperature and the mixture was stirred at the same temperature for 1.5 hours. Insoluble materials were filtered off and then the filtrate was evaporated to dryness under reduced pressure. The residue thus obtained was dissolved in 50% aqueous ethanol and cooled to −10°−−20° C. and then adjusted to pH 9 with aqueous ammonium. The solution was allowed to stand at the same temperature for two hours. Insoluble materials were filtered off and the filtrate was evaporated to dryness under reduced pressure. The residue was passed through a column packed with activated carbon (10 ml). The column was washed with water (30 ml) and eluted with 70% aqueous acetone. The fraction containing the object compound was collected and evaporated to dryness under reduced pressure. The residue was pulverized with a mixture of methanol and ether to give D—Lac—L—Ala—γ—D—Glu(α—OH)—(L-)—meso—DAP(L)GlyOH (2) (84 mg), whose structure was confirmed in comparision of data of the products prepared in Example 72-1.

EXAMPLE 73

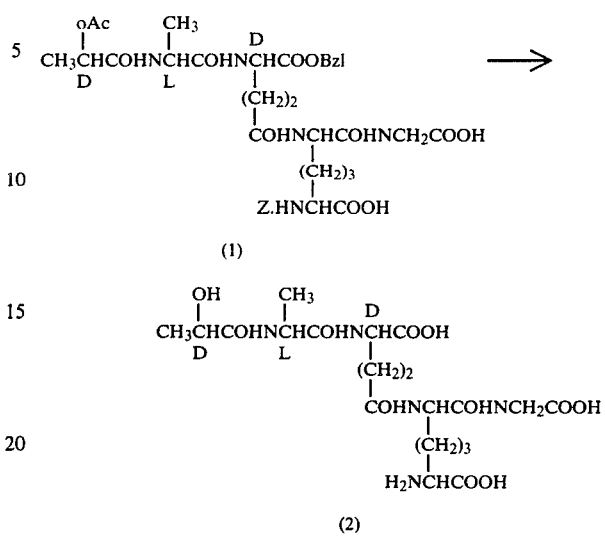

D—Lac(oAc)—L—Ala—γ—D—Glu(α—oBzl)—Z-DAP(OH)GlyOH (1) (2.80 g) was dehydrogenated in acetic acid (15 ml) over 10% palladium black (0.50 g) under two atmospheric pressure of hydrogen for six hours. The reaction mixture was filtered and the filtrate was concentrated to give an oil. The oil was dissolved in water and the solution was adjusted to pH 9.0–9.5 with diluted aqueous solution of potassium carbonate, and then stirred under ice-cooling for four hours. The reaction mixture was adjusted to pH 7 with dil. hydrochloric acid and concentrated. The concentrate was dissolved in methanol and insoluble materials were filtered off. The methanolic filtrate was evaporated to dryness under reduced pressure, and the residue was dissolved in water (3 ml) adjusted to pH 3–3.2, passed through a column packed with a macroporous non-ionic adsorption resin, HP20 (200 ml) and then eluted with water. The fractions containing the object compound were collected and concentrated to give a powder (400 mg). The power was dissolved in water and the solution was again passed through a column packed with a macroporous non-ionic adsorption resin, HP20 (100 ml). Elution was carried out with water and the fraction containing the object compound was collected and concentrated to give D—Lac—L—Ala—γ—D—Glu(α—OH)—DAP(OH)GlyOH (2) (100 mg), whose structure was confirmed in comparision of data of the products prepared in Example 72-1.

EXAMPLE 74

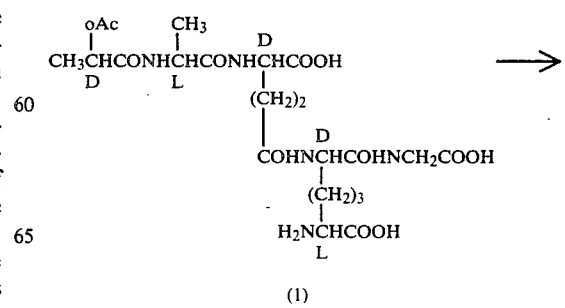

-continued

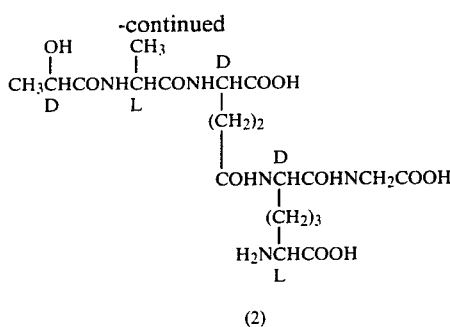

(2)

5% Aqueous potassium bicarbonate (3.25 ml) was added to a solution of D—Lac(oAc-)—L—Ala—γ—D—Glu(α—OH)—(D-)—mesoDAP(D)GlyOH (1) (278 mg) in 5% aqueous methanol (6 ml) at ambient temperature. The mixture was stirred at ambient temperature with occasional addition of 5% aqueous potassium bicarbonate in order to maintain pH 9. The reaction mixture was acidified to pH 3.5 with 1N aqueous hydrochloric acid and evaporated to dryness. The residue was dissolved in water and the solution was concentrated to about 2 ml. The concentrate was chromatographed on macroporous non-ionic adsorption resin, HP20 (15 ml) and elution was carried out with water. The fraction containing the object compound was eveporated, and the residue was dissolved in a small amount of water and lyophilized to give D—Lac—L—Ala—γ—D—Glu(α—OH)—(D-)—mesoDAP—(D)—GlyOH (135 mg), whose structure was confirmed in comparision of data of the products prepared in Example 72-1.

EXAMPLE 75

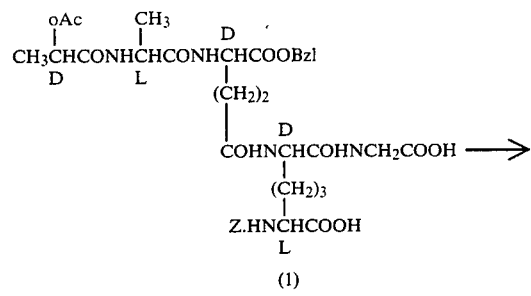

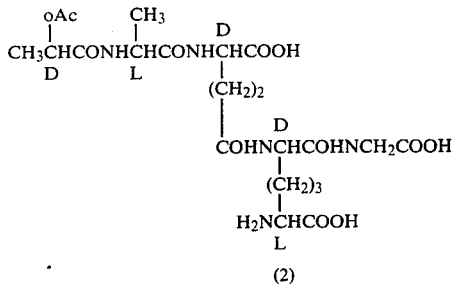

(2)

A mixture of D—Lac(oAc)—L—Ala—γ—D—Glu(α—oBzl)—(D)—Z—(L)—mesoDAP—(D)—GlyOH (1) (440 mg) and 10% palladium black (90 mg) in acetic acid (5 ml) was stirred under hydrogen atmosphere for four hours. Additional 10% palladium black (60 mg) and acetic acid (3 ml) were added to the reaction mixture and the stirring was continued under hydrogen atmosphere for four hours. The reaction mixture was filtered. The filtrate was concentrated under reduced pressure and the residue was dissolved in water. The aqueous solution was evaporated to dryness. The residue was again dissolved in water and concentrated. The concentrate was lyophilized to give D—Lac(oAc)—L—Ala—γ—D—Glu(α—OH)—(D-)—meso—DAP(D)GlyOH (2) (301 mg).

N.M.R. (D$_2$), δ(ppm): 1.42 (3H, d, J=7 Hz), 1.47 (3H, d, J=7 Hz), 2.14 (3H, s), 1.0-2.8 (10H, m), 3.80 (1H, t, J=7 Hz), 3.94 (2H, s), 4.1-4.6 (3H, m) 5.02 (1H, q, J=7 Hz).

EXAMPLE 76

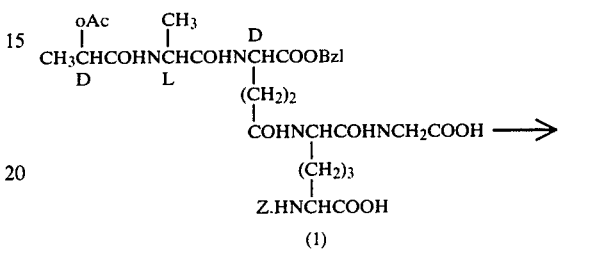

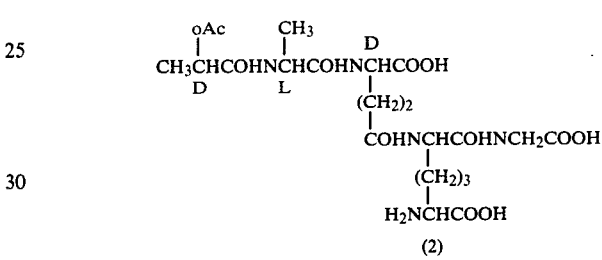

A solution of D—Lac(oAc)—L—Ala—γ—D—Glu(α—oBzl)—Z—DAP(OH)GlyOH in methanol (1) (20 mg) was hydrogenated over 10% palladium black (50 mg). The reaction mixture was filtered and the filtrate was evaporated to dryness to give D—Lac(oAc-)—L—Ala—γ—D—Glu(α—OH)—DAP(OH)GlyOH (2) (10 mg), whose structure was confirmed in comparision of data of the products prepared in Example 75.

EXAMPLE 77

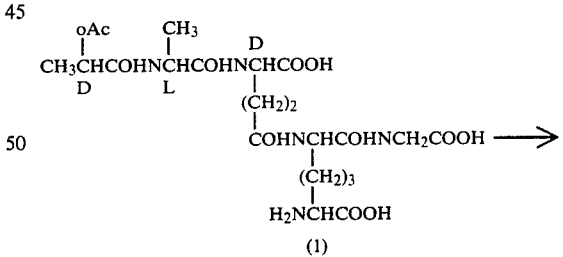

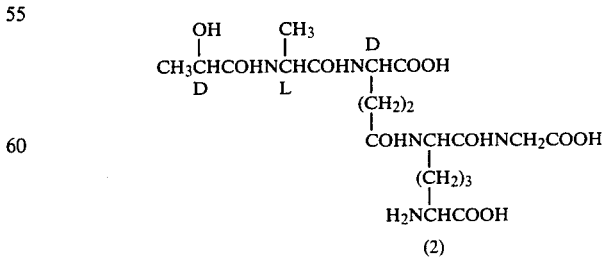

D—Lac(oAc)—L—Ala—γ—D—Glu(α—OH-)—DAP(OH)GlyOH (1) (10 mg) was added to 0.05M solution of potassium carbonate in 70% methanol (0.6 ml) at 0° C. and the mixture was stirred at ambient temperature for an hour. The reaction mixture was neutralized with acetic acid and then evaporated to give a residue. The residue was purified by suing carbon column chromatography. Elution was carried out with 50% aqueous acetone to give D—Lac—L—Ala—γ—D—Glu(α—OH)—DAP(OH)-GlyOH (2) (7 mg), whose structure was confirmed in comparision of data of the products prepared in Example 72-1.

EXAMPLE 78

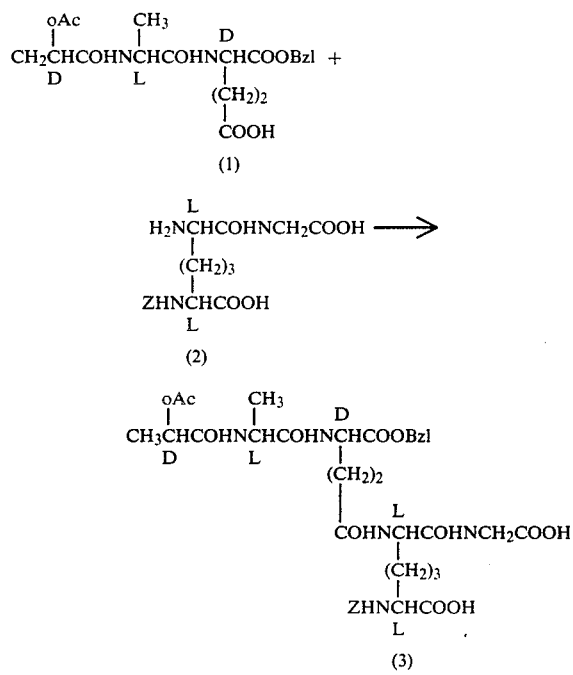

To a mixture of D—Lac(oAc)—L—Ala—D—Glu(OH)oBzl (1) (2.45 g) and succinic acid (740 mg) in dioxane (20 ml) was added N,N'-dicyclohexylcarbodimido (1.25 g) at 12° C. and the mixture was stirred at ambient temperature for 16 hours. The reaction mixture was filtered and N,N'-dicyclohexylurea was washed with dioxane. The filtrate and the washings were combined and concentrated. The concentrate was dissolved in dioxane (18 ml). This solution was used for the next reaction. To a mixture of Z—(α)—L—DAP—(ε)—GlyOH (2) (1.21 g) and N-methylmorpholine (1.02 ml) in water (20 ml) was added the above solution at 5° C. and the mixture was stirred at 5° C. for 40 minutes and at ambient temperature for 4 hours. An additional N-methylmorpholine (0.2 ml) was added to the reaction mixture and the resulting mixture was stirred at the same temperature for two hours. The reaction mixture was concentrated and the concentrate was diluted with water. The solution was washed with ether and acidified with dil. hydrochloric acid to pH 2. To the solution was added a mixture of methylene chloride and ethyl acetate and the mixture was shaked and then filtered to give insoluble materials and the organic layer. The organic layer was washed with water, dried over magnesium sulfate and concentrated. The residue was combined with the insoluble materials described above and dissolved in a mixture of chloroform and methanol (1:1). The solution was concentrated and the concentrate was triturated with a mixture of ethyl acetate and ether (1:2) to give a powder (1.8 g), which was dissolved in a mixture of chloroform and methanol and ethyl acetate (1:1:1) and concentrated. The concentrate was triturated with a mixture of ethyl acetate and ether (5:1) to give D—Lac(oAc)—L—Ala—γ—D—Glu(α—oBzl)—(α)—Z—(ε)—L—DAP—(α)—GlyOH (3) (1.654 g).

N.M.R. (CDCl$_3$-CD$_3$OD), δ(ppm): 1.37 (3H, d, J=7 Hz), 1.46 (3H, d, J=7 Hz), 2.11 (3H, s), 1.2–2.6 (10H, m), 3.95 (2H, s), 4.0–4.6 (4H, m), 4.96 (1H, q, J=7 Hz), 5.08 (2H, s), 5.15 (2H, s), 7.33 (10H, s).

EXAMPLE 79

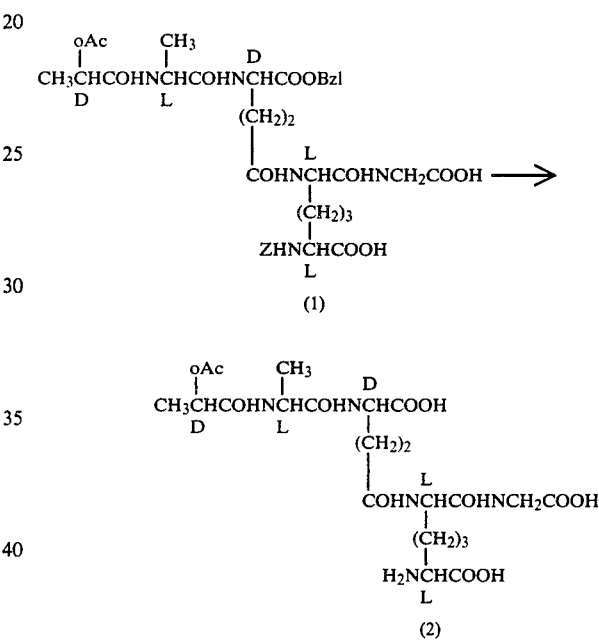

A solution of D—Lac(oAc)—L—Ala—γ—D—Glu(α—oBzl)—(α)—Z—(ε)—L—DAP—(α)—GlyOH (1) (1.59 g) in acetic acid (40 ml) was hydrogenated over 10% palladium black (500 mg) for 4 hours. The reaction mixture was filtered and the filter cake was washed with 50% aqueous methanol. The filtrate and the washings were combined and evaporated and pumped to give a residue (1.5 g). Contaminated acetic acid was removed by co-eveporation with water and this operation was repeated once more. The residue was dissolved in water and lyophilized to give D—Lac(oAc)—L—Ala—γ—D—Glu(α—OH)—(α)—L—DAP—(α)—GlyOH (2) (1.10 g).

N.M.R. (D$_2$O), δ(ppm): 1.43 (3H, d, J=7 Hz), 1.48 (3H, d, J=7 Hz), 1.3–2.7 (10H, m), 2.15 (3H, s), 3.80 (1H, broad t, J=6 Hz), 3.95 (2H, s), 4.0–4.6 (3H, m), 5.05 (1H, q, J=7 Hz).

EXAMPLE 80

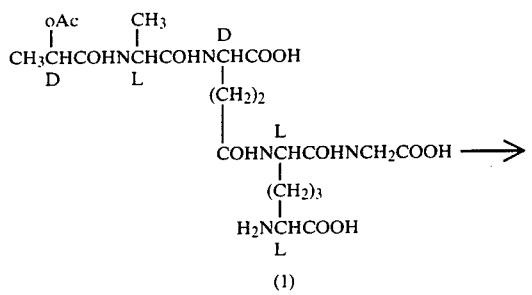

To a solution of D—Lac(oAc)—L—Ala—γ—D—Glu(α—OH)—(α)—L—DAP—(α)—GlyOH (1) in a mixture of methanol (15 ml) and water (5 ml) was added 1N sodium hydroxide (7.5 ml) at 5° C. The solution was stirred at the same temperature for 30 minutes and at ambient temperature for 2.25 hours.

The resulting solution was acidified to pH 4 with 3N hydrochloric acid and concentrated. The concentrate was diluted with water to 10 ml, acidified to pH 2.2 with 3N hydrochloric acid and chromatographed on a column of a macroporous non-ionic adsorption resin, HP 20 (135 ml). Elution was carried out with water and the eluate was concentrated and lyophilized to give D—Lac—L—Ala—γ—D—Glu(α—OH)—(α)—L—DAP—(α)—GlyOH (2) (681 mg). mp. 130° C. (dec.)

N.M.R. (D$_2$O), δ(ppm): 1.39 (3H, d, J=7 Hz), 1.45 (3H, d, J=7 Hz), 1.1–2.6 (10H, m), 3.86 (1H, t, J=6 Hz), 4.00 (2H, s), 4.1–4.6 (4H, m).

$[\alpha]_D^{15} = -23.3°$ (C=0.322, water).

EXAMPLE 81

(1) Step 1

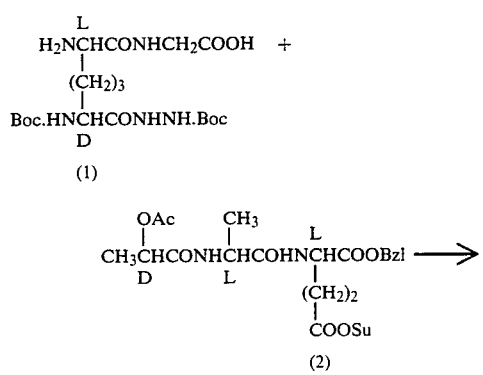

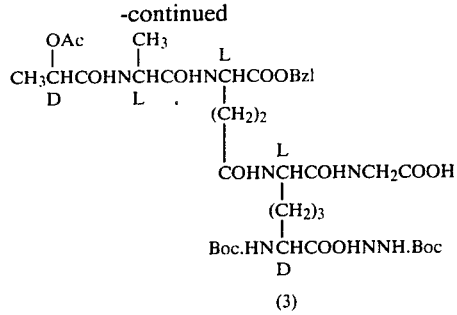

D—Lac(OAc)—L—Ala—γ—L—Glu(α—OBzl)—(L)—Boc—(D)—meso—DAP(L)—GlyOH—(D-)—NHNHBoc (3) was prepared from Boc(-D)—meso—DAP—(L)GlyOH—(D)—NHNHBoc (1) and D—Lac(OAc)—L—Ala—L—Glu(α—OBzl) (2) in substantially the same manner as that of Example 65-1.

IR(Nujol): 3300, 1735, 1695 1645 cm$^{-1}$.

NMR(CD$_3$OD): 1.40(9H, S), 1.42(9H, S), 2.08(3H, S), 3.90(2H, broad S), 4.00~5.00(5H, m), 5.10(2H, S), 7.30(5H, S).

(2) Step 2

Compound (3) ⟶

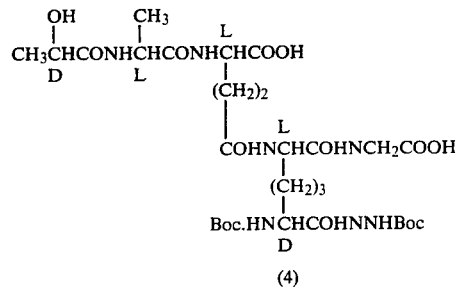

D—Lac(OH)—L—Ala—γ—L—Glu(α—OH)—(L-)—Boc—(D)—meso—DAP—(L)—GlyOH—(D-)—NHNHBoc (4) was prepared in substantially the same manner as that of Example 71.

NMR (CD$_3$OD), δ(ppm): 1.44(9H, S), 1.46(9H, S), 3.90(2H, broad S), 4.00~4.60(5H, m).

(3) Step 3

Compound (4) ⟶

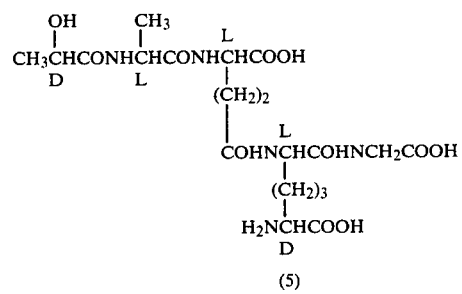

D—Lac(OH)—L—Ala—γ—L—Glu(α—OH)—(L-)—meso—DAP(L)GlyOH (5) was prepared in substantially the same manner as that of Example 72-1.

NMR (D₂O), δ(ppm): 1.38(3H, d, J=7 Hz), 1.00~2.60(10H, m), 3.98(2H, S), 3.84(1H, t, J=7 Hz), 4.1~4.5(4H, m).

[α]_D= −34.7 (c=0.15 water).

EXAMPLE 82

(1) Step 1

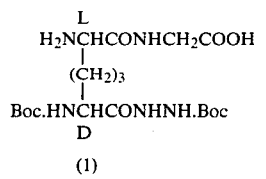
(1)

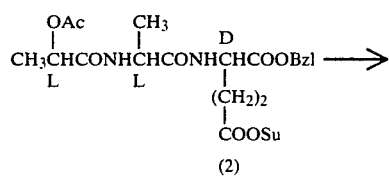
(2)

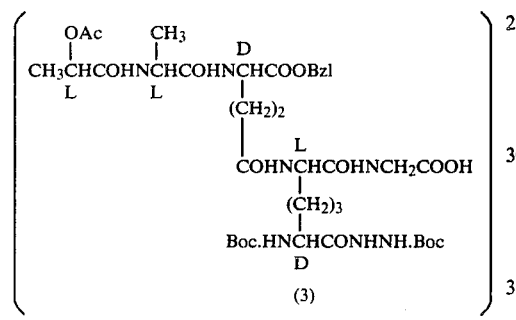
(3)

L—Lac(OAC)—L—Ala—γ—D—Glu(α—OBzl)—(L)—Boc—(D)—meso—DAP(L)—GlyOH—(D-)—NHNHBoc (3) was prepared from Boc(D)—mesoDAP—(L)—GlyOH—(D)—NHNHBoc (1) and L—Lac(OAC)—L—Ala—D—Glu(α—OBzl) (2) in substantially the same manner as that of Example 65-1.

(2) Step 2

Compound (3) →

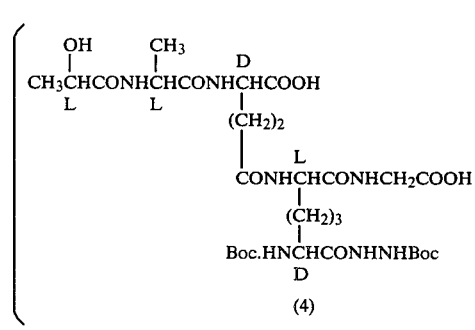
(4)

L—Lac(OH)—L—Ala—γ—D—Glu(α—OH)—(L-)—Boc—(D)—meso—DAP(L)—GlyOH—(D-)—NHNHBoc (4) was prepared in substantially the same manner as that of Example 71.

Step (3)

Compound (4) →

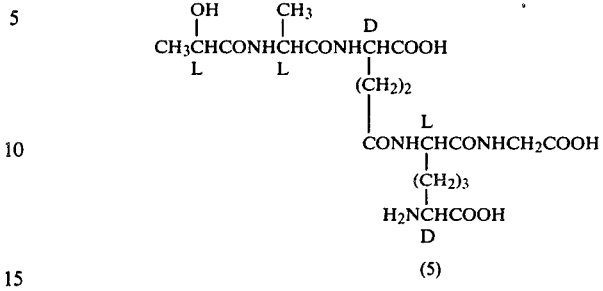
(5)

L—Lac(OH)—L—Ala—γ—D—Glu(α—OH)—(L-)—meso—DAP(L)GlyOH (5) was prepared in substantially the same manner as that of Example 72-1.

mp 170°~174° C. (dec.).

[α]_D= −33.2° (C=0.25, water).

NMR (D₂O), δ(ppm): 1.38(3H, J=7 Hz), 1.45(3H, J=7 Hz), 3.89(1H, t, J=7 Hz), 4.01(2H, s), 4.20 4.55(m).

EXAMPLE 83

(1) Step 1

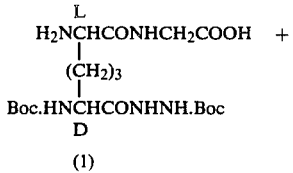
(1)

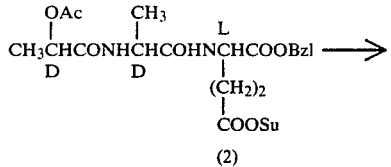
(2)

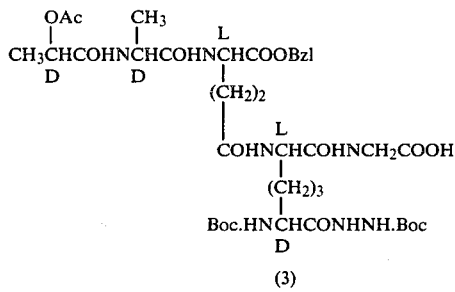
(3)

D—Lac(OAC)—D—Ala—γ—L—Glu(α—OBzl)—(L)—Boc—(D)—meso—DAP(L)—GlyOH—(D-)—NHNHBoc (3) was prepared from Boc(-D)—mesoDAP—(L)—GlyOH—(D)—NHNHBoc (1) and D—Lac(OAC)—D—Ala—L—Glu(α—OBzl) (2) in substantially the same manner as that of Example 65-1.

NMR (CD₃OD), δ(ppm): 1.40(9H, s), 1.42(9H, s), 2.06(3H, s), 3.90(2H, broad s), 3.90~5.00(5H, m), 5.15(2H, s), 7.35(5H, s).

(2) Step 2

Compound (3) →

-continued

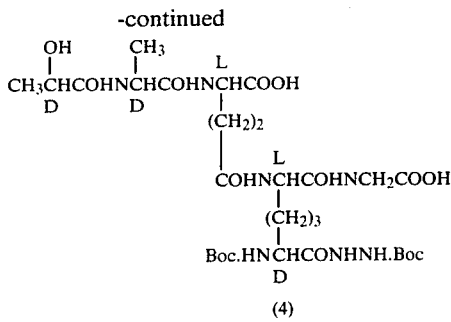

(4)

D—Lac(OH)—D—Ala—γ—L—Glu(α—OH)—(L-)—Boc—(D)—meso—DAP(L)—GlyOH—(D-)—NHNHBoc (4) was prepared in substantially the same manner as that of Example 71.

IR (Nujol): 3300, 1740, 1690 1740 (Broad) cm$^{-1}$.

NMR (CD$_3$OD), δ(ppm): 3.90(2H, broad s), 4.00~4.60(5H, m).

(3) Step 3

Compound (4) ⟶

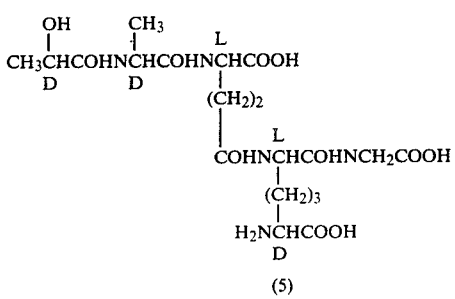

(5)

D—Lac(OH)—D—Ala—γ—L—Glu(α—OH)—(L-)—mesoDAP(L)GlyOH (5) was prepared in substantially the same manner as that of Example 72-1.

NMR (D$_2$O), δ(ppm): 1.35(3H, d, J=7 Hz), 1.40(3H, d, J=7 Hz), 1.00~2.60(10H, m), 3.80(1H, t, J=7 Hz), 3.90(2H, s), 4.10~4.5(4H, m).

[α]$_D$ = +0.76 (c=0.35, water).

EXAMPLE 84

(1) Step 1

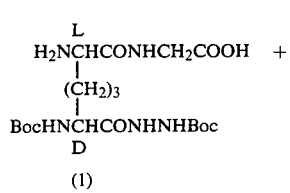

(1)

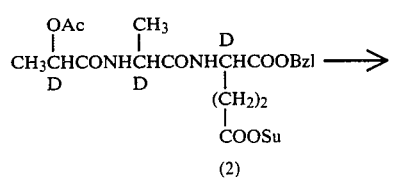

(2)

-continued

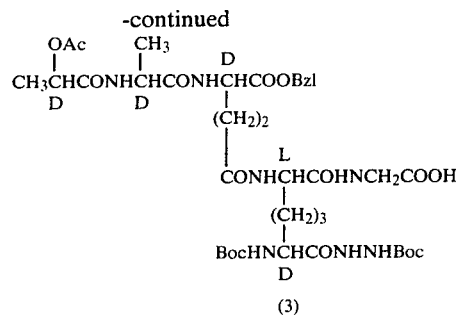

(3)

D—Lac(OAC)—D—Ala—γ—D—Glu(α—oBzl)—(L)—Boc—(D)—mesoDAP—(D)—NHNHBoc—(L)—GlyOH (3) was prepared from Boc(-D)—mesoDAP—(D)—NHNHBoc—(L)—GlyOH (1) and D—Lac(oAC)—D—Ala—D—Glu(α—OBzl) (2) in substantially the same manner as that of Example 65-1.

N.M.R. (CD$_3$OD), δ(ppm): 1.41 (18H, s), 2.12 (3H, s), 3.92 (2H, broad s), 4.00-5.10 (5H, m), 5.16 (2H, s), 7.36 (5H, s).

(2) Step 2

Compound (3) ⟶

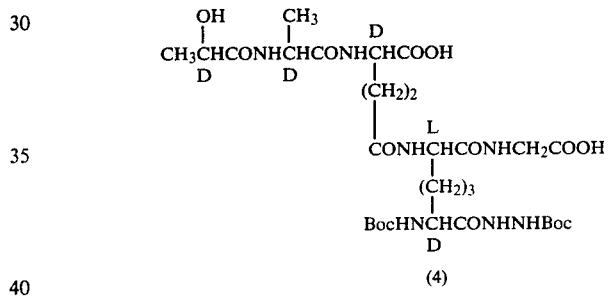

(4)

D—Lac(OH)—D—Ala—γ—D—Glu(α—OH)—(L-)—Boc—(D)—mesoDAP—(D)—NHNHBoc'(L)—GlyOH (4) was prepared in substantially the same manner as that of Example 71.

N.M.R. (CD$_3$OD), δ(ppm): 1.41 (18H, s), 3.92 (2H, broad s), 4.00-4.60 (5H, m).

(3) Step 3

Compound (4) ⟶

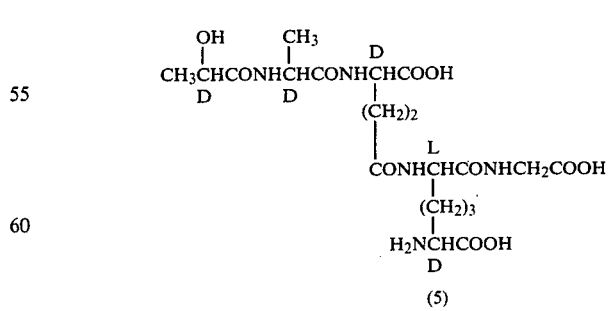

(5)

D—Lac(OH)—D—Ala—γ—D—Glu(α—OH)—(L-)—mesoDAP—(L)—GlyOH (5) was prepared in substantially the same manner as that of Example 72-1.

[α]$_D$ = 11.6 (c=0.25, water).

N.M.R. (CD₃OD), δ(ppm): 1.36 (3H, d, J=7 Hz), 1.44 (3H, d, J=7 Hz), 1.00-2.60 (10H, m), 3.88 (1H, t, J=7 Hz), 3.98 (2H, broad s), 4.10-4.50 (5H, m).

The following compounds were prepared in substantially the same manner as that of Steps 1 and 2 of Example 1.

EXAMPLE 85

(1) Step 1

Benzenesulfonyl—L—Ala—γ—D—Glu(α—OH-)—(L)—Boc—(D)—mesoDAP—(D)—NHNH-Boc—(L)—GlyOH.

NMR (CD₃OD), δ(ppm): 1.24 (3H, d, J=7 Hz), 1.47 (18H, s), 1.25-2.46 (10H, m), 3.94 (2H, s), 3.82-4.54 (4H, m), 7.55-8.00 (5H, m)

(2) Step 2

Benzenesulfonyl—L—Ala—γ—D—Glu(α—OH-)—(L)—mesoDAP—(L)—GlyOH.

NMR (D₂O), δ(ppm): 1.38 (3H, d, J=7 Hz), 1.5-2.42 (10H, m), 3.67-4.42 (4H, m), 4.10 (2H, s), 7.54-7.97 (5H, m).

EXAMPLE 86

(1) Step 1

Cinnamoyl—L—Ala—γ—D—Glu(α—OH)—(L-)—Boc—(D)—mesoDAP—(D)—NHNHBoc—(L)—GlyOH was prepared in substantially the same manner as that of Step 1 of Example 1.

NMR (CD₃OD), δ(ppm): 1.34 (13H, m), 1.44 (18H, s), 3.95 (2H, s), 3.90-4.67 (4H, m), 6.74 (1H, d, J=7 Hz), 7.57 (1H, d, J=16 Hz), 7.32-7.70 (5H, m).

(2) Step 2

Cinnamoyl—L'Ala—γ—D—Glu(α—OH)—(L-)—mesoDAP—(D)—NHNH₂—(L)—GlyOH was prepared in substantially the same manner as that of Step 3 of Example 11.

NMR (D₂O), δ(ppm): 1.47 (3H, d, J=7 Hz), 1.34-2.42 (10H, m), 3.95 (2H, s), 3.78-4.58 (4H, m), 6.64 (1H, d, J=16 Hz), 7.37-7.70 (6H, m).

(3) Step 3

Cinnamoyl—L—Ala—γ—D—Glu(α—OH)—(L-)—mesoDAP—(L)—GlyOH was prepared in substantially the same manner as that of Step 4 of Example 11.

NMR (D₂O), δ(ppm): 1.46 (3H, d, J=7 Hz), 1.28-2.44 (10H, m), 3.72 (1H, t, J=7 Hz), 3.88 (2H, s), 4.20-4.46 L (4H, m), 6.67 (1H, d, J=7 Hz), 7.38-7.46 (6H, m).

EXAMPLE 87

(1) Step 1

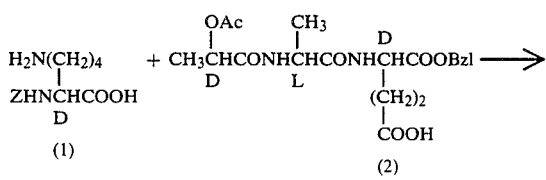

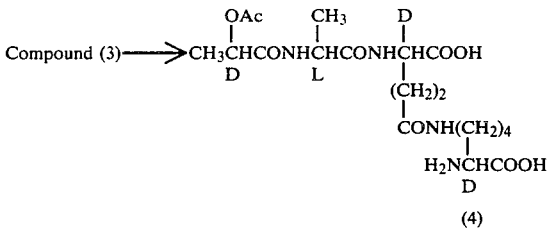

To a mixture of D—Lac(OAc)—L—Ala—D—GluOBzl (2) (1.20 g) and N-methylmorpholine (0.28 ml) in methylene chloride (17 ml) was added isobutyl chlorocarbonate (0.33 ml). The resulting mixture was stirred at −15° C. to −10° C. for 30 minutes and then cooled to −40° C. To the resulting mixture was added a mixture of Z—D—LysOH (1) (725 ml) and bis(trimethylsilyl)acetamide (3 ml) in dimethylformamide (3 ml) and methylene chloride (8 ml) at −40° C. The resulting mixture was stirred at −15° C. to −10° C. for an hour and gradually allowed to warm to ambient temperature. The resulting mixture was concentrated, taken up into ethyl acetate (80 ml) and washed with dil hydrochloric acid, water and brine, in turn. The concentrate was dried over magnesium sulfate and the solvent was distilled off to give an oil which was crystallized from a mixture of chloroform and isopropyl ether to give D—Lac(OAc)—L—Ala—γ—D—Glu(α—OBzl)—ε—Z—D—LysOH (3) (1.60 g).

NMR (DMSO-d₆), δ(ppm): 1.28 (3H, d, J=7 Hz), 1.37 (3H, d, J=7 Hz), 1.0-2.4 (10H, m), 2.10 (3H, s), 3.1 (2H, m), 4.0 (1H, m), 4.40 (2H, broad t, J=7 Hz), 5.05 (1H, q, J=6.5 Hz), 5.10 (2H, s), 5.20 (2H, s), 7.42 (10H, s), 7.3-8.0 (2H, m), 8.0-8.4 (2H, m).

(2) Step 2

Compound (3) ⟶
```
         OAc      CH₃    D
          |        |     |
      CH₃CHCONHCHCONHCHCOOH
       D        L     |
                     (CH₂)₂
                      |
                     CONH(CH₂)₄
                      |
                     H₂NCHCOOH
                      D
                     (4)
```

A solution of D—Lac(OAc)—L—Ala—γ—D—Glu(α—OBzl)—ε—Z—D—LysOH (3) (1.50 g) in acetic acid (40 ml) was hydrogenated over 10% palladium black (500 mg) at ambient temperature under an atmospheric pressure of hydrogen. The reaction mixture was filtered and the catalyst was washed with 50% aqueous methanol. The filtrates were combined and evaporated. Acetic acid was removed by co-evaporation with water. The residue was dissolved in water and lyophilized to give D—Lac(OAc)—L—Ala—γ—D—Glu(α—OH)—ε—D—LysOH (4) (1.00 g).

NMR (D₂O), δ(ppm): 1.42 (3H, d, J=7 Hz), 1.47 (3H, d, J=7 Hz), 2.16 (3H, s), 1.2-2.5 (10H, m), 3.0-3.4 (2H, m), 3.83 (1H, t, J=6 Hz), 4.1-4.6 (2H, m), 5.07 (1H, q, J=7 Hz).

(3) Step 3

Compound (4) ⟶
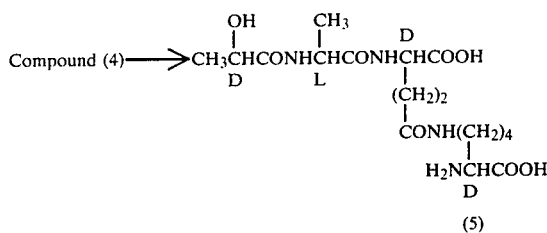
(5)

To a solution of D-Lac(OAc)—L—Ala—γ—D—Glu(α—OH)—ε—D—LysOH (4) (930 mg) in a mixture of methanol (9 ml) and water (3 ml) was added dropwise 1N sodium hydroxide (6 ml). The resulting solution was stirred at 5° C. for an hour and at ambient temperature for two hours.

The reaction mixture was neutralized to pH 7 with 1N hydrochloric acid and concentrated. The concentrate was adjusted to pH 2.2 with 1N hydrochloric acid and chromatographed on a macroporous non-ionic adsorption resin, HP 20 (90 ml), eluting with water. Fractions containing the object compound (5) were collected, concentrated and lyophilized to give D—Lac(OH)—L—Ala—γ—D—Glu(α—OH)—ε—D—LysOH (5) (700 mg).

$[\alpha]_D = -17.1°$ C. (C=0.509, water).

NMR (D$_2$O), δ(ppm): 1.36 (3H, d, J=7 Hz), 1.42 (3H, d, J=7 Hz), 1.1–2.6 (10H, m), 3.19 (2H, broad t, J=7 Hz), 3.83 (1H, t, J=6 Hz), 4.1–4.5 (3H, m).

EXAMPLE 88

(1) Step 1

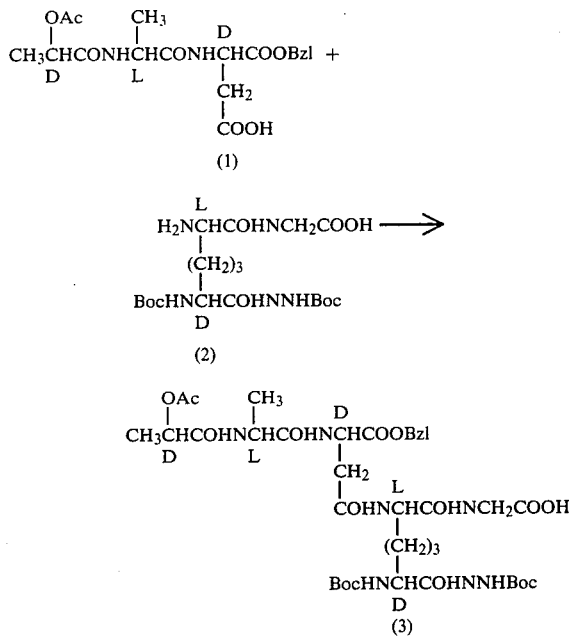

D—Lac(OAc)—L—Ala—β—D—Asp(α—OBzl)—(L)—Boc—(D)—mesoDAP—(D)—NHNH-Boc—(L)—GlyOH (3) was prepared from D—Lac(OAc)—L—Ala—D—Asp(OH)OBzl (1) and Boc—(D)—mesoDAP—(D)—NHNHBoc—(L)—GlyOH (2) in substantially the same manner as that of Example 66.

m.p. 120°–123° C. (dec.).

I.R. (Nujol): 3550, 3300, 1730, 1650, 1550 cm$^{-1}$.

NMR (DMSO-d$_6$), δ(ppm): 1.10–1.9 (30H, m), 2.06 (3H, s), 3.0–5.0 (13H, m), 3.18 (2H, s), 5.14 (2H, s), 6.63 (1H, m), 7.40 (5H, s), 7.9–8.6 (6H, m), 9.56 (1H, s).

(2) Step 2

Compound (3) ⟶
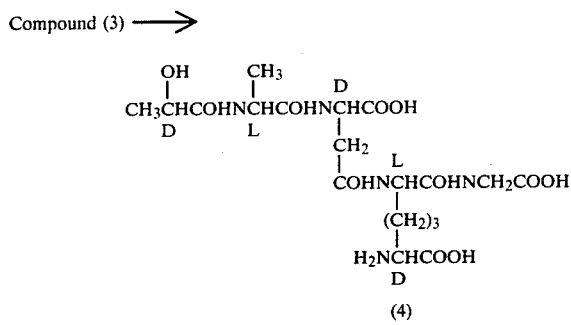
(4)

To a suspension of D—Lac(OAc)—L—Ala—β—D—Asp(α—OBzl)—(L)—Boc—(D)—mesoDAP—(D)—NHNHBoc—(L)—GlyOH (3) (0.74 g) in water (10 ml) was added 1N sodium hydroxide (3.0 ml) at 0° C. and the mixture was stirred for 1 hour at the same temperature. The reaction mixture was neutralized to pH 3 with 1N hydrochloric acid (3.0 ml) and evaporated to give an oil, which was dissolved in water (3 ml) and applied to a column of HP-20 (20 ml). The column was washed with water and eluted with methanol:water (7:3) and the eluate was evaporated to give an oil (0.42 g), which was then dissolved in trifluoroacetic acid (5 ml) and stirred for 15 minutes at room temperature. After evaporation of trifluoroacetic acid, the resulting residue was pulverized with ether and filtered to give a powder, which was dissolved in 1N sulfuric acid (2.5 ml) and sodium periodate (0.09 g) was added at 0° C. After stirring for 10 minutes at the same temperature, the reaction mixture was treated with 0.5N aqueous sodium hydrogen sulfite (0.2 ml). This solution was neutralized to pH 2 with 1M sodium carbonate (1.4 ml) and evaporated and methanol (3 ml) was added and an undissolved material was filtered off. The filtrate was evaporated to give an oil (0.30 g), which was dissolved in a small amount of water and applied to a column of HP-20 (40 ml). The column was eluted with water and the eluate was evaporated to give an oil (140 mg), which was again applied to a column of HP-20 (60 ml) and eluted with water. The eluate was evaporated and the residue was dissolved in a small amount of water and lyophilized to give D—Lac—L—Ala—β—D—Asp(α—OH)—(L)—mesoDAP—(L)—GlyOH (4) (120 mg) as a white powder.

I.R. (Nujol): 3270, 1720, 1640, 1520 cm$^{-1}$.

NMR (D$_2$O), δ(ppm): 1.36 (3H, d, J=7 Hz), 1.38 (3H, d, J=7 Hz), 1.2–2.1 (6H, m), 2.6–3.0 (2H, m). 3.87 (1H, t, J=6 Hz), 3.95 (2H, s), 4.1–4.5 (4H, m).

EXAMPLE 89

(1) Step 1

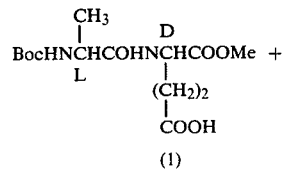
(1)

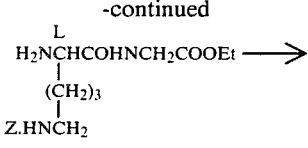

(2)

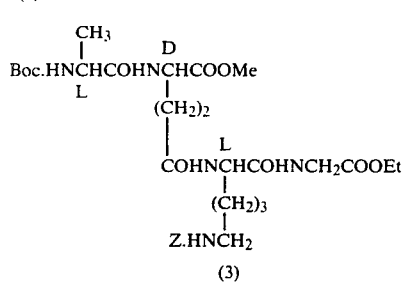

(3)

To a mixture of Boc—L—Ala—D—Glu(OH)OMe (1) (1.94 g), L—Lys(ε—Z)—GlyOEt (2) (1.67 g) and 1-(4-chlorobenzenesulfonyloxy)-6-chlorobenzotriazole (1.72 g) in methylene chloride (100 ml) was added N-methylmorpholine (1.01 g) and the mixture was stirred for 2 days at room temperature. The reaction mixture was washed sccessively with 5% aqueous sodium bicarbonate, water, 5% hydrochloric acid and water and dried over magnesium sulfate. After evaporation of the solvent, the resulting crystalline mass was filtered and washed with ether, to give Boc—L—Ala—γ—D—Glu(α—OMe)—L—Lys(ε—Z)—GlyOEt (3) (1.34 g). m.p.126°-127° C.

I.R. (Nujol): 3550, 3255, 1750, 1720, 1700, 1680, 1660, 1650, 1640 cm⁻¹.

NMR (CD₃OD), δ(ppm): 1.22 (3H, t, J=7 Hz), 1.30 (3H, d, J=7 Hz), 1.42 (9H, s), 1.34-1.60 (6H, m), 2.70 (2H, t J=7 Hz), 3.08 (2H, m), 3.68 (3H, s), 3.92 (2H, s), 4.15 (2H, q, J=7 Hz), 4.00-4.42 (3H, m), 5.07 (2H, s), 7.34 (5H, s).

(2) Step 2

Compound (3) ⟶

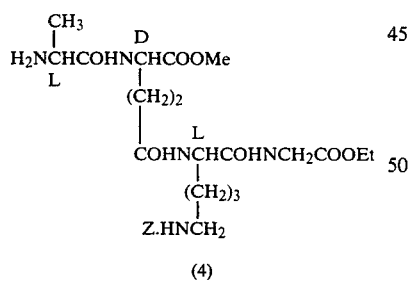

(4)

To a solution of Boc—L—Ala—γ—D—Glu(α—OMe)—L—Lys(ε—Z)—GlyOEt (3) (1.20 g) in a mixture of ethyl acetate (20 ml) and methanol (5 ml) was added a saturated solution of hydrogen chloride in ethyl acetate (20 ml) at 0° C. and the mixture was stirred for 20 minutes at the same temperature and for 30 minutes at room temperature. The reaction mixture was evaporated to give a powder, which was washed successively with ethyl acetate and ether to give L—Ala—γ—D—Glu(α—OMe)—L—Lys(ε—Z)—GlyOEt.HCl (4) (0.97 g).

NMR (D₂O), δ(ppm): 1.25 (3H, t, J=7 Hz), 1.62 (3H, t, J=7 Hz), 1.34-1.84 (8H, m), 2.44 (2H, t, J=6 Hz), 3.17 (2H, t, J=6 Hz), 3.82 (3H, s), 4.04 (2H, s), 4.12 (2H, q, J=7 Hz), 4.17-4.68 (3H, m), 5.12 (2H, s), 7.42 (5H, s)

(3) Step 3

Compound (4) ⟶

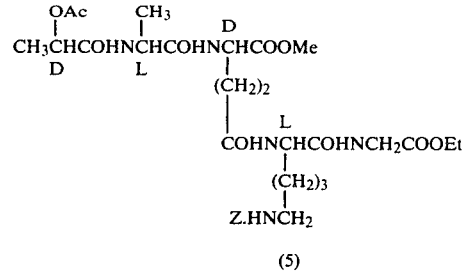

(5)

To a mixture of L—Ala—γ—D—Glu(α—OMe)—L—Lys(ε—Z)—GlyOEt.HCl (4) (0.90 g) and triethylamine (0.17 g) in methylene chloride (15 ml) was added a solution of acetyl D-lactyl chloride (0.26 g) in methylene chloride (5 ml) at 5° C. and the mixture was stirred for 1 hour at the same temperature. The reaction mixture was washed successively with 5% aqueous sodium bicarbonate, water, 5% hydrochloric acid and water, dried over magnesium sulfate and evaporated to give a crystalline mass, which was washed with ethyl acetate to give D—Lac(OAc)—L—Ala—γ—D—Glu(α—OMe)—L—Lys(ε—Z)—GlyOEt (5) (0.97 g).

I.R. (Nujol): 3400, 1730-1640 (broad) cm⁻¹.

NMR (D₂O), δ(ppm): 1.17 (3H, t, J=7 Hz), 1.45 (3H, d, J=7 Hz), 1.34-1.67 (8H, m), 2.04 (3H, s), 1.96-2.13 (2H, m), 3.07-2.87 (2H, m), 3.64 (3H, s), 4.07 (2H, d, J=7 Hz), 4.25 (2H, q, J=7 Hz), 3.57-4.34 (3H, m), 5.00 (2H, s), 7.34 (5H, s), 8.25-7.84 (4H, m).

(4) Step 4

Compound (5) ⟶

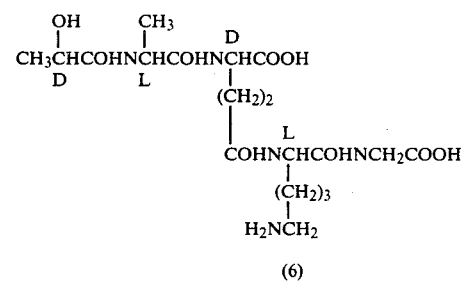

(6)

To a solution of D—Lac(OAc)—L—Ala—γ—D—Glu—L—Lys(ε—Z)—GlyOEt (5) (0.90 g) in methanol (15 ml) was added 1N sodium hydroxide (30 ml) at 5° C. and the mixture was stirred for 4 hours at the same temperature and overnight at room temperature. Methanol was evaporated and the resulting aqueous layer was adjusted to pH 5.5 with diluted hydrochloric acid and washed with ethyl acetate. The aqueous layer was acidified to pH 1 with diluted hydrochloric acid and extracted with ethyl acetate. The extract was washed with water saturated with sodium chloride, dried over magnesium sulfate and evaporated to give an amorphous solid (0.50 g). This solid was dissolved in MeOH (15 ml) and hydrogenated over 5% palladium-charcoal (0.10 g). After removal of the catalyst by filtration, the filtrate was evaporated and the resulting residue was pulverized with acetone to give D—Lac—L—Ala—γ—D—Glu(α—OH)—L—Lys—GlyOH (0.25 g) as a powder.

I.R. (Nujol): 3350, 1710, 1670–1640 cm$^{-1}$.

NMR (D$_2$O+NaHCO$_3$), δ(ppm): 1.37 (3H, d, J=7 Hz), 1.44 (3H, d, J=7 Hz), 1.34–2.00 (8H, m), 1.84–2.25 (2H, m), 3.04 (2H, t, J=7 Hz), 3.79 (2H, s), 4.17–4.50 (3H, m).

EXAMPLE 90

(1) Step 1

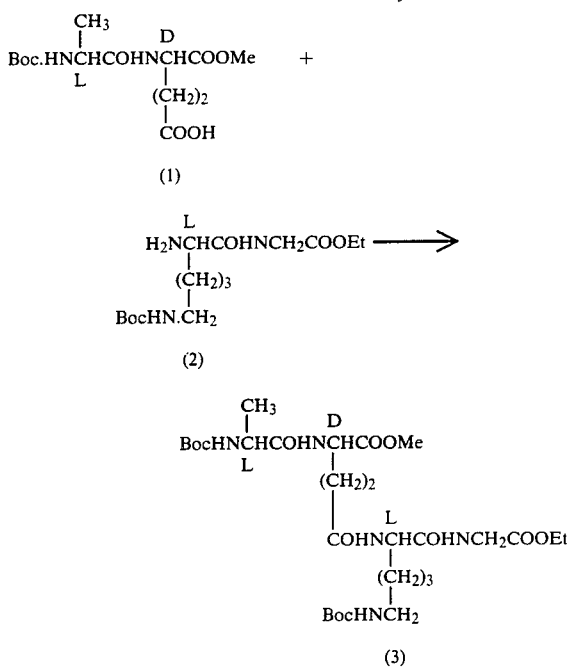

To a mixture of Boc—L—Ala—D—Glu(OH)OMe (1) (1.33 g), L—Lys(ε—Boc)—GlyOEt (2) (2.02 g) and 1-(4-chlorobenzenesulfonyloxy)-6-chlorobenzotriazole (1.38 g) in methylene chloride (50 ml) was added N-methylmorphorine (0.808 g) at 0° C. and the mixture was stirred for 30 minutes at the same temperature and for 2 days at room temperature. The reaction mixture was washed successively with 5% aqueous sodium bicarbonate, water, 5% hydrochloric acid and water, dried over magnesium sulfate and evaporated to give a crystalline mass, which was washed with ether to give Boc—L—Ala—γ—D—Glu(α—OMe)—L—Lys(-ε—Boc)—GlyOEt (3) (1.96 g).

m.p. 163°–4° C.

I.R. (Nujol): 3550, 3275, 1740, 1690, 1650 cm$^{-1}$.

NMR (DMSO-d$_6$), δ(ppm): 1.17 (3H, t, J=7 Hz), 1.32 (3H, d, J=7 Hz), 1.35 (18H, s), 1.42–1.54 (8H, m), 2.08–2.18 (2H, m), 3.25–2.82 (2H, m), 3.62 (3H, s), 3.80 (2H, d, J=6 Hz), 4.07 (2H, q, J=7 Hz), 3.80–4.07 (3H, m), 6.58–6.77 (2H, m), 7.83–8.25 (3H, m).

(2) Step 2

Compound (3) ⎯⎯⎯→

-continued

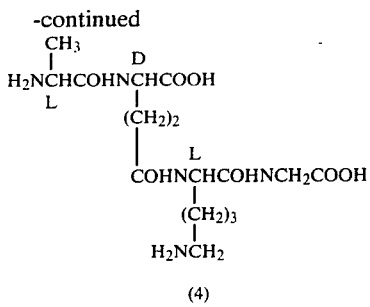

To a solution of Boc—L—Ala—γ—D—Glu(α—OMe)—L—Lys(ε—Boc)—GlyOEt (3) (0.50 g) in methanol (5 ml) was added 1N sodium hydroxide (2 ml) at 0° C. and the mixture was stirred for 1 hour at the same temperature and overnight at room temperature. The reaction mixture was evaporated and the residue was dissolved in water and washed with ethyl acetate. The aqueous layer was acidified with diluted hydrochloric acid to pH 2 and extracted with ethyl acetate. The extract was washed with water, dried over magnesium sulfate and evaporated to give an oil (0.37 g). This oil was dissolved in ethyl acetate (10 ml) and a saturated solution of hydrogen chloride in ethyl acetate (5 ml) was added at 0° C. The mixture was stirred for 10 minutes at the same temperature and for 30 minutes at room temperature. The resulting precipitate was filtered and washed with ethyl acetate to give L—Ala—γ—D—Glu(α—OH)—L—Lys—GlyOH (4) (0.17 g) as a powder.

I.R. (Nujol): 3450, 3200, 1730, 1680, 1660–1640 cm$^{-1}$.

NMR (D$_2$O), δ(ppm): 1.65 (3H, d, J=7 Hz), 1.92–1.42 (8H, m), 2.34 (2H, t, J=6 Hz), 2.64 (2H, t, J=6 Hz), 3.95 (2H, s), 4.10–4.67 (3H, m).

EXAMPLE 91

(1) Step 1

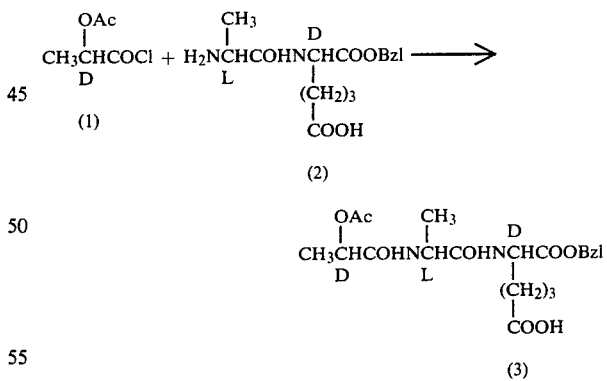

D—Lac(OAc)—L—Ala—D—Aad(OH)OBzl(3) was prepared from O—acetyl—D—lactyl chloride (1) and L—Ala—D—GluOBzl (2) in substantially the same manner as that of Step 1 of Example 1.

I.R. (CHCl$_3$): 3400, 1730, 1710, 1665 cm$^{-1}$.

NMR (CDCl$_3$), δ(ppm): 1.36 (3H, d, J=7 Hz), 1.41 (3H, d, J=7 Hz), 1.4–2.0 (4H, m), 2.08 (3H, s), 2.2–2.4 (2H, m), 4.4–4.7 (2H, m), 4.9–5.2 (1H, m), 5.10 (2H, s), 6.96 (1H, d, J=8 Hz), 7.15 (1H, d, J=8 Hz), 7.20 (5H, s), 7.4–8.2 (1H, broad s)

(2) Step 2

Compound (3) + H₂NCHCOHNCH₂COOH ⟶
                               L
                               |
                              (CH₂)₃
                               |
                        BocHNCHCOHNNHBoc
                               D (4)

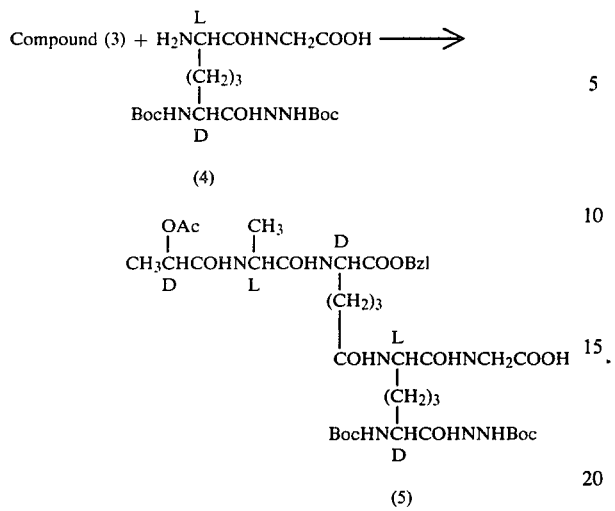

(5)

D—Lac(OAc)—L—Ala—δ—D—Aad(α—OBzl)—(L)—Boc—(D)—mesoDAP—(D)—NHNHBoc—(L)—GlyOH (5) was prepared from D—Lac(OAc)—L—Ala—D—Aad(OH)oBzl(3) and Boc—(D)—mesoDAP—(D)—NHNHBoc—(L)—GlyOH (4) in substantially the same manner as that of Example 66.

m.p. 108°–110° C.

I.R. (Nujol): 3260, 1725, 1670, 1650, 1630, 1540, 1520 cm⁻¹.

NMR (CDCl₃), δ(ppm): 1.40 (3H, d, J=7 Hz), 1.4–2.0 (13H, m), 1.44 (18H, s), 2.10 (3H, s), 2.1–2.5 (2H, m), 3.90 (2H, s), 3.8–4.2 (1H, m), 4.3–4.6 (3H, m), 4.7–5.1 (1H, m), 5.12 (2H, s), 7.30 (5H, s).

(3) Step 3

Compound (5) ⟶

OH     CH₃
    |        |     D
CH₃CHCOHNCHCOHNCHCOOH
  D       L     |
                 (CH₂)₃
                 |     L
             COHNCHCOHNCH₂COOH
                 |
                 (CH₂)₃
                 |
             H₂NCHCOOH
                 D (6)

D—Lac—L—Ala—δ—D—Aad(α—OH)—(L)—mesoDAP—(L)—GlyOH (6) was prepared from D—Lac(OAc)—L—Ala—δ—D—Aad—(α—OBzl)—(L)—Boc—(D)—mesoDAP—(D)—NHNHBoc—(L)—GlyOH (5) in substantially the same manner as that of Step 2 of Example 88.

I.R. (Nujol): 3270, 1720, 1620, 1530 cm⁻¹.

NMR (D₂O), δ(ppm): 1.36 (3H, d, J=7 Hz), 1.43 (3H, d, J=7 Hz), 1.5–2.1 (10H, m), 2.2–2.5 (2H, m), 3.84 (1H, t, J=6 Hz), 3.96 (2H, s), 4.1–4.5 (4H, m).

EXAMPLE 92

(1) Step 1

L
H₂NCHCOHNCH₂COOH   +
  |
(CH₂)₃
  |
BocHNCHCOHNNHBoc
      D

OAc    CH₃
     |       |
CH₃CHCONHCHCONH(CH₂)₃COOH ⟶
     D      L

OAc    CH₃                         L
     |       |
CH₃CHCONHCHCONH(CH₂)₃COHNCHCONHCH₂COOH
     D      L                             |
                                              (CH₂)₃
                                              |
                                   BocHNCHCONHNHBoc
                                           D (3)

D—Lac(OAc)—L—Ala—γ—Abu—(L)—Boc—(D)—mesoDAP—(D)—NHNHBoc—(L)—GlyOH (3) was prepared in substantially the same manner as that of Example 66.

NMR (CDCl₃), δ(ppm): 1.2–2.0 (4H, m), 1.42 (18H, s), 2.0–2.5 (2H, m), 2.15 (3H, s), 3.1–3.4 (2H, m), 3.8–4.1 (2H, m), 4.3–4.7 (1H, m), 4.9–5.2 (1H, m), 5.5–6.0 (2H, m), 7.3–7.6 (2H, m), 7.6–8.1 (2H, m).

(2) Step 2

Compound (3) ⟶

OH     CH₃                            L
    |        |
CH₃CHCOHNCHCOHN(CH₂)₃COHNCHCOHNCH₂COOH
    D      L                           |
                                        (CH₂)₃
                                        |
                                     H₂NCHCOOH
                                          D (4)

D—Lac(OH)—L—Ala—γ—Abu—(L)—mesoDAP—(L)—GlyOH (4) was prepared in substantially the same manner as that of Example 88.

NMR (D₂O), δ(ppm): 1.39 (3H, d, J=7 Hz), 1.40 (3H, d, J=7 Hz), 1.5–2.1 (8H, m), 2.33 (2H, t, J=7 Hz), 3.21 (2H, t, J=7 Hz), 3.79 (1H, t, J=7 Hz), 3.95 (2H, s), 4.1–4.5 (4H, m).

The following compounds were prepared in substantially the same manner as Steps 1 and 2 of Example 1, respectively.

EXAMPLE 93

(1) Step 1

Thienylacetyl—γ—D—Glu(α—OH)—(L)—Boc—(D)—mesoDAP—(D)—NHNHBoc.

NMR (DMSO-d₆), δ(ppm): 1.36 (18H, s), 1.00–2.33 (10H, m), 3.66 (2H, s), 3.83–4.33 (3H, m), 6.87 (2H, m), 7.27 (1H, m), 7.83–8.66 (3H, m), 9.02 (2H, broad s).

(2) Step 2

Thienylacetyl—γ—D—Glu(α—OH)—(L)—mesoDAP.

NMR (D₂O), δ(ppm): 1.20–2.60 (10H, m), 3.78 (1H, t, J=7 Hz), 3.86 (2H, s), 4.28 (1H, t, J=7 Hz), 7.04 (2H, m), 7.32 (2H, m).

EXAMPLE 94

For fermentation (1) A vegetative medium 1 (pH 7.0) was prepared from the following ingredients:

Vegetative medium 1
Soluble starch: 2% by wt.
Gluten meal: 1% by wt.
Dried yeast: 1% by wt.
Corn Steep Liquor: 1% by wt.
Tap water: q.s.

100 ml. of the medium 1 in each of ten 500 ml. flasks were sterilised in conventional manner and then inoculated with a loopful of culture from a stock slant of *Streptomyces olivaceogriceus* ATCC 31427. The organism was grown in the medium at 30° C. for 48 hours on a shaker.

Into a 30-liter Jar-fermentor, there were placed 20 liters of the vegetative medium 2 prepared from the following ingredients:

Vegetative medium 2
Soluble starch: 2% by wt.
Cottonseed meal: 0.5% by wt.
Gluten meal: 0.5% by wt.
Dried yeast: 0.5% by wt.
Corn Steep Liquor: 0.5% by wt.
Tap water: q.s.

The vegetative medium 2 (pH 7.0) was sterilised in a conventional manner and then inoculated aseptically with the whole volume of the vegetative inoculum culture prepared above. The organism was grown in the medium 2 at 30° C. for 24 hours.

The whole volume of the vegetative inoculum thus prepared was aseptically inoculated into a 2000-liter fermentor, containing 1600 liters of the fermentation medium prepared from the following ingredients:

Fermentation medium
Soluble starch: 2% by wt.
Cottonseed meal: 0.5% by wt.
Wheat germ: 0.5% by wt.
Dried yeast: 0.25% by wt.
Corn Steep Liquor: 0.25% by wt.
$KH_2PO_4$: 0.5% by wt.
$Na_2HPO_4.12H_2O$: 0.5% by wt.
$CoCl_2.6H_2O$: 1.25 mg/l
Tap water: q.s.

The organism was cultured in the fermentation medium for 72 hours at 30° C. During the growth period, the broth was stirred with a propeller operating at 170 r.p.m. and sterile air was passed through the broth at a rate of 1600 liters per minute.

After the fermentation was completed, 20 kg "Radiolite" (trade name, a filter aid material sold by Showa Chemical Company, Japan) was added to the culture broth and the mixture was filtered to remove mycelia. 1600 liters of the filtrate was passed through a column of activated charcoal (800 liters) and then was washed with 1600 liters of water. Elution was carried out with 3000 liters of 50% aqueous acetone and then the eluate was concentrated to a volume of about 600 liters.

The concentrate was passed through a column of DEAE-Sephadex (trade name, made by Pharmacia A.B.) (200 liters) which has previously been buffered with phosphate buffer (pH 6.0). The column was successively washed with 200 liters of water and 200 liters of 0.1M sodium chloride solution and then eluted with 400 liters of 0.3M sodium chloride solution. The aqueous eluate was passed through a column of an activated charcoal (200 l), washed with 200 liters of water and then eluted with 400 liters of 50% aqueous acetone. The eluate was concentrated and then freeze-dried to give 800 g of a white powder. The powder was dissolved into 25 liters of water and the solution was passed through a column of CM-Sephadex ($H^+$ form) (25 l). The column was eluted with 25 liters of water and the eluate was concentrated and then freeze-dried to give 33 g. of yellowish white powder. The powder was placed on the top of a column of cellulose (1.2 l). The column was washed with 1000 ml. of 70% aqueous propanol and then eluted with 1000 ml. of 60% aqueous propanol. The eluate was concentrated and freeze-dried to give 4 g. of white powder. The powder was dissolved into 150 ml. of water and then the solution was subjected to column chromatography on Sephadex G-15 (2.8 l).

The column was developed and eluted with water. The active fractions were collected and concentrated and then freeze-dried to give 4 g. of a white powder. The powder dissolved into 25 ml. of water and the solution was subjected to column chromatography on CM-Sephadex ($H^+$ form) (400 ml). The column was developed and eluted with water. The active fractions were collected, concentrated and then freeze-dried to give 40 mg. of the FR-900156 substance in the form white powders (purity: about 70%).

(2) Fermentation was carried out in the same manner as described in Example 94 (1). After the fermentation was completed, 20 kg. "Radiolite" (trade name, a filter aid material sold by Showa Chemical Company) was added to the culture broth and the mixture was filtered to remove mycelia. 1600 liters of the filtrate was passed through a column of activated charcoal (800 liters) and then was washed with 1600 liters of water. Elution was carried out with 3000 liters of 50% aqueous acetone and then the eluate was concentrated to a volume of about 600 liters. The concentrate was passed through a column of DEAE-Sephadex (trade name, made by Pharmacia A.B.) (200 liters) which has previously been buffered with phosphate buffer (pH 6.0). The column was successively washed with 200 liters of water and 200 liters of 0.1M sodium chloride solution and then eluted with 400 liters of 0.3M sodium chloride solution. The aqueous eluate was passed through a column of an activated charcoal (200 liters), washed with 200 liters of water and then eluted with 400 liters of 50% aqueous acetone. The eluate was concentrated and then freeze-dried to give 800 g. of white powder. The powder was dissolved into 25 liters of water and the solution was passed through a column of CM-Sephadex ($H^+$ form) (25 liters). The column was eluted with 25 liters of water and the eluate was concentrated and then freeze-dried to give 33 g. of yellowish white powders. The powders were placed on top of a column of cellulose (1.2 liters). The column was washed with 1000 ml. of 70% aqueous propanol and then eluted with 1000 ml. of 60% aqueous propanol. The eluate was concentrated and freeze-dried to give 4 g. of white powder. The powder was dissolved into 300 ml. of water and then passed through a column of DEAE-Sephadex (trade name, made by Pharmacia A.B.) (1.4 liters) of which has previously been buffered with phosphate buffer (pH 6.0). The column was washed with 1.5 liters of 0.1M sodium chloride solution and then eluted with 3 liters of 0.2M sodium chloride solution The active fractions were collected and then passed through a column of activated charcoal (300 ml). The column was washed with water and then eluated with 800 ml. of 50% aqueous acetone. The eluate was concentrated and then freeze-dried to give 700 mg. of white powders. The powders were dissolved into 20 ml. of water and then passed through a column of CM-Sephadex (H+ form) (500 ml). The column was eluted with water and the active fractions were collected, and then concentrated to give 10 ml. of concentrate. The concentrate was subjected to a column chromatography on Sephadex G 15 (500 ml) and developed with water. The active fractions were collected and concentrated and then freeze-dried to give 70 mg. of white powders. The powders were dissolved into 25 ml. of water and subjected to preparative thin layer chromatography on cellulose (made by Eastman Kodak Co.): a developing solvent was mixture of butanol, acetic acid and water (4:1:2). Elution was carried out with 50 ml. of water and the eluate was concentrated and then freeze-dried to give 20 mg of the FR-900156 substance in the form of a white powder.

(3) Fermentation was carried out in the same manner as described in Example 94 (1). After the fermentation was completed, 20 kg. "Radiolite" (trade name, a filter aid material sold by Showa Chemical Company) was added to the culture broth and the mixture was filtered to remove mycelia. 1600 liters of the filtrate was passed through a column of activated charcoal (800 liters) and then was washed with 1600 liters of water. Elution was carried out with 3000 liters of 50% aqueous acetone and then the eluate was concentrated to a volume of about 600 liters. The concentrate was passed through a column of DEAE-Sephadex (trade name, made by Pharmacia A.B.) (200 liters) which has previously been buffered with phosphate buffer (pH 6.0). The column was successively washed with 200 liters of water and 200 liters of 0.1M sodium chloride solution and then eluted with 400 liters of 0.3M sodium chloride solution. The aqueous eluate was passed through a column of an activated charcoal (200 liters), washed with 200 liters of water and then eluted with 400 liters of 50% aqueous acetone. The eluate was concentrated and then freeze-dried to give 800 g. of white powder. The powder was dissolved into 25 liters of water and the solution was passed through a column of CM-Sephadex (H+ form) (25 liters). The column was eluted with 25 liters of water and the eluate was concentrated and then freezdried to give 33 g. of yellowish white powder. The powder was placed on top of a column of cellulose (1.2 liters). The column was washed with 1000 ml. of 70% aqueous propanol and then eluted with 1000 ml. of 60% aqueous propanol. The eluate was concentrated and freeze-dried to give 4 g. of white powder.The powder was dissolved into 300 ml. of water and then passed through a column of DEAE-Sephadex (trade name, made by Pharmacia A.B.) (1.4 liters) which has previously been buffered with phosphate buffer (pH 6.0). The column was washed with 1.5 liters of 0.1M sodium chloride solution and then eluted with 300 liters of 0.2M sodium chloride solution. The active fractions were collected and then passed through a column of activated charcoal (300 ml). The column was washed with water and then eluated with 800 ml. of 50% aqueous acetone. The eluate was concentrated and then freeze-dried to give 700 mg. of white powders. The powders were dissolved into 20 ml. of water and then passed through a column of CM-Sephadex (H+ form) (500 ml). The column was eluted with water and the active fractions were collected, and then concentrated to give 10 ml. of concentrate. The concentrate was freeze-dried to give 400 mg of a powder. The powder was placed on the top of a column of cellulose (500 ml). Elution was carried out with a mixture of n-butanol, acetic acid and water (4:1:2). The active fractions were collected and freeze-dried to give 200 mg of a powder. The powder was dissolved into 7 ml. of water and then placed on Sephadex G 15 (250 ml). The active fractions were collected, concentrated and then freeze-dried to give 100 mg of the FR-900156 substance in the form of a white powder.

(4) A white powder of FR-900156 substance obtained by the Example 94 (3) was further purified by conducting repeatedly the above purification means to give a more purified product of FR-900156 substance.

(5) 100 ml of a medium containing corn starch 2% (by wt.), gluten meal 1%, dried yeast 1% and corn steep liquor 1% were poured into each of ten 500 ml flasks and sterilised in a cenventional manner and then inoculated with a loopful of culture from a stock slant of Streptomyces violaceus ATCC 31481.

The organism was grown in the medium at 30° C. for 48 hours on a shaker.

Into a 30-liters Jar-fermentor, there were placed 20-liters of the same medium as above. The medium was sterilised in a conventional manner and then inoculated aseptically with the whole volume of the inoculum culture prepared above. The organism was grown in the medium at 30° C. for 30 hours.

The whole volume of the inoculum thus prepared was aseptically inoculated into a 400-liters fermentor, containing 320 liters of the medium (pH 6.5) containing soluble starch 2% (by wt.), gluten meal 1%, cottonseed meal 1% and sodium sulfate (10 hydrates) 2%.

The organism was cultured in the medium at 30° C. for 72 hours. During the growth period, the broth was stirred with a propeller operating at 170 r.p.m. and sterile air was passed through the broth at a rate of 320 liters per minute. After the fermentation was complete, 4 kg of "Radiolite" was added to the cultured broth and the mixture was filtered to remove mycelia. 300 liters of the filtrate was passed through a column of activated charcoal (150 liters) and then, washed with 300 liters of water. Elution was carried out with 600 liters of 50% aqueous acetone and then the eluate was concentrated to a volume of about 120 liters.

The concentrate was passed through a column of DEAE-Sephadex (30 liters) which has previously been buffered with phosphate buffer (pH 6.0). The column was successively washed with 30 liters of water and 30 liters of 0.1M sodium chloride and then eluted with 0.3M sodium chloride. The eluate (60 liters) was passed through a column of an activated charcoal (30 liters), washed with 60 liters of water and then eluted with 60 liters of 50% aqueous acetone. The eluate was freeze-dried to give 120 g of a white powder. The powder was dissolved in 4 liters of water and the solution was passed through a column of CM-Sephadex (H+ form) (14 liters). The column was eluted with water and the eluate was concentrated and then freeze-dried to give 20 g of a powder. The powder was placed on the top of the column of cellulose. Elution was carried out with an aqueous propanol and the active fractions were collected and freeze-dried to give 5 g of a powder. The powder was dissolved in 500 ml of water and the solution was passed through a column of DEAE-Sephadex (1.3 liters) which has previously been buffered with phosphate buffer (pH 6). The column was washed with 0.1M sodium chloride and eluted with 0.2M sodium chloride. The active fractions were collected and passed through a column of an activated charcoal (900 ml). The column was washed with water and eluted with 50% aqueous acetone (200 ml). The eluate was concentrated and freeze-dried to give 1 g of a powder.

The powder was dissolved in 300 ml of water and the solution was passed through a column of CM-Sephadex (H+ form) (250 ml). The column was developed and eluted with water. The active fractions were collected, concentrated and then freeze-dried to give 800 mg of a powder. The powder was dissolved in 20 ml of water and the solution was mixed with a small amount of cellulose. The mixture was subjected to column chromatograph on cellulose. The column was washed successively with 100 ml of acetone and 300 ml of mixture of n-butanol:acetic acid:water (4:1:1) and then developed and eluted with a mixture of n-butanol:acetic acid:water (4:1:2) (1 liter). The active fractions were collected and freeze-dried to give 30 mg of a powder. The powder was dissolved in 20 ml of water and the solution was passed through a column of Sephadex G 15 (250 ml). The column was developed and eluted with water and the active fractions were collected and then freeze-dried to give 5 mg of Fr-900156 substance.

EXAMPLE 95

For the Pharmaceutical Composition (1) Preparation for injection

The required quantities of the FR-900156 substance were distributed into vials, each containing 500 mg of the active ingredient. The vials were sealed hermetically to exclude bacteria. Whenever the vial is required for use, 2 ml of sterile distilled water for injection is added to the vial and then the aqueous solution is administered by injection.

(2) Preparation of tablet

A suitable formulation for a table consists of the following mixture.

FR-900156 substance: 200 mg
Mannitol: 400 mg
Starch: 50 mg
Magnesium stearate: 10 mg (3) Preparation of capsule FR-900156 substance: 300 mg
Magnesium stearate: 15 mg.

The above ingredients were mixed and then inserted into a hard gelatin capsule in a conventional manner.

PREPARATION 66

(1) Step 1

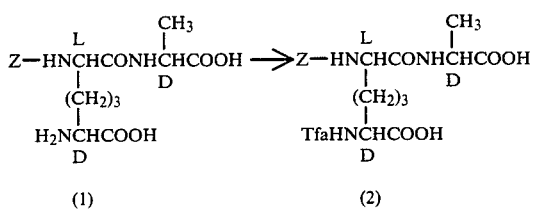

Z—(L)—mesoDAP—(L)—D—AlaOH (1) (1.80 g) was suspended in a mixture of methylene chloride (50 ml), bis(trimethylsilyl)acetamide (5.60 g) and dimethylformamide (6 ml). The suspension was stirred for 4 hours at ambient temperature and treated with trifluoroacetic anhydride (1.0 g) and further stirred for an hour. The reaction mixture was concentrated under reduced pressure and the residual oil was extracted with ethyl acetate. The organic layer was washed with water, dried over magnesium sulfate and then evaporated to give Z—(L)—Tfa—(D)—mesoDAP—(L)—D—AlaOH (2).

NMR (DMSO-d$_6$), δ(ppm): 1.18 (3H, d, J=7 Hz), 1.10–2.0 (6H, m), 3.90–4.30 (3H, m), 5.03 (2H, s), 7.33 (5H, s), 8.18 (1H, d, J=7 Hz), 9.55 (1H, d, J=7 Hz).

(2) Step 2

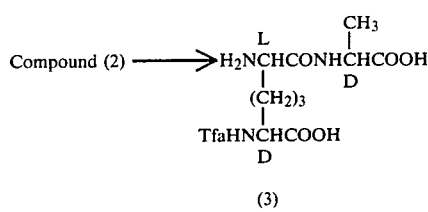

Tfa—(D)—mesoDAP—(L)—D—AlaOH (3) was prepared in substantially the same manner as Preparation 25 from compound (2).

IR (Nujol): 3250, 2600–2400 (broad), 1700, 1670 cm$^{-1}$.

NMR (D$_2$O), δ(ppm): 1.33 (3H, d, J=7 Hz), 1.20–2.20 (6H, m), 3.83–4.43 (3H, m).

PREPARATION 67

(1) Step 1

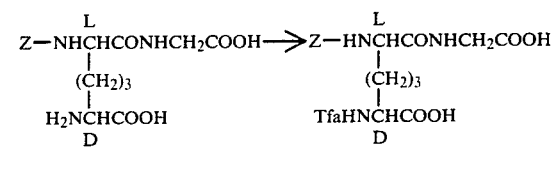

Z—(L)—Tfa—(D)—mesoDAP—(L)—GlyOH (2) was prepared in substantially the same manner as step 1 of Preparation 66 from compound (1).

NMR (DMSO-d$_6$), δ(ppm): 1.10–2.10 (6H, m), 3.73 (2H, d, J=7 Hz), 3.90–4.50 (2H, m), 5.06 (2H, s), 7.33 (5H, s), 7.0–7.30 (1H, broad), 8.13 (1H, t, J=7 Hz), 9.56 (1H, d, J=7 Hz).

(2) Step 2

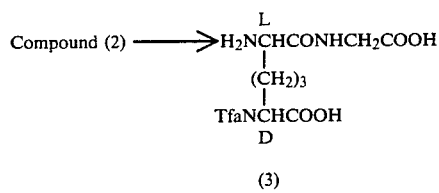

Tfa—(D)—mesoDAP—(L)—GlyOH (3) was prepared in substantially the same manner as Preparation 25 from compound (2).

IR (Nujol): 3250 (shoulder), 2600–2300 (broad), 1720 (shoulder), 1700, 1680 (shoulder), 1210, 1180, 1150 cm$^{-1}$.

NMR (D$_2$O), δ(ppm): 1.20–2.20 (6H, m), 3.90 (2H, s), 4.00–4.50 (2H, m).

PREPARATION 68

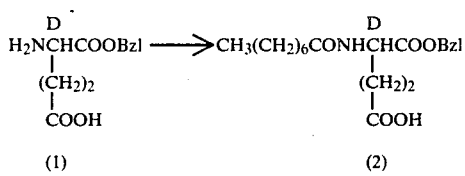

D—Glu(α—oBzl) (1) (4.74 g) was added to a mixture of methylene chloride (50 ml) and bis(trimethylsilyl-)acetamide (4.10 g). The mixture was stirred until a clear solution was obtained and n-octanoyl chloride (3.17 g) was added dropwise thereto. The mixture was reacted for an hour at ambient temperature and then evaporated to give an oily residue to which water was added. The mixture was extracted with ethyl acetate and the extract was washed with water, dried over magnesium sulfate and then evaporated to give a crystalline residue (7.10 g). The residue was recrystallized from diisopropyl ether to give n—octanoyl—D—Glu(OH)oBzl (2) (6.0 g).

NMR (CD Cl$_3$), δ(ppm): 0.87 (3H, t, J=7 Hz), 1.0-2.60 (16H, m), 4.50-5.10 (1H, m), 5.20 (2H, s), 6.35 (1H, d, J=7 Hz), 7.40 (5H, s), 9.90 (1H, broad s).

The following compounds were prepared in substantially the same manner as Preparation 68.

PREPARATION 69 n—Heptanoyl—D—Glu(OH)oBzl.

NMR (CDCl$_3$), δ(ppm): 0.86 (3H, t, J=7 Hz), 1.0-2.60 (14H, m), 4.50-5.10 (1H, m), 5.16 (2H, s), 6.45 (1H, d, J=7 Hz), 7.35 (5H, s), 10.00 (1H, s).

PREPARATION 70

Phenoxyacetyl—D—Glu(OH)oBzl.

NMR (CDCl$_3$), δ(ppm): 1.80-2.56 (4H, m), 4.50 (2H, s), 4.50-5.10 (1H, m), 5.20 (2H, s), 6.80-7.20 (5H, m), 7.35 (5H, s), 9.40 (1H, broad s).

PREPARATION 71

D—Acetylmandelyl—D—Glu(OH)oBzl.

NMR (CDCl$_3$), δ(ppm): 1.90-2.50 (4H, m), 2.10 (3H, s), 4.20-4.80 (1H, m), 5.10 (2H, s), 6.00 (1H, s), 7.20-7.50 (10H, m).

PREPARATION 72 n—Hexanoyl—D—Glu(OH)oBzl.

NMR (CDCl$_3$), δ(ppm); 0.90 (3H, t, J=7 Hz), 1.0-2.70 (2H, m), 4.50-5.0 (1H, m), 5.17 (2H, s), 6.50 (1H, d, J=7 Hz), 7.37 (5H, s), 10.60 (1H, s).

PREPARATION 73

N-Phenylcarbamoyl—D—Glu(OH)oBzl.

NMR (DMSO-d$_6$), δ(ppm): 1.70-2.50 (4H, m), 4.15-4.60 (1H, m), 5.13 (2H, s), 6.57 (1H, d, J=8 Hz), 6.70-7.60 (10H, m), 8.50 (1H, s).

PREPARATION 74

O—Benzylsalicyloyl—D—Glu(OH)oBzl.

NMR (CDCl$_3$), δ(ppm): 0.83-2.30 (26H, m), 2.83 (2H, broad s), 4.70-5.0 (1H, m), 5.13 (2H, s), 5.20 (2H, s), 7.0-7.68 (14H, m).

PREPARATION 75

D—Lac(oAc)—D—Glu(OH)oBzl dicyclohexylamine salt.

NMR (CDCl$_3$), δ(ppm): 0.80-2.40 (26H, m), 1.43 (3H, d, J=7 Hz), 2.10 (3H, s), 2.90 (2H, broad s), 4.40 (1H, q, J=7 Hz), 5.17 (2H, s), 5.17 (1H, q, J=7 Hz), 7.40 (5H, s), 7.90 (1H, d, J=7 Hz), 9.10 (1H, s).

PREPARATION 76

Nicotinoyl—D—Glu(OH)oBzl.

NMR (DMSO-d$_6$), δ(ppm): 1.83-2.67 (4H, m), 4.40-4.85 (1H, m), 5.20 (2H, s), 7.40 (5H, s), 7.50-7.70 (1H, m), 8.10-8.40 (1H, m), 8.67-9.20 (3H, m).

PREPARATION 77

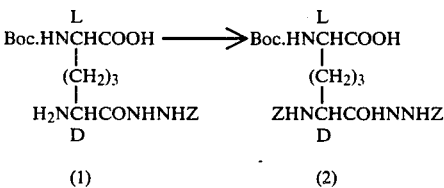

To a mixture of bis(trimethylsilyl)acetamide (2.4 ml) and methylene chloride (25 ml) was added Boc—(L-)—mesoDAP—(D)—NHNHZ (1) (1.0 g). The resulting mixture was stirred for two hours at ambient temperature and cooled to 15° C. and then carbobenzyl chloride (505 mg) was added thereto.

The reaction mixture was stirred for an hour at ambient temperature and concentrated to about 5 ml. To the concentrate were added ethyl acetate (30 ml) and 2% hydrochloric acid (10 ml). Ethyl acetate layer was separated and washed with water and dried over magnesium sulfate. Ethyl acetate was evaporated to dryness under reduced pressure and the residue was pulverized with isopropylether to give Boc—(L)—Z—(D-)—mesoDAP—(D)—NHNHZ (2) (0.60 g).

NMR (CD$_3$OD), δ(ppm): 1.43 (9H, s), 1.3-2.1 (6H, m), 3.9-4.3 (2H, m), 5.08 (2H, s), 5.13 (2H, s), 7.32 (10H, s).

PREPARATION 78

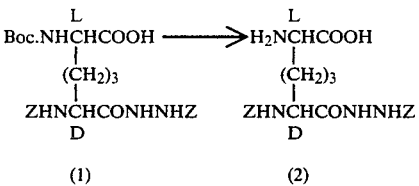

Boc—(L)—Z—(D)—mesoDAP—(D)—NHNHZ (1) (500 mg) was dissolved in trifluoroacetic acid (5 ml) and the solution was stirred for 15 minutes at ambient temperature. After evaporation of trifluoroacetic acid, the residue was dissolved in water (3 ml) and neutralized with 5% sodium bicarbonate. The resulting crystal was filtered and washed with water to give Z—(D-)—mesoDAP—(D)—NHNHZ (2) (280 mg), which was identical with that of product prepared in Preparation 62.

PREPARATION 79

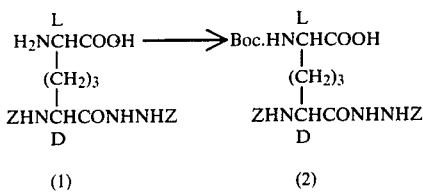

To a solution of 50% aqueous dioxane (20 ml) were added Z—(D)—mesoDAP—(D)—NHNHZ (1) (500 mg) and triethylamine (250 mg).

Di—tert—butyldicarbonate (300 mg) was added to the mixture. The resulting mixture was stirred for three hours at ambient temperature and then evaporated. The resulting aqueous solution was acidified to pH 3 with 5% hydrochloric acid and extracted with ethyl acetate (30 ml). Ethyl acetate layer was separated and the residue was washed with water, dried over magnesium sulfate. Ethyl acetate was evaporated to dryness under reduced pressure and the residue was pulverized with isopropyl ether to give Boc—(L)—Z—(D)—mesoDAP—(D)—NHNHZ (2) (0.47 g), which was identified with that of the product prepared in Preparation 77.

PREPARATION 80

(1) Step 1

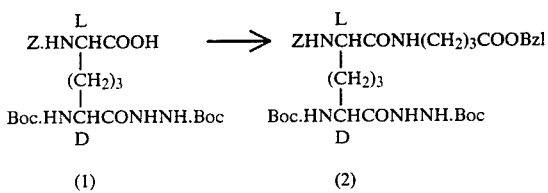

Z—(L)—Boc—(D)—mesoDAP—(D)—NHNH-Boc—(L)—γ—AbuoBzl (2) was prepared in substantially the same manner as step 1 of Preparation 43 from compound (1).

NMR (DMSO-d$_6$), δ(ppm): 0.9–2.0 (26H, m), 2.3 (2H, m), 2.9–3.4 (2H, m), 3.6–4.2 (2H, m), 5.02 (2H, s), 5.09 (2H, s), 6.7 (1H, m), 7.2 (1H, m), 7.35 (10H, s), 7.80 (1H, m), 8.65 (1H, m), 9.58 (1H, broad s).

(2) Step 2

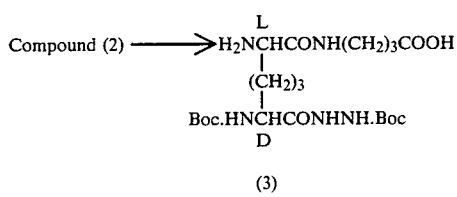

Boc—(D)—MesoDAP—(D)—NHNH.Boc—(L-)—γ—AbuOH (3) was prepared in substantially the same manner as step 2 of Preparation 43 from compound (2).

NMR (D$_2$O), δ(ppm): 1.0–2.6 (10H, m), 3.28 (2H, t, J=6.5 Hz), 3.7–4.3 (2H, m).

PREPARATION 81

(1) Step 1

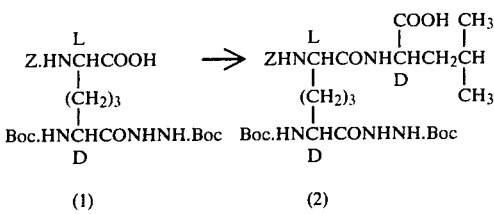

Z—(L)—Boc—(D)—mesoDAP—(D)—NHNH-.Boc—(L)—D—LeuOH (2) was prepared in substantially the same manner as step 1 of Preparation 43 from compound (1).

NMR (DMSO-d$_6$), δ(ppm): 0.6–2.0 (33H, m), 3.6–4.6 (3H, m), 5.01 (2H, s), 5.10 (2H, s), 6.7 (1H, m), 7.2 (1H, m), 7.34 (10H, s), 8.1–8.9 (2H, m), 9.57 (1H, broad s).

(2) Step 2

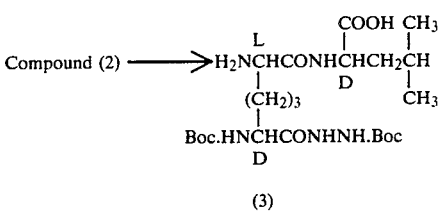

Boc—(D)—mesoDAP—(D)—NHNH.Boc—(L-)—D—LeuOH (3) was prepared in substantially the same manner as step 2 of Preparation 43 from compound (2).

IR (Nujol): 1680 (broad) and 1540 (broad) cm$^{-1}$.

NMR (CD$_3$OD), δ(ppm): 1.0 (6H, m), 1.50 (18H, s), 1.2–2.3 (9H, m), 3.6–4.6 (3H, m).

PREPARATION 82

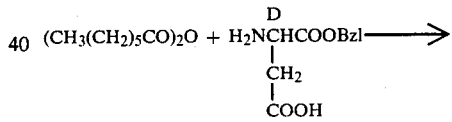

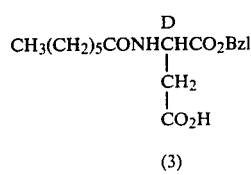

Heptanoyl—β—D—Asp(OH)oBzl (3) was prepared in substantially the same manner as Preparation 56 from compounds (1) and (2).

NMR (CDCl$_3$), δ(ppm): 0.7–1.0 (3H, m), 1.0–2.0 (8H, m), 2.95 (t 2H, 4 Hz), 4.90 (t, t, 1H, 4 Hz, 8 Hz), 5.14 (2H, s), 6.72 (1H, 8 Hz), 7.25 (5H, s), 10.00 (1H, s).

PREPARATION 83

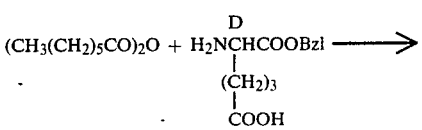

-continued

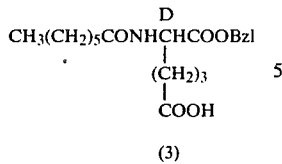

Heptanoyl—δ—D—Aad(OH)oBzl (3) was prepared in substantially the same manner as Preparation 56 from compounds (1) and (2).

(as dicyclohexylamine salt).

NMR (CDCl₃), δ(ppm): 0.7–1.1 (3H, m), 1.1–2.5 (34H, m), 2.5–3.1 (2H, m), 4.3–4.8 (1H, m), 5.13 (2H, s), 6.60 (1H, d, J=8 Hz), 7.33 (5H, s), 8.50 (3H, s).

PREPARATION 84

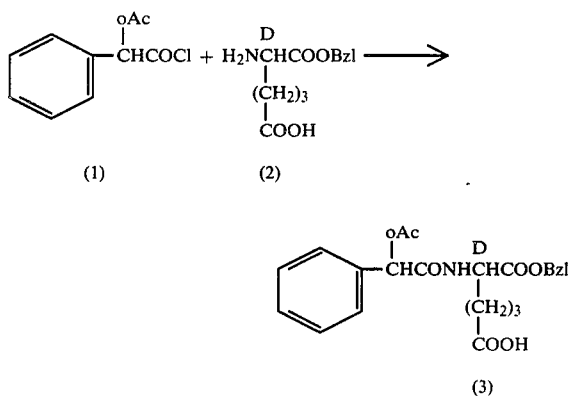

Mandelyl(oAc)—δ—D—Aad(OH)oBzl (3) was prepared in substantially the same manner as Preparation 56 from compounds (1) and (2).

NMR (CDCl₃), δ(ppm): 1.5–2.0 (4H, m), 2.13 (3H, s), 2.0–2.5 (2H, m), 4.4–4.8 (1H, m), 5.13 (2H, s), 6.07 (1H, s), 6.7–7.0 (1H, m), 7.33 (10H, s), 9.33 (1H, broad s).

EXAMPLE 96

(1) Step 1

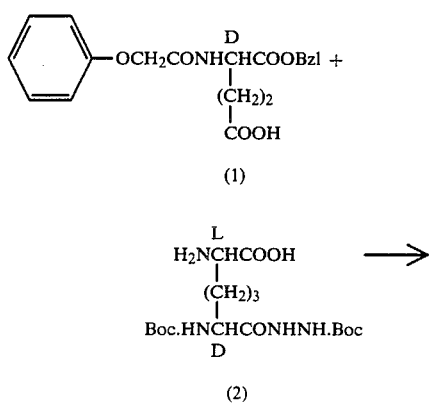

-continued

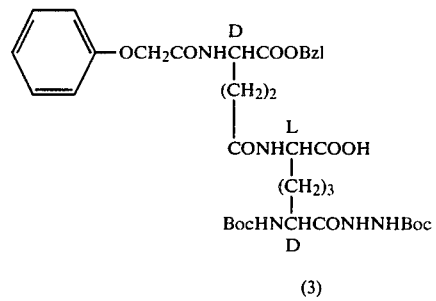

Phenoxyacetyl—D—Glu(α—oBzl) (1) (742 mg) was dissolved in methylene chloride and N-methylmorpholine (202 mg) was added thereto. This solution was cooled under a dryice-carbontetrachloride and isobutylchloroformate (274 mg) was added thereto. The mixture was allowed to react for 60 minutes at the same temperature. To the resulting reaction mixture was added the solution Boc—(D)mesoDAP—(D-)—NHNHBoc (2) (808 mg) in a mixture of methylene chloride (20 ml), dimethylformamide (2 ml) and bis(-trimethylsilyl)acetamide (2 ml). The reaction mixture was stirred for two hours and concentrated in vacuo to give an oily residue, which was dissolved in ethyl acetate, washed with 1N hydrochloric acid and brine, dried over magnesium sulfate. Evaporation of the solvent gave a white foam, which was pulverized with isopropylether to give a phenoxyacetyl—γ—D—Glu(α—oBzl)—(L)—Boc—(D)—mesoDAP—(D-)—NHNHBoc (3) (1.21 g).

NMR (CD₃OD), δ(ppm): 1.42 (18H, s), 3.9–4.6 (3H, m), 4.54 (2H, s), 5.17 (2H, s), 6.85–7.30 (5H, m), 7.35 (5H, s).

(2) Step 2

Compound (3) ⟶

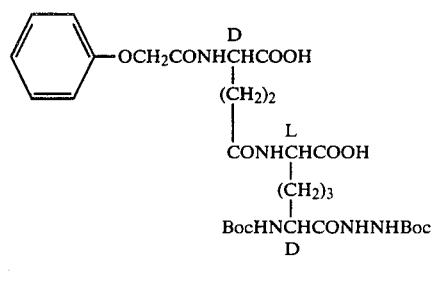

Phenoxyacetyl—γ—D—Glu(α—oBzl)—(L-)—Boc—(D)—mesoDAP—(D)—NHNHBoc (3) (1.13 g) was dissolved in methanol (20 ml) and 1N sodium hydroxide (3.0 ml) was added thereto at ambient temperature. The reaction mixture was stirred for 4 hours at the same temperature and concentrated under reduced pressure to give an oily residue, which was dissolved in a mixture of ethyl acetate (60 ml), water (10 ml) and 1N hydrochloric acid (4 ml). The organic layer was with brine, dried over magnesium sulfate and then concentrated in vacuo to give phenoxyacetyl—γ—D—Glu(α—OH)—(L)—Boc—(D)—mesoDAP—(D-)—NHNHBoc (4) (670 mg).

NMR (CD₃OD), δ(ppm): 1.43 (18H, s), 4.00–4.70 (3H, m), 4.60 (2H, s), 7.24–7.50 (5H, m).

(3) Step 3

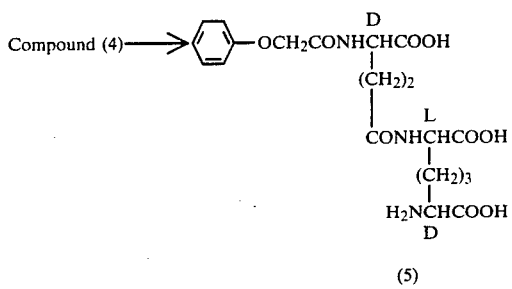

Phenoxyacetyl—γ—D—Glu(α—OH)—(L-)—Boc—(D)—mesoDAP—(D)—NHNHBoc (4) (615 mg) was dissolved in trifluoroacetic acid (3 ml) and the solution was kept for an hour at ambient temperature. The solvent was distilled off to give an oily paste, which was pulverized with ether to give a white powder. The powder was dissolved in a mixture of water (25 ml) and 1N sulfuric acid and the solution was cooled in an ice-bath. To the solution was added sodium periodate (300 mg) and the mixture was stirred for two hours at 0° C. The mixture was treated with an aqueous sodium bisulfite and then passed through a column packed with a macroporous non-ionic adsorption resin, HP-20. Elution was carried out with a mixture of water and methanol (7:3) and the eluate was concentrated in vacuo to give a white powder, which was dissolved in water and lyophilized to give phenoxyacetyl—γ—D—Glu(α—OH)—(L)—mesoDAP (5) (150 mg).

NMR (D₂O+NaHCO₃), δ(ppm): 1.25–2.35 (10H, m), 3.72 (1H, t, J=6 Hz), 4.00–4.35 (2H, m), 4.63 (2H, s), 7.0–7.5 (5H, m).

EXAMPLE 97

(1) Step 1

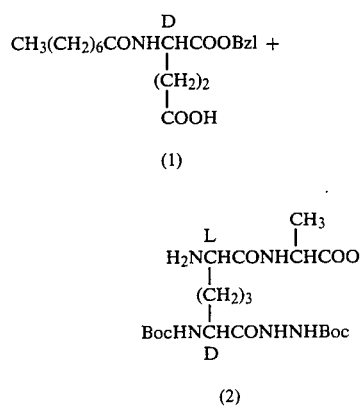

-continued

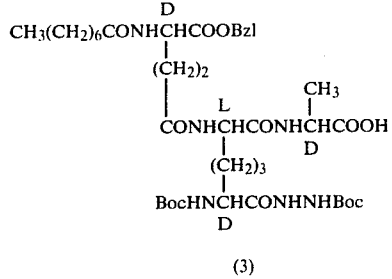

n—Octanoyl—γ—D—Glu(α—oBzl)—(L-)—Boc—(D)—mesoDAP—(D)—NHNHBoc—(L-)—D—AlaOH (3) was prepared in substantially the same manner as step (1) of Example 96 from compounds (1) and (2).

NMR (DMSO-d₆+D₂O), δ(ppm): 0.83 (3H, t, J=6 Hz), 1.37 (18H, s), 3.80–4.50 (4H, m), 5.08 (2H, s), 7.33 (5H, s), 7.66–8.33 (6H, m), 9.20 (1H, broad s).

(2) Step 2

Compound (3) ⟶

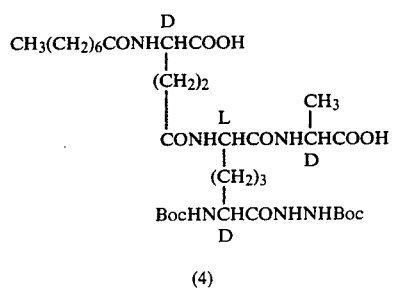

n—Octanoyl—γ—D—Glu(α—OH)—(L-)—Boc—(D)—mesoDAP—(D)—NHNHBoc—(L-)—D—AlaOH (4) was prepared in substantially the same manner as step 2 of Example 96 from compound (3).

NMR (DMSO-d₆+D₂O), δ(ppm): 0.87 (3H, t, J=6 Hz), 1.35 (18H, s), 4.00–4.66 (4H, m), 7.66–8.33 (6H, m), 9.55 (2H, broad s).

(3) Step 3

Compound (4) ⟶

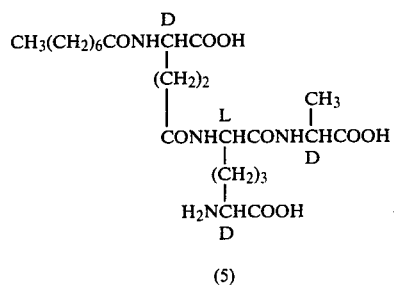

n—Octanoyl—γ—D—Glu(α—OH)—(L-)—mesoDAP—(L)—D—AlaOH (5) was prepared in substantially the same manner as step 3 of Example 96 from compound (4).

NMR (D₂O), δ(ppm): 0.88 (3H, t, J=7 Hz), 1.40 (3H, d, J=7 Hz), 1.00-2.50 (22H, m), 3.80 (1H, t, J=7 Hz), 4.00-4.50 (3H, m).

EXAMPLE 98

(1) Step 1

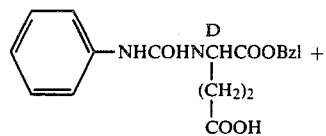

(1)

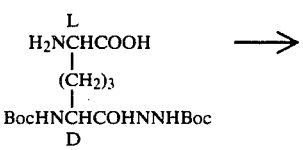

(2)

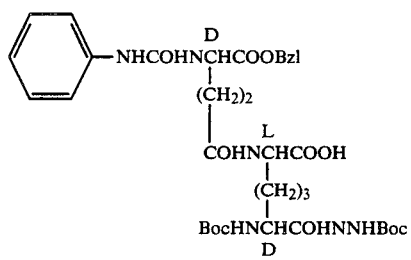

(3)

Phenylcarbamoyl—γ—D—Glu(α—oBzl)—(L-)—Boc—(D)—mesoDAP—(D)—NHNHBoc (3) was prepared in substantially the same manner as step 1 of Example 96 from Compounds (1) and (2).

NMR (CD₃OD) δ(ppm): 1.41 (18H, s), 3.90-4.62 (3H, m), 5.19 (2H, s), 6.95-7.52 (10H, m).

(2) Step 2

Compound (3) ⟶

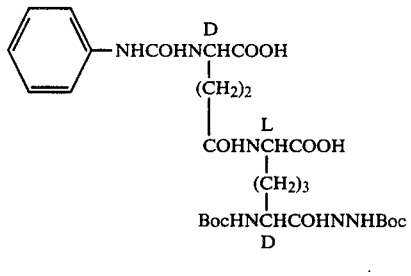

(4)

Phenylcarbamoyl—γ—D—Glu(α—OH)—(L-)—Boc—(D)—mesoDAP—(D)—NHNHBoc (4) was prepared in substantially the same manner as step (2) of Example 96 from compound (3).

NMR (CD₃OD) δ(ppm): 1.48 (18H, s), 3.95-4.55 (3H, m), 7.32 (5H, s).

(3) Step 3

Compound (4) ⟶

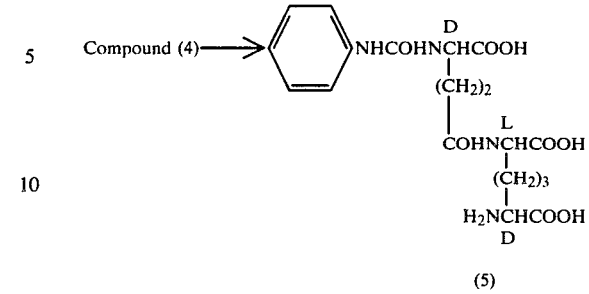

(5)

Phenylcarbamoyl—γ—D—Glu(α—OH)—(L-)—mesoDAP (5) was prepared in substantially the same manner as step 3 of Example 96 from Compound (4).

NMR (D₂O+NaOD) δ(ppm): 1.1-2.6 (10H, m), 3.16 (1H, m), 4.00-4.20 (2H, m), 7.00-7.45 (5H, m).

EXAMPLE 99

(1) Step 1

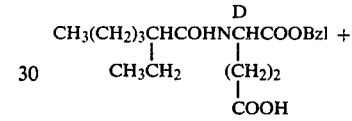

(1)

(2)

(3)

α—Ethylhexanoyl—γ—D—Glu(α—oBzl)—(L-)—Boc—(D)—mesoDAP—(D)—NHNHBoc (3) was prepared in substantially the same manner as step 1 of Example 96 from compound (1) and (2).

NMR (CD₃OD) δ(ppm): 0.86 (6H, m), 1.45 (18H, s), 3.90-4.30 (3H, m), 5.16 (2H, s), 7.36 (5H, s).

(2) Step 2

Compound (3) ⟶

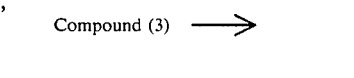

-continued

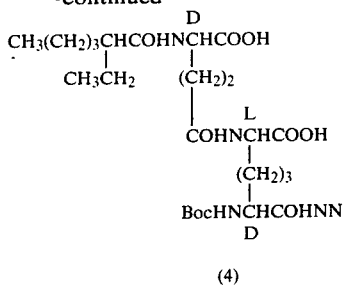

(4)

α—Ethylhexanoyl—γ—D—Glu(α—OH)—(L-)—Boc—(D)—mesoDAP—(D)—NHNHBoc (4) was prepared in substantially the same manner as step 2 of Example 96 from compound (3).

NMR (CD₃OD) δ(ppm): (0.88 (6H, m), 1.43 (18H, s), 4.02 (1H, m), 4.36 (2H, m).

(3) Step 3

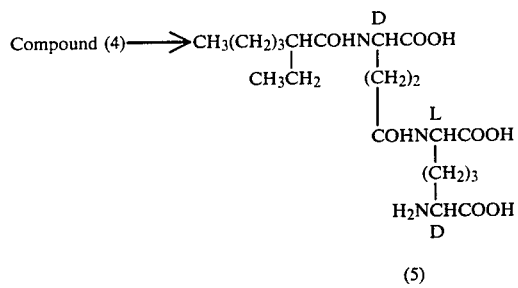

(5)

α—Ethylhexanoyl—γ—D—Glu(α—OH)—(L-)—mesoDAP (5) was prepared in substantially the same manner as step 3 of Example 96 from Compound (4).

NMR (D₂O) δ(ppm): 0.83 (6H, m), 1.08–2.56 (19H, m), 3.82 (1H, t, J=7 Hz), 4.23–4.48 (2H, m).

EXAMPLE 100

(1) Step 1

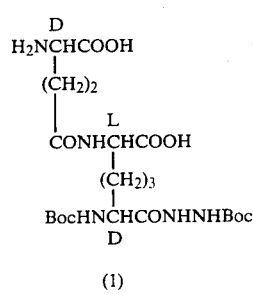

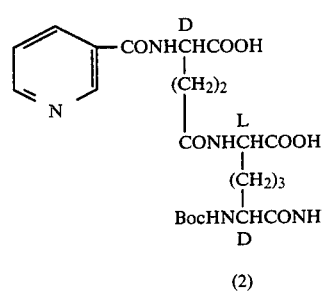

(2)

To a solution of γ—D—Glu(α—OH)—(L-)—Boc—(D)—mesoDAP—(D)—NHNHBoc (1) (800 mg) in the mixture of water (8 ml) and dioxane (8 ml) were added N-hydroxysuccinylnicotinate (330 mg) and triethylamine (364 mg). The reaction mixture was left for 20 hours at ambient temperature and concentrated in vacuo. To the residue was added 1N hydrochloric acid (3 ml) and the mixture was passed through a column packed with a macroporous non-ionic adsorption resin, HP 20 (120 ml).

The fraction eluted with a mixture of water and methanol (2:3) was concentrated in vacuo to give nicotinoyl—γ—D—Glu(α—OH)—(L)—Boc—(D-)—mesoDAP—(D)—NHNHBoc (2).

NMR (CD₃OD), δ(ppm): 1.44 (18H, s), 3.9–4.6 (3H, m), 7.59 (1H, d.d., J=8 & 5 Hz), 8.35 (1H, m), 8.75 (1H, d, J=5 Hz), 9.11 (1H, m).

(2) Step 2

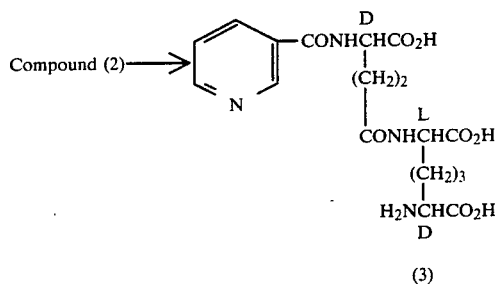

(3)

Nicotinoyl—γ—D—Glu(α—OH)—(L)—mesoDAP (3) was prepared in substantially the same manner as Step 2 of Example 96 from Compound (2).

NMR (D₂O, δ(ppm): 1.25–2.60 (10H, m), 3.87 (1H, t, J=6 Hz), 4.23 (1H, m), 4.51 (1H, m), 7.98 (1H, d.d., J=6 and 8 Hz), 8.71 (1H, d, J=8 Hz), 8.88 (1H, d, J=6 Hz), 9.10 (1H, s).

EXAMPLE 101

(1) Step 1

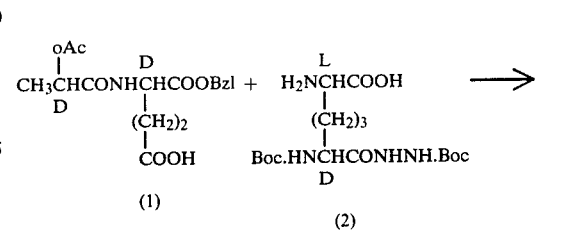

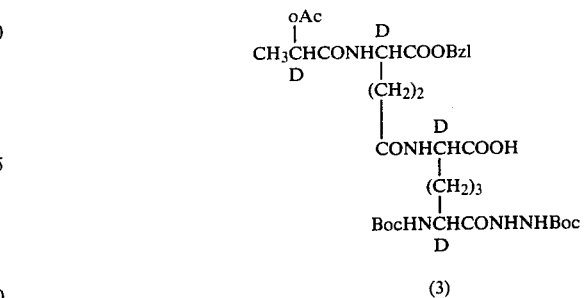

(3)

D—Lac(oAc)—γ—D—Glu(α—oBzl)—(L-)—Boc—(D)—mesoDAP—(D)—NHNHBoc (3) was prepared in substantially the same manner as Step 1 of Example 59 from Compounds (1) and (2).

IR (Nujol): 3280, 1730, 1660, 1530 cm⁻¹.

NMR (CD₃OD), δ(ppm): 1.38 (18H, s), 2.05 (3H, s), 3.85–4.60 (3H, m).

(2) Step 2

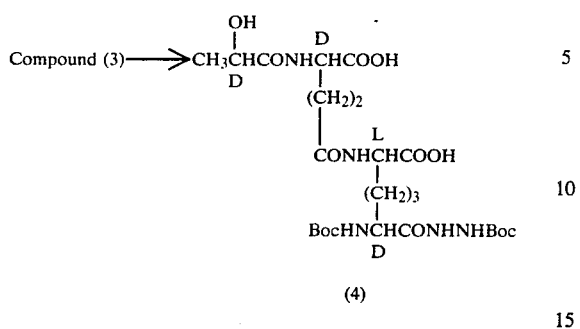

To a solution of D—Lac(oAc)—γ—D—Glu(α—oBzl)—(L)—Boc—(D)—mesoDAP—(D-)—NHNHBoc (4) (1.14 g) in methanol (15 ml) was added 1N sodium hydroxide (6.2 ml).

The reaction mixture was left for 3.5 hours at ambient temperature and 1N hydrochloric acid (6.2 ml) was added thereto. The mixture was concentrated in vacuo and the residue was passed a column packed with a macroporous non-ionic adsorption resin, HP 20 (100 ml) and eluted with a mixture of water and methanol (1:1). The fractions containing the object Compound (4) were collected and concentrated in vacuo to give D—Lac(OH)—γ—D—Glu(α—OH)—(L)—Boc—(D-)—mesoDAP—(D)—NHNHBoc (4) (510 mg).

IR (Nujol): 3300, 1720(sh), 1650, 1520 cm$^{-1}$.

NMR (CD$_3$OD), δ(ppm): 1.45 (18H, s), 3.97-4.70 (4H, m).

(3) Step 3

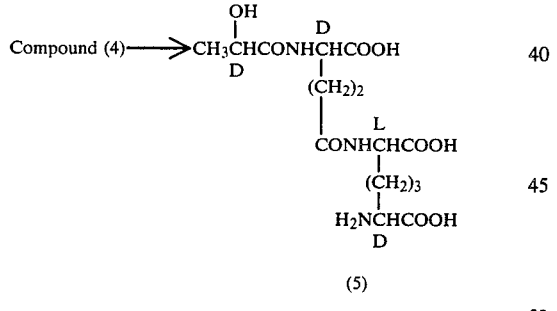

D—Lac(OH)—γ—D—Glu(α—OH)—(L-)—mesoDAP (5) was prepared in substantially the same manner as Step 3 of Example 59 from Compound (4).

IR (Nujol): 3250 (sh), 1720, 1650, 1530 cm$^{-1}$.

NMR (D$_2$O), δ(ppm): 1.25-2.50 (10H, m), 1.36 (3H, d, J=7 Hz), 3.91 (1H, t, J=7 Hz), 4.28-4.45 (3H, m).

EXAMPLE 102

(1) Step 1

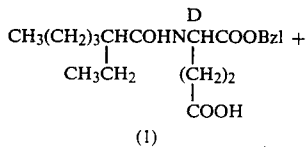

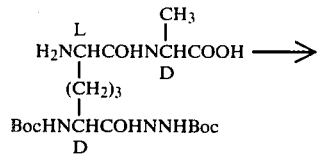

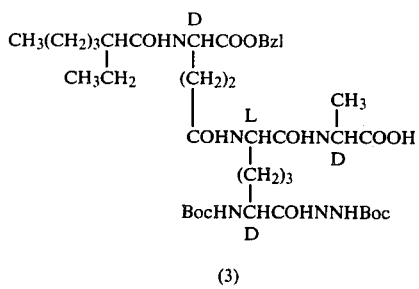

α—Ethylhexanoyl—γ—D—Glu(α—oBzl)—(L-)—Boc—(D)—mesoDAP—(D)—NHNHBoc—(L-)—D—AlaOH (3) was prepared in substantially the same manner as step 1 of Example 96 from compounds (1) and (2).

NMR (DMSO-d$_6$+D$_2$O, δ(ppm): 0.80-1.00 (6H, m), 1.40 (18H, s), 1.00-2.33 (22H, m), 4.00-4.50 (4H, m), 5.10 (2H, s), 7.33 (5H, s), 7.66-8.33 (6H, m), 9.50 (1H, broad s).

(2) Step (2)

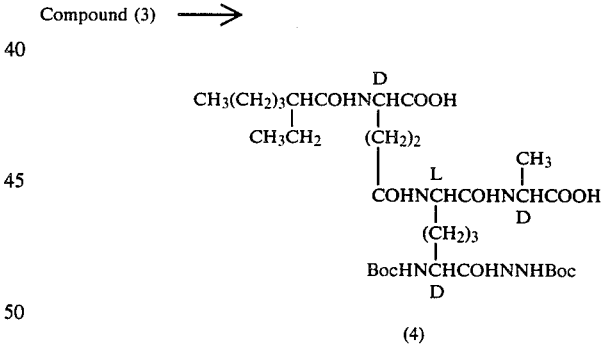

α—Ethylhexanoyl—γ—D—Glu(α—OH)—(L-)—Boc—(D)—mesoDAP—(D)—NHNHBoc—(L-)—D—AlaOH (4) was prepared in substantially the same manner as step 2 of Example 96 from compound (3).

NMR (DMSO-d$_6$+D$_2$O), δ(ppm): 0.83-1.00 (6H, m), 1.43 (18H, s), 1.00-2.33 (22H, m), 3.50-4.66 (4H, m), 7.66-8.33 (6H, m), 9.53 (2H, broad s).

(3) Step 3

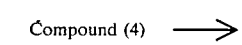

-continued

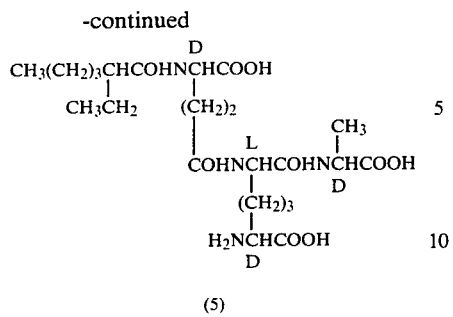

(5)

α—Ethylhexanoyl—γ—D—Glu(α—OH)—(L-)—mesoDAP—(L)—D—AlaOH (5) was prepared in substantially the same manner as step 3 of Example 96 from compound (4).

NMR (D$_2$O), δ(ppm): 0.84 (6H, t, J=7 Hz), 1.24–2.30 (19H, m), 1.36 (3H, t, J=7 Hz), 3.82 (1H, t, J=6 Hz), 4.25–4.44 (3H, m).

EXAMPLE 103

(1) Step 1

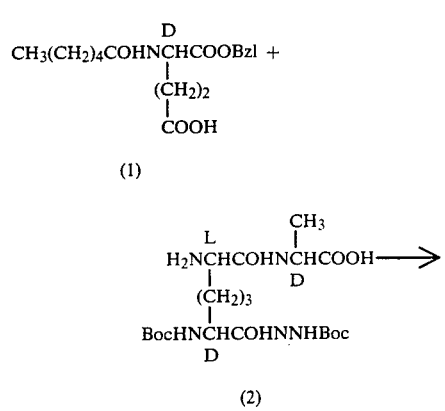

Hexanoyl—γ—D—Glu(α—oBzl)—(L)—Boc—(D-)—mesoDAP—(D)—NHNHBoc—(L)—D—AlaOH (3) was prepared in substantially the same manner as step 1 of Example 96 from compound (1) and (2).

NMR (DMSO-d$_6$+D$_2$O), δ(ppm): 0.83 (3H, t, J=7 Hz), 1.44 (18H, s), 3.83–4.50 (4H, m), 5.13 (2H, s), 7.33 (5H, s), 7.73–8.73 (5H, m), 9.56 (1H, broad s).

(2) Step 2

Compound (3) ⟶

-continued

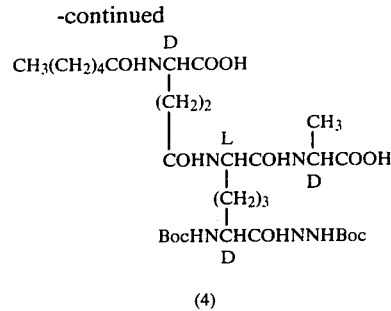

(4)

Hexanoyl—γ—D—Glu(α—OH)—(L)—Boc—(D-)—mesoDAP—(D)—NHNHBoc—(L)—D—AlaOH (4) was prepared in substantially the same manner as step 2 of Example 96.

NMR (DMSO-d$_6$+D$_2$O), δ(ppm): 0.86 (3H, t, J=7 Hz), 1.37 (18H, s), 3.83–4.33 (4H, m), 7.66–8.77 (6H, m).

(3) Step 3

Compound (4) ⟶

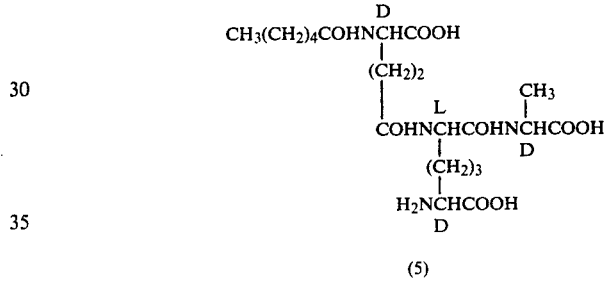

(5)

Hexanoyl—γ—D—Glu(α—OH)—(L-)—mesoDAP—(L)—D—AlaOH (5) was prepared in substantially the same manner as step 3 of Example 96 from compound (4).

NMR (DMSO-d$_6$+D$_2$O), δ(ppm): 0.80 (3H, t, J=7 Hz), 1.38 (5H, d, J=7 Hz), 1.28–2.40 (18H, m), 3.75 (1H, t, J=7 Hz), 4.20–4.35 (3H, m).

EXAMPLE 104

(1) Step 1

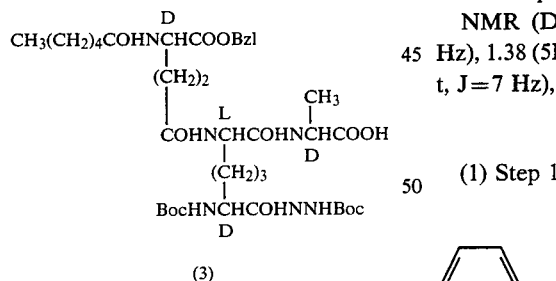

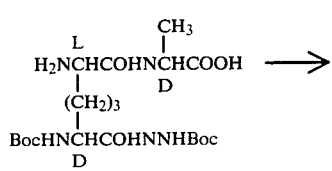

-continued

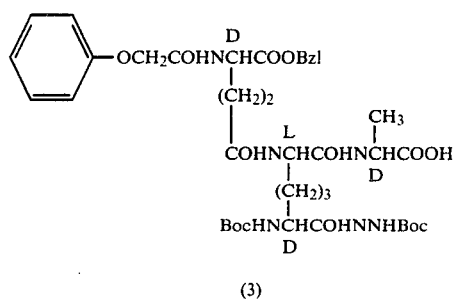
(3)

Phenoxyacetyl—γ—D—Glu(α—oBzl)—(L-)—Boc—(D)—mesoDAP—(D)—NHNHBoc—(L-)—D—AlaOH (3) was prepared in substantially the same manner as step 1 of Example 96 from compound (1) and (2).

NMR (DMSO-d$_6$+D$_2$O, δ(ppm): 1.38 (18H, s), 3.66–4.50 (4H, m), 4.53 (2H, s), 5.15 (2H, s), 6.87–7.33 (5H, m), 7.37 (5H, s), 7.85–8.60 (6H, m), 9.57 (1H, broad s).

(2) Step 2

Compound (3) ⟶

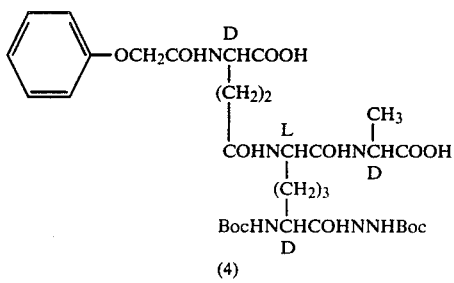
(4)

Phenoxyacetyl—γ—D—Glu(α—OH)—(L-)—Boc—D—mesoDAP—(D)—NHNHBoc—(L-)—D—AlaOH (4) was prepared in substantially the same manner as step 2 of Example 96 from compound (3).

NMR (DMSO-d$_6$+D$_2$O, δ(ppm): 1.40 (18H, s), 3.73–4.50 (4H, m), 4.53 (2H, s), 6.90–7.43 (5H, m), 7.73–8.66 (6H, m), 9.50 (2H, broad s).

(3) Step 3

Compound (4) ⟶

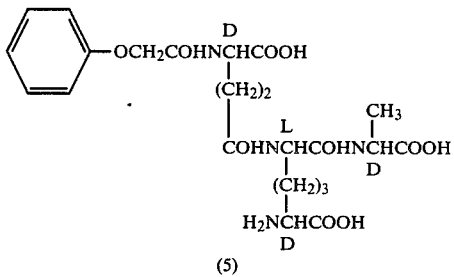
(5)

Phenoxyacetyl—γ—D—Glu(α—OH)—(L-)—mesoDAP—(L)—D—AlaOH (5) was prepared in substantially the same manner as step 3 of Example 96 from compound (4).

NMR (D$_2$O), δ(ppm): 1.39 (3H, d, J=7 Hz), 1.60–2.50 (10H, m), 3.85 (1H, t, J=7 Hz), 4.00–4.50 (3H, m), 4.64 (2H, s), 6.80–7.50 (5H, m).

EXAMPLE 105

(1) Step 1

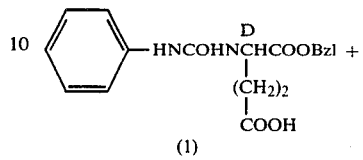
(1)

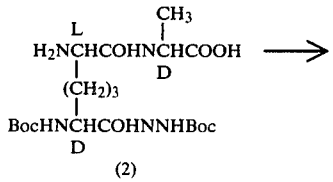
(2)

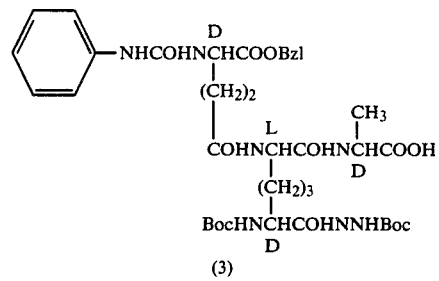
(3)

Phenylcarbamoyl—γ—D—Glu(α—oBzl)—(L-)—Boc—(D)—mesoDAP—(D)—NHNHBoc—(L-)—D—AlaOH (3) was prepared in substantially the same manner as step 1 of Example 96 from compounds (1) and (2).

NMR (DMSO-d$_6$+D$_2$O), δ(ppm): 1.37 (18H, s), 3.83–4.50 (4H, m), 5.13 (2H, s), 7.33 (5H, s), 6.50–7.20 (5H, m), 7.33–8.50 (7H, m), 9.50 (1H, broad s).

(2) Step 2

Compound (3) ⟶

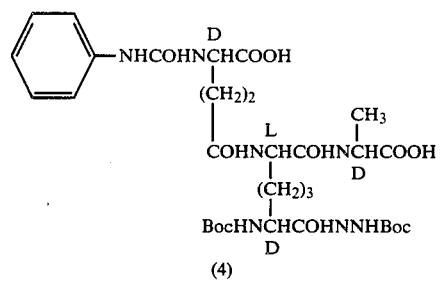
(4)

Phenylcarbamoyl—γ—D—Glu(α—OH)—(L-)—Boc—(D)—mesoDAP—(D)—NHNHBoc—(L-)—D—AlaOH (4) was prepared in substantially the same manner as step 2 of Example 96 from compound (3).

NMR (DMSO-d$_6$+D$_2$O), δ(ppm): 1.42 (18H, s), 3.83–4.20 (4H, m), 6.40–7.50 (5H, m), 7.66–8.60 (7H, m), 9.50 (2H, broad s).

(3) Step 3

Compound (4) →

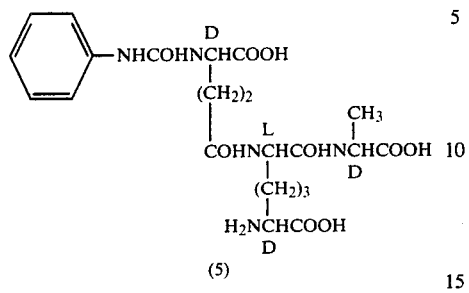

(5)

Phenylcarbamoyl—γ—D—Glu(α—OH)—(L-)—mesoDAP—(L)—D—AlaOH (5) was prepared in substantially the same manner as step 3 of Example 96.

NMR (D₂O), δ(ppm): 1.40 (5H, d, J=7 Hz), 1.30–2.50 (10H, m), 3.76 (1H, t, J=7 Hz), 4.20–4.50 (3H, m), 7.00–7.70 (5H, m).

EXAMPLE 106

(1) Step 1

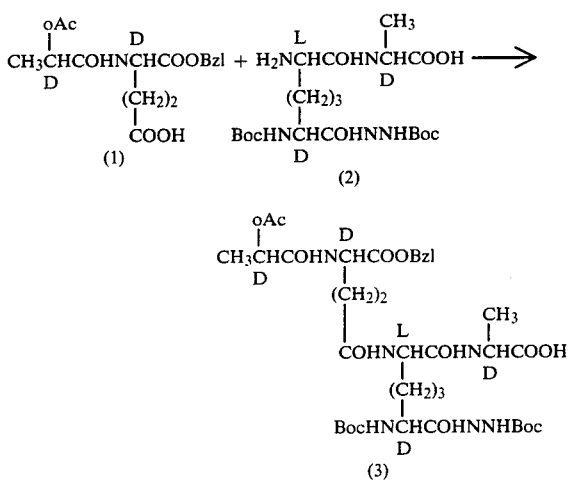

D—Lac(oAc)—γ—D—Glu(α—oBzl)—(L-)—Boc—(D)—mesoDAP—(D)—NHNHBoc—(L-)—D—Ala OH (3) was prepared in substantially the same manner as step 1 of Example 96 from compounds (1) and (2).

NMR (DMSO-d₆+D₂O), δ(ppm): 1.40 (18H, s), 2.06 (3H, s), 1.10–2.30 (16H, m), 3.66–4.57 (5H, m), 5.13 (2H, s), 7.37 (5H, s), 7.66–8.38 (6H, m), 9.56 (1H, broad s).

(2) Step 2

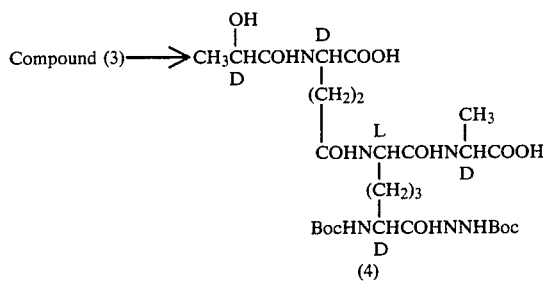

D—Lac(OH)—γ—D—Glu(α—OH)—(L-)—Boc—(D)—mesoDAP—(D)—NHNHBoc—(L-)—D—AlaOH (4) was prepared in substantially the same manner as step 2 of Example 96 from compound (3).

NMR (CD₃OD), δ(ppm): 1.40 (9H, s), 1.43 (9H, s), 1.33–2.50 (16H, m), 3.83–4.66 (5H, m).

(3) Step 3

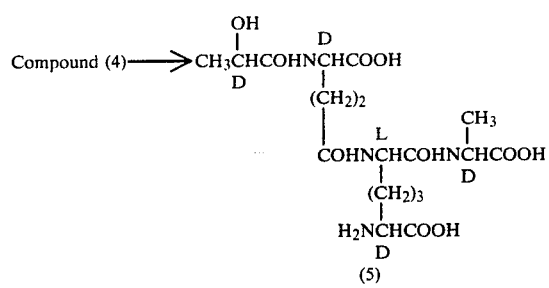

D—Lac(OH)—γ—D—Glu(α—OH)—(L-)—mesoDAP—(L)—D—AlaOH (5) was prepared in substantially the same manner as step 3 of Example 96 from compound (4).

NMR (D₂O), δ(ppm): 1.32 (3H, d, J=7 Hz), 1.33 (3H, d, J=7 Hz), 1.20–2.40 (10H, m), 3.82 (1H, t, J=7 Hz), 4.20–4.44 (4H, m).

EXAMPLE 107

(1) Step 1

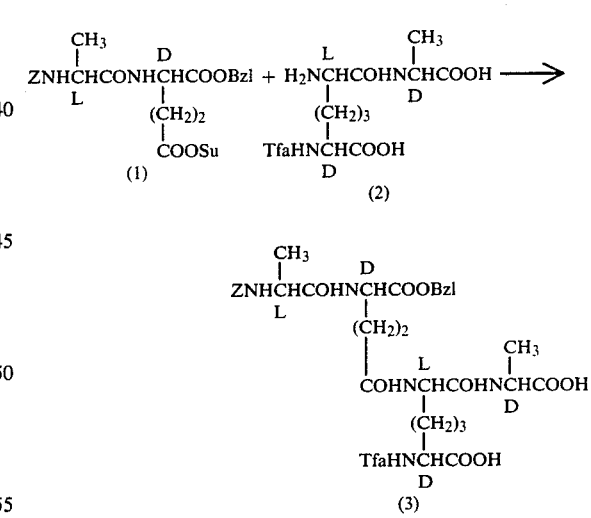

Z—L—Ala—γ—D—Glu(α—oBzl)—(L)—Tfa—(D-)—mesoDAP—(L)—D—AlaOH (3) was prepared in substantially the same manner as step 1 of Example 32 from compounds (1) and (2).

NMR (DMSO-d₆), δ(ppm): 1.23 (6H, d, J=7 Hz), 1.20–2.30 (10H, m), 4.0–4.63 (5H, m), 5.07 (2H, s), 5.15 (2H, s), 7.40 (5H, s), 7.73–8.50 (3H, m), 9.63 (1H, d, J=7 Hz).

(2) Step 2

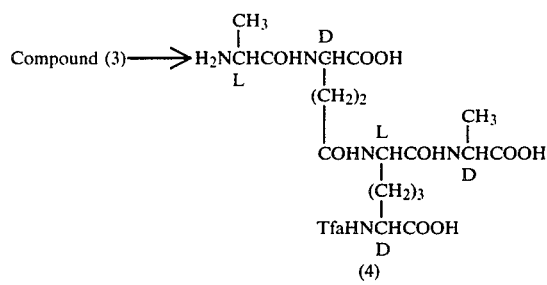

L—Ala—γ—D—Glu(α—OH)—(L)—Tfa—(D-)—mesoDAP—(L)—D—AlaOH (4) was prepared in substantionally the same manner as step 2 of Example 32 from compound (3).

NMR (D₂O), δ(ppm): 1.43 (3H, d, J=7 Hz), 1.60 (3H, d, J=7 Hz), 1.40–2.70 (10H, m), 4.00–4.50 (5H, m).

(3) Step 3

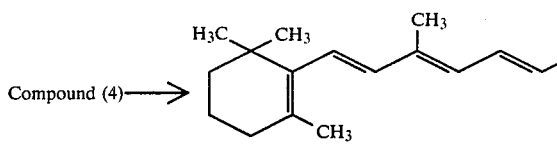

L—Ala—γ—D—Glu(α—OH)—(L)—Tfa—(D-)—mesoDAP—(L)—D—Ala(OH) (4) (810 mg) was dissolved in a mixture of methylene chloride (30 ml), methanol (3 ml) and triethylamine (594 mg). To this solution was added retinoic acid N-hydroxysuccimide ester (584 mg) and the mixture was reacted for two days at ambient temperature. Triethylamine (150 mg) was added to the reaction mixture and reacted for another day further. The resulting mixture was evaporated and the oily residue was extracted with ethyl acetate after acidification with 1N sulfuric acid. The organic layer was washed with water, dried over magnesium sulfate and evaporated to give a yellow foamyl residue (1.10 g) which was throughly washed with a mixture of ethyl ether and isopropylether to give retinoyl—L—Ala—γ—D—Glu(α—OH)—(L)—Tfa—(D)—mesoDAP—(L)—D—AlaOH (5) (940 mg.).

NMR (DMSO-d₆), δ(ppm): 1.00 (6H, s), 1.03 (3H, d, J=7 Hz), 1.23 (3H, d, J=7 Hz), 1.0–2.40 (16H, m), 1.66 (3H, s), 1.93 (3H, s), 2.25 (3H, s), 4.0–4.50 (5H, m), 5.83–6.50 (5H, m), 6.70–7.30 (1H, m), 7.70–8.40 (4H, m).

(4) Step 4

Retinoyl—L—Ala—γ—D—Glu(α—OH)—(L)—Tfa—(D)—mesoDAP—(L)—D—AlaOH (5) (0.90 g) was dissolved in a mixture of water (15 ml) and 1N sodium hydroxide (4.50 ml). The resulting solution was maintained for 2 hours at ambient temperature and then acidified with 1N sulfuric acid. The mixture was extracted with n-butanol (100 ml). The organic layer was washed three times with water (20 ml) and evaporated to give a yellow solid residue which was throughly washed with ethyl ethre to give retinoyl—L—Ala—γ—D—Glu(α—OH)—(L-)—mesoDAP—(L)—D—AlaOH (6);

NMR (DMSO-d₆), δ(ppm): 1.06 (6H, s), 1.20 (3H, d, J=7 Hz), 1.30 (3H, d, J=7 Hz), 1.73 (3H, s), 2.00 (3H, s), 2.30 (3H, s), 1.00–2.50 (16H, m), 3.30–3.70 (1H, m), 4.00–4.66 (4H, m), 5.86–6.50 (5H, m), 6.70–7.30 (1H, m), 7.70–8.30 (4H, m).

EXAMPLE 108

(1) Step 1

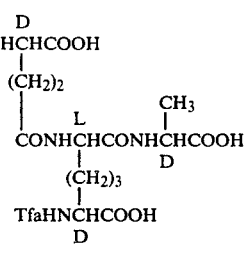

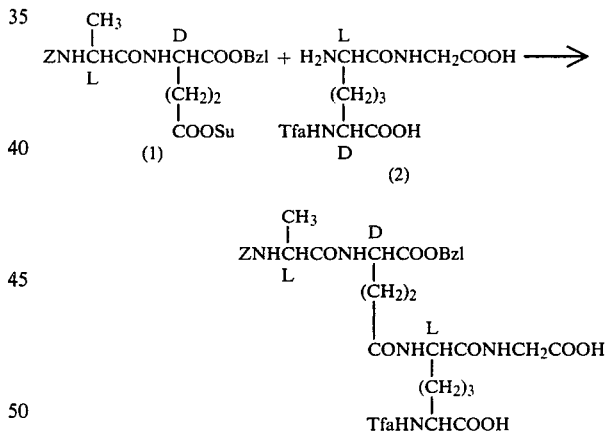

Z—L—Ala—γ—D—Glu(α—oBzl)—(L)—Tfa—(D-)—mesoDAP—(L)—GlyOH (3) was prepared in sub-

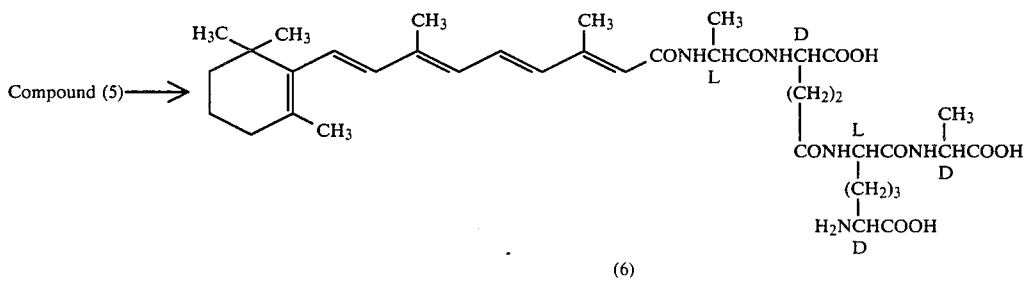

stantially the same manner as step 1 of Example 107 from compounds (1) and (2).

NMR (DMSO-d₆), δ(ppm): 1.23 (3H, d, J=7 Hz), 1.20-2.50 (10H, m), 3.75 (2H, d, J=6 Hz), 4.0-4.60 (4H, m), 5.03 (2H, s), 5.13 (2H, s), 7.10-7.30 (1H, broad), 7.33 (10H, s), 7.83-8.50 (3H, m), 9.60 (1H, d, J=7 Hz).

(2) Step 2

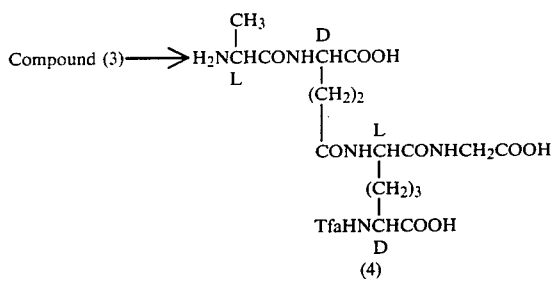

L—Ala—γ—D—Glu(α—OH)—(L)—Tfa—(D-)—mesoDAP—(L)—GlyOH (4) was prepared in substantially the same manner as step 2 of Example 107 from compound (3).

NMR (D₂O), δ(ppm): 1.56 (3H, d, J=7 Hz), 1.20-2.63 (10H, m), 3.95 (2H, s), 4.00-4.50 (4H, m).

(3) Step 3

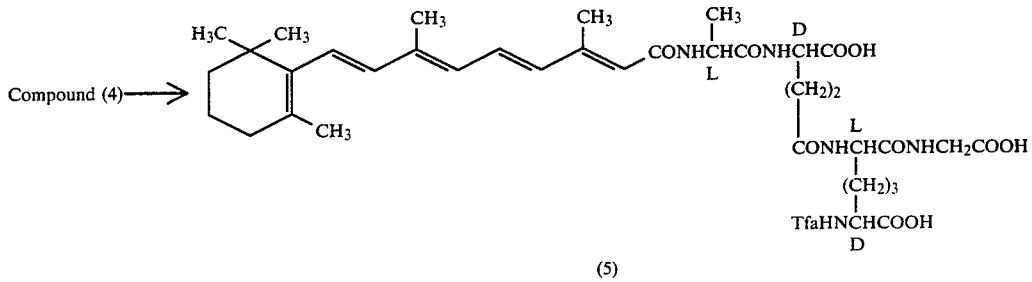

Retinoyl—L—Ala—γ—D—Glu(α—OH)—(L)—Tfa—(D)—mesoDAP—(L)—GlyOH (5) was prepared in substantially the same manner as step 3 of Example 107 from compound (4).

NMR (DMSO-d₆), δ(ppm): 1.00 (6H, s), 1.06 (3H, d, J=7 Hz), 1.00-2.40 (16H, m), 1.66 (3H, s), 1.90 (3H, s), 2.33 (3H, s), 3.70 (2H, broad), 4.0-4.50 (4H, m), 5.83-6.50 (5H, m), 6.70-7.30 (1H, m), 7.70-8.40 (4H, m).

(4) Step 4

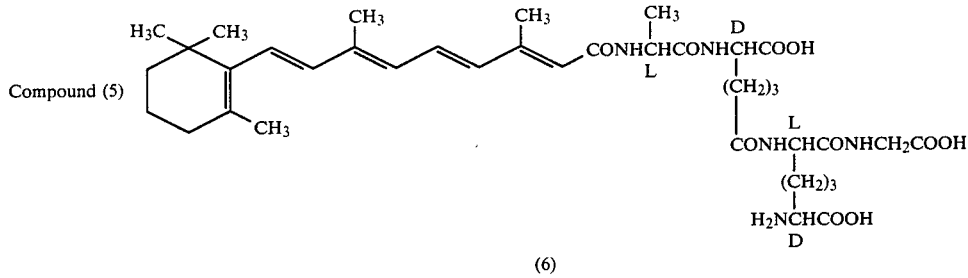

Retinoyl—L—Ala—γ—D—Glu(α—OH)—(L-)—mesoDAP—(L)—GlyOH (6) was prepared in substantially the same manner as step 4 of Example 107 from compound (5).

NMR (DMSO-d₆), δ(ppm): 1.00 (6H, s), 1.23 (3H, d, J=7 Hz), 1.70 (3H, s), 1.96 (3H, s), 2.26 (3H, s), 1.00-2.50 (16H, m), 3.50 (1H, broad s), 3.76 (2H, broad s), 4.0-4.50 (4H, m), 5.70-7.30 (6H, m), 7.70-8.30 (4H, m).

EXAMPLE 109

(1) Step 1

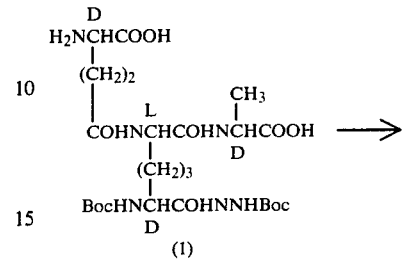

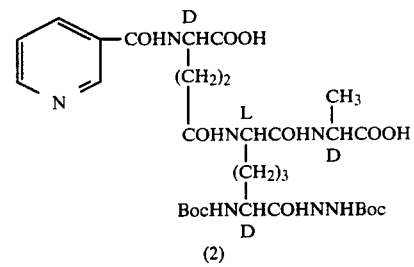

Nicotinoyl—γ—D—Glu(α—OH)—(L)—Boc—(D-)—mesoDAP—(D)—NHNHBoc—(L)—D—AlaOH (2) was prepared in substantially the same manner as step 1 of Example 100 from compound (1).

NMR (D₂O), δ(ppm): 1.43 (18H, s), 1.35-2.66 (13H, m), 3.87 (1H, t, J=7 Hz), 4.00-4.66 (3H, m), 7.90 (1H, m), 8.50-9.20 (3H, m).

(2) Step 2

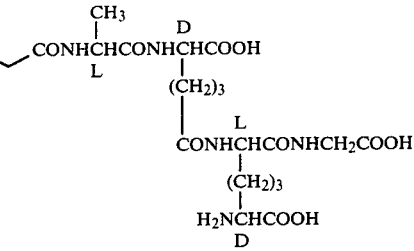

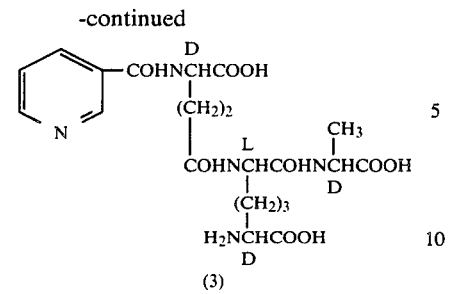

(3)

Nicotinoyl—γ—D—Glu(α—OH)—(L-)—mesoDAP—(L)—D—AlaOH (3) was prepared in substantially the same manner as step 2 of Example 100 from compound (2).

NMR (NaOD-D₂O), δ(ppm): 1.33 (3H, d, J=8 Hz), 1.20–2.50 (10H, m), 3.20 (1H, t, J=6 Hz), 4.04–4.60 (3H, m), 7.64 (1H, dd, J=4 and 8 Hz), 8.33 (1H, dd, J=2 and 8 Hz), 8.72 (1H, dd, J=2 and 4 Hz), 8.94 (1H, dd, J=J=1.5 and 2 Hz).

EXAMPLE 110

(1) Step 1

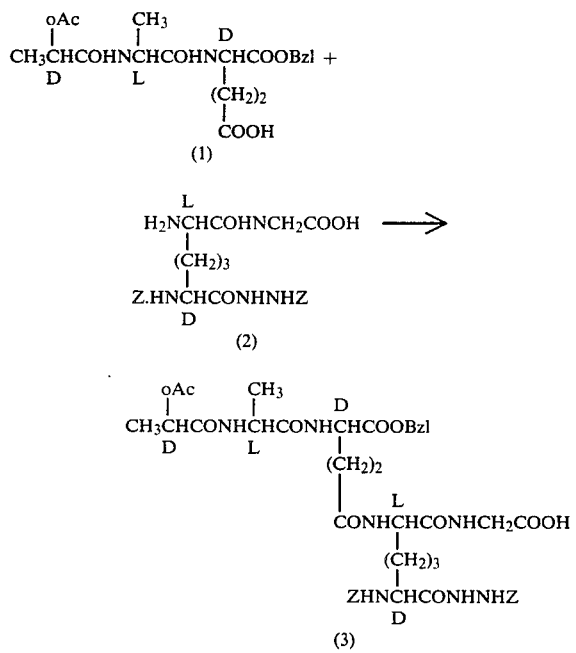

D—Lac(oAc)—L—Ala—γ—D—Glu(α—oBz-l)—(L)—Z—(D)—mesoDAP—(D)—NHNHZ—(L-)—GlyOH (3) was prepared in substantially the same manner as step 1 of Example 96 from compounds (1) and (2).

NMR (CD₃OD), δ(ppm): 1.36 (3H, d, J=7 Hz), 1.44 (3H, d, J=7 Hz), 2.07 (3H, s), 1.3–2.4 (10H, m), 3.92 (2H, s), 4.1–4.6 (4H, m), 5.07 (2H, s), 5.13 (2H, s), 5.15 (2H, s), 7.32 (15H, s).

(2) Step 2

Compound (3) ⟶

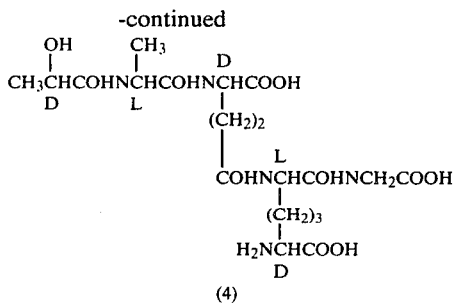

(4)

D—Lac(oAc)—L—Ala—γ—D—Glu(α—oBz-l)—(L)—Z—(D)—mesoDAP—(D)—NHNHZ—(L-)—GlyOH (3) (180 mg) was hydrogenated in acetic acid (25 ml) over 10% palladium black (150 mg) for 3.5 hours under two atmospheric pressure of hydrogen at ambient temperature. After completion of the reaction, the catalyst was filtered off and the filtrate was evaporated to dryness under reduced pressure and then the residue was dissolved in water (10 ml). To the solution was added 1N hydrochloric acid (0.4 ml) and a solution of sodium periodate (84 mg) in water (1 ml) was added to the solution. The mixture was stirred for 30 minutes under ice-cooling and then the excess reagent was decomposed with sodium bisulfite. The resulting solution was adjusted to pH 2 with 1N sodium hydroxide and concentrated to 5 ml under reduced pressure. The concentrate was passed through a column packed with activated carbon (5 ml). The column was washed with water (30 ml) and eluted with a mixture of methanol and water. The eluate was evaporated to dryness under reduced pressure. The residue was dissolved in 50% aqueous methanol (10 ml) and the solution was stirred for 2.5 hours at ambient temperature, maintaining the pH at 9.0 with 10% aqueous sodium carbonate. The solution was concentrated to about 5 ml. The concentrate was adjusted to pH 2.0 and passed through a column packed with non-ionic adsorption resin, HP 20 (20 ml) and eluted with water. The eluate was lyophilized to give D—Lac(OH—L—Ala—γ—D—Glu(α—OH-)—(L)—mesoDAP—(L)—GlyOH (4) (78 mg), which was identical with that of product prepared in Example 72-1.

EXAMPLE 111

(1) Step 1

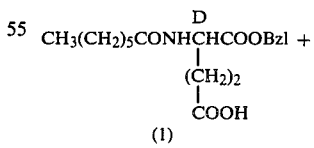

(1)

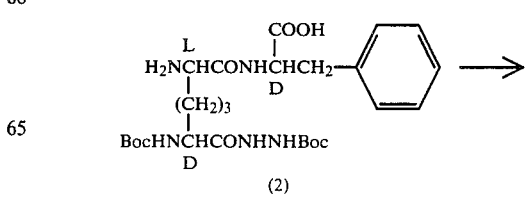

(2)

-continued

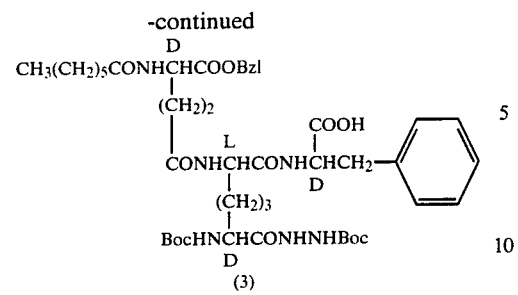
(3)

Heptanoyl—γ—D—Glu(α—oBzl)—(L)—Boc—(D-)—mesoDAP—(D)—NHNHBoc—(L)—D—PheOH (3) was prepared in substantially the same manner as step 1 of Example 96 from compounds (1) and (2).

NMR (DMSO-d$_6$), δ(ppm): 0.7-2.4 (41H, m), 2.8-3.2 (2H, s), 3.4-4.8 (4H, m), 5.15 (2H, s), 6.7 (1H, m), 7.26 (5H, s), 7.40 (5H, s), 7.8 (1H, m), 8.2 (2H, m), 8.7 (1H, m), 9.60 (1H, broad s).

(2) Step 2

Compound (3) ⟶

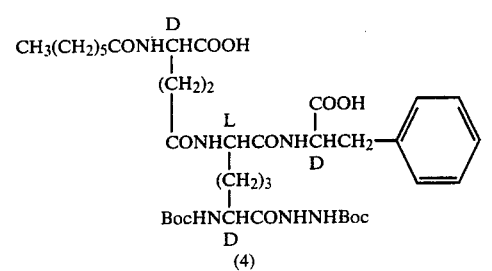
(4)

Heptanoyl—γ—D—Glu(α—OH)—(L)—Boc—(D-)—mesoDAP—(D)—NHNHBoc—(L)—D—PheOH (4) was prepared in substantially the same manner as step 2 of Example 96.

NMR (CD$_3$OD), δ(ppm): 0.91 (3H, m), 1.1-2.7 (20H, m), 1.46 (18H, s), 3.1 (2H, m), 3.8-4.6 (4H, m), 7.19 (5H, s).

(3) Step 3

Compound (4) ⟶

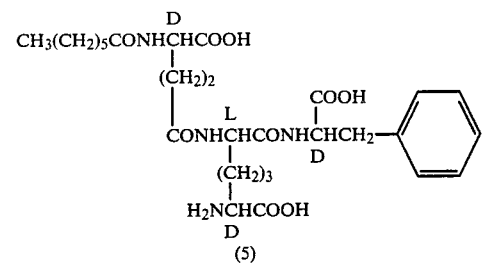
(5)

Heptanoyl—γ—D—Glu(α—OH)—(L-)—mesoDAP—(L)—D—PheOH (5) was prepared in substantially the same manner as step 3 of Example 96.

NMR (D$_2$O-NaOD), δ(ppm): 0.83 (3H, t, J=6 Hz), 1.0-2.1 (16H, m), 2.28 (4H, t, J=7.5 Hz), 3.10 (2H, AB part of ABX system, J=14, 8, 4 Hz), 3.15 (1H, t, J=7.5 Hz), 4.16 (2H, broad t, J=8 Hz), 4.50 (1H, dd, J=8, 4 Hz), 7.3 (5H, m).

EXAMPLE 112

(1) Step 1

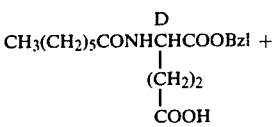
(1)

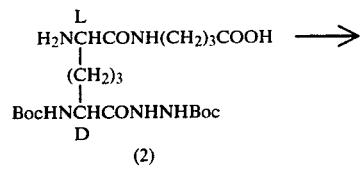
(2)

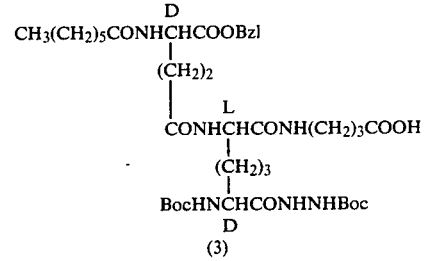
(3)

Heptanoyl—γ—D—Glu(α—oBzl)—(L)—Boc—(D-)—mesoDAP—(D)—NHNHBoc—(L)—γ—AbuOH (3) was prepared in substantially the same manner as step 1 of Example 96 from compounds (1) and (2).

NMR (DMSO-d$_6$), δ(ppm): 0.7-2.6 (27H, m), 1.40 (18H, s), 2.8-4.6 (5H, m), 5.11 (2H, s), 6.65 (1H, m), 7.34 (5H, s), 7.82 (2H, m), 8.16 (1H, d, J=7 Hz), 8.60 (1H, m), 9.52 (1H, broad s).

(2) Step 2

Compound (3) ⟶

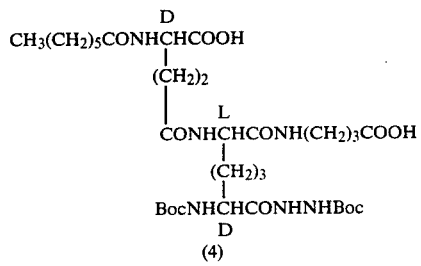
(4)

Heptanoyl—γ—D—Glu(α—OH)—(L)—Boc—(D-)—mesoDAP—(D)—NHNHBoc—(L)—γ—AbuOH (4) was prepared in substantially the same manner as step 2 of Example 96.

IR (Nujol): 1700 (broad), 1640 (broad), 1520 (broad) cm$^{-1}$.

NMR (CD$_3$OD), δ(ppm): 0.88 (3H, m), 1.1-2.6 (27H, m), 1.43 (18H, s), 3.8-4.6 (3H, m).

(3) Step 3

Compound (4) ⟶

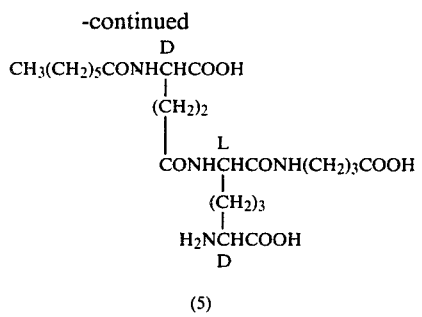

(5)

Heptanoyl—γ—D—Glu(α—OH)—(L-)—mesoDAP—(L)—γ—AbmOH (5) was prepared in substantially the same manner as step 3 of Example 96.

IR (Nujol): 1710, 1635 and 1540 cm$^{-1}$.

NMR (D$_2$O), δ(ppm): 0.85 (3H, brt, J=6 Hz), 1.0–2.8 (24H, m), 3.28 (2H, t, J=6, 5 Hz), 3.83 (1H, t, J=6 Hz), 4.1–4.5 (2H, m).

EXAMPLE 113

(1) Step 1

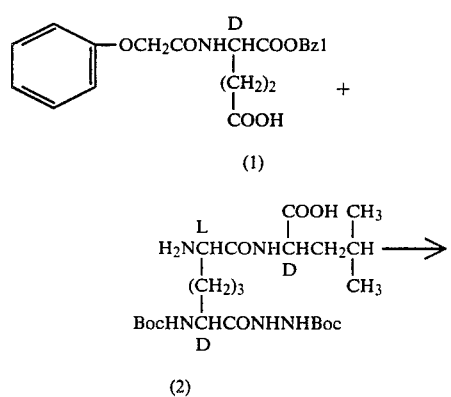

Phenoxyacetyl—γ—D—Glu(α—oBzl)—(L-)—Boc—(D)—mesoDAP—(D)—NHNHBoc—(L-)—D—LeuOH (3) was prepared in substantially the same manner as step 1 of Example 96 from compounds (1) and (2).

NMR (DMSO-d$_6$), δ(ppm): 0.7–2.4 (19H, m), 1.40 (18H, s), 3.6–4.7 (4H, m), 4.55 (2H, s), 5.15 (2H, s), 6.5–8.8 (10H, m), 7.34 (5H, s), 9.55 (1H, broad s).

(2) Step 2

Compound (3) ⟶

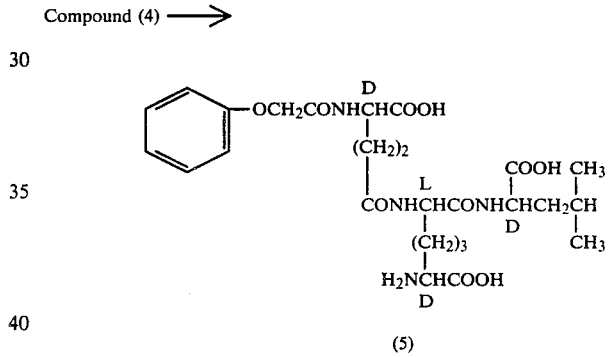

Phenoxyacetyl—γ—D—Glu(α—OH)—(L-)—Boc—(D)—mesoDAP—(D)—NHNHBoc—(L-)—D—LeuOH (4) was prepared in substantially the same manner as step 2 of Example 96.

NMR (CD$_3$OD), δ(ppm): 0.90 (6H, broad d, J-5 Hz), 1.3–2.7 (13H, m), 1.43 (18H, s), 3.8–5.0 (4H, m), 4.60 (2H, s), 6.8–7.6 (5H, m).

(3) Step 3

Compound (4) ⟶

(5)

Phenoxyacetyl—γ—D—Glu(α—OH)—(L-)—mesoDAP—(L)—D—LeuOH (5) was prepared in substantially the same manner as step 3 of Example 96.

NMR (CD$_3$OD), δ(ppm): 0.88 (6H, m), 1.2–2.7 (13H, m), 3.73 (1H, brs), 4.2–4.7 (3H, m), 4.55 (2H, s), 6.8–7.5 (5H, m).

EXAMPLE 114

(1) Step 1

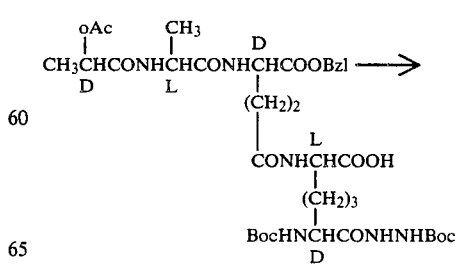

(1)

-continued

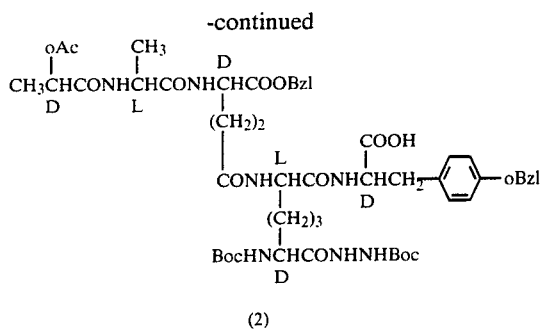

(2)

A suspension of D—TyrOH(oBzl)(596 mg) in a mixture of bis(trimethylsilyl)acetamide (2 ml), dimethylformamide (2 ml) and methylene chloride (2 ml) was stirred at ambient temperature for two hours. The resulting solution was added to a solution of the mixed anhydride of D—Lac(oAc)—L—Ala—γ—D—Glu(α'oBzl)—(L)—Boc—(D)—mesoDAP—(D)—NHNHBoc (1) (1.64 g) in a mixture of methylene chloride (10 ml) and ethyl acetate (5 ml). The reaction mixture was stirred at −15° C. for an hour and kept overnight in a refrigerator. The resulting solution was concentrated, taken up into ethyl acetate (50 ml) and washed in turn with dil. hydrochloric acid, water (X2) and brine. The resulting solution was dried over magnesium sulfate and the solvent was distilled off to give an amorphous solid (2.11 g). The solid was triturated with ether and supernatant was discarded to give D—Lac-(oAc)—L—Ala—γ—D—Glu(α—oBzl)—(L-)—Boc—(D)—mesoDAP—(D)—NHNHBoc—(L-)—D—TyrOH (oBzl)(2)(1.74 g).

(2) Step 2

Compound (2) ⟶

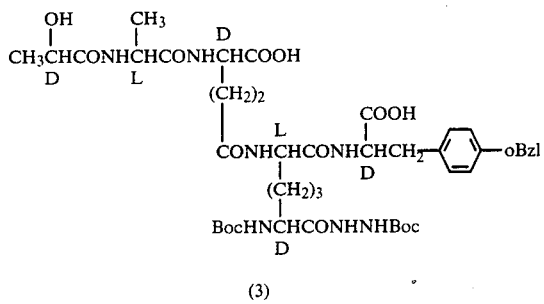

(3)

1N Sodium hydroxide (18 ml) was added to a solution of D—Lac(oAc)—L—Ala—γ—D—Glu(α—oBzl)—(L)—Boc—(D)—mesoDAP—(D)—NHNHBoc—(L)—D—TyrOH (oBzl)(2)(1.74 g) in a mixture of methanol (15 ml) and water (7 ml) and the solution was stirred at 5° C. for 30 minutes and at ambient temperature for 1.5 hours. The reaction mixture was neutralized to pH 7 with 1N hydrochloric acid and concentrated in vacuo. The concentrate was diluted with water, acidified to pH 7 with 1N hydrochloric acid and then extracted with ethyl acetate. The extract was washed with water and brine, dried over magnesium sulfate and evaporated to give D—Lac(OH)—L—Ala—γ—D—Glu(α—OH)—(L)—Boc—(D)—mesoDAP—(D)—NHNHBoc—(L)—D—TyrOH (oBzl)(3).

(3) Step 3

Compound (3) ⟶

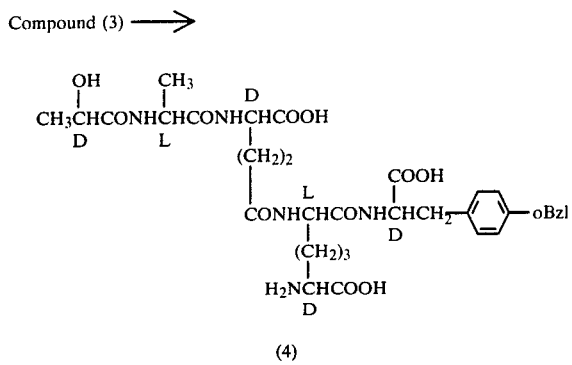

(4)

D—Lac(OH)—L—Ala—γ—D—Glu(α—OH)—(L-)—mesoDAP—(L)—D—TyrOH(oBzl)(4) was prepared in substantially the same manner as step 3 of Example 96.

(4) Step 4

Compound (4) ⟶

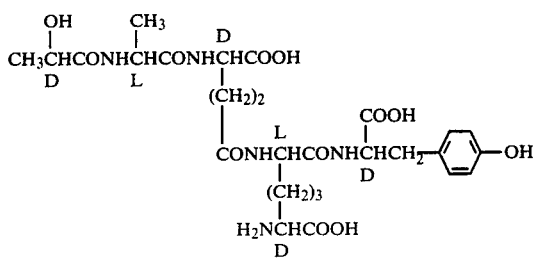

(5)

A solution of D—Lac(OH)—L—Ala—γ—D—(-Glu(α—OH)—(L)—mesoDAP—(L)—D—TyrOH-(oBzl)(4)(258 mg) in a mixture of 0.25N hydrochloric acid (2 ml) and methanol (8 ml) was hydrogenated over 10% palladium black (120 mg) for 21.5 hours. The reaction mixture was filtered and the filtrate was evaporated to dryness. The residue was dissolved in metanol (5 ml) and the solution was treated with 1N sodium hydroxide (1.5 ml) at 5° C. The resulting solution was neutralized to pH 7, concentrated, adjusted to pH 2 and passed through a column packed with HP 20 (16 ml). Elution was carried out with aqueous methanol and then menanol. Fractions containing the object compound were collected, evaporated, dissolved in water and then lyophillized to give D—Lac(OH)—L—Ala—γ—D—Glu(α—OH)—(L)—mesoDAP—(L)—D—TyrOH (5)(100 mg).

NMR ($D_2O$), δ(ppm): 1.0–2.5 (10H, m), 1.38 (3H, d, J=7 Hz), 1.41 (3H, d, J=7 Hz), 2.6–3.4 (2H, m), 3.74 (1H, t, J=6 Hz), 4.0–4.6 (5H, m), 6.82 (2H, d, J=9 Hz), 7.10 (2H, d, J=9 Hz).

EXAMPLE 115

(1) Step 1

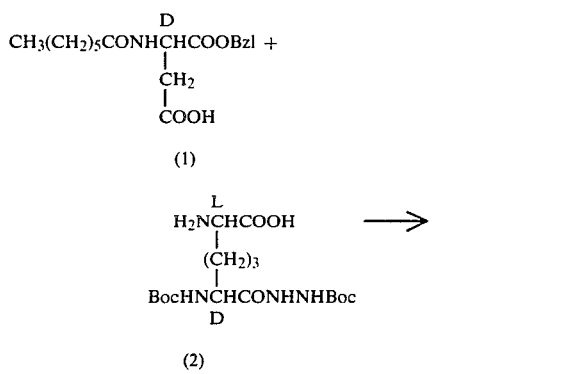

Heptanoyl—β—D—Asp(α—oBzl)—(L)—Boc—(D-)—mesoDAP—(D)—NHNHBoc (3) was prepared in substantially the same manner as step 1 of Example 96 from compounds (10) and (2).

NMR (CDCl₃), δ(ppm): 0.7-1.0 (3H, m), 1.0-2.0 (32H, m), 2.0-2.5 (2H, m), 2.8-3.1 (2H, m), 4.1-4.9 (2H, m), 4.9-5.1 (1H, m), 5.27 (2H, s), 5.5-6.0 (1H, m), 7.0-7.3 (2H, m), 7.50 (5H, s), 8.9-9.2 (1H, m), 9.2-9.6 (1H, m).

(2) Step 2

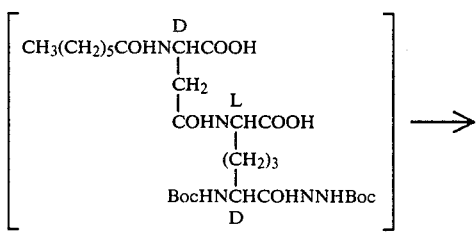

Heptanoyl—β—D—Asp(α—OH)—(L)—mesoDAP (4) was prepared in substantially the same manner as steps 1 and 2 of Example 96 from compound (3).

NMR (D₂O), δ(ppm): 0.84 (3H, t, J=6 Hz), 1.2-2.0 (14H, m), 2.2-2.4 (2H, m), 2.5-3.0 (2H, m), 3.75 (1H, t, J=6 Hz), 4.0-4.3 (2H, m).

EXAMPLE 116

(1) Step 1

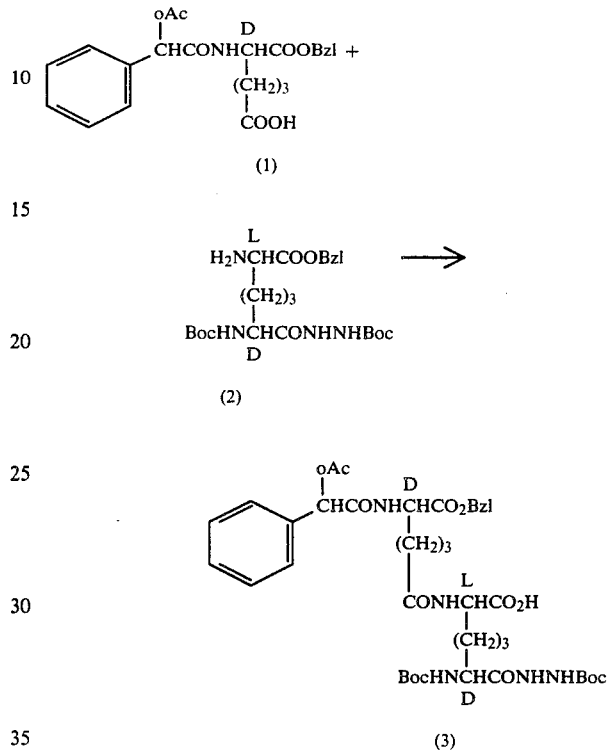

Mandelyl(oAc)—δ—D—Aad(α—oBzl)—(L-)—Boc—(D)—mesoDAP—(D)—NHNHBoc (3) was prepared in substantially the same manner as step 1 of Example 96 from compounds (1) and (2).

NMR (CDCl₃), δ(ppm): 1.4 (18H, s), 1.2-2.0 (10H, m), 2.16 (3H, s), 2.0-2.4 (2H, m), 4.0-4.2 (1H, m), 4.3-4.7 (2H, m), 5.08 (2H, s), 5.3-5.6 (1H, m), 6.08 (1H, s), 6.7-7.1 (3H, m), 7.30 (10H, s), 8.8-9.0 (1H, m).

(2) Step 2

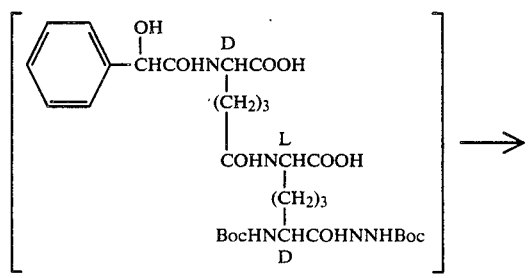

-continued

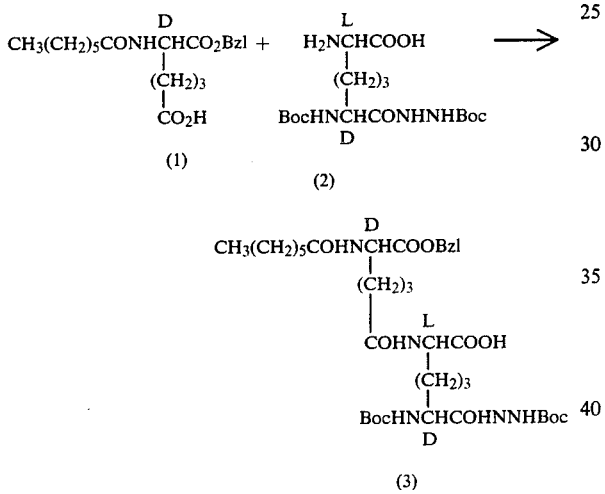

(4)

Mandelyl—δ—D—Aad(α—OH)—(L)—mesoDAP (4) was prepared in substantially the same manner as steps 2 and 3 of Example 96 from compound (3).

NMR (D₂O), δ(ppm): 1.2–2.0 (10H, m), 2.1–2.4 (3H, m), 3.6–3.9 (1H, m), 4.2–4.5 (2H, m), 5.17 (1H, s), 7.42 (5H, s).

EXAMPLE 117

(1) Step 1

CH₃(CH₂)₅CONHCHCO₂Bzl + H₂NCHCOOH
       |                    |
       (CH₂)₃               (CH₂)₃
       |                    |
       CO₂H                 BocHNCHCONHNHBoc
       D                    D (1)                         (2)

⟶

CH₃(CH₂)₅COHNCHCOOBzl
         |
    D    (CH₂)₃
         |
         L
         COHNCHCOOH
         |
         (CH₂)₃
         |
         BocHNCHCOHNNHBoc
         D (3)

Heptanoyl—δ—D—Aad(α—oBzl)—(L)—Boc—(D-)—mesoDAP—(D)—NHNHBoc (3) was prepared in substantially the same manner as step 1 of Example 96 from compounds (1) and (2).

(2) Step 2

Compound (3) ⟶ CH₃(CH₂)₅CONHCHCO₂H
                           |
                      D    (CH₂)₃
                           |
                           L
                           CONHCHCO₂H
                           |
                           (CH₂)₃
                           |
                           BocHNCHCONHNHBoc
                           D (4)

Heptanoyl—δ—D—Aad(α—OH)—(L)—Boc—(D-)—mesoDAP—(D)—NHNHBoc (3) was prepared in substantially the same manner as step 2 of Example 96.

NMR (CD₃OD): 0.7–1.1 (3H, m), 1.1–2.1 (36H, m), 2.1–2.6 (4H, m), 3.9–4.6 (3H, m).

IR (Nujol): 3270, 1700, 1640, 1520, 1160 cm⁻¹.

(3) Step 3

Compound (4) ⟶ CH₃(CH₂)₅CONHCHCO₂H
                           |
                      D    (CH₂)₃
                           |
                           L
                           CONHCHCO₂H
                           |
                           (CH₂)₃
                           |
                           H₂NCHCO₂H
                           D (5)

Heptanoyl—δ—D—Aad(α—OH)—(L)—mesoDAP (5) was prepared in substantially the same manner as step 3 of Example 96.

NMR (D₂O), δ(ppm): 0.7–1.0 (3H, m), 1.1–2.1 (18H, m), 2.1–2.5 (4H, m), 3.76 (1H, t, J=6 Hz), 4.2–4.4 (2H, m).

IR (Nujol): 3260, 1715, 1625, 1540 cm⁻¹.

EXAMPLE 118

(1) Step 1 oAc
          |
CH₃(CH₂)₁₆CHCHCOCl +
          |
          (CH₂)₁₅CH₃

(1)

CH₃
       |    D
H₂NCHCONHCHCOOH
  L    |
       (CH₂)₂              CH₃
       |         L         |
       CONHCHCONHCHCOOH
       |
       (CH₂)₃
       |
       Boc.HNCHCOOH
       D (2)

⟶ oAc        CH₃         D
         |          |
CH₃(CH₂)₁₆CHCHCONHCHCONHCHCOOH
         |          L           |
         (CH₂)₁₅CH₃              (CH₂)₂          CH₃
                                 |       L      |
                                 CONHCHCONHCHCOOH
                                 |
                                 (CH₂)₃
                                 |
                                 Boc.HNCHCOOH
                                 D (3)

To a solution of L—Ala—γ—D—Glu(α—OH)—(L-)—Boc—(D)—mesoDAP—(L)—D—AlaOH (2) (561 mg) in the mixture of methylene chloride (20 ml) and bis(trimethylsilyl)acetamide (3.25 g) was added a solution of 2-hexadesyl-3-acetoxyeicosanoyl chloride (1)(630 mg) in methylene chloride (5 ml).

The reaction mixture was left for 5 days at ambient temperature and concentrated to give an oily residue to which water (20 ml) and ether (50 ml) were added.

The organic layer was separated, dried over magnesium sulfate and concentrated in vacuo. The residual paste was column chromatographed on silicic acid and eluted with a mixture of chloroform and methanol (2:1) to give a 2—hexadesyl—3—acetoxyeicosanoyl—L—Ala—γ—D—Glu(α—OH)—(L-)—Boc—(D)—mesoDAP—(L)—D—AlaOH (3) (283 mg).

NMR (CDCl₃+CD₃OD), δ(ppm): 0.85 (6H, m), 1.94 (3H, s), 3.65-4.55 (m), 5.02 (1H, m), 6.34 (1H, m), 6.98 (1H, m).

(2) Step 2

Compound (3) ⟶

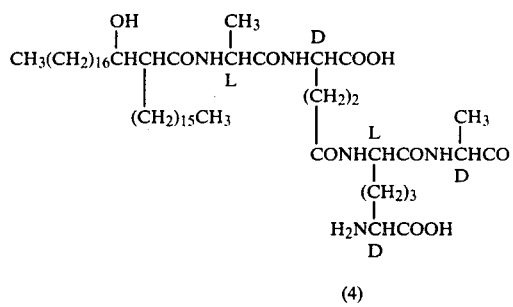

(4)

2—Hexadesyl—3—acetoxyeicosanoyl—L—Ala—γ—D—Glu(α—OH)—(L-)—Boc—(D)—mesoDAP—(L)—D—Ala—OH(3) (200 mg) was dissolved in trifluoroacetic acid (2 ml) and the mixture was left for 30 minutes at ambient temperature. The reaction mixture was concentrated and the residual oil was dissolved in n-butanol (15 ml) and then 1N sodium hydroxide (1 ml) was added thereto. After standing for 2 hours at ambient temperature, water (10 ml) and n-butanol (20 ml) were added to the reaction mixture. The n-butanol layer was separated and concentrated in vacuo to give 2—hexadesyl—3—hydroxyeicosanoyl—L—Ala—γ—D—Glu (α—OH)—(L-)—mesoDAP—(L)—D—AlaOH (4) (150 mg.).

NMR (CD₃OD), δ(ppm): 0.89 (6H, m), 3.65 (1H, m), 4.00 (1H, m), 4.25-4.60 (4H, m).

EXAMPLE 119

(1) Step 1

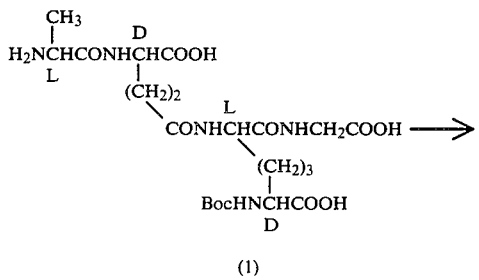

(1)

-continued

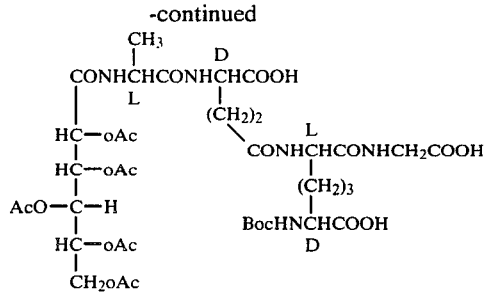

(2)

(Pentaacetyl—D—Gluco.nyl—L—Ala—γ—D—Glu(α—OH)—(L)—Boc—(D)—mesoDAP—(L)—GlyOH (2) was prepared in substantially the same manner as step 1 of Example 1.

IR (Nujol): 3350-3300, 1730-1710, 1700-1690 1650 cm⁻¹.

(2) Step 2

Compound (2) ⟶

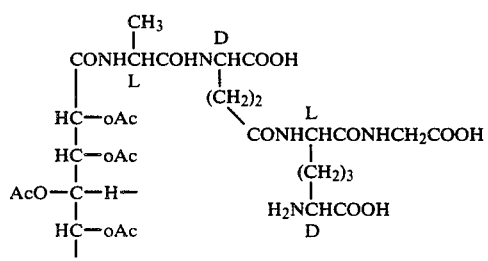

(3)

(Pentaacetyl—D—Gluconyl—L—Ala—γ—D—Glu(α—OH)—(L)—mesoDAP—(L)—GlyOH (3) was prepared in substantially the same manner as step 2 of Example 17.

N.M.R. (CD₃OD), δ(ppm): 1.37 (3H, d, J=7 Hz), 1.50-2.34 (10H, m), 2.00 (9H, s), 2.10 (3H, s), 2.17 (3H, s), 3.92 (2H, s), 3.95-4.50 (6H, m), 5.10-5.75 (4H, m).

(3) Step 3

Compound (3) ⟶

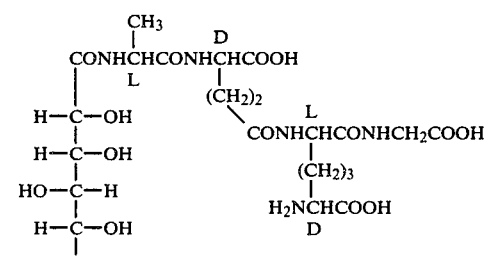

(4)

D—Gluconyl—L—Ala—γ—Glu(α—OH)—(L-)—mesoDAP—(L)—GlyOH (4) was prepared in substantially the same manner as step 2 of Example 19.

N.M.R. (D₂O), δ(ppm): 1.44 (3H, d, J=7 Hz), 1.34–2.50 (10H, m), 3.75 (2H, s), 3.85 (2H, d, J=10 Hz), 3.84–4.67 (8H, m).

EXAMPLE 120

(1) Step 1

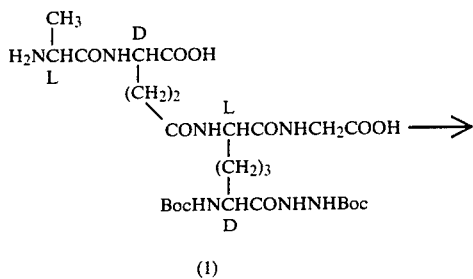

(1)

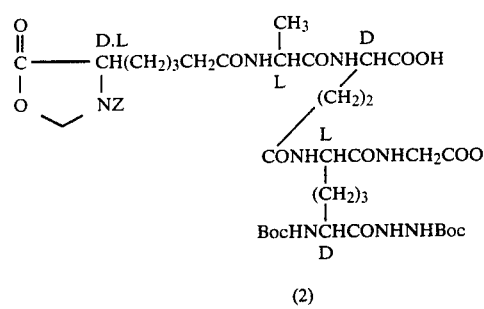

(2)

5—(N—Z—5—oxo—4—oxozolidinyl)-valeryl—L—Ala—γ—D—Glu—(α—OH)—(L-)—Boc—(D)—mesoDAP—(D)—NHNHBoc—(L)—GlyOH (2) was prepared in substantially the same manner as Step 1 of Example 1.

N.M.R. (CD₃OD), δ(ppm): 1.38 (3H, d, J=7 Hz), 1.50 (18H, s), 1.38–2.50 (18H, m), 4.00 (2H, s), 4.10–4.60 (5H, m), 4.27 (2H, s), 6.60 (2H, ABq, J=4 and 6 Hz), 7.43 (5H, s).

(2) Step 2

Compound (2) ⟶

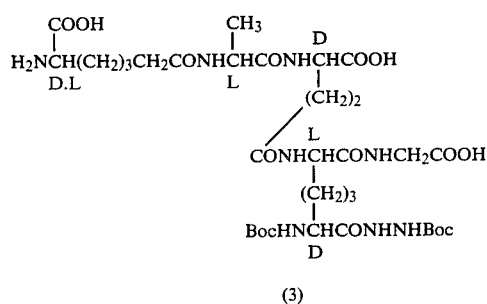

(3)

α—Aminopimelyl—L—Ala—γ—D—Glu(α—OH)—(L)—Boc—(D)—mesoDAP—(D)—NHNHBoc—(L)—GlyOH (3) was prepared in substantially the same number as step 2 of Example 11.

N.M.R. (CD₃OD), δ(ppm): 1.35 (3H, d, J=7 Hz), 1.42 (18H, s), 1.34–2.50 (18H, m), 3.92 (2H, s), 3.63–4.50 (5H, m).

(3) Step 3

Compound (3) ⟶

-continued

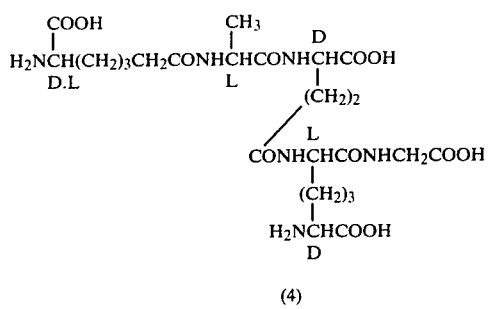

(4)

α—Aminopimelyl—L—Ala—γ—D—Glu(α—OH)—(L)—mesoDAP—(L)—GlyOH (4) was prepared in substantially the same manner as step 2 of Example 17.

N.M.R. (D₂O), δ(ppm): 1.38 (3H, d, J=7 Hz), 1.33–2.50 (18H, m), 3.73 (1H, t, J=7 Hz), 3.83 (1H, t, J=7 Hz), 3.97 (2H, s), 4.07–4.30 (3H, m).

PREPARATION 85

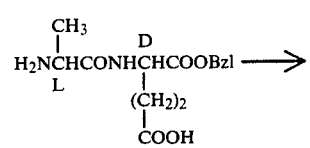

(1)

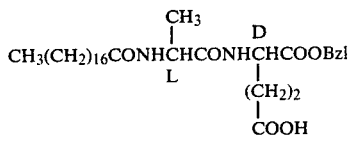

(2)

L—Ala—D—Glu(OH)OBzl (1) (942 mg) was suspended in methylene chloride (40 ml), and bis(trimethylsilyl)acetamide (1.20 g) was added to the suspension under stirring. The resulting solution was treated with stearoyl chloride (900 mg) at ambient temperature and left for an hour. Evaporation of the solvent gave an oily residue which was treated with water to give white solides. The solides were collected by filtration, washed with water and dried over magnesium sulfate to give stearoyl—L—Ala—D—Glu(OH)OBzl (2) (1.60 g).

IR(Nujol): 3300, 2700–2500 (broad), 1720, 1710, 1660 (sh), 1640 cm⁻¹.

NMR(Pyridine-d₅): δ0.90 (3H, m), 1.0–3.0 (36H, m), 1.55 (3H, d, J=7 Hz), 4.90–5.40 (2H, m), 5.23 (2H, s).

PREPARATION 86

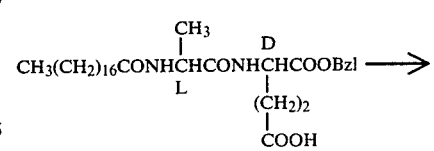

(1)

-continued $$\text{CH}_3(\text{CH}_2)_{16}\text{CONH}\overset{\text{L}}{\underset{|}{\text{CH}}}\text{CONH}\overset{\text{CH}_3}{\underset{|}{\text{CH}}}\text{CONH}\overset{\text{D}}{\underset{\underset{\underset{\text{COOSu}}{|}}{\underset{(\text{CH}_2)_2}{|}}}{\text{CH}}}\text{COOBzl}$$

(2)

Stearoyl—L—Ala—D—Glu(OH)OBzl (1) (1.41 g) and N-hydroxysuccimide (280 mg) were dissolved in tetrahydrofuran (50 ml). To the solution was added N,N'-dicyclohexylcarbodiimide (500 mg) under ice-cooling and the resulting solution was left in a refrigerator overnight. The precipitates separated were filtered and the filtrate was evaporated to give a white solid, which was recrystallized from a mixture of isopropylalcohol and isopropyl ether to give stearoyl—L—Ala—D—Glu(α—OBzl)OSu (2) (1.45 g).

IR(Nujol): 3300, 1805, 1780, 1740, 1660 (sh), 1640 cm$^{-1}$.

NMR(CDCl$_3$): δ0.87 (3H, m), 1.0–2.90 (39H, m), 2.80 (4H, s), 4.20–4.80 (2H, m), 5.17 (2H, s), 6.20 (1H, d, 7 Hz), 7.37 (5H, s).

PREPARATION 87

2—Hexadecyloctadecanoyl—L—Ala—D—Glu(OH)OBzl was prepared in substantially the same manner as that of Preparation 85.

IR(Nujol): 3300 (sh), 3280, 1740 (broad), 1640 (sh), 1625 cm$^{-1}$.

NMR(CDCl$_3$): δ0.83–2.67 (73H, m), 4.33–5.00 (2H, m), 5.15 (2H, s), 6.42 (2H, d, J=8 Hz), 7.16 (5H, s).

PREPARATION 88

2—Hexadecyloctadecanoyl—L—Ala—D—Glu(α—OBzl) (γ—OSu) was prepared in substantially the same manner as that of Preparation 86.

IR(Nujol): 3300, 1810, 1780, 1740, 1650 (sh), 1635 cm$^{-1}$.

NMR(CDCl$_3$): δ0.67–2.83 (73H, m), 2.80 (4H, s), 4.40–4.86 (2H, m), 5.16 (2H, s), 6.60 (2H, d, J=7 Hz), 7.16 (5H, s).

PREPARATION 89

Stearoyl—D—Glu(OH)OBzl was prepared in substantially the same manner as that of Preparation 85.

IR(Nujol): 3300, 1750, 1710, 1650 cm$^{-1}$.

NMR(CDCl$_3$): δ0.87 (3H, m), 1.0–2.70 (34H, m), 4.50–5.00 (1H, m), 5.17 (2H, s), 6.33 (1H, d, J=8 Hz), 7.33 (5H, s), 10.30 (1H, s).

PREPARATION 90

Stearoyl—D—Glu(α—OBzl)OSu was prepared in substantially the same manner as that of Preparation 86.

IR(Nujol): 3300, 1810, 1780, 1740, 1650 cm$^{-1}$.

NMR(CDCl$_3$): δ0.87 (3H, m), 1.0–2.80 (36H, m), 2.76 (4H, s), 4.50–5.00 (1H, m), 5.16 (2H, s), 6.32 (1H, d, J=8 Hz), 7.33 (5H, s).

PREPARATION 91

2—Hexadecyloctadecanoyl—D—Glu(OH)OBzl was prepared in substantially the same manner as that of Preparation 85.

IR(Nujol): 3280, 1740, 1710, 1640 cm$^{-1}$.

NMR(CDCl$_3$): δ0.83–2.63 (70H, m), 4.33–5.00 (1H, m), 5.15 (2H, s), 6.20 (1H, d, J=7 Hz), 7.30 (5H, s).

PREPARATION 92

2—Hexadecyloctadecanoyl—D—Glu(α—OBzl)OSu was prepared in substantially the same manner as that of Preparation 86.

IR(Nujol): 3300, 1810, 1780, 1745, 1640 cm$^{-1}$.

NMR(CDCl$_3$): δ0.83–2.83 (71H, m), 2.80 (4H, s), 4.50–5.00 (1H, m), 6.20 (1H, d, J-7 Hz), 7.35 (5H, s).

PREPARATION 93

2—Docosyltetracosanoyl—L—Ala—D—Glu(OH)OBzol was prepared in substantially the same manner as that of Preparation 85.

IR(Nujol): 3270, 1740, 1640 (sh), 1625 cm$^{-1}$.

NMR(CDCl$_3$): δ0.67–2.50 (98H, m), 4.40–4.80 (2H, m), 5.10 (2H, s), 6.16–6.40 (2H, m), 7.28 (5H, s).

PREPARATION 94

2—Docosyltetracosanoyl—L—Ala—D—Glu(α—OBzl)OSu was prepared in substantially the same manner as that of Preparation 86.

IR(Nujol): 3300, 1815, 1780, 1750, 1650 (sh), 1640 cm$^{-1}$.

NMR(CDCl$_3$): δ0.67–3.00 (98H, m), 2.76 (4H, s), 4.40–4.83 (2H, m), 5.13 (2H, s), 6.13 (2H, d, J=7 Hz), 7.30 (5H, s).

PREPARATION 95

2—Docosyltetracosanoyl—D—Glu(OH)OBzl was prepared in substantially the same manner as Preparation 85.

IR(Nujol): 3250, 2600 (broad sh), 1740, 1710, 1645 cm$^{-1}$.

NMR(CDCl$_3$): 0.67–2.83 (95H, m), 4.50–5.00 (1H, m), 5.20 (2H, s), 6.20 (1H, d, J=7 Hz), 7.36 (5H, s).

PREPARATION 96

2—Docosyltetracosanoyl—D—Glu(α—OBzl)OSu was prepared in substantially the same manner as that of Preparation 86.

IR(Nujol): 3300, 1810, 1780, 1740, 1640 cm$^{-1}$.

NMR(CDCl$_3$): δ0.68–2.87 (96H, m), 2.87 (4H, s), 4.50–5.00 (1H, m), 5.20 (2H, s), 6.25 (1H, d, J=7 Hz), 7.36 (5H, s).

PREPARATION 97

$$\underset{(1)}{\text{BocHN}\overset{\text{L}}{\underset{\underset{\underset{\text{D}}{|}}{\underset{\text{ZHNCHCONHNHBoc}}{|}}}{\text{CH}}}\text{COOH}} \quad \longrightarrow \quad \underset{(2)}{\text{BocHN}\overset{\text{L}}{\underset{\underset{\underset{\text{D}}{|}}{\underset{\text{ZHNCHCONHNHBoc}}{|}}}{\text{CH}}}\text{CONH}\overset{\text{CH}_3}{\underset{|}{\text{CH}}}\text{COOEt}}$$

To a solution of Boc—(L)—Z—(D-)—mesoDAP—(D)—NHNHBoc (1) (2.16 g) and N-methylmorpholine (404 mg) in methylene chloride (40 ml) was added isobutylchloroformate (546 mg) at −10°∼−15° C. The mixture was stirred for 30 minutes at ambient temperature. A solution of D-AlaOEt, prepared from D—AlaOEt hydrochloric acid salt (614 mg) and N-methylmorphorin (404 mg) by stirring 10 minutes in methylene chloride at ambient temperature, was added to the mixture. The resulting mixture was stirred for 1.5 hours at −10°∼−15° C. Methylene chloride was evaporated in vacuo and the residue was dissolved in a mixture of ethyl acetate (100 ml) and 2.5% hydrochloric acid (50 ml). The organic layer was separated and washed with water (50 ml) and 2% sodium bicarbonate (50 ml), dried over magnesium sulfate and then the solvent was evaporated in vacuo. The residue was crystallized from ether (30 ml) to give Boc—(L-)—Z—(D)—mesoDAP—(L)—D—AlaOEt—(D-)—NHNHBoc (2) (2.2 g).

IR(Nujol): 3300, 3230, 1720, 1705, 1675, 1645, 1630 cm$^{-1}$.

NMR(CD$_3$OD), δ: 1.45 (18H, s), 1.2–2.20 (12H, m), 4.0–4.6 (5H, m), 5.13 (2H, s), 7.37 (10H, s).

PREPARATION 98

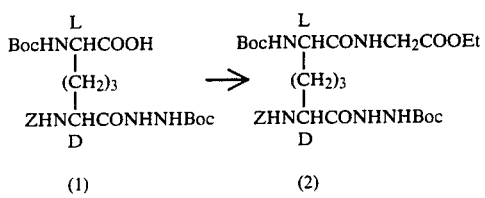

(1) → (2)

Boc—(L)—Z—(D)—mesoDAP—(L)—GlyO-Et—(D)—NHNHBoc (2) was prepared in substantially the same manner as that of Preparation 97.

IR(Nujol): 3270, 1670 (broad), 1240, 1160, 1040, 1020, 860 cm$^{-1}$.

NMR(CD$_3$OD), δ: 1.28 (3H, t, J=7 Hz), 1.48 (18H, s), 1.4–2.0 (6H, m), 3.98 (2H, s), 4.20 (2H, q, J=7 Hz), 3.9–4.2 (1H, m), 5.10 (2H, s), 7.35 (5H, s).

PREPARATION 99

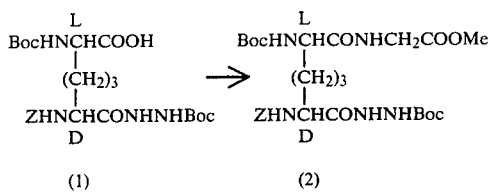

(1) → (2)

Boc—(L)—Z—(D)—mesoDAP—(L)—GlyOMe—(D)—NHNHBoc (2) was prepared in substantially the same manner as that of Preparation 97.

IR(Nujol): 3300, 3230, 1730, 1710, 1680, 1650, 1630 cm$^{-1}$.

NMR(CD$_3$OD), δ: 1.47 (18H, s), 1.4–2.0 (6H, s), 3.68 (3H, s), 3.94 (2H, s), 3.9–4.3 (2H, m), 5.04 (2H, s), 7.30 (5H, s).

PREPARATION 100

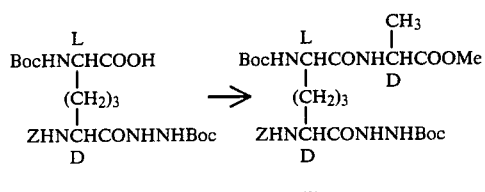

(1) → (2)

Boc—(L)—Z—(D)—mesoDAP—(L-)—D—AlaOMe—(D)—NHNHBoc (2) was prepared in substantially the same manner as that of Preparation 97.

IR(Nujol): 3300, 3230, 1725, 1705, 1680, 1645, 1630 cm$^{-1}$.

NMR(CD$_3$OD), δ: 1.33 (3H, d, J=7 Hz), 1.48 (18H, s), 1.4–2.1 (6H, m), 3.67 (3H, s), 3.8–4.3 (2H, m), 4.35 (1H, q, J=7 Hz), 5.02 (2H, s), 7.30 (5H, s).

PREPARATION 101

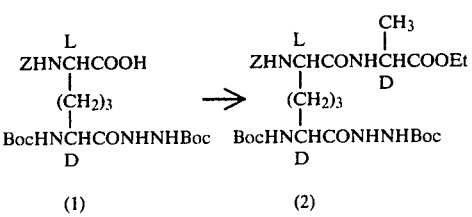

(1) → (2)

Z—(L)—Boc—(D)—mesoDAP—(L)—D—AlaO-Et—(D)—NHNHBoc (2) was prepared in substantially the same manner as that of Preparation 97.

IR(Nujol): 3300, 3220 (schoulder), 1735, 1710, 1680, 1645, 1630 cm$^{-1}$.

NMR(CD$_3$OD), δ: 1.23 (3H, t, J=7 Hz), 1.37 (2H, d, J=7 Hz), 1.40 (9H, s), 1.4–2.0 (6H, m), 3.9–4.6 (5H, m), 5.10 (2H, s), 7.33 (5H, s).

PREPARATION 102

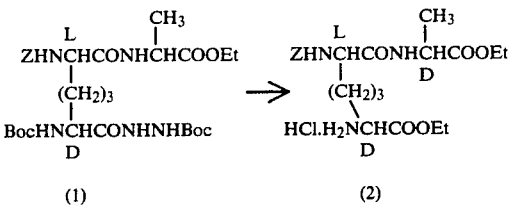

(1) → (2)

Z—(L)—Boc—(D)—mesoDAP—(L)—D—AlaO-Et—(D)—NHNHBoc (1) (0.5 g) was added to trifluoroacetic acid (5 ml) and the mixture was stirred for 30 minutes at ambient temperature. After evaporation of trifluoroacetic acid, the residue was dissolved in ethanol (10 ml) and the solution was cooled to 0° C.

To the solution was added N-bromosuccinimide (420 mg) and the mixture was stirred for 10 minutes at 0° C. Ethanol was evaporated in vacuo and the residue was dissolved in water (10 ml). The solution was cooled to 0° C. and the excess reagent was decomposed with aqueous sodium bisufite. The mixture was neutralized to pH 8.0 with sodium bicarbonate and extracted with ethyl acetate (30 ml).

The extract was dried over magnesium sulfate and 2N hydrochloric acid in ethyl acetate (4 ml) was added to the extract. The solvent was evaporated in vacuo and the residue was crystallized from ether to give hydrochloric acid salt of Z—(L)—mesoDAP—(L-)—D—AlaOEt—(D)—OEt (2) (280 mg).

IR(Nujol): 3280, 1730, 1690, 1650 cm$^{-1}$.

NMR(CD$_3$OD), δ: 1.23 (3H, t, J=7 Hz), 1.30 (3H, t, J=7 Hz), 1.35 (3H, d, J=7 Hz), 1.5–2.1 (6H, m), 3.9–4.6 (7H, m), 5.10 (2H, s), 7.32 (5H, s).

PREPARATION 103

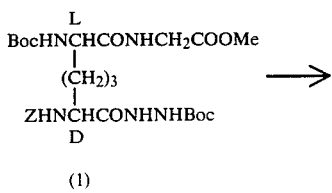

(1) →

-continued

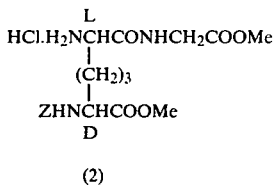

(2)

Z—(D)—mesoDAP—(L)—GlyOMe—(D)—OMe hydrochloric acid salt (2) was prepared in substantially the same manner as that of Preparation 102.

IR(CHCl$_3$): 1745, 1720, 1680 cm$^{-1}$.

PREPARATION 104

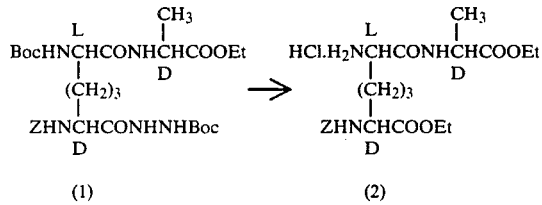

Z—(D)—mesoDAP—(L)—AlaOEt—(D)—OEt hydrochloric acid salt (2) was prepared in substantially the same manner as that of Preparation 102.

IR(Nujol): 3300, 1725, 1680, 1655 cm$^{-1}$.

NMR(CD$_3$OD), δ: 1.1–2.0 (15H, m), 3.9–4.5 (7H, m), 5.08 (2H, s), 7.32 (5H, s).

PREPARATION 105

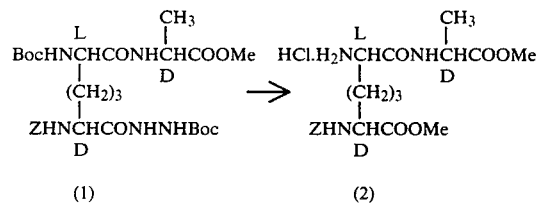

Z—(D)—mesoDAP—(L)—D—AlaOMe—(D-)—OMe hydrochloric acid salt (2) was prepared in substantially the same manner as that of Preparation 102.

NMR(CD$_3$CD), δ: 1.42 (3H, d, J=7 Hz), 1.4–2.0 (6H, m), 3.72 (6H, s), 3.95 (1H, t, J=6 Hz), 4.23 (1H, t, J=6 Hz), 4.47 (1H, q, J=7 Hz), 5.10 (1H, s), 7.38 (5H, s).

PREPARATION 106

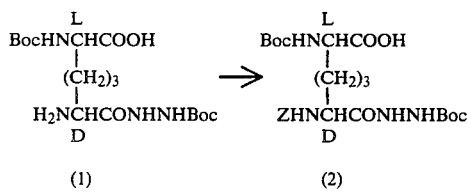

To a solution of bis(trimethylsilyl)acetamide (15 ml) and methylene chloride (60 ml) was added Boc—(L-)—mesoDAP—(D)—NHNHBoc (1) (6.08 g). The mixture was stirred for an hour at ambient temperature and cooled to 0° C. and carbobenzyloxy chloride (5.1 g) was added thereto. The resulting mixture was stirred for an hour at ambient temperature. After evaporation of methylene chloride, the residue was poured into a mixture of ethyl acetate (60 ml) and 2.5% hydrochloric acid (50 ml). The organic layer was separated and washed with aqueous sodium chloride, dried over magnesium sulfate and then evaporated. The residue was pulverized with isopropyl ether to give Boc—(L)—Z—(D-)—mesoDAP—(D)—NHNHBoc (2) (5.4 g).

NMR(CD$_3$OD), δ: 1.43 (18H, s), 1.42–2.0 (6H, m), 3.9–4.3 (2H, m), 5.08 (2H, s), 7.32 (5H, s).

IR(Nujol): 3270, 3100–2200, 1690, 1370, 1240, 1160, 1050, 1020 cm$^{-1}$.

PREPARATION 107

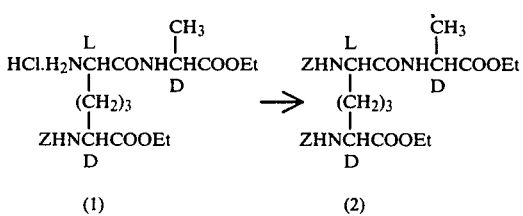

DiZ—mesoDAP—(L)—D—AlaOEt—(D)—OEt (2) was prepared in substantially the same manner as that of Preparation 106.

[α]$_D$= +16.3° (C=1, MeOH).

IR(Nujol): 3300, 1740 (schoulder), 1730, 1685, 1650 cm$^{-1}$.

NMR(CD$_3$OD), δ: 1.20 (6H, t, J=7 Hz), 1.37 (3H, d, J=7 Hz), 1.4–2.0 (6H, m), 4.0–4.5 (7H, m), 5.10 (4H, s), 7.33 (10H, s).

PREPARATION 108

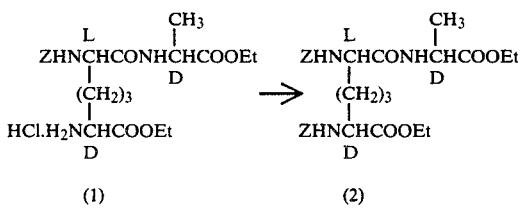

DiZ—mesoDAP—(L)—D—AlaOEt—(D)—OEt (21) was prepared in substantially the same manner as that of Preparation 106. This compound was identified with the product prepared in Preparation 107.

PREPARATION 109

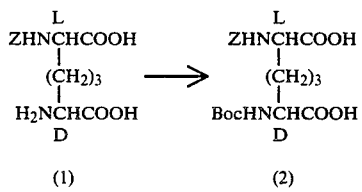

Z—(L)—Boc—(D)—mesoDAP (2) was prepared in substantially the same manner as that of Preparation 106.

IR(Nujol): 3300, 2600 (broad, sh), 1750–1650 (broad) cm$^{-1}$.

NMR(DMSO-d$_6$), δ: 1.20–2.0 (15H, m), 3.63–4.16 (2H, m), 5.06 (2H, s), 6.93 (1H, d, J=8 Hz), 7.33 (5H, s).

PREPARATION 110

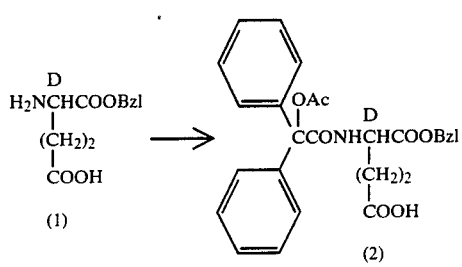

O—acetylbenziloyl—D—Glu(OH)OBzl (2) was prepared in substantially the same manner as that of Preparation 85.

NMR(CDCl$_3$), δ: 2.16 (3H, s), 1.9-2.5 (4H, m), 4.5-4.9 (1H, m), 5.16 (2H, s), 7.03 (1H, d, J=8 Hz), 7.1-7.7 (15H, m), 9.55 (1H, s).

IR(film): 1730, 1680, 1510, 1210, 1025, 750, 695 cm$^{-1}$.

PREPARATION 111

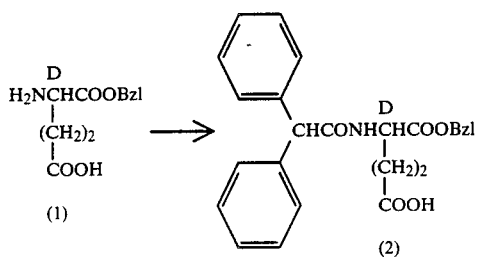

Diphenylacetyl—D—Glu(OH)OBzl (2) was prepared in substantially the same manner as that of Preparation 85.

NMR(CDCl$_3$), δ: 1.7-2.5 (4H, m), 4.5-4.9 (1H, m), 4.95 (1H, s), 5.10 (2H, s), 6.37 (1H, d, J=8 Hz), 7.23 (10H, s), 7.30 (5H, s), 9.40 (1H, s).

IR(CHCl$_3$): 3400, 1730, 1710, 1670, 1490 cm$^{-1}$.

PREPARATION 112

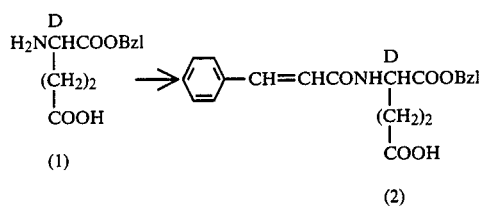

Cinnamoyl—D—Glu(OH)OBzl (2) was prepared in substantially the same manner as that of Preparation 85.

NMR(CDCl$_3$), δ: 1.9-2.7 (4H, m), 4.7-5.0 (1H, m), 5.17 (2H, s), 6.43 (1H, d, J=16 Hz), 6.74 (1H, d, J=8 Hz), 7.30 (10H, s), 7.63 (1H, d, J=16 Hz), 10.07 (1H, s).

IR(Nujol): 3300, 1735, 1690, 1650, 1620, 1525, 1280, 1205, 975, 750, 695 cm$^{-1}$.

PREPARATION 113

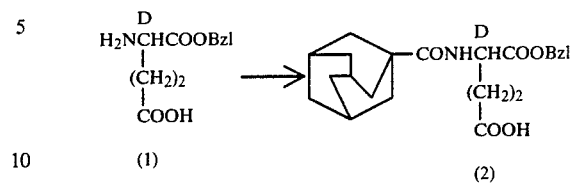

Adamantane—1—carbonyl—D—Glu(OH)OBzl (2) was prepared in substantially the same manner as that of Preparation 85.

NMR(CDCl$_3$), δ: 1.5-2.6 (19H, m), 4.5-4.9 (1H, m), 5.16 (2H, s), 6.52 (1H, d, J=8 Hz), 7.33 (5H, s), 9.80 (1H, s).

IR(film): 4300, 1730, 1710, 1630, 1520, 1210 cm$^{-1}$.

PREPARATION 114

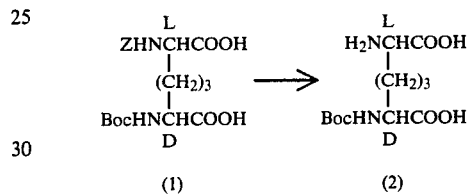

Z—(L)—Boc—(D)—mesoDAP (1) was dissolved in acetic acid (50 ml) and hydrogenated over palladium black (450 mg) at ambient temperature. The catalyst was removed by filtration and the filtrate was evaporated in vacuo to give a white solid. The solid was dissolved in water (100 ml) and chromatographed on a column of macroporous non-ionic adsorption resin, Hp 20 (200 ml). The column was eluted successively with water and 50% aqueous methanol. The latter fractions were combined and evaporated to give Boc—(D-)—mesoDAP (2) (3.80 g).

IR(Nujol): 3400, 2600 (broad), 1710, 1640, 1580 cm$^{-1}$.

NMR(D$_2$O): δ1.16-2.16 (15H, m), 3.60-4.20 (2H, m).

EXAMPLE 121

(1) Step 1

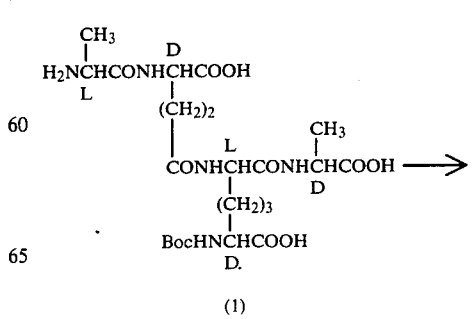

-continued

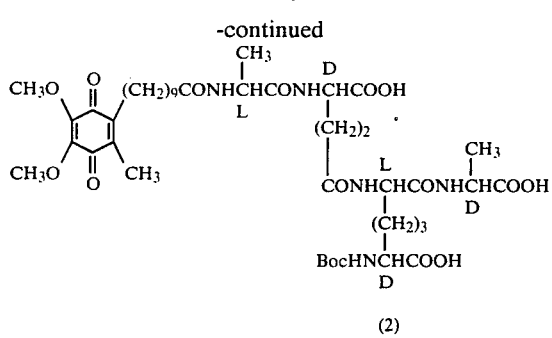

(2)

L—Ala—γ—D—Glu(α—OH)—(L)—Boc—(D-)—mesoDAP—(L)—D—AlaOH (1.64 g) (1) was dissolved in a mixture of dioxane (30 ml) and water (30 ml). To this solution, triethylamine (606 mg) was added. To the mixture was added 10-(2,3-dimethoxy-5-methyl-1,4-benzoquino-6-yl) decanoic acid N-hydroxy-succinimide ester (872 mg). The reaction mixture was kept at room temperature for 24 hours. The reaction mixture was concentrated and extracted with ethylacetate. The organic layer was washed successively with aqueous hydrochloric acid, water and brine, and dried over magnesium sulfate. Evaporation of the solvent gave a foam, which was pulvirized with ether to afford 10—(2-,3—dimethoxy—5—methyl—1,4—benzoquino—6—yl)decanoyl—L—Ala—γ—D—Glu(α—OH)—(L)—Boc—(D)—mesoDAP—(L-)—D—AlaOH (2) (0.97 g).

IR(Nujol): 3280, 1710, 1640, 1610 cm$^{-1}$.

NMR(CDCl$_3$), δ: 1.48 (9H, s), 2.00 (3H, s), 4.00 (6H, s), 3.66-4.66 (5H, m).

(2) Step 2

Compound (2) ⟶

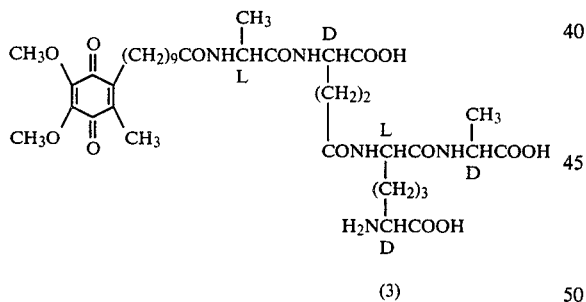

(3)

10—(2,3—dimethoxy—5—methyl—1,4—benzoquino—6—yl)decanoyl—L—Ala—γ—D—Glu(α—OH)—(L)—Boc—(D)—mesoDAP—(L-)—D—AlaOH (2) (0.945 g) was dissolved in trifluoroacetic acid (20 ml). The solution was kept for 1 hour at room temperature. The reaction mixture was concentrated in vacuo. The residue was dissolved in water. The pH of the aqueous solution was adjusted to 2-3, and the whole solution was subjected to Hp-20 column (100 ml). The column was eluted with a mixture of water and MeOH—H$_2$O (1:2). Evaporation of the latter fractions gave an orange foam, which was dissolved in water and lyophilized to give 10—(2,3—dimethoxy—5—methyl—1,4—benzoquino—6—yl)—L—Ala—γ—D—Glu(α—OH)—(L)—mesoDAP—(L)—D—AlaOH (3) (0.80 g).

IR(Nujol): 3300, 1720, 1640, 1610, 1530 cm$^{-1}$.

NMR(CD$_3$CD), δ: 2.00 (3H, s), 3.92 (6H, s) 3.60-4.50 (5H, m).

EXAMPLE 122

(1) Step 1

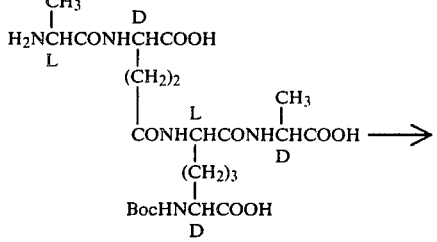

(1)

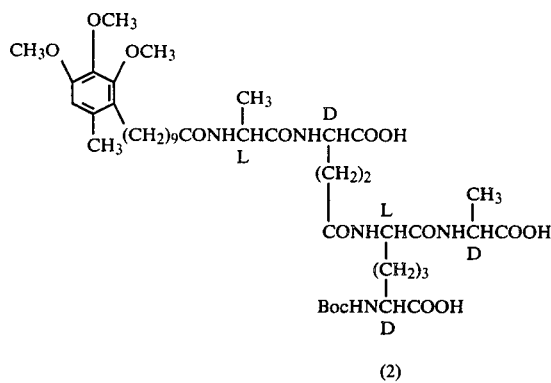

(2)

10—(2,3,4—Trimethoxy—6—methyl phenyl-)—decanoyl—L—Ala—γ—D—Glu(α—OH)—(L-)—Boc—(D)—mesoDAP—(L)—D—AlaOH (2) was prepared in substantially the same manner as that of Step 1 of Example 121.

IR(Nujol): 1710, 1640, 1530 cm$^{-1}$.

NMR(CDCl$_3$): δ 1.46 (9H, s), 2.27 (3H, s), 3.90 (9H, s), 4.00-5.00 (5H, m) 6.50 (1H, s).

(2) Step 2

Compound (2) ⟶

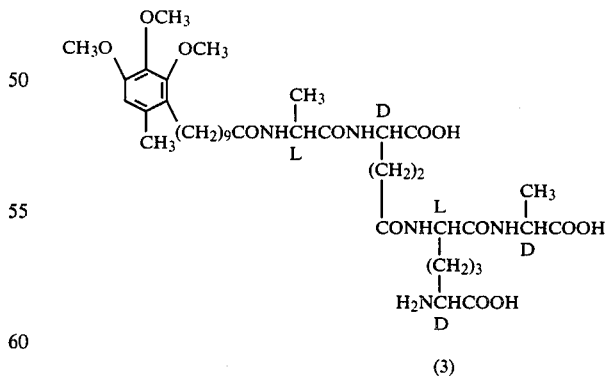

(3)

10—(2,3,4—Trimethoxy—6—methylphenyl-)—decanoyl—L—Ala—γ—D—Glu(α—OH)—(L-)—mesoDAP—(L)—D—AlaOH (3) was prepared in substantially the same manner as that of step 2 of Example 121.

IR(Nujol): 3260, 1720, 1620, 1530 cm$^{-1}$.

NMR(CD₃OD): δ 2.26 (3H, s), 3.83 (9H, s), 6.60 (1H, s).

EXAMPLE 123

(1) Step 1

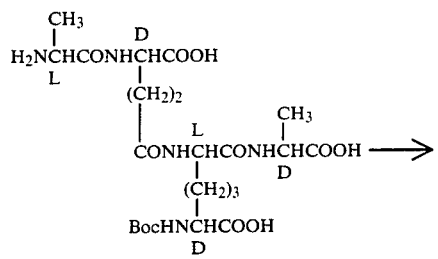

(1)

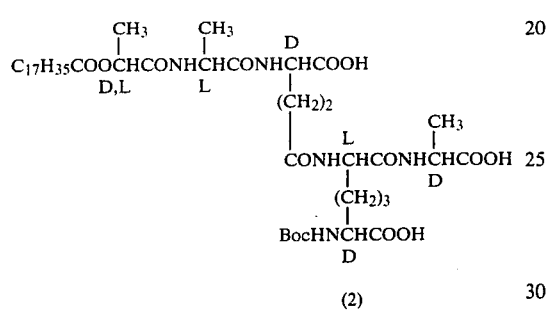

(2)

O—Stearoyl—Lac—L—Ala—γ—D—Glu(α—OH-)—(L)—Boc—(D)—mesoDAP—(L)—D—AlaOH (2) was prepared in substantially the same manner as step 1 of Example 121.

IR(Nujol): 3300, 1720, 1630 cm⁻¹.

NMR(CDCl₃), δ: 0.90 (3H, m), 4.15–4.90 (5H, m), 5.17 (1H, m).

(2) Step 2

Compound (2) ⟶

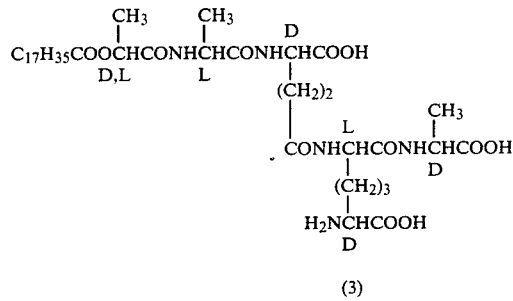

(3)

O—Stearoyl—Lac—L—Ala—γ—D—Glu(α—OH-)—(L)—mesoDAP—(L)—D—AlaOH (3) was prepared in substantially the same manner as step 2 of Example 121.

IR(Nujol): 3370, 1740, 1650 (sh), 1630 cm⁻¹.

NMR(D₂O—NaHCO₃), δ: 0.87 (3H, m), 3.74 (1H, m), 4.0–4.5 (4H, m), 5.10 (1H, m),

[α]_D = −38.24° (C=0.30, 5% NaHCO₃).

EXAMPLE 124

(1) Step 1

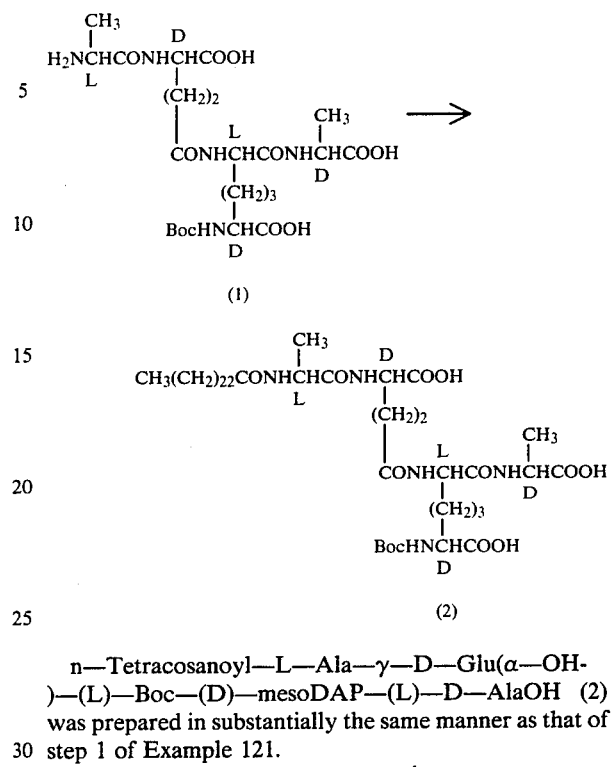

n—Tetracosanoyl—L—Ala—γ—D—Glu(α—OH-)—(L)—Boc—(D)—mesoDAP—(L)—D—AlaOH (2) was prepared in substantially the same manner as that of step 1 of Example 121.

IR(Nujol): 3300, 1750, 1630 cm⁻¹.

NMR(CDCl₃), δ: 0.89 (3H, m), 4.0–4.9 (5H, m).

(2) Step 2

Compound (2) ⟶

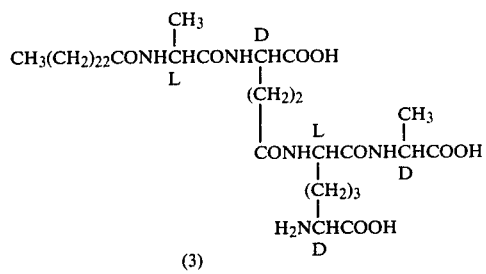

(3)

n—Tetracosanoyl—L—Ala—γ—D—Glu(α—OH-)—(L)—mesoDAP—(L)—D—AlaOH (3) was prepared in substantially the same manner as that of step 2 of Example 121.

IR(Nujol): 3280, 1730, 1630 cm⁻¹.

NMR(D₂O+NaHCO₃), δ: 0.88 (3H, m), 3.72 (1H, m), 3.95–4.6 (4H, m).

EXAMPLE 125

(1) Step 1

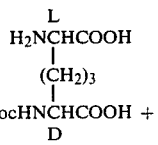

(1)

-continued

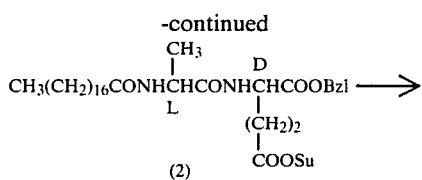

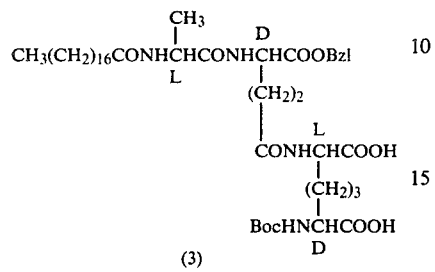

(D)—Boc—mesoDAP (1) (580 mg) was dissolved in a mixture of methanol (10 ml), methylene chloride (40 ml) and triethylamine (404 mg). To this solution was added stearoyl—L—Ala—D—Glu(α—OBzl)OSu (1.34 g). The resulting solution was left overnight at ambient temperature, evaporated and extracted with ethyl acetate after acidification. The organic layer was washed with water, dried over magnesium sulfate and evaporated to give stearoyl—L—Ala—γ—D—Glu(α—OBzl)—(L)—Boc—(D)—mesoDAP—(3) (1.10 g).

IR(Nujol): 3300, 2700-2500 (broad), 1720 (broad), 1650 (sh), 1630 cm⁻¹.

NMR(DMSO-d₆): δ 0.88 (3H, m), 1.0-2.50 (54H, m), 4.0-4.50 (4H, m), 5.12 (2H, s), 7.36 (5H, s), 7.84 (1H, d, J=7 Hz), 8.04 (1H, d, J=7 Hz), 8.28 (1H, d, J=7 Hz).

(2) Step 2

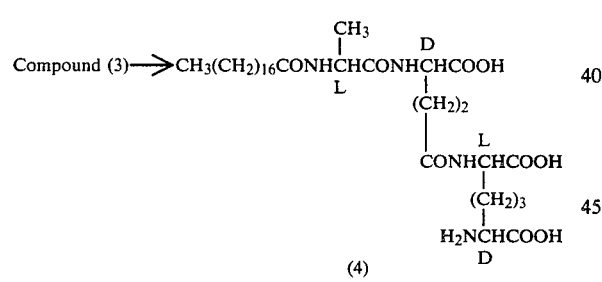

Stearoyl—L—Ala—γ—Glu(α—OBzl)—(L)—Boc—(D)—DAP (3) (1.10 g) was dissolved in acetic acid (80 ml) and hydrogenated over 10% palladium black (120 mg). The catalyst was removed by filtration and the filtrate was evaporated to give a gummyresidue which was dissolved in trifluoroacetic acid (5 ml). After standing for 15 minutes at ambient temperature, the solvent was evaporated to give a foam which was triturated with diethyl ether to give stearoyl—L—Ala—γ—D—Glu(α—OH)—(L)—mesoDAP (4) (0.90 g).

IR(Nujol): 3300, 2600-2300, 1720, 1650 (sh), 1630 cm⁻¹.

NMR(NaOD-D₂O): δ 0.84 (3H, m), 1.0-2.60 (45H, m), 3.10-3.40 (1H, m), 4.0-4.50 (3H, m).

EXAMPLE 126

(1) Step 1

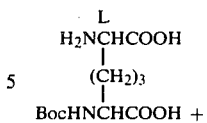

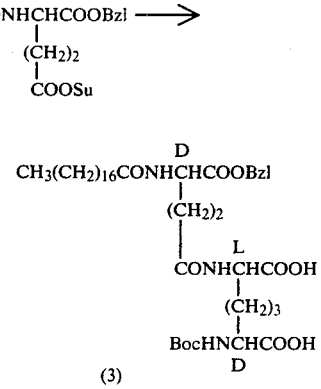

Stearoyl—γ—D—Glu(α—OBzl)—(L)—Boc—(D-)—mesoDAP (3) was prepared in substantially the same manner as step 1 of Example 125.

IR(Nujol): 3300, 2600-2300 (broad), 1750-1700 (broad), 1650 (broad) cm⁻¹.

NMR(DMSO-d₆): δ 0.86 (3H, m), 1.0-2.40 (5H, m), 4.0-4.50 (3H, m), 5.13 (2H, s), 6.90 (1H, m), 7.36 (5H, s), 7.70-8.30 (2H, m).

(2) Step 2

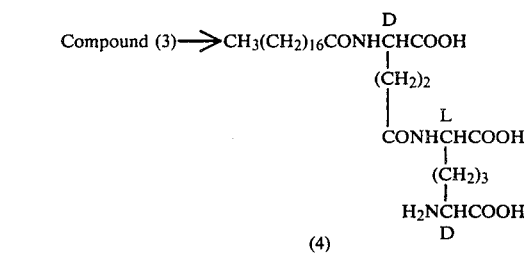

Stearoyl—γ—D—Glu(α—OH)—(L)—mesoDAP (4) was prepared in substantially the same manner that of step 2 of Example 125.

IR(Nujol): 3250 (sh), 1720, 1640 cm⁻¹.

NMR(NaOD-D₂₆): δ 0.80-2.80 (45H, m), 3.12-3.40 (1H, m), 4.0-4.32 (2H, m).

EXAMPLE 127

(1) Step 1

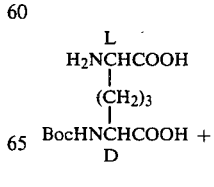

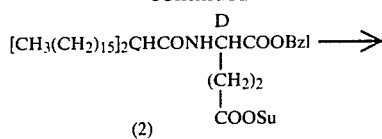

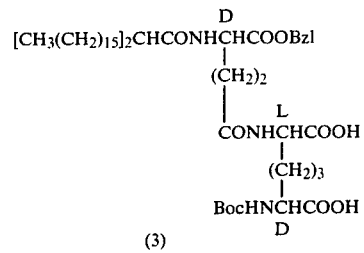

2-Hexadecyloctadecanoyl—γ—D—Glu(α—OBzl)—(L)—Boc—(D)—mesoDAP (3) was prepared in substantially the same manner as that of step 1 of Example 125.

IR(Nujol): 3300, 1730 (broad), 1680, 1640 cm⁻¹.

NMR(CDCl₃): δ 0.87–2.87 (77H, m), 4.33–4.80 (3H, m), 5.16 (2H, s), 7.33 (5H, s).

(2) Step 2

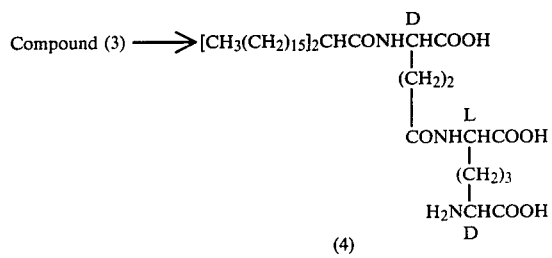

2—Hexadecyloctadecanoyl—γ—D—Glu(α—OH)—(L)—mesoDAP (4) was prepared in substantially the same manner as that of step 2 of Example 125.

IR(Nujol): 3250, 1720, 1630 cm⁻¹.

NMR(CDCl₃): δ 0.68–2.68 (77H, m), 3.68–4.00 (1H, m), 4.16–4.83 (2H, m).

EXAMPLE 128

(1) Step 1

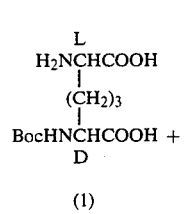

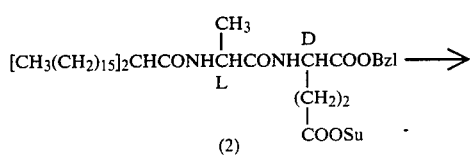

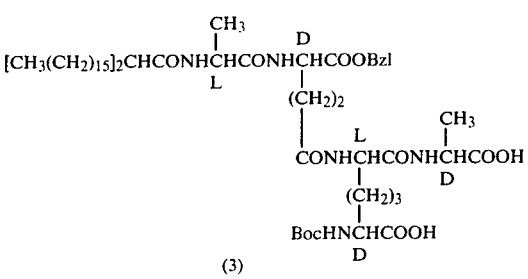

2—Hexadecyloctadecanoyl—L—Ala—γ—D—Glu(α—OBzl)—(L)—Boc—(D)—mesoDAP—(L-)—D—AlaOH (3) was prepared in substantially the same manner as that of step 1 of Example 125.

IR(Nujol): 3300, 1745, 1660 (sh), 1640 cm⁻¹.

(2) Step 2

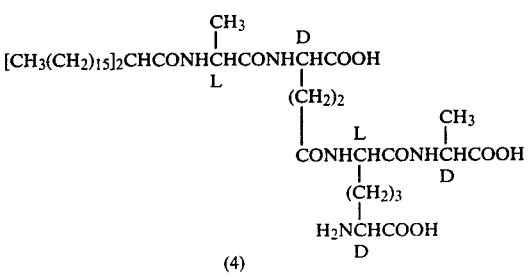

2—Hexadecyloctadecanoyl—L—Ala—γ—D—Glu(α—OH)—(L)—mesoDAP—(L)—D—AlaOH (4) was prepared in substantially the same manner as that of step 2 of Example 125.

IR(Nujol): 3270, 1730, 1630 cm⁻¹.

NMR(CF₃CO₂H): δ 0.92 (6H, m) 4.30–5.00 (5H, m).

EXAMPLE 129

(1) Step 1

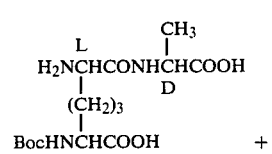

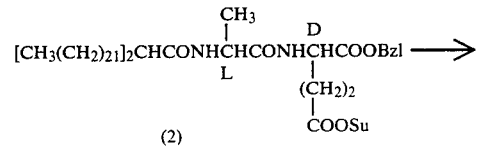

-continued $$[CH_3(CH_2)_{21}]_2CHCONH\overset{L}{C}H(CH_3)CONH\overset{D}{C}H((CH_2)_2-CONH\overset{L}{C}H(CH_3)COOBzl)COOH$$

(with (CH₂)₃—BocHN\overset{D}{C}HCOOH side chain on the meso-DAP)

(3)

2—Docosyltetracosanoyl—L—Ala—γ—D—Glu(α—OBzl)—(L)—Boc—(D)—mesoDAP—(L-)—D—AlaOH (3) was prepared in substantially the same manner as that of step 1 of Example 125.

IR(Nujol): 3250, 1750 (sh), 1715 (sh), 1690, 1660, 1640 cm⁻¹.

(2) Step 2

Compound (3) ⟶

$$[CH_3(CH_2)_{21}]_2CHCONH\overset{L}{C}H(CH_3)CONH\overset{D}{C}H((CH_2)_2-CONH\overset{L}{C}H(CH_3)COOH \cdots (CH_2)_3-H_2N\overset{D}{C}HCOOH)$$

(4)

2—Docosyltetracosanoyl—L—Ala—γ—D—Glu(α—OH)—(L)—mesoDAP—(L)—D—AlaOH (4) was prepared in substantially the same manner as that of step 2 of Example 125.

IR(Nujol): 3300, 1720, 1645-1625 (broad) cm⁻¹.

NMR (CDCl₃): δ 0.67–3.00 (107H, m), 4.33–4.67 (3H, m).

EXAMPLE 130

(1) Step 1

$$\overset{L}{H_2N}\overset{}{C}HCOOH-(CH_2)_3-BocHN\overset{D}{C}HCOOH$$

(1)

+

$$[CH_3(CH_2)_{21}]_2CHCONH\overset{D}{C}H((CH_2)_2-COOSu)COOBzl$$

(2)

⟶

$$[CH_3(CH_2)_{21}]_2CHCONH\overset{D}{C}H((CH_2)_2-CONH\overset{L}{C}H((CH_2)_3-BocHN\overset{D}{C}HCOOH)COOH)COOBzl$$

(3)

2-Docosyltetrcosanoyl—γ—D—Glu(α—OBzl)—(L)—Boc—(D)—mesoDAP (3) was prepared in substantially the same manner as that of step 1 of Example 125.

IR(Nujol): 3300, 1740 (sh), 1720 (broad), 1690, 1640 cm⁻¹.

NMR(CDCl₃): δ 0.86–2.50 (101H, m), 4.10–4.83 (3H, m), 5.13 (2H, s), 7.30 (5H, s).

(2) Step 2

Compound (3) ⟶

$$[CH_3(CH_2)_{21}]_2CHCONH\overset{D}{C}H((CH_2)_2-CONH\overset{L}{C}H((CH_2)_3-H_2N\overset{D}{C}HCOOH)COOH)COOH$$

(4)

2—Docosyltetracosanoyl—γ—D—Glu(α—OH)—(L)—mesoDAP (4) was prepared in substantially the same manner as that of step 2 of Example 125.

IR(Nujol): 3300, 1720, 1640-1620 (broad) cm⁻¹.

NMR(CDCl₃): δ 0.68–2.86 (101H, m), 4.33–4.86 (2H, m).

EXAMPLE 131

(1) Step 1

$$[CH_3(CH_2)_{21}]_2CHCONH\overset{L}{C}H(CH_3)CONH\overset{D}{C}H((CH_2)_2-CONH\overset{L}{C}H(CH_3)((CH_2)_3-BocHN\overset{D}{C}HCOOH)COOH)COOBzl$$

(1)

⟶

$$[CH_3(CH_2)_{21}]_2CHCONH\overset{L}{C}H(CH_3)CONH\overset{D}{C}H((CH_2)_2-CONH\overset{L}{C}H(CH_3)((CH_2)_3-BocHN\overset{D}{C}HCOOCH_3)COOMe)COOBzl$$

(2)

2—Docosyltetracosanoyl—L—Ala—γ—D—Glu(α—OBzl)—(L)—Boc—(D)—mesoDAP—(L-)—D—AlaOH (1) (1.50 g) was dissolved in a mixture of tetrahydrofuran (50 ml) and methylene dichloride (20 ml). To this solution was added etheral solution (6 ml) of diazomethane (0.5 Mole solution) under stirring and reacted for 1 hour. The excess of diazomethane was destroyed by adding acetic acid and the resulting solution was evaporated to give a waxy residue, which was subjected to a silica gel column. Elution with chloroform-methanol (20:1) and subsequent evaporation gave 2—docosyltetracosanoyl—L—Ala—γ—D—Glu(α—OBzl)—(L)—Boc—(D)—mesoDAP—(L-)—D—Ala(OMe)—(D)—OMe (2) (0.90 g).

IR(Nujol): 3300, 1755 (sh), 1745, 1690, 1660, 1640 cm$^{-1}$.

NMR(CDCl$_3$): δ 0.86–2.50 (116H, m), 3.68 (3H, m), 3.72 (3H, s), 4.16–4.83 (5H, m), 5.15 (2H, s), 7.33 (5H, s).

(2) Step 2

Compound (3) ⟶

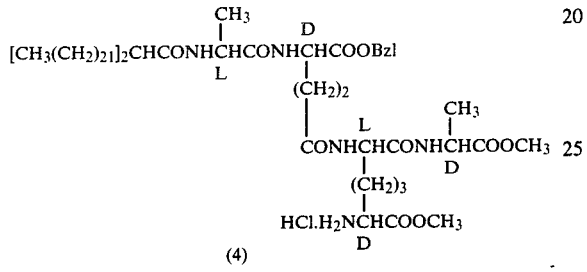

(4)

2—Docosyltetracosanoyl—L—Ala—γ—D—Glu(α—OBzl)—(L)—Boc—(D)—mesoDAP—(L-)—D—Ala(OMe)—(D)—OMe (3) (1.0 g) was dissolved in acetic acid (40 ml) and then treated with hydrogen chloride saturated acetic acid (2 ml). After standing for 2 hours at ambient temperature, the solution was evaporated to give a white residue, which was throughly washed with diisopropylether to afford 2—docosyltetracosanoyl—L—Ala—γ—D—Glu(α—OBzl)—(L-)—mesoDAP—(L)—D—Ala(OMe)—(D)—OMe (4) (0.90 g).

IR(Nujol): 3300, 1750, 1660, 1640 cm$^{-1}$.

NMR(CDCl$_3$): δ 0.68–3.00 (107H, m), 3.68–4.00 (6H, broad), 4.33–5.86 (4H, m), 5.16 (2H, s), 7.36 (5H, s).

EXAMPLE 132

(1) Step 1

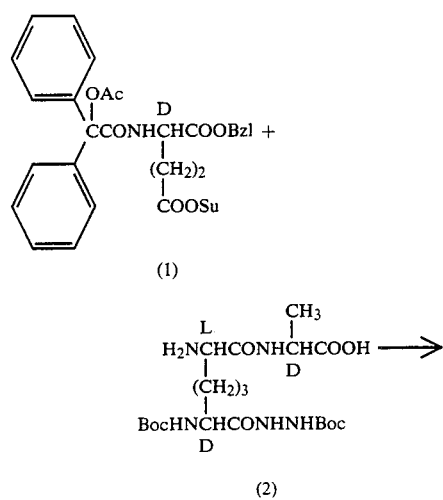

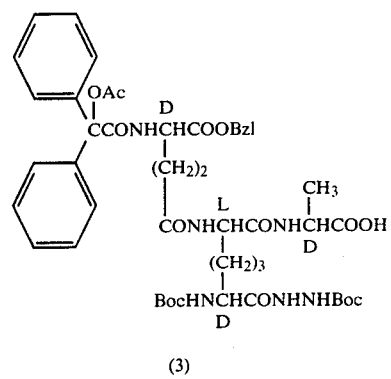

(3)

To a solution of Boc—(D)—mesoDAP—(L-)—D—AlaOH—(D)—NHNHBoc (2) (2.76 g) and triethylamine in aceton-water (2:1, 90 ml) was added a solution of O—acetylbenziloyl-γ—D—Glu(α—OBzl)—1—succinimidyl ester (3.4 g: 5.8 mM) in acetone at 0° C. with stirring. Stirring was continued overnight, allowing the temperature of the mixture to reach to room temperature. After evapolation of acetone, the residue was added ethyl acetate (60 ml), and the organic layer was washed with dil sodium bicarbonate, saturated sodium chloride, dil hydrochloric acid and water. After drying over magnesium sulfate, the solvent was removed in vacuo and triturated with isopropyl ether to give O—acetylbenziloyl—γ—D—Glu(α—OBzl)—(L-)—Boc—(D)—mesoDAP—(L)—D—AlaOH—(D-)—NHNHBoc (3) (4.63 g).

NMR(CDCl$_3$): δ 1.0–2.0 (29H, m), 2.05 (3H, s), 2.0–2.6 (2H, m), 4.0–5.0 (4H, m), 5.13 (2H, s), 5.66 (1H, broads), 6.80 (3H, m), 7.07 (2H, m), 7.33 (15H, s), 8.94 (1H, s).

IR(Nujol): 3300, 1735, 1670, 1520, 1240, 1165, 700 cm$^{-1}$.

(2) Step 2

Compound (3) ⟶

(4)

To a solution of O—acetylbenziloyl—γ—D—Glu(α—OBzl)—(L)—Boc—(D)—mesoDAP—(L-)—D—AlaOH—(D)—NHNHBoc (3) (4.2 g) in methanol (25 ml) was added 1N sodium hydroxide (16 ml) at 0° C. with stirring. The mixture was stirred in an ice bath for 30 minutes and then at room temperature for 30 minutes. After addition of 1N. hydrochloric acid (16 ml), the solvent was removed in vacuo, and the residue was dissolved in ethyl acetate (60 ml) and water (40 ml). The organic layer was washed with saturated sodium chloride and dried over magnesium sulfate and evaporated and then triturated with diethyl ether to give benziloyl—γ—D—Glu(α—OH)—(L)—Boc—(D-)—mesoDAP—(L)—D—AlaOH—(D)—NHNHBoc (4) (2.97 g).

NMR(CD₃OD): δ 1.23 (3H, d, 7 Hz), 1.0-2.0 (26H, m), 2.0-2.6 (2H, m), 3.9-4.7 (4H, m), 7.1-7.7 (10H, m).

IR(Nujol): 3300, 1720, 1650, 1510, 1240, 1160, 700 cm⁻¹.

(3) Step 3

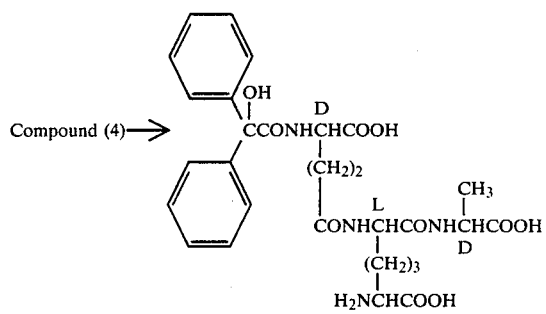

Benziloyl—γ—D—Glu(α—OH)—(L)—Boc—(D-)—mesoDAP—(L)—D—AlaOH—(D)—NHNHBoc (4) (2.5 g) was treated with trifluoroacetic acid (10 ml) for 15 minutes at room temperature. Resulting trifluoroacetic acid salt of benziloyl—γ—D—Glu(α—OH-)—(L)—mesoDAP—(L)—D—AlaOH—(D)—NHNH₂ (2.44 g) was dissolved in 1N sulfuric acid (18 ml) and added sodium metaperiodate (0.62 g) at 0° C. with stirring. After stirring for 20 minutes at 0° C., the reaction mixture was treated with sodium bisulfite, and put on a column of Hp-20 (170 ml). After removal of inorganic salts with water, elution was carried out with methanol-water (1:1). The eluate was lyophilized to give benziloyl—γ—D—Glu(α—OH)—(L)—mesoDAP—(L-)—D—AlaOH (5) (1.0 g).

$[\alpha]_D^{21} = +11.90$ (CO.36H₂O).

NMR(D₂O): δ 1.36 (3H, d, 7 Hz), 1.3-2.1 (8H, m), 2.1-2.5 (2H, m), 3.76 (1H, t, 6 Hz), 4.0-4.6 (3H, m), 7.45 (10H, d, 3 Hz).

IR(Nujol): 3300, 1710, 1645, 1520, 1220, 700 cm⁻¹.

EXAMPLE 133

(1) Step 1

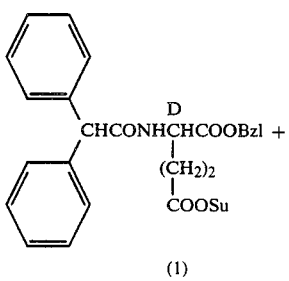

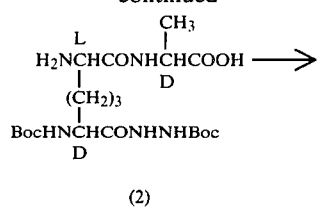

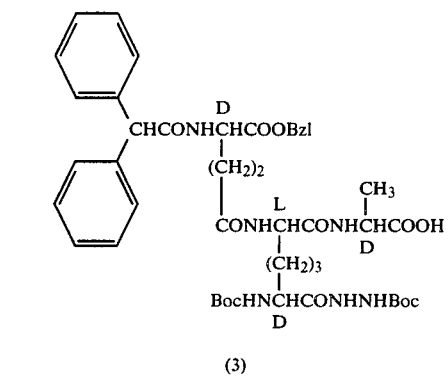

Diphenylacetyl—γ—D—Glu(α—OBzl)—(L-)—Boc—(D)—mesoDAP—(L)—D—AlaOH—(D-)—NHNHBoc (3) was prepared in substantially the same manner as that of step 1 of Example 132.

NMR(DMSO-d₆): δ 1.0-2.3 (31H, m), 3.7-4.5 (4H, m), 5.0 (1H, s), 5.06 (2H, s), 6.3-7.0 (1H, m), 7.23 (10H, s), 7.28 (5H, s), 7.5-8.1 (3H, m), 7.3-9.0 (2H, m), 9.5 (1H, s).

IR(Nujol): 3300, 1725, 1630, 1525, 1220, 1160, 700 cm⁻¹.

(2) Step 2

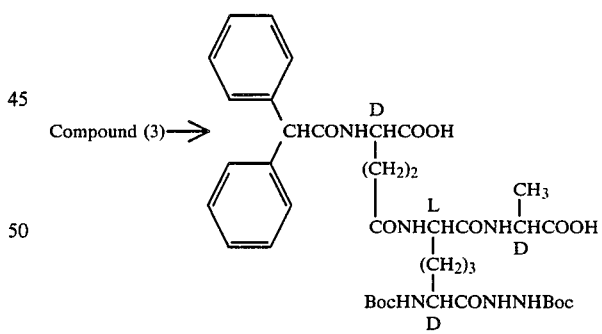

Diphenylacetyl—γ—D—Glu(α—OH)—(L-)—Boc—(D)—mesoDAP—(L)—D—AlaOH—(D-)—NHNHBoc (4) was prepared in substantially the same manner as that of step 2 of Example 132.

NMR(CD₃OD): δ 1.36 (3H, d, J=7 Hz), 1.3-2.5 (28H, m), 3.9-4.6 (4H, m), 5.10 (1H, s), 7.30 (10H, d, J=3 Hz).

IR(Nujol): 3300, 1720, 1650, 1520, 1220, 1160, 700 cm⁻¹.

(3) Step 3

Compound (4)⟶ 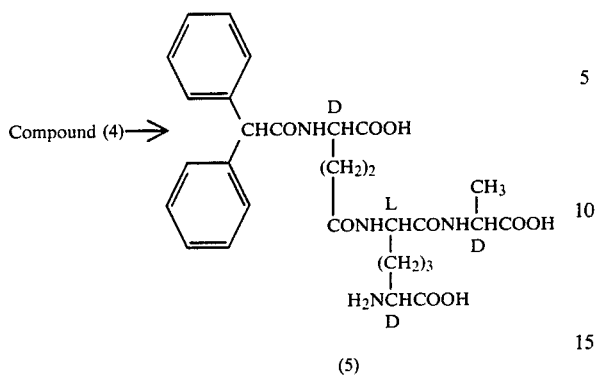

(5)

Diphenylacetyl—γ—D—Glu(α—OH)—(L-)—mesoDAP—(L)—D—AlaOH (5) was prepared in substantially the same manner as that of step 3 of Example 132.

$[α]_D^{22}= +4.02$ (C0.2H$_2$O).

NMR(D$_2$O): δ 1.35 (3H, d, J=7 Hz), 1.3–2.6 (10H, m), 3.73 (1H, t, J=6 Hz9, 4.0–4.6 (3H, m), 5.20 (1H, s), 7.36 (10H, s).

IR(Nujol): 3250, 1720, 1620, 1525, 1220, 700 cm$^{-1}$.

EXAMPLE 134

(1) Step 1

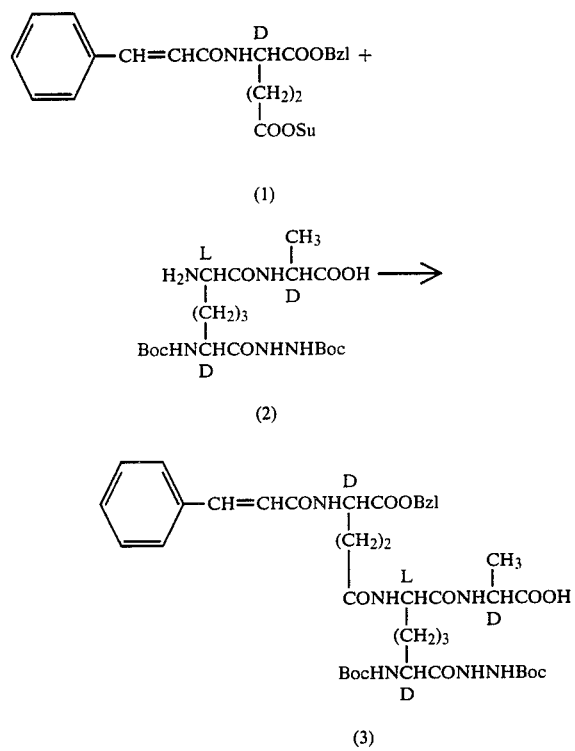

Cinnamoyl—γ—D—Glu(α—OBzl)—(L-)—Boc—(D)—mesoDAP—(L)—D—AlaOH—(D-)—NHNHBoc (3) was prepared in substantially the same manner as that of step 1 of Example 132.

NMR(CD$_3$OD): δ1.1–2.6 (3H, m), 3.9–4.7 (4H, m), 5.19 (2H, s), 6.67 (1H, d, J=16 Hz), 7.1–7.9 (1H, m).

IR(Nujol): 3260, 1730, 1650, 1625, 1520, 1160 cm$^{-1}$.

(2) Step 2

Compound (3) ⟶ 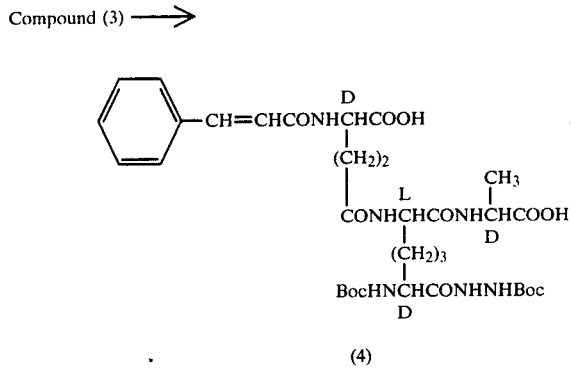

(4)

Cinnamoyl—γ—D—Glu(α—OH)—(L)—Boc—(D-)—mesoDAP—(L)—D—AlaOH—(D)—NHNHBoc (4) was prepared in substantially the same manner as that of step 2 of Example 132.

NMR(CD$_3$OD): δ 1.1–2.6 (31H, m), 3.9–4.7 (4H, m), 6.67 (1H, d, J=16 Hz), 7.3–7.9 (6H, m).

IR(Nujol): 3260, 1740, 1690, 1655, 1620, 1550, 1160 cm$^{-1}$.

(3) Step 3

Compound (4) ⟶ 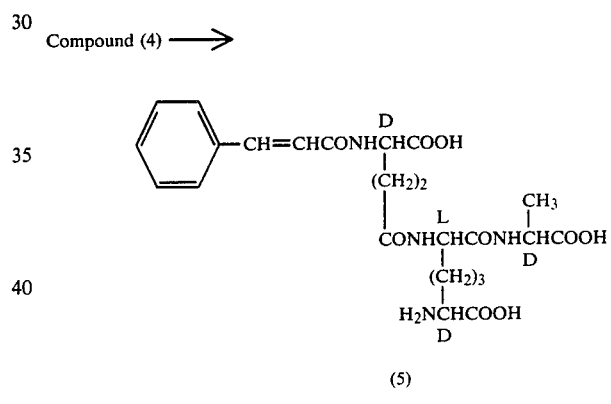

(5)

Cinnamoyl—γ—D—Glu(α—OH)—(L-)—mesoDAP—(L)—D—AlaOH (5) was prepared in substantially the same manner as that of step 3 of Example 132.

$[α]_D^{22}= +5.69°$ (C0.22H$_2$O).

NMR(D$_2$O): δ 1.38 (3H, d, J=7 Hz), 1.5–2.6 (10H, m), 3.74 (1H, t, J=6 Hz), 4.1–4.6 (3H, m), 6.65 (1H, d, J=16 Hz), 7.2–7.7 (6H, m).

IR(Nujol): 3250, 1720, 1650, 1620, 1530, 1220 cm$^{-1}$.

EXAMPLE 135

(1) Step 1

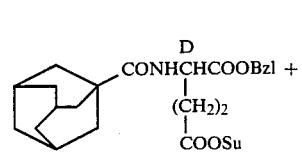

(1)

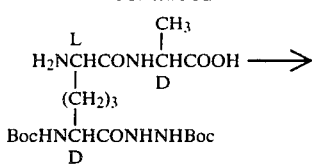

(2)

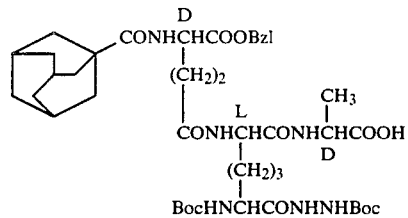

(3)

Adamantane—1—carbonyl—γ—D—Glu(α—OBzl)—(L)—Boc—(D)—mesoDAP—(L-)—D—AlaOH—(D)—NHNHBoc (3) was prepared in substantially the same manner as that of step 1 of Example 132.

NMR(DMSO-d6): δ 1.0–2.3 (46H, m), 4.0–4.5 (4H, m), 5.10 (2H, s), 6.5–6.9 (1H, m), 7.33 (5H, s), 7.5–8.6 (5H, m), 9.53 (1H, s).

IR(Nujol): 3300, 1740 (sholder), 1720, 1685, 1630, 1520, 1240, 1160, 700 cm$^{-1}$.

(2) Step 2

Compound (3) ⟶

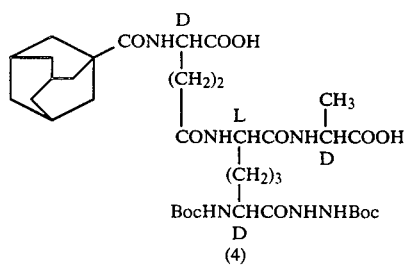

(4)

Adamantane—1—carbonyl—γ—D—Glu(α—OH)—(L)—Boc—(D)—mesoDAP—(L-)—D—AlaOH—(D)—NHNHBoc (4) was prepared in substantially the same manner as that of step 2 of Example 132.

NMR(CD3OD): 1.3–2.5 (46H, m), 3.9–4.6 (4H, m).
IR(Nujol): 3300, 1720, 1640, 1520, 1240, 1160 cm$^{-1}$.

(3) Step 3

Compound (4) ⟶

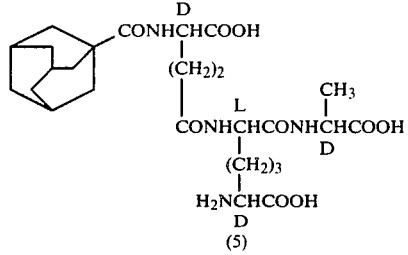

(5)

Adamantane—1—carbonyl—γ—D—Glu(α—OH-)—(L)—mesoDAP—(L)—D—AlaOH (5) was prepared in substantially the same manner as that of step 3 of Example 132.

$[\alpha]_D^{22} = -2.64$ (C0.23H2O).

NMR(D2O): δ 1.40 (3H, d, J=7 Hz), 1.2–2.6 (25H, m), 3.80 (1H, t, J=6 Hz), 4.2–4.5 (3H, m).

IR(Nujol): 3250, 1720, 1635, 1520 cm$^{-1}$.

EXAMPLE 136

(1) Step 1

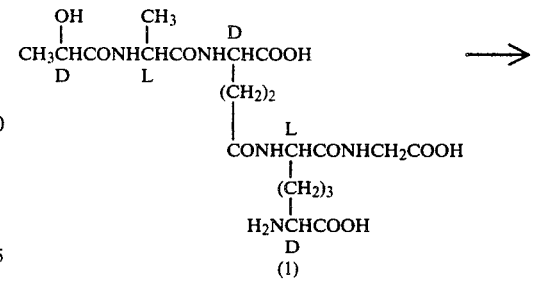

(1)

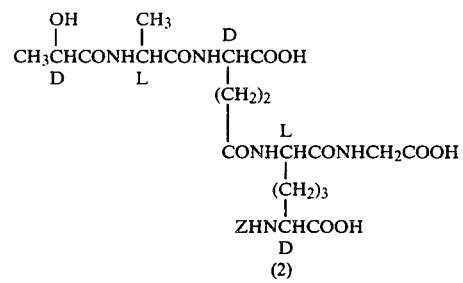

(2)

To a solution of D—Lac—L—Ala—γ—D—Glu(α—OH)—(L)—mesoDAP—(L)—GlyOH (1) (1.2 g) in water (5 ml) was added triethylamine (0.96 g) and a solution of benzyloxycarbonyloxyimino-2-phenylacetonitrile (0.69 g) in acetone (5 ml) at 0° C. with stirring and the mixture was stirring over night at room temperature. After evapolation of acetone to the residue was added water (5 ml) and ethyl acetate (5 ml). The aqueous layer was separated, washed with ethyl acetate (5 ml), acidified with 1N-hydrochloric acid, and extracted with ethyl acetate (20 ml). The extract was washed with water (5 ml×2) and dried over magnesium sulfate. Evaporation of the solvent gave 1.42 g (94.7%) of D—Lac—L—Ala—γ—D—Glu(α—OH)—(L-)—Z—(D)—mesoDAP—(L)—GlyOH (2).

(2) Step 2

Compound (2) ⟶

-continued

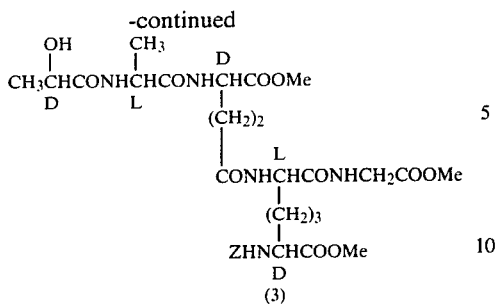

To a solution of D—Lac—L—Ala—γ—D—Glu(α—OH)—(L)—Z—(D)—mesoDAP—(L)—GlyOH (2) (1.42 g) in methanol (30 ml) was added a solution of diazomethane in diethyl ether at 0° C. with stirring. The mixture was stirred for 4 hours at 0° C. and for 2 hours at room temperature and allowed to stand overnight. After addition of acetic acid (0.1 ml) the solvent was evapolated in vacuo and crystallized from ethyl acetate to give D—Lac—L—Ala—γ—D—Glu(α—OMe)—(L)—Z—(D)—mesoDAP—(L)—GlyOMe—(D)—OMe (3) (1.30 g).

NMR(CD₃OD): δ 1.33 (3H, d, J=7 Hz), 1.36 (3H, d, J=7 Hz), 1.5–2.5 (10H, m), 3.67 (9H, s), 3.95 (2H, s), 4.0–4.6 (4H, m), 5.06 (2H, s), 7.47 (5H, s).

IR(Nujol): 3310, 1760, 1740, 1690, 1660, 1630, 1550, 1280 cm⁻¹.

(3) Step 3

Compound (3) ⟶

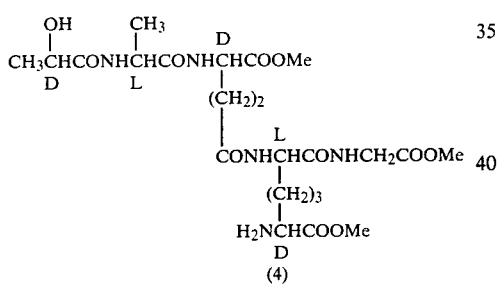

A solution of D—Lac—L—Ala—γ—D—Glu(α—OMe)—(L)—Z—(D)—mesoDAP—(L)—GlyOMe—(D)—OMe (3) in 80% methanol (30 ml) was hydrogenolyzed in the presence of 10% palladium charcoal (0.12 g). After the catalyst was removed, the solvent was evaporated in vacuo and crystallized from methanol-diethylether to give D—Lac—L—Ala—γ—D—Glu(α—OMe)—(L-)—mesoDAP—(L)—GlyOMe—(D)—OMe (4) (0.86 g).

NMR(D₂O): δ 1.43 (3H, d, J=7 Hz), 1.53 (3H, d, J=7 Hz), 1.5–2.6 (10H, m), 3.6–3.8 (1H, m), 3.77 (9H, s), 4.03 (2H, s), 4.1–4.6 (4H, m).

IR(Nujol): 3370, 1730, 1630, 1520, 1210 cm⁻¹.

EXAMPLE 137

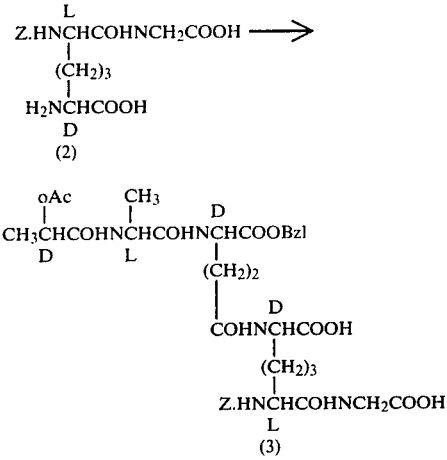

A solution of Z—(L)—mesoDAP—(L)—GlyOH (2) (186 mg) in water (3 ml) was adjusted to pH 8 with triethylamine and a solution of D—Lac(oAc-)—L—Ala—D—Glu(oSu)(α—oBzl) (1) (260 mg) in dioxane (2 ml) was added thereto.

The mixture was stirred at ambient temperature for five hours, maintaining the pH 8 with triethylamine, and then evaporated.

The aqueous layer was diluted with water (10 ml) and adjusted to pH 4 with 1N hydrochloric acid.

This solution was washed with ethyl acetate and adjusted to pH 2 with 1N hydrochloric acid and then extracted with ethyl acetate. The extract was washed with a saturated sodium chloride, dried over magnesium sulfate and evaporated to give D—Lac(oAc-)—L—Ala—γ—D—Glu(α—oBzl)—(D)—Z—(L-)—mesoDAP—(L)—GlyOH (3) (203 mg).

N.M.R. (CD₃OD), δ (ppm): 1.38 (3H, d, J=7 Hz), 1.45 (3H, d, J=7 Hz), 1.4–2.0 (6H, m), 2.10 (3H, s), 2.0–2.4 (4H, m), 3.93 (2H, s), 4.1–4.7 (4H, m), 4.9–5.1 (1H, m), 5.12 (2H, s), 5.20 (2H, s), 7.37 (10H, s).

EXAMPLE 138

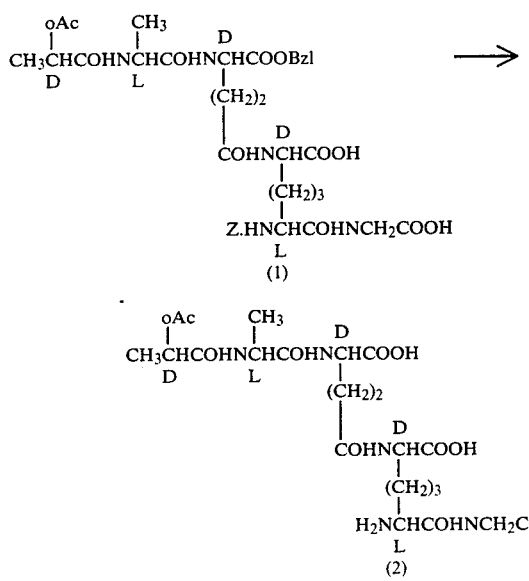

A solution of D—Lac(oAc)—L—Ala—γ—D—Glu(α—OBzl)—(D)—Z—(L)—mesoDAP—(L)—GlyOH (1) (180 mg) in methanol (30 ml) was hydrogenated over 10% palladium-black (50 mg) under an ordinary atmospheric pressure of hydrogen. The reaction mixture was filtered and the filtrate was concentrated. The concentrate was dissolved in methanol (1 ml) and triturated with ether and then filtered. The powder obtained was washed with ether to give D—Lac(oAc)—L—Ala—γ—D—Glu(α—OH)—(D-)—mesoDAP—(L)—GlyOH (2) (98 mg).

N.M.R. (D₂O), δ (ppm): 1.38 (3H, d, J=7 Hz), 1.43 (3H, d, J=7 Hz), 1.5-2.2 (10H, m), 2.0 (3H, s), 3.90 (2H, s), 4.0-4.5 (5H, m).

EXAMPLE 139

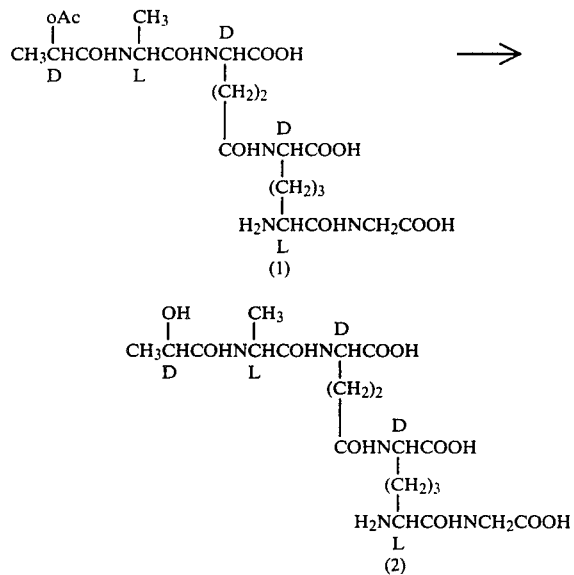

A solution of D—Lac(oAc)—L—Ala—γ—D—Glu(α—OH)—(D)—mesoDAP—(L)—GlyOH (1) (105 mg) in methanol (5 ml) was stirred at ambient temperature for three hours, maintaining the pH at 9 with 5% aqueous potassium carbonate.

The solution was evaporated and the residue was adjusted to pH 3.5 and put on a column of activated carbon. The column was washed with water and eluted with 70% aqueous acetone. The eluate was evaporated and the residue was dissolved in methanol (0.5 ml) and triturated with ether. The precipitate thus obtained was filtered and washed ether to give D—Lac—L—Ala—γ—D—Glu(α—OH)—(D-)—mesoDAP—(L)—GlyOH (2) (60 mg).

N.M.R. (D₂O), δ (ppm): 1.38 (3H, d, J=7 Hz), 1.44 (3H, d, J=7 Hz), 1.7-2.5 (10H, m), 3.98 (2H, s), 4.08 (1H, t, J=6 Hz), 4.2-4.5 (5H, m).

EXAMPLE 140

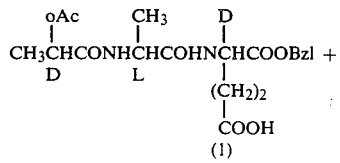

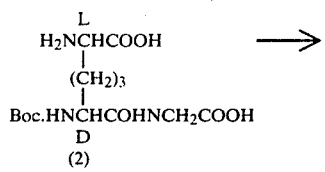

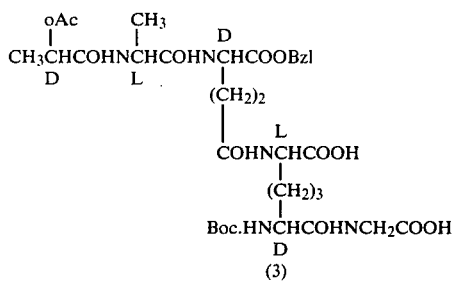

To a cold mixture of D—Lac(oAc)—L—Ala—γ—D—Glu(OH)(α—oBzl) (1) (1.05 g) and N-hydroxysuccinimide (317 mg) in a mixture of dioxane (10 ml) and tetrahydrofuran (2 ml) was added N,N'-dicyclohexylcarbodiimide (557 mg).

The mixture was stirred at 10° C. for ten minutes and at ambient temperature overnight.

The precipitated N,N'-dicyclohexylurea was filtered off and washed with dioxane and then filtered. The combined filtrate was evaporated and the residue was dissolved in dioxane (6 ml). To this solution was added a solution of Boc—(D)meso—DAP—(D)GlyOH (2) (600 mg) and N-methylmorpholine (0.57 ml) in dimethylformamide (6 ml).

The resulting solution was stirred at °C. for 30 minutes and the stirring was continued at ambient temperature for 2.3 hours and then an additional N-methylmorpholine (0.10 ml) was added thereto. The mixture was stirred at the same temperature for 2 hours. The reaction mixture was concentrated, diluted with water and then washed with ether. The aqueous layer was cooled, acid acidified to pH 2 with 1N aqueous hydrochloric acid and then extracted four times with a mixture of methylene chloride and ethyl acetate (1:1).

The combined extracts were washed twice with water and brine, dried over anhydrous magnesium sulfate and then evaporated to give amorphous solid (1.2 g).

The solid was dissolved in methylene chloride (2 ml) and diluted with ether (30 ml) to give an oily precipitate and the supernatant was decanted. This operation was repeated three times. The resulting precipitate was dissolved in methylene chloride and the solution was evaporated and pumped to give D—Lac(oAc)—L—Ala—γ—D—Glu(α—oBzl)—(L)—Boc—(D-)meso—DAP—(D)—GlyOH (3) (932 mg) as an amorphous solid.

N.M.R. (CDCl₃—CD₃OD), δ (ppm): 1.38 (3H, d, J=7 Hz), 1.47 (9H, s), 1.49 (3H, d, J=7 Hz), 1.2-2.0 (6H, m), 2.0-2.5 (4H, m), 2.15 (3H, s), 3.99 (2H, broad s), 5.02 (1H, q, J=7 Hz), 5.20 (2H, s), 7.39 (5H, s).

EXAMPLE 141

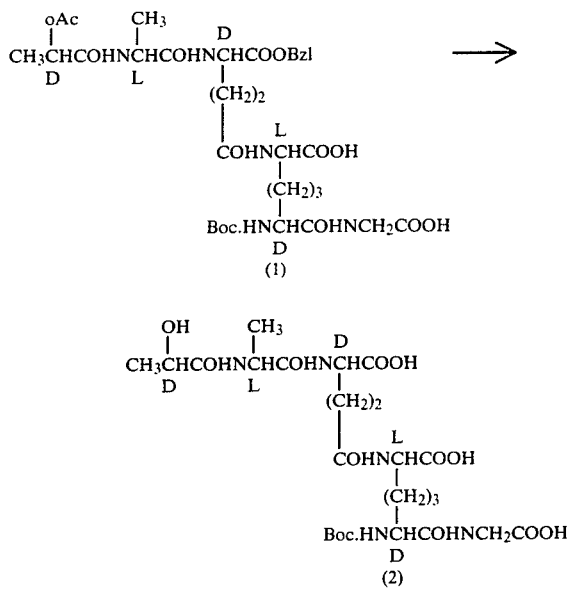

1N Aqueous sodium hydroxide (4.6 ml) was added to a solution of D—Lac(oAc)—L—Ala—γ—D—Glu(α—oBzl)—(L)—Boc—(D)—meso—DAP—(D-)—GlyOH (1) (865 mg) in a mixture of methanol (8 ml) and water (4 ml) was stirred at ambient temperature for two hours.

The reaction mixture was cooled to 0° C., neutralized to pH 7 with 1N aqueous hydrochloric acid and then concentrated. The concentrate was diluted with water and washed with ether. The aqueous layer was concentrated and the concentrate was acidified to pH 2 with 1N aqueous hydrochloric acid and then chromatographed on a macroporous non-ionic adsorption resin, HP20 (40 ml) eluting with 50% aqueous methanol. The eluate was concentrated, triturated in ether and then evaporated to give D—Lac—L—Ala—γ—D—Glu(α—OH)—(L)—Boc—(D)—meso—DAP—(D)—GlyOH (2) (600 mg).

N.M.R. (D$_2$O), δ (ppm): 1.0-2.8 (16H, m), 1.43 (9H, s), 3.83-4.5 (4H, m), 3.96 (2H, s).

EXAMPLE 142

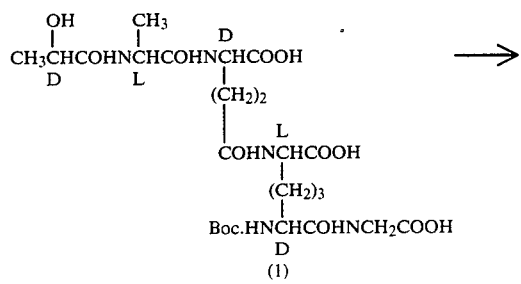

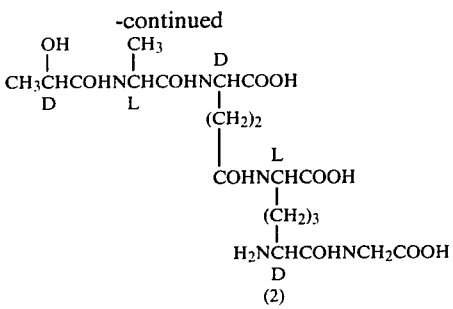

D—Lac—L—Ala—γ—D—Glu(α—OH)—(L-)—Boc—(D)—meso—DAP—(D)—GlyOH (1) (560 mg) was dissolved in tetrahydrofuran (5 ml) and the solution was stirred at ambient temperature for 15 minutes. The reaction mixture was evaporated to dryness. The residue was triturated with ether and the supernatant was discarded. The residue thus obtained was pumped to give a solid materials (647 mg). The solid materials were dissolved in water and the solution was adjusted to pH 3.0 with 1N aqueous hydrochloric acid and chromatographed on a macroporous non-ionic adsorption resin, HP20 (40 ml). The fractions containing the object compound were collected, concentrated and then lyophilized to give D—Lac—L—Ala—γ—D—Glu(α—OH)—(L)—meso—DAP(D)GlyOH (2) (324 mg).

N.M.R. (D$_2$O), δ (ppm): 1.1-2.5 (10H, m), 1.37 (5H, d, J=7 Hz), 1.43 (3H, d, J=7 Hz), 4.01 (2H, s), 4.09 (1H, t, J=6 Hz), 4.2-4.6 (5H, m).

[α]$_D^{25}$ = −35.4° (C=0.26, water).

EXAMPLE 143

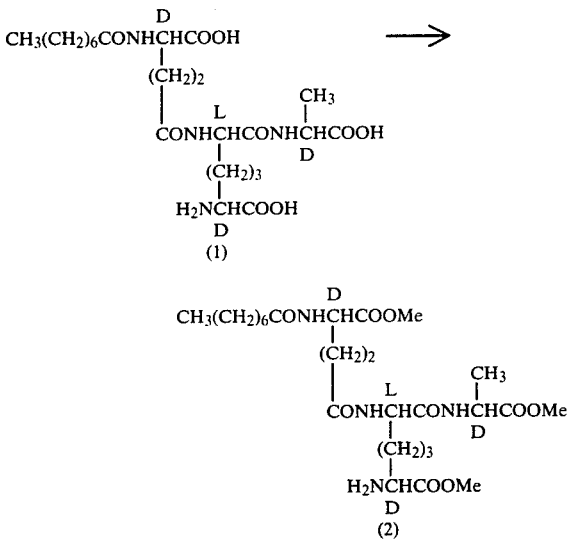

To a solution of n-octanoyl—γ—D—Glu(α—OH-)—(L)—mesoDAP—D—AlaOH (1) (150 mg) in methanol (150 ml) was added conc. hydrochloric acid (1 ml) was added at ambient temperature. The mixture was stood for two weeks at the same temperature. To the reaction mixture was added triethylamine in order to adjust the pH of the solution to 7 to 8. Evaporation of the solvent in vacuo gave an oily residue, which was extracted with ethyl acetate. The extract was washed with water and brine, and then dried over magnesium sulfate. After evaporation of the solvent in vacuo, the residue was pulverized with isopropyl ether to give n—octanoyl—γ—D—Glu(α—oMe)—(L-)—mesoDAP—D—AlaOMe—(D)—oMe (2) (102 mg).

NMR (CDCl₃), δ(ppm): 0.90 (3H, t, J=7 Hz), 1.00–2.33 (25H, m), 3.73 (9H, s), 4.33–4.66 (4H, m), 6.50–7.50 (5H, m).

EXAMPLE 144

(1) Step 1

DL—2,3—Diacetoxypropionyl—L—Ala—γ—D—Glu(α—oBzl)—(L)—Z—(D)—mesoDAP—(D-)—NHNHZ—(L)—GlyOH was prepared substantially in the same manner as that of Step 1 of Example 1.

NMR (CDCl₃), δ(ppm): 1.36 (3H, d, J=7 Hz), 2.01 (3H, s), 2.12 (3H, s), 3.95 (2H, s), 4.25–4.65 (6H, m), 5.03–5.30 (8H, m), 7.35 (15H, s).

(2) Step 2

DL—2,3—Diacetoxypropionyl—L—Ala—γ—D—Glu(α—OH)—(L)—mesoDAP—(L)—GlyOH was prepared substantially in the same manner as that of Step 3 of Example 27.

NMR (D₂O), δ(ppm): 1.42 (3H, d, J=7 Hz), 2.10 (3H, s), 2.21 (3H, s), 3.83 (1H, m), 3.96 (2H, s), 5.30 (1H, t, J=5 Hz).

(3) Step 3

DL—2,3—Dihydroxypropionyl—L—Ala—γ—D—Glu(α—OH)—(L-)—mesoDAP—(L)—GlyOH was prepared substantially in the same manner as that of Step 2 of Example 12.

NMR (D₂O), δ(ppm): 1.47 (3H, d, J=7 Hz), 3.85 (2H, d, J=4 Hz), 4.00 (2H, s), 4.27–4.63 (5H, m).

EXAMPLE 145

(1) Step 1

Stearoyl—L—Ala—γ—D—Glu(α—oBzl)—(L-)—Boc—(D)—mesoDAP—(L)—D—AlaOH was prepared substantially in the same manner as that of Step 1 of Example 27.

NMR (DMSO-d₆), δ(ppm): 0.80–2.40 (60H, m), 4.10–4.60 (5H, m), 5.12 (2H, s), 7.33 (5H, s), 7.80–8.43 (4H, m), 6.80–7.10 (1H, m).

(2) Step 2

Stearoyl—L—Ala—γ—D—Glu(α-oBzl)—(L-)—Boc—(D)—mesoDAP—(L)—D—AlaoMe—(D-)—oMe was prepared substantially in the same manner as that of Step 1 of Example 131.

NMR (CDCl₃), δ(ppm): 0.68–2.53 (65H, m), 3.67 (3H, s), 3.70 (3H, s), 4.10–4.70 (5H, m), 5.13 (2H, s), 6.33–6.67 (1H, m), 7.00 (1H, d, J=8 Hz), 7.30 (5H, s), 7.30–7.70 (2H, m).

(3) Step 3

Stearoyl—L—Ala—γ—D—Glu(α—OH)—(L-)—mesoDAP—(L)—D—AlaoMe—(D)—oMe was prepared substantially in the same manner as that of Step 2 of Example 131.

NMR (DMSO-d₆), δ(ppm): 0.68–2.50 (51H, m), 3.68 L (3H, s), 3.77 (3H, s), 4.0–4.70 (5H, m), 7.80–8.50 (5H, m).

EXAMPLE 146

(1) Step 1

Stearoyl—L—Ala—γ—D—Glu(α—oMe)—(L-)—Boc—(D)—mesoDAP—(D)—oMe—(L-)—D—AlaoMe was prepared substantially in the same manner as that of Step 1 of Example 131.

NMR (CDCl₃), δ(ppm): 0.80–2.68 (60H, m), 3.90 (9H, s), 4.33–4.66 (5H, m).

(2) Step 2

Stearoyl—L—Ala—γ—D—Glu(α—oMe)—(L-)—mesoDAP—(D)—oMe—(L)—D—AlaoMe was prepared substantially in the same manner as that of Step 2 of Example 131.

NMR (CDCl₃-CD₃OD), δ(ppm): 0.68–2.50 (51H, m), 3.87 (6H, s), 3.90 (3H, s), 4.27–4.66 (5H, m).

EXAMPLE 147

(1) Step 1

Stearoyl—L—Val—γ—D—Glu(α—oBzl)—(L-)—Boc—(D)—mesoDAP—(L)—D—AlaOH was prepared substantially in the same manner as that of Step 1 of Example 27.

NMR (DMSO-d₆), δ(ppm): 0.70–2.50 (64H, m), 4.0–4.60 (5H, m), 5.15 (2H, s), 6.70–7.10 (1H, m), 7.36 (5H, s), 7.50–8.50 (4H, m).

(2) Step 2

Stearoyl—L—Val—γ—D—Glu(α—OH)—(L-)—mesoDAP—(L)—D—AlaOH was prepared substantially in the same manner as that of Step 3 of Example 27.

NMR (DMSO-d₆), δ(ppm): 0.68–2.50 (55H, m), 3.67–3.90 (1H, m), 4.0–4.50 (4H, m), 7.50–8.40 (4H, m).

PREPARATION 115

(1) Step 1

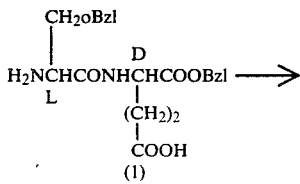

Stearoyl—L—Ser(oBzl)—D—Glu(α—oBzl) (2) was prepared substantially in the same manner as Preparation 85.

NMR (CDCl₃-CD₃OD), δ(ppm): 0.90 (3H, m), 1.1–1.9 (30H, m), 1.95–2.65 (6H, m), 3.60–3.90 (3H, m), 4.32 (2H, s), 5.19 (2H, s), 7.35 (10H, s).

(2) Step 2

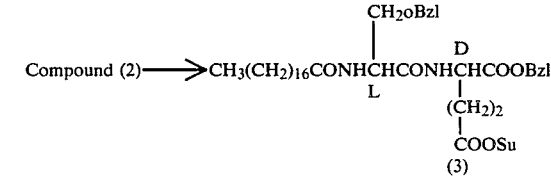

Stearoyl—L—Ser(oBzl)—D—Glu(α—oBzl)—γ—OSu (3) was prepared substantially in the same manner as Preparation 86.

NMR (CDCl₃, δ): 0.89 (3H, m), 1.28 (30H, s), 2.81 (4H, s), 4.56 (2H, s), 5.20 (2H, s), 7.33 (5H, s), 7.36 (5H, s).

PREPARATION 116

(1) Step 1

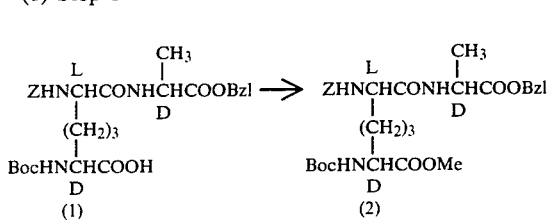

Z—(L)—Boc—(D)—mesoDAP—(L)—D—Alaobzl (1) (11.0 g) was dissolved in methanol (100 ml) and the solution of diazomethane in ether was added thereto. After stirring for 15 minutes, the resultant mixture was treated with acetic acid, concentrated in vacuo. The residue was dissolved in ethyl acetate and washed with 3% sodium bicarbonate, dried over magnesium sulfate and then concentrated in vacuo to give Z—(L-)—Boc—(D)—mesoDAP—(L)—D—Ala(oBzl)—(D-)—OMe (2) (9.1 g).

NMR (CDCl$_3$), δ(ppm): 1.3-2.0 (18H, m), 3.72 (3H, s), 4.32 (1H, m), 4.82 (1H, t, J=7), 5.12 (2H, s), 5.18 (2H, s), 5.59 (1H, d, J=8), 6.82 (1H, d, J=8), 7.37 (10H, s).

(2) Step 2

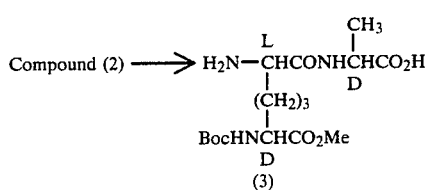

Z—(L)—Boc—(D)—mesoDAP—(L-)—D—Ala(oBzl)—(D)—OMe (2) (9.1 g) was dissolved in a mixture of methanol (100 ml) and water (20 ml), and hydrogenated under 32 atmospheric pressure of hydrogen over 10% palladium-carbon. After removal of the catalyst, the mixture was concentrated and treated with ether to give a crystalline mass (5.7 g), which was purified by using HP° to give Boc—(D-)—mesoDAP—(L)—D—AlaOH—(D)—OMe (3) (5.02 g).

NMR (CDCl$_3$), δ(ppm): 1.30-2.00 (18H, m), 3.72 (3H, s), 3.90-4.45 (3H, m).

PREPARATION 117

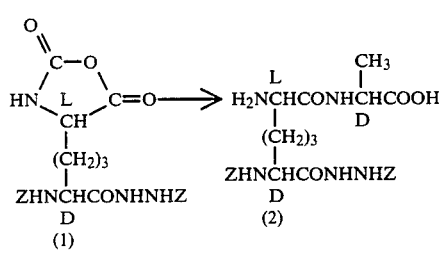

Z—(D)—mesoDAP—(D)—NHNHZ—(L-)—D—AlaOH (2) was prepared substantially in the same manner as Preparation 63.

mp. 161°-165° C. (dec.).

PREPARATION 118

(1) Step 1

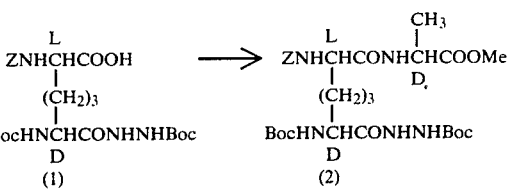

Z—(L)—Boc—(D)—mesoDAP—(L-)—D—AlaOMe—(D)—NHNHBoc (2) was prepared substantially in the same manner as step 1 of Preparation 53.

NMR (DMSO-d$_6$), δ(ppm): 1.05-1.95 (2H, m), 3.65 (3H, s), 3.70-4.65 (3H, m), 5.08 (2H, s), 6.70 (1H, m), 7.35 (5H, s), 8.34 (2H, m), 8.68 (1H, m), 9.61 (1H, s).

(2) Step 2

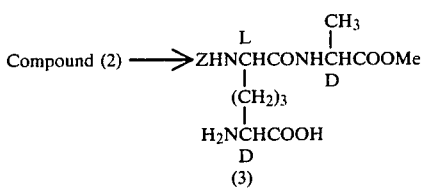

Z—(L)—mesoDAP—(L)—D—AlaOMe (3) was prepared substantially in the same manner as step 2 of Preparation 53.

NMR (CD$_3$OD), δ(ppm): 1.35 (3H, d, J=7 Hz), 1.45-2.10 (6H, m), 3.71 (3H, s), 4.15 (1H, m), 4.42 (1H, q, J=7 Hz), 5.11 (2H, s), 7.36 (5H, s).

(3) Step 3

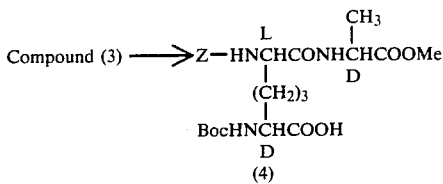

Z—(L)—Boc—(D)—mesoDAP—(L-)—D—AlaOMe (4) was prepared substantially in the same manner as step 3 of Preparation 53.

NMR (CD$_3$OD), δ(ppm): 1.35 (3H, d, J=7 Hz), 1.43 (9H, s), 3.69 (3H, s), 4.16 (1H, m), 4.41 (1H, q, J=7 Hz), 5.10 (2H, s), 7.34 (5H, s).

(4) Step 4

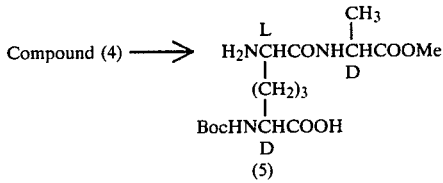

Boc—(D)—mesoDAP—(L)—D—AlaOMe (5) was prepared substantially in the same manner as step 4 of Preparation 53.

NMR (CD$_3$OD), δ(ppm): 1.2-2.0 (18H, m), 3.77 (3H, s), 3.7-4.1 (2H, m), 4.51 (1H, q, J=7 Hz).

PREPARATION 119

(1) Step 1

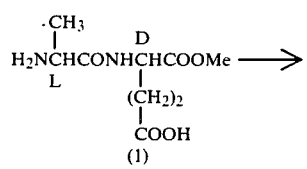

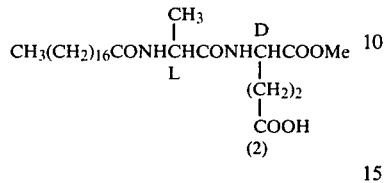

Stearoyl—L—Ala—D—GluOMe (2) was prepared substantially in the same manner as Preparation 85.

NMR (CDCl₃-CD₃OD), δ(ppm): 0.90 (3H, m), 1.30 (30H, s), 1.42 (9H, s), 3.79 (3H, s).

(2) Step 2

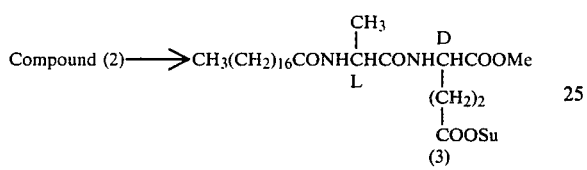

Stearoyl—L—Ala—D—Glu(α—OMe)(γ—OSu) (3) was prepared substantially in the same manner as Preparation 86.

NMR (CDCl₃), δ(ppm): 0.89 (3H, m), 1.30 (30H, s), 1.45 (9H, s), 2.88 (4H, s), 4.4–4.9 (2H, m), 6.61 (1H, d, J=7 Hz), 7.57 (1H, d, J=7 Hz).

PREPARATION 10

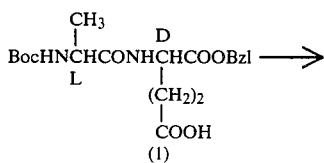

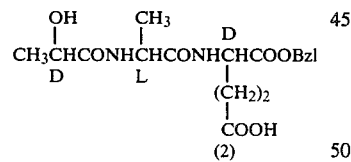

Boc—L—Ala—D—Glu(α—OBzl)(1) (1.68 g) was added to trifluoroacetic acid (10 ml) and the mixture was stirred for 15 minutes at ambient temperature. After evaporation of trifluoroacetic acid, the residue was dissolved in dioxane (30 ml). The solution was neutralized with triethylamine and then a solution of D—LacOSu (0.77 g) in methyl cyanide (10 ml) was added thereto. The resulting mixture was stirred for 5 hours at ambient temperature and the solvent was removed under reduced pressure. The residue was dissolved in ethyl acetate and the ethyl acetate layer was washed with water (30 ml×2), dried over magnesium sulfate and then concentrated under reduced pressure to give an oil. The oil was chromatographed on silica gel and eluted with a mixture of chloroform and methanol (20:1) to give D—Lac—L—Ala—D—Glu(α—OBzl) (2) (0.77 g).

NMR (CDCl₃), δ(ppm): 1.40 (6H, d, J=7 Hz), 1.8–2.6 (4H, m), 4.2–4.8 (3H, m), 5.17 (2H, s), 7.35 (5H, s).

PREPARATION 121

(1) Step 1

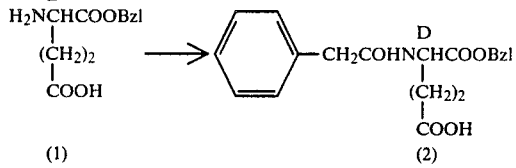

Phenylacetyl—D—Glu(α—OBzl)(2) was prepared substantially in the same manner as Preparation 85.

NMR (CDCl₃), δ(ppm): 1.80–2.50 (4H, m), 3.50 (2H, s), 4.50–4.90 (1H, m), 5.13 (2H, s), 6.33 (1H, d, J=8 Hz), 7.26 (5H, s), 7.33 (5H, s), 9.76 (1H, s).

(2) Step 2

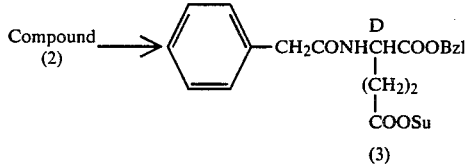

Phenylacetyl—D—Glu(α—OBzl)—γ—OSu (3) was prepared substantially in the same manner as Preparation 86.

NMR (CDCl₃), δ(ppm): 2.06–2.72 (4H, m), 2.76 (4H, s), 3.66 (2H, s), 4.60–4.88 (1H, m), 5.20 (2H, s), 6.64 (1H, d, J=8 Hz), 7.40 (5H, s), 7.48 (5H, s).

PREPARATION 122

(1) Step 1

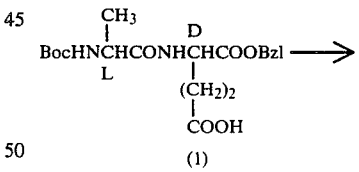

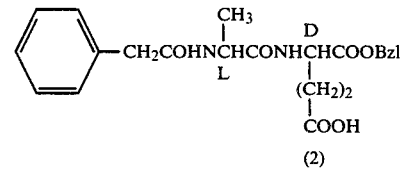

Phenylacetyl—L—Ala—D—Glu(α—OBzl) (2) was prepared substantially in the same manner as Preparation 85.

NMR (CDCl₃), δ(ppm): 1.23 (3H, d, J=7 Hz), 1.80–2.50 (4H, m), 3.53 (2H, s), 4.33–4.80 (2H, m), 5.10 (2H, s), 6.90 (1H, d, J=7 Hz), 7.30 (5H, s), 7.40 (5H, s), 7.60 (1H, d, J=7 Hz), 8.83 (1H, s).

(2) Step 2

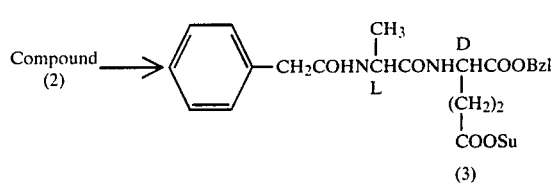

Phenylacetyl—L—Ala—D—Glu(α—OBzl)—γ—OSu (3) was prepared substantially in the same manner as Preparation 86.

NMR (CDCl₃), δ(ppm): 1.23 (3H, d, J=7 Hz), 1.84-2.67 (4H, m), 2.76 (4H, s), 3.53 (2H, s), 4.40-4.86 (2H, m), 5.13 (2H, s), 6.40 (1H, d, J=8 Hz), 7.27 (5H, s), 7.33 (5H, s).

PREPARATION 123

(1) Step 1

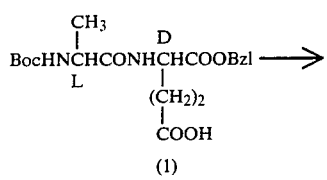

n—Octanoyl—L—Ala—D—Glu(α—OBzl)(2) was prepared substantially in the same manner as Preparation 85.

NMR (CDCl₃), δ(ppm): 0.68-2.50 (22H, m), 4.40-4.80 (2H, m), 5.15 (2H, s), 6.70 (1H, d, J=7 Hz), 7.30 (5H, s), 7.54 (1H, d, J=7 Hz), 9.50 (1H, s).

(2) Step 2

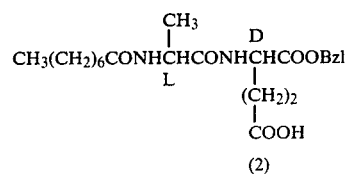

n—Octanoyl—L—Ala—D—Glu(α—OBzl)—γ—OSu (3) was prepared substantially in the same manner as Preparation 86.

NMR (CDCl₃), δ(ppm): 0.92 (3H, t, J=7 Hz), 1.10-1.80 (15H, m), 2.0-2.80 (4H, m), 2.82 (4H, s), 4.50-4.84 (2H, m), 5.24 (2H, s), 6.68 (1H, d, J=8 Hz), 7.44 (5H, s), 7.68 (1H, d, J=8 Hz).

PREPARATION 124

(1) Step 1

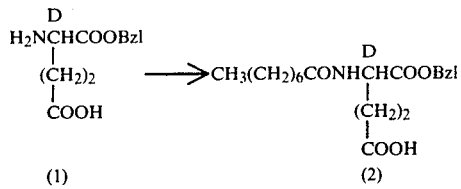

n—Octanoyl—D—Glu(α—Obzl)(2) was prepared substantially in the same manner as Preparation 85.

NMR (CDCl₃), δ(ppm): 0.87 (3H, t, J=7 Hz), 1.0-2.60 (16H, m), 4.50-5.00 (1H, m), 5.20 (2H, s), 6.35 (1H, d, J=7 Hz), 7.40 (5H, s), and 9.90 (1H, s).

(2) Step 2

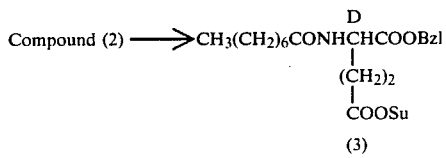

n—Octanoyl—D—Glu(α—Obzl)—γ—Osu (3) was prepared substantially in the same manner as Prepation 86.

NMR (CDCl₃), δ(ppm): 0.90 (3H, t, J=7 Hz), 1.20-1.80 (12H, m), 2.16-2.80 (4H, m), 2.86 (4H, s), 4.68-4.96 (1H, m), 5.62 (2H, s), 6.52 (1H, d, J=8 Hz), 7.48 (5H, s).

PREPARATION 125

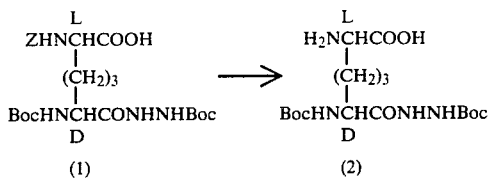

Boc—(D)—mesoDAP—(D)—NHNHBoc (2) was prepared substantially in the same manner as Preparation 20.

NMR (CD₃OD-D₂O), δ(ppm): 1.50-2.20 (24H, m), 3.60-3.90 (1H, m), 4.00-4.20 (1H, m).

EXAMPLE 148

(1) Step 1

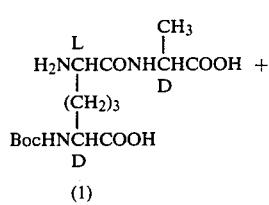

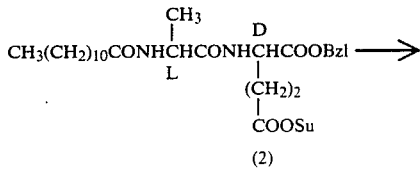

-continued

```
         CH3   D
CH3(CH2)10CONHCHCONHCHCOOBzl
         L    |
              (CH2)2
                   L    CH3
                   CONHCHCONHCHCOOH
                        |         D
                        (CH2)3
                        |
                        BocHNCHCOOH
                             D
```
(3)

Lauroyl—L—Ala—γ—D—Glu(α—oBzl)—(L-)—Boc—(D)—mesoDAP—(L)—D—Ala(OH) (3) was prepared substantially in the same manner as step 1 of Example 125.

NMR (DMSO-$d_6$): δ, 0.80–2.50 (48H, m), 4.0–4.50 (5H, m), 5.10 (2H, s), 6.80–7.00 (1H, m), 7.33 (5H, s), 7.70–8.40 (4H, m).

(2) Step 2

Compound (3) ⟶

```
         CH3   D
CH3(CH2)10CONHCHCONHCHCOOMe
         L    |
              (CH2)2
                   L    CH3
                   CONHCHCONHCHCOOMe
                        |         D
                        (CH2)3
                        |
                        BocHNCHCOOMe
                             D
```
(4)

Lauroyl—L—Ala—γ—D—Glu(α—oMe)—(L-)—Boc—(D)—mesoDAP—(L)—D—Ala(oMe)—(D-)—oMe (4) was prepared substantially in the same manner as step 1 of Example 131.

NMR (CDCl$_3$): δ, 0.80–2.50 (48H, m), 3.73 (9H, s), 4.10–4.70 (5H, m), 5.30 (1H, d, J=8 Hz), 6.50 (1H, broad s), 6.96 (1H, d, J=8 Hz), 7.33–7.65 (2H, m).

(3) Step 3

Compound (4) ⟶

```
         CH3   D
CH3(CH2)10CONHCHCONHCHCOOMe
         L    |
              (CH2)2
                   L    CH3
                   CONHCHCONHCHCOOMe
                        |         D
                        (CH2)3
                        |
                        HClH2NCHCOOMe
                             D
```
(5)

Lauroyl—L—Ala—γ—D—Glu(α—oMe)—(L-)—mesoDAP—(L)—D—Ala(oMe)—(D)—oMe hydrochloric acid salt (5) was prepared substantially in the same manner as step 1 of Example 131.

NMR (DMSO-$d_6$): δ, 0.80–2.40 (39H, m), 3.68 (6H, s), 3.78 (3H, s), 3.88–4.00 (1H, m), 4.12–4.50 (4H, m), 8.04 (2H, t, J=8 Hz), 8.20 (2H, t, J=8 Hz), 8.64 (2H, broad).

EXAMPLE 149

(1) Step 1

```
      L   CH3
H2NCHCONHCHCOOH   +
      |        D
      (CH2)3
      |
BocHNCHCOOH
      D
```
(1)

```
         CH2oBzl  D
CH3(CH2)16CONHCHCONHCHCOOBzl  ⟶
         L      |
                (CH2)2
                |
                COOSu
```
(2)

```
         CH2oBzl  D
CH3(CH2)16CONHCHCONHCHCOOBzl
         L      |
                (CH2)2
                     L    CH3
                     CONHCHCONHCHCOOH
                          |         D
                          (CH2)3
                          |
                          BocHNCHCOOH
                               D
```
(3)

Stearoyl—L—Ser(oBzl)—γ—D—Glu(α—oBzl)—(L)—Boc—(D)—mesoDAP—(L)—D—AlaOH (3) was prepared substantially in the same manner as step 1 of Example 125.

NMR (CDCl$_3$-CD$_3$OD), δ(ppm): 0.88 (3H, m), 1.1–1.4 (30H, m), 1.45 (9H, s), 3.6–3.9 (2H, m), 4.53 (2H, s), 5.15 (2H, s), 7.31 (10H, s).

(2) Step 2

Compound (3) ⟶

```
         CH2OH   D
CH3(CH2)16CONHCHCONHCHCO2H
         L      |
                (CH2)2
                     L    CH3
                     CONHCHCONHCHCO2H
                          |         D
                          (CH2)3
                          |
                          BocHNCHCO2H
                               D
```
(4)

Stearoyl—L—Ser—γ—D—Glu(α—OH)—(L-)—Boc—(D)—mesoDAP—(L)—D—Ala(OH) (4) was prepared substantially in the same manner as step 2 of Example 96.

NMR (CDCl$_3$-CD$_3$OD), δ(ppm): 0.90 (3H, m), 1.30 (30H, s), 1.46 (9H, s), 2.1–2.55 (4H, m), 3.65–4.80 (7H, m).

(3) Step 3

Compound (4) ⟶

-continued

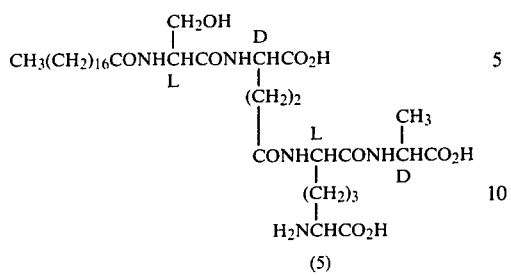
(5)

Stearoyl—L—Ser—γ—D—Glu(α—OH)—(L-)—mesoDAP—(L)—D—Ala(OH) (5) was prepared substantially in the same manner as step 3 of Example 96.

NMR (CDCl₃, CD₃OD), δ(ppm): 0.90 (3H, m), 1.05–2.60 (45H, m), 4.02 (1H, m), 4.30–4.95 (6H, m).

EXAMPLE 150

(1) Step 1

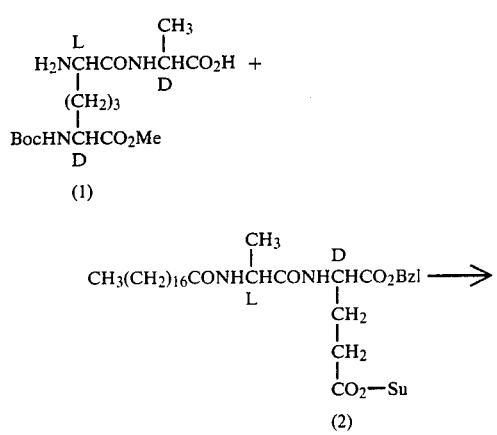

Stearoyl—L—Ala—γ—D—Glu(α—oBzl)—(L-)—Boc—(D)—mesoDAP—(L)—D—Ala—(D)—oMe (3) was prepared substantially in the same manner as step 1 of Example 125.

NMR (CDCl₃-CD₃OD), δ(ppm): 0.90 (3H, s), 1.28 (30H, s), 1.40 (9H, s), 3.74 (3H, s), 4.05–4.60 (5H, m), 5.18 (2H, s), 7.36 (5H, s).

(2) Step 2

Compound (3) ⟶

-continued

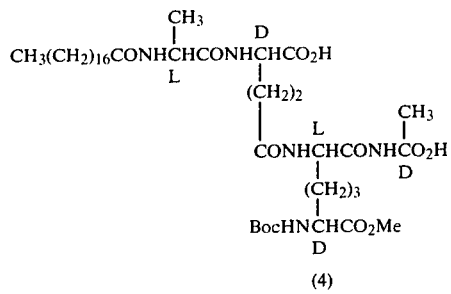
(4)

Stearoyl—L—Ala—γ—D—Glu(α—OH)—(L-)—Boc(D)—mesoDAP—(L)—D—Ala(OH)—(D-)—oMe (4) was prepared substantially in the same manner as step 2 of Example 96.

NMR (CDCl₃-CD₃OD), δ(ppm): 0.89 (3H, m), 1.30 (30H, s), 1.46 (9H, s), 3.77 (3H, s), 4.05–4.60 (5H, m).

(3) Step 3

Compound (4) ⟶

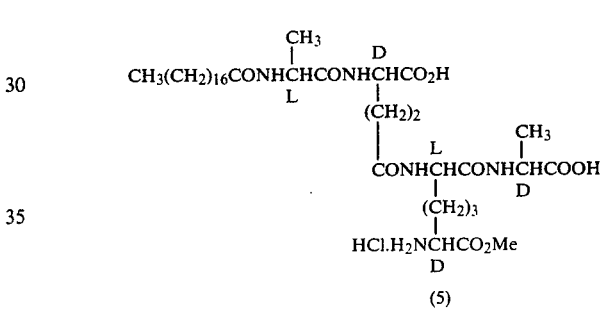
(5)

Stearoyl—L—Ala—γ—D—Glu(α—OH)—(L-)—mesoDAP—(L)—D—Ala(OH)—(D)—oMe hydrochloric acid salt (5) was prepared substantially in the same manner as step 3 of Example 96.

NMR (DMSO-d₆), δ(ppm): 0.85 (3H, m), 3.74 (3H, s), 3.8–4.55 (5H, m).

EXAMPLE 151

(1) Step 1

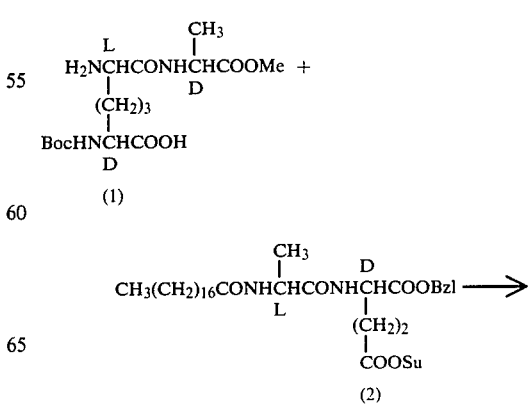

-continued

```
         CH3     D
         |      |
CH3(CH2)16CONHCHCONHCHCOOBzl
         L      |
                (CH2)2
                |       CH3
                |    L  |
                CONHCHCONHCHCOOMe
                    |         D
                    (CH2)3
                    |
                    BocHNCHCOOH
                         D
                    (3)
```

Stearoyl—L—Ala—γ—D—Glu(α—oBzl)—(L-)—Boc—(D)—mesoDAP—(L)—D—AlaOMe (3) was prepared substantially in the same manner as step 1 of Example 125.

NMR (CDCl$_3$-CD$_3$OD), δ(ppm): 0.88 (3H, m), 1.27 (30H, s), 1.42 (9H, s), 3.71 (3H, s), 4.03–4.65 (5H, m), 5.18 (2H, s), 7.35 (5H, s).

(2) Step 2

Compound (3) ⟶

```
         CH3     D
         |      |
CH3(CH2)16CONHCHCONHCHCOOH
         L      |
                (CH2)2
                |       CH3
                |    L  |
                CONHCHCONHCHCOOMe
                    |         D
                    (CH2)3
                    |
                    BocHNCHCOOH
                         D
                    (4)
```

Stearoyl—L—Ala—γ—D—Glu(α—OH)—(L-)—Boc—(D)—mesoDAP—(L)—D—AlaOMe (4) was prepared substantially in the same manner as step 2 of Example 96.

NMR (CDCl$_3$-CD$_3$OD), δ(ppm): 0.88 (3H, m), 1.31 (30H, s), 1.46 (9H, s), 3.73 (3H, s), 4.00–4.65 (5H, m).

(3) Step 3

Compound (4) ⟶

```
         CH3     D
         |      |
CH3(CH2)16CONHCHCONHCHCOOH
         L      |
                (CH2)2
                |       CH3
                |    L  |
                CONHCHCONHCHCOOMe
                    |         D
                    (CH2)3
                    |
                    HClH2NCHCOOH
                         D
                    (5)
```

Stearoyl—L—Ala—γ—D—Glu(α—OH)—(L-)—mesoDAP—(L)—D—AlaOMe hydrochloric acid salt (5) was prepared substantially in the same manner as step 2 of Example 131.

NMR (DMSO-d$_6$), δ(ppm): 0.86 (3H, m), 3.68 (3H, s), 3.85 (1H, s), 4.10–4.50 (4H, m).

EXAMPLE 152

(1) Step 1

```
    L      CH3
    |      |
H2NCHCONHCHCOOH  +
    |      D
    (CH2)3
    |
BocHNCHCOOH
    D
    (1)
```

```
         CH3     D
         |      |
CH3(CH2)16CONHCHCONHCHCOOMe  ⟶
         L      |
                (CH2)2
                |
                COOSu
                (2)
```

```
         CH3     D
         |      |
CH3(CH2)16CONHCHCONHCHCOOMe
         L      |
                (CH2)3
                |       CH3
                |    L  |
                CONHCHCONHCHCOOH
                    |         D
                    (CH2)3
                    |
                    BocHNCHCOOH
                         D
                    (3)
```

Stearoyl—L—Ala—γ—D—Glu(α—OMe)—(L-)—Boc(D)—mesoDAP—(L)—D—AlaOH (3) was prepared substantially in the same manner as step 1 of Example 125.

NMR (CDCl$_3$-CD$_3$OD), δ(ppm): 0.89 (3H, m), 1.28 (30H, s), 1.45 (9H, s), 3.76 (3H, s).

(2) Step 2

Compound (3) ⟶

```
         CH3     D
         |      |
CH3(CH2)16CONHCHCONHCHCOOMe
         L      |
                (CH2)2
                |       CH3
                |    L  |
                CONHCHCONHCHCOOH
                    |         D
                    (CH2)3
                    |
                    HClH2NCHCOOH
                         D
                    (4)
```

Stearoyl—L—Ala—γ—D—Glu(α—OMe)—(L-)—mesoDAP—(L)—D—AlaOH hydrochloric acid salt (4) was prepared substantially in the same manner as step 2 of Example 131.

NMR (CDCl$_3$-CD$_3$OD), δ(ppm): 0.98 (3H, m), 1.0–2.5 (38H, m), 3.73 (3H, s), 3.94 (1H, m), 4.20–4.57 (4H, m).

EXAMPLE 153

(1) Step 1

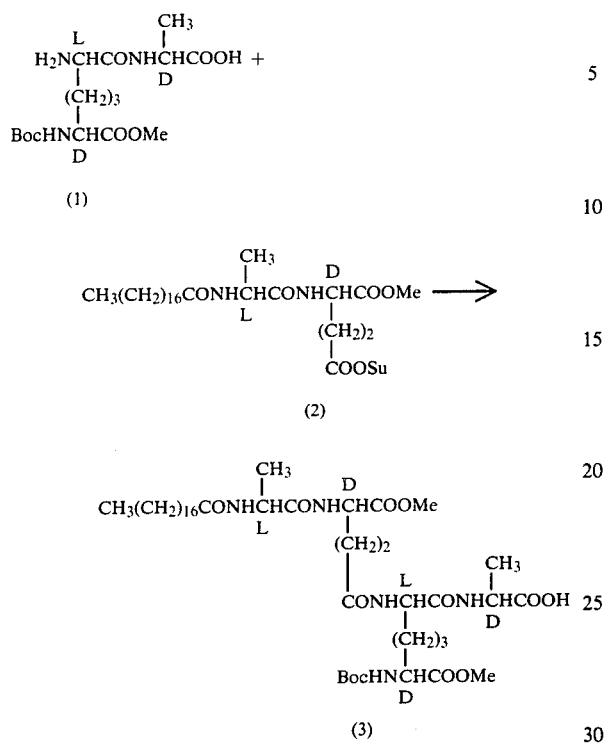

(1)

(2)

(3)

Stearoyl—L—Ala—γ—D—Glu(α—OMe)—(L-)—Boc—(D)—mesoDAP—(L)—D—Ala—(D)—OMe (3) was prepared substantially in the same manner as step 1 of Example 125.

NMR (CDCl$_3$-CD$_3$OD), δ(ppm): 0.92 (3H, m), 1.31 (30H, s), 1.48 (9H, s), 3.77 (6H, s).

(2) Step 2

Compound (3) ⟶

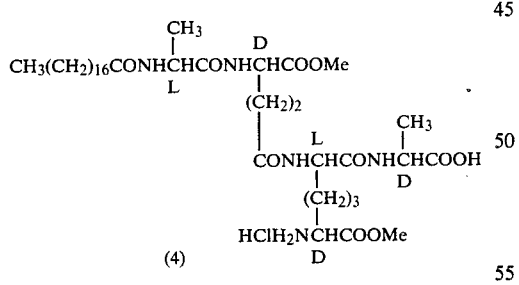

(4)

Stearoyl—L—Ala—γ—D—Glu(α—OMe)—(L-)—mesoDAP—(L)—D—Ala—(D)—OMe hydrochloric acid salt (4) was prepared substantially in the same manner as step 2 of Example 131.

NMR (CDCl$_3$-CD$_3$OD), δ(ppm): 0.90 (3H, m), 1.08–2.47 (48H, m), 3.74 (3H, s), 3.85 (3H, s), 3.93–4.09 (1H, m), 4.25–4.80 (4H, m).

EXAMPLE 154

(1) Step 1

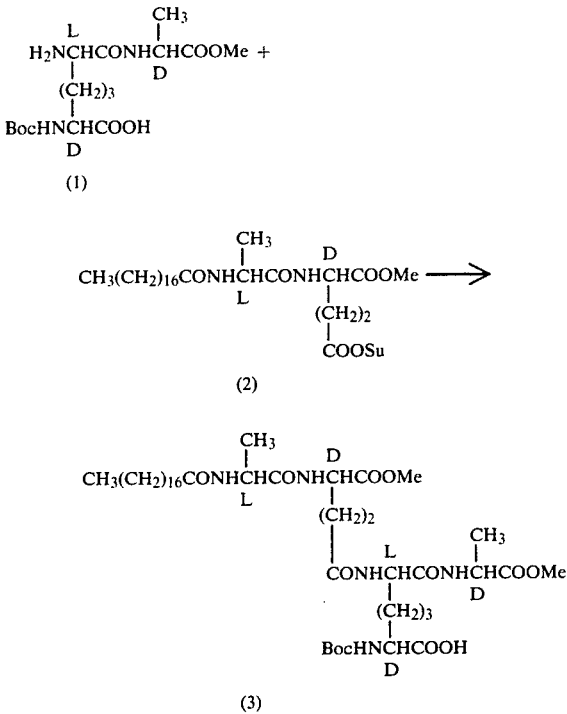

(1)

(2)

(3)

Stearoyl—L—Ala—γ—D—Glu(α—OMe)—(L-)—Boc—(D)—mesoDAP—(L)—D—AlaOMe (3) was prepared substantially in the same manner as step 1 of Example 125.

NMR (CDCl$_3$-CD$_3$OD), δ(ppm): 0.88 (3H, m), 1.28 (30H, s), 1.46 (9H, s), 3.75 (6H, s).

(2) Step 2

Compound (3) ⟶

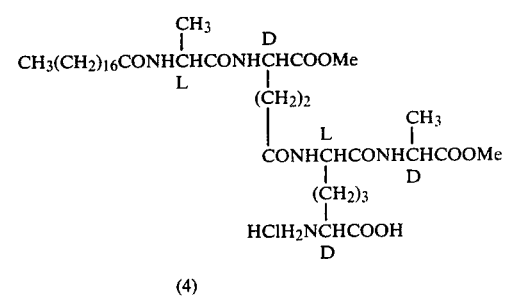

(4)

Stearoyl—L—Ala—γ—D—Glu(α—OMe)—(L-)—mesoDAP—(L)—D—AlaOMe hydrochloric acid salt (4) was prepared substantially in the same manner as step 2 of Example 131.

NMR (CDCl$_3$-CD$_3$OD), δ(ppm): 0.89 (3H, m), 1.0–2.5 (48H, m), 3.75 (6H, s), 3.95 (1H, m), 4.15–4.95 (4H, m).

EXAMPLE 155

(1) Step 1

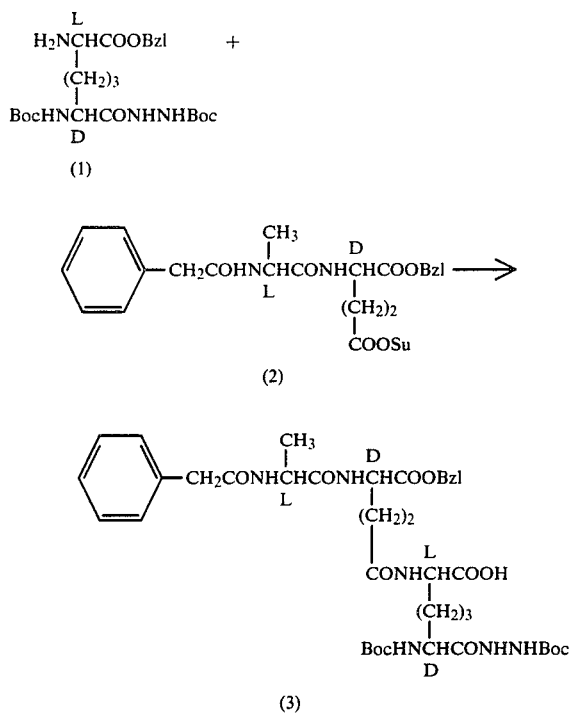

(1), (2), (3)

Phenylacetyl—L—Ala—γ—D—Glu(α—OBzl)—(L)—Boc—(D)—mesoDAP—(D)—NHNHBoc (3) was prepared substantially in the same manner as step 1 of Example 125.

NMR (CD₃OD), δ(ppm): 1.47 (18H, s), 3.60 (2H, s), 5.20 (2H, s), 7.33 (5H, s), 7.40 (5H, s).

(2) Step 2

Compound (3) ⟶

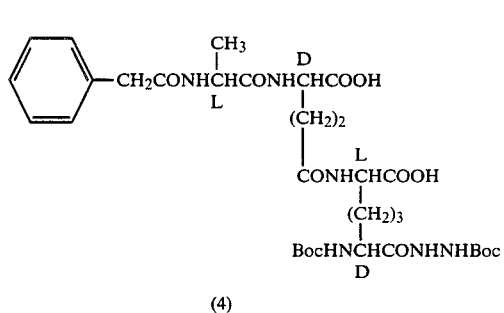

(4)

Phenylacetyl—L—Ala—γ—D—Glu(α—OH)—(L)—Boc—(D)—mesoDAP—(D)—NHNHBoc (4) was prepared substantially in the same manner as step 2 of Example 96.

NMR (CD₃OD), δ(ppm): 1.47 (18H, s), 3.60 (2H, s), 4.00–4.66 (4H, s), 7.30 (5H, s).

(3) Step 3

Compound (4) ⟶

-continued

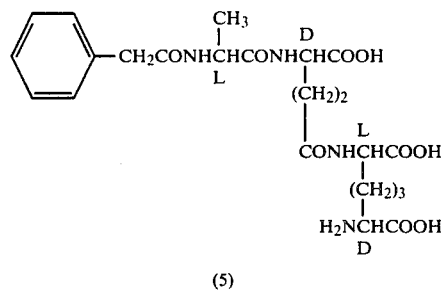

(5)

Phenylacetyl—L—Ala—γ—D—Glu(α—OH)—(L)—mesoDAP (5) was prepared substantially in the same manner as step 3 of Example 96.

NMR (D₂O), δ(ppm): 1.40 (3H, d, J=8 Hz), 3.60 (2H, s), 3.80 (1H, m), 4.24 (2H, t, J=7 Hz), 7.36 (5H, s).

EXAMPLE 156

(1) Step 1

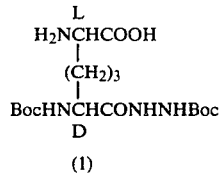

(1)

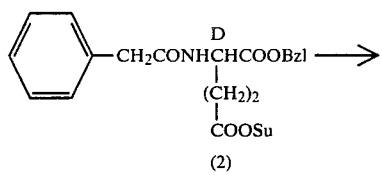

(2)

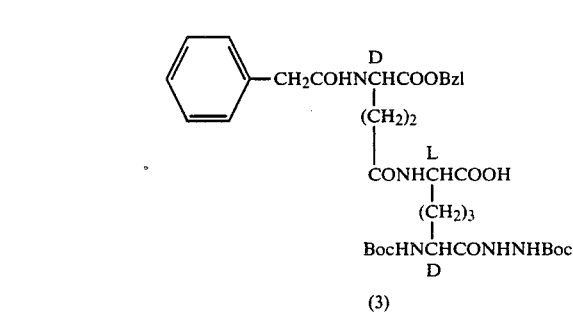

(3)

Phenylacetyl—γ—D—Glu(α—OBzl)—(L)—Boc—(D)—mesoDAP—(D)—NHNHBoc (3) was prepared substantially in the same manner as step 1 of Example 125.

NMR (CD₃OD), δ(ppm): 1.47 (18H, s), 3.65 (2H, broad s), 5.17 (2H, s), 7.30 (5H, s), 7.36 (5H, s).

(2) Step 2

Compound (3) ⟶

-continued

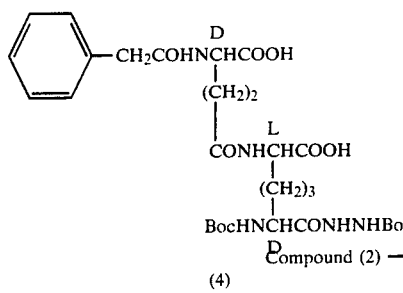
(4)

Phenylacetyl—γ—D—Glu(α—OH)—(L-)—Boc—(D)—mesoDAP—(D)—NHNHBoc (4) was prepared substantially in the same manner as step 2 of Example 96.

(3) Step 3

Compound (4) ⟶ 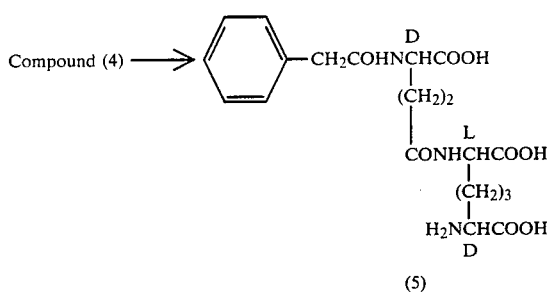
(5)

Phenylacetyl—γ—D—Glu(α—OH)—(L-)—mesoDAP (5) was prepared substantially in the same manner as step 3 of Example 96.

NMR (D$_2$O), δ(ppm): 1.20–2.50 (10H, m), 3.64 (2H, s), 3.72 (1H, t, J=7 Hz), 4.24 (1H, t, J=7 Hz), 4.30 (1H, t, J=7 Hz), 5.36 (5H, s).

EXAMPLE 157

(1) Step 1

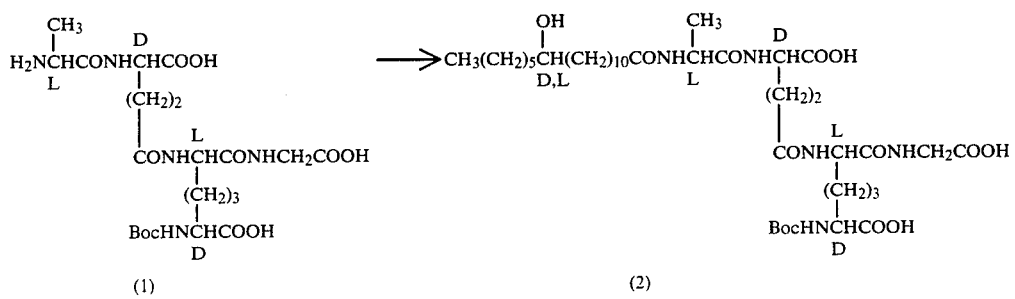

(12—Hydroxy)stearoyl—L—Ala—γ—D—Glu(α—OH)—(L)—Boc—(D)—mesoDAP—(L)—GlyOH (2) was prepared substantially in the same manner as step 1 of Example 1.

NMR (CD$_3$OD), δ(ppm): 0.90 (3H, t, J=5 Hz), 1.25 (9H, s), 1.15–1.83 (39H, m), 2.15–2.42 (4H, m), 3.93 (2H, s), 4.25–4.53 (5H, m).

(2) Step 2

Compound (2) ⟶ 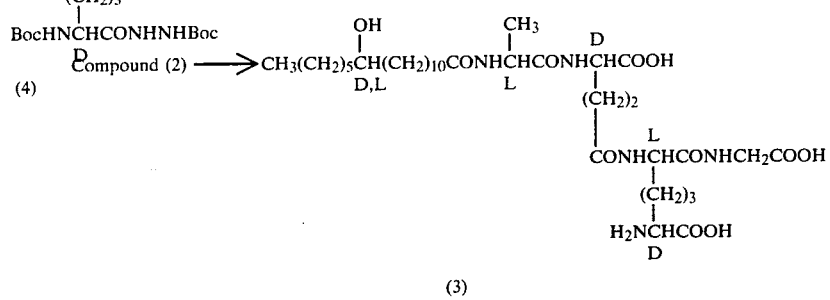
(3)

(12—Hydroxy)stearoyl—L—Ala—D—Glu(α—OH)—(L)—mesoDAP—(L)—GlyOH (3) was prepared substantially in the same manner as step 2 of Example 1.

NMR (DMSO-d$_6$), δ(ppm): 0.83 (3H, t, J=5 Hz), 1.16–1.66 (39H, m), 1.92–2.25 (4H, m), 3.73 (2H, broad s), 4.07–4.25 (5H, m).

EXAMPLE 158

(1) Step 1

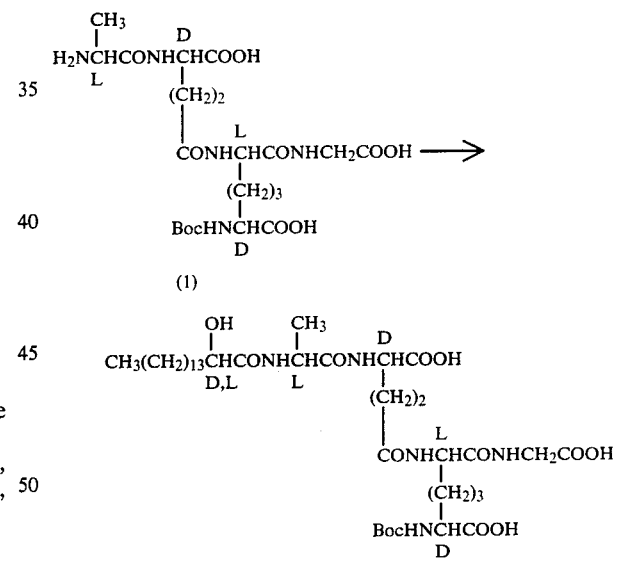

α—D,L—Hydroxypalmitoyl—L—Ala—γ—D—Glu(α—OH)—(L)—Boc—(D)—mesoDAP—(L)—GlyOH (2) was prepared substantially in the same manner as step 1 of Example 1.

NMR (CD₃OD), δ(ppm): 0.92 (3H, t, J=5 Hz), 1.30–1.75 (37H, m), 1.45 (9H, s), 2.30–2.63 (2H, m), 3.97 (2H, s), 4.00–4.58 (5H, m).

(2) Step 2

Compound (2) ⟶

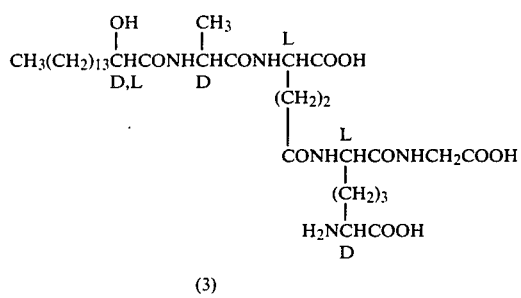

(3)

α—D,L—Hydroxypalmitoyl—L—Ala—γ—D—Glu(α—OH)—(L)—mesoDAP—(L)—GlyOH (3) was prepared substantially in the same manner as step 2 of Example 1.

NMR (DMSO-d₆), δ(ppm): 8.66 (3H, t, J=5 Hz), 1.23–1.75 (37H, m), 2.08–2.23 (2H, m), 3.63 (2H, broad s), 4.13–4.43 (5H, m).

EXAMPLE 159

(1) Step 1

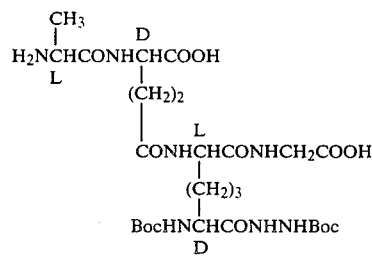

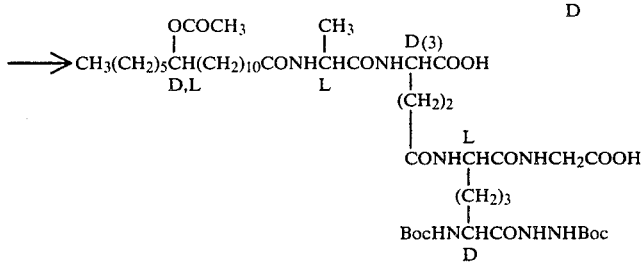

(12—D,L—Acetoxy)stearoyl—L—Ala—γ—D—Glu(α—OH)—(L)—Boc—(D)—mesoDAP—(D-)—NHNHBoc—(L)—GlyOH (2) was prepared substantially in the same manner as step 1 of Example 1.

NMR (CD₃OD), δ(ppm): 0.90 (3H, t, J=5 Hz), 1.30–1.73 (37H, m), 1.43 (9H, s), 2.02 (3H, s), 2.13–2.36 (4H, m), 3.95 (2H, s), 4.33–4.53 (5H, m).

(2) Step 2

Compound (2) ⟶ 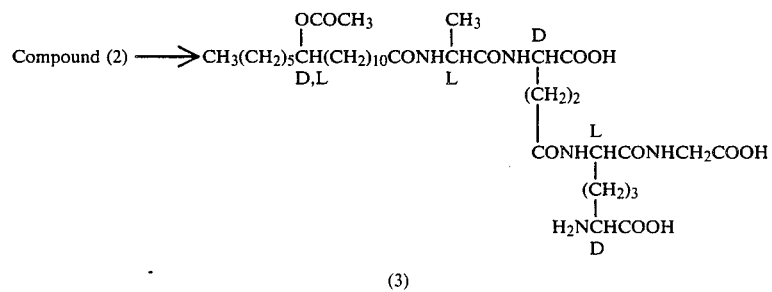

(3)

(12—D,L—Acetoxy)stearoyl—L—Ala—γD—Glu(α—OH)—(L)—mesoDAP—(L)—GlyOH (3) was prepared substantially in the same manner as step 2 of Example 1.

NMR (CD₃OD), δ(ppm): 0.87 (3H, t, J=5 Hz), 1.28–1.73 (37H, m), 2.00 (3H, s), 2.13–2.33 (4H, m), 3.92 (2H, s), 4.30–4.50 (5H, m).

EXAMPLE 160

(1) Step 1

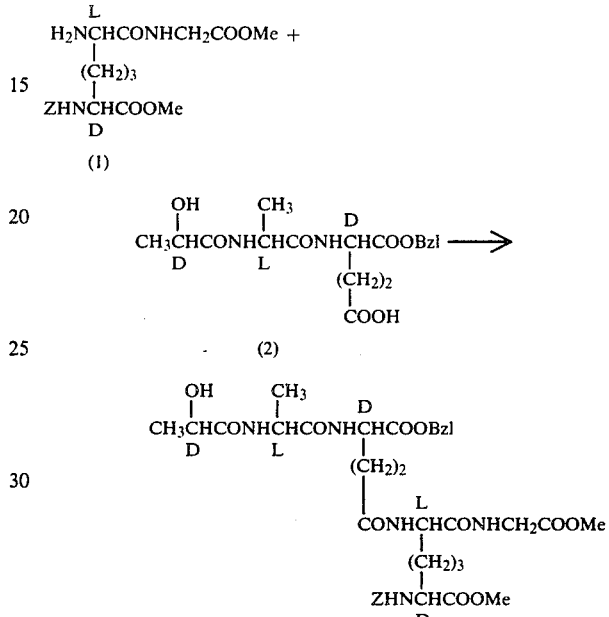

D—Lac—L—Ala—γ—D—Glu(α—OBzl)—(L-)—Z—(D)—mesoDAP—(L)—GlyOMe—(D)—OMe (3) was prepared substantially in the same manner as step 1 of Example 125.

NMR (CD$_3$OD), δ(ppm): 1.37 (6H, d, J=7 Hz), 1.3–2.5 (10H, m), 3.67 (3H, s), 3.70 (3H, s), 3.95 (2H, s), 4.0–4.6 (5H, m), 5.09 (2H, s), 5.17 (2H, s), 7.35 (10H, s).

(2) Step 2

Compound (3) ⟶

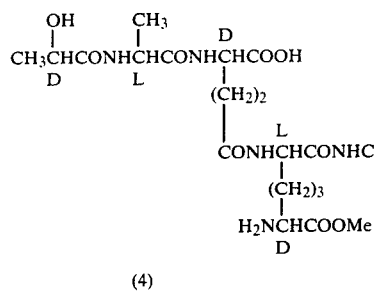

(4)

D—Lac—L—Ala—γ—D—Glu(α—OH)—(L-)—mesoDAP—(L)—GlyOMe—(D)—OMe (4) was prepared substantially in the same manner as Example 73.

NMR (D$_2$O), δ(ppm): 1.37 (3H, d, J=6 Hz), 1.41 (3H, d, J=6 Hz), 1.5–2.4 (10H, m), 3.73 (3H, s), 3.82 (3H, s), 4.00 (2H, s), 4.0–4.5 (5H, m).

EXAMPLE 161

(1) Step 1

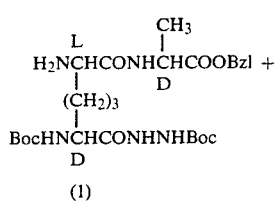

(1)

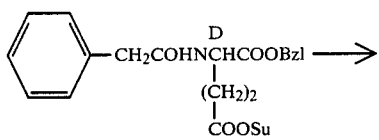

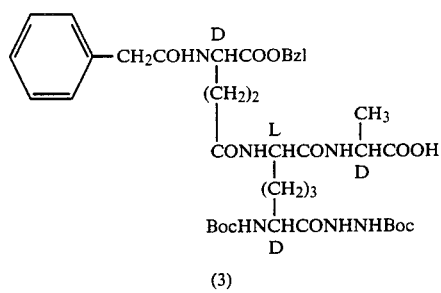

(3)

Phenylacetyl—γ—D—Glu(α—OBzl)—(L-)—Boc—(D)—mesoDAP—(L)—D—Ala—(D-)—NHNHBoc (3) was prepared substantially in the same manner as step 1 of Example 125.

NMR (CDCl$_3$—CD$_3$OD), δ(ppm): 1.48 (18H, s), 3.62 (2H, s), 3.67 (1H, m), 5.19 (2H, s), 7.34 (5H, s), 7.39 (5H, s).

(2) Step 2

Compound (3) ⟶

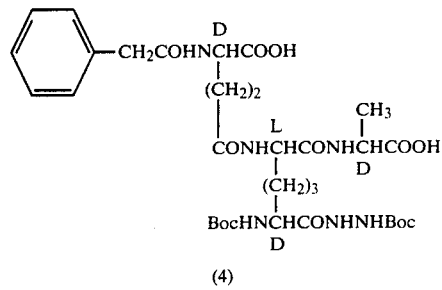

(4)

Phenylacetyl—γ—D—Glu(α—OH)—(L-)—Boc—(D)—mesoDAP—(L)—D—Ala—(D-)—NHNHBoc (4) was prepared substantially in the same manner as step 2 of Example 89.

NMR (DMSO-d$_6$), δ(ppm): 1.30 (3H, d, J=7), 3.55 (2H, s), 3.8–4.8 (4H, m), 6.77 (1H, d, J=8), 7.36 (5H, s), 7.8–8.9 (5H, m), 8.63 (1H, s).

(3) Step 3

Compound (4) ⟶

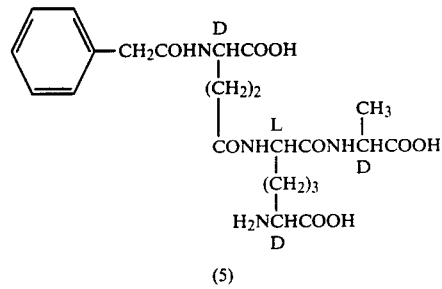

(5)

Phenylacetyl—γ—D—Glu(α—OH)—(L-)—mesoDAP—(L)—D—AlaOH (5) was prepared substantially in the same manner as step 3 of Example 89.

NMR (D$_2$O), δ(ppm): 1.39 (3H, d, J=7 Hz), 1.20–2.55 (10H, m), 3.66 (2H, s), 3.80 (1H, t, J=6 Hz), 4.20–4.55 (3H, m), 7.36 (5H, s).

EXAMPLE 162

(1) Step 1

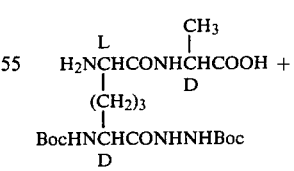

(1)

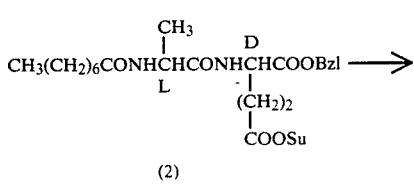

(2)

-continued

```
         CH3  D
CH3(CH2)6COHNCHCONHCHCOOBzl
         L     |
               (CH2)2
                |      CH3
                |   L   |
               CONHCHCONHCHCOOH
                      |    D
                      (CH2)3
                      |
                      BocHNCHCONHNHBoc
                           D
```
(3)

n—Octanoyl—L—Ala—γ—D—Glu(α—OBzl)—(L-)—Boc—(D)—mesoDAP—(L)—D—Ala—(D-)—NHNHBoc (3) was prepared substantially in the same manner as step 1 of Example 125.

NMR (CDCl₃—CD₃OD), δ(ppm): 0.90 (3H, m), 1.15–2.53 (46H, m), 4.27–4.69 (5H, m), 5.21 (2H, s), 7.40 (5H, s).

(2) Step 2

Compound (3) ⟶

```
         CH3  D
CH3(CH2)6CONHCHCONHCHCOOH
         L    |
              (CH2)2
               |     CH3
               |  L   |
              CONHCHCONHCHCOOH
                     |   D
                     (CH2)3
                     |
                     BocHNCHCONHNHBoc
                          D
```
(4)

n—Octanoyl—L—Ala—γ—D—Glu(α—OH)—(L-)—Boc—(D)—mesoDAP—(L)—D—Ala—(D-)—NHNHBoc (4) was prepared substantially in the same manner as step 2 of Example 96.

NMR (DMSO-d₆), δ(ppm): 0.6–2.4 (49H, m), 3.8–4.6 (5H, m), 6.71 (1H, m), 7.75–8.80 (5H, m), 9.60 (1H, s).

(3) Step 3

Compound (4) ⟶

```
         CH3  D
CH3(CH2)6CONHCHCONHCHCOOH
         L    |
              (CH2)2
               |     CH3
               |  L   |
              CONHCHCONHCHCOOH
                     |   D
                     (CH2)3
                     |
                     H2NCHCOOH
                          D
```
(5)

n—Octanoyl—D—Ala—γ—D—Glu(α—OH)—(L-)—mesoDAP—(L)—D—AlaOH (5) was prepared substantially in the same manner as step 3 of Example 96.

NMR (D₂O), δ(ppm): 0.87 (3H, m), 1.1–2.6 (28H, m), 3.85 (1H, t, J=6), 4.2–4.6 (4H, m).

EXAMPLE 163

(1) Step 1

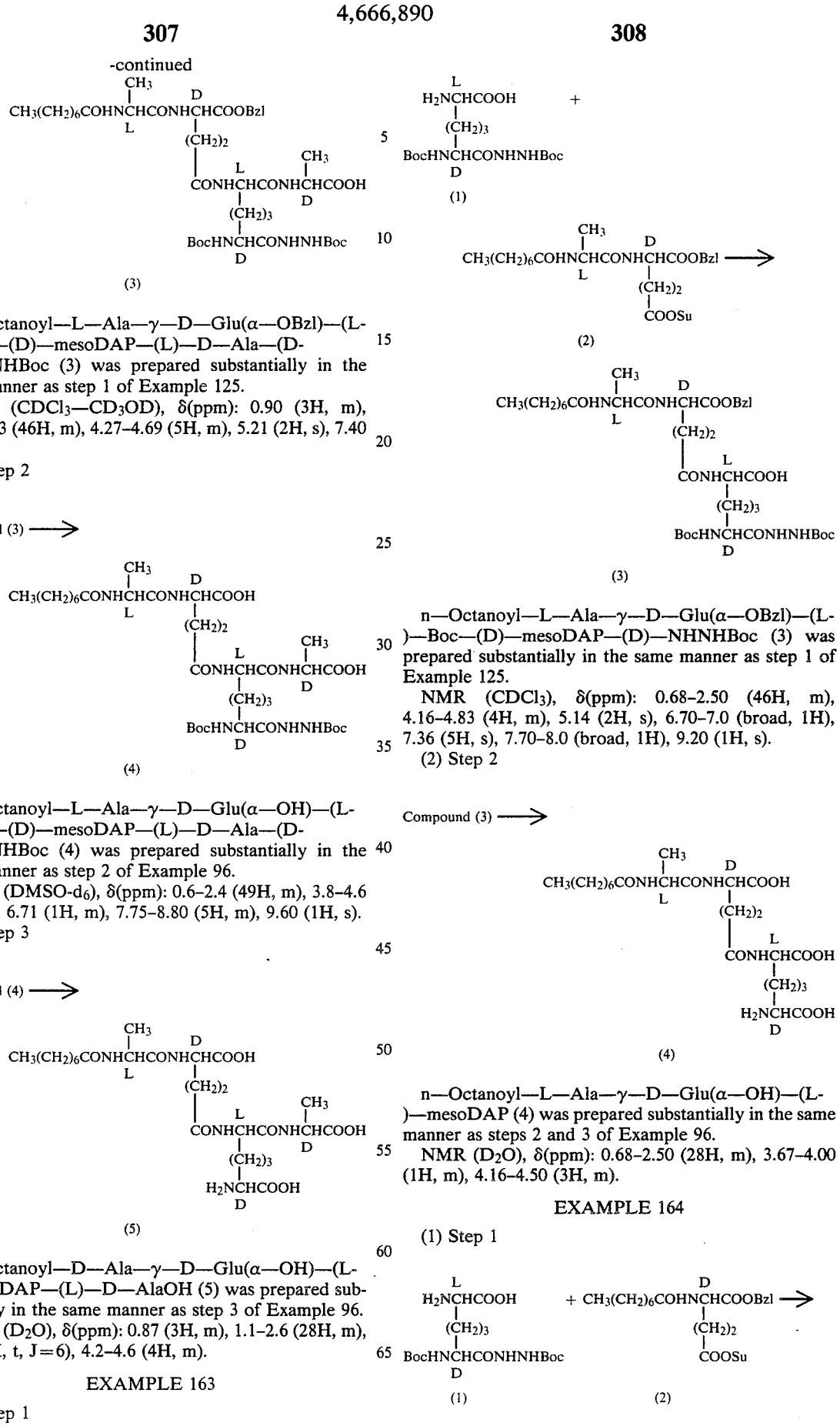

n—Octanoyl—L—Ala—γ—D—Glu(α—OBzl)—(L-)—Boc—(D)—mesoDAP—(D)—NHNHBoc (3) was prepared substantially in the same manner as step 1 of Example 125.

NMR (CDCl₃), δ(ppm): 0.68–2.50 (46H, m), 4.16–4.83 (4H, m), 5.14 (2H, s), 6.70–7.0 (broad, 1H), 7.36 (5H, s), 7.70–8.0 (broad, 1H), 9.20 (1H, s).

(2) Step 2

Compound (3) ⟶ n—Octanoyl—L—Ala—γ—D—Glu(α—OH)—(L-)—mesoDAP (4) was prepared substantially in the same manner as steps 2 and 3 of Example 96.

NMR (D₂O), δ(ppm): 0.68–2.50 (28H, m), 3.67–4.00 (1H, m), 4.16–4.50 (3H, m).

EXAMPLE 164

(1) Step 1

-continued $$\text{CH}_3(\text{CH}_2)_6\text{CONH}\overset{D}{\underset{|}{\text{CH}}}\text{COOBzl}$$
$$\underset{|}{(\text{CH}_2)_2}$$
$$\underset{|}{\text{CONH}\overset{L}{\underset{|}{\text{CH}}}\text{COOH}}$$
$$\underset{|}{(\text{CH}_2)_3}$$
$$\text{BocHN}\overset{D}{\underset{|}{\text{CH}}}\text{CONHNHBoc}$$

(3)

n—Octanoyl—L—Ala—γ—D—Glu(α—OBzl)—(L-)—Boc—(D)—mesoDAP—(D)—NHNHBoc (3) was prepared substantially in the same manner as step 1 of Example 125.

NMR (CDCl$_3$), δ(ppm): 0.70–2.50 (43H, m), 4.0–4.80 (3H, m), 5.20 (2H, s), 5.50–5.80 (1H, m), 6.30–6.60 (2H, m), 6.80–7.10 (2H, m), 7.35 (5H, s), 9.10 (1H, s).

(2) Step 2

$$\text{Compound (3)} \longrightarrow \text{CH}_3(\text{CH}_2)_6\text{CONH}\overset{D}{\underset{|}{\text{CH}}}\text{COOH}$$
$$\underset{|}{(\text{CH}_2)_2}$$
$$\underset{|}{\text{CONH}\overset{L}{\underset{|}{\text{CH}}}\text{COOH}}$$
$$\underset{|}{(\text{CH}_2)_3}$$
$$\text{H}_2\text{N}\overset{D}{\underset{|}{\text{CH}}}\text{COOH}$$

(4)

n—Octanoyl—γ—D—Glu(α—OH)—(L-)—mesoDAP (4) was prepared substantially in the same manner as steps 2 and 3 of Example 96.

NMR (D$_2$O), δ(ppm): 0.68–2.60 (25H, m), 3.80 (1H, t, J=7 Hz), 4.16–4.50 (2H, m).

PREPARATION 126

$$\text{BocHN}\overset{L}{\underset{|}{\text{CH}}}\text{COOSu} + \text{H}_2\text{N}\overset{D}{\underset{|}{\text{CH}}}\text{COOH} \longrightarrow$$
$$\underset{|}{(\text{CH}_2)_4} \quad \underset{}{\text{CH}_3}$$
$$\underset{}{\text{NHZ}}$$

(1)        (2)

$$\text{H}_2\text{N}\overset{L}{\underset{|}{\text{CH}}}\text{CONH}\overset{\text{CH}_3}{\underset{D}{\overset{|}{\text{CH}}}}\text{COOH}$$
$$\underset{|}{(\text{CH}_2)_4}$$
$$\underset{}{\text{NHZ}}$$

(3)

D—AlaOH (2) (1.78 g) was dissolved in a mixture of water (40 ml), dioxane (40 ml) and triethylamine (4.04 g). To this solution was added Boc—L—Lys(ε—Z)OSu (1) (9.26 g) and the resulting solution was left overnight at ambient temperature and then filtered.

The filtrate was evaporated to give an oily residue which was dissolved in water. The solution was acidified with dil hydrochloric acid and then extracted with ethyl acetate. The organic layer was washed with water, dried over magnesium sulfate and then evaporated to give a white foam. The foam was dissolved in trifluoroacetic acid (30 ml) and reacted for 30 minutes at ambient temperature. Excess trifluoroacetic acid was evaporated to give a paste which was dissolved in water. The solution was passed through HP20 column.

The column was eluted with water and water-methanol (1:1), successively. The latter fractions were combined and evaporated to give L—Lys(ε—Z-)—D—AlaOH (3) (4.50 g).

IR (Nujol): 3350, 3300, 1685, 1660, 1640 cm$^{-1}$.

NMR (CD$_3$OD): δ 1.30 (3H, d, J=7 Hz), 1.20–1.70 (6H, m), 2.86–3.50 (2H, m), 4.16 (1H, q, J=7 Hz), 5.00 (2H, s), 7.30 (5H, s).

PREPARATION 127

$$\text{ZHN}\overset{L}{\underset{|}{\text{CH}}}\text{CONHCH}_2\text{COOMe} \longrightarrow$$
$$\underset{|}{(\text{CH}_2)_3}$$
$$\text{BocHN}\overset{D}{\underset{|}{\text{CH}}}\text{COOMe}$$

(1)

$$\text{H}_2\text{N}\overset{L}{\underset{|}{\text{CH}}}\text{CONHCH}_2\text{COOMe}$$
$$\underset{|}{(\text{CH}_2)_3}$$
$$\text{BocHN}\overset{D}{\underset{|}{\text{CH}}}\text{COOMe}$$

(2)

Z—(L)—Boc—(D)—mesoDAP—(L)—GlyOMe—(D)—OMe (1) (0.66 g) was dissolved in methanol (10 ml) and hydrogenated over 10% palladium charcoal (0.12 g). After removal of the catalyst by filtration, the filtrate was concentrated under reduced pressure to give Boc—(D)—mesoDAP—(L)—GlyOMe—(D)—OMe (2) (0.48 g).

IR (CH$_2$Cl$_2$): 3400, 3360, 1735, 1705, 1670 cm$^{-1}$.

NMR (CDCl$_3$) δ: 1.42 (9H, s), 1.3–2.2 (6H, m), 3.3–3.6 (1H, m), 3.77 (6H, s), 4.05 (2H, d, J=5 Hz), 4.1–4.5 (1H, m).

PREPARATION 128

$$\text{Z.HN}\overset{L}{\underset{|}{\text{CH}}}\text{CONHCH}_2\text{CO}_2\text{Me} \longrightarrow$$
$$\underset{|}{(\text{CH}_2)_3}$$
$$\text{BocHN}\overset{D}{\underset{|}{\text{CH}}}\text{CONHNHBoc}$$

(1)

$$\left[\begin{array}{c} \text{Z.HN}\overset{L}{\underset{|}{\text{CH}}}\text{CONHCH}_2\text{CO}_2\text{Me} \\ \underset{|}{(\text{CH}_2)_3} \\ \text{H}_2\text{N}\overset{D}{\underset{|}{\text{CH}}}\text{CONHNH}_2 \end{array}\right] \longrightarrow$$

$$\left[\begin{array}{c} \text{Z.HN}\overset{L}{\underset{|}{\text{CH}}}\text{CONHCH}_2\text{CO}_2\text{Me} \\ \underset{|}{(\text{CH}_2)_3} \\ \text{H}_2\text{N}\overset{D}{\underset{|}{\text{CH}}}\text{CO}_2\text{Me} \end{array}\right] \longrightarrow$$

-continued

```
        L
Z.HNCHCONHCH₂CO₂Me
     |
   (CH₂)₃
     |
  BocHNCHCO₂Me
     D
    (2)
```

Z—(L)—Boc—(D)—mesoDAP—(L)—GlyOMe—(D)—NHNHBoc (1) (1.8 g) was added to trifluoroacetic acid and the mixture was stirred for 15 minutes at room temperature. After evaporation of the solvent, the residue was dissolved in methanol (50 ml) and treated with N-bromosuccinimide (1.58 g), and the mixture was stirred for 10 minutes at 0°–5° C. and concentrated in vacuo. The residue was dissolved in water (40 ml) and the excess reagent was decomposed by adding 5% sodium bisulfite. The mixture was neutralized to pH 9 with sodium bicarbonate, and extracted with ethyl acetate (40 ml). The extract was washed with water and dried over magnesium sulfate, and the solvent was removed in vacuo. The residue was dissolved in a mixture of dioxane (20 ml) and water (10 ml). To this mixture triethylamine (0.66 g) and di-t-butyldicarbonate (1.42 g) was added and stirred for an hour at room temperature. After evaporation of the solvent, the residue was dissolved in ethylacetate (40 ml), and washed successively with 2.5% hydrochloric acid (15 ml) and water (20 ml), dried over magnesium sulfate and evaporated. The residue was pulverized with isopropylether to give Z—(L)—Boc—(D-)—mesoDAP—(L)—GlyOMe—(D)—OMe (2) (0.7 g).

NMR (CD₃OD) δ: 1.43 (9H, s), 1.4–2.0 (6H, m), 3.72 (6H, s), 3.8–4.3 (4H, m), 5.12 (2H, s), 7.35 (5H, s).

PREPARATION 129

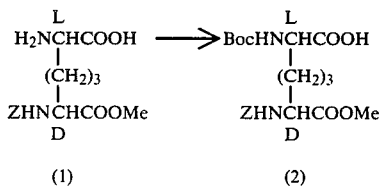

To a mixture of Z—(D)—mesoDAP—(D)—OMe (1) (90 mg) and triethylamine (50 mg) in 50% aqueous dioxane was added di-t-butyldicarbonate (120 mg) and the mixture was stirred for overnight at room temperature. After evaporation of dioxane, the aqueous solution was washed with ether (10 ml) and acidified t pH3 with 5% hydrochloric acid and extracted with ethyl acetate (30 ml). The extract was washed with water and dried over magnesium sulfate. The solvent was removed under reduced pressure to give Boc—(L)—Z—(D-)—mesoDAP—(D)—OMe (2) (110 mg).

IRcm⁻¹ in CH₂Cl₂: 3390, 1730 (shoulder), 1710.

NMR (CDCl₃) δ: 1.45 (9H, s), 1.4–2.0 (6H, m), 3.68 (3H, s), 4.0–4.4 (2H, m), 5.08 (2H, s), 7.30 (5H, s).

PREPARATION 130

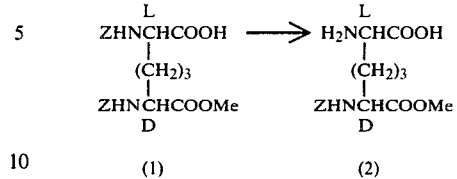

To a situation of diZDAP(D)—OMe (1) (2.20 g) in benzene (50 ml) was added thionyl chloride (5 ml) and the mixture was refluxed for an hour. The reaction mixture was concentrated under reduced pressure. The residual oil was dissolved in a mixture of dioxane (20 ml) and water (20 ml) and then stood overnight at room temperature. After concentration of dioxane, the concentrate was washed with ethyl acetate (20 ml). The aqueous layer was concentrated to about 10 ml and neutralized to pH 5 with 5% aqueous sodium bicarbonate. The resulting crystalline solid was filtered and washed with water to give Z(D)—mesoDAP—(D-)—OMe (2) (0.58 g).

IR cm⁻¹ (Nujol): 3100, 1745, 1695, 1610.

NMR (DCl-D₂O), δ: 1.3–2.3 (6H, m), 3.73 (3H, s), 4.0–4.5 (2H, m), 5.15 (2H, s), 7.43 (5H, s).

PREPARATION 131

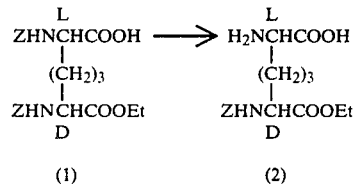

Z—(D)—mesoDAP—(D)—OEt (2) was prepared substantially in the same manner as Preparation 130.

IR cm⁻¹ (Nujol): 3300–2200, 1725, 1690, 1615.

NMR (D₂O-DCl), δ: 1.25 (3H, t, J=7 Hz), 1.5–2.2 (6H, m), 3.9–4.5 (4H, m), 5.13 (2H, s), 7.42 (5H, s).

PREPARATION 132

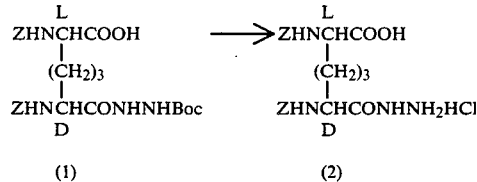

Into a solution of diZ—mesoDAP—(D)—NHNH-Boc (1) (30.3 g) in ethyl acetate (240 ml) was passed a stream of hydrogen chloride gas for 40 minutes under ice-bath cooling. The reaction mixture was stirred for an hour at the same temperature. The precipitated crystals were filtered and washed with ether to give diZ—mesoDAP—(D)—NHNH₂—HCl (2) (24.2 g).

IR cm⁻¹ (Nujol): 3280, 3400–2200, 1720, 1680, 1660.

NMR (DMSO-d₆), δ: 1.3–2.0 (6H, m), 3.8–4.2 (2H, m), 5.04 (4H, s), 7.36 (10H, s).

PREPARATION 133

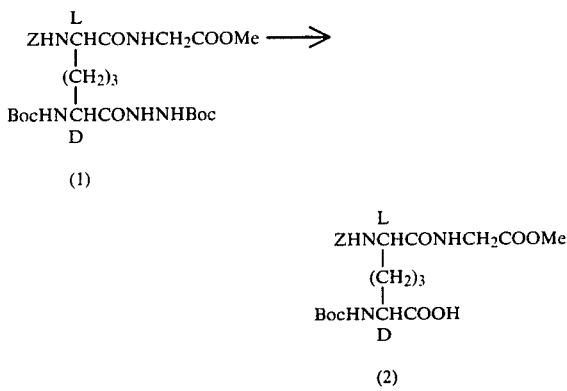

Z—(L)—Boc—(D)—mesoDAP—(L)—GlyOMe—(D)—NHNHBoc (1) (9.57 g) was added to trifluoroacetic acid (96 ml) and the mixture was stirred for an hour at ambient temperature. After evaporation of trifluoroacetic acid, the residue was dissolved in 50% aqueous dioxane (180 ml) and the mixture was treated with N-bromosuccinimide (6.43 g). After stirring for an hour under ice-bath cooling, the excess reagent was decomposed with 10% sodium bisulfite. The resulting solution was adjusted to pH 8 with 50% sodium bicarbonate and then a solution of di-t-butylcarbonate (8.56 g) in dioxane (35 ml) was added thereto.

The resulting mixture was stirred for 20 hours at ambient temperature and evaporated. The aqueous solution was washed with ethyl acetate (100 ml) and adjusted to pH 3 with 5% hydrochloric acid and then extracted with ethyl acetate (250 ml). The extract was washed with water and dried over magnesium sulfate. The solvent was removed under reduced pressure to leave an oil, which was chromatographed on silica gel (220 g) eluting with a mixture of chloroform and methanol (20:1) to give Z—(L)—Boc—(D)—mesoDAP—(L-)—GlyOMe (2) (4.78 g).

NMR (CD$_2$OD), δ: 1.47 (9H, s), 1.4–2.0 (6H, m), 3.73 (3H, s), 3.97 (2H, s), 4.0–4.35 (2H, m), 5.13 (2H, s), 7.37 (5H, s).

PREPARATION 134

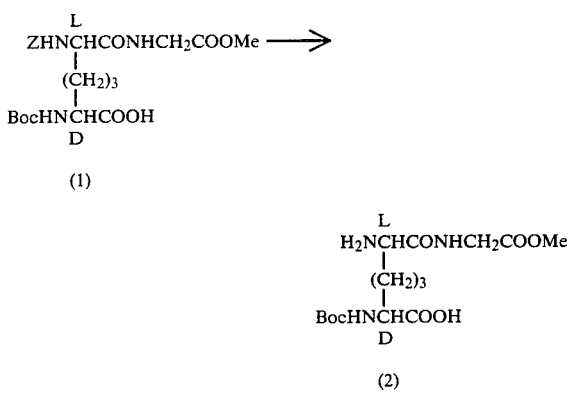

A solution of Z—(L)—Boc—(D)—mesoDAP—(L-)—GlyOMe (1) (4.78 g) in a mixture of methanol (100 ml) and water (15 ml) was hydrogenated over 10% palladium-charcoal (1.45 g). After removal of the catalyst, the filtrate was evaporated to dryness under reduced pressure. The residue was pulverized with ether to give Boc—(D)—mesoDAP—(L)—GlyOMe (2) (3.26 g).

IR cm$^{-1}$ (Nujol): 3600–2200, 1740, 1680, 1220, 1170, 1050, 1030, 860.

PREPARATION 135

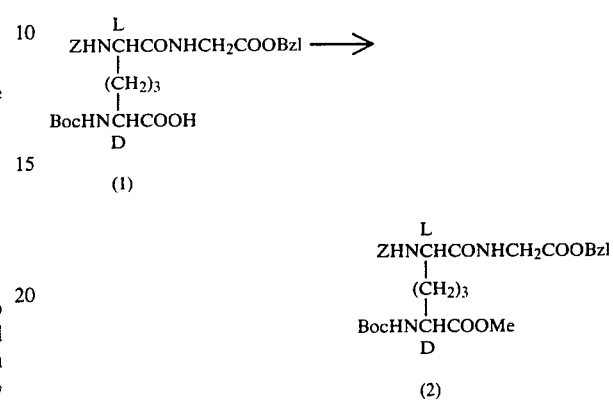

A solution of Z—(L)—Boc—(D)—mesoDAP—(L-)—GlyOBzl (1) (13.7 g) in methanol (140 ml) was treated with ethereal diazomethane under ice-bath cooling. The mixture was stirred for an hour at the same temperature and concentrated under reduced pressure. The residue was pulverized with isopropylether to give Z—(L)—Boc—(D)—mesoDAP—(L)—GlyOBzl—(D-)—OMe (2) (11.9 g).

NMR (CD$_3$OD), δ: 1.44 (9H, s), 1.3–2.0 (6H, m), 3.68 (3H, s), 3.96 (2H, d, J=4 Hz), 4.0–4.3 (2H, m), 5.06 (2H, s), 5.14 (2H, s), 7.30 (10H, s).

PREPARATION 136

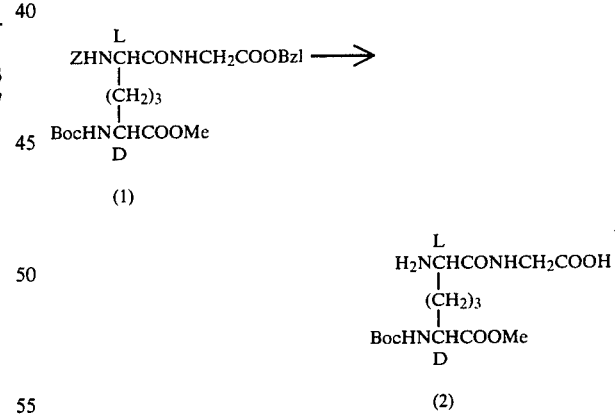

A solution of Z—(L)—Boc—(D)—mesoDAP—(L-)—GlyOBzl—(D)—OMe (1) (10.17 g) in a mixture of methanol (150 ml) and water (15 ml) was hydrogenated over 10% palladium charcoal (3.0 g) for 4 hours. After removal of the catalyst, the filtrate was evaporated to dryness under reduced pressure. The residue was pulverized with ether to give Boc—(D)—mesoDAP—(L)—GlyOH—(D)—OMe (2)(5.85 g).

IR cm$^{-1}$ (Nujol): 3325, 1750, 1690, 1640, 1610.

NMR (CD$_3$OD), δ: 1.40 (9H, s), 1.5–2.0 (6H, m), 3.70 (3H, s), 3.82 (2H, s), 3.8–4.2 (2H, m).

PREPARATION 137

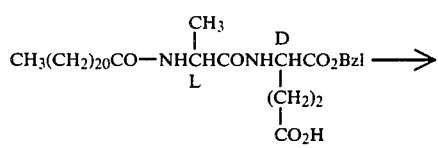

(1)

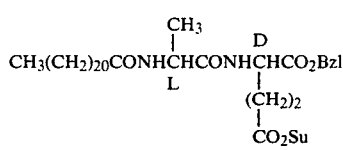

(2)

To a solution of n—docosonoyl—L—Ala—D—Glu(α—OBzl) (1) (4.76 g) in a mixture of tetrahydrofuran (50 ml) and chloroform (100 ml) were added dicyclohexylcarbodiimide (1.56 g) and N-hydroxysuccinimide (0.87 g). The mixture was kept for 17 hours at room temperature. The precipitate was filtered off and washed with chloroform (150 ml). The filtrate was concentrated in vacuo to give a crystal line residue, which was collected and washed with diisopropylether to give n—docosanoyl—L—Ala—D—Glu(α—OBzl)—OSu (2) (5.70 g).

IR (Nujol): 3380, 1820, 1790, 1750, 1640 cm$^{-1}$

NMR (CDCl$_3$-CD$_3$OD), δ: 0.91 (3H, m), 1.06–2.53 (47H, m), 2.84 (4H, s), 4.35–4.75 (2H, m), 5.19 (2H, s), 7.33 (5H, s).

PREPARATION 138

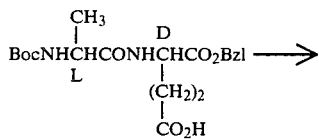

(1)

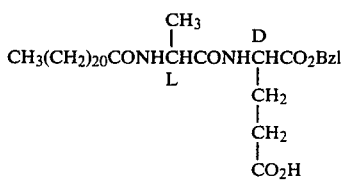

(2)

Boc—L—Ala—D—Glu(α—OBzl) (1) (4.0 g) was dissolved in trifluoroacetic acid (30 ml) and stirred for two hours at room temperature. The reaction mixture was concentrated in vacuo, and the residual oil was washed with ethylether. The oil was dissolved in methylenechloride (40 ml) and triethylamine (2.48 g) and methanol (12 ml) were added thereto. After the solution turned clean, n-docosanoic acid succinimidoester (4.28 g) and another 0.5 equivalent mole of triethylamine were added. After stirring for 19 hours, the reaction mixture was concentrated in vacuo. Water (15 ml) and 1N-hydrochloric acid (30 ml) were added to the solution to give a crystalline mass. The precipitate was collected and washed with water (50 ml) to give a crude crystal (5.78 g), which was purified by washing with hot dissopropylether to give n—docosanoyl—L—Ala'-D—Glu(α—OBzl) (2) (5.1 g).

IR (Nujol): 3300, 1725, 1700, 1650, 1630 cm$^{-1}$.

NMR (CDCl$_3$),: 0.88 (3H, m), 1.05–2.50 (47H, m), 4.3–4.8 (2H, m), 5.15 (2H, s), 7.32 (5H, s).

PREPARATION 139

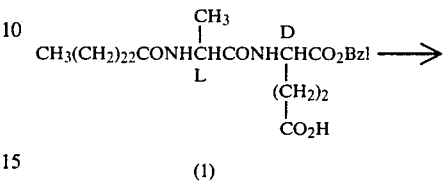

(1)

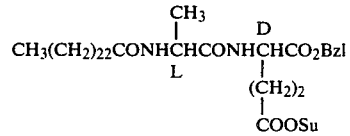

(2)

n—Tetracosanoyl—L—Ala—d—Glu(≢—OBzl)OSu (2) was prepared substantially in the same manner as Preparation 137.

IR (Nujol): 3380, 1820, 1790, 1745, 1630 cm$^{-1}$.

NMR (CDCl$_3$-CD$_3$OD), δ: 0.87 (3H, m), 1.05–1.50 (51H, m), 2.82 (4H, s), 4.30–4.75 (2H, m), 5.17 (2H, s), 7.33 (5H, s).

PREPARATION 140

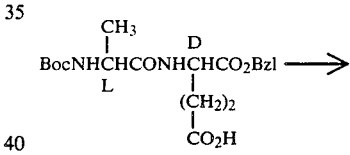

(1)

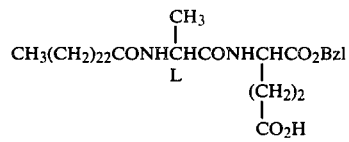

(2)

n—Tetracosanoyl—L—Ala—D—Glu(α—OBzl) (2) was prepared substantially in the same manner as Preparation 138.

IR (Nujol): 3360, 1740, 1710, 1640 cm$^{-1}$.

NMR (CDCl$_3$-CD$_3$OD), δ: 0.88 (3H, m), 1.06–1.70 (47H, m), 2.00–2.50 (4H, m), 5.16 (2H, s), 7.36 (5H, s).

EXAMPLE 165

(1) Step 1

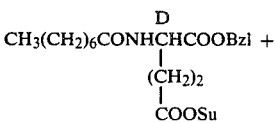

(1)

-continued

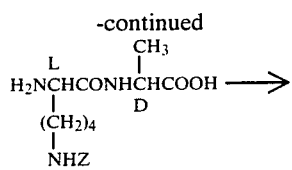

(2)

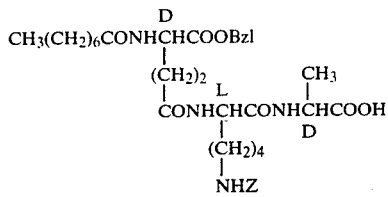

(3)

L—Lys(ε—Z)—D—AlaOH (2) (0.915 g) was dissolved in a mixture of methylene chloride (40 ml) methanol (40 ml) and triethylamine (0.53 g).

To this solution was added n—octanoyl—D—Glu(α—OBzl)—γ—OSu (1) (1.20 g) and the resulting solution was left overnight at ambient temperature. The reaction mixture was evaporated to give a paste, to which were added water (50 ml), ether (50 ml) and 1N hydrogen chloride. The resulting mixture was stirred well and ether was evaporated to separate crystals from the aqueous layer. The crystals were filtered, washed with water and then dried to give n—octanoyl—γ—D—Glu(α—OBzl)—L—Lys(ε—Z-)—D—AlaOH (3) (1.50 g).

IR (Nujol): 3300, 1725, 1685, 1650, 1630 cm$^{-1}$.

NMR (DMSO-d$_6$): δ 0.84 (3H, t, J=7 Hz), 1.00–2.40 (25H, m), 2.84–3.12 (2H, m), 4.10–4.50 (3H, m), 5.00 (2H, s), 5.10 (2H, s), 7.32 (10H, s), 8.10 (2H, t, J=8 Hz), 8.84 (1H, d, J=8 Hz).

(2) Step 2

Compound (3) ⟶

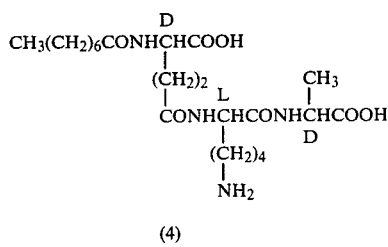

(4)

Octanoyl—γ—D—Glu(α—OBzl)—L—Lys(ε—Z-)—D—AlaOH (3) (1.20 g) was dissolved in acetic acid (50 ml) and hydrogenated over palladium black (150 mg). The catalyst was removed by filtration and the filtrate was evaporated to give a paste. The paste was allowed to stand to give crystals. The crystals were washed throughly with diethyl ether to give octanoyl—γ—D—Glu(α—OH)—L—Lys—D—AlaOH (4) (0.80 g).

[α]$_D$= +41.7 (C=0.2, acetic acid).

IR (Nujol): 3360, 1710 (sh), 1640 cm$^{-1}$.

NMR (D$_2$O): δ 0.84 (3H, obscure t, J=7 Hz), 1.00–2.50 (25H, m), 2.80–3.10 (2H, m), 4.00–4.40 (3H, m).

EXAMPLE 166

(1) Step 1

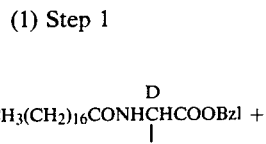

(1)

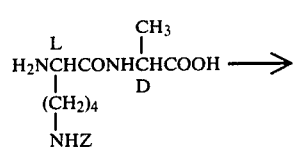

(2)

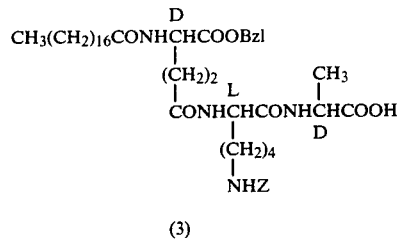

(3)

Stearoyl—γ—D—Glu(α—OBzl)—L—Lys(ε—Z-)—D—AlaOH (3) was prepared substantially in the same manner as step (1) of Example 165.

NMR (DMSO-d$_6$): δ 0.84 (3H, t, J=7 Hz), 1.00–2.40 (45H, m), 2.80–3.10 (2H, m), 4.00–4.80 (3H, m), 5.00 (2H, s), 5.08 (2H, s), 7.32 (10H, s), 7.80 (1H, d, J=8 Hz), 8.08 (2H, t, J=8 Hz).

(2) Step 2

Compound (3) ⟶

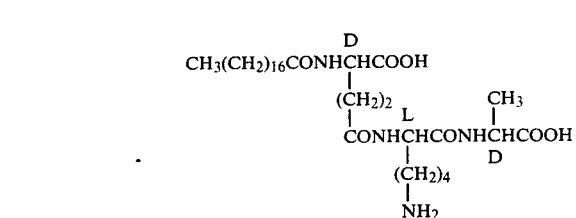

(4)

Stearoyl—γ—D—Glu(α—OH-)—L—Lys—D—AlaOH (4) was prepared substantially in the same manner as step (2) of Example 165.

[α]$_D$= −11.10 (C=0.21, acetic acid).

IR (Nujol): 3350, 1730, 1640 cm$^{-1}$.

NMR (NaOD-D$_2$O), δ: 0.68–2.80 (50H, m), 4.10–4.50 (3H, m).

EXAMPLE 167

(1) Step 1

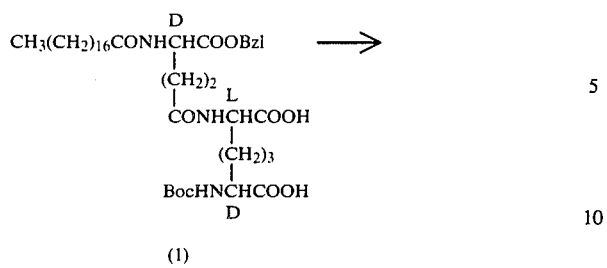

(1)

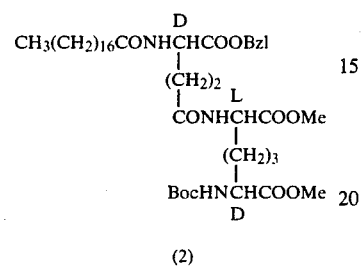

(2)

Stearoyl—γ—D—Glu(α—OBzl)—(L)—Boc—(D-)—mesoDAP—(1) (2.20 g) was dissolved in tetrahydrofuran (50 ml), and ethereal diazomethane solution was added thereto until pale yellow of the solution persisted. After 10 minutes, excess diazomethane was destroyed by adding acetic acid thereto. The resulting solution was evaporated to give a white crystalline residue, which was washed with diisopropyl ether to give stearoyl—γ—D—Glu(α—OBzl)—(L)—Boc—(D-)—mesoDAP—(L)—(OMe)—(D)—(OMe) (2) (2.10 g).

IR (Nujol): 3300, 1740, 1680, 1640 cm$^{-1}$.

NMR (CDCl$_3$), δ: 0.83–2.50 (45H, m), 3.71 (3H, s), 3.75 (3H, s), 4.10–5.00 (3H, m), 5.20 (2H, s), 7.36 (5H, s).

(2) Step 2

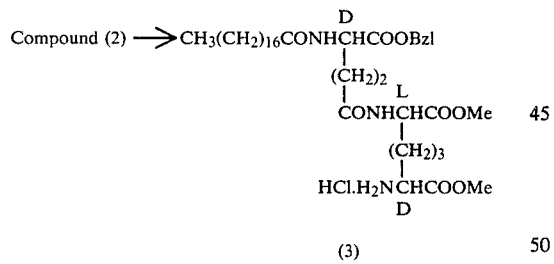

(3)

Stearoyl—γ—D—Glu(α—OBzl)—(L)—Boc—(D-)—mesoDAP—(L)—(OMe)—(D)—(OMe) (2) (0.90 g) was dissolved in a mixture of acetic acid (10 ml) and hydrogen chloride-saturated acetic acid (4 ml). The solution was allowed to stand for 15 minutes at ambient temperature and then evaporated to give a crystalline residue. The crystalline residue was throughly washed with isopropyl ether to give stearoyl—γ—D—Glu(α—OBzl)—(L)—mesoDAP—(L)—(OMe)—(D-)—(OMe) hydrochloric acid salt (3).

IR (Nujol): 3300, 1740, 1640 cm$^{-1}$.

NMR (DMSO-d$_6$), δ: 0.76–2.40 (45H, m), 3.64 (3H, s), 3.76 (3H, s), 3.84–4.40 (3H, m), 5.12 (2H, s), 7.38 (5H, s).

(3) Step 3

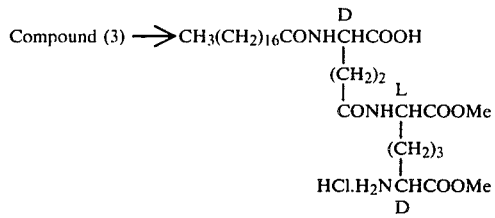

(4)

Stearoyl—γ—D—Glu(α—OH)—(L-)—mesoDAP—(L)—(OMe)—(D)—(OMe) (4) was prepared substantially in the same manner as step (2) of Example 165.

[α]$_D$= +3.901 (C=0.2, acetic acid).

IR (Nujol): 3300, 1730, 1640, 1600 cm$^{-1}$.

NMR (DMSO-d$_6$), δ: 0.70–2.32 (45H, m), 3.62 (3H, s), 3.74 (3H, s), 3.80–4.32 (3H, m), 8.02 (1H, d, J=8 Hz), 8.30 (1H, d, J=8 Hz).

EXAMPLE 168

(1) Step 1

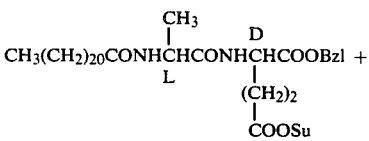

(1)

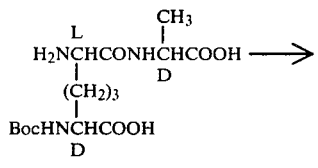

(2)

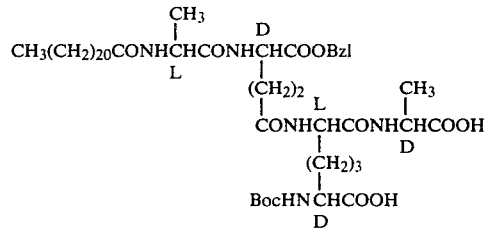

(3)

To a suspension of n—docosanoyl—L—Ala—D—Glu(α—OBzl)—γ—OSu (1) (2.91 g) in methylene chloride (50 ml) were added triethylamine (0.89 g) and Boc—(D)—mesoDAP—(L)—D—AlaOH (2) (1.44 g). The mixture was kept for 66 hours at ambient temperature and then concentrated in vacuo. To the residue were added water (100 ml), 1N hydrochloric acid (10 ml) and ethylether (30 ml). The resulting mixture was stirred for 15 minutes and ethylether was removed. The precipitate was collected by filtration and then washed with water to give a crude product which was washed with diisopropylether to give n—docosanoyl—L—Ala—γ—D—Glu(α—OBzl)—(L-)—Boc—(D)—mesoDAP—(L)—D—AlaOH (3) (3.60 g).

IR (Nujol): 3300, 1720, 1680, 1630 cm$^{-1}$.

NMR (CDCl$_3$-CD$_3$OD), δ: 0.94 (3H, m), 1.1–2.5 (65H, m), 5.21 (2H, s), 7.38 (5H, s).

(2) Step 2

Compound (3) ⟶

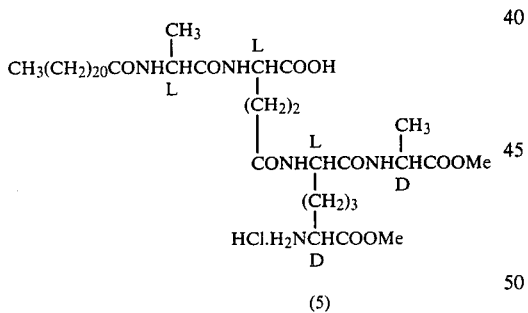

(4)

To a solution of n—docosanoyl—L—Ala—γ—D—Glu(α—OBzl)—(L)—Boc—(D)—mesoDAP—(L-)—AlaOH (3) (1.5 g) in a mixture of tetrahydrofuran (40 ml) and chloroform (20 ml) was added 0.6M diazomethane in ethylether (10 ml). The resulting mixture was stirred for 30 minutes at ambient temperature and then the excess reagent was decomposed with acetic acid. The reaction mixture was concentrated and the residue was washed with ethylether and collected by filtration to give n—docosanoyl—L—Ala—γ—D—Glu(α—OBzl)—(L)—Boc—(D)—mesoDAP—(L-)—D—Ala(OMe)—(D)—OMe (4) (1.36 g).

NMR (CDCl$_3$-CD$_3$OD), δ: 0.90 (3H, m), 1.1–2.6 (65H, m), 3.71 (3H, s), 3.74 (3H, s), 5.19 (2H, s), 7.48 (5H, s).

(3) Step 3

Compound (4) ⟶

```
              CH3           L
              |             |
CH3(CH2)20CONHCHCONHCHCHCOOH
              L             |
                           (CH2)2
                            |       CH3
                            |   L   |
                           CONHCHCONHCHCOOMe
                                    |      D
                                   (CH2)3
                                    |
                              HCl.H2NCHCOOMe
                                    |
                                    D
```

(5)

n—Docosanoyl—L—Ala—γ—D—Glu(α—OBzl)—(L)—Boc—(D)—mesoDAP—(L-)—D—AlaOMe—(D)—OMe (4) (1.25 g) was dissolved in acetic acid (20 ml) and hydrogenated under an atmospheric pressure of hydrogen over 10% palladium charcoal. After removal of the catalyst, acetic acid (8 ml) saturated with hydrogen chloride was added to the filtrate. The resulting mixture was kept for 3 hours at ambient temperature and concentrated in vacuo to give a crystalline residue, which was collected and washed with diisopropylether to give n—docosanoyl—L—Ala—γ—D—Glu(α—OH)—(L-)—D—AlaOMe—(D)—OMe hydrochloric acid salt (5) (1.08 g).

[α]$_D$= −11.42° (C=0.30, acetic acid).

IR (Nujol): 3380, 1745, 1630 cm$^{-1}$.

NMR (DMSO-d$_6$), δ: 0.87 (3H, m), 1.05–2.45 (56H, m), 3.63 (3H, s), 3.75 (3H, s).

EXAMPLE 169

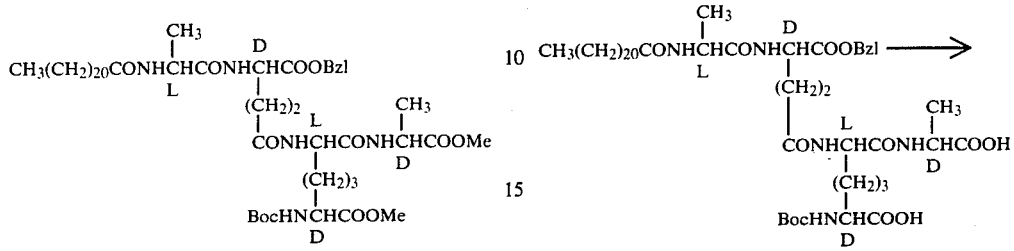

(1)

```
              CH3           D
              |             |
CH3(CH2)20CONHCHCONHCHCHCOOH
              L             |
                           (CH2)2
                            |       CH3
                            |   L   |
                           CONHCHCONHCHCOOH
                                    |      D
                                   (CH2)3
                                    |
                              H2NCHCOOH
                                    |
                                    D
```

(2)

n—Docosanoyl—L—Ala—γ—D—Glu(α—OH-)—(L)—mesoDAP—(L)—D—AlaOH (2) was prepared substantially in the same manner as step 3 of Example 168.

[α]$_D$= −19.34° (C=0.20, acetic acid).

IR (Nujol): 3380, 1740, 1630 cm$^{-1}$.

NMR (NaOD-D$_2$O), δ: 0.91 (3H, m), 3.25 (1H, m), 4.0–4.6 (5H, m).

EXAMPLE 170

(1) Step 1

```
              CH3           D
              |             |
CH3(CH2)22CONHCHCONHCHCOOBzl    +
              L             |
                           (CH2)2
                            |
                           COOSu
```

(1)

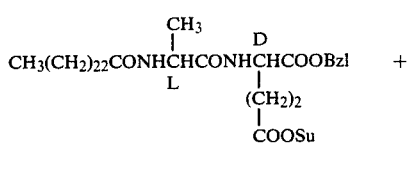

(2)

-continued

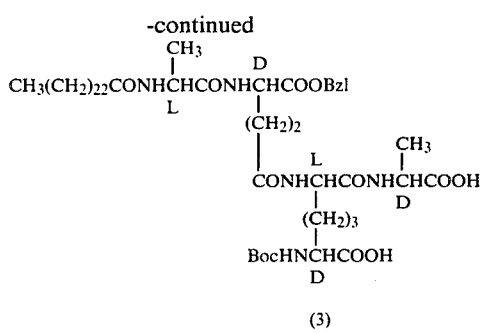

(3)

n—Tetracosanoyl—L—Ala—γ—D—Glu(α—OBzl)—(L)—Boc—(D)—mesoDAP—(L)—D—AlaOH (3) was prepared substantially in the same manner as step 1 of Example 168.

IR (Nujol): 3300, 1720, 1680, 1630 cm$^{-1}$.

NMR (CDCl$_3$-CD$_3$OD), δ: 0.90 (3H, m), 1.05–2.50 (69H, m), 5.15 (2H, s), 7.34 (5H, s).

(2) Step 2

Compound (3) ⟶

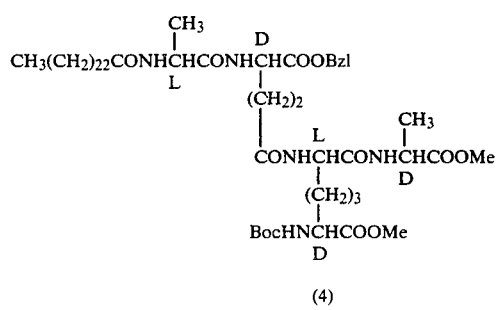

(4)

n—Tetracosanoyl—L—Ala—γ—D—Glu(α—OBzl)—(L)—Boc—(D)—mesoDAP—(L-)—D—AlaOMe—(D)—OMe (4) was prepared substantially in the same manner as step 2 of Example 168.

IR (Nujol): 3300, 1735, 1685, 1630 cm$^{-1}$.

NMR (CDCl$_3$-CD$_3$OD), δ: 0.89 (3H, m), 1.05–2.50 (69H, m), 3.69 (3H, s), 3.73 (3H, s), 5.18 (2H, s), 7.42 (15H, s).

(3) Step 3

Compound (4) ⟶

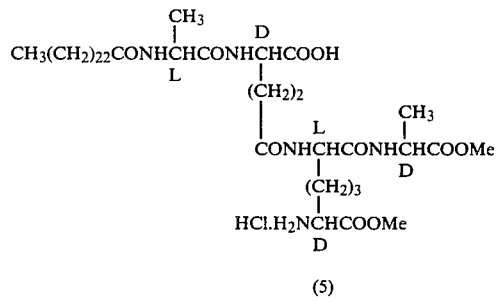

(5)

n—Tetracosanoyl—L—Ala—γ—D—Glu(α—OH-)—(L)—mesoDAP—(L)—D—AlaOMe—(D)—OMe hydrochloric acid salt (5) was prepared substantially in the same manner as step 3 of Example 168.

[α]$_D$ = −14.01 (C=0.26, acetic acid).

IR (Nujol): 3380, 1745, 1630 cm$^{-1}$.

NMR (DMSO-d$_6$), δ: 0.85 (3H, m), 1.0–2.4 (60H, m), 3.60 (3H, s), 3.72 (3H, s).

(4) Step 4

Compound (3) ⟶

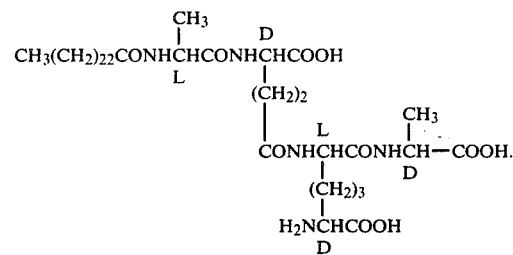

(6)

D—Tetracosanoyl—L—Ala—γ—D—Glu(α—OH-)—(L)—mesoDAP—(L)—D—AlaOH (6) was prepared substantially in the same manner as step 3 of Example 168.

IR (Nujol): 3280, 1730, 1630 cm$^{-1}$.

NMR (D$_2$O+NaHCO$_3$), δ: 0.88 (3H, m), 3.72 (1H, m), 3.95–4.6 (4H, m).

EXAMPLE 171

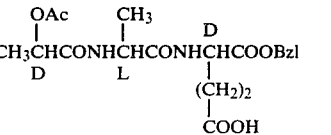

(1)

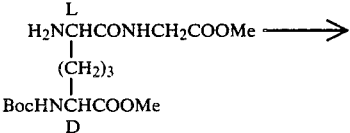

(2)

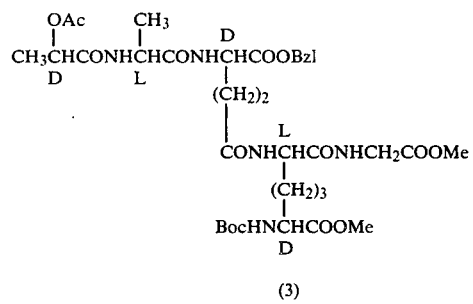

(3)

D—Lac(OAc)—L—Ala—γ—D—Glu(α—OBzl)—(L)—Boc—(D)—mesoDAP—(L)—GlyOMe—(D-)—OMe (3) was prepared substantially in the same manner as step 1 of Example 168.

IR (Nujol): 3250, 1720, 1680, 1630 cm$^{-1}$.

NMR (CD$_3$OD), δ: 1.2–1.9 (17H, m), 2.12 (3H, s), 1.9–2.6 (2H, m), 3.70 (6H, s), 3.97 (2H, s), 4.0–4.6 (4H, m), 4.98 (1H, q, J=7 Hz), 5.18 (2H, s), 7.35 (5H, s).

EXAMPLE 172

(1) Step 1

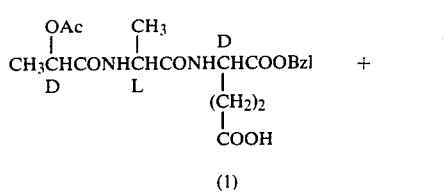

(1)

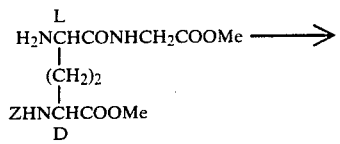

(2)

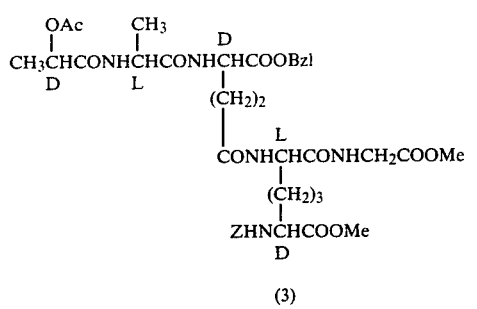

(3)

D—Lac(OAc)—L—Ala—γ—D—Glu(α—OBzl)—(L)—Z—(D)—mesoDAP—(L)—GlyOMe—(D-)—OMe (3) was prepared substantially in the same manner as step 1 of Example 168.

IR (Nujol): 3260, 1735, 1635 cm$^{-1}$.

NMR (CDCl$_3$), δ: 1.1–2.5 (10H, m), 1.35 (3H, d, J=7 Hz), 1.42 (3H, d, J=7 Hz), 2.08 (3H, s), 3.60 (3H, s), 3.67 (3H, s), 3.94 (2H, d, J=7 Hz), 4.1–4.8 (4H, m), 4.9–5.2 (1H, m), 5.06 (2H, s), 5.09 (2H, s), 7.30 (10H, s).

(2) Step 2

Compound (3) ⟶

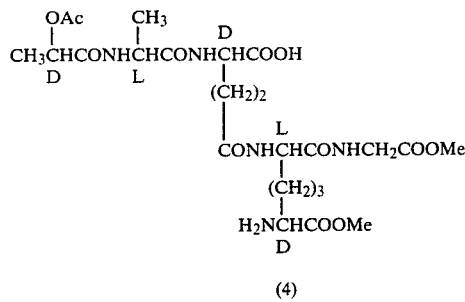

(4)

D—Lac(OAc)—L—Ala—γ—D—Glu(α—OBzl)—(L)—Z—(D)—mesoDAP—(L)—GlyOMe—(D-)—OMe (3) (1.32 g) was hydrogenated in acetic acid (15 ml) over 10% palladium charcoal (0.4 g) for 1.5 hours under an atmospheric pressure of hydrogen at ambient temperature. After completion of the reaction, the catalyst was filtered off and the filtrate was evporated to dryness. The residue was pulverized with ether to give D—Lac(OAc)—L—Ala—γ—D—Glu(α—OH)—(L-)—mesoDAP—(L)—GlyOMe—(D)—OMe (4) (1.1 g).

NMR (D$_2$O), δ: 1.2–2.3 (10H, m), 1.43 (3H, d, J=7 Hz), 1.47 (3H, d, J=7 Hz), 3.77 (3H, s), 3.87 (3H, s), 4.03 (2H, s), 4.1–4.5 (4H, m), 5.07 (1H, q, J=7 Hz).

EXAMPLE 173

(1) Step 1

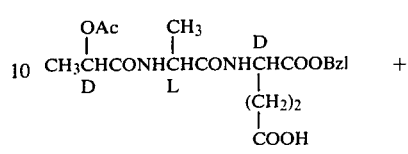

(1)

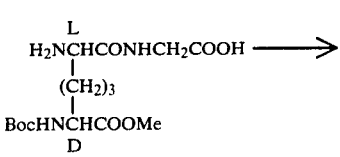

(2)

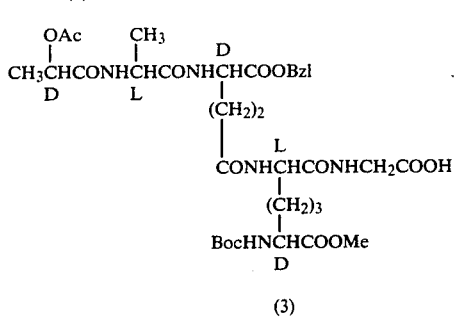

(3)

D—Lac(OAc)—L—Ala—γ—D—Glu(α—OBzl)—(L)—Boc—(D)—mesoDAP—(L)—GlyOH—(D-)—OMe (3) was prepared substantially in the same manner as step 1 of Example 168.

IR (Nujol): 3270, 1735, 1650 cm$^{-1}$.

NMR (CDCl$_3$), δ: 1.2–2.7 (16H, m), 1.43 (9H, s), 2.12 (3H, s), 3.70 (3H, s), 3.8–4.5 (7H, m), 4.9–5.3 (1H, m), 5.13 (2H, s), 7.32 (5H, s).

(2) Step 2

Compound (3) ⟶

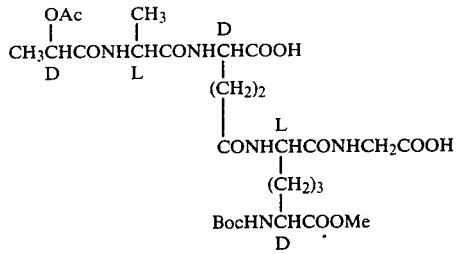

(4)

D—Lac(OAc)—L—Ala—γ—D—Glu(α—OH-)—(L)—Boc—(D)—mesoDAP—(L)—GlyOH—(D-)—OMe (4) was prepared substantially in the same manner as step 2 of Example 172.

IR (Nujol): 3300, 1725, 1650 cm$^{-1}$.

NMR (CD$_3$OD), δ: 1.3–2.6 (16H, m), 1.43 (9H, s), 2.11 (3H, s), 3.70 (3H, s), 3.93 (2H, s), 4.2–4.6 (4H, m), 5.08 (1H, q, J=7 Hz).

EXAMPLE 174

(1) Step 1

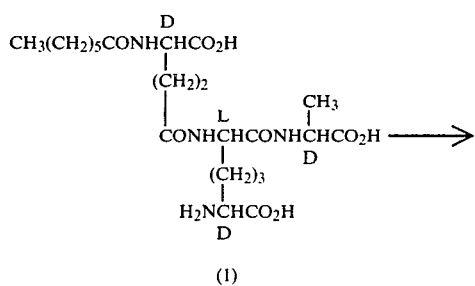

Heptanoyl—γ—D—Glu(α—OH)—(L-)—mesoDAP—(L)—D—AlaOH (1) (1.00 g) was dissolved in the mixture of water (10 ml) and dioxane (20 ml). Triethylamine (730 mg) and 2-(tert-butoxycarbonyloxyimino)-2-phenylacetonitrile (640 mg) was added to the solution. After stirring for 16 hours at ambient temperature, the reaction mixture was concentrated. To the residue was added waters (30 ml), 1N hydrochloric acid (8 ml) and ethyl acetate. The organic layer was separated and washed with brine, dried over magnesium sulfate and concentrated in vacuo to give an oily residue, which was treated with ethylether and diisopropylether to give heptanoyl—γ—D—Glu(α—OH)—(L)—Boc—(D)—mesoDAP—(L-)—D—AlaOH (2) (925 mg).

IR (Nujol): 3300, 1720, 1630 cm$^{-1}$.

NMR (CD$_3$OD), δ: 0.90 (3H, m), 1.1–2.6 (23H, m), 3.70 (1H, t, J=6 Hz), 3.90–4.65 (3H, m).

(2) Step 2

Compound (2) ⟶

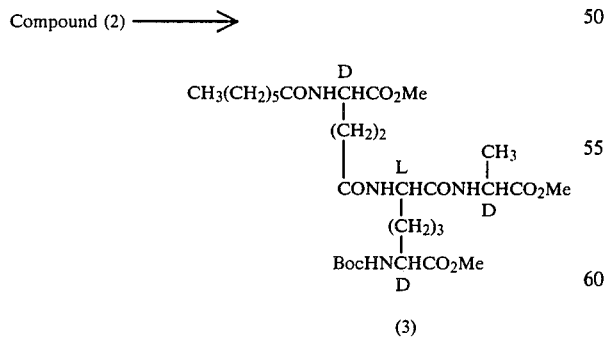

Heptanoyl—γ—D—Glu(α—OMe)—(L)—Boc—(D-)—mesoDAP—(L)—D—AlaOMe—(D)—OMe (3) was prepared substantially in the same manner as step 2 of Example 168.

IR (Nujol): 3300, 1735, 1685, 1630 cm$^{-1}$.

NMR (CD$_3$OD), δ: 0.91 (3H, m), 1.15–1.90 (16H, m), 2.00–2.45 (4H, m), 3.71 (9H, s), 4.06 (1H, m), 4.24–4.56 (3H, m).

(3) Step 3

Compound (3) ⟶

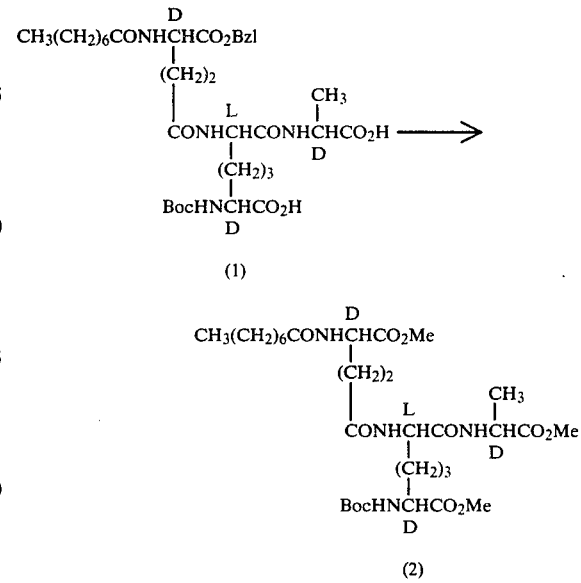

Heptanoyl—γ—D—Glu(α—OMe)—(L-)—mesoDAP—(L)—D—AlaOMe—(D)—OMe (4) was prepared substantially in the same manner as step 3 of Example 168.

IR (Nujol): 3320, 3080, 1740, 1635 cm$^{-1}$.

NMR (CD$_3$OD), δ: 0.92 (3H, m), 1.16–2.46 (26H, m), 3.74 (9H, s), 4.21–4.60 (4H, m).

EXAMPLE 175

(1) Step 1

```
              D
CH3(CH2)6CONHCHCO2Bzl
       |
       (CH2)2
       |              CH3
       |     L        |
       CONHCHCONHCHCO2H  ⟶
       |              D
       (CH2)3
       |
       BocHNCHCO2H
       D
```

(1)

```
              D
CH3(CH2)6CONHCHCO2Me
       |
       (CH2)2
       |              CH3
       |     L        |
       CONHCHCONHCHCO2Me
       |              D
       (CH2)3
       |
       BocHNCHCO2Me
       D
```

(2)

Octanoyl—γ—D—Glu(α—OMe)—(L)—Boc—(D-)—mesoDAP—(L)—D—AlaOMe—D—OMe (2) was prepared substantially in the same manner as step 2 of Example 168.

IR (Nujol): 3370, 1750, 1690, 1640 cm$^{-1}$.

NMR (CDCl$_3$), δ: 0.89 (3H, m), 1.05–2.75 (37H, m), 3.72 (9H, s), 4.20 (1H, m), 4.35–4.75 (3H, m), 5.35 (1H, d, J=8 Hz), 6.75 (1H, d, J=8 Hz), 6.85 (1H, d, J=8 Hz), 7.42 (1H, d, J=7 Hz).

(2) Step 2

Compound (2) ⟶

-continued

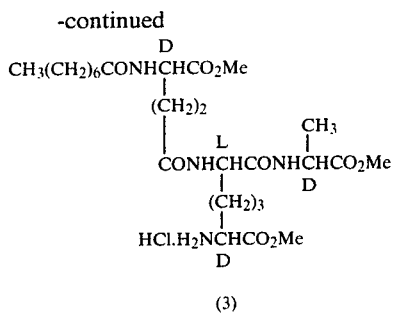

(3)

Octanoyl—γ—D—Glu(α—OMe)—(L-)—mesoDAP—(L)—D—AlaOMe—(D)—OMe hydrochloric acid salt (3) was prepared substantially in the same manner as step 3 of Example 168.

IR (Nujol): 3280, 1735, 1630 cm$^{-1}$.

NMR (CD$_3$OD), δ: 0.89 (3H, m), 1.2–2.5 (22H, m), 3.72 (6H, s), 3.86 (3H, s), 4.07 (1H, t, J=6 Hz), 4.19–4.65 (3H, m).

EXAMPLE 176

(1) Step 1

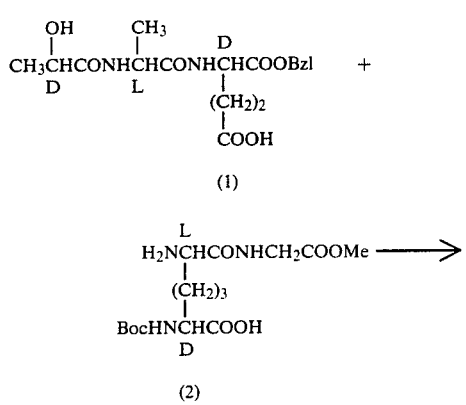

D—Lac—L—Ala—γ—D—Glu(α—OBzl)—(L-)—Boc—(D)—mesoDAP—(L)—GlyOMe (3) was prepared substantially in the same manner as step 1 of Example 168.

NMR (CD$_3$OD), δ: 1.38 (6H, d, J=7 Hz), 1.47 (9H, s), 1.3–2.5 (10H, m), 3.75 (3H, s), 4.00 (2H, s), 4.0–4.6 (5H, m), 5.20 (2H, s), 7.40 (5H, s).

(2) Step 2

Compound (3) ⟶

-continued

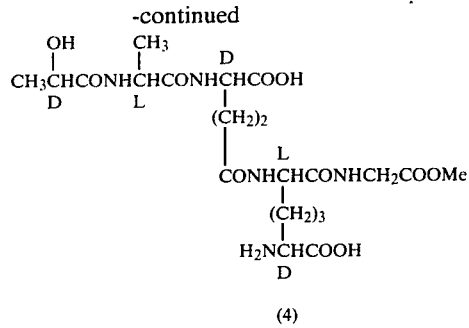

(4)

D—Lac—L—Ala—γ—D—Glu(α—OH)—(L-)—mesoDAP—(L)—GlyOMe (4) was prepared substantially in the same manner as step 3 of Example 168.

IR cm$^{-1}$ Nujol: 3280, 1740, 1640.

NMR (D$_2$O), δ: 1.38 (3H, d, J=7 Hz), 1.41 (3H, d, J=7 Hz), 1.3–2.5 (10H, m), 3.75 (3H, s), 3.98 (2H, s), 4.0–4.6 (5H, m).

EXAMPLE 177

(1) Step 1

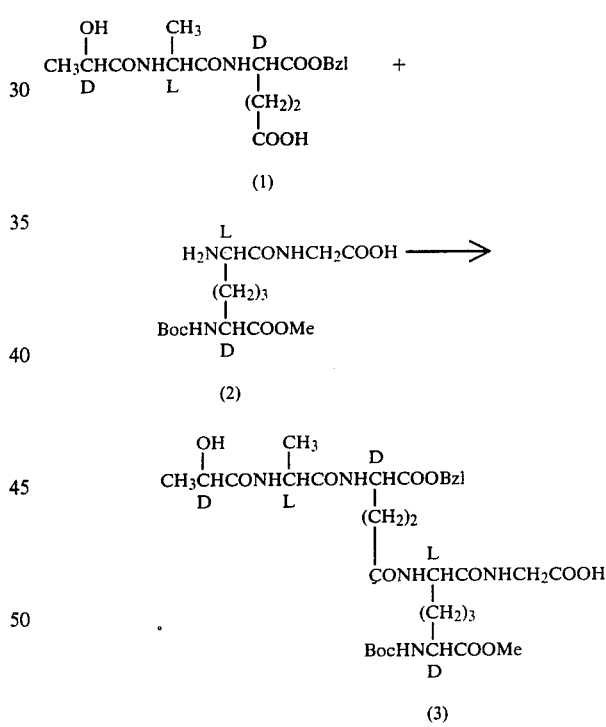

D—Lac—L—Ala—γ—D—Glu(α—OBzl)—(L-)—Boc—(D)—mesoDAP—(L)—GlyOH—(D)—OMe (3) was prepared substantially in the same manner as step 1 of Example 168.

NMR (CD$_3$OD), δ: 1.42 (9H, s), 1.2–2.5 (16H, m), 3.70 (3H, s), 3.92 (2H, s), 4.0–4.6 (5H, m), 5.17 (2H, s), 7.35 (5H, s).

(2) Step 2

Compound (2) ⟶

-continued

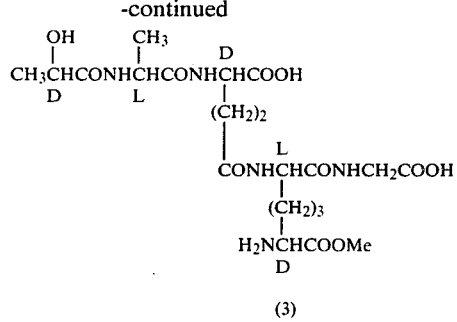

(3)

D—Lac—L—Ala—γ—D—Glu(α—OH)—(L-)—mesoDAP—(L)—GlyOH—(D)—OMe (3) was prepared substantially in the same manner as step 3 of Example 168.

IR (KBr): 3700-2500, 1730, 1650 cm$^{-1}$.

NMR (D$_2$O), δ: 1.37 (3H, d, J=7 Hz), 1.40 (3H, d, J=7 Hz), 1.3-2.5 (10H, m), 3.80 (2H, s), 3.83 (3H, s), 4.0-4.6 (5H, m).

PREPARATION 141

(1) Step 1

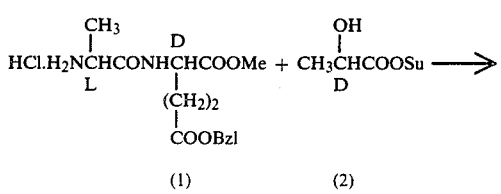

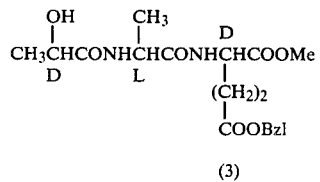

To a mixture of L—Ala—D—Glu(γ—OBzl)OMe hydrochloric acid salt (1) (2.9 g) and triethylamine (0.91 g) in acetonitrile (30 ml) was added D—lactic acid N-hydroxysuccinimide ester (2) (2.53 g) under ice-bath cooling. The mixture was stirred for 1.5 hours at ambient temperature. After evaporation of acetonitrile, the residue was dissolved in ethyl acetate (70 ml), washed succesively with 2.5% hydrochloric acid (30 ml×2), water (30 ml), 2.5% sodium bicarbonate (30 ml) and water (30 ml×2), dried over magnesium sulfate and then evaporated. The residue was chromatographed on silica gel column (60 g) eluting with a mixture of chloroform and ethyl acetate (1:1) to give D—Lac—L—Ala—D—Glu(γ—OBzl)OMe (3) (2.23 g).

NMR (CDCl$_3$), δ: 1.30 (3H, d, J=7 Hz), 1.43 (3H, d, J=7 Hz), 2.0-2.7 (4H, m), 3.30 (1H, broad s), 4.73 (3H, s), 4.0-4.8 (3H, m), 5.13 (2H, s), 7.35 (5H, s).

(2) Step 2

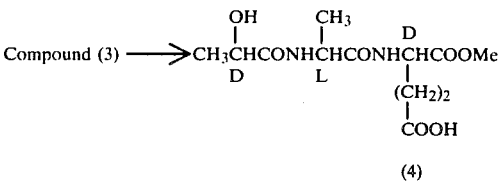

(4)

A solution of D—Lac—L—Ala—D—Glu(γ—OBzl)OMe (3) (2.09 g) in methanol (100 ml) was hydrogenated over 10% palladium charcoal (0.6 g). After removal of the catalyst, the filtrate was evaporated under reduced pressure to give D—Lac—L—Ala—D—GluOMe (4) (1.6 g).

NMR (CDCl$_3$), δ: 1.40 (3H, d, J=7 Hz), 1.43 (3H, d, J=7 Hz), 1.9-2.6 (4H, m), 4.75 (3H, s), 4.18 (1H, q, J=7 Hz), 4.3-4.6 (2H, m).

Preparation 142

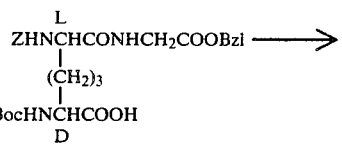

(1)

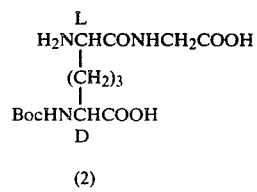

(2)

A solution of Z—(L)—Boc—(D)—mesoDAP—(L-)—GlyZBzl (1) (3.8 g) in a mixture of methanol (100 ml) and water (10 ml) was hydrogenated over 10% palladium charcoal (0.18 g). After removal of the catalysts, the filtrate was evaporated to dryness under reduced pressure. The residue was pulverized with ether to give Boc—(D)—mesoDAP—(L)—GlyOH (2) (2.10 g).

NMR (CD$_3$OD), δ: 1.43 (9H, s), 1.3-2.1 (6H, m), 3.8-4.2 (4H, m).

PREPARATION 143

(1) Step 1

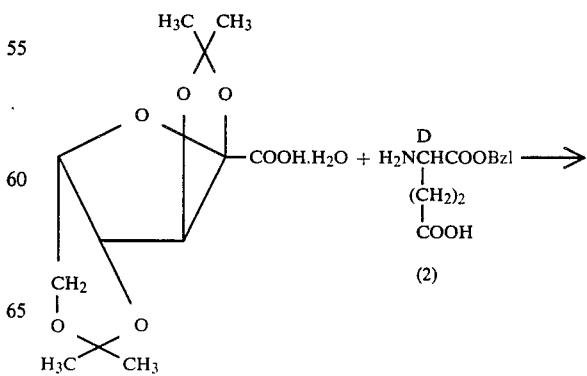

(2)

-continued

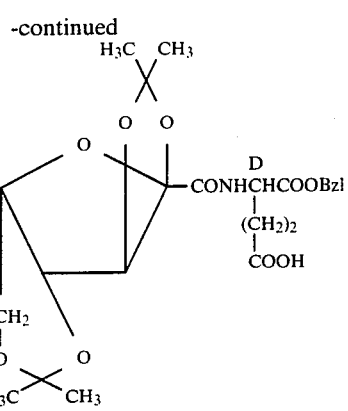

A mixture of phosphorus oxychloride (120 mg) and N,N-dimethylformamide (1 ml) was stirred at 25°-30° C. for 3 hours and then was cooled to 0° C. To the solution was added methylene chloride solution (2 ml) of 2,3;4,6—di—isopropylidene—2—keto—L—gulonic acid mono hydrate (1) (150 mg), keeping the temperature at 0° to 5° C. for 30 minutes.

The resulting solution was cooled at −20° to −30° C. On the other hand, D—Glu(OBzl) (2) (120 mg) was dissolved in a mixture of methylene chloride (100 ml) and bis-trimethylsilyl-acetamide (800 mg).

The solution thus prepared was added to the above solution at −20° to −30° C. The temperature of the mixture was raised to ambient temperature and then the mixture was stirred for 15 hours. The reaction mixture was evaporated in vacuo and extracted with ethyl acetate. The organic layer was washed with water (x2) and brine and then dried over magnesium sulfate. The solvent was evaporated to give an oily residue which was subjected to silica gel column. The column was eluted with chloroform and methanol (20:1). The solvent of the fraction containing, the object compound was evaporated to give 2,3;4,6—di—isopropylidene—2—keto—L—gulonoyl—γ—D—Glu(α—OBzl)OH (3) (220 mg).

NMR (CDCl₃), δ: 1.33 (3H, s), 1.43 (3H, s), 1.53 (6H, s), 2.10-2.40 (4H, m), 4.15 (2H, s), 4.33-4.66 (3H, m), 4.73 (1H, t, J=7 Hz), 5.16 (2H, s), 7.33 (5H, s).

(2) Step 2

Compound (3) ⟶

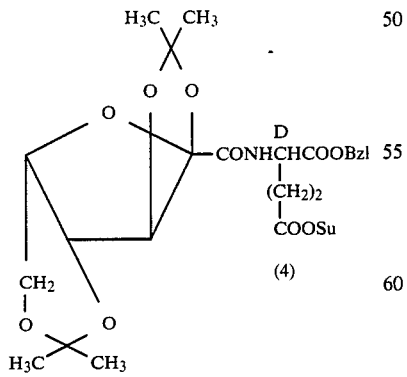

2,3;4,6—Di—iso-propylidene—2—keto—L—gulonoyl—D—Glu—(α—OBzl)OH (3) (950 mg) and N-hydroxysuccinimide (230 mg) was dissolved in tetrahydrofuran (10 ml). To the solution was added dicyclohexylcarbodiimide (410 mg) at 0° C. The reaction mixture was stirred at 0° C. and stood overnight in a refrigerator. The precipitates were filtered and washed with tetrahydrofuran. The filtrate was evaporated to give a viscous oil which was pulverized with diethylether to give 2,3;4,6—di—isopropylidene—2—keto—L—gulonoyl—D—Glu(α—OBzl)OSu (4) (1.1 g).

NMR (CDCl₃), δ: 1.30 (3H, s), 1.40 (3H, s), 1.50 (6H, s), 2.77 (4H, s), 4.10-4.90 (6H, s), 5.16 (2H, s), 7.30 (5H, s).

PREPARATION 144

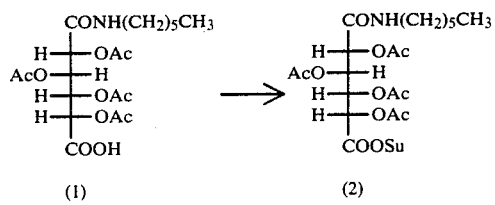

1—N—n—hexyl—2,3,4,5—O—tetraacetyl—D—glucaramide N—hydroxylsuccinimyl ester (2) was prepared substantially in the same manner as step 2 of Preparation 143.

NMR (CDCl₃), δ: 0.7-1.1 (3H, m), 1.1-2.0 (8H, m), 2.10 (3H, s), 2.22 (9H, s), 2.88 (4H, s), 3.0-3.5 (2H, m), 5.2-6.0 (4H, m), 6.23 (1H, m).

PREPARATION 145

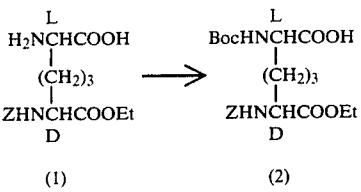

Boc—(L)—Z—(D)—mesoDAP—(D)—OEt (2) was prepared substantially in the same manner as Preparation 129.

NMR (CDCl₃), δ: 1.17 (3H, t, J=7 Hz), 1.40 (9H, s), 1.30-2.0 (6H, m), 4.13 (2H, q, J=7 Hz), 4.25 (1H, m), 5.07 (2H, s), 5.30 (1H, broad), 7.25 (5H, s), 8.12 (1H, broad s).

PREPARATION 146

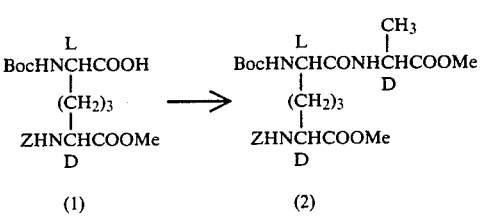

Boc—(L)—Z—(D)—mesoDAP—(L-)—D—AlaOMe—(D)—OMe (2) was prepared substantially in the same manner as Preparation 126.

IR (Nujol): 3300, 1740, 1685, 1655 cm⁻¹.

PREPARATION 147

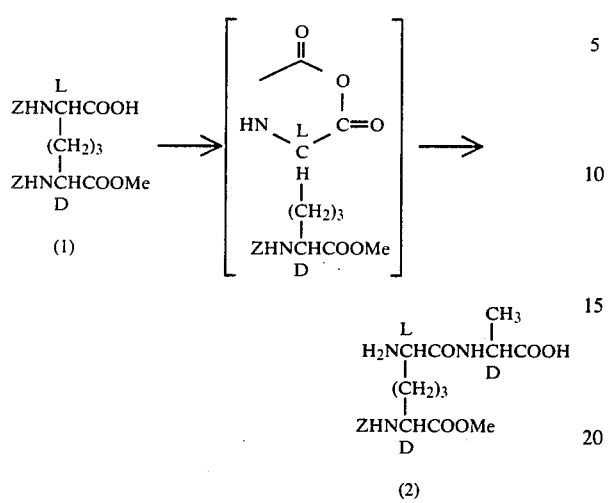

To a solution of diZ—mesoDAP—(D)—OMe (1) (37.0 g) in methylene chloride (200 ml) was added thionyl chloride (74 ml) and the mixture was refluxed for an hour. After evaporation of the solvent, the residue was dissolved in acetonitrile (200 ml). This solution was added to a mixture of D-alanine (21.0 g) and sodium carbonate (8.3 g) in a mixture of 0.5N sodium hydride (400 ml) and acetonitrile (200 ml) under ice-bath cooling. After stirring for 30 minutes at the same temperature, the mixture was diluted with ethyl acetate (150 ml). The aqueous layer was evaporated and the organic layer was extracted with water (150 ml). The aqueous layer and the extract were combined, washed with ethyl acetate and then acidified to pH 4 with 20% hydrochloric acid. This solution was put on a column of HP 20 (700 ml). After washing with water, the column was eluted with a mixture of methanol and water (4:1) to give Z—(D)—mesoDAP—(L)—D—AlaOH—(D)—OMe (2) (20.0 g).

NMR (D$_2$O-NaHCO$_3$), δ: 1.2–2.1 (6H, m), 1.35 (3H, d, J=7 Hz), 3.73 (3H, s), 3.9–4.4 (3H, m), 5.10 (2H, s), 7.07 (5H, s).

PREPARATION 148

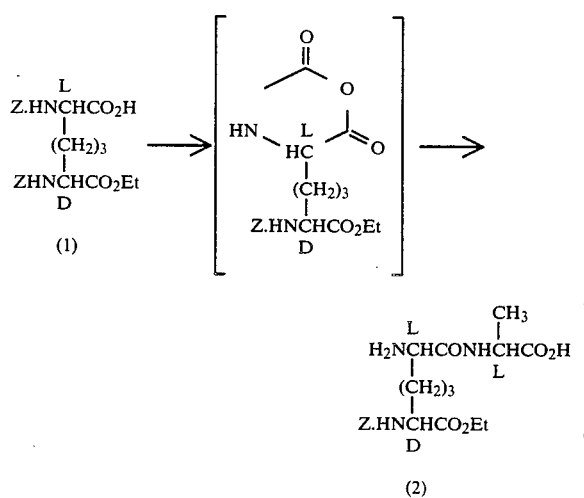

Z—(D)—mesoDAP—(L)—L—AlaOH—(D)—OEt (2) was prepared substantially in the same manner as Preparation 147.

NMR (D$_2$O-NaHCO$_3$), δ: 1.22 (3H, t, J=7 Hz), 1.37 (3H, d, J=7 Hz), 1.5–2.1 (6H, m), 3.8–4.4 (5H, m), 5.12 (2H, s), 7.40 (5H, s).

PREPARATION 149

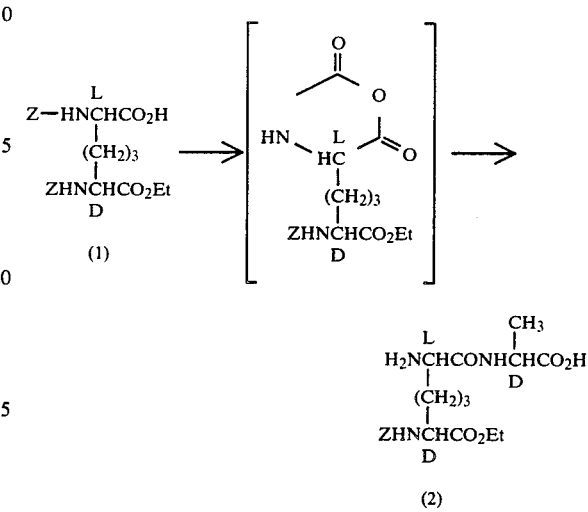

Z—(D)—mesoDAP—(L)—D—AlaOH—(D)—OEt (2) was prepared substantially in the same manner as Preparation 147.

NMR (D$_2$O-NaHCO$_3$), δ: 1.23 (3H, t, J=8 Hz), 1.35 (3H, d, J=7 Hz), 1.1–2.0 (6H, m), 3.9–4.5 (5H, m), 5.15 (2H, s), 7.34 (5H, s).

PREPARATION 150

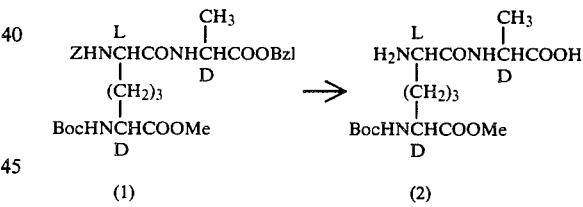

Boc—(L)—mesoDAP—(L)—D—AlaOH—(D)—OMe (2) was prepared substantially in the same manner as Preparation 142.

PREPARATION 151

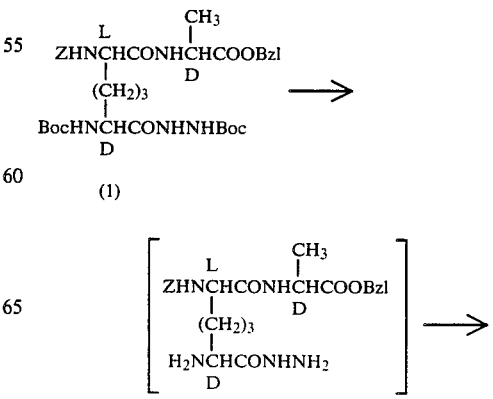

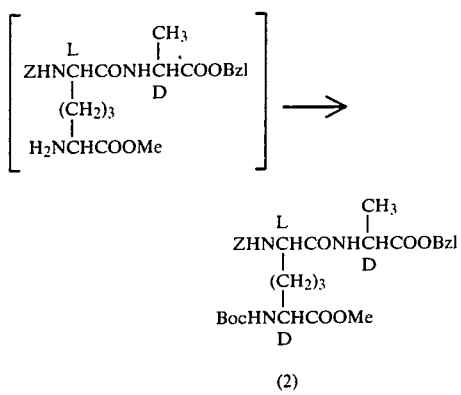

(2)

Z—(L)—Boc—(D)—mesoDAP—(L)—D—AlaOBzl—(D)—OMe (2) was prepared substantially in the same manner as Preparations (102) and (106).

NMR (CDCl$_3$), δ: 1.42 (9H, s), 1.0–2.1 (9H, s), 3.66 (3H, s), 4.0–4.7 (3H, m), 5.07 (2H, s), 5.10 (2H, s), 7.29 (10H, s).

GlyOH—(D)—NHNHZ (1) (1.23 g), and triethylamine (0.30 g) in a mixture of acetone (12 ml) and water (2 ml) was added a solution of 1—N—n—hexyl—2,3,4,5—O—tetraacetyl—D—glucaramide N-hydroxysuccinimyl ester (2) (0.84 g) in acetone (12 ml). The mixture was stirred overnight, allowing the temperature of the mixture to reach to ambient temperature.

After evaporation, the residue was added to a mixture of water (50 ml) and ethyl acetate (100 ml). The organic layer was washed with aqueous sodium bicarbonate (30 ml), water (30 ml), 10% hydrochloric acid (30 ml) and water (30 ml×2) and then dried over magnesium sulfate. The solvent was removed in vacuo to give 1—N—n—hexyl—2,3,4,5—O—tetraacetyl—D—glucaramidyl—L—Ala—γ—D—Glu(α—OBzl)—(L-)—(D)—Z—mesoDAP—(L)—GlyOH—(D-)—NHNHZ (3) (1.15 g).

NMR (DMSO-d$_6$), δ: 0.7–1.0 (3H, m), 1.1–1.7 (19H, m), 1.7–2.3 (2H, m), 1.96 (3H, s), 2.00 (3H, s), 2.07 (3H, s), 2.12 (3H, s), 2.8–3.1 (2H, m), 3.8–4.5 (10H, m), 5.00 (2H, s), 5.06 (2H, s), 5.10 (2H, s), 5.30 (1H, m), 5.60 (1H, m), 7.34 (15H, s), 7.7–8.2 (5H, m), 8.40 (1H, m), 9.98 (1H, s).

(2) Step 2

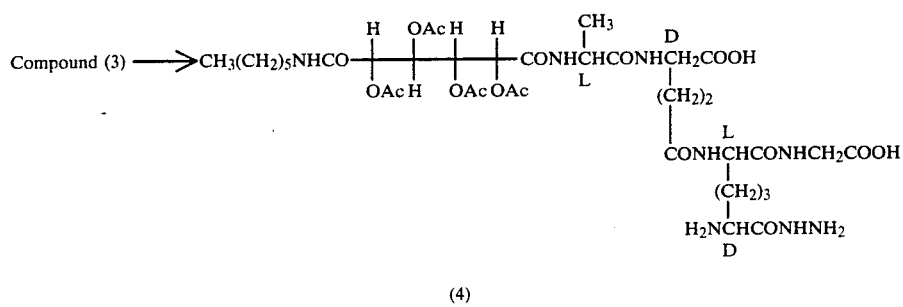

(4)

EXAMPLE 178

(1) Step 1

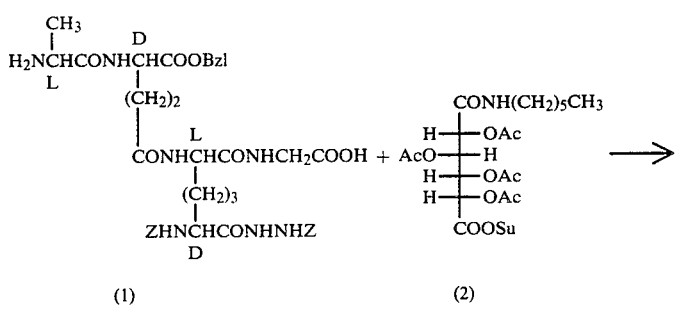

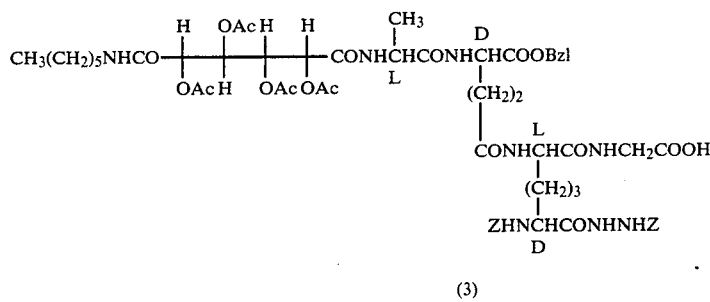

To an ice-cooling solution of L—Ala—γ—D—Glu(α—OBzl)—(L)—Z—(D)—mesoDAP—(L)—

1—N—n—hexyl—2,3,4,5—O—tetraacetyl—D—Glucaramidoyl—L—Ala—γ—D—Glu(α—OH)—(L-)—mesoDAP—(L)—GlyOH—(D)—NHNH$_2$ (4) was prepared substantially in the same manner as step 2 of Example 165.

NMR (CD₃OD), δ: 0.8–1.1 (3H, m), 1.1–2.5 (21H, m), 2.03 (6H, s), 2.17 (3H, s), 2.23 (3H, s), 3.0–3.6 (2H, m), 3.7–4.8 (6H, m), 5.1–6.0 (4H, m).

(3) Step 3

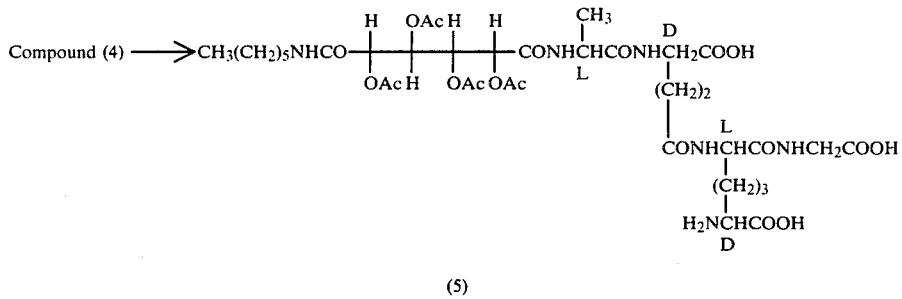

(5)

To an ice-cooling solution of 1—N—n—hexyl—2,3,4,5—O—tetraacetyl—D—glucaramidoyl—L—Ala—γ—D—Glu(α—OH)—(L-)—mesoDAP—(L)—GlyOH—(D)—NHNH₂ (4) (0.64 g) in a mixture of 10% hydrochloric acid (3 ml) and 1,4-dioxane (6 ml) was added N-bromosuccinimide (0.2 g). After stirring for an hour at ambient temperature, the mixture was treated with sodium bisulfite and then adjusted to pH 4 with aqueous sodium carbonate. After evaporation, the residue was dissolved in 1N hydrochloric acid (2 ml) and put on a column of HP-20 (40 ml). After removal of inorganic salts with water, the product was obtained by eluting with 70% methanol. The eluate was lyophilized to give 1—N—n—hexyl—2,3,4,5—O—tetraacetyl—D—glucaramidoyl—L—Ala—γ—D—Glu(α—OH)—(L-)—mesoDAP—(L)—GlyOH (5) (0.43 g).

NMR (D₂O), δ: 0.7–1.0 (3H, m), 1.0–1.6 (19H, m), 1.6–2.5 (2H, m), 2.14 (3H, s), 2.16 (3H, s), 2.22 (3H, s), 2.24 (3H, s), 3.0–3.3 (2H, m), 3.76 (1H, m), 4.0–4.6 (5H, m), 5.1–5.8 (4H, m).

(4) Step 4

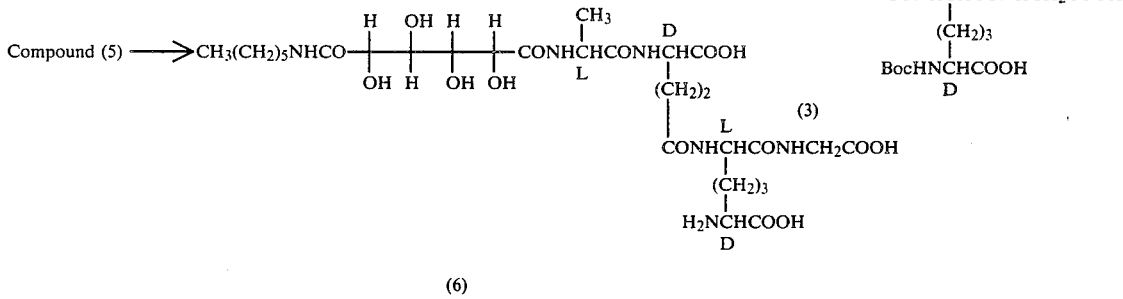

(6)

To an ice-cooling solution of 1—N—n—hexyl—2,3,4,5—O—tetraacetyl—D—glucaramidoyl—L—Ala—γ—D—Glu(α—OH)—(L-)—mesoDAP—(L)—GlyOH (5) (0.33 g) in 50% methanol was added 2N potassium carbonate (2 ml). The mixture was stirred for two hours at the same temperature and then acidified to pH 4 with 10% hydrochloric acid. After evaporation, the residue was dissolved in 1N hydrochloric acid (1 ml) and put on a column of HP-20 (15 ml). Inorganic salts were removed with water and then eluted with 80% methanol. The eluate was lyophilized to give 1—N—n—hexyl—D—glucaramidoyl—L—Ala—γ—D—Glu(α—OH)—(L-)—mesoDAP—(L)—GlyOH (6) (0.26 g).

IR (Nujol): 3300, 1720, 1640, 1540, 1230 —m⁻¹.

NMR (D₂O), δ: 0.7–1.0 (3H, m), 1.0–2.5 (21H, m), 3.1–3.5 (2H, m), 3.5–4.5 (10H, m).

EXAMPLE 179

(1) Step 1

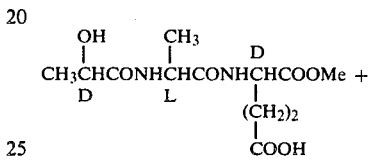

(1)

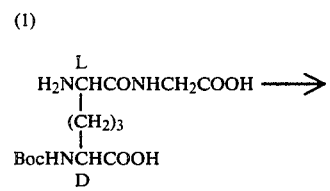

(2)

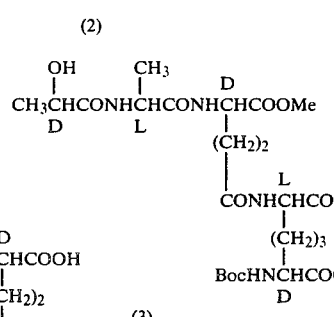

(3)

D—Lac—L—Ala—γ—D—Glu(α—OMe)—(L-)—Boc—(D)—mesoDAP—(L)—GlyOH (3) was prepared substantially in the same manner as step 1 of Example 168.

NMR (CD₃OD), δ: 1.46 (9H, s), 1.2–2.4 (10H, m), 3.72 (3H, s), 3.93 (2H, s), 4.0–4.6 (5H, m).

(2) Step 2

Compound (3) ⟶

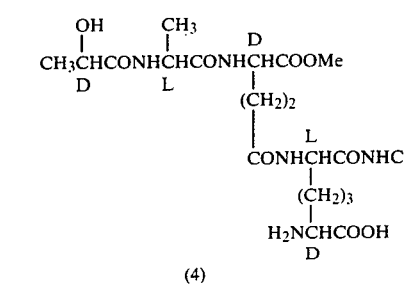

(4)

D—Lac—L—Ala—γ—D—Glu(α—OMe)—(L-)—mesoDAP—(L)—GlyOH (4) was prepared substantially in the same manner as step 3 of Example 168.

NMR (D$_2$O), δ: 1.40 (3H, d, J=7 Hz), 1.45 (3H, d, J=7 Hz), 1.3–2.6 (10H, m), 3.77 (3H, s), 3.87 (2H, s), 4.2–4.6 (4H, m).

EXAMPLE 180

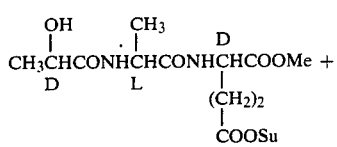

(1)

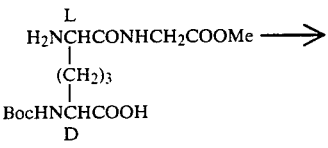

(2)

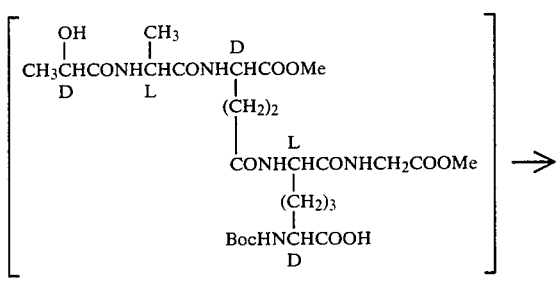

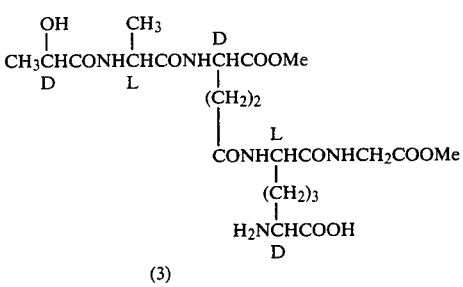

(3)

D—Lac—L—Ala—γ—D—Glu(α—OMe)—(L-)—mesoDAP—(L)—GlyOMe (3) was prepared substantially in the same manner as steps 1 and 3 of Example 168.

NMR (D$_2$O), δ: 1.36 (3H, d, J=7 Hz), 1.42 (3H, d, J=7 Hz), 1.2–2.4 (10H, m), 3.72 (6H, s), 3.98 (2H, s), 4.2–4.5 (4H, m).

EXAMPLE 181

(1) Step 1

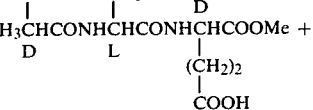

(1)

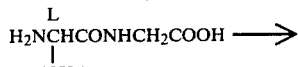

(2)

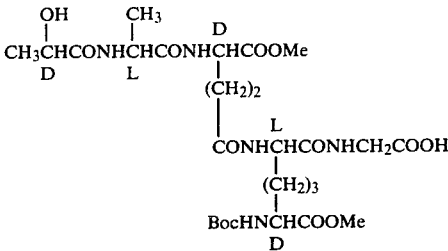

(3)

D—Lac—L—Ala—γ—D—Glu(α—OMe)—(L-)—Boc—(D)—mesoDAP—(D)—OMe—(L)—GlyOH (3) was prepared substantially in the same manner as step 1 of Example 168.

IR cm$^{-1}$ Nujol: 3300, 1730, 1660.

NMR (CD$_3$OD), δ: 1.47 (9H, s), 1.4–2.5 (16H, m), 3.73 (6H, s), 3.95 (2H, s), 4.0–4.6 (5H).

(2) Step 2

Compound (3) ⟶

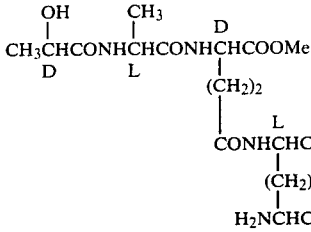

(4)

D—Lac—L—Ala—γ—D—Glu(α—OMe)—(L-)—mesoDAP—(D)—OMe—(L)—GlyOH (4) was prepared substantially in the same manner as Step 3 of Example 168.

[α]$_D$ = −22.9° (C=0.2, H$_2$O)

IR cm$^{-1}$ Nujol: 3400, 1745, 1650.

NMR (D$_2$O), δ: 1.33 (3H, d, J=7 Hz), 1.40 (3H, d, J=7 Hz), 1.2–2.6 (10H, m), 3.77 (3H, s), 3.83 (3H, s), 4.0–4.6 (5H, m).

EXAMPLE 182

(1) Step 1

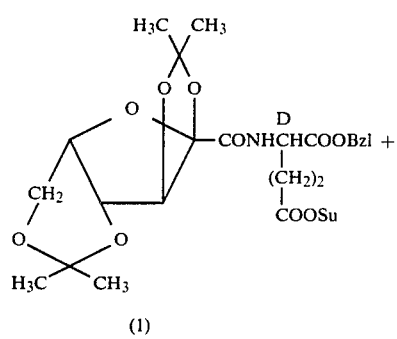

(1)

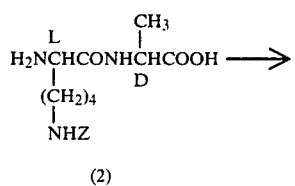

(2)

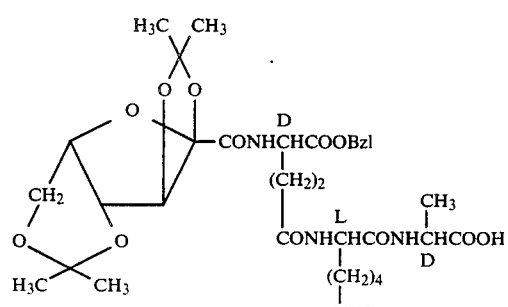

(3)

2,3;4,6—diisopropylidene—L—2—ketogulonoyl—γ—D—Glu(α—OBzl)—L—Lys(Z)—D—AlaOH (3) was prepared substantially in the same manner as step 1 of Example 165.

IR (Nujol), 3300, 1750–1620, 1250–1060⁻¹.

(2) Step 2

Compound (3) ⟶

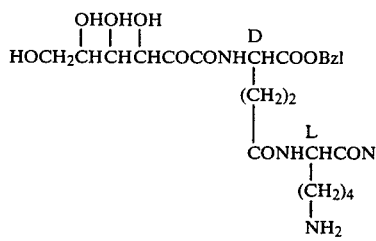

(4)

2,3;4,6—Diisopropylidene 2—ketogulonoyl—γ—D—Glu(α—OBzl)—L—Lys(Z)—D—AlaOH (3) (0.9 g) was dissolved in dioxane. To the solution was added conc. hydrochloric acid (5 ml), and the mixture was stirred for 20 hours and then adjusted to pH 6–7 with aqueous sodium bicarbonate solution. The resultant mixture was concentrated in vacuo and the residue was dissolved in water. The solution was subjected to carbon column (30 ml). The column was eluted with methanol and ethanol (1:1). The fractions containing the object compound (4) were collected and the solvent was evaporated to give a foam which was lyophilized to give 2—keto—L—gulonoyl—γ—D—Glu(α—OBzl)—L—Lys—D—AlaOH (4) (400 mg).

NMR (D$_2$O), δ: 1.32 (3H, d, J=7 Hz), 3.15 (2H, t, J=7 Hz), 3.66–4.50 (8H, m), 5.10 (2H, s), 7.43 (5H, s).

(3) Step 3 .

Compound (4) ⟶

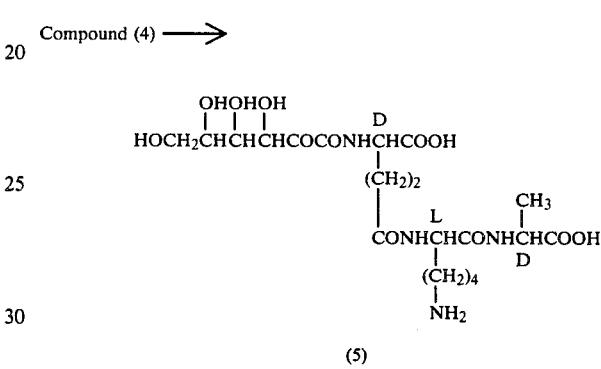

(5)

2—Keto—L—gulonoyl—γ—D—Glu(α—OH)—L—Lys—D—AlaOH (5) was prepared substantially in the same manner as step 2 of Example 165.

NMR (D$_2$O), δ: 1.36 (3H, d, J=7 Hz), 3.05 (2H, t, J=7 Hz), 3.70–4.50 (8H, m).

EXAMPLE 183

(1) Step 1

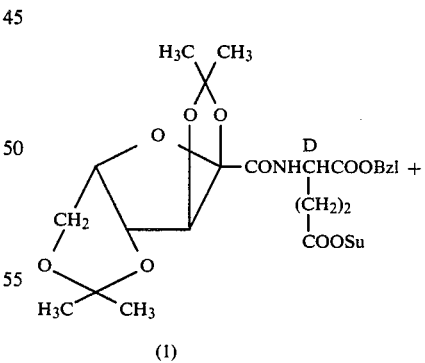

(1)

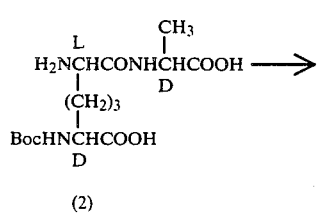

(2)

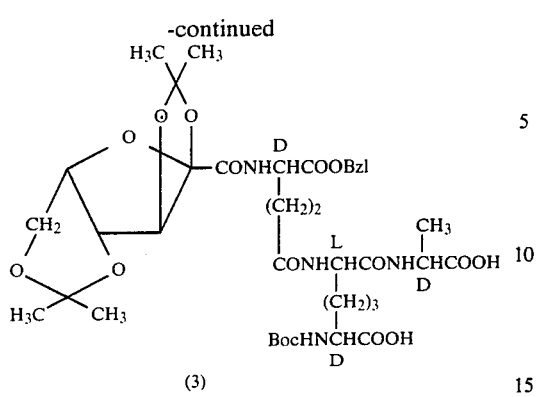

(3)

2,3;4,6—di—iso-propylidene—2—keto—L—gulonoyl—γ—D—Glu(α-OBzl)—(L)—Boc—(D)—mesoDAP—(L-)—D—AlaOH (3) was prepared substantially in the same manner as step 1 of Example 165.

IR (Nujol),: 3300, 1730, 1680, 1520, 1250-1060 cm$^{-1}$.

NMR (CD$_3$OD), δ: 1.06 (3H, s), 1.20 (3H, s), 1.47 (15H, s), 4.16-4.50 (9H, m), 5.20 (2H, s), 7.40 (5H, s).

(2) Step 2

Compound (3) ⟶

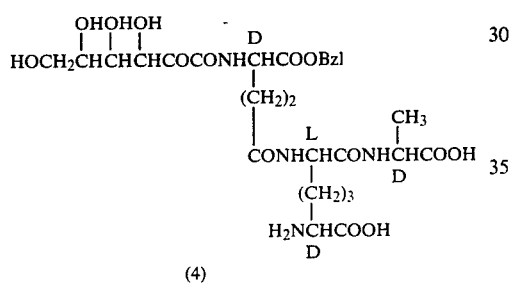

(4)

2—Keto—L—gulonoyl—γ—D—Glu(α—OBzl)—(L)—mesoDAP—(L)—D—AlaOH (4) was prepared substantially in the same manner as step 2 of Example 182.

IR (Nujol),: 3300, 1730, 1650, 1530, 1220, 1180, 1050 cm$^{-1}$.

NMR (D$_2$O), δ: 1.33 (3H, d, J=8 Hz), 3.66-4.50 (8H, m), 5.30 (2H, s), 7.47 (5H, s).

(3) Step 3

Compound (4) ⟶

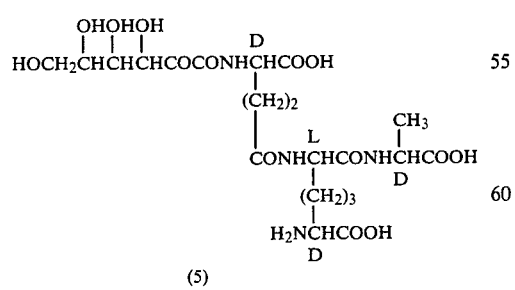

(5)

2—Keto—L—gulonoyl—γ—D—Glu(α—OH)—(L-)—mesoDAP—(L)—D—AlaOH (5) was prepared substantially in the same manner as step 2 of Example 165.

IR (Nujol),: 3300, 1720, 1670 cm$^{-1}$.

NMR (D$_2$O), δ: 1.38 (3H, d, J=7 Hz), 1.70-2.50 (10H, m), 3.60-4.40 (8H, m).

EXAMPLE 184

(1) Step 1

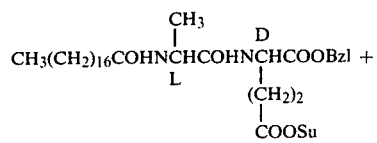

Stearoyl—γ—D—Glu(α—OBzl)—(L)—Z—(D-)—mesoDAP—(D)—OEt—(L)—D—AlaOEt (3) was prepared substantially in the same manner as step 1 of Example 168.

IR (Nujol): 3280, 1750, 1710, 1650 cm$^{-1}$.

NMR (CDCl$_3$),: δ: 0.87 (3H, m), 3.96-4.60 (9H, m), 5.10 (2H, s), 5.13 (2H, s), 7.32 (10H, s).

(2) Step 2

Compound (3) ⟶

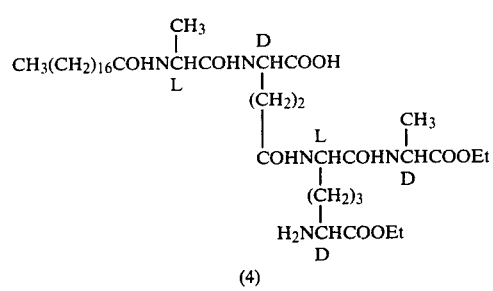

(4)

Stearoyl—L—Ala—γ—D—Glu(α—OBzl)—(L-)—Z—(D)—mesoDAP—(D)—OEt—(L-)—D—AlaOEt (3) (584 mg) was dissolved in acetic acid (20 ml) and hydrogenated under 2.5 atmospheric pressures of hydrogen over 10% palladium charcoal. After removal of the catalyst by filtration, the filtrate was evaporated in vacuo. To the residue was added hexane to give crystals which were washed with hot isopropylether to give stearoyl—L—Ala—γ—D—Glu(α—OH)—(L)—mesoDAP—(D)—OEt—(L-)—D—AlaOEt (4) (340 mg).

IR (Nujol): 3290, 1740, 1630 cm⁻¹.

NMR (CF₃COOH), δ: 0.87 (3H, m), 1.1–2.9 (54H, m), 4.13–5.00 (9H, m).

EXAMPLE 185

(1) Step 1

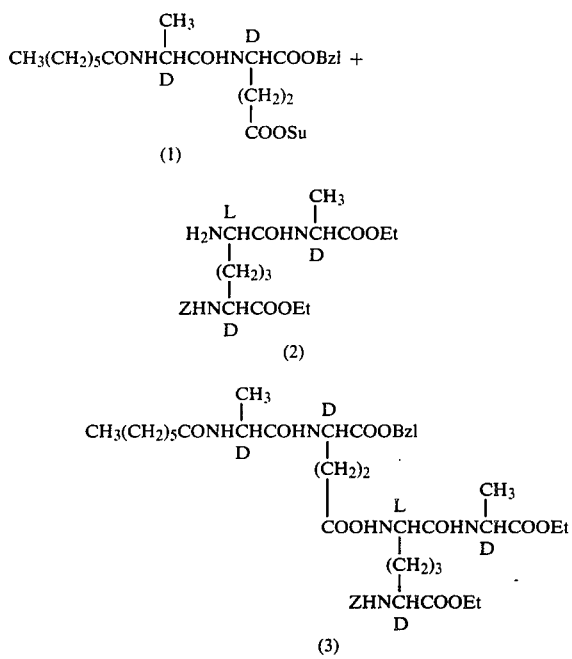

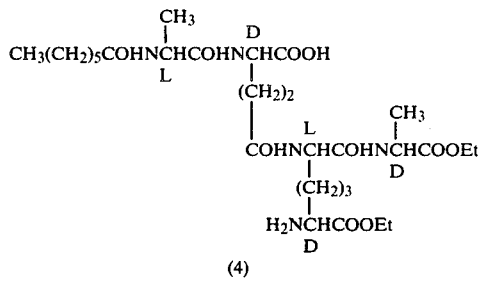

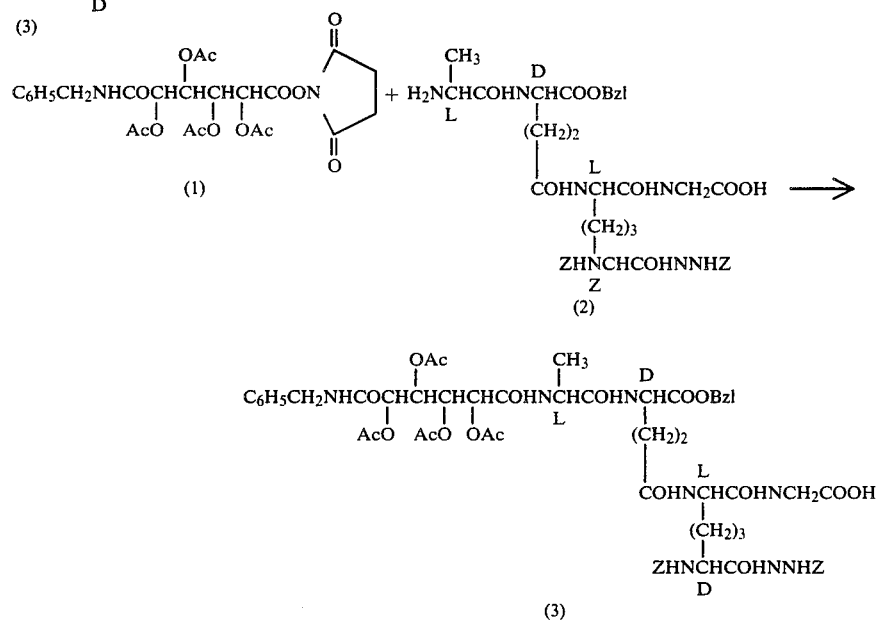

Heptanoyl—L—Ala—γ—D—Glu(α—OBzl)—(L-)—Z—(D)—mesoDAP—(D)—OEt—(L-)—D—AlaOEt (3) was prepared substantially in the same manner as Step 1 of Example 168.

IR (Nujol): 3260, 1730, 1680, 1620 cm⁻¹.

NMR (CDCl₃), δ: 0.85 (3H, m), 1.05–2.40 (29H, m), 3.93–4.70 (8H, m), 5.06 (2H, s), 5.11 (2H, s), 5.58 (1H, d, J=8 Hz), 6.60 (2H, d, J=8 Hz), 7.20 (1H, d, J=8 Hz), 7.31 (10H, s).

(2) Step 2

Compound (3) ⟶

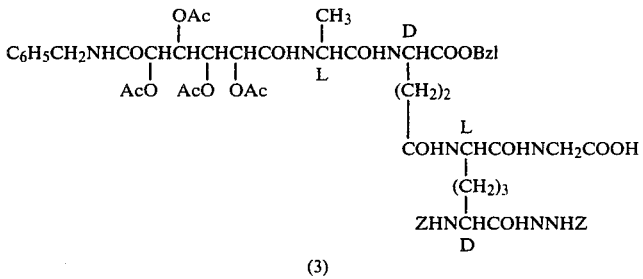

Heptanoyl—L—Ala—γ—D—Glu(α—OH)—(L-)—mesoDAP—(D)—OEt—(L)—D—AlaOEt (4) was prepared substantially in the same manner as step 2 of Example 184.

IR (Nujol): 3280, 1740, 1635 cm⁻¹.

NMR (DMSO-d₆), δ: 0.87 (3H, m), 1.02–2.33 (27H, m), 3.40 (1H, m).

EXAMPLE 186

(1) Step 1

1—N—Benzyl—2,3,4,5—O—tetraacetyl—D—glucaramidoyl—L—Ala—γ—D—Glu(α—OBzl)—(L-)—Z—(D)—mesoDAP—(D)—NHNHZ—(L)—GlyOH (3) was prepared in a similar manner to Step 1 of the Example 168.

mp. 176°–178° C.

IR (Nujol): 3350, 1750, 1670, 1530 cm⁻¹.

NMR (DMSO-d₆): δ1.0–2.2 (13H, m), 1.85 (3H, s), 1.94 (3H, s), 2.00 (3H, s), 2.10 (3H, s), 3.6–4.5 (8H, m), 4.95 (2H, s), 5.00 (2H, s), 5.06 (2H, s), 5.1–5.7 (2H, m), 7.20 (5H, s), 7.28 (15H, s), 7.6–8.6 (3H, m).

(2) Step 2

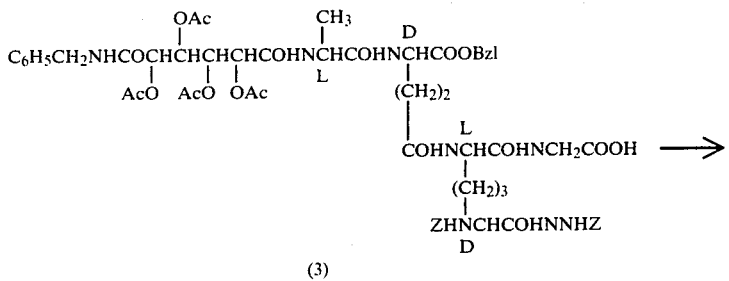

(3)

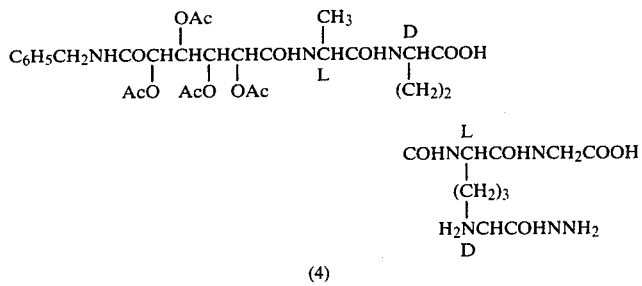

(4)

1—N—Benzyl—2,3,4,5—O—tetraacetyl—D—glucaramidoyl—L—Ala—γ—D—Glu(α—OH)—(L-)—mesoDAP—(D)—NHNH$_2$—(L)—GlyOH (4) was prepared in a similar manner to the Example 165 Step 2.
mp. 178°–181° (dec).
IR (Nujol): 3300, 1750, 1650, 1530 cm$^{-1}$.
NMR (CH$_3$OD): δ1.1–2.5 (13H, m), 1.83 (3H, s), 2.00 (3H, s), 2.13 (3H, s), 2.23 (3H, s), 3.85 (2H, s), 7.25 (5H, s).
(3) Step 3

1—N—Benzyl—2,3,4,5—O—tetraacetyl—D—glucaramidoyl—L—Ala—γ—D—Glu(α—OH)—(L-)—mesoDAP—(L)—GlyOH (5) was prepared in a similar manner to the Example 178 Step 3.
mp. 145°–150° C.
IR (Nujol): 3350, 1760, 1660 (sh), 1650, 1530 cm$^{-1}$.
NMR (D$_2$O): δ1.43 (3H, d, J=7 Hz), 1.3–2.5 (10H, m), 2.00 (3H, s), 2.10 (3H, s), 2.23 (6H, s), 3.7–4.0 (3H, m), 4.0–4.5 (3H, m), 5.1–6.0 (4H, m), 7.37 (5H, s).
(4) Step 4

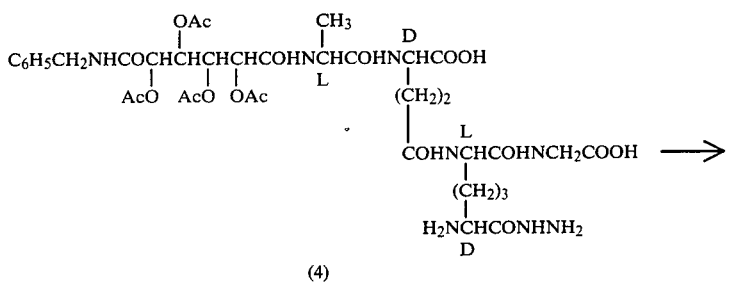

(4)

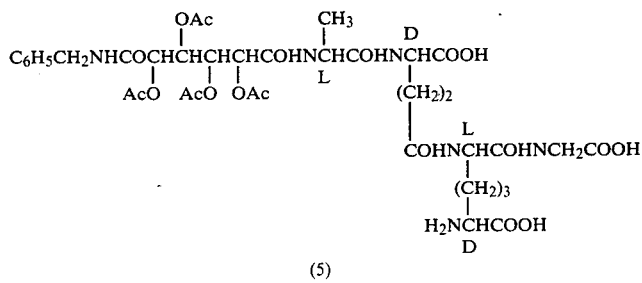

(5)

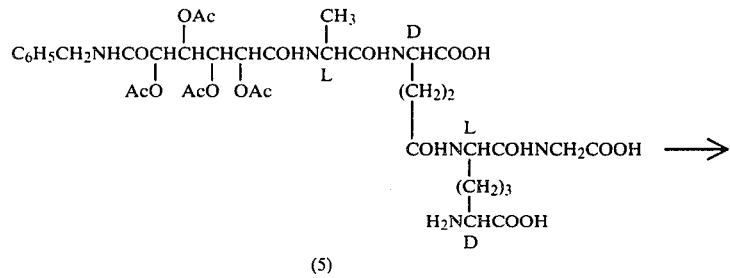

(5)

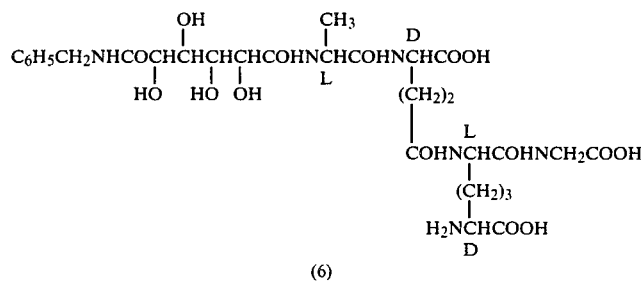

(6)

1—N—Benzyl—D—glucaramidoyl—L—Ala—γ—D—Glu(α—OH)—(L-)—mesoDAP—(L)—GlyOH (6) was prepared in a similar manner to the Example 178 Step 4.

mp. 117°–120° C.

IR (Nujol): 3350, 1730, 1640 (sh), 1540 cm$^{-1}$.

NMR (D$_2$O): δ1.42 (3H, d, J=7 Hz), 1.2–2.5 (10H, m), 3.86 (2H, s), 3.5–5.0 (10H, m), 7.35 (5H, s).

EXAMPLE 187

(1) Step 1

1—N—Lauryl—2,3,4,5—O—tetraacetyl—D—glucaramidoyl—L—Ala—γ—D—Glu(α—OBzl)—(L-)—(D)—mesoDAP—(D)—NHNHZ—(D)-GlyOH (III) was prepared in a similar manner to the Example 168, step 1.

IR (Nujol): 3350, 1760, 1670, 1650, 1540 cm$^{-1}$.

NMR (DMSOD$_6$): δ0.9 (3H, m), 1.0–2.3 (33H, m), 1.95 (3H, s), 2.00 (3H, s), 2.07 (3H, s), 2.15 (3H, s), 3.00 (2H, m), 3.2–4.6 (10H, m), 5.08 (2H, s), 5.13 (2H, s), 5.18 (2H, s), 5.2–5.8 (2H, m), 7.37 (15H, s), 7.7–8.5 (5H, m), 9.20 (1H, m), 9.90 (1H, s).

(2) Step 2

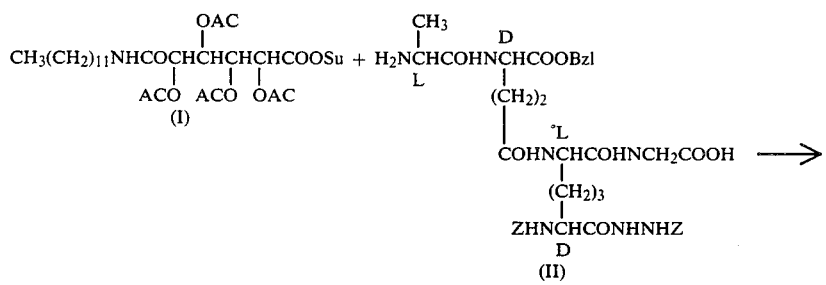

(II)

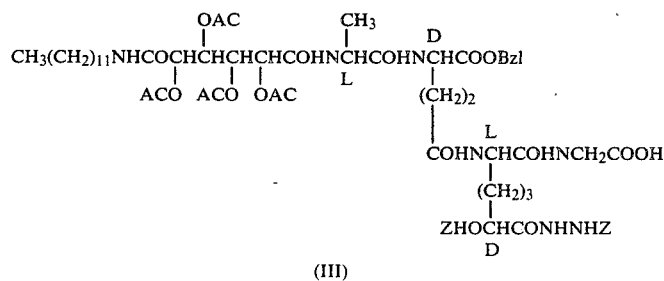

(III)

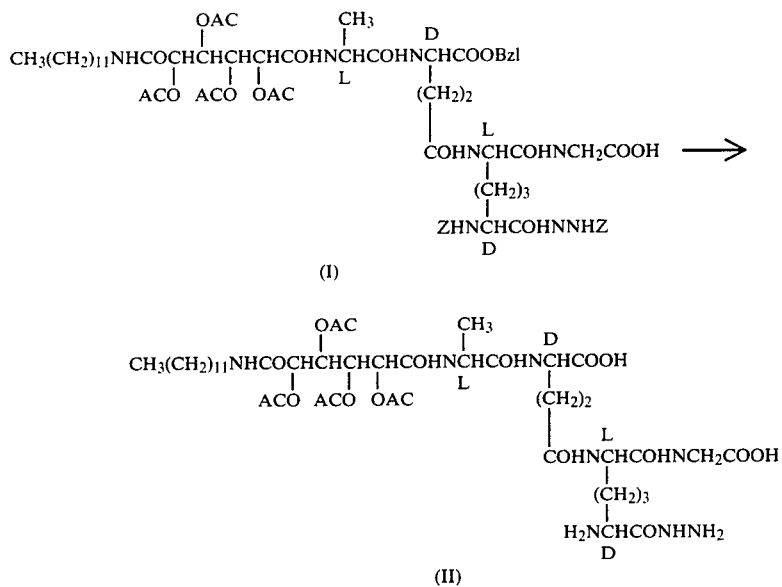
1—N—Lauryl—2,3,4,5—O—tetraacetyl—D—glucaramidoyl—L—Ala—γ—D—Glu(α—OH)—(L)-mesoDAP—(D)—NHNH$_2$—(L)—GlyOH (II) was prepared in a similar manner to the Example 165 step 2.
IR(Nujol): 3350, 1760, 1660, 1540 cm$^{-1}$.
NMR (CD$_3$OD): δ0.90 (3H, m), 1.0–2.4 (33H, m), 2.02 (6H, s), 2.13 (3H, s), 2.20 (3H, s), 2.9–3.3 (2H, m), 3.80 (2H, s).
(3) Step 3
1—N—Lauryl—2,3,4,5—O—tetraacetyl—D—glucaramidoyl—L—Ala—γ—D—Glu(α—OH)—(L)-mesoDAP—(L)—GlyOH (II) was prepared in a similar manner to the Example 178 step 3.
IR (Nujol): 3350, 1760, 1660, 1540 cm$^{-1}$.
NMR (D$_2$O): δ0.80 (3H, m), 1.0–2.5 (33H, m), 2.08 (6H, s), 2.16 (3H, s), 2.20 (3H, s), 3.10 (2H, m), 3.78 (2H, s).
(4) Step 4
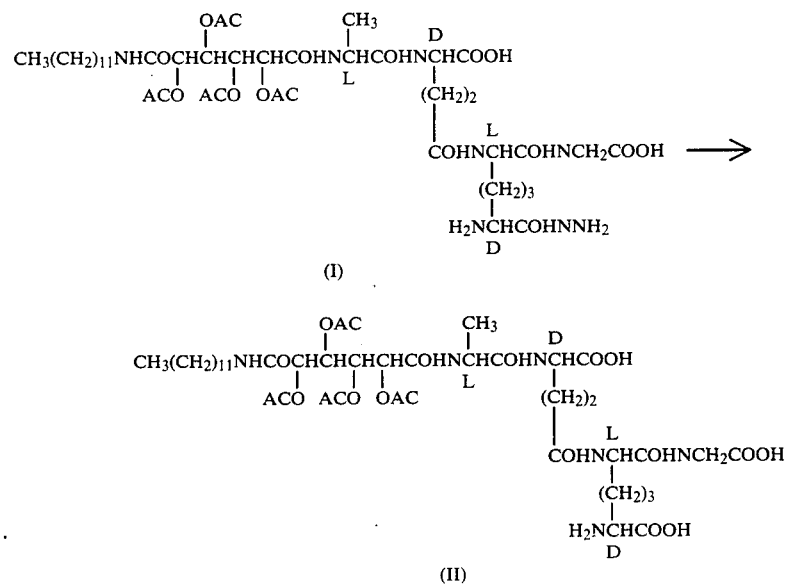

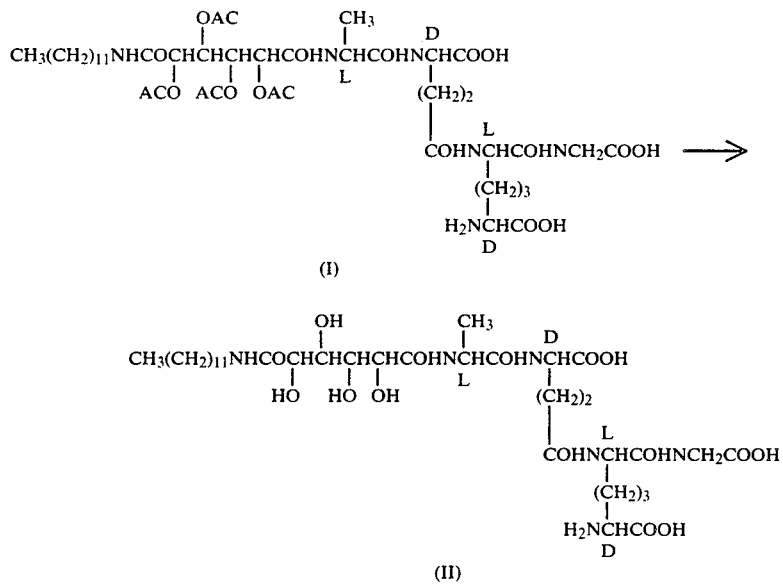

1—N—Lauryl—D—glucaramidoyl—L—Ala—γ—D—Glu(α—OH)—(L-)—mesoDAP—(L)—GlyOH (II) was prepared in a similar manner to the Example 178 step 4.

IR (Nujol): 3300, 1720, 1640, 1540 cm⁻¹.

NMR (D$_2$O): δ0.80 (3H, m), 1.0-2.5 (33H, m), 3.20 (2H, m), 3.80 (2H, m).

PREPARATION 152

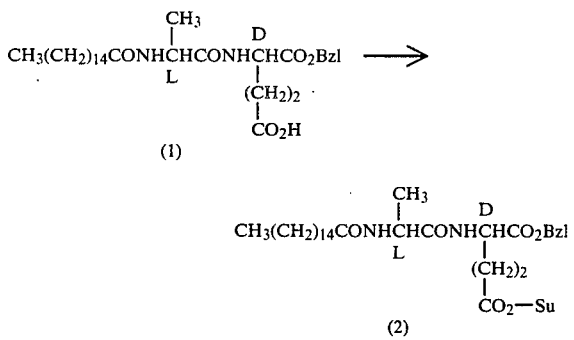

To a solution of palmitoyl—L—Ala—D—Glu(OH-)OBzl (1)(1.84 g) in a mixture of tetrahydrofuran (20 ml) and chloroform (30 ml) were added N-hydroxysuccinimide (425 mg) and dicyclohexylcarbodiimide (728 mg). The reaction mixture was kept for 18 hours at room temperature and the precipitate was filtered off and washed with chloroform. The filtrate was concentrated in vacuo and the diisopropylether was added to the residue. The product was collected and dried to afford palmitoyl—L—Ala—D—Glu(OSu)OBzl (2)(1.70 g).

IR (Nujol): 3300, 1805, 1780, 1745, 1640 cm⁻¹.

NMR (CDCl$_3$, δ): 0.89 (3H, m), 1.05-2.70 (35H, m), 2.80 (4H, s), 4.20-4.83 (2H, m), 5.15 (2H, s), 6.23 (1H, d, J=8 Hz), 7.30 (5H, s).

PREPARATION 153

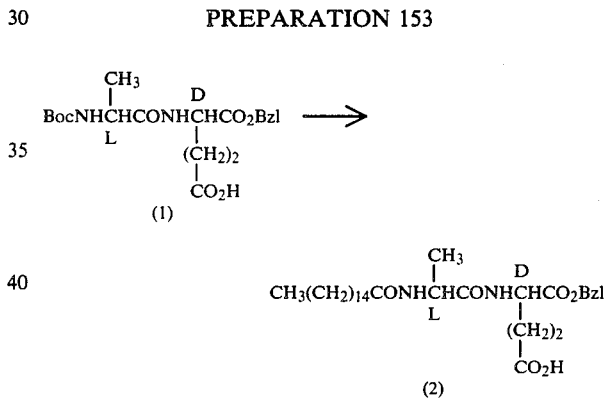

Trifluoroacetic acid (15 ml) was added to Boc—L—Ala—D—Glu—(OH)OBzl (1)(3.26 g) and the mixture was stirred for 20 minutes at room temperature, concentrated in vacuo and washed with diisopropylether. The oil was dissolved in a mixture of water (15 ml) and sodium bicarbonate was added until the pH of the solution became 8-9. The mixture of water (6 ml) and acetone (20 ml) was added to the solution and palmitoyl chloride (2.20 g) was added in one portion. After stirring for 30 minutes at room temperature, the pH of the solution was adjusted to 3 was 1N-hydrochloric acid and the reaction mixture was concentrated. To the residue was added water (30 ml) and the precipitates was collected and dried to give a crude product, which was purified by column chromatography of Silicagel (90 g) with chloroform-methanol (30:1, v/v) as an eluent to give palmitoyl-L-Ala-D-Glu(OH)OBzl (2)(2.00 g). mp. 131°-132° C.

[α]$_D$—23.38° (C=0.2, CHCl$_3$).

IR (Nujol): 3300, 1730, 1700, 1650, 1635 cm⁻¹.

NMR (CDCl$_3$, δ): 0.88 (3H, m), 1.1-1.75 (31H, m), 2.0-2.5 (4H, m), 4.4-4.8 (2H, m), 5.11 (2H, s), 7.34 (5H, s).

PREPARATION 154

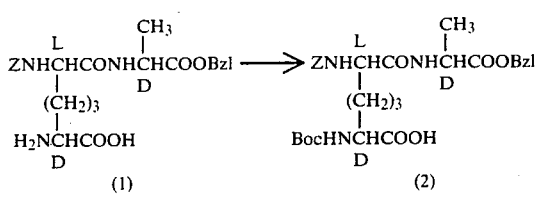

To a solution of Z—(L)—mesoDAP—(L-)—D—AlaOBzl (1) (5.97 g) in a mixture of water (60 ml), dioxane (60 ml) and triethylamine (2.73 g) was dropped a solution of di-tert-butyl carbonate (3.21 g) in dioxane (18 ml) at room temperature and the pH of the mixture was adjusted between 9 and 10 with triethylamine. After stirring for 1 hour, the mixture was diluted with water and ethyl acetate (100 ml) was added. The organic layer was extracted with water three times and the aqueous layers were combined. The pH of the aqueous layer was adjusted to 4–5 with 5% hydrochloric acid and extracted with ethyl acetate. The extract was washed with brine, dried over magnesium sulfate and concentrated in vacuo. The resulting residue was crystallized with diisopropylether to give Z—(L-)—Boc—(D)—mesoDAP—(L)—D—AlaOBzl (2)(5.28 g). mp. −143° C. (dec.).

NMR (CD$_3$OD): δ1.33 (2H, d, J=8 Hz), 1.40 (9H, s), 1.2–2.0 (6H, m), 3.9–4.2 (2H, m), 4.40 (1H, q, J=8 Hz), 5.05 (2H, s), 5.10 (2H, s), 7.30 (10H, s).

PREPARATION 155

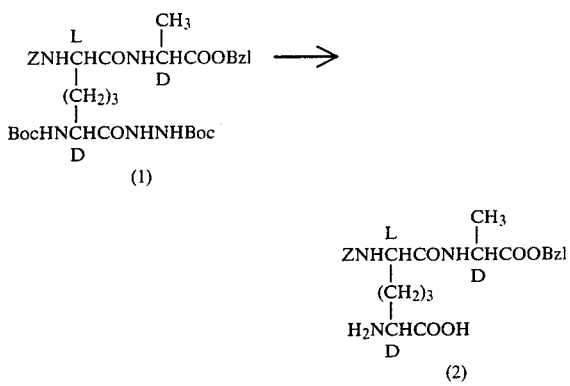

Z—(L)—Boc—(D)—mesoDAP—(L)—D—AlaOBzl—(D)—NHNHBoc (1) (28 g) was added to trifluoroacetic acid (280 ml) and the mixture was stirred for 1 hour at room temperature. After evaporation of trifluoroacetic acid, the residue was dissolved in a mixture of water (240 ml), 1N hydrochloric acid (40 ml) and dioxane (200 ml), and N-bromosuccinimide (16.4 g) was added at 0° C. After stirring for 0.5 hours at the same temperature, the reaction mixture was treated with an aqueous solution of sodium sulfite and concentrated in vacuo. To the residue was added 30% aqueous sodium hydroxide until the pH of the mixture reached to 4–5. The resulting precipitate was collected and washed with water to give Z—(L)—mesoDAP—(L-)—D—AlaOBzl (2).

IR (Nujol): 3280, 1725, 1685, 1640 cm$^{-1}$.

NMR (DMSO-d$_6$): 1.34 (3H, d, J=8 Hz), 1.2–2.0 (6H, m), 4.37 (1H, q, J=8 Hz), 5.08 (2H, s), 5.16 (2H, s), 7.43 (10H, s).

EXAMPLE 188

(1) Step 1

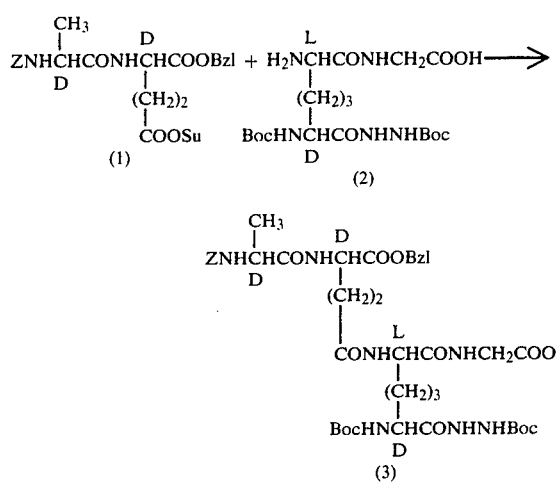

Boc—(D)—mesoDAP—(L)—Gly—(D)—NHNHBoc (1)(2.31 g) was dissolved in a mixture of dioxane (60 ml) and water (50 ml) and triethylamine (610 mg) and Z—D—Ala—D—Glu(α—OBzl)—γ—OSu (1)(2.70 g) were added. The mixture was left for 18 hours at room temperature and concentrated at a reduced pressure. The mixture of water (30 ml), 1N-hydrochloric acid (10 ml) and ethyl acetate (100 ml) were added to the residue. The organic layer was separated and washed with brine, dried over magnesium sulfate, concentrated in vacuo. The resulting amorphous powder was washed with diisopropyl ether and collected to give a crude product, which was purified by silica gel chromatography (100 ml) eluting with chloroform-methanol (10:1–5:1, v/v). The fractions containing the object compound (3) were collected and concentrated to dryness to yield Z—D—Ala—γ—D—Glu—α—OBzl—(L)—Boc—(D)—mesoDAP—(L)—Gly—(D-)—NHNHBoc (3) (1.09 g).

mp −125° C. (dec.).

[α]$_D$−4.39 (C=0.21, CHCl$_3$).

IR (Nujol): 3300, 1720, 1670 cm$^{-1}$.

(2) Step 2

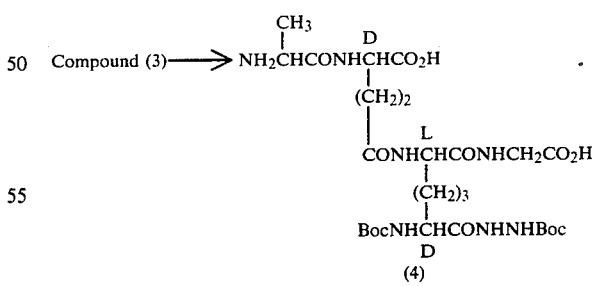

Z—D—Ala—γ—D—Glu(α—OBzl)—(L-)—Boc—(D)—mesoDAP—(L)—Gly—(D)—NHNHBoc (3) (980 ml) was dissolved in acetic acid (20 ml) and hydrogenated under an atomspheric pressure of hydrogen over 10% palladium-charcoal (200 mg). After removal of the catalyst, the filtrate was concentrated at a reduced pressure. The resulting syrup was dissolved in water (5 ml) and applied for HP-20 column chromatography (50 ml) eluting with water-methanol (1:1, v/v). The fractions containing the object compound (4) were collected and evaporated to dryness to yield H—D—Ala—γ—D—Glu—(L)—Boc—(D-)—mesoDAP—(L)—Gly—(D)—NHNHBoc (4) (610 mg).

mp −159° C. (dec.).
[α]$_D$−17.30 (C=0.1, meOH).
IR (Nujol): 3270, 1670 cm$^{-1}$.
NMR (CD$_2$OD): δ1.1–2.4 (3H, m), 3.70–4.55 (6H, m).

EXAMPLE 189

(1) Step 1

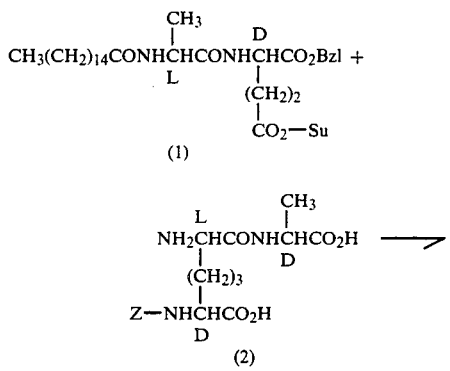

To a solution of Z—(D)—meso—DAP—(L-)—D—AlaOH (2) (918 mg) in the mixture of methylene chloride (25 ml) and methanol (6 ml) was added triethylamine (760 mg). After the solution turned clear, palmitoyl—L—Ala—D—Glu(OSu)OBzl (1) (1.61 g) was added to the solution. The mixture was kept for 18 hours at the room temperature and concentrated in vacuo. To the residue were added water (30 ml) and 1N-hydrochloric acid (8 ml). The precipitate was collected, washed with water and dried to give a crude product (2.06 g), which was washed with hot diisopropylether to give palmitoyl—L—Ala—γ—D—Glu—(α—OBzl)—(L)—Z—(D)—mesoDAP—(L-)—D—AlaOH (3) (2.00 g).

mp 185°–187° C.
[α]$_D$−15.38°(C=0.21, AcOH).
IR (Nujol): 3300, 1725, 1690, 1630 cm$^{-1}$.
NMR (CDCl$_3$-CD$_3$OD): δ 0.87 (3H, m), 1.0–2.4 (44H, m), 4.1–4.6 (5H, m), 5.06 (2H, s).

(2) Step 2

Compound (3) ⟶

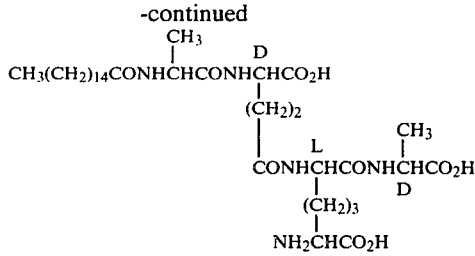

Palmitoyl—L—Ala—γ—D—Glu—(α—O—Bz-l)—(L)—Z—(D)—mesoDAP—(L)—D—Ala—OH (3) (1.86 g) was dissolved in acetic acid (40 ml) and hydrogenated under an atmospheric pressure of hydrogen over 10% palladium-charcoal (1.0 g). After removal of the catalyst, acetic acid was evaporated off in vacuo. To the residue was added diisopropylether and the crystalline mass was collected to give palmitoyl—L—Ala—γ—D—Glu—(L)—mesoDAP—(L-)—D—AlaOH (4) (1.30 g).

mp. 185°–190° C.
[α]$_D$−14.07°(C=0.21, AcOH).
IR (Nujol): 3320, 1730(sh), 1710, 1625 cm$^{-1}$.
NMR (NaOD-D$_2$O, δ): 0.87 (3H, m), 1.05–2.60 (44H, m), 3.91–4.54 (5H, m).

EXAMPLE 190

(1) Step 1

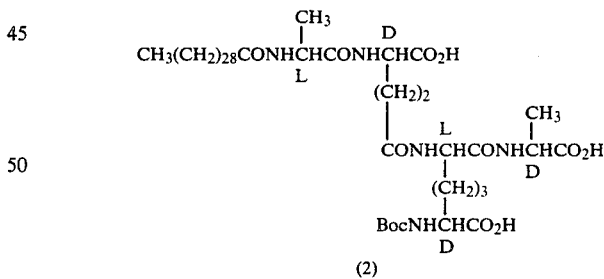

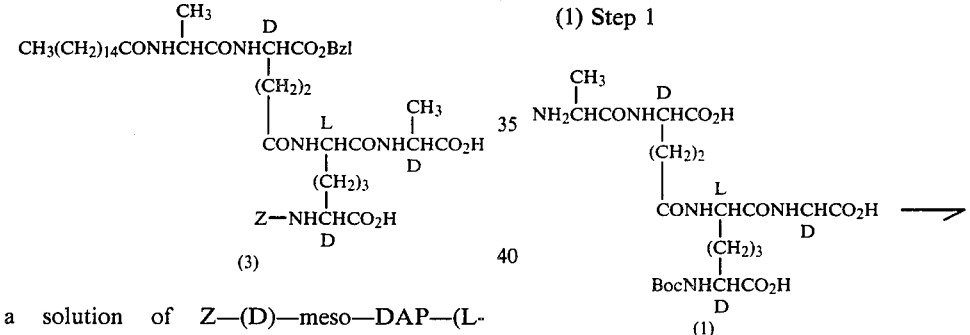

To the solution of H—L—Ala—γ—D—Glu—(α—OH)—(L)—Boc—(D)—meso—DAP—(L-)—D—Ala—OH (1) (528 mg) in a mixture of methylene chloride (20 ml) and methanol (6 ml) were added triethylamine (314 mg) and triacontanoic acid-N-hydroxysuccinimide ester (518 mg). After stirring for 16 hours at room temperature, the reaction mixture was concentrated in vacuo and the mixture of water (10 ml) and 1N-hydrochloric acid (4 ml) was added to the residue. The precipitates were collected, washed with water and dried to give a crude product, which was washed with hot diisopropylether to give triacontanoyl—L—Ala—γ—D—Glu—(α—OH)—(L-

)—Boc—(D)—mesoDAP—(L)—D—AlaOH (2) (610 mg).

mp—157° C. (dec.).

[α]$_D$—14.67°(C=0.20, AcOH).

IR (Nujol): 3280, 1720, 1625 cm$^{-1}$.

NMR (CDCl$_3$-CD$_3$OD, δ): 0.92 (3H, m), 1.1–2.1 (77H, m), 2.15–2.50 (4H, m).

(2) Step 2

Compound (2) ⟶

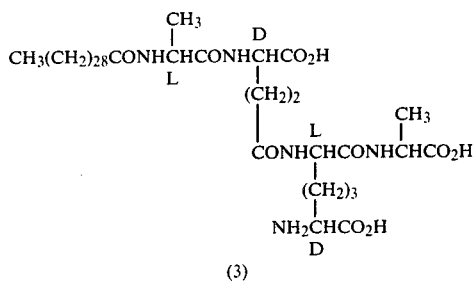

To the suspension of triacontanoyl—L—Ala—γ—D—Glu—(α—OH)—(L-)—Boc—(D)—mesoDAP—(L)—D—Ala—OH (2) (500 mg) in acetic acid (20 ml) was added acetic acid saturated with hydrogen chloride (10 ml) and the mixture was stirred on a steam bath for 5 minutes and cooled to room temperature and kept for 1.5 hours at the same temperature. The reaction mixture was concentrated in vacuo and the residue was washed with water and the precipitates were collected and dried to give triacontanoyl—L—Ala—γ—D—Glu—(α—OH-)—(L)—meso—DAP—(L)—D—AlaOH (412 mg).

mp —185° C. (dec.).

IR (Nujol): 3300, 1720, 1625 cm$^{-1}$.

NMR (CF$_3$CO$_2$H, δ): 0.90 (3H, m).

EXAMPLE 191

(1) Step 1

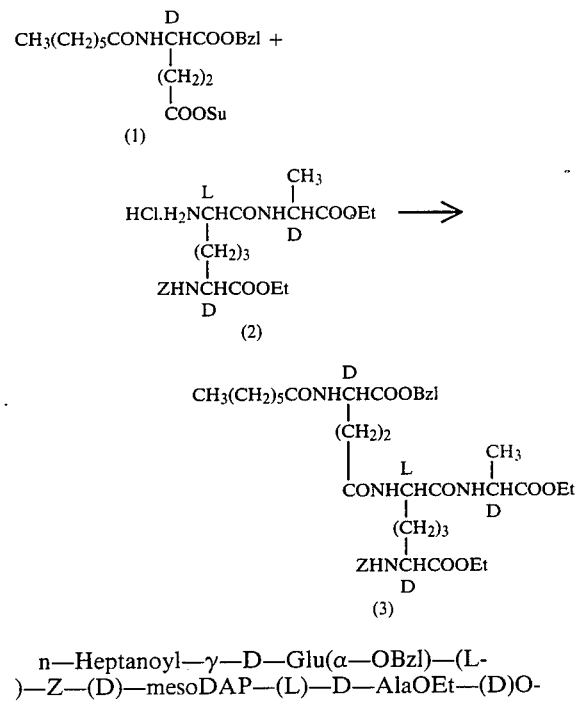

n—Heptanoyl—γ—D—Glu(α—OBzl)—(L-)—Z—(D)—mesoDAP—(L)—D—AlaOEt—(D)O-

Et(3) was prepared substantially in the same manner as step 1 of Example 189.

mp 141°–142° C.

[α]$_D$= —10.31° (C=0.22, CHCl$_3$).

NMR (DMSO-d$_6$), δ: 0.85 (3H, m), 1.05–2.40 (29H, m), 3.93–4.70 (8H, m), 5.06 (2H, s), 5.11 (2H, s), 5.58 (1H, d, J=8 Hz), 6.60 (2H, d, J=8 Hz), 7.20 (1H, d, J=8 Hz), 7.31 (10H, s).

(2) Step 2

Compound (3) ⟶

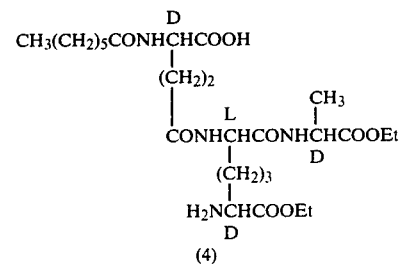

n—Heptanoyl—γ—D—Glu(α—OH)—(L-)—mesoDAP—(L)—D—AlaOEt—(D)—OEt (4) was prepared substantially in the same manner as step 2 of Example 189.

mp. 179°–182° C.

[α]$_D$= —13.85° (C=0.29, AcOH).

NMR (DMSO-d$_6$): 0.87 (3H, m), 1.02–2.33 (27H, m), 3.40 (1H, m).

EXAMPLE 192

(1) Step 1

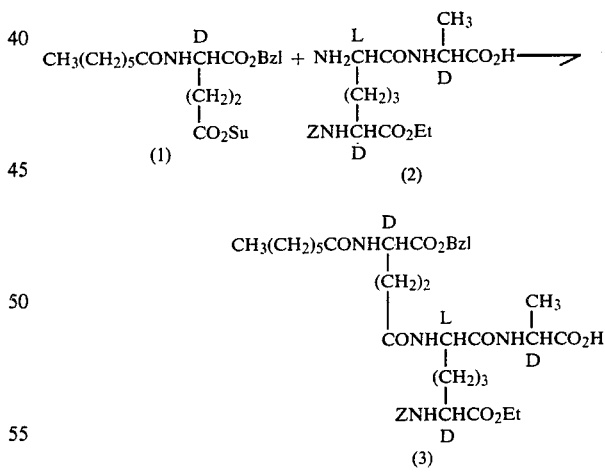

Heptanoyl—γ—D—Glu—(α—Obzl)—(L)—Z—(D-)—mesoDAP—(D)—OEt—(L)—D—AlaOH (3) was prepared substantially in the same manner as step 1 of Example 189.

mp. 94°–102° C.

[α]$_D$—1.06 (C=0.21, CHCl$_3$).

IR (Nujol): 3280, 1735, 1685, 1630 cm$^{-1}$.

NMR (CDCl$_3$, δ): 0.86 (3H, m), 1.05–2.55 (26H, m), 3.9–4.9 (6H, m), 5.10 (2H, s), 5.16 (2H, s), 7.32 (10H, s).

(2) Step 2

Compound (3) ⟶

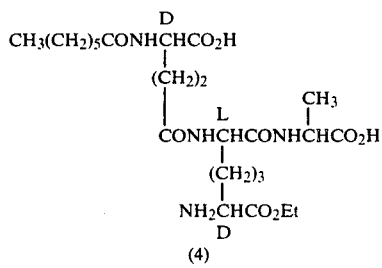
(4)

Heptanoyl—γ—D—Glu—(α—OBzl)—(L)—Z—(D-)—mesoDAP—(D)—OEt—(L)—D—AlaOH (3) (930 mg) was dissolved in acetic acid (20 ml) and hydrogenated under an atmospheric pressure of hydrogen over 10% palladium-charcoal (200 mg). After removal of the catalyst, acetic acid was evaporated in vacuo. The residue was purified by column chromatography of HP-20 (50 ml) with ethanol-H20 (3:7, v/v) as an eluent to give heptanoyl—γ—D—Glu—(α—OH)—(L-)—mesoDAP—(D)—OMe—(L)—D—AlaOH (4) (490 mg).

mp. 218° C.

$[\alpha]_D - 14.63°$ (C=0.2, H$_2$O).

IR (Nujol): 3280, 1740, 1635 cm$^{-1}$.

NMR (D$_2$O, δ): 0.90 (3H, m), 1.2–2.6 (26H, m), 4.1–4.55 (6H, m).

We claim:

1. A compound of the formula:

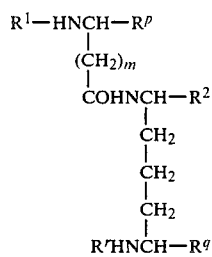

wherein

R$^1$ is alkanoyl;

R$^2$ is R$^q$ are each hydrogen, carboxy, protected carboxy, or a group of the formula:

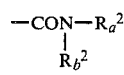

wherein R$_a^2$ is mono- or di-carboxy (or protected carboxy) lower alkyl or ar(carboxy or protected carboxy) lower alkyl whose aryl moiety may be substituted by hydroxy, R$_b^2$ is hydrogen or lower alkyl;

R$^p$ is hydrogen, carboxy, protected carboxy, with proviso that when one of R$^2$ and R$^q$ is hydrogen, then the outer is carboxy or protected carboxy or a group of the formula:

wherein R$_a^2$ and R$_b^2$ are each as defined above;

R$^r$ is hydrogen or amino protective group; m is an integer 1 to 3;

or its pharmaceutically acceptable salt.

2. A compound according to claim 1, wherein R$^1$ is alkanoyl selected from acetyl, hexanoyl, heptanoyl, octanoyl, lauroyl, stearoyl, 2-ethylhexanoyl, 2-hexadecyloctadecanoyl and 2-docosyltetracosanoyl, and R$^2$, R$^p$, R$^q$, R$^r$ and m are each as defined in the preceding claim 1.

3. A compound according to claim 2, wherein R$^2$ is carboxy, methoxycarbonyl, carboxymethylcarbamoyl, 1-carboxyethylcarbamoyl, 1-methoxycarbonylethylcarbamoyl, 1-ethoxycarbonylethylcarbamoyl, 1-carboxy-2-phenylethylcarbamoyl, 1-carboxy-3-methylbutylcarbamoyl or 3-carboxypropylcarbamoyl, R$^1$, R$^p$, R$^q$, R$^r$ and m are each as defined in the preceding claim 2.

4. A compound according to claim 3, wherein R$^p$ and R$^q$ are each hydrogen, carboxy, methoxycarbonyl or ethoxycarbonyl, R$^r$ is hydrogen, m is an integer of 2, and R$^1$ and R$^2$ are each as defined in the preceding claim 3.

5. A compound according to claim 1, wherein R$^1$ is acetyl or heptanoyl, R$^p$ is carboxy, m is an integer of 2, R$^2$ is carboxymethylcarbamoyl, R$^q$ is carboxy and R$^r$ is hydrogen.

6. A compound according to claim 1, wherein R$^1$ is stearoyl, heptanoyl, lauroyl, octanoyl, 2-ethylhexanoyl or hexanoyl, R$^p$ is carboxy, m is an integer of 2, R$^2$ is 1-carboxyethylcarbamoyl, R$^q$ is carboxy and R$^r$ is hydrogen.

7. A compound according to claim 1, wherein R$^1$ is heptanoyl, 2-ethylhexanoyl, stearoyl, 2-hexadecyloctadecanoyl, 2-docosyltetracosanoyl or octanoyl, R$^p$ is carboxy, m is an integer of 2, R$^2$ and R$^q$ are each carboxy, and R$^r$ is hydrogen.

8. A compound according to claim 1, wherein R$^1$ is heptanoyl, R$^p$ is carboxy, m is an integer of 2, R$^2$ is 1-carboxy-2-phenylethylcarbamoyl or 3-carboxypropylcarbamoyl, R$^q$ is carboxy and R$^r$ is hydrogen.

9. A compound according to claim 1, wherein R$^1$ is heptanoyl, R$^p$ is carboxy, m is an integer of 1 or 3, R$^2$ and R$^q$ are each carboxy and R$^r$ is hydrogen.

10. A compound according to claim 1, wherein R$^1$ is octanoyl, R$^p$ is methoxycarbonyl, m is an integer of 2, R$^2$ is 1-methoxycarbonylethylcarbamoyl, R$^q$ is methoxycarbonyl and R$^r$ is hydrogen.

11. A compound according to claim 1, wherein R$^1$ is octanoyl or stearoyl R$^p$ is carboxy, m is an integer of 2, R$^2$ is 1-carboxyethylcarbamoyl, and R$^q$ and R$^r$ are each hydrogen.

12. A compound according to claim 1, wherein R$^1$ is stearoyl, R$^p$ is carboxy, m is an integer of 2, R$^2$ and R$^q$ are each methoxycarbonyl and R$^r$ is hydrogen.

13. A compound according to claim 1, wherein R$^1$ is heptanoyl or octanoyl, R$^p$ is methoxycarbonyl, m is an integer of 2, R$^2$ is 1-methoxycarbonylethylcarbamoyl, R$^q$ is methoxycarbonyl and R$^r$ is hydrogen.

14. A compound according to claim 1, wherein R$^1$ is heptanoyl,

R$^p$ is carboxy, m is an integer of 2,

R$^2$ is 1-ethoxycarbonylethylcarbamoyl,

R$^q$ is ethoxycarbonyl and R$^r$ is hydrogen.

15. A compound according to claim 1, wherein R$^p$ is carboxy, m is an integer of 2, R$^2$ is 1-carboxyethylcarbamoyl, R$^q$ is carboxy and R$^r$ is hydrogen.

16. A compound according to claim 1, where $R^1$ is stearoyl, $R^p$ is carboxy, m is an integer of 2, $R^2$ is 1-carboxyethylcarbamoyl, $R^q$ is carboxy and $R^r$ is hydrogen.

17. A compound according to claim 1, where $R^1$ is heptanoyl, $R^p$ is carboxy, m is an integer of 2, $R^2$ is 1-carboxyethylcarbamoyl, $R^q$ is carboxy and $R^r$ is hydrogen.

18. A compound according to claim 1, where $R^1$ is lauroyl, $R^p$ is carboxy, m is an integer of 2, $R^2$ is 1-carboxyethylcarbamoyl, $R^q$ is carboxy and $R^r$ is hydrogen.

19. A compound according to claim 1, where $R^1$ is octanoyl, $R^p$ is carboxy, m is an integer of 2, $R^2$ is 1-carboxyethylcarbamoyl, $R^q$ is carboxy and $R^r$ is hydrogen.

20. A compound according to claim 1, where $R^1$ is 2-ethylhexanoyl, $R^p$ is carboxy, m is an integer of 2, $R^2$ is 1-carboxyethylcarbamoyl, $R^q$ is carboxy and $R^r$ is hydrogen.

21. A compound according to claim 1, where $R^1$ is hexanoyl, $R^p$ is carboxy, m is an integer of 2, $R^2$ is 1-carboxyethylcarbamoyl, $R^q$ is carboxy and $R^r$ is hydrogen.

22. A compound according to claim 1, wherein $R^1$ is octanoyl, $R^p$ is carboxy, m is an integer of 2, $R^2$ is 1-carboxyethylcarbamoyl, and $R^q$ and $R^r$ are each hydrogen.

23. A compound according to claim 1, wherein $R^1$ is stearoyl, $R^p$ is carboxy, m is an integer of 2, $R^2$ is 1-carboxyethylcarbamoyl, and $R^q$ and $R^r$ are each hydrogen.

24. A pharmaceutical composition for enhancing protective efficacy in infection comprising an enhancing effective amount of a compound as defined in claim 1 or its pharmaceutically acceptable salt, in admixture with a carrier.

* * * * *